(12) United States Patent
Gersbach et al.

(10) Patent No.: US 12,214,054 B2
(45) Date of Patent: Feb. 4, 2025

(54) THERAPEUTIC TARGETS FOR THE CORRECTION OF THE HUMAN DYSTROPHIN GENE BY GENE EDITING AND METHODS OF USE

(71) Applicant: Duke University, Durham, NC (US)

(72) Inventors: Charles A. Gersbach, Durham, NC (US); Jacqueline N. Robinson-Hamm, Durham, NC (US)

(73) Assignee: Duke University, Durham, NC (US)

( * ) Notice: Subject to any disclaimer, the term of this patent is extended or adjusted under 35 U.S.C. 154(b) by 245 days.

(21) Appl. No.: 15/779,633

(22) PCT Filed: Nov. 30, 2016

(86) PCT No.: PCT/US2016/064285
§ 371 (c)(1),
(2) Date: May 29, 2018

(87) PCT Pub. No.: WO2017/095967
PCT Pub. Date: Jun. 8, 2017

(65) Prior Publication Data
US 2018/0353615 A1 Dec. 13, 2018

Related U.S. Application Data

(60) Provisional application No. 62/330,336, filed on May 2, 2016, provisional application No. 62/260,712, filed on Nov. 30, 2015.

(51) Int. Cl.
| | |
|---|---|
| *A61K 48/00* | (2006.01) |
| *A61K 31/7105* | (2006.01) |
| *A61K 47/26* | (2006.01) |
| *A61K 47/54* | (2017.01) |
| *C12N 15/10* | (2006.01) |
| *C12N 15/113* | (2010.01) |
| *C12N 15/80* | (2006.01) |
| *C12N 15/85* | (2006.01) |
| *C12Q 1/68* | (2018.01) |

(52) U.S. Cl.
CPC ........ *A61K 48/005* (2013.01); *A61K 31/7105* (2013.01); *A61K 47/26* (2013.01); *A61K 47/549* (2017.08); *A61K 48/0016* (2013.01); *C12N 15/102* (2013.01); *C12N 15/113* (2013.01); *C12N 15/80* (2013.01); *C12N 15/8509* (2013.01); *C12Q 1/68* (2013.01); *C12N 2310/20* (2017.05)

(58) Field of Classification Search
CPC ..... A61K 47/549; A61P 21/00; C12N 15/102; C12N 15/113; C12N 2310/20; C12Q 1/68
USPC ..... 435/6.1, 91.1, 91.31, 455, 458; 536/23.1
See application file for complete search history.

(56) References Cited

U.S. PATENT DOCUMENTS

| | | | |
|---|---|---|---|
| 3,687,808 | A | 8/1972 | Merigan, Jr. |
| 4,469,863 | A | 9/1984 | Ts'o et al. |
| 4,476,301 | A | 10/1984 | Imbach et al. |
| 4,501,729 | A | 2/1985 | Boucher et al. |
| 4,554,101 | A | 11/1985 | Hopp |
| 4,587,044 | A | 5/1986 | Miller et al. |
| 4,605,735 | A | 8/1986 | Miyoshi et al. |
| 4,667,025 | A | 5/1987 | Miyoshi et al. |
| 4,737,323 | A | 4/1988 | Martin et al. |
| 4,762,779 | A | 8/1988 | Snitman |
| 4,789,737 | A | 12/1988 | Miyoshi et al. |
| 4,824,941 | A | 4/1989 | Gordon et al. |
| 4,828,979 | A | 5/1989 | Klevan et al. |
| 4,835,263 | A | 5/1989 | Nguyen et al. |
| 4,845,205 | A | 7/1989 | Huynh et al. |
| 4,876,335 | A | 10/1989 | Yamane et al. |
| 4,904,582 | A | 2/1990 | Tullis |
| 4,948,882 | A | 8/1990 | Ruth |
| 4,958,013 | A | 9/1990 | Letsinger |
| 5,013,830 | A | 5/1991 | Ohsuka et al. |
| 5,023,243 | A | 6/1991 | Tullis |
| 5,034,506 | A | 7/1991 | Summerton et al. |
| 5,082,830 | A | 1/1992 | Brakel et al. |
| 5,109,124 | A | 4/1992 | Ramachandran et al. |
| 5,112,963 | A | 5/1992 | Pieles et al. |
| 5,118,802 | A | 6/1992 | Smith et al. |
| 5,130,302 | A | 7/1992 | Spielvogel et al. |
| 5,134,066 | A | 7/1992 | Rogers et al. |
| 5,138,045 | A | 8/1992 | Cook et al. |
| 5,149,797 | A | 9/1992 | Pederson et al. |
| 5,166,315 | A | 11/1992 | Summerton et al. |
| 5,175,273 | A | 12/1992 | Bischofberger et al. |
| 5,177,196 | A | 1/1993 | Meyer et al. |
| 5,185,444 | A | 2/1993 | Summerton et al. |
| 5,188,897 | A | 2/1993 | Suhadolnik et al. |
| 5,214,134 | A | 5/1993 | Weis et al. |

(Continued)

FOREIGN PATENT DOCUMENTS

| | | |
|---|---|---|
| AU | 2022318664 A1 | 2/2024 |
| CA | 2749305 A1 | 7/2010 |

(Continued)

OTHER PUBLICATIONS

US 11,898,176 B2, 02/2024, Gersbach et al. (withdrawn)

(Continued)

*Primary Examiner* — Jane J Zara

(74) *Attorney, Agent, or Firm* — Michael Best & Friedrich LLP

(57) ABSTRACT

Disclosed herein are therapeutic targets for the correction of the human dystrophin gene by gene editing and methods of use.

16 Claims, 39 Drawing Sheets

Specification includes a Sequence Listing.

(56) References Cited

U.S. PATENT DOCUMENTS

| | | |
|---|---|---|
| 5,214,136 A | 5/1993 | Lin et al. |
| 5,216,141 A | 6/1993 | Benner |
| 5,218,105 A | 6/1993 | Cook et al. |
| 5,219,740 A | 6/1993 | Miller et al. |
| 5,220,007 A | 6/1993 | Pederson et al. |
| 5,235,033 A | 8/1993 | Summerton et al. |
| 5,245,022 A | 9/1993 | Weis et al. |
| 5,254,469 A | 10/1993 | Warren, III |
| 5,256,775 A | 10/1993 | Froehler |
| 5,258,506 A | 11/1993 | Urdea et al. |
| 5,262,536 A | 11/1993 | Hobbs, Jr. |
| 5,264,423 A | 11/1993 | Cohen et al. |
| 5,264,562 A | 11/1993 | Matteucci |
| 5,264,564 A | 11/1993 | Matteucci |
| 5,272,250 A | 12/1993 | Spielvogel et al. |
| 5,276,019 A | 1/1994 | Cohen et al. |
| 5,278,302 A | 1/1994 | Caruthers et al. |
| 5,286,717 A | 2/1994 | Cohen et al. |
| 5,292,873 A | 3/1994 | Rokita et al. |
| 5,317,098 A | 5/1994 | Shizuya et al. |
| 5,321,131 A | 6/1994 | Agrawal et al. |
| 5,366,878 A | 11/1994 | Pederson et al. |
| 5,367,066 A | 11/1994 | Urdea et al. |
| 5,371,241 A | 12/1994 | Brush |
| 5,391,723 A | 2/1995 | Priest |
| 5,399,676 A | 3/1995 | Froehler |
| 5,403,711 A | 4/1995 | Walder et al. |
| 5,405,938 A | 4/1995 | Summerton et al. |
| 5,405,939 A | 4/1995 | Suhadolnik et al. |
| 5,414,077 A | 5/1995 | Lin et al. |
| 5,416,203 A | 5/1995 | Letsinger |
| 5,432,272 A | 7/1995 | Benner |
| 5,434,257 A | 7/1995 | Matteucci et al. |
| 5,451,463 A | 9/1995 | Nelson et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,459,255 A | 10/1995 | Cook et al. |
| 5,466,677 A | 11/1995 | Baxter et al. |
| 5,470,967 A | 11/1995 | Huie et al. |
| 5,476,925 A | 12/1995 | Letsinger et al. |
| 5,478,745 A | 12/1995 | Samulski et al. |
| 5,484,908 A | 1/1996 | Froehler et al. |
| 5,486,603 A | 1/1996 | Buhr |
| 5,489,677 A | 2/1996 | Sanghvi et al. |
| 5,491,133 A | 2/1996 | Walder et al. |
| 5,502,177 A | 3/1996 | Matteucci et al. |
| 5,510,473 A | 4/1996 | Camerini-otero et al. |
| 5,510,475 A | 4/1996 | Agrawal et al. |
| 5,512,439 A | 4/1996 | Horner et al. |
| 5,512,667 A | 4/1996 | Reed et al. |
| 5,514,785 A | 5/1996 | Van Ness et al. |
| 5,519,126 A | 5/1996 | Hecht |
| 5,525,465 A | 6/1996 | Haralambidis et al. |
| 5,525,711 A | 6/1996 | Hawkins et al. |
| 5,536,821 A | 7/1996 | Agrawal et al. |
| 5,541,306 A | 7/1996 | Agrawal et al. |
| 5,541,307 A | 7/1996 | Cook et al. |
| 5,541,313 A | 7/1996 | Ruth |
| 5,545,730 A | 8/1996 | Urdea et al. |
| 5,550,111 A | 8/1996 | Suhadolnik et al. |
| 5,552,538 A | 9/1996 | Urdea et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,552 A | 10/1996 | Magda et al. |
| 5,567,810 A | 10/1996 | Weis et al. |
| 5,571,799 A | 11/1996 | Tkachuk et al. |
| 5,574,142 A | 11/1996 | Meyer et al. |
| 5,578,717 A | 11/1996 | Urdea et al. |
| 5,578,718 A | 11/1996 | Cook et al. |
| 5,580,731 A | 12/1996 | Chang et al. |
| 5,585,481 A | 12/1996 | Arnold, Jr. et al. |
| 5,587,361 A | 12/1996 | Cook et al. |
| 5,587,371 A | 12/1996 | Sessler et al. |
| 5,587,469 A | 12/1996 | Cook et al. |
| 5,591,584 A | 1/1997 | Chang et al. |
| 5,593,972 A | 1/1997 | Weiner et al. |
| 5,595,726 A | 1/1997 | Magda et al. |
| 5,596,086 A | 1/1997 | Matteucci et al. |
| 5,596,091 A | 1/1997 | Switzer |
| 5,597,696 A | 1/1997 | Linn et al. |
| 5,599,923 A | 2/1997 | Sessler et al. |
| 5,599,928 A | 2/1997 | Hemmi et al. |
| 5,602,240 A | 2/1997 | De Mesmaeker et al. |
| 5,608,046 A | 3/1997 | Cook et al. |
| 5,610,289 A | 3/1997 | Cook et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,633,360 A | 5/1997 | Bischofberger et al. |
| 5,652,355 A | 7/1997 | Metelev et al. |
| 5,652,356 A | 7/1997 | Agrawal |
| 5,663,312 A | 9/1997 | Chaturvedula et al. |
| 5,677,437 A | 10/1997 | Teng et al. |
| 5,677,439 A | 10/1997 | Weis et al. |
| 5,681,941 A | 10/1997 | Cook et al. |
| 5,688,941 A | 11/1997 | Cook et al. |
| 5,700,922 A | 12/1997 | Cook et al. |
| 5,714,331 A | 2/1998 | Buchardt et al. |
| 5,719,262 A | 2/1998 | Buchardt et al. |
| 5,750,692 A | 5/1998 | Cook et al. |
| 5,773,700 A | 6/1998 | Van Grinsven et al. |
| 5,962,428 A | 10/1999 | Carrano et al. |
| 6,140,081 A | 10/2000 | Barbas |
| 6,207,453 B1 | 3/2001 | Maass et al. |
| 6,268,490 B1 | 7/2001 | Imanishi et al. |
| 6,287,860 B1 | 9/2001 | Monia et al. |
| 6,453,242 B1 | 9/2002 | Eisenberg et al. |
| 6,462,254 B1 | 10/2002 | Vernachio et al. |
| 6,534,261 B1 | 3/2003 | Cox, III et al. |
| 6,734,291 B2 | 5/2004 | Kochkine et al. |
| 6,770,748 B2 | 8/2004 | Imanishi et al. |
| 6,794,499 B2 | 9/2004 | Wengel et al. |
| 7,034,133 B2 | 4/2006 | Wengel et al. |
| 7,053,207 B2 | 5/2006 | Wengel |
| 7,060,809 B2 | 6/2006 | Wengel et al. |
| 7,074,596 B2 | 7/2006 | Darzynkiewicz et al. |
| 7,084,125 B2 | 8/2006 | Wengel |
| 7,449,561 B1 | 11/2008 | Sommer et al. |
| 7,572,582 B2 | 8/2009 | Wengel et al. |
| 7,728,118 B2 | 6/2010 | Wood et al. |
| 7,745,651 B2 | 6/2010 | Heyes et al. |
| 7,799,565 B2 | 9/2010 | Maclachlan et al. |
| 8,278,036 B2 | 10/2012 | Kariko et al. |
| 8,450,107 B1 | 5/2013 | Zhang et al. |
| 8,586,526 B2 | 11/2013 | Gregory et al. |
| 8,889,356 B2 | 11/2014 | Zhang |
| 9,139,554 B2 | 9/2015 | Hope et al. |
| 9,458,205 B2 | 10/2016 | Gregory et al. |
| 9,890,364 B2 | 2/2018 | Joung et al. |
| 10,266,850 B2 | 4/2019 | Doudna et al. |
| 11,421,251 B2 | 8/2022 | Gersbach et al. |
| 11,427,817 B2 | 8/2022 | Josephs et al. |
| 2002/0160940 A1 | 10/2002 | Case et al. |
| 2004/0142025 A1 | 7/2004 | Maclachlan et al. |
| 2004/0175727 A1 | 9/2004 | Draghia-Akli et al. |
| 2004/0192593 A1 | 9/2004 | Draghia-Akli et al. |
| 2004/0204345 A1 | 10/2004 | Case et al. |
| 2006/0068395 A1 | 3/2006 | Wood et al. |
| 2006/0211647 A1 | 9/2006 | Khan |
| 2007/0042031 A1 | 2/2007 | Maclachlan et al. |
| 2007/0042462 A1 | 2/2007 | Hildinger |
| 2007/0059795 A1 | 3/2007 | Moore et al. |
| 2007/0185042 A1 | 8/2007 | Tsai et al. |
| 2007/0192880 A1 | 8/2007 | Muyan et al. |
| 2008/0070299 A1 | 3/2008 | Wood et al. |
| 2008/0090291 A1 | 4/2008 | Wood et al. |
| 2009/0018031 A1 | 1/2009 | Trinklein et al. |
| 2010/0035968 A1 | 2/2010 | Rasmussen et al. |
| 2010/0076057 A1 | 3/2010 | Sontheimer et al. |

(56) References Cited

U.S. PATENT DOCUMENTS

| | | |
|---|---|---|
| 2010/0261175 A1 | 10/2010 | Rasmussen et al. |
| 2010/0267018 A1 | 10/2010 | Wengel et al. |
| 2011/0145940 A1 | 6/2011 | Voytas et al. |
| 2011/0197290 A1 | 8/2011 | Fahrenkrug et al. |
| 2011/0263682 A1 | 10/2011 | De Kimpe et al. |
| 2011/0301073 A1 | 12/2011 | Gregory et al. |
| 2012/0195917 A1 | 8/2012 | Sahin et al. |
| 2012/0207744 A1 | 8/2012 | Mendlein et al. |
| 2013/0274129 A1 | 10/2013 | Katzen et al. |
| 2014/0179006 A1 | 6/2014 | Zhang |
| 2014/0234975 A1 | 8/2014 | Silva et al. |
| 2014/0295557 A1 | 10/2014 | Joung et al. |
| 2014/0356956 A1 | 12/2014 | Church et al. |
| 2015/0024499 A1 | 1/2015 | Brouns et al. |
| 2015/0031089 A1 | 1/2015 | Lindstrom |
| 2015/0044772 A1 | 2/2015 | Zhao |
| 2015/0045413 A1 | 2/2015 | De Visser et al. |
| 2015/0056705 A1 | 2/2015 | Conway et al. |
| 2015/0079064 A1 | 3/2015 | Gersbach et al. |
| 2015/0159178 A1 | 6/2015 | Green et al. |
| 2015/0225717 A1 | 8/2015 | Lee et al. |
| 2015/0252358 A1 | 9/2015 | Maeder et al. |
| 2016/0002634 A1 | 1/2016 | Sazani et al. |
| 2016/0040189 A1 | 2/2016 | Kennedy et al. |
| 2016/0058889 A1 | 3/2016 | Olson et al. |
| 2016/0177278 A1 | 6/2016 | Wolfe et al. |
| 2016/0199419 A1 | 7/2016 | Miura |
| 2016/0201089 A1 | 7/2016 | Gersbach et al. |
| 2016/0281166 A1 | 9/2016 | Bhattacharjee et al. |
| 2016/0354487 A1 | 12/2016 | Zhang et al. |
| 2017/0002316 A1 | 1/2017 | Gascón Jiménez et al. |
| 2017/0198308 A1 | 7/2017 | Qi et al. |
| 2017/0204407 A1 | 7/2017 | Gilbert et al. |
| 2017/0283831 A1 | 10/2017 | Zhang et al. |
| 2017/0362635 A1 | 12/2017 | Chamberlain et al. |
| 2018/0073012 A1 | 3/2018 | Liu et al. |
| 2018/0127780 A1 | 5/2018 | Liu et al. |
| 2018/0135109 A1 | 5/2018 | Jayaram et al. |
| 2018/0201951 A1 | 7/2018 | Guilak et al. |
| 2018/0237771 A1 | 8/2018 | Kim et al. |
| 2018/0251735 A1 | 9/2018 | Ko |
| 2018/0271069 A1 | 9/2018 | Min et al. |
| 2018/0280539 A1 | 10/2018 | Debs et al. |
| 2018/0305689 A1 | 10/2018 | Sætrom et al. |
| 2018/0305704 A1 | 10/2018 | Zhang |
| 2018/0305719 A1 | 10/2018 | Perez-Pinera et al. |
| 2018/0319850 A1 | 11/2018 | Payne et al. |
| 2018/0320197 A1 | 11/2018 | Gersbach et al. |
| 2018/0327740 A1 | 11/2018 | Gifford et al. |
| 2018/0334685 A1 | 11/2018 | Yeo et al. |
| 2019/0032049 A1 | 1/2019 | Naldini et al. |
| 2019/0038776 A1 | 2/2019 | Pyle et al. |
| 2019/0048337 A1* | 2/2019 | Hsu .................. C12N 9/22 |
| 2019/0062790 A1 | 2/2019 | Doudna et al. |
| 2019/0078119 A1 | 3/2019 | Wilson et al. |
| 2019/0106710 A1 | 4/2019 | Zhang et al. |
| 2019/0127713 A1 | 5/2019 | Gersbach et al. |
| 2019/0134221 A1 | 5/2019 | Bumcrot et al. |
| 2019/0151476 A1 | 5/2019 | Gersbach et al. |
| 2019/0183932 A1 | 6/2019 | Mackall et al. |
| 2019/0201402 A1 | 7/2019 | Jiang et al. |
| 2019/0264232 A1 | 8/2019 | Hou et al. |
| 2019/0374655 A1 | 12/2019 | Kabadi et al. |
| 2020/0002731 A1 | 1/2020 | Frendewey et al. |
| 2020/0056206 A1 | 2/2020 | Tremblay et al. |
| 2020/0123533 A1 | 4/2020 | Wang et al. |
| 2020/0216549 A1 | 7/2020 | Fukumura et al. |
| 2020/0216810 A1 | 7/2020 | Metelitsa et al. |
| 2020/0275641 A1 | 9/2020 | Min et al. |
| 2021/0322577 A1 | 10/2021 | Lande et al. |
| 2022/0098561 A1 | 3/2022 | Gersbach et al. |
| 2022/0177879 A1 | 6/2022 | Gersbach et al. |
| 2022/0184229 A1 | 6/2022 | Gersbach et al. |
| 2022/0195406 A1 | 6/2022 | Gersbach et al. |
| 2022/0305141 A1 | 9/2022 | Gersbach et al. |
| 2022/0307015 A1 | 9/2022 | Gersbach et al. |
| 2022/0364124 A1 | 11/2022 | Gersbach et al. |
| 2022/0396790 A1 | 12/2022 | Gersbach et al. |
| 2023/0032846 A1 | 2/2023 | Gersbach et al. |
| 2023/0047669 A1 | 2/2023 | Josephs et al. |
| 2023/0201375 A1 | 6/2023 | Gersbach et al. |
| 2023/0348870 A1 | 11/2023 | Gersbach et al. |
| 2023/0349888 A1 | 11/2023 | Gersbach et al. |
| 2023/0383270 A1 | 11/2023 | Gersbach et al. |
| 2023/0383297 A1 | 11/2023 | Gersbach et al. |
| 2023/0392132 A1 | 12/2023 | Gersbach et al. |
| 2024/0026352 A1 | 1/2024 | Gersbach et al. |
| 2024/0052328 A1 | 2/2024 | Kwon et al. |
| 2024/0058425 A1 | 2/2024 | Gersbach et al. |
| 2024/0067968 A1 | 2/2024 | Cosgrove et al. |

FOREIGN PATENT DOCUMENTS

| | | |
|---|---|---|
| CA | 2981508 A1 | 10/2016 |
| CA | 3086885 A1 | 7/2019 |
| CA | 3101477 A1 | 12/2019 |
| EP | 3009511 A2 | 4/2016 |
| EP | 3199632 A1 | 8/2017 |
| EP | 3712272 A1 | 9/2020 |
| EP | 3209783 B1 | 11/2021 |
| EP | 3995584 A1 | 5/2022 |
| JP | 2013-509159 A | 3/2013 |
| JP | 2015-534817 A | 12/2015 |
| JP | 2016-521452 A | 7/2016 |
| JP | 2016-521975 A | 7/2016 |
| JP | 2016-523082 A | 8/2016 |
| KR | 20190134673 A | 12/2019 |
| WO | 1991/18114 A1 | 11/1991 |
| WO | WO1992/000387 A1 | 1/1992 |
| WO | WO1993/007883 A1 | 4/1993 |
| WO | WO 1993/024640 A2 | 12/1993 |
| WO | WO 1994/016737 A1 | 8/1994 |
| WO | WO1998/053058 A1 | 11/1998 |
| WO | WO1998/053059 A1 | 11/1998 |
| WO | WO1998/053060 A1 | 11/1998 |
| WO | WO 2000/028004 A1 | 5/2000 |
| WO | 2001/083793 A2 | 11/2001 |
| WO | WO 2001/083783 A2 | 11/2001 |
| WO | WO 2001/092551 A2 | 12/2001 |
| WO | WO2002/016536 A1 | 2/2002 |
| WO | WO2003/016496 A2 | 2/2003 |
| WO | WO2003/072788 A1 | 9/2003 |
| WO | WO2007/019301 A2 | 2/2007 |
| WO | WO 2008/006028 A2 | 1/2008 |
| WO | WO2008/070859 A2 | 6/2008 |
| WO | WO2010/075424 A2 | 7/2010 |
| WO | WO2010/144740 A1 | 12/2010 |
| WO | WO 2011/036640 A2 | 3/2011 |
| WO | WO 2011/154427 A1 | 12/2011 |
| WO | WO2012/136476 A1 | 10/2012 |
| WO | WO2013/098244 A1 | 7/2013 |
| WO | WO 2013/163628 A2 | 10/2013 |
| WO | WO2014/018423 A2 | 1/2014 |
| WO | WO2014/059255 A1 | 4/2014 |
| WO | 2014/081855 A1 | 5/2014 |
| WO | WO2014/065596 A2 | 5/2014 |
| WO | 2014/093595 A1 | 6/2014 |
| WO | 2014/093622 A2 | 6/2014 |
| WO | 2014/093712 A2 | 6/2014 |
| WO | 2014/099744 A1 | 6/2014 |
| WO | WO2014/089290 A1 | 6/2014 |
| WO | WO2014/093479 A1 | 6/2014 |
| WO | WO2014/093709 A1 | 6/2014 |
| WO | WO2014/144592 A2 | 9/2014 |
| WO | 2014/197568 A2 | 12/2014 |
| WO | WO 2014/197748 A2 | 12/2014 |
| WO | WO2014/204726 A1 | 12/2014 |
| WO | WO2015/006747 A2 | 1/2015 |
| WO | 2015/021457 A2 | 2/2015 |
| WO | 2015/035139 A2 | 3/2015 |
| WO | WO2015/035136 A2 | 3/2015 |
| WO | WO2015/048690 A1 | 4/2015 |
| WO | 2015/070083 A1 | 5/2015 |
| WO | 2015/089462 A1 | 6/2015 |

(56) References Cited

FOREIGN PATENT DOCUMENTS

| | | |
|---|---|---|
| WO | WO2015/089427 A1 | 6/2015 |
| WO | WO2015/155686 A2 | 10/2015 |
| WO | WO2015/161276 A2 | 10/2015 |
| WO | 2015/195621 A1 | 12/2015 |
| WO | 2016/011080 A2 | 1/2016 |
| WO | WO2016/011070 A2 | 1/2016 |
| WO | WO2016/049258 A2 | 3/2016 |
| WO | WO2016/063264 A1 | 4/2016 |
| WO | 2016/070070 A1 | 5/2016 |
| WO | WO2016/081924 A1 | 5/2016 |
| WO | WO2016/114972 A1 | 7/2016 |
| WO | WO2016/123578 A1 | 8/2016 |
| WO | WO 2016/130600 A2 | 8/2016 |
| WO | WO 2016/161380 A1 | 10/2016 |
| WO | 2016/205613 A1 | 12/2016 |
| WO | WO2016/187717 A1 | 12/2016 |
| WO | 2017/016915 A1 | 2/2017 |
| WO | WO2017/049266 A2 | 3/2017 |
| WO | WO2017/049407 A1 | 3/2017 |
| WO | WO2017/070632 A2 | 4/2017 |
| WO | WO2017/072590 A1 | 5/2017 |
| WO | WO2017/075478 A1 | 5/2017 |
| WO | 2017/139505 A2 | 8/2017 |
| WO | WO2017/165859 A1 | 9/2017 |
| WO | 2017/180976 A1 | 10/2017 |
| WO | WO 2017/180915 A2 | 10/2017 |
| WO | 2017/193029 A3 | 11/2017 |
| WO | 2018/002812 A1 | 1/2018 |
| WO | 2018/005805 A1 | 1/2018 |
| WO | 2018/017483 A1 | 1/2018 |
| WO | WO 2018/013932 A1 | 1/2018 |
| WO | WO2018/017751 A1 | 1/2018 |
| WO | WO2018/035388 A1 | 2/2018 |
| WO | WO2018/035495 A1 | 2/2018 |
| WO | 2018/039145 A1 | 3/2018 |
| WO | 2018/098480 A1 | 5/2018 |
| WO | WO2018/081504 A1 | 5/2018 |
| WO | 2018/107003 A1 | 6/2018 |
| WO | WO2018/129296 A1 | 7/2018 |
| WO | 2018/162702 A1 | 9/2018 |
| WO | 2018/179578 A1 | 10/2018 |
| WO | WO2018/191388 A1 | 10/2018 |
| WO | 2019/009682 A2 | 1/2019 |
| WO | 2019/023291 A2 | 1/2019 |
| WO | WO2019/002590 A1 | 1/2019 |
| WO | WO 2019/036599 A1 | 2/2019 |
| WO | 2019/046755 A1 | 3/2019 |
| WO | WO2019/067786 A1 | 4/2019 |
| WO | WO2019/077001 A1 | 4/2019 |
| WO | WO 2019/079514 A1 | 4/2019 |
| WO | 2019/084050 A1 | 5/2019 |
| WO | WO 2019/092505 A1 | 5/2019 |
| WO | 2019/113472 A1 | 6/2019 |
| WO | 2019/123014 A1 | 6/2019 |
| WO | 2019/136216 A1 | 7/2019 |
| WO | 2019/204750 A1 | 10/2019 |
| WO | 2019/213626 A1 | 11/2019 |
| WO | WO2019/232069 A1 | 12/2019 |
| WO | 2020/018918 A1 | 1/2020 |
| WO | WO2020/124257 A1 | 6/2020 |
| WO | WO 2020/132226 A1 | 6/2020 |
| WO | 2020/168133 A1 | 8/2020 |
| WO | WO2020/163396 A1 | 8/2020 |
| WO | WO 2020/214613 A1 | 10/2020 |
| WO | WO2020/257665 A1 | 12/2020 |
| WO | WO2021/055956 A1 | 3/2021 |
| WO | 2022/038264 A1 | 2/2022 |
| WO | 2022/087321 A1 | 4/2022 |
| WO | 2022/104159 A1 | 5/2022 |
| WO | WO 2022/103935 A1 | 5/2022 |
| WO | 2022/133062 A1 | 6/2022 |
| WO | WO2022/187288 A2 | 9/2022 |
| WO | WO 2023/010133 A2 | 2/2023 |
| WO | WO 2023/137471 A1 | 7/2023 |
| WO | WO 2023/137472 A2 | 7/2023 |
| WO | WO2023/200998 A2 | 10/2023 |
| WO | WO 2024/015881 A2 | 1/2024 |
| WO | 2024/040253 A1 | 2/2024 |
| WO | WO 2024/064642 A2 | 3/2024 |
| WO | 2024/081937 A1 | 4/2024 |
| WO | WO 2024/040254 A3 | 5/2024 |

OTHER PUBLICATIONS

Sequence alignment: SEQ ID No. 15.*
Sequence alignment: SEQ ID No. 15 a.*
Sequence alignment: SEQ ID No. 16.*
Sequence alignment: SEQ ID No. 1 a.*
Xie et al., "sgRNAcas9: a software package for designing CRISPR sgRNA and evaluating potential off-target cleavage sites," PLoS One, 2014, 9(6): e100448.
United States Patent Office Action for U.S. Appl. No. 16/098,464 dated Jun. 21, 2021 (12 pages).
United States Patent Office Action for U.S. Appl. No. 16/318,745 dated Jul. 13, 2021 (9 pages).
Israeli Patent Office Action for Application No. 259100 dated Apr. 27, 2021 (6 pages, English translation included).
Friedland et al., "Characterization of *Staphylococcus aureus* Cas9: a smaller Cas9 for all-in-one adeno-associated virus delivery and paired nickase applications," Genome Biology, 2015, 16(16):257, 10 pages.
Friedland et al., "*Staphyloccocus aureus* Cas9: An Alternative Cas9 for Genome Editing Applications," Retrieved from the Internet: <http://www.editasmedicine.com/data/doc uments/ASGCT%20poster 2015 Ari.pdf> Retrieved on Feb. 28, 2018.
Eurasian Patent Office Action for Application No. 201891317/28 dated Nov. 19, 2019 (6 pages, English translation included).
U.S. Appl. No. 61/831,481, filed Jun. 5, 2013.
U.S. Appl. No. 61/839,127, filed Jun. 25, 2013.
U.S. Appl. No. 61/967,466, filed Mar. 19, 2014.
PCT/US2014/041190, Jun. 5, 2014, WO 2014/197748, Dec. 11, 2014.
U.S. Appl. No. 14/895,316, filed Dec. 2, 2015, 2016/0201089, Jul. 14, 2016.
U.S. Appl. No. 15/991,333, filed May 29, 2018.
U.S. Appl. No. 62/332,297, filed May 5, 2016.
PCT/US2017/031351, May 5, 2017, WO 2017/193029, Nov. 9, 2017.
U.S. Appl. No. 62/363,888, filed Jul. 19, 2016.
PCT/US2017/042921, Jul. 19, 2017, WO 2018/017754, Jan. 25, 2018.
Aartsma-Rus, A. et al., "Antisense-mediated exon skipping: a versatile tool with therapeutic and research applications," RNA 13, 2007, 1609-1624.
Aartsma-Rus, A. et al., "Exploring the frontiers of therapeutic exon skipping for Duchenne muscular dystrophy by double targeting within one or multiple exons," Mol Ther, 2006, 14:401-407.
Aartsma-Rus, A. et al., "Theoretic applicability of antisense-mediated exon skipping for Duchenne muscular dystrophy mutations," Hum Mutat, 2009, 30:293-299.
Adler, A.F. et al., "Nonviral direct conversion of primary mouse embryonic fibroblasts to neuronal cells," Molecular therapy, 2012 Nucleic acids 1, e32.
Aiuti, A. et al., "Lentiviral hematopoietic stem cell gene therapy in patients with Wiskott-Aldrich syndrome," Science, 2013, 341(6148): p. 1233151.
Anders, S. et al., "Differential expression analysis for sequence count data," Genome biology 11, 2010, R106.
Anguela, X. M. et al., "Robust ZFN-mediated genome editing in adult hemophilic mice," Blood, 2013, 122:3283-3287.
Aoki, Y. et al., "Bodywide skipping of exons 45-55 in dystrophic mdx52 mice by systemic antisense delivery," Proc Natl Acad Sci USA, 2012, 109:13763-13768.
Bae et al., "Cas-OFFinder: a fast and versatile algorithm that searches for potential off-target sites of Cas9 RNA-guided endonucleases," Bioinformatics, 2014, 30: 1473-1475.
Bartsevich, V.V. et al., "Engineered zinc finger proteins for controlling stem cell fate," Stem Cells 21, 2003, 632-637.

(56) References Cited

OTHER PUBLICATIONS

Bauer et al., "An erythroid enhancer of BCL11A subject to genetic variation determines fetal hemoglobin level," Science 342, 2013, 253-257.
Beerli, R. R. et al., "Chemically regulated zinc finger transcription factors," J Biol Chem, 2000, 275(42): p. 32617-27.
Beerli, R.R. et al., "3rd Engineering polydactyl zinc-finger transcription factors," Nat Biotechnol 20, 2002, 135-141.
Beerli, R.R. et al., "3rd Positive and negative regulation of endogenous genes by designed transcription factors," Proc Natl Acad Sci U S A 97, 2000, 1495-1500.
Beerli, R.R. et al., "3rd Toward controlling gene expression at will: specific regulation of the erbB-2/HER-2 promoter by using polydactyl zinc finger proteins constructed from modular building blocks," Proc Natl Acad Sci U S A 95, 1998, 14628-14633.
Beltran, A. et al., "Re-activation of a dormant tumor suppressor gene maspin by designed transcription factors," Oncogene 26, 2007, 2791-2798.
Benedetti, S. et al., "Repair or Replace? Exploiting Novel Gene and Cell Therapy Strategies for Muscular Dystrophies," FEBS Journal (2013).
Berghella, L. et al., "Reversible immortalization of human myogenic cells by site-specific excision of a retrovirally transferred oncogene," Human gene therapy 10, 1999, 1607-1617.
Bhakta, M. S. et al., "Highly active zinc-finger nucleases by extended modular assembly," Genome Res, 2013, 530-538.
Bidou, L. et al., "Sense from nonsense: therapies for premature stop codon diseases," Trends in Molecular Medicine 18, 2012, 679-688.
Bladen et al., "The TREAT-NMD DMD Global Database: analysis of more than 7,000 Duchenne muscular dystrophy mutations," Human Mutation, 2015, 36(4):395-402.
Blancafort, P. et al., "3rd Scanning the human genome with combinatorial transcription factor libraries," Nat Biotechnol 21, 2003, 269-274.
Boch, J. et al., "Breaking the code of DNA binding specificity of TAL-type III effectors," Science 326, 2009, 1509.
Bowles, D. E. et al., "Phase 1 Gene Therapy for Duchenne Muscular Dystrophy Using a Translation Optimized AAV Vector," Molecular Therapy 20, 2012, 443-455.
Brunet, E. et al., "Chromosomal translocations induced at specific loci in human stem cells," Proc Natl Acad Sci USA, 2009, 106:10620-10625.
Buler et al. "Energy-sensing factors coactivator peroxisome proliferator-activated receptor gamma coactivator 1-alpha (PGC-1 alpha) and AMP-activated protein kinase control expression of inflammatory mediators in liver." The Journal of Biological Chemistry, vol. 287, No. 3, pp. 1847-1860, Jan. 13, 2012.
Bultmann, S. et al., "Targeted transcriptional activation of silent oct4 pluripotency gene by combining designer TALEs and inhibition of epigenetic modifiers," Nucleic Acids Res 40, 2012, 5368-5377.
Canver et al., "BCL11A enhancer dissection by Cas9-mediated in situ saturating mutagenesis," Nature, 2015, 527:192-197.
Cerletti, M. et al., "Highly efficient, functional engraftment of skeletal muscle stem cells in dystrophic muscles," Cell 134, 2008, 37-47.
Cermak, T. et al., "Efficient design and assembly of custom TALEN and other TAL effector-based constructs for DNA targeting," Nucleic Acids Res 30, 2011, e82.
Chapdelaine, P. et al., "Meganucleases can restore the reading frame of a mutual dystrophin," Gene therapy 17, 2010, 846-858.
Cheng, A. W. et al., "Multiplexed activation of endogenous genes by CRISPR-on, an RNA-guided transcriptional activator system," Cell Res, 2013, 23(10): p. 1163-1171.
Cho, S. W. et al., "Analysis of off-target effects of CRISPR/Cas-derived RNA-guided endonucleases and nickases," Genome Res, 2014, 24:132-141.
Cho, S.W. et al., "Targeted genome engineering in human cells with the Cas9 RNA-guided endonuclease," Nat Biotechnol 31, 2013, 230-232.
Christian, M. et al., "Targeting DNA double-strand breaks with TAL effector nucleases," Genetics 186, 2010, 757-761.
Cirak, S. et al., "Exon skipping and dystrophin restoration in patients with Duchenne muscular dystrophy after systemic phosphorodiamidate morpholino oligomer treatment: an open-label, phase 2, dose-escalation study," Lancet 378, 2011, 595-605.
Cong, L. et al., "Multiplex Genome Engineering Using CRISPR/Cas Systems," Science 339, 2013, 819-823.
Cornu et al., "Quantification of zinc finger nuclease-associated toxicity," Meth Mol Biol, 2010, 649:237-245.
Cornu, T. I. et al., "DNA-binding specificity is a major determinant of the activity and toxicity of zinc-finger nucleases," Mol Ther, 2008, 16:352-358.
Cradick, T. J. et al., "CRISPR/Cas9 systems targeting beta-globin and CCR5 genes have substantial off-target activity," Nucleic Acids Res, 2013, 41(20): p. 9584-92.
Darabi, R. et al., "Human ES- and iPS-derived myogenic progenitors restore dystrophin and improve contractility upon transplantation in dystrophic mice," Cell Stem Cell 10, 2012, 610-619.
Dezawa, M. et al., "Bone marrow stromal cells generate muscle cells and repair muscle degeneration," Science Signaling 309, 2005, 314.
Ding, Q. et al., "A TALEN Genome-Editing System for Generating Human Stem Cell-Based Disease Models," 2013, Cell Stem Cell 12, 238-251.
Ding, Q. et al., "Enhanced efficiency of human pluripotent stem cell genome editing through replacing TALENs with CRISPRs," Cell Stem Cell, 2013, 12:393-394.
Doyle, E. L. et al., "TAL Effector-Nucleotide Targeter (TALE-NT) 2.0: tools for TAL effector design and target prediction," Nucleic Acids Res 40, 2012, W117-122.
Doyon, Y. et al., "Enhancing zinc-finger-nuclease activity with improved obligate heterodimeric architectures," Nat Methods 8, 2010, 74-79.
Edelstein et al. "Gene therapy clinical trials worldwide 1989-2004—an overview." J. Gene Med. vol. 6, pp. 597-602, 2004.
Esvelt et al., "Orthogonal Cas9 proteins for RNA-guided gene regulation and editing," Nature Methods 2013, 10(11): p. 1116-21.
Fagerlund et al., "The Cpf1 CRISPR-Cas protein expands genome-editing tools," Genome Biology, 2015, 16:251.
Farinelli, G. et al., "Lentiviral vectors for the treatment of primary immunodeficiencies," J Inherit Metab Dis, 2014.
Farzadfard, F. et al., "Tunable and Multifunctional Eukaryotic Transcription Factors Based on CRISPR/Cas," ACS Synth Biol, 2013, 604-613.
Flanigan, K. M. et al., "Mutational spectrum of DMD mutations in dystrophinopathy patients: application of modern diagnostic techniques to a large cohort," Human mutation 30, 2009, 1657-1666.
Fonfara, I. et al., "Phylogeny of Cas9 determines functional exchangeability of dual-RNA and Cas9 among orthologous type II CRISPR-Cas systems," Nucleic Acids Res, 2013.
Forget, "Molecular basis of hereditary persistence of fetal hemoglobin," Ann N Y Acad Sci, 1998, 850, 38-44.
Fu, Y. et al., "High-frequency off-target mutagenesis induced by CRISPR-Cas nucleases in human cells," Nat Biotechnol, 2013, 31(9): p. 822-6.
Fu, Y. et al., "Improving CRISPR-Cas nuclease specificity using truncated guide RNAs," 2014, Nat Biotechnol 32, 279-284.
Gaj, T. et al., "Targeted gene knockout by direct delivery of zinc-finger nuclease proteins," Nature Methods, 2012.
Gaj, T. et al., "ZFN, TALEN, and CRISPR/Cas-based methods for genome engineering," Trends Biotechnol, 2013, 31:397-405.
Garg, A. et al., "Engineering synthetic TAL effectors with orthogonal target sites," Nucleic Acids Res 40, 2012, 7584-7595.
GenBank Accession AF214528.1 (2000).
GenBank Accession X51934.1 (1997).
Gertz, J. et al., "Transposase mediated construction of RNA-seq libraries," Genome Res 22, 2012, 134-141.
Gilman et al., "Distal CCAAT box deletion in the A gamma globin gene of two black adolescents with elevated fetal A gamma globin," Nucleic Acids Res 16, 1988, 10635-10642.

(56) References Cited

OTHER PUBLICATIONS

Goemans, N. M. et al., "Systemic administration of PRO051 in Duchenne's muscular dystrophy," The New England journal of medicine 364, 2011, 1513-1522.

Gou, D. et al., "A novel approach for the construction of multiple shRNA expression vectors," J Gene Med, 2007, 9(9): p. 751-63.

Graslund, T. et al., "3rd Exploring strategies for the design of artificial transcription factors: targeting sites proximal to known regulatory regions for the induction of gamma-globin expression and the treatment of sickle cell disease," J Biol Chem 280, 2005, 3707-3714.

Gregorevic, P. et al., "Systemic delivery of genes to striated muscles using adeno-associated viral vectors," Nat Med, 2004, 10:828-834.

Guo, J. et al., "Directed evolution of an enhanced and highly efficient Fok1 cleavage domain for zinc finger nucleases," J Mol Biol, 2010.

Guschin, D. Y. et al., "A rapid and general assay for monitoring endogenous gene modification," Methods Mol Biol 649, 2010, 247-256.

Hakim et al., "Systemic gene transfer reveals distinctive muscle transduction profile of tyrosine mutant AAV-1, -6, and -9 in neonatal dogs," Mol. Ther. Methods Clin. Dev., 2014, 1:14002.

Hockemeyer, D. et al., "Efficient targeting of expressed and silent genes in human ESCs and iPSCs using zinc-finger nucleases," Nat Biotechnol, 2009, 27(9): p. 851-7.

Hockemeyer, D. et al., "Genetic engineering of human pluripotent cells using TALE nucleases," Nat Biotechnol 29, 2011, 731-734.

Hoffman, E. P. et al., "Dystrophin: the protein product of the Duchenne muscular dystrophy locus," Cell, 1987, 51:919.

Hou, Z. et al., "Efficient genome engineering in human pluripotent stem cells using Cas9 from Neisseria meningitidis," Proc Natl Acad Sci USA, 2013, 110:15644-15649.

Hsu et al. (2012) "Dissecting Neural Function Using Targeted Genome Engineering Technologies", ACS Chem. Neurosci., pp. 603-610.

Hsu et al., "DNA targeting specificity of RNA-guided Cas9 nucleases," Nature Biotechnology 31, 2013, 827-832 doi:10.1038/nbt.2647.

Humbert et al., "Targeted gene therapies: tools, applications, optimization", Critical Reviews in Biochemistry and Molecular Biology, CRC Press, vol. 47, No. 3, Apr. 2012, pp. 264-281.

Hwang, W. Y. et al., "Efficient genome editing in zebrafish using CRISPR-Cas system," Nat Biotechnol, 2013, 31(3):p. 227-9.

Iyombe-Engembe et al., "Efficient Restoration of the Dystrophin Gene Reading Frame and Protein Structure in DMD Myoblasts Using the CinDel Method," Molecular Therapy—Nucleic Acids, 2016, 5:e283.

Jinek, M. et al., "A programmable dual-RNA-guided DNA endonuclease in adaptive bacterial immunity," Science 337, 2012, 816-821.

Jinek, M. et al., "RNA-programmed genome editing in human cells. eLife 2," e00471, 2013.

Jinek, M. et al., "Structures of Cas9 endonucleases reveal RNA-mediated conformational activation," Science, 2014, 343(6176): p. 1247997.

Joung, J. K. et al., "TALENs: a widely applicable technology for targeted genome editing," Nature Reviews Molecular Cell Biology 14, 2013, 49-55.

Kayali et al., "Site-directed gene repair of the dystrophin gene mediated by PNA-ssODNs," Human Molecular Genetics, vol. 19, No. 16, Aug. 15, 2010, pp. 3266-3281.

Kearns, N. A. et al., "Cas9 effector-mediated regulation of transcription and differentiation in human pluripotent stem cells," Development, 2014, 141(1): p. 219-23.

Kim, H. et al., "Surrogate reporters for enrichment of cells with nuclease-induced mutations," Nat Methods, 2011, 8:941-943.

Kim, Y. et al., "TALENs and ZFNs are associated with different mutation signatures," Nat Methods, 2013.

Kimura, E. et al., "Cell-lineage regulated myogenesis for dystrophin replacement: a novel therapeutic approach for treatment of muscular dystrophy," Hum Mol Genet 17, 2008, 2507-2517.

Kleinstiver et al., "Broadening the targeting range of *Staphylococcus aureus* CRISPR-Cas9 by modifying PAM recognition," Nature Biotechnology, 2015, 7 pages.

Konermann, S. et al., "Optical control of mammalian endogenous transcription and epigenetic states," Nature, 2013, 500(7463): p. 472-6.

Konieczny, P. et al., "Gene and cell-mediated therapies for muscular dystrophy," Muscle Nerve, 2013, 47:649-663.

Kubokawa, I. et al., "Molecular characterization of the 5'-UTR of retinal dystrophin reveals a cryptic intron that regulates translational activity," Molecular Vision, 2010, vol. 16, pp. 2590-2597.

Kyte et al., "A Simple Method for Displaying the Hydropathic Character of a Protein," J. Mol. Biol., 1982, 157:105-132.

Lai et al., "Partial restoration of cardiac function with ΔPDZ nNOS in aged mdx model of Duchenne cardiomyopathy," Hum Mol Genet., 2014, 23(12): 3189-3199.

Langmead, B. et al., "Ultrafast and memory-efficient alignment of short DNA sequences to the human genome," Genome biology 10, 2009, R25.

Larson, M. H. et al., "CRISPR interference (CRISPRi) for sequence-editing control of gene expression," Nat Protoc, 2013, 8(11): p. 2180-96.

Latta-Mahieu et al. "Gene transfer of a chimeric trans-activator is immunogenic and results in short-lived transgene expression." Human Gene Therapy, vol. 13, No. 13, pp. 1611-1620, Sep. 2002.

Lattanzi, L. et al., "High efficiency myogenic conversion of human fibroblasts by adenoviral vector-mediated MyoD gene transfer. An alternative strategy for ex vivo gene therapy of primary myopathies," The Journal of clinical investigation 101, 1998, 2119-2128.

Lee, H. J. et al., "Targeted chromosomal deletions in human cells using zinc finger nucleases," Genome research 20, 2010, 81-89.

Li, D. et al., "Marginal level dystrophin expression improves clinical outcome in a strain of dystrophin/utrophin double knockout mice," PLoS One, 2010, 5:e15286.

Li, H. et al, "In vivo genome editing restores haemostasis in a mouse model of haemophilia," Nature 475, 2011, 217-221.

Li, T. et al., "Modularly assembled designer TAL effector nucleases for targeted gene knockout and gene replacement in eukaryotes," Nucleic Acids Research, 2011, vol. 39, No. 14, pp. 6315-6325.

Li, Y. et al., "Transcription activator-like effector hybrids for conditional control and rewiring of chromosomal transgene expression," Scientific reports 2, 2012, 897.

Liang, J.C. et al., "Engineering biological systems with synthetic RNA molecules," Mol Cell 43, 2011, 915-926.

Lohmueller, J.J. et al., "A tunable zinc finger-based framework for Boolean logic computation in mammalian cells," Nucleic Acids Res 40, 2012, 5180-5187.

Long et al., "Postnatal genome editing partially restores dystrophin expression in a mouse model of muscular dystrophy," Science, 2016, 351(6271):400-403.

Lovric, J. et al., "Terminal Differentiation of Cardiac and Skeletal Myocytes Induces Permissivity to AAV Transduction by Relieving Inhibition Imposed by DNA Damage Response Proteins," Molecular Therapy, 2012, 2087-2097.

Lu, Q. L. et al., "The status of exon skipping as a therapeutic approach to duchenne muscular dystrophy," Molecular Therapy 19, 2011, 9-15.

Lund et al. "Promoter-targeted phage display selections with preassembled synthetic zinc finger libraries for endogenous gene regulation." Journal of Molecular Biology, vol. 340, pp. 599-613, 2004.

Luo et al. "Synthetic DNA delivery systems." Nature Biotechnology, vol. 18, pp. 33-37, 2000.

Maeder et al. "Robust, synergistic regulation of human gene expression using TALE activators." Nature Methods, vol. 10, No. 3, pp. 243-246, Feb. 10, 2013, including pp. 1/14-14/14 of Supplementary Material.

Maeder, M. L., "Targeted DNA demethylation and activation of endogenous genes using programmable TALE-TET1 fusion proteins," Nat Biotechnol, 2013, 31(12): p. 1137-42.

Maeder, M.L. et al., "Robust, synergistic regulation of human gene expression using TALE activators," Nat Methods 10, 2013, 243-245.

(56) References Cited

OTHER PUBLICATIONS

Mali, P. et al., "Cas9 as a versatile tool for engineering biology," Nat Methods, 2013, 10(10): p. 957-63.
Mali, P. et al., "CAS9 transcriptional activators for target specificity screening and paired nickases for cooperative genome engineering," Nat Biotechnol, 2013, 31(9): p. 833-8.
Mali, P. et al., "RNA-Guided Human Genome Engineering via Cas9," Science 339, 2013, 823-826.
Mamchaoui, K. et al., "Immortalized pathological human myoblasts: towards a universal tool for the study of neuromuscular disorders," Skelet Muscle 1, 2011, 1-11.
Mendell, J. R. et al., "Dystrophin immunity in Duchenne's muscular dystrophy," New England Journal of Medicine 363, 2010, 1429-1437.
Mendenhall, E. M. et al., "Locus-specific editing of histone modification at endogenous enhancers," Nat Biotechnol, 2013, 31(12): p. 1133-6.
Mercer, A. C. et al., "Regulation of Endogenous Human Gene Expression by Ligand-Inducible TALE Transcription Factors," ACS Synth Biol, 2013.
Miller, J.C. et al., "A TALE nuclease architecture for efficient genome editing," Nat Biotechnol 29, 2011, 143-148.
Moscou, M. J. et al., "A simple cipher governs DNA recognition by TAL effectors," Science 326, 2009, 1501.
Muir et al., "Engraftment potential of dermal fibroblasts following in vivo myogenic conversion in immunocompetent dystrophic skeletal muscle," Mol. Ther. Methods Clin. Dev., 2014, 1:14025.
Murphy et al., "The in vitro transcription of the 7SK RNA gene by RNA polymerase III is dependable only on the presence of an upstream promoter," Cell, 1987, 51:81-87.
Mussolino, C. et al., "A novel TALE nuclease scaffold enables high genome editing activity in combination with low toxicity," Nucleic Acids Res 39, 2011, 9283-9293.
Myslinski et al., "An unusually compact external promoter for RNA polymerase III transcription of the human HIRNA gene," Nucleic Acids Res, 2001, 29:2502-2509.
Negroni, E. et al., "In Vivo Myogenic Potential of Human CD133+ Muscle-derived Stem Cells: A Quantitative Study," Molecular Therapy 17, 2009, 1771-1778.
Nelson et al., "In vivo genome editing improves muscle function in a mouse model of Duchenne muscular dystrophy," Science, 2016, 351(6271):403-7.
Nishimasu, H. et al., "Crystal structure of cas9 in complex with guide RNA and target DNA Cell," 2014, 156(5): p. 935-49.
Ohshima et al., "Nucleotide sequence of mouse genomic loci including a gene or pseudogene for U6 (4.85) nuclear RNA," Nucleic Acids Res, 1981, 9:5145-5158.
Ousterout et al., "Correction of dystrophin expression in cells from duchenne muscular dystrophy patients through genomic excision of exon 51 by zinc finger nucleases," Molecular Therapy 23, 2015, 523-532.
Ousterout et al., "Multiplex CRISPR/Cas9-based genome editing for correction of dystrophin mutations that cause Duchenne muscular dystrophy," Nature Communications, 2015, 6:6244.
Ousterout et al., "Reading frame correction by targeted genome editing restores dystrophin expression in cells from Duchenne muscular dystrophy patients," Mol Ther, 2013, 21:1718-1726.
Palu et al. "In pursuit of new developments for gene therapy of human diseases." J. Biotechnol. vol. 68, pp. 1-13, 1999.
Papayannakos, C. et al., "Understanding lentiviral vector chromatin targeting: working to reduce insertional mutagenic potential for gene therapy," Gene Ther, 2013, 20(6): p. 581-8.
Park et al., "Multi-Parametric MRI at 14T for Muscular Dystrophy Mice Treated with AAV Vector-Mediated Gene Therapy," PLoS One, 2015, 10(4): e0124914.
Park, K.S. et al., "Phenotypic alteration of eukaryotic cells using randomized libraries of artificial transcription factors," Nat Biotechnol 21, 2003, 1208-1214.

Pattanayak, V. et al., "High-throughput profiling of off-target DNA cleavage reveals RNA-programmed Cas9 nuclease specificity," Nat Biotechnol, 2013, 31(9): p. 839-43.
Peault, B. et al., "Stem and progenitor cells in skeletal muscle development, maintenance, and therapy," Molecular Therapy 15, 2007, 867-877.
Perez, E. et al., "Establishment of HIV-1 resistance in CD4+ T cells by genome editing using zinc-finger nucleases," Nature biotechnology 26, 2008, 808-816.
Perez-Pinera et al. Abstract 855. "Synergistic Transcriptional Activation by Combinations of Engineered TALEs" presented at the American Society of Gene & Cell Therapy's 15th Annual Meeting in Philadelphia, Pennsylvania May 19, 2012.
Perez-Pinera et al. "Synergistic and tunable human gene activation by combinations of synthetic transcription factors." Nature Methods, vol. 10, No. 3, pp. 239-244, Feb. 3, 2013, including pp. 1/12-12-12 of Supplementary Material.
Perez-Pinera et al., "Gene targeting to the ROSA26 locus directed by engineered zinc finger nucleases," Nucleic Acids Research, 2012, 40:3741-3752.
Perez-Pinera et al., "RNA-guided gene activation by CRISPR-Cas9-based transcription factors," Nat Methods, 2013, 10:973-976.
Perez-Pinera, P. et al., "Advances in targeted genome editing," Current Opinion in Chemical Biology 16, 2012, 268-277.
Perez-Pinera, P. et al., "Synergistic and tunable human gene activation by combinations of synthetic transcription factors," Nat Methods 10, 2013, 239-242.
Persons, D. A., "Lentiviral vector gene therapy: effective and safe?" Mol Ther, 2010, 18(5): p. 861-2.
Piacentino et al., "X-Linked Inhibitor of Apoptosis Protein-Mediated Attenuation of Apoptosis, Using a Novel Cardiac-Enhanced Adeno-Associated Viral Vector," Human Gene Therapy, 2012, 23:635-646.
Pichavant, C. et al., "Current status of pharmaceutical and genetic therapeutic approaches to treat DMD," Molecular Therapy 19, 2011, 830-840.
Polstein, L. R. and Gersbach, C. A., "Light-inducible spatiotemporal control of gene activation by customizable zinc finger transcription factors," J Am Chem Soc, 2012, 134(40): p. 16480-3.
Popplewell, L. et al., "Gene correction of a duchenne muscular dystrophy mutation by meganuclease-enhanced exon knock-in," Hum Gene Ther, 2013, 24:692-701.
Qi, L.S. et al., "Repurposing CRISPR as an RNA-guided platform for sequence-specific control of gene expression," Cell 152, 2013, 1173-1183.
Ran et al., "In vivo genome editing using *Staphylococcus aureus* Cas9," Nature 520, 2015, 186-191.
Ran, F. A. et al., "Double nicking by RNA-guided CRISPR Cas9 for enhanced genome editing specificity," Cell, 2013, 154(6): p. 1380-9.
Rebar, E.J. et al., "Induction of angiogenesis in a mouse model using engineered transcription factors," Nat Med 8, 2002, 1427-1432.
Reyon, D. et al., "FLASH assembly of TALENs for high-throughput genome editing," Nat Biotechnol 30, 2012, 460-465.
Rousseau, J. et al., "Endonucleases: tools to correct the dystrophin gene" The Journal of Gene Medicine, 2011, vol. 13, pp. 522-537.
Saito et al., "Specific activation of microRNA-127 with downregulation of the proto-oncogene BCL6 by chromatin-modifying drugs in human cancer cells," Cancer Cell, 2006, vol. 9, pp. 435-443.
Salmon, P. and Trono, D., "Production and titration of lentiviral vectors," Curr Protoc Neurosci, 2006, Chapter 4: Unit 4 21.
Salva et al., "Design of tissue-specific regulatory cassettes for high-level rAAV-mediated expression in skeletal and cardiac muscle," Mol. Ther., 2007, 15:320-329.
Schmid-Burgk, J. L. et al., "A ligation-independent cloning technique for high-throughput of transcription activator-like effector genes," Nat Biotechnol 31, 2012, 76-81.
Scholze et al. "TAL effectors are remote controls for gene activation." Current Opinion in Microbiology, vol. 14, pp. 47-53, Jan. 2011.
Schultz, B. R. & Chamberlain, J. S., "Recombinant adeno-associated virus transduction and integration," Molecular Therapy 16, 2008, 1189-1199.

(56) References Cited

OTHER PUBLICATIONS

Sebastiano, V. et al., "In Situ Genetic Correction of the Sickle Cell Anemia Mutation in Human Induced Pluripotent Stem Cells Using Engineered Zinc Finger Nucleases," Stem Cells 29, 2011, 1717-1726.
Seidel et al., "Chromatin-modifying agents in anti-cancer therapy," Biochimie, 2012, vol. 94, pp. 2264-2279.
Seto et al., "Gene Replacement Therapies for Duchenne Muscular Dystrophy Using Adeno-Associated Viral Vectors," Current Gene Therapy, 2012, 12:139-151.
Sharma, S. et al., "Efficiency of nonhomologous DNA and joining varies among somatic tissues, despite similarity in mechanism," Cellular and Molecular Life Science 68, 2011, 661-676.
Shen et al., "Engraftment of a galactose receptor footprint onto adeno-associated viral capsids improves transduction efficiency," J. Biol. Chem., 2013, 288:28814-28823.
Silva, G. et al., "Meganucleases and other tools for targeted genome engineering: perspective and challenges for gene therapy," Current gene therapy, 2011, 11:11-27.
Şöllü, C. et al., "Autonomous zinc-finger nuclease pairs for targeted chromosomal deletion," Nucleic acids research 38, 2010, 8269-8276.
Song, L. et al., "Dnase-seq: a high-resolution technique for mapping active gene regulatory elements across the genome from mammalian cells," Cold Spring Harbor protocols 2010, pdb prot5384.
Song, L. et al., "Open chromatin defined by DNaseI and FAIRE identifies regulatory elements that shape cell-type identify," Genome Res 21, 2011, 1757-1767.
Sun, N. et al., "Optimized TAL effector nucleases (TALENs) for use in treatment of sickle cell disease," Molecular bioSystems 8, 2012, 1255-1263.
Szyf, M., "Epigenetics, DNA methylation, and chromatin modifying drugs," Annual Review of Pharmacology and Toxicology, 2009, vol. 49, pp. 243-263.
Tabebordbar et al., "In vivo gene editing in dystrophic mouse muscle and muscle stem cells," Science, 2015, 351(6271):407-411.
Taniguchi-Ikeda, M. et al., "Pathogenic exon-trapping by SVA retrotransposon and rescue in Fukuyama muscular dystrophy," Nature 478, 2011, 127-131.
Tebas, P. et al., "Gene editing of CCR5 in autologous CD4 T cells of persons infected with HIV," N Engl J Med, 2014, 370:901-910.
Tedesco, F. S. et al., "Repairing skeletal muscle: regenerative potential of skeletal muscle stem cells," J Clin Invest, 2010, 120:11-19.
Tedesco, F. S. et al., "Stem Cell-Mediated Transfer of a Human Artificial Chromosome Ameliorates Musculat Dystrophy," Science Translational Medicine 3, 96ra78-96ra78, 2011.
Tedesco, F. S. et al., "Transplantation of Genetically Corrected Human iPSC-Derived Progenitors in Mice with Limb-Girdle Muscular Dystrophy," Science Translational Medicine 4, 140ra189, 2012.
Tycko et al., "Screening *S. aureus* CRISPR-Cas9 Paired Guide RNAs for Efficient Targeted Deletion in Duchenne Muscular Dystrophy," Editas, Poster presented on May 5, 2016.
Urnov, F. et al., "Highly efficient endogenous human gene correction using designed zinc-finger nucleases," Nature 435, 2005, 646-651.
Van Putten, M. et al., "Low dystrophin levels in heart can delay heart failure in mdx mice," J Mol Cell Cardiol, 2014, 69C:17-23.
Van Putten, M. et al., "Low dystrophin levels increase survival and improve muscle pathology and function in dystrophin/utrophin double-knockout mice," FASEB J, 2013, 27:2484-2495.
Verma and Weitzman. "Gene Therapy: Twenty-first century medicine." Annual Review of Biochemistry, vol. 74, pp. 711-738, 2005.
Verma et al. "Gene therapy—promises, problems and prospects." Nature, vol. 389, pp. 239-242, 1997.
Vierbuchen, T. et al., "Direct conversion of fibroblasts to functional neurons by defined factors," Nature 463, 2010, 1035-1041.

Wang et al., "Adeno-associated virus vector carrying human minidystrophin genes effectively ameliorates muscular dystrophy in mdx mouse model," Proc Natl Acad Sci USA. (2000) 97(25):13714-13719.
Wang, H. et al., "One-Step Generation of Mice Carrying Mutations in Multiple Genes by CRISPR-Cas-Mediated Genome Engineering," Cell, 2013, 153(4): p. 910-8.
Wein, N. et al., "Efficient bypass of mutations in dysferlin deficient patient cells by antisense-induced exon skipping," Hum Mutat 31, 2010, 136-142.
Welch, E. M. et al., "PTC124 targets genetic disorders caused by nonsense mutations," Nature 447, 2007, 87-91.
Wienert et al., "Editing the genome to introduce a beneficial naturally occurring mutation associated with increased fetal globin," Nat Commun 6, 2015, 7085.
Yan et al., "Drugging the Undruggable: Transcription Therapy for Cancer," Biochimica et Biophysica Acta, vol. 1835, No. 1, pp. 76-85, Jan. 2013.
Yang, L., "Optimization of scarless human stem cell genome editing," Nucleic Acids Res, 2013, 41:9049-9061.
Yusa, K. et al., "Targeted gene correction of α1-antitrypsin deficiency in induced pluripotent stem cells," Nature 478, 2011, 391-394.
Zetsche et al., "Cpf1 Is a Single RNA-Guided Endonuclease of a Class 2 CRISPR-Cas System," Cell, 2015, 163(3):759-71.
Zhang, F. et al. "Efficient construction of sequence-specific TAL effectors for modulating mammalian transcription," Nat Biotechnol 29, 2011, 149-153.
Zhu, C. H. et al., "Cellular senescence in human telomerase reverse transcriptase and cyclin-dependent kinase 4: consequences in aging muscle and therapeutic strategies for muscular dystrophies," Aging cell 6, 2007, 515-523.
Zou, J. et al., "Site-specific gene correction of a point mutation in human iPS cells derived from an adult patient with sickle cell disease," Blood 118, 2011, 4599-4608.
Invitation to Pay Additional Fees for Application No. PCT/US2017/042921 dated Sep. 22, 2017 (3 pages).
International Search Report and Written Opinion for Application No. PCT/US2017/042921 dated Nov. 9, 2017 (21 pages).
International Search Report and Written Opinion for Application No. PCT/US2016/064285 dated Apr. 6, 2017 (21 pages).
International Search Report and Written Opinion for Application No. PCT/US2017/031351 dated Nov. 21, 2017 (22 pages).
Eurasian Patent Office Action for Application No. 201891317/28 dated Oct. 2, 2020 (3 pages, English translation included).
India Patent Office Examination Report for Application No. 201837014278 dated Oct. 14, 2020 (8 pages).
Hilton et al., "Enabling functional genomics with genome engineering," Genome Research, 2015, 25(10):1442-1455.
Riordan et al., "Application of CRISPR/Cas9 for biomedical discoveries," Cell & Bioscience, 2015, 5(1):11 pages.
Tsuchiya et al., "The "Spanning Protocol": A new DNA extraction method for efficient single-cell genetic diagnosis," Journal of Assisted Reproduction Genetics, 2005, 22(11-12):407-14.
Wood, "Neuromuscular disease: CRISPR/Cas9 gene-editing platform corrects mutations associated with Duchenne muscular dystrophy," Nature Reviews Neurology, 2015, 11(4):184.
Eurasian Patent Office Search Report for Application No. 201891317 dated Feb. 25, 2019 (4 pages).
European Patent Office Extended Search Report for Application No. 16871452.5 dated Mar. 20, 2019 (12 pages).
Acosta et al., "Use of two gRNAs for CRISPR/Cas9 improves bi-allelic homologous recombination efficiency in mouse embryonic stem cells," Genesis, 2018, 56(5): 1-8.
Adamson et al., "A Multiplexed Single-Cell CRISPR Screening Platform Enables Systematic Dissection of the Unfolded Protein Response," Cell, 2016, 167: 1867-1882 e1821.
Aguilar et al., "Transcriptional and Chromatin Dynamics of Muscle Regeneration after Severe Trauma," Stem Cell Rep, 2016, 7: 983-997.
Ahlenius et al., "FoxO3 regulates neuronal reprogramming of cells from postnatal and aging mice," Proc Natl Acad Sci U S A, 2016, 113: 8514-8519.

(56) References Cited

OTHER PUBLICATIONS

Albuquerque et al., "Mammalian nicotinic acetylcholine receptors: from structure to function," Physiol Rev, 2009, 89: 73-120.

Amoasii et al., "Gene editing restores dystrophin expression in a canine model of Duchenne muscular dystrophy," Science, 2018, 362: 86-91.

Amoasii et al., "Single-cut genome editing restores dystrophin expression in a new mouse model of muscular dystrophy," Sci Transl Med, Nov. 2017, 9(418): eaan8081.

Andersen et al., "Dual role of delta-like 1 homolog (DLK1) in skeletal muscle development and adult muscle regeneration," Development, 2013, 140: 3743-3753.

Arnett et al., "Adeno-associated viral vectors do not efficiently target muscle satellite cells," Molecular Therapy Methods & Clinical Development, 2014, 1: 14038.

Asokan et al., "Reengineering a receptor footprint of adeno-associated virus enables selective and systemic gene transfer to muscle," Nat Biotechnol, 2010, 28: 79-82.

Balboa et al., "Conditionally Stabilized dCas9 Activator for Controlling Gene Expression in Human Cell Reprogramming and Differentiation," Stem Cell Rep, 2015, 5: 448-459.

Barberi et al., "Derivation of engraftable skeletal myoblasts from human embryonic stem cells," Nat Med, 2007, 13: 642-648.

Barr et al., "Predominant Expression of Alternative PAX3 and PAX7 Forms in Myogenic and Neural Tumor Cell Lines," Cancer Res, 1999, 59: 5443-5448.

Bengtsson et al., "Muscle-specific CRISPR/Cas9 dystrophin gene editing ameliorates pathophysiology in a mouse model for Duchenne muscular dystrophy," Nat Commun, 2017, 8: 1-10.

Bernstein et al., "An integrated encyclopedia of DNA elements in the human genome," Nature, 2012, 489: 57-74.

Black et al., "Targeted Epigenetic Remodeling of Endogenous Loci by CRISPR/Cas9-Based Transcriptional Activators Directly Converts Fibroblasts to Neuronal Cells," Cell Stem Cell, 2016, 19: 406-414.

Boldrin et al., "Donor satellite cell engraftment is significantly augmented when the host niche is preserved and endogenous satellite cells are incapacitated," Stem Cells, 2012, 30: 1971-1984.

Bolger et al., "Trimmomatic: a flexible trimmer for Illumina sequence data," Bioinformatics, 2014, 30: 2114-2120.

Boshart et al., "A very strong enhancer is located upstream of an immediate early gene of human cytomegalovirus," Cell, 1985, 41(2): 521-530.

Boyle et al., "High-resolution mapping and characterization of open chromatin across the genome," Cell, 2008, 132: 311-322.

Briguet et al., "Histological parameters for the quantitative assessment of muscular dystrophy in the mdx-mouse," Neuromuscul. Disord., 2004, 14: 675-682.

Brunger et al., "CRISPR/Cas9 Editing of Murine Induced Pluripotent Stem Cells for Engineering Inflammation-Resistant Tissues," Arthritis Rheumatol, 2017, 69: 1111-1121.

Brunger et al., "Genome Engineering of Stem Cells for Autonomously Regulated, Closed-Loop Delivery of Biologic Drugs," Stem Cell Reports, 2017, 8: 1202-1213.

Buenrostro et al., "Transposition of native chromatin for fast and sensitive epigenomic profiling of open chromatin, DNA-binding proteins and nucleosome position," Nat Methods, 2013, 10: 1213-1218.

Busskamp et al., "Rapid neurogenesis through transcriptional activation in human stem cells," Mol Syst Biol, 2014, 10: 760.

Chakraborty et al., "A CRISPR/Cas9-based system for reprogramming cell lineage specification," Stem Cell Reports, 2014, 3: 940-947.

Chal et al., "Differentiation of pluripotent stem cells to muscle fiber to model Duchenne muscular dystrophy," Nat Biotechnol, 2015, 33: 962-969.

Chamberlain et al., "Progress toward Gene Therapy for Duchenne Muscular Dystrophy," Mol. Ther., 2017, 25: 1125-1131.

Chanda et al., "Generation of induced neuronal cells by the single reprogramming factor ASCL1," Stem Cell Reports, 2014, 3: 282-296.

Chavez et al., "Highly efficient Cas9-mediated transcriptional programming," Nat Methods, 2015, 12: 326-328.

Cheloufi et al., "The histone chaperone CAF-1 safeguards somatic cell identity," Nature, 2015, 528: 218-224.

Chen et al., "Dynamic imaging of genomic loci in living human cells by an optimized CRISPR/Cas systemm," Cell, 2013, 155: 1479-1491.

Chen et al., "Enrichr: interactive and collaborative HTML5 gene list enrichment analysis tool," BMC Bioinformatics, 2013, 14: 128.

Chen et al., "microRNA-1 and microRNA-206 regulate skeletal muscle satellite cell proliferation and differentiation by repressing Pax7," J Cell Biol, 2010, 190: 867-879.

Childers et al., "Gene therapy prolongs survival and restores function in murine and canine models of myotubular myopathy," Sci Transl Med, 2014, 6: 220ra210.

Chronis et al., "Cooperative Binding of Transcription Factors Orchestrates Reprogramming," Cell, 2017, 168: 442-459 e420.

Cooper et al., "Improved induction of immune tolerance to factor IX by hepatic AAV-8 gene transfer," Hum Gene Ther, 2009, 20: 767-776.

Cordier et al., "Muscle-specific promoters may be necessary for adeno-associated virus-mediated gene transfer in the treatment of muscular dystrophies," Hum. Gene Ther., 2001, 12: 205-215.

D'Alessio et al., "A Systematic Approach to Identify Candidate Transcription Factors that Control Cell Identity," Stem Cell Reports, 2015, 5: 763-775.

Daley et al., "CRISPhieRmix: a hierarchical mixture model for CRISPR pooled screens," Genome Biol, 2018, 19: 159.

Darabi et al., "Functional skeletal muscle regeneration from differentiating embryonic stem cells," Nat Med, 2008, 14: 134-143.

Darmanis et al., "A survey of human brain transcriptome diversity at the single cell level," Proc Natl Acad Sci U S A, 2015, 112: 7285-7290.

Deconinck et al., "Utrophin-Dystrophin-Deficient Mice as a Model for Duchenne Muscular Dystrophy," Cell, 1997, 90(4): 717-727.

Dijkema et al., "Cloning and expression of the chromosomal immune interferon gene of the rat," EMBO J, 1985, 4(3): 761-767.

Dobin et al., "STAR: ultrafast universal RNA-seq aligner," Bioinformatics, 2013, 29: 15-21.

Du et al., "Genetic interaction mapping in mammalian cells using CRISPR interference," Nat Methods, 2017, 14: 577-580.

Duan et al., "Expanding AAV packaging capacity with transsplicing or overlapping vectors: a quantitative comparison," Molecular Therapy, 2001, 4: 383-391.

Duan, "Systemic AAV Micro-dystrophin Gene Therapy for Duchenne Muscular Dystrophy," Molecular Therapy, 2018, 26(10): 2337-2356.

Dumont et al., "Dystrophin expression in muscle stem cells regulates their polarity and asymmetric division," Nat Med, 2015, 21: 1455-1463.

Dumont et al., "Intrinsic and extrinsic mechanisms regulating satellite cell function," Development, 2015, 142: 1572-1581.

Dunbar et al., "Gene therapy comes of age," Science, 2018, 359: eaan4672.

Eguchi et al., "Reprogramming cell fate with a genome-scale library of artificial transcription factors," Proc Natl Acad Sci U S A, 2016, 113: E8257-E8266.

Ernsberger, "Role of neurotrophin signalling in the differentiation of neurons from dorsal root ganglia and sympathetic ganglia," Cell Tissue Res, 2009, 336: 349-384.

Erwin et al., "Synthetic transcription elongation factors license transcription across repressive chromatin," Science, 2017, 358: 1617-1622.

Fairclough et al., "Therapy for Duchenne muscular dystrophy: renewed optimism from genetic approaches," Nat. Rev. Genet., 2013, 14: 373-378.

FDA approval brings first gene therapy to the United States, <https://www.fda.gov/newsevents/newsroom/pressannouncements/ucm574058.htm> (Aug. 30, 2017).

(56) References Cited

OTHER PUBLICATIONS

FDA approves first drug for spinal muscular atrophy, <https://www.fda.gov/newsevents/newsroom/pressannouncements/ucm534611.htm> (Dec. 23, 2016).

FDA approves first-of-its kind targeted RNA-based therapy to treat a rare disease, <https://www.fda.gov/newsevents/newsroom/pressannouncements/ucm616518.htm> (Aug. 10, 2018).

FDA approves novel gene therapy to treat patients with a rare form of inherited vision loss, <https://www.fda.gov/newsevents/newsroom/pressannouncements/ucm589467.htm> (Dec. 18, 2017).

FDA grants accelerated approval to first drug for Duchenne muscular dystrophy, <https://www.fda.gov/newsevents/newsroom/pressannouncements/ucm521263.htm> (Sep. 19, 2016).

Flandin et al., "Lhx6 and Lhx8 coordinately induce neuronal expression of Shh that controls the generation of interneuron progenitors," Neuron, 2011, 70: 939-950.

Friedland et al., "*Staphyloccocus aureus* Cas9: An Alternative Cas9 for Genome Editing Applications," Molecular Therapy, 2015, 23(Suppl. 1):S224.

Gaj et al., "Structure-Guided Reprogramming of Serine Recombinase DNA Sequence Specificity," Proc Natl Acad Sci U S A, 2011, 108(2): 498-503.

Gao et al., "Complex transcriptional modulation with orthogonal and inducible dCas9 regulators," Nat Methods, 2016, 13: 1043-1049.

Gascon et al., "Direct Neuronal Reprogramming: Achievements, Hurdles, and New Roads to Success," Cell Stem Cell, 2017, 21: 18-34.

Gersbach et al., "Targeted plasmid integration into the human genome by an engineered zinc-finger recombinase," Nucleic Acids Res, 2011, 39: 7868-7878.

Gilbert et al., "Genome-Scale CRISPR-Mediated Control of Gene Repression and Activation," Cell, 2014, 159: 647-661.

Goldstein et al., "In Situ Modification of Tissue Stem and Progenitor Cell Genomes," Cell Reports, 2019, 27: 1254-1264.e7.

Gorman et al., "The Rous sarcoma virus long terminal repeat is a strong promoter when introduced into a variety of eukaryotic cells by DNA-mediated transfection," Proc. Natl. Acad. Sci. USA, 1982, 79(22): 6777-6781.

Gregorevic et al., "Systemic microdystrophin gene delivery improves skeletal muscle structure and function in old dystrophic mdx mice," Mol Ther, 2008, 16: 657-664.

Hakim et al., "Evaluation of Muscle Function of the Extensor Digitorum Longus Muscle Ex vivo and Tibialis Anterior Muscle In situ in Mice," J. Vis. Exp., 2013, 1-8.

Hall et al., "Prevention of Muscle Aging by Myofiber-Associated Satellite Cell Transplantation," Sci Transl Med, 2010, 2: 57ra83.

Hardy et al., "Comparative Study of Injury Models for Studying Muscle Regeneration in Mice," PLoS One, 2016, 11: e0147198.

Harper et al., "Modular flexibility of dystrophin: implications for gene therapy of Duchenne muscular dystrophy," Nat. Med., 2002, 8: 253-261.

Harrow et al., "GENCODE: The reference human genome annotation for The ENCODE Project," Genome Res, 2012, 22: 1760-1774.

Heagerty et al., "Time-dependent ROC curves for censored survival data and a diagnostic marker," Biometrics, 2000, 56: 337-344.

Hilton et al., "Epigenome editing by a CRISPR-Cas9-based acetyltransferase activates genes from promoters and enhancers," Nat Biotechnol, 2015, 33: 510-517.

Himeda et al., "Design and Testing of Regulatory Cassettes for Optimal Activity in Skeletal and Cardiac Muscles," Methods Mol Biol, 2011, 709: 3-19 (Published Online Dec. 2010).

Horlbeck et al., "Compact and highly active next-generation libraries for CRISPR-mediated gene repression and activation," eLife, 2016, 5: e19760.

Huang et al., "Impaired respiratory function in mdx and mdx/utrn+/− mice," Muscle & Nerve, 2011, 43(2): 263-267.

Inoue et al., "Runx transcription factors in neuronal development," Neural Dev, 2008, 3: 20.

Isaac et al., "Dystrophin and utrophin "double knockout" dystrophic mice exhibit a spectrum of degenerative musculoskeletal abnormalities," Journal of Orthopaedic Research, 2013, 31(3): 343-349.

Jiang et al., "Notch signaling deficiency underlies age-dependent depletion of satellite cells in muscular dystrophy," Disease Models & Mechanisms, 2014, 7: 997-1004.

Jiwlawat et al., "Current Progress and Challenges for Skeletal Muscle Differentiation from Human Pluripotent Stem Cells Using Transgene-Free Approaches," Stem Cells Int, Apr. 2018, Article ID 6241681, 18 pages.

Jooss et al., "Transduction of dendritic cells by DNA viral vectors directs the immune response to transgene products in muscle fibers," J. Virol., 1998, 72: 4212-4223.

Kabadi et al., "Multiplex CRISPR/Cas9-based genome engineering from a single lentiviral vector," Nucleic Acids Res, 2014, 42: e147.

Keefe et al., "Muscle stem cells contribute to myofibers in sedentary adult mice," Nat Commun, 2015, 6: 7087.

Keil et al., "Brain transcriptome databases: a user's guide," J Neurosci, 2018, 38(10): 2399-2412.

Khambata-Ford et al., "Identification of Promoter Regions in the Human Genome by Using a Retroviral Plasmid Library-Based Functional Reporter Gene Assay," Genome Research, 2003, 13: 1765-1774.

Kim et al., "Expansion and Purification Are Critical for the Therapeutic Application of Pluripotent Stem Cell-Derived Myogenic Progenitors," Stem Cell Rep, 2017, 9: 12-22.

Kim et al., "Use of the human elongation factor 1α promoter as a versatile and efficient expression system," Gene, 1990, 91(2): 217-223.

Klann et al., "CRISPR-based methods for high-throughput annotation of regulatory DNA," Curr Opin Biotechnol, 2018, 52: 32-41.

Klann et al., "CRISPR-Cas9 epigenome editing enables high-throughput screening for functional regulatory elements in the human genome," Nat Biotechnol, 2017, 35: 561-568.

Kodaka et al., "Skeletal Muscle Cell Induction from Pluripotent Stem Cells," Stem Cells Int, Apr. 2017, Article ID 1376151, 16 pages.

Koerber et al., "DNA shuffling of adeno-associated virus yields functionally diverse viral progeny," Mol Ther, 2008, 16: 1703-1709.

Konermann et al., "Genome-scale transcriptional activation by an engineered CRISPR-Cas9 complex," Nature, 2015, 517: 583-588.

Koopmans et al., "SynGO: An Evidence-Based, Expert-Curated Knowledge Base for the Synapse," Neuron, 2019, 103: 217-234 e214.

Koppanati et al., "Improvement of the mdx mouse dystrophic phenotype by systemic in utero AAV8 delivery of a minidystrophin gene," Gene Ther, 2010, 17: 1355-1362.

Kreis et al., "The Multifaceted p21 (Cip1/Waf1/CDKN1A) in Cell Differentiation, Migration and Cancer Therapy," Cancers (Basel), 2019, 11(9): 1220.

Kwon et al., "Myogenic Progenitor Cell Lineage Specification by CRISPR/Cas9-Based Transcriptional Activators," Stem cell reports, 2020, 14: 755-769.

Lake et al., "Integrative single-cell analysis of transcriptional and epigenetic states in the human adult brain," Nat Biotechnol, 2018, 36: 70-80.

Lam et al., "Rapid and Efficient Differentiation of Human Pluripotent Stem Cells into Intermediate Mesoderm That Forms Tubules Expressing Kidney Proximal Tubular Markers," J Am Soc Nephrol JASN, 2014, 25: 1211-1225.

Lambert et al., "The Human Transcription Factors," Cell, 2018, 172: 650-665.

Lamey et al., "Pax genes in myogenesis: alternate transcripts add complexity," Histol Histopathol, 2004, 19: 1289-1300.

Langmead et al., "Fast gapped-read alignment with Bowtie 2," Nat Methods, 2012, 9: 357-359.

Lee et al., "Activation of innate immunity is required for efficient nuclear reprogramming," Cell, 2012, 151: 547-558.

Lee et al., "Nanoparticle delivery of Cas9 ribonucleoprotein and donor DNA in vivo induces homology-directed DNA repair," Nat Biomed Eng, 2017, 1: 889-901.

(56) References Cited

OTHER PUBLICATIONS

Li et al., "Engineering and selection of shuffled AAV genomes: a new strategy for producing targeted biological nanoparticles," Mol Ther, 2008, 16: 1252-1260.
Li et al., "Precise correction of the dystrophin gene in duchenne muscular dystrophy patient induced pluripotent stem cells by TALEN and CRISPR-Cas9," Stem Cell Reports, 2015, 4: 143-154.
Li et al., "Preservation of muscle force in Mdx3cv mice correlates with low-level expression of a near full-length dystrophin protein," Am. J. Pathol., 2008, 172: 1332-1341.
Li et al., "RSEM: accurate transcript quantification from RNA-Seq data with or without a reference genome," BMC Bioinformatics, 2011, 12: 323.
Li et al., "Synthetic muscle promoters: activities exceeding naturally occurring regulatory sequences," Nature Biotechnology, 1999, 17: 241-245.
Lian et al., "Robust cardiomyocyte differentiation from human pluripotent stem cells via temporal modulation of canonical Wnt signaling," Proc Natl Acad Sci, 2012, 109: E1848-E1857.
Liao et al., "The Subread aligner: fast, accurate and scalable read mapping by seed-and-vote," Nucleic Acids Res, 2013, 41: e108.
Lim et al., "Application of CRISPR/Cas9 for the Treatment of Duchenne Muscular Dystrophy," Journal of Personalized Medicine, 2018, 8(4): 1-20.
Limberis et al., "Transduction efficiencies of novel AAV vectors in mouse airway epithelium in vivo and human ciliated airway epithelium in vitro," Molecular therapy: the journal of the American Society of Gene Therapy, 2009, 17: 294-301.
Liu et al., "Adeno-associated virus-mediated microdystrophin expression protects young mdx muscle from contraction-induced injury," Mol. Ther., 2005, 11: 245-256.
Liu et al., "CRISPR Activation Screens Systematically Identify Factors that Drive Neuronal Fate and Reprogramming," Cell Stem Cell, 2018, 23: 758-771 e758.
Liu et al., "CRISPR-Based Chromatin Remodeling of the Endogenous Oct4 or Sox2 Locus Enables Reprogramming to Pluripotency," Cell Stem Cell, 2018, 22: 252-261 e254.
Love et al., "Moderated estimation of fold change and dispersion for RNA-seq data with DESeq2," Genome Biol, 2014, 15: 550.
Madigan et al., "Engineering AAV receptor footprints for gene therapy," Curr Opin Virol, 2016, 18: 89-96.
Madisen et al., "A robust and high-throughput Cre reporting and characterization system for the whole mouse brain," Nat Neurosci, 2010, 13: 133-140.
Maeder et al., "CRISPR RNA-guided activation of endogenous human genes," Nat Methods, 2013, 10: 977-979.
Magli et al., "PAX7 Targets, CD54, Integrin $\alpha 9\beta 1$, and SDC2, Allow Isolation of Human ESC/iPSC-Derived Myogenic Progenitors," Cell Rep, 2017, 19: 2867-2877.
Maheshri et al., "Directed evolution of adeno-associated virus yields enhanced gene delivery vectors," Nat Biotechnol, 2006, 24: 198-204.
Maniatis et al., "Regulation of inducible and tissue-specific gene expression," Science, 1987, 236(4806): 1237-1245.
Mann et al., "Improved antisense oligonucleotide induced exon skipping in the mdx mouse model of muscular dystrophy," J. Gene Med., 2002, 4: 644-654.
Manning et al., "What has the mdx mouse model of duchenne muscular dystrophy contributed to our understanding of this disease? ," Journal of Muscle Research and Cell Motility, 2015, 36: 155-167.
Maruyama et al., "Epigenetic Regulation of Cell Type-Specific Expression Patterns in the Human Mammary Epithelium," PLoS Genetics, 2011, 7(4): e1001369, 15 pages.
McFadden et al., "The Hand1 and Hand2 transcription factors regulate expansion of the embryonic cardiac ventricles in a gene dosage-dependent manner," Development, 2005, 132: 189-201.
McGreevy et al., "Animal models of Duchenne muscular dystrophy: from basic mechanisms to gene therapy," Disease Models Mechanisms, 2015, 8(3): 195-213.

Mertens et al., "Evaluating cell reprogramming, differentiation and conversion technologies in neuroscience," Nat Rev Neurosci, 2016, 17: 424-437.
Miller et al., "Transcriptional landscape of the prenatal human brain," Nature, 2014, 508: 199-206.
Mizushima et al., "pEF-BOS, a powerful mammalian expression vector," Nuc. Acids. Res., 1990, 18(17): 5322.
Montalbano et al., "High-Throughput Approaches to Pinpoint Function within the Noncoding Genome," Molecular Cell, 2017, 68: 44-59.
Montarras, "Direct Isolation of Satellite Cells for Skeletal Muscle Regeneration," Science, 2005, 309: 2064-2067.
Morris et al., "Dissecting engineered cell types and enhancing cell fate conversion via CellNet," Cell, 2014, 158: 889-902.
Najm et al., "Orthologous CRISPR-Cas9 enzymes for combinatorial genetic screens," Nat Biotechnol, 2018, 36: 179-189.
Naldini, "Gene therapy returns to centre stage," Nature, 2015, 526: 351-360.
Nance et al., "AAV9 Edits Muscle Stem Cells in Normal and Dystrophic Adult Mice," Molecular Therapy, 2019, 27: 1568-1585.
Nelson et al., "Engineering Delivery Vehicles for Genome Editing," Annual review of chemical and biomolecular engineering, 2016, 7: 637-662.
Nelson et al., "Genome engineering: a new approach to gene therapy for neuromuscular disorders," Nat Rev Neurol, 2017, 13: 647-661.
Nelson et al., "Long-term evaluation of AAV-CRISPR genome editing for Duchenne muscular dystrophy," Nature Medicine, 2019, 25(3): 427-432.
Odom et al., "Microutrophin Delivery Through rAAV6 Increases Lifespan and Improves Muscle Function in Dystrophic Dystrophin/Utrophin-deficient Mice," Molecular Therapy, 2008, 16(9): 1539-1545.
O'Geen et al., "Ezh2-dCas9 and KRAB-dCas9 enable engineering of epigenetic memory in a context-dependent manner," Epigenetics Chromatin, 2019, 12: 26.
Olguin et al., "Pax-7 up-regulation inhibits myogenesis and cell cycle progression in satellite cells: a potential mechanism for self-renewal," Dev Biol, 2004, 275: 375-388.
Pang et al., "Induction of human neuronal cells by defined transcription factors," Nature, 2011, 476: 220-223.
Papapetrou, "Induced pluripotent stem cells, past and future," Science, 2016, 353: 991-992.
Parekh et al., "Mapping Cellular Reprogramming via Pooled Overexpression Screens with Paired Fitness and Single-Cell RNA-Sequencing Readout," Cell Systems, 2018, 7: 548-555.e548.
Pawlikowski et al., "Regulation of skeletal muscle stem cells by fibroblast growth factors," Dev Dyn, 2017, 246: 359-367.
Pigozzo et al., "Revertant Fibers in the mdx Murine Model of Duchenne Muscular Dystrophy: An Age- and Muscle-Related Reappraisal," PLoS One, 2013, 8(8): e72147.
Polstein et al., "A light-inducible CRISPR-Cas9 system for control of endogenous gene activation," Nature Chemical Biology, 2015, 11: 198-200.
Polstein et al., "Genome-wide specificity of DNA-binding, gene regulation, and chromatin remodeling by TALE- and CRISPR/Cas9-based transcriptional activators," Genome Res, 2015, 25: 1158-1169.
Rackham et al., "A predictive computational framework for direct reprogramming between human cell types," Nature Genetics, 2016, 48: 331-335.
Ramachandran et al., "Nitric Oxide Signaling Pathway in Duchenne Muscular Dystrophy Mice: Upregulation of L-arginine Transport," Biochem. J., 2012, 449: 133-142.
Rao et al., "Engineering human pluripotent stem cells into a functional skeletal muscle tissue," Nat Commun, 2018, 9: 126.
Roadmap Epigenomics Consortium, "Integrative analysis of 111 reference human epigenomes," Nature, 2015, 518: 317-330.
Roudaut et al., "Restriction of calpain3 expression to the skeletal muscle prevents cardiac toxicity and corrects pathology in a murine model of limb-girdle muscular dystrophy," Circulation, 2013, 128: 1094-1104.

(56) References Cited

OTHER PUBLICATIONS

Sacco et al., "Short Telomeres and Stem Cell Exhaustion Model Duchenne Muscular Dystrophy in mdx/mTR Mice," Cell, 2010, 143: 1059-1071.
Sagal et al., "Proneural transcription factor Atoh1 drives highly efficient differentiation of human pluripotent stem cells into dopaminergic neurons," Stem Cells Transl Med, 2014, 3: 888-898.
Salmon et al., "Production and titration of lentiviral vectors," Curr Protoc Hum Genet, 2007, Chapter 12, Unit 12.10, Supplement 54, 24 pages.
Sambasivan et al., "Embryonic founders of adult muscle stem cells are primed by the determination gene Mrf4," Developmental Biology, 2013, 381: 241-255.
Sanson et al., "Optimized libraries for CRISPR-Cas9 genetic screens with multiple modalities," Nat Commun, 2018, 9: 5416.
Sharma et al., "In vivo genome editing of the albumin locus as a platform for protein replacement therapy," Blood, 2015, 126: 1777-1784.
Shelton et al., "Derivation and Expansion of PAX7-Positive Muscle Progenitors from Human and Mouse Embryonic Stem Cells," Stem Cell Rep, 2014, 3: 516-529.
Shen et al., "Combinatorial CRISPR-Cas9 screens for de novo mapping of genetic interactions," Nat Methods, 2017, 14: 573-576.
Shin et al., "Microdystrophin Ameliorates Muscular Dystrophy in the Canine Model of Duchenne Muscular Dystrophy," Mol. Ther., 2013, 21: 750-757.
Skene et al., "Genetic identification of brain cell types underlying schizophrenia," Nat Genet, 2018, 50: 825-833.
Song et al., "Non-immunogenic utrophin gene therapy for the treatment of muscular dystrophy animal models," Nature Medicine, 2019, 25(10): 1505-1511.
Stuelsatz et al., "A Contemporary Atlas of the Mouse Diaphragm: Myogenicity, Vascularity, and the Pax3 Connection" J Histochem Cytochem, 2012, 60(9): 638-657.
Suzuki et al., "In vivo genome editing via CRISPR/Cas9 mediated homology-independent targeted integration," Nature, 2016, 540: 144-149.
T Hoen et al., "Generation and characterization of transgenic mice with the full-length human DMD gene," J. Biol. Chem., 2008, 283: 5899-5907.
Takahashi et al., "A decade of transcription factor-mediated reprogramming to pluripotency," Nature Reviews, 2016, 17: 183-193.
Takahashi et al., "Induction of pluripotent stem cells from mouse embryonic and adult fibroblast cultures by defined factors," Cell, 2006, 126: 663-676.
Takeshima et al., "Mutation spectrum of the dystrophin gene in 442 Duchene/Becker muscular dystrophy cases from one Japanese referral center," Journal of Human Genetics, 2010, 55: 379-388.
Tan et al., "Efficient derivation of lateral plate and paraxial mesoderm subtypes from human embryonic stem cells through GSKi-mediated differentiation," Stem Cells Dev, 2013, 22: 1893-1906.
Teratani-Ota et al., "Induction of specific neuron types by overexpression of single transcription factors," In Vitro Cell Dev Biol Anim, 2016, 52(9): 961-973.
Thakore et al., "Editing the epigenome: technologies for programmable transcription and epigenetic modulation," Nat Methods, 2016, 13: 127-137.
Thakore et al., "Highly specific epigenome editing by CRISPR-Cas9 repressors for silencing of distal regulatory elements," Nat Methods, 2015, 12: 1143-1149.
Thakore et al., "RNA-guided transcriptional silencing in vivo with S. aureus CRISPR-Cas9 repressors," Nat Commun, 2018, 9: 1674.
Theodorou et al., "A high throughput embryonic stem cell screen identifies Oct-2 as a bifunctional regulator of neuronal differentiation," Genes Dev, 2009, 23: 575-588.
Thorgeirsson et al., "A variant associated with nicotine dependence, lung cancer and peripheral arterial disease," Nature, 2008, 452: 638-642.
Tian et al., "CRISPR Interference-Based Platform for Multimodal Genetic Screens in Human iPSC-Derived Neurons," Neuron, 2019, 104: 239-255 e212.
Tinsley et al., "Amelioration of the dystrophic phenotype of mdx mice using a truncated utrophin transgene," Nature, 1996, 384(6607): 349-353.
Tsunemoto et al., "Diverse reprogramming codes for neuronal identity," Nature, 2018, 557: 375-380.
Uetsuki et al., "Isolation and Characterization of the Human Chromosomal Gene for Polypeptide Chain Elongation Factor-1α," J. Biol. Chem., 1989, 264(10): 5791-5798.
Van Arensbergen et al., "Genome-wide mapping autonomous promoter activity in human cells," Nature Biotechnology, 2017, 35(2): 145-153.
Van Deutekom et al., "Advances in Duchenne muscular dystrophy gene therapy," Nat. Rev. Genet., 2003, 4: 774-783.
Vaquerizas et al., "A census of human transcription factors: function, expression and evolution," Nat Rev Genet, 2009, 10: 252-263.
Verkhusha et al., "GFP-like flourescent proteins and chromoproteins of the class Anthozoa," Protein Structures: Kaleidoscope of Structural Properties and Functions, 2003, 405-439.
Vierbuchen et al., "Direct lineage conversions: unnatural but useful?," Nat Biotechnol, 2011, 29: 892-907.
Vierbuchen et al., "Molecular roadblocks for cellular reprogramming," Mol Cell, 2012, 47: 827-838.
Vorobyov et al., "Expression of two protein isoforms of PAX7 is controlled by competing cleavage-polyadenylation and splicing," Gene, 2004, 342: 107-112.
Voss et al., "The role of enhancers in the regulation of cell-type-specific transcriptional control," Trends Biochem. Sci., 1986, 11(7): 287-289.
Waddell et al., "Dlk1 Is Necessary for Proper Skeletal Muscle Development and Regeneration," PLoS One, 2010, 5(11): e15055.
Waldrop et al., "Update in Duchenne and Becker muscular dystrophy," Current Opinion in Neurology, 2019, 32: 722-727.
Wang et al., "Adeno-associated virus serotype 8 efficiently delivers genes to muscle and heart," Nat. Biotechnol., 2005, 23: 321-328.
Wang et al., "Construction and analysis of compact muscle-specific promoters for AAV vectors," Gene Ther, 2008, 15: 1489-1499.
Wang et al., "Systemic human minidystrophin gene transfer improves functions and life span of dystrophin and dystrophin/utrophin-deficient mice," J. Orthop. Res., 2009, 27: 421-426.
Wapinski et al., "Hierarchical mechanisms for direct reprogramming of fibroblasts to neurons," Cell, 2013, 155: 621-635.
Weltner et al., "Human pluripotent reprogramming with CRISPR activators," Nat Commun Lond, 2018, 9: 1-12.
Westendorp et al., "E2F7 represses a network of oscillating cell cycle genes to control S-phase progression," Nucleic Acids Res, 2012, 40: 3511-3523.
Willmann et al., "Mammalian animal models for Duchenne muscular dystrophy," Neuromuscular Disorders, 2009, 19(4): 241-249.
Wu et al., "A Myogenic Double-Reporter Human Pluripotent Stem Cell Line Allows Prospective Isolation of Skeletal Muscle Progenitors," Cell Rep, 2018, 25: 1966-1981.e4.
Wüst et al., "Metabolic Maturation during Muscle Stem Cell Differentiation Is Achieved by miR-1/133a-Mediated Inhibition of the Dlk1-Dio3 Mega Gene Cluster," Cell Metab, 2018, 27: 1026-1039.e6.
Wylie et al., "Distinct transcriptomes define rostral and caudal serotonin neurons," J Neurosci, 2010, 30: 670-684.
Xu et al., "Direct lineage reprogramming: strategies, mechanisms, and applications," Cell Stem Cell, 2015, 16: 119-134.
Xu et al., "Human Satellite Cell Transplantation and Regeneration from Diverse Skeletal Muscles," Stem Cell Rep, 2015, 5: 419-434.
Xu et al., "Recent advances in neuroepigenetic editing," Curr Opin Neurobiol, 2019, 59: 26-33.
Xue et al., "Synthetic mRNAs Drive Highly Efficient iPS Cell Differentiation to Dopaminergic Neurons," Stem Cells Transl Med, 2019, 8: 112-123.
Yang et al., "Generation of pure GABAergic neurons by transcription factor programming," Nat Methods, 2017, 14: 621-628.

(56) References Cited

OTHER PUBLICATIONS

Young et al., "A Single CRISPR-Cas9 Deletion Strategy that Targets the Majority of DMD Patients Restores Dystrophin Function in hiPSC-Derived Muscle Cells," Cell Stem Cell, 2016, 18: 533-540.
Young et al., "Creation of a Novel Humanized Dystrophic Mouse Model of Duchenne Muscular Dystrophy and Application of a CRISPR/Cas9 Gene Editing Therapy," Journal of Neuronuscular Diseases, 2017, 4(2): 139-145.
Zhang et al., "Comprehensive Structure-Function Study of Neurogenin3 Disease-Causing Alleles during Human Pancreas and Intestinal Organoid Development," Dev Cell, 2019, 50(3): 367-380.e7.
Zhang et al., "Rapid single-step induction of functional neurons from human pluripotent stem cells," Neuron, 2013, 78: 785-798.
Zhao et al., "The LIM-homeobox gene Lhx8 is required for the development of many cholinergic neurons in the mouse forebrain," Proc Natl Acad Sci U S A, 2003, 100: 9005-9010.
Zhou et al., "Haploinsufficiency of utrophin gene worsens skeletal muscle inflammation and fibrosis in mdx mice," Journal of the Neurological Sciences, 2008, 264(1): 106-111.
Zincarelli et al., "Analysis of AAV serotypes 1-9 mediated gene expression and tropism in mice after systemic injection," Mol Ther, 2008, 16: 1073-1080.
International Search Report and Written Opinion for Application No. PCT/US2020/028154 dated Sep. 30, 2020 (17 pages).
International Search Report and Written Opinion for Application No. PCT/US2020/028148 dated Jul. 28, 2020 (13 pages).
International Search Report and Written Opinion for Application No. PCT/US2020/045544 dated Oct. 6, 2020 (16 pages).
International Search Report and Written Opinion for Application No. PCT/US2020/047083 dated Feb. 2, 2021 (17 pages).
International Search Report and Written Opinion for Application No. PCT/US2020/047080 dated Feb. 12, 2021 (14 pages).
Japanese Patent Office Action for Application No. 2018-547872 dated Jan. 4, 2021 (8 pages, English translation included).
European Patent Office Action for Application No. 16871452.5 dated Jan. 27, 2021 (7 pages).
Brazilian Patent Office Action for Application No. BR11201811133-3 dated Mar. 23, 2021 (7 pages, English translation included).
International Search Report and Written Opinion for Application No. PCT/US2020/063150 dated Mar. 10, 2021 (11 pages).
Nelson et al., "Local and Systemic Gene Editing in a Mouse Model of Duchenne Muscular Dystrophy," Molecular Therapy, 2016, 24(Supp 1):S191.
Xu et al., "CRISPR-mediated Genome Editing Restores Dystrophin Expression and Function in mdx Mice," Molecular Therapy: The Journal of the American Society of Gene Therapy, 2016, 24(3):564-569.
Kleinstiver et al., "Genome-wide specificities of CRISPR-Cas Cpf1 nucleases in human cells," Nature Biotechnology, 2016, 34(8):869-874.
European Patent Office Action for Application No. 16871452.5 dated Feb. 4, 2020 (5 pages).
Zhang et al., "Efficient precise knockin with a double cute HDR donor after CRISPR/Cas9-mediated double-stranded DNA cleavage," Genome Biol, 2017 18(35): 18 pages.
Guo et al., "Harnessing accurate non-homologous end joining for efficient prease deletion in CRISPR/Cas9-mediated genome editing," Genome Biology, 2018, 19: 170, 20 pages.
Koo et al., "Functional Rescue of Dystrophin Deficiency in Mice Caused by Frameshift Mutations Using Campylobacter jejuni Cas9," Molecular Therapy, 2018 26(6): 1529-1538.
Veltrop et al., "A dystrophic Duchenne mouse model for testing human antisense oligonucleotides," PLoS One, 2018, 13(2): e0193289, 18 pages.
International Search Report and Written Opinion for Application No. PCT/US2021/0029482 dated Sep. 1, 2021 (13 pages).
South Arabia Patent Office Action for Application No. 518391703 dated Aug. 31, 2021 (11 pages, English translation included).
International Search Report and Written Opinion for Application No. PCT/US2021/029424 dated Sep. 17, 2021 (15 pages).
International Search Report and Written Opinion for Application No. PCT/US2021/029498 dated Sep. 17, 2021 (15 pages).
Prykhozhij et al., "CRISPR MultiTargeter: A Web Tool to Find Common and Unique CRISPR Single Guide RNA Targets in a Set of Similar Sequences," PLoS One, 2015, 10(3): e011932.
Saudi Arabia Patent Office Action for Application No. 521431236 dated Jun. 13, 2022 (14 pages, English translation included).
United Arab Emirates Patent Office Examination Report for Application No. 6000731 dated Jul. 19, 2022 (9 pages).
Israeli Patent Office Action for Application No. 259100 dated Apr. 11, 2022 (7 pages, English translation included).
Eurasian Patent Office Action for Application No. 201891317/28 dated Apr. 28, 2022 (5 pages, English translation included).
European Patent Office Action for Application No. 16871452.5 dated Jun. 23, 2022 (4 pages).
Adamson et al., "A Multiplexed Single-Cell CRISPR Screening Platform Enables Systematic Dissection of the Unfolded Protein Response," Cell, 2016, 167: 1867-1882.e21.
Aloia, "Epigenetic Regulation of Cell-Fate Changes That Determine Adult Liver Regeneration After Injury," Front. Cell Dev. Biol., 2021, 9: 643055.
Amabile et al., "Inheritable Silencing of Endogenous Genes by Hit-and-Run Targeted Epigenetic Editing," Cell, 2016, 167(1): 219-232.e14.
Amabile et al., "Permanent Epigenetic Silencing of Human Genes With Artificial Transcriptional Repressors,", Molecular Therapy, 2015, 23(Suppl. 1): S275.
Arechavala-Gomeza et al., "Comparative analysis of antisense oligonucleotide sequences for targeted skipping of exon 51 during dystrophin pre-mRNA splicing in human muscle," Human Gene Therapy, 2007, 18: 798-810.
Asrani et al., "Burden of liver diseases in the world," J Hepatol, 2019, 70(1): 151-171.
Baratta et al., "Cellular organization of normal mouse liver: a histological, quantitative immunocytochemical, and fine structural analysis," Histochem Cell Biol, 2009, 131(6): 713-726.
Barrangou et al., "CRISPR provides acquired resistance against viruses in prokaryotes," Science, 2007, 315(5819): 1709-1712.
Bartel et al., "Isolation of new ribozymes from a large pool of random sequences," Science, 1993, 261(5127): 1411-1418.
Beaudry et al., "Directed evolution of an RNA enzyme," Science, 1992, 257(5070): 635-641.
Bieth et al., "Highly restricted deletion of the SNORD116 region is implicated in Prader-Willi Syndrome," Eur J Hum Genet, 2015, 23: 252-255.
Bittel et al., "Prader-Willi syndrome: clinical genetics, cytogenetics and molecular biology," Expert Rev Mol Med, 2005, 7(14): 1-20.
Blakemore et al., "Editing of Human Genes May Begin by Year's End in the U.S." Smithsonian.com, <https://www.smithsonianmag.com/smart-news/editing-human-genes-may-begin-years-end-us-180959532/?no-ist> 2016.
Blancafort et al., "Writing and rewriting the epigenetic code of cancer cells: from engineered proteins to small molecules," Mol. Pharmacol., 2013, 83(3): 563-576.
Braasch et al., "Novel Antisense and Peptide Nucleic Acid Strategies for Controlling Gene Expression," Biochemistry, 2002, 41: 4503-4510.
Breaker et al., "Inventing and improving ribozyme function rational design versus iterative selection methods," Tibtech, 1994, 12: 268-274.
Breaker, "Are engineered proteins getting competition from RNA?," Curr. Op. Biotech., 1996, 7(4): 442-448.
Briner et al., "Guide RNA Functional Modules Direct Cas9 Activity and Orthogonality," Molecular Cell, 2014, 56(2): 333-339.
Briner et al., "Lactobacillus buchneri genotyping on the basis of clustered regularly interspaced short palindromic repeat (CRISPR) locus diversity," Appl. Environ. Microbiol., 2014, 80: 994-1001.
Brummelkamp et al., "A system for stable expression of short interfering RNAs in mammalian cells," Science, 2002, 296(5567): 550-553.
Buiting, "Prader-Willi syndrome and Angelman syndrome," Am J Med Genet C Semin Med Genet, 2010, 154C(3): 365-376.

(56) References Cited

OTHER PUBLICATIONS

Burnett et al., "Deficiency in prohormone convertase PC1 impairs prohormone processing in Prader-Willi syndrome," J Clin Invest, 2017, 127: 293-305.
Cano-Rodriguez et al., "Writing of H3K4Me3 overcomes epigenetic silencing in a sustained but context-dependent manner," Nat Commun, 2016, 7: 12284.
Carroll, "A CRISPR approach to gene targeting, " Molecular Therapy, 2012, 20: 1658-1660.
Cassidy et al., "Prader-Willi syndrome," Eur J Hum Genet, 2009, 17(1): 3-13.
Cassidy et al., "Prader-Willi syndrome," Genet Med, 2012, 14: 10-26.
Cencic et al., "Protospacer adjacent motif (PAM)-distal sequences engage CRISPR Cas9 DNA target cleavage," PLoS one, 2014, 9, e109213, 13 pages.
Chang et al., "Integrating Combinatorial Lipid Nanoparticle and Chemically Modified Protein for Intracellular Delivery and Genome Editing," Acc. Chem. Res., 2019, 52: 665-675.
Chen et al., "Acetylation of RelA at discrete sites regulates distinct nuclear functions of NF-kB," The EMBO Journal, 2002, 21(23): 6539-6548.
Chen et al., "Genome-wide CRISPR screen in a mouse model of tumor growth and metastasis," Cell, 2015, 160: 1246-1260.
Chen et al., "Targeted activation of diverse CRISPR-Cas systems for mammalian genome editing via proximal CRISPR targeting," Nature Communications, 2017, 8: 14958.
Chen et al., "Vitamin D receptor suppresses proliferation and metastasis in renal cell carcinoma cell lines via regulating the expression of the epithelial Ca2+ channel TRPV5," PLoS One, 2018, 13: e0195844.
Christoffersen et al., "Ribozymes as human therapeutic agents," J. Med. Chem., 1995, 38(12): 2023-2037.
Concise Encyclopedia of Polymer Science and Engineering, 1990, pp. 858-859.
Corces et al., "The chromatin accessibility landscape of primary human cancers," Science, 2018, 362(6413): eaav1898.
Crooke et al., "Pharmacokinetic properties of several novel oligonucleotide analogs in mice," J. Pharmacol. Exp. Ther., 1996, 277(2): 923-937.
Cruvinel et al., "Reactivation of maternal SNORD116 cluster via SETDB1 knockdown in Prader-Willi syndrome iPSCs," Hum Mol Genet, 2014, 23: 4674-4685.
Dahlman et al., "Orthogonal gene knockout and activation with a catalytically active Cas9 nuclease," Nat Biotechnol, 2015, 33(11): 1159-1161, correction in Nat Biotechnol, Apr. 2016, 34(4): 441.
Datlinger et al., "Pooled CRISPR screening with single-cell transcriptome readout," Nat. Methods, 2017, 14: 297-301.
De Mesmaeker et al., "Antisense Oligonucleotides," Ace. Chem. Res., 1995, 28: 366-374.
De Smith et al., "A deletion of the HBII-85 class of small nucleolar RNAs (snoRNAs) is associated with hyperphagia, obesity and hypogonadism," Hum Mol Genet, 2009, 18: 3257-3265.
Dempster et al., "Extracting Biological Insights from the Project Achilles Genome-Scale CRISPR Screens in Cancer Cell Lines," Cold Spring Harbor Laboratory, 2019, 35 pages.
Diao et al., "A new class of temporarily phenotypic enhancers identified by CRISPR/Cas9-mediated genetic screening," Genome Res, 2016, 26: 397-405.
Dirks et al., "Triggered amplification by hybridization chain reaction," Proceedings of the National Academy of Sciences of the United States of America, 2004, 101(43): 15275-15278.
Dixit et al., "Perturb-Seq: Dissecting Molecular Circuits with Scalable Single-Cell RNA Profiling of Pooled Genetic Screens," Cell, 2016, 167: 1853-1866.e17.
Duan et al., "Genome-wide identification of CRISPR/Cas9 off-targets in human genome," Cell research, 2014, 24(8): 1009-12.
Duker et al., "Paternally inherited microdeletion at 15q11.2 confirms a significant role for the SNORD116 C/D box snoRNA cluster in Prader-Willi syndrome," Eur J Hum Genet, 2010, 18: 1196-1201.
Dykeman, "An implementation of the Gillespie algorithm for RNA kinetics with logarithmic time update," Nucleic Acids Research, 2015, 45(12): 5708-5715.
ENCODE Project Consortium, "Expanded encyclopaedias of DNA elements in the human and mouse genomes," Nature, 2020, 583: 699-710.
Englisch et al., Chemically Modified Oligonucleotides as Probes and Inhibitors, Angewandle Chemie, International Edition, 1991, 30(6): 613-629.
Eraslan et al., "Deep learning: new computational modelling techniques for genomics," Nat. Rev. Genet., 2019, 20: 389-403.
Ernst et al., "ChromHMM: automating chromatin-state discovery and characterization," Nat. Methods, 2012, 9: 215-216.
Farasat et al., "A Biophysical Model of CRISPR/Cas9 Activity for Rational Design of Genome Editing and Gene Regulation," PLOS Computational Biology, 2016, 12(1):e1004724.
Farasat, "Sequence-to-Function Models for Efficient Optimization of Metabolic Pathways and Genetic Circuits," Ph. D. Thesis, 2015, 254 pages.
Flamm et al., "RNA folding at elementary step resolution," Rna, 2000, 6: 325-338.
Fluiter et al., "Filling the gap in LNA antisense oligo gapmers: the effects of unlocked nucleic acid (UNA) and 4'-C-hydroxymethyl-DNA modifications on RNase H recruitment and efficacy of an LNA gapmer," Mol. Biosyst., 2009, 5: 838-843.
Frank et al., "HDAC inhibitors cause site-specific chromatin remodeling at PU.1-bound enhancers in K562 cells," Epigenetics Chromatin, 2016, 9: 15.
Fu et al., "Landscape of target: guide homology effects on Cas9-mediated cleavage," Nucleic Acids Research, 2014, 42(22): 13778-13787.
Fulco et al., "Activity-by-contact model of enhancer-promoter regulation from thousands of CRISPR perturbations," Nature Genetics, 2019, 51: 1664-1669.
Fulco et al., "Systematic mapping of functional enhancer-promoter connections with CRISPR interference," Science, 2016, 354: 769-773.
Fulmer-Smentek et al., "Association of acetylated histones with paternally expressed genes in the Prader-Willi deletion region," Hum Mol Genet, 2001, 10: 645-652.
Gait, "Oligoribonucleotides," Antisense Research and Applications, 1993, Chapter 16, pp. 290-299.
Gasiunas et al., "Cas9-crRNA ribonucleoprotein complex mediates specific DNA cleavage for adaptive immunity in bacteria," Proc. Natl. Acad. Sci., 2012, 109: E2579-E2586.
Gasperini et al., "A Genome-wide Framework for Mapping Gene Regulation via Cellular Genetic Screens," Cell, 2018, 176(1-2); 377-390.e19.
Gaudelli et al., "Directed evolution of adenine base editors with increased activity and therapeutic application," Nat Biotechnol, Jul. 2020, 38(7): 892-900.
Gaudelli et al., "Programmable base editing of A•T to G•C in genomic DNA without DNA cleavage," Nature, Nov. 2017, 551(7681): 464-471.
Gebeyehu et al., "Novel biotinylated nucleotide—analogs for labeling and colorimetric detection of DNA," Nucl. Acids Res., 1987, 15(11): 4513-4534.
Gee et al., "Cellular Reprogramming Genome Editing, and Alternative CRISPR Cas9 Technologies for Precise Gene Therapy of Duchenne Muscular Dystrophy," Stem Cells International, 2017, pp. 1-11.
Gemberling et al., "Transgenic mice for in vivo epigenome editing with CRISPR-based systems," Nat Methods, 2021, 18(8): 965-974.
Genbank Accenssion AP006627.1 (2016).
Genbank Accenssion BA000004.3 (2016).
Genbank Accenssion BAB04055.1 (2016).
GenBank Accession No. AAC75803.1 (2018).
GenBank Accession No. AIN33136.1 (2014).
GenBank Accession No. BAB04055.1 (2017).
GenBank Accession No. EOT14076.1 (2013).
GenBank Accession No. AK019325 (2010).
GenBank Accession No. BB730912 (2001).
GenBank Accession No. BC010291 (2006).

(56) References Cited

OTHER PUBLICATIONS

GenBank Accession No. BC026642.1 (2007).
GenBank Accession No. BI143915 (2011).
GenBank Accession No. NM_020562.1 (2004).
GenBank P38036.2 (2013).
Ghisletti et al., "Identification and characterization of enhancers controlling the inflammatory gene expression program in macrophages," Immunity, 2010, 32: 317-328.
Gibson et al., "Enzymatic assembly of DNA molecules up to several hundred kilobases," Nature Methods, 2009, 6(5): 343-345.
Gilbert et al., "CRISPR-mediated modular RNA-guided regulation of transcription in eukaryotes," Cell, 2013, 154: 442-451.
Gillespie, "A general method for numerically simulating the stochastic time evolution of coupled chemical reactions," Journal of computational physics, 1976, 22: 403-434.
Gomaa et al., "Programmable Removal of Bacterial Strains by Use of Genome-Targeting CRISPR-Cas Systems," 2014, mBio 5(1): e00928-13.
Gonda "Aerosols for delivery of therapeutic and diagnostic agents to the respiratory tract," Critical Reviews in Therapeutic Drug Carrier Systems, 1990 6:273-313.
Gong et al., "Molecular insights into DNA interference by CRISPR-associated nuclease-helicase Cas3," Proc Natl Acad Sci U S A, 2014, 111(46):16359-64.
Gray et al., "G quadruplexes are genomewide targets of transcriptional helicases XPB and XPD," Nat. Chem. Biol, 2014, 10: 313-318.
Grissa et al., "CRISPRFinder: a web tool to identify clustered regularly interspaced short palindromic repeats," Nucleic Acids Res., 2007, 35(Web Server issue):W52-57.
Guo et al., "Directed evolution of an enhanced and highly efficient FokI cleavage domain for zinc finger nucleases," J Mol Biol, 2010, 400: 96-107.
Hacein-Bey-Abina et al., "LMO2-associated clonal T cell proliferation in two patients after gene therapy for SCID-X1," Science, 2003, 302: 415-419.
Hart et al., "High-Resolution CRISPR Screens Reveal Fitness Genes and Genotype-Specific Cancer Liabilities," Cell, 2015, 163: 1515-1526.
Hayward et al., "Whole-genome landscapes of major melanoma subtypes," Nature, 2017, 545: 175-180.
He et al., "Molecular Genetic Mechanisms of Hereditary Spherocytosis: Current Perspectives," Acta Haematol., 2018, 139: 60-66.
Heasman, "Morpholino oligos: making sense of antisense?," Dev. Biol., 2002, 243(2): 209-214.
Henikoff et al., "Amino acid substitution matrices from protein blocks," Proc. Natl. Acad. Sci. USA, 1992, 89: 10915-9.
Henning et al., "Epigenetic control of CD8 + T cell differentiation," Nat Rev Immunol, 2018, 18(5): 340-356.
Hori et al., "Simple and reproducible hepatectomy in the mouse using the clip technique," World J Gastroenterol, 2012, 18(22): 2767-2774.
Howarth et al., "A monovalent streptavidin with a single femtomolar biotin binding site," Nature methods, 2006, 3(4): 267-273.
Hsu et al., "Development and applications of CRISPR-Cas9 for genome engineering," Cell, 2014, 157(6): 1262-1278.
Huang et al., "Generation and comparison of CRISPR-Cas9 and Cre-mediated genetically engineered mouse models of sarcoma," Nature Communications, 2017, 8(15999): 1-11.
Huntriss et al., "Imprinted expression of SNRPN in human preimplantation embryos," Am J Hum Genet, 1998, 63: 1009-1014.
Jansen et al., "Identification of genes that are associated with DNA repeats in prokaryotes," Mol Microbiol, 2002, 43(6): 1565-1575.
Jeltsch et al., "Application of DNA methyltransferases in targeted DNA methylation," Appl. Microbiol. Biotechnol., 2007, 75(6): 1233-1240.
Jepsen et al., "Locked nucleic acid: a potent nucleic acid analog in therapeutics and biotechnology," Oligonucleotides, 2004, 14(2): 130-146.

Jiang et al., "A Cas9-guide RNA complex preorganized for target DNA recognition," Science, 2015, 348, 1477-1481.
Jiang et al., "RNA-guided editing of bacterial genomes using CRISPR-Cas systems," Nat. Biotechnol., 2013, 31:233-239.
Jimenez et al., "Activation of the beta-globin locus control region precedes commitment to the erythroid lineage," Proceedings of the National Academy of Sciences, 1992, 89: 10618-10622.
Jobling et al., "Chitayat-Hall and Schaaf-Yang syndromes:a common aetiology: expanding the phenotype of MAGEL2-related disorders," J Med Genet, 2018, 55: 316-321.
Josephs et al., "Structure and specificity of the RNA-guided endonuclease Cas9 during DNA interrogation, target binding and cleavage," Nucleic Acids Research, 2015, 43(18): 8924-8941.
Joyce, "Amplification, mutation and selection of catalytic RNA," Gene, 1989, 82(1): 83-87.
Joyce, "Directed molecular evolution," Scientific American, 1992, 267(6): 90-97.
Jurkowska and Jeltsch, "Silencing of Gene Expression by Targeted DNA Methylation: Concepts and Approaches," Methods Mol. Biol. 649, 2010, Chapter 9: 149-161.
Kabadi et al., "Engineering Synthetic TALE and CRISPR/Cas9 Transcription Factors for Regulating Gene Expression," Methods, 2014, 69(2): 188-197.
Kabanov et al., "A new class of antivirals: antisense oligonucleotides combined with a hydrophobic substituent effectively inhibit influenza virus reproduction and synthesis of virus-specific proteins in MDCK cells," FEBS Lett., 1990, 259: 327-330.
Karlin et al., "Applications and statistics for multiple high-scoring segments in molecular sequences," Proc. Natl. Acad. Sci. USA, 1993, 90: 5873-77.
Kauppinen et al., "Locked nucleic acid (LNA): High affinity targeting of RNA for diagnostics and therapeutics," Drug Discov Today Technol, 2005, 2(3): 287-290.
Kempfer et al., "Methods for mapping 3D chromosome architecture," Nat. Rev. Genet., 2020, 21: 207-226.
Keys et al., "A genome-wide screen in the mouse liver reveals sex-specific and cell non-autonomous regulation of cell fitness," bioRxiv preprint doi: https://doi.org/10.1101/2021.01.30.428976, posted Feb. 1, 2021.
Khodakov et al., "Protected DNA strand displacement for enhanced single nucleotide discrimination in double-stranded DNA," Scientific reports, 2015, 5: 8721.
Khurana et al., "Role of non-coding sequence variants in cancer," Nat. Rev. Genet., 2016, 17: 93-108.
Kim et al., "Epigenetic therapy of Prader-Willi Syndrome," Transl Res, 2019, 208: 105-118.
Kim et al., "Histone acetylation contributes to chromatin looping between the locus control region and g]obin gene by influencing hypersensitive site formation," Biochim Biophys Acta, 2013, 1829: 963-969.
Kim et al., "Targeting the histone methyltransferase G9a activates imprinted genes and improves survival of a mouse model of Prader-Willi syndrome," Nat Med, 2017, 23: 213-222.
Kim et al., "Engineering and Application of Zinc Finger Proteins and TALEs for Biomedical Research," Mol Cells, 2017, 40(8): 533-541.
Klann et al., "Genome-wide annotation of gene regulatory elements linked to cell fitness," bioRxiv doi: 10.1101/2021.03.08.434470. Preprint posted Mar. 9, 2021, 42 pages.
Kleinstiver et al., "Engineered CRISPR-Cas9 nucleases with altered PAM specificities," Nature, 2015, 523(7561): 481-485.
Koblan et al., "Improving cytidine and adenine base editors by expression optimization and ancestral reconstruction," Oct. 2018, 36(9): 843-846.
Kocak, "Synthetic Transcription Factors and their Effects on Endogenous DNA Methylation in Human Cells," Thesis submitted in partial fulfillment of the requirements for the degree of Master of Science in the Department of Biomedical Engineering in the Graduate School of Duke University, 2013, p. 1-29.
Kocher et al., "Phylogenetic Analysis of the SNORD116 Locus," Genes, 2017, 8(12): 358.

(56) References Cited

OTHER PUBLICATIONS

Komor et al., "Programmable editing of a target base in genomic DNA without double-stranded DNA cleavage," Nature, 2016, 533(7603): 420-424.
Korkmaz et al., "Functional genetic screens for enhancer elements in the human genome using CRISPR-Cas9," Nat Biotechnol, 2016, 34: 192-198.
Kornberg et al., "DNA Replication," 1980, pp. 75-77.
Koshkin et al., "LNA (Locked Nucleic Acids): Synthesis of the adenine, cytosine, guanine, 5-methylcytosine, thymine and uracil bicyclonucleoside monomers, oligomerisation, and unprecedented nucleic acid recognition," Tetrahedron, 1998, 54(14): 3607-3630.
Kuhnel et al., "Tumor-specific adenoviral gene therapy: Transcriptional repression of gene expression by utilizing p53-signal transduction pathways," Cancer Gene Ther., 2004, 11: 28-40.
Kumar et al., "Artificial evolution and natural ribozymes," FASEB Journal, 1995, 9: 1183-1195.
Kurreck, "Antisense technologies. Improvement through novel chemical modifications," European Journal of Biochemistry, 2003, 270(8): 1628-1644.
Kwa et al., "Chromatin modifying agents—the cutting edge of anticancer therapy," Drug Discovery Today, 2011, 16(13/14):543-547.
Lacerra et al., "Restoration of hemoglobin A synthesis in erythroid cells from peripheral blood of thalassemic patients," Proc. Natl. Acad. Sci., 2000, 97(17): 9591-9596.
Landry et al., "Expression of the leukemia oncogene Lmo2 is controlled by an array of tissue-specific elements dispersed over 100 kb and bound by Tal1/Lmo2, Ets, and Gata factors," Blood, 2009, 113: 5783-5792.
Langouet et al., "Zinc finger protein 274 regulates imprinted expression of transcripts in Prader-Willi syndrome neurons," Hum Mol Genet, 2018, 27: 505-515.
Laumont et al., "Noncoding regions are the main source of targetable tumor-specific antigens," Sci. Transl. Med., 2018, 10(470): eaau5516, 11 pages.
Lawrence et al., "Discovery and saturation analysis of cancer genes across 21 tumour types," Nature, 2014, 505: 495-501.
Lee et al., "Expression of small interfering RNAs targeted against HIV-1 rev transcripts in human cells," Nature Biotechnol, 2002, 20(5): 500-505.
Lenoir et al., "PICKLES: the database of pooled in-vitro CRISPR knockout library essentiality screens," Nucleic Acids Res, 2018, 46: D776-D780.
Lesnik et al., "Relative thermodynamic stability of DNA, RNA, and DNA: RNA hybrid duplexes: relationship with base composition and structure," Biochemistry, 1995, 34(34): 10807-10815.
Letsinger et al., "Cholesteryl-conjugated oligonucleotides: synthesis, properties, and activity as inhibitors of replication of human immunodeficiency virus in cell culture," Proc. Natl. Acad. Sci. USA, 1989, 86(17): 6553-6556.
Levin et al., "Position-dependent effects of locked nucleic acid (LNA) on DNA sequencing and PCR primers," Nuc. Acids. Res., 2006, 34: e142.
Levskaya et al., "Synthetic biology: engineering *Escherichia coli* to see light," Nature, 2005, 438:441-442.
Li et al., "Chimeric DNA methyltransferases target DNA methylation to specific DNA sequences and repress expression of target genes," Nucleic Acids Res., 2007, 35(1): 100-112.
Li et al., "Ex vivo cell-based CRISPR/Cas9 genome editing for therapeutic applications," Biomaterials, 2020, 234: 119711.
Li et al., "The autism-related gene SNRPN regulates cortical and spine development via controlling nuclear receptor Nr4a1," Sci Rep, 2016, 6: 29878.
Liao et al., "In Vivo Target Gene Activation via CRISPR/Cas9-Mediated Trans-epigenetic Modulation," Cell, 2017, 171: 1495-1507.

Lin et al., "Essential Role of the 58-kDa Microspherule Protein in the Modulation of Daxx-dependent Transcriptional Repression as Revealed by Nucleolar Sequestration," J Biol Chem, 2002, 277: 25446-25456.
Liu et al., "Editing DNA Methylation in the Mammalian Genome," Cell, Sep. 2016, 167(1): 233-247.
Liu et al., "Monte Carlo simulation for single RNA unfolding by force," Biophysical journal, 2005, 88(1): 76-84.
Luo et al., "Repurposing endogenous type I CRISPR-Cas systems for programmable gene repression," Nucleic Acids Research, 2014, 43(1): 674-681.
Ma et al., "Targeted gene suppression by inducing de novo DNA methylation in the gene promoter," Epigenetics Chromatin, 2014, 7: 20.
Machinek et al., "Programmable energy landscapes for kinetic control of DNA strand displacement," Nature communications, 2014, 5: 5324, 9 pages.
MacPherson et al., "Flexible guide-RNA design for CRISPR applications using Protospacer Workbench," Nature biotechnology, 2015, 33(8): 805-806.
Mader et al., "CRISPR RNA-guided activation of endogenous human genes," Nature Methods, 2013, 10(10): 977-979.
Maeder et al., "Robust, synergistic regulation of human gene expression using TALE activators," Nat Methods, 2013, 10(3): 243-245.
Majzner et al., "Clinical lessons learned from the first leg of the CAR T cell journey," Nature Medicine, 2019, 25(9): 1341-1355.
Makarova et al., "An updated evolutionary classification of CRISPR-Cas systems," Nature Reviews Microbiology, 2015, 13:722-736.
Makarova et al., "Evolution and classification of the CRISPR-Cas systems," Nature Reviews Microbiology, 2011, pp. 467-477.
Manoharan et al., "Chemical Modifications to Improve Uptake and Bioavailability of Antisense Oligonucleotides," Ann. N. Y. Acad. Sci., 1992, 660: 306-309.
Manoharan et al., "Cholic acid-oligonucleotide conjugates for antisense applications," Bioorg. Med. Chem. Let., 1994, 4(8): 1053-1060.
Manoharan et al., "Introduction of a lipophilic thioether tether in the minor groove of nucleic acids for antisense applications," Bioorg. Med. Chem. Let., 1993, 3(12): 2765-2770.
Manoharan et al., "Lipidic Nucleic Acids," Tetrahedron Lett, 1995, 36: 3651-3654.
Manoharan et al., "Oligonucleotide Conjugates: Alteration of the Pharmacokinetic Properties of Antisense Agents," Nucleosides & Nucleotides, 1995, 14: 969-973.
Martin et al, "A New Access to 2'-O-Alkylated Ribonucleosides and Properties of 2'-O-Alkylated Oligoribonucleotides," Helv. Chim. Acta, 1995, 78: 486-504.
Mastellos et al., "Inducing and characterizing liver regeneration in mice: Reliable models, essential 'readouts' and critical perspectives," Curr Protoc Mouse Biol., 2013, 3(3): 141-170.
Mathews et al., "Expanded sequence dependence of thermodynamic parameters improves prediction of RNA secondary structure," Journal of Molecular Biology, 1999, 288(5): 911-940.
Maurano et al., "Systematic localization of common disease-associated variation in regulatory DNA," Science, 2012, 337: 1190-1195.
Maxwell et al., "A detailed cell-free transcription-translation-based assay to decipher CRISPR protospacer-adjacent motifs," Methods, 2018, 143: 48-57.
McCarthy et al., "Schaaf-Yang syndrome overview: Report of 78 individuals," Am J Med Genet A, 2018, 176(12): 2564-2574.
McTigue et al., "Sequence-dependent thermodynamic parameters for locked nucleic acid (LNA)-DNA duplex formation," Biochemistry, 2004, 43(18): 5388-5405.
Mevissen et al., "Molecular basis of Lys11-polyubiquitin specificity in the deubiquitinase Cezanne," Nature, 2016, 538(7625): 402-405.
Meyers et al., "Computational correction of copy number effect improves specificity of CRISPR-Cas9 essentiality screens in cancer cells," Nat. Genet., 2017, 49: 1779-1784.
Min et al., "CRISPR Correction of Duchene Muscular Dystrophy," Annual Review of Medicine, Epub Oct. 2018, 70: 239-255.

(56) References Cited

OTHER PUBLICATIONS

Mishra et al., "Improved leishmanicidal effect of phosphorotioate antisense oligonucleotides by LDL-mediated delivery," Biochim. Biophys. Acta, 1995, 1264(2): 229-237.

Miyagishi et al., "U6 promoter-driven siRNAs with four uridine 3' overhangs efficiently suppress targeted gene expression in mammalian cells," Nature Biotechnol, 2002, 20(5): 497-500.

Mojica et al., "Intervening sequences of regularly spaced prokaryotic repeats derive from foreign genetic elements," J Molec Evolution, 2005, 60(2): 174-182.

Mojica et al., "Short motif sequences determine the targets of the prokaryotic CRISPR defence system," Microbiology, 2009, 155: 733-740.

Moore et al., "Transcription Activator-like Effectors: A Toolkit for Synthetic Biology," ACS Synth Biol, 2014, 3(10): 708-716.

Murray et al., "Codon usage in plant genes," Nucl. Acids Res., 1989, 17:477-498.

Naguibneva et al., "An LNA-based loss-of-function assay for micro-RNAs," Biomed Pharmacother, 2006, 60: 633-638.

Nam et al., "Cas5d protein processes pre-crRNA and assembles into a Cascade-like interference complex in Subtype I-C/Dvulg CRISPR-Cas system," Structure, 2012, 20:1574-1584.

Nasevicius et al., "Effective targeted gene 'knockdown' in zebrafish," Nat. Genet., 2000, 26(2): 216-220.

Nguyen et al., "Transcriptional Enhancers in the Regulation of T Cell Differentiation," Front. Immunol., 2015, 6: 462.

Nielsen et al., "Sequence-selective recognition of DNA by strand displacement with a thymine-substituted polyamide," Science, 1991, 254: 1497-1500.

Nikfarjam et al., "A Model of Partial Hepatectomy in Mice," Journal of Investigative Surgery, 2004, 17(5): 291-294.

Nowotny et al., "Crystal structures of RNase H bound to an RNA/DNA hybrid: substrate specificity and metal-dependent catalysis," Cell, 2005, 121(7): 1005-1016.

Nuñez et al., "Genome-wide programmable transcriptional memory by CRISPR-based epigenome editing," Cell, 2021, 184(9): P2503-2519.

O'Brien et al., "GT-Scan: identifying unique genomic targets," Bioinformatics, 2014, 30: 2673-2675.

Oberhauser et al., "Effective incorporation of 2'-O-methyl-oligoribonucleotides into liposomes and enhanced cell association through modification with thiocholesterol," Nucl. Acids Res., 1992, 20(3): 533-538.

Obika et al., "Stability and structural features of the duplexes containing nucleoside analogues with a fixed N-type conformation, 2'-O,4'-C-methyleneribonucleosides," Tetrahedron Lett. 1998, 39(30): 5401-5404.

O'Connell et al., "Programmable RNA recognition and cleavage by CRISPR/Cas9," Nature, 2014, 516: 263-266.

O'Geen et al., "dCas9-based epigenome editing suggests acquisition of histone methylation is not sufficient for target gene repression," Nucleic Acids Res, 2017, 45: 9901-9916.

Orgel, "Selection in vitro," Proc. R. Soc. B, 1979, 205: 435-442.

Orlando et al., "Promoter capture Hi-C-based identification of recurrent noncoding mutations in colorectal cancer," Nat. Genet., 2018, 50: 1375-1380.

Orom et al., "LNA-modified oligonucleotides mediate specific inhibition of microRNA function," Gene, 2006, 372: 137-141.

Ousterout, "Genetic Correction of Duchenne Muscular Dystrophy using Engineered Nucleases," Dept. of Biomedical Engineering Duke University (Dissertation), 2014, pp. 1-204.

Paddison et al., "Short hairpin RNAs (shRNAs) induce sequence-specific silencing in mammalian cells," Genes & Dev, 2002, 16(8): 948-958.

Paez-Espino et al., "CRISPR immunity drives rapid phage genome evolution in Streptococcus thermophilus," mBio, 2015, 6(2): e00262-15.

Paul et al., "Effective expression of small interfering RNA in human cells," Nature Biotechnol, 2002, 20(5): 505-508.

Penczek et al., "Three-dimensional reconstruction of single particles embedded in ice," Ultramicroscopy, 1992, 40, 33-53.

Perez-Pinera et al., "Synergistic and tunable human gene activation by combinations of synthetic transcription factors," Nat Methods, 2013, 10: 239-242.

Pinello et al., "Analyzing CRISPR genome-editing experiments with CRISPResso," Nat Biotechnol, 2016, 34(7):695-697.

Ponting et al., "Evolution and functions of long noncoding RNAs," Cell, 2009, 136(4): 629-641.

Povero et al., "Lipid-induced toxicity stimulates hepatocytes to release angiogenic microparticles that require Vanin-1 for uptake by endothelial cells," Sci Signal, 2013, 6(296): ra88.

Powell et al., "A Prader-Willi locus lncRNA cloud modulates diurnal genes and energy expenditure," Hum Molec Genet, 2013, 22: 4318-4328.

Puccini et al., "Colorectal cancer: epigenetic alterations and their clinical implications", Biochim Biophys Acta, 2017, vol. 1868, No. 2, pp. 439-448.

Raeburn et al., "Techniques for drug delivery to the airways, and the assessment of lung function in animal models," J. Pharmacol. Toxicol. Meth., 1992, 27:143-159.

Rajagopal et al., "High-throughput mapping of regulatory DNA," Nat. Biotechnol, 2016, 34: 167-174.

Ran et al., "Genome engineering using the CRISPR-Cas9 system," Nature Protocols, 2013, 8(11): 2281-2308.

Ratcliff et al., "A novel single-molecule study to determine protein-protein-protein association constants," Journal of the American Chemical Society, 2001, 123(24): 5632-5635.

Rauscher et al., "GenomeCRISPR—a database for high-throughput CRISPR/Cas9 screens," Nucleic Acids Res, 2017, 45: D679-D686.

Rheinbay et al., "Analyses of non-coding somatic drivers in 2,658 cancer whole genomes," Nature, 2020, 578: 102-111.

Rhodes et al., "G-quadruplexes and their regulatory roles in biology," Nucleic Acids Res, 2015, 43: 8627-8637.

Richter et al., "Phage-assisted evolution of an adenine base editor with improved Cas domain compatibility and activity," Nat Biotechnol, Jul. 2020, 38(7): 883-891.

Rmilah et al., "Understanding the marvels behind liver regeneration," Wiley Interdiscip Rev Dev Biol., 2019, 8(3): e340.

Rodriguez et al., "Clustering by fast search and find of density peaks," Science, 2014, 344(6191): 1492-1496.

Russa et al. "The New State of the Art: Cas9 for Gene Activation and Repression," Molecular and Cellular Biology, 2015, 35(22):3800-3809.

Rutkauskas et al., "Directional R-loop formation by the CRISPR-Cas surveillance complex cascade provides efficient off-target site rejection," Cell reports, 2015, 10, 1534-1543.

Sahoo et al., "Prader-Willi phenotype caused by paternal deficiency for the HBII-85 C/D box small nucleolar RNA cluster," Nat Genet, 2008, 40: 719-721.

Saitoh et al., "Parent-of-Origin Histone Acetylation and Reactivation of a Key Imprinted Gene Locus in Prader-Willi Syndrome," Am J Hum Genet, 2000, 66: 1958-1962.

Sanghvi et al., "Heterocyclic Base Modifications in Nucleic Acids and their Applications in Antisense Oligonucleotides," 1993, Antisense Research and Applications, Chapter 15, pp. 274-285.

Sanjana et al., "High-resolution interrogation of functional elements in the noncoding genome," Science, 2016, 353: 1545-1549.

SantaLucia et al., "Improved nearest-neighbor parameters for predicting DNA duplex stability," Biochemistry, 1996, 35(11): 3555-3562.

Schaaf et al., "Truncating mutations of MAGEL2 cause Prader-Willi phenotypes and autism," Nat Genet, 2013, 45(11): 1405-1408.

Schifrut et al., "Genome-wide CRISPR Screens in Primary Human T Cells Reveal Key Regulators of Immune Function," Cell, 2018, 175(7): 1958-1971.e15.

Schmidt et al., "GenomeRNAi: a database for cell-based and in vivo RNAi phenotypes, 2013 update," Nucleic Acids Res, 2013, 41: D1021-6.

Schmittgen et al., "Analyzing real-time PCR data by the comparative CT method," Nature Protocols, 2008, 3(6): 1101-1108.

(56) References Cited

OTHER PUBLICATIONS

Schreck et al., "DNA hairpins destabilize duplexes primarily by promoting melting rather than by inhibiting hybridization," Nucleic Acids Research, 2015, 43(13): 6181-6190.
Schreck et al., "DNA hairpins primarily promote duplex melting rather than inhibiting hybridization," 2014, arXiv preprint arXiv:1408.4401.
Segal and Meckler, "Genome Engineering at the Dawn of the Golden Age," Annu. Rev. Genomics Hum. Genet., 2013, 14: 135-158.
Semenova et al., "The Cas6e ribonuclease is not required for interference and adaptation by the *E. coli* type I-E CRISPR-Cas system," Nucleic Acids Res, 2015, 43(12):6049-61.
Sengupta et al., "Super-Enhancer-Driven Transcriptional Dependencies in Cancer," Trends Cancer Res, 2017, 3: 269-281.
Sentmanat et al., "A Survey of Validation Strategies for CRISPR-Cas9 Editing," Scientific Reports, 2018, 8: 888.
Serra et al., "Predicting thermodynamic properties of RNA," Methods in Enzymology, 1995, 259: 242-261.
Shalem et al., "Genome-scale CRISPR-Cas9 knockout screening in human cells," Science, 2014, 343: 84-87.
Shea et al., "Synthesis, hybridization properties and antiviral activity of lipid-oligodeoxynucleotide conjugates," Nucl. Acids Res, 1990, 18: 3777-3783.
Shlyakhtenko et al., "Silatrane-based surface chemistry for immobilization of DNA, protein-DNA complexes and other biological materials," Ultramicroscopy, 2003, 97: 279-287.
Siddique et al., "Targeted methylation and gene silencing of VEGF-A in human cells by using a designed Dnmt3a-Dnmt3L single-chain fusion protein with increased DNA methylation activity," J. Mol. Biol., 2013, 425(3): 479-491.
Simpson, "Contacts between *Escherichia coli* RNA polymerase and thymines in the lac UV5 promoter," Proc. Natl. Acad. Sci. USA, 1979, 76: 3233-3237.
Singh et al. "Protein Engineering Approaches in the Post-Genomic Era," Current Protein and Peptide Science, 2017, 18: 1-11.
Soejima et al., "Imprinting centers, chromatin structure, and disease," J Cell Biochem, 2005, 95(2): 226-233.
Stanton et al., "Chemical modification study of antisense gapmers," Nucleic Acid Ther., 2012, 22(5): 344-359.
Stemmer et al., "CCTop: An Intuitive, Flexible and Reliable CRISPR/Cas9 Target Prediction Tool," PLoS One, 2015, 10(4): e0124633.
Stephens, "False discovery rates: a new deal," Biostatistics, 2017, 18: 275-294.
Stepper et al., "Efficient targeted DNA methylation with chimeric dCas9-Dnmt3a-Dnmt3L methyltransferase," Nucleic Acids Res., 2017, 45(4): 1703-1713.
Stolzenburg et al., "Targeted silencing of the oncogenic transcription factor SOX2 in breast cancer," Nucleic Acids Res., 2012, 40(14): 6725-6740.
Su et al., "Identification of biologically relevant enhancers in human erythroid cells," J Biol Chem, 2013, 288: 8433-8444.
Sugimoto et al., "Thermodynamic parameters to predict stability of RNA/DNA hybrid duplexes," Biochemistry, 1995, 34: 11211-11216.
Sugimoto et al., "Thermodynamics-structure relationship of single mismatches in RNA/DNA duplexes," Biochemistry, 2000, 39: 11270-11281.
Sui et al., "A DNA vector-based RNAi technology to suppress gene expression in mammalian cells," PNAS, 2002, 99(8): 5515-5520.
Sun et al., "Phage mutations in response to CRISPR diversification in a bacterial population," Environmental microbiology, 2013, 15(2): 463-470.
Sur et al., "The role of enhancers in cancer," Nat. Rev. Cancer., 2016, 16: 483-493.
Sutcliffe et al., "Deletions of a differentially methylated CpG island at the SNRPN gene define a putative imprinting control region," Nature Genetics, 1994, 8: 52-58.
Svinarchuk et al., "Inhibition of HIV proliferation in MT-4 cells by antisense oligonucleotide conjugated to lipophilic groups," Biochimie, 1993, 75: 49-54.
Szczelkun et al., "Direct observation of R-loop formation by single RNA-guided Cas9 and Cascade effector complexes," Proceedings of the National Academy of Sciences, 2014, 6 pages.
Szostak, "in Vitro Genes," TIBS, 1993, 17: 89-93.
Szymczak et al., "Correction of multi-gene deficiency in vivo using a single 'self-cleaving' 2A peptide-based retroviral vector," Nature Biotechnology, 2004, 22(5): 589-594.
Takami et al., "Complete Genome Sequence of the Alkaliphilic Bacterium Bacillus halodurans and Genomic Sequence Comparison with Bacillus subtilis," Nucleic Acids Research, 2000, 28(21): 4317-4331.
Tam et al., "Benefits and limitations of genome-wide association studies," Nat. Rev. Genet., 2019, 20: 467-484.
Tan et al., "Rationally engineered *Staphylococcus aureus* Cas9 nucleases with high genome-wide specificity," Proc. Nat. Acad. Sci. USA, 2019, 116(46): 20969-20976.
Tracy, "Human DNA sequence from clone RP11-34D15 on chromosome 10, complete sequence," Genbank entry, National Center for Biotechnology Information, <https://www.ncbi.nlm.nih.gov/nucleotide/AL139819.8> 2012.
Tsai et al., "GUIDE-seq enables genome-wide profiling of off-target cleavage by CRISPR-Cas nucleases," Nature biotechnology, 2015, 33(2): 187-197.
Tyle, "Iontophoretic Devices for Drug Delivery," Pharm. Res., 1986, 3: 318-326.
U.S. Appl. No. 17/471,935, filed Sep. 10, 2021, by Gersbach et al.
U.S. Appl. No. 17/636,750, filed Feb. 18, 2022, by Gersbach et al.
U.S. Appl. No. 17/636,754, filed Feb. 18, 2022, by Gersbach et al.
Urrutia, "KRAB-containing zinc-finger repressor proteins," Genome Biol., 2003, 4(10): 231.
Usman et al., "Catalytic RNA (Ribozymes) as Drugs," Ann. Rep. Med. Chem., 1995, Chapter 30, pp. 285-294.
Van der Oost et al., "Unravelling the structural and mechanistic basis of CRISPR-Cas systems," Nature Reviews Microbiology, 2014, 12: 479-492.
Wada et al., "Codon usage tabulated from the GenBank genetic sequence data," Nucl. Acids Res., 1990, 18: 2367-2411.
Wang et al., "Cyclohexene Nucleic Acids (CeNA): Serum Stable Oligonucleotides that Activate RNase H and Increase Duplex Stability with Complementary RNA," J. Am. Chem. Soc., 2000, 122: 8595-8602.
Wang et al., "Gene Essentiality Profiling Reveals Gene Networks and Synthetic Lethal Interactions with Oncogenic Ras," Cell, 2017, 168: 890-903.e15.
Wang et al., "Genetic screens in human cells using the CRISPR-Cas9 system," Science, 2014, 343: 80-84.
Wang et al., "Identification and characterization of essential genes in the human genome," Science, 2015, 350: 1096-1101.
Wang et al., "Potential of Epigenetic Therapy for Pader-Willi Syndrome," Trends in Pharmacological Sciences, 2019, 40(9): 605-608.
Wang et al., "Unbiased detection of off-target cleavage by CRISPR-Cas9 and TALENs using integrase-defective lentiviral vectors," Nature biotechnology, 2015, 33(2): 175-8.
Watkins et al., "Thermodynamic contributions of single internal rA.dA, rC.dC, rG.dG and rU.dT mismatches in RNA/DNA duplexes," Nucleic acids research, 2011, 39(5): 1894-1902.
Wei et al., "Targeting Regnase-1 programs long-lived effector T cells for cancer therapy," Nature, 2019, 576(7787): 471-476.
Wherry, "T cell exhaustion," Nat. Immunology, 2011, 12: 492-499.
Wiggins et al., "High flexibility of DNA on short length scales probed by atomic force microscopy," Nature nanotechnology, 2006, 1(2): 137-141.
Wilbie et al., "Delivery Aspects of CRISPR/Cas for in Vivo Genome Editing," Acc Chem Res, 2019, 52(6): 1555-1564.
Wiles et al., "CRISPR-Cas9_mediated genome editing and guide RNA design," Mammalian Genome, 2015, 26(9): 501-510.
Wu et al., "Genome-wide binding of the CRISPR endonuclease Cas9 in mammalian cells," Nature biotechnology, 2014, 32(7): 670-6.

(56) References Cited

OTHER PUBLICATIONS

Wu et al., "Induction of anion exchanger-1 translation and its opposite roles in the carcinogenesis of gastric cancer cells and differentiation of K562 cells," Oncogene, 2010, 29: 1987-1996.
Wu et al., "Unusual Processing Generates SPA LncRNAs that Sequester Multiple RNA Binding Proteins," Mol Cell, 2016, 64: 534-548.
Xie et al., "Multiplexed Engineering and Analysis of Combinatorial Enhancer Activity in Single Cells," Mol. Cell, 2017, 66: 285-299. e5.
Yang et al., "Determination of protein-DNA binding constants and specificities from statistical analyses of single molecules: MutS-DNA interactions," Nucleic acids research, 2005, 33(13): 4322-4334.
Yang et al., "Gene Reactivation by 5-Aza-2'-Deoxycytidine-Induced Demethylation Requires SRCAP-Mediated HZA.Z Insertion to Establish Nucleosome Depleted Regions", PLoS Genetics, 2012, vol. 8, Issue 3, e1002604, 12 pages.
Yin et al., "Long noncoding RNAs with snoRNA ends," Mol Cell, 2012, 48(2): 219-230.
Yin et al., "Programming biomolecular self-assembly pathways," Nature, 2008, 451(7176): 318-323.
You et al., "Design of LNA probes that improve mismatch discrimination," Nuc. Acids. Res., 2006, 34(8): e60.
Younossi et al., "Epidemiology of chronic liver diseases in the USA in the past three decades," Gut, 2020, 69(3): 564-568.
Yu et al., "RNA interference by expression of short-interfering RNAs and hairpin RNAs in mammalian cells," PNAS, 2002, 99(9): 6047-6052.
Zenser et al., "A new TAP system for isolation of plant protein complexes and subsequent mass-spec analysis," <https://www.sigmaaldrich.com/deepweb/assets/sigmaaldrich/product/documents/388/028/flag_ha_tap_poster.pdf> published 2008, printed as pp. 1/4-4/4.
Zhang et al., "Gene activation in human cells using CRISPR/Cpf1-p300 and CRISPR/Cpf1-SunTag systems," Protein Cell, 2018, 9: 380-383.
Zhang et al., "Myoediting: Toward Prevention of Muscular Dystrophy by Therapeutic Genome Editing," Physiological Reviews, 2018, 98(3): 1205-1240.
Zhang et al., "Propagated Perturbations from a Peripheral Mutation Show Interactions Supporting WW Domain Thermostability," Structure, 2018, 26: 1474-1485.
Zhao et al., "High-efficiency transfection of primary human and mouse T lymphocytes using RNA electroporation," Mol. Ther., 2006, 13: 151-159.
Zhao et al., "Intracellular delivery of artificial transcription factors fused to the protein transduction domain of HIV-1 Tat," Protein Expr Purif, 2013, 90(1): 27-33.
Zheng et al., "Foxp3 in control of the regulatory T cell lineage," Nat. Immunol. 2007, 8: 457-462.
Zhu et al., "The role of histone deacetylase 7 (HDAC7) in cancer cell proliferation: regulation on c-Myc," J. Mol. Med, 2011, 89: 279-289.
NCBI Reference Sequence XM011532698.1 (2015).
NCBI Reference Sequence NM_004020.2 (2010).
NCBI Reference Sequence NG_028016.2 (2013).
Chinese Patent Office Action for Application No. 201680080439.7 dated Sep. 5, 2022 (19 pages, English translation included).
Saudi Arabia Patent Office Examination Report for Application No. 521431236 dated Nov. 3, 2022 (20 pages, English translation included).
Canadian Patent Office Action for Application No. 3,001,623 dated Jan. 16, 2023 (5 pages).
United States Patent Office Notice of Allowance for U.S. Appl. No. 16/318,745 dated Oct. 27, 2022 (9 pages).
United States Patent Office Action for U.S. Appl. No. 16/098,464 dated Nov. 3, 2022 (13 pages).
Ifuku et al., "Restoration of Dystrophin Protein Expression by Exon Skipping Utilizing CRISPR-Cas9 in Myoblasts Derived from DMD Patient iPS Cells," Methods Mol Biol, 2018, Chapter 12, pp. 191-217.
Min et al., "CRISPR Correction of Duchene Muscular Dystrophy Exon 44 Deletion Mutations in Mice and Human Cells," Science Advances, 2019, 5: eaav4324.
Robinson-Hamm et al., "Gene therapies that restore dystrophin expression for the treatment of Duchenne muscular dystrophy," Human Genetics, 2016, 135(9): 1029-1040.
Yu et al., "Dystrophin-deficient large animal models: translational research and exon skipping," Am J Transl Res, 2015, 7(8): 1314-1331.
Chinese Patent Office Action for Application No. 201680080439.7 dated Apr. 18, 2023 (12 pages, English translation included).
Mexican Patent Office Action for Application No. MX/a/2018/005377 dated Apr. 19, 2023 (10 pages, English translation included).
Park et al., "Cas-Designer: a web-based tool for choice of CRISPR-Cas9 target sites," Bioinformatics, 2015, 31(24): 4014-4016.
Shen et al., "Massively parallel cis-regulatory analysis in the mammalian central nervous system," Genome Research, 2015, 26(2): 238-255.
Chhatwal et al., "Identification of cell-type-specific promoters within the brain using lentiviral vectors," Gene Therapy, 2007, 14(7): 575-583.
Trinklein et al., "Identification and functional analysis of human transcriptional promoters," Genome Research, 2003, 13(2): 308-312.
United States Patent Office Action for U.S. Appl. No. 16/098,464 dated Aug. 1, 2023 (16 pages).
United States Office Action for U.S. Appl. No. 16/318,745 dated Aug. 11, 2023 (12 pages).
European Patent Office Action for Application No. 16871452.5 dated Jul. 20, 2023 (6 pages).
U.S. Appl. No. 63/335,122, filed Apr. 26, 2022.
U.S. Appl. No. 63/342,027, filed May 13, 2022.
Adikusuma et al., "Versatile single-step-assembly CRISPR/Cas9 vectors for dual gRNA expression," 2017, 12(12): e0187236.
Carcagno et al., "Neurogenin3 Restricts Serotonergic Neuron Differentiation to the Hindbrain," The Journal of Neuroscience, 2014, 34(46): 15223-15233.
Kalsner et al., "Prader-Willi, Angelman, and 15q11-q13 Duplication Syndromes," Pediatric Clinics of North America United States, 2015, 62(3): 587-606.
Ohta et al., "Imprinting-Mutation Mechanisms in Prader-Willi Syndrome," The American Journal of Human Genetics, 1999, 64(2): 397-413.
Yang et al., "A dual AAV system enables the Cas9-mediated correction of a metabolic liver disease in newborn mice," Nature Biotechnology, 2016, 34(3): 334-338.
Chinese Patent Office Action for Application No. 201680080439.7 dated Sep. 27, 2023 (14 pages, English translation included).
Japanese Patent Office Action for Application No. 2022-110179 dated Aug. 24, 2023 (7 pages, English translation included).
United Arab Emirates Patent Office Examination Report for Application No. 6000731 dated Sep. 27, 2023 (7 pages).
U.S. Publication 20190183932.
U.S. Publication 20190264232.
U.S. Publication 20190062790.
WO2016/011080.
WO2017/180976.
WO2019/113472.
WO2019/204750.
WO2022/038264.
WO2022/133062.
Mexican Patent Office Action for Application No. MX/a/2018/005377 dated Nov. 28, 2023 (14 pages, English translation included).
Echevarria et al., "Exon-skipping advances for Duchenne muscular dystrophy," Human Molecular Genetics, 2018, 27 (R2): R163-R172.
Miller, "Non-viral CRISPR/Cas gene editing in vitro and in vivo enabled by synthetic nanoparticle co-delivery of Cas9 mRNA and sgRNA," Angew Chem Int Engl, 2017, 56(4): 1059-1063.

(56) References Cited

OTHER PUBLICATIONS

Ryu et al., "Adenine base editing in mouse embryos and an adult mouse model of Duchenne muscular dystrophy," Nature Biotechnology, 2018, 36(6):536-539.
Rees et al., "Base editing: precision chemistry on the genome and transcriptome of living cells," Nature Reviews Genetics, 2018, 19(12): 770-788.
Nelson et al., "Long-term evaluation of genome editing for Duchenne muscular dystrophy," Duke Presentation, 2019, 123 pages. Retrieved from the Internet: <https://static.seekingalpha.com/uploads/sa_presentations/453/41453/original.pdf>.
Young, "Development of a Therapeutic CRISPR/Cas9 Plataform for Duchenne Muscular Dystrophy," UCLA Electronic Theses and Dissertations, Jan. 1, 2018, 136 pages.
Kwon et al., "In Vivo Gene Editing of Muscle Stem Cells with Adeno-Associated Viral Vectors in a Mouse Model of Duchenne Muscular Dystrophy," Molecular Therapy, 2020, 19: 320-329.
United States Patent Office Action for U.S. Appl. No. 16/098,464 dated Feb. 12, 2024 (16 pages).
United States Patent Office Corrected Notice of Allowance for U.S. Appl. No. 16/318,715 dated Mar. 27, 2024 (2 pages).
Abaandou et al., "Affecting HEK293 Cell Growth and Production Performance by Modifying the Expression of Specific Genes," Cells, 2021, 10: 1667, 21 pages.
Alerasool et al., "An efficient KRAB domain for CRISPRi applications in human cells," Nat Methods, 2020, 17: 1093-1096.
Alonso-Camino et al., "CARbodies: Human Antibodies Against Cell Surface Tumor Antigens Selected From Repertoires Displayed on T Cell Chimeric Antigen Receptors," Mol Ther Nucl Acids, 2013, 2: e93, 11 pages.
Azuma et al., "Robust expansion of human hepatocytes in Fah-/-/Rag2-/-/Il2rg-/- mice" Nat Biotechnol., 2007, 25(8): 903-910.
Bhakta et al., "The generation of zinc finger proteins by modular assembly," Methods Mol. Biol., 2010, 649: 3-30.
Bloomfield, "Quasi-Elastic Light Scattering Applications in Biochemistry and Biology," Ann. Rev. Biophys. Bioeng., 1981, 10: 421-450.
Boris-Lawrie et al., "Recent advances in retrovirus vector technology," Cur. Opin. Genet. Develop., 1993, 3: 102-109.
Bouhairie et al., "familial hypercholesterolemia," Cardiol. Clin., 2015, 33(2): 169-179.
Braliou et al., "The v-ErbA oncoprotein quenches the activity of an erythroid-specific enhancer," Oncogene, 2001, 20(7): 775-87.
Brash et al., "Strontium phosphate transfection of human cells in primary culture: stable expression of the simian virus 40 large-T-antigen gene in primary human bronchial epithelial cells," Mol. Cell Biol., 1987, 7(5): 2031-2034.
Broude et al., "p21 (CDKN1A) is a negative regulator of p53 stability," Cell Cycle, 2007, 6(12): 1468-1471.
Buckingham, M. et al. "The role of Pax genes in the development of tissues and organs: Pax3 and Pax7 regulate muslce progenitor cell functions." Annu. Rev. Cell Dev. Biol. 23 (2007): 645-673.
Burns et al., "Vesicular stomatitis virus G glycoprotein pseudotyped retroviral vectors: concentration to very high titer and efficient gene transfer into mammalian and nonmammalian cells," Proc. Natl. Acad. Sci. USA, 1993, 90: 8033-8037.
Cano-Rodriguez et al., "Epigenetic Editing: On the Verge of Reprogramming Gene Expression at Will," Curr Genet Med Rep Rep, 2016, 4: 170-179.
Carlens et al., "Ex vivo T lymphocyte expansion for retroviral transduction: influence of serum-free media on variations in cell expansion rates and lymphocyte subset distribution," Exp Hematol, 2000, 28(10): 1137-46.
Cavalieri et al., "Human T lymphocytes transduced by lentiviral vectors in the absence of TCR activation maintain an intact immune competence," Blood, 2003, 102(2): 497-505.
Chakraborty et al. "553. AAV-fVlediated Delivery of HSV-Specific Homing Endonucleases To Neurons of the Trigeminal Ganglia for HSV-1 Inhibition." Molecular Therapy 22 (2014).

Chen et al., "Fusion protein linkers: property, design, and functionality," Adv. Drug Deliv. Rev., 2013, 65(10): 1357-1369.
Chicaybam et al., "An efficient low cost method for gene transfer to T lymphocytes," PLoS ONE, 2013, 8(3): e60298, 11 pages.
Chylinski et al., "The tracrRNA and Cas9 families of type II CRISPR-Cas immunity systems," RNA Biol., 2013, 10(5): 726-737.
Cooper et al., "T-cell clones can be rendered specific for CD19: toward the selective augmentation of the graft-versus-B-lineage leukemia effect," Blood, 2003, 101(4): 1637-1644.
Cortés-Mancera et al., "Gene-Targeted DNA Methylation: Towards Long-Lasting Reprogramming of Gene Expression?" Adv Exp Med Biol., 2022, 1389: 515-533.
Das et al., "Tet-On Systems For Doxycycline-inducible Gene Expression," Current Gene Therapy, 2016, 16: 156-167.
Defesche et al., "Familial hypercholesterolaemia," Nat. Rev. Dis. Primers, 2017, 3: 17093, 20 pages.
Deng et al., "Highly sensitive electrochemical methyltransferase activity assay," Anal Chem., 2014, 86: 2117-2123.
Fuks, "DNA methylation and histone modifications: teaming up to silence genes," Current Opinion in Genetics & Development, 2005, 15(5): 490-495.
Gersbach et al., "Synthetic zinc finger proteins: the advent of targeted gene reguulation and genome modification technologies," Acc. Chem. Res., 2014, 47(8): 2309-18.
Gowher et al., "Mechanism of stimulation of catalytic activity of Dnmt3A and Dnmt3B DNA-(cytosine-C5)-methyltransferases by Dnmt3L," J. Biol. Chem., 2005, 280(14): 13341-13348.
Gowher et al., "Molecular enzymology of the catalytic domains of the Dnmt3a and Dmnt3b DNA methyltransferases," J. Biol. Chem., 2002, 277(23): 20409-20414.
Hochstrasser et al., "CasA mediates Cas3-catalyzed target degradation during CRISPR RNA-guided interference," PNAS, 2014, 111(18): 6618-23.
Huang et al., "Ch 9: DNA transposons for modification of human primary T lymphocytes," Methods Mol Biol, 2009, 506: 115-126.
Jia et al., "Structure of Dnmt3a bound to Dnmt3L suggests a model for de novo DNA methylation," Nature, 2007, 449(7159): 248-251.
Johnston, "Biolistic transformation: microbes to mice," Nature, 1990, 346: 776-777.
Kao et al., "Ectopic DNMT3L triggers assembly of a repressive complex for retroviral silencing in somatic cells," J Virol., 2014, 88(18): 10680-95.
Kim et al., "Zinc-fingers and homeoboxes 1 (ZHX1) binds DNA methyltransferase (DNMT) 3B to enhance DNMT3B-mediated trascriptional repression," Biochemical and Biophysical Research Communications, 2007, 355(2): 318-323.
Koste et al., "T-cell receptor transfer into human T cells with ecotropic retroviral vectors," Gene Ther, 2014, 21(5): 533-538.
Lagace, "PCSK9 and LDLR degradation: regulatory mechanisms in circulation and in cells," Curr. Opin. Lipidol., 2014, 25(5): 387-393.
Lei et al., "Targeted DNA methylation in vivo using an engineered dCas9-MQ1 fusion protein," Nat. Commun, 2017, 8: 16026, 10 pages.
Li et al., "Development of fluorescent methods for DNA methyltransferase assay," Methods Appl. Fluoresc., 2017, 5: 012002, 8 pages.
Li et al., "The histone methyltransferase SETDB1 and the DNA methyltransferase DNMT3A interact directly and localize to promoters silenced in cancer cells," J. Biol. Chem., 2006, 281(28): 19489-19500.
Liu et al., "Design of polydactly zinc-finger proteins for unique addressing within complex genomes," PNAS, 1997, 94(11): 5525-5530.
Ma et al., "Pol III Promoters to Express Small RNAs: Delineation of Transciption Initiation," Molecular Therapy—Nucleic Acids, 2014, 3: e161, 11 pages.
Makarova et al., "Annotation and Classification of CRISPR-Cas Systems," Methods Mol. Biol, 2015, 1311: 47-75.
Manuri et al., "piggyBac transposon/transposase system to generate CD19-specific T cells for the treatment of B-lineage malignancies," Hum Gene Ther, 2010, 21(4): 427-437.
Mavrothalassitis et al., "Proteins of the ETS family with trascriptional repressor activity," Oncogene, 2000, 19: 6524-6532.

(56) References Cited

OTHER PUBLICATIONS

Miller et al., "Improved retroviral vectors for gene transfer and expression," BioTechniques, 1989, 7(9): 980-990.
Miller, "Retrovirus packaging cells," Human Gene Therapy, 1990, 1: 5-14.
Millone et al., "Clinical use of lentiviral vectors," Leukemia, 2018, 32(7): 1529-1541.
Mok et al., "Stabilized plasmid-lipid particles: factors influencing plasmid entrapment and transfection properties," Biochimica et Biophysica Acta, 1999, 1419(2): 137-150.
Moon et al., "Recent advances in the CRISPR genome editing tool set," Exp. Mol. Med., 2019, 51(11): 130, 11 pages.
Moussa et al., "Here to stay: Writing lasting epigenetic memories," Cell, 2021, 184(9): 2281-2283.
Murphy et al., "The Transcriptional Repressive Activity of KRAB Zinc Finger Proteins Does Not Correlate with Their Ability to Recruit TRIM28," PLoS ONE, 2016, 11(9): e0163555, 19 pages.
O'Geen et al., "Determinants of heritable gene silencing for KRAB-dCas9 + DMNT3 and Ezh2-dCas9 + DNMT3 hit-and-run epigenome editing," Nucleic Acids Res, 2022, 50(6): 3239-3253.
Orth et al., "Structural basis of gene regulation by the tetracycline inducible Tet repressor-operator system," natural structural biology, 2000, 7(3): 215-219.
Park et al., "Treating cancer with genetically engineered T cells," Trends Biotechnol, 2011, 29(11): 550-557.
Peterson et al., "PCSK9 function and physiology," J. Lipid Res., 2008, 49(6): 1152-1156.
Pickar-Oliver et al., "The next generation of CRISPR-Cas technologies and applications," Nature Reviews Molecular Cell Biology, 2019, 20(8): 490-507.
Poh et al., "DNA Methyltransferase Activity Assays: Advances and Challenges," Theranostics, 2016, 6(3): 369-391.
Poirier et al., "The proprotein convertase PCSK9 induces the degradation of low density lipoprotein receptor (LDLR) and its closest family members VLDLR and ApoER2"J. Biol. Chem., 2008, 283: 2363-2372.
Policarpi et al., "Epigenetic editing: Dissecting chromatin function in context," Bioessays, 2021, 43(5): e2000316, 16 pages.
Saha et al., "The NIH Somatic Cell Genome Editing program," Nature, 2021, 592: 195-204.
Scarpa et al., "Characterization of recombinant helper retroviruses from moloney-based vectors in ecotropic and amphotropic packaging cell lines," Virology, 1991, 180: 849-852.
Schellenberger et al., "A recombinant polypeptide extends the in vivo half-life of peptides and proteins in a tunable manner," Nature Biotechnology, 2009, 27(12): 1186-1190.
Sharma et al., "Efficient Sleeping Beauty DNA Transposition From DNA Minicircles," Molec Ther Nucl Acids, 2013, 2(2): e74, 10 pages.
Stepper, "Dissertation: CRISPR-Cas9 fusions for synthetic epigenetics," Von der Fakultat 4: Energie-, Verfahrens-und Biotechnik, Institut für Biochemie und Technische Biochemie der Universität Stuttgart, 2020, 148 pages.
Thakore et al., "385. Inhibiting the Myostatin Singaling Pathway using CRISPR/Cas9-Based Repressors." Molecular Therapy 2016, 24: S153.
Tycko et al., "High-Throughput Discovery and Characterization of Human Transcriptional Effectors," Cell, 2020, 183(7): 2020-2035.
Van Tedeloo et al., "High-level transgene expression in primary human T lymphocytes and adult bone marroe CD34+ cells via electroporation-mediated gene delivery," Gene Therapy, 2000, 7(16): 1431-1437.
Verhoeyen et al., "Ch 8: Lentiviral vector gene transfer into human T cells," Methods Mol Biol, 2009, 506: 97-114.
Wang et al., "Phenotypic and functional attributes of lentivirus modified CD19-specific human CD8+ central memory T cells manufactured at clinical scale," J. Immunother, 2012, 35(9): 689-701.
Wright et al., "Rational design of a split-Cas9 enzyme complex," PNAS, 2015, 112(10): 2984-2989.

Wright et al., "Standardized reagents and protocols for engineering zinc finger nucleases by modular assembly," Nat. Protoc., 2006, 1(3): 1637-1652.
Zetsche et al., "A split-Cas9 architecture for inducible genome editing and transcription modulation," Nat. Biotechnol, 2015, 33(2): 139-142.
Chao et al., "Several log increase in therapeutic transgene delivery by distinct adeno-associated viral serotype vectors," (2000) Molecular Therapy 2:619.
Chen et al., "In vivo CD8+ T cell CRISPR screening reveals control by Fli1 in infection and cancer," Cell, 2021, 184(5): 1262-1280.
Corces et al., "An improved ATAC-seq protocol reduces background and enables interrogation of frozen tissues," Nature Methods, 2017, 14: 959-962.
Galletti et al., "Two subsets of stem-like CD8+ memory T cell progenitors with distinct fate commitments in humans," Nature Immunology, 2020, 21: 1552-1562.
Gao et al., "Clades of Adeno-Associated Viruses Viruses Are Widely Disseminated in Human Tissues," (2004) J. Virology 78:6381-6388.
GenBank Accession No. AF028704.1, (1998).
GenBank Accession No. AF028705.1, (1998).
GenBank Accession No. AF043303.1, (2010).
GenBank Accession No. AF063497.1, (1999).
GenBank Accession No. AF288061.1, (2001).
GenBank Accession No. AF513851.1, (2002).
GenBank Accession No. AFS13852.1, (2015).
GenBank Accession No. AH009962.2, (2016).
GenBank Accession No. AY028223.1, (2001).
GenBank Accession No. AY028226.1, (2001).
GenBank Accession No. AY530579.1, (2004).
GenBank Accession No. J01901.1, (1993).
GenBank Accession No. J02275.1, (1995).
GenBank Accession No. NC_000883.2, (2018).
GenBank Accession No. NC_001358.1, (2015).
GenBank Accession No. NC_001401, (2018).
GenBank Accession No. NC_001510.1, (2018).
GenBank Accession No. NC_001540.1, (2018).
GenBank Accession No. NC_001701.1, (2018).
GenBank Accession No. NC_001729, (2018).
GenBank Accession No. NC_001829.1, (2018).
GenBank Accession No. NC_001862.1, (2004).
GenBank Accession No. NC_001863.1, (2004).
GenBank Accession No. NC_002077, (2018).
GenBank Accession No. NC_006152.1, (2018).
GenBank Accession No. NC_006261.1, (2018).
GenBank Accession No. U89790.1, (1997).
GenBank Accession No. X01457.1, (2005).
Hao et al., "Integrated analysis of multimedia single-cell data," Cell, 2021, 184: 3573-3587. e29.
Hart et al., "Kruppel-like factors in lymphocyte biology," J Immunol, 2012, 188(2): 521-526.
Joung et al., "Transcription Factor Atlas of Directed Diffrentiation," Cell, 2023, 186(1): 209-229.e26.
Jung et al. "BLIMP1 and NR4A3 transcription factors reciprocally regulate antitumor CAR T cell stemness and exhaustion," Cancer Immunotherapy, 2022, 14: eabn7336.
Kaminskiy et al., "Neglected, yet significant role of FOXP1 in T-cell quiescence, differentiation and exhaustion," Front. Immunol, 2022, 13: 971045.
Krishna et al., "Stem-like CD8 T cells mediate response of adoptive cell immunotherapy against human cancer," Science, 2020, 370: 1328-1334.
Kuleshov et al., "Enrichr: a comprehensive gene set enrichment analysis web server 2016 update," Nucleic Acids Research, 2016, 44: 90-97.
Liao et al., "featureCounts: an efficient general purpose program for assigning sequence reads to genomic features," Bioinformatics, 2013, 30(7): 923-30.
Martin et al., "CCR7 Deficiency in NOD Mice Leads to Thyroiditis and Primary Hyperthyroidism," The Journal of Immunology, 2009, 183(5): 3073-3080.

(56) References Cited

OTHER PUBLICATIONS

Mimitou et al., "Expanding the CITE-seq tool kit: Detection of proteins, transcriptomes, clonotypes and CRISPR perturbations with multiplexing, in a single assay," Nat. Methods, 2019, 16: 409-412.
Mori et al., "Two-novel adeno-associated viruses from cynomolgus monkey: pseudotyping characterization of capsid protein," (2004) Virology 330: 375-383.
Muzyczka, "Use of adeno-associated virus as a general transduction vector for mammalian cells," (1992) Curr. Topics Microbial. Immunol. 158: 97-129.
Philip et al., "Chromatin states define tumour-specific T cell dysfunction and reprogramming," Nature, 2017, 545: 452-456.
Pritykin et al., "A unified atlas of CD8 T cell dysfunctional states in cancer and infection," Mol. Cell 2021, 81: 2477-2493.
Ramirez et al., "deepTools: a flexible platform for exploring deep-sequencing data," Nucleic Acids Research, 2014, 42:W187-91.
Schubert et al., "Autosomal dominant immune dysregulation syndrome in humans with CTLA4 mutations," Nature Medicine, 2014, 20(2): 1410-1416.
Sen et al., "The epigenetic landscape of T cell exhaustion," Science, 2016, 354(6316): 1165-1169.
Vojta et al., "Repurposing the CRISPR-Cas9 system for targeted DNA methylation," Nucleic Acids Research, 2016, 44(12): 5615-5628.
Wherry et al., "Molecular Signature of CD8+ T Cell Exhaustion during Chronic Viral Infection," Immunity, 2007, 27(4): 670-684.
Woolf et al., "Runx3 and Runx1 are required for CD8 T cell development during thymopoiesis," PNAS, 2003, 100(13): 7731-7736.
Yang et al., "The transcriptional regulators Id2 and Id3 control the formation of distinct memory CD8+ T cell subsets," Nat Immunol, 2011, 12: 1221-1229.
Yu et al., "ChIPseeker: an R/Bioconductor package for CHIP peak annotation, comparison and visualization," Bioinformatics, 2015, 31(14): 2382-2383.
Yuan et al., "Genetic Modulation of RNA Splicing with a CRISPR-Guided Cytidine Deaminase," Molecular Cell, 2018, 72(2): 380-394.
Zhang et al., "Model-based analysis of ChIP-Seq (MACS)," Genome Biology, 2008, 9(9): R137.
Zheng et al., "Landscape of Infiltrating T Cells in Liver Cancer Revealed by Single-Cell Sequencing," Cell, 2017, 169: 1342-1356.
Canadian Patent Office Action for Application No. 3,001,623 dated Apr. 17, 2024 (5 pages).
Korean Patent Office Action for Application No. 10-2018-7018218 dated Mar. 15, 2024 (8 pages, English translation included).
Mexican Patent Office Action for Application No. MX/a/2018/005377 dated Apr. 24, 2024 (3 pages, English language summary included).
Saudi Arabia Patent Office Examination Report for Application No. 521431236 dated Jun. 18, 2023 (11 pages, English translation).
Bulcha et al., "Viral vector platforms within the gene therapy landscape," Signal Transduction and Targeted Therapy, 2021, 6: 53.
Duchêne et al., "CRISPR-Induced Deletion with SaCas Restores Dystrophin Expression in Dystrophic Models in Vitro and In Vivo." Molecular Therapy: The Journal of the American Society of Gene Therapy, 2018, 26(11):2604-2616.
Hideki et al., Geneseq Accession No. BFK30060, 2018. Reference cited by examiner in U.S. Appl. No. 16/963,034, U.S. Patent Office Action dated Jun. 27, 2024.
Kotterman et al., "Engineering adeno-associated viruses for clinical gene therapy," Nature Reviews, 2014, 15(7): 445-451.
Lenzi et al., "Oversight and Review of Clinical Gene Transfer Protocols: Assessing the Role of the Recombinant DNA Advisory Committee," NCBI Bookshelf, A Service of the National Library of Medicine, National Institute of Health, Washington, DC, National Academies Press, US, 2014, pp. 1-16.
Liao, "Targeted disruption of DNMT1, DNMT3A, and DMNT3B in human embryonic stem cells," Nature Genetics, 2015, 47(5): 469-478.
Long et al., "Correction of Diverse Muscular Dystrophy Mutations in Human Engineered Heart Muscle by Single-Site Genome Editing," Sci Adv, 2018, 4(1): eaap9004.
Maggio et al., "Adenoviral vectors encoding CRISPR/Cas9 multiplexes rescue dystrophin synthesis in unselected populations of DMD muscle cells," Scientifc Reports, 2016, 6: 37051.
Shim et al., "Nonviral Delivery Systems for Cancer Gene Therapy: Strategies and Challenges," Current Gene Therapy, 2017, 17(5): 1-18.
Swiech et al., "In vivo interrogation of gene function in the mammalian brain using CRISPR-Cas9," Nature Biotechnology, 2014, 33(1): 102-106 (Supplementary information included).
Thule et al., "Engineered Insulin Secretion in Human Primary Thyroid Cells," Molecular Therapy, 2012, 20(Supplement 1): S164, Article 421.
Mexican Patent Office Action for Application No. MX/a/2018/005377 dated Aug. 20, 2024 (9 pages, English language summary included).
New Zealand Patent Office Examination Report 1 for Application No. 741354 dated Jul. 16, 2024 (5 pages).
United States Patent Office Notice of Allowance for U.S. Appl. No. 16/318,745 dated Aug. 22, 2024 (8 pages).
Liu et al., "A CRISPR-Cas9 Strategy for Activating the Saccharopolyspora erythraea Erythromycin Biosynthetic Gene Cluster with Knock-in Bidirectional Promotes," ACS Synth. Biol. 2019, 8(5): 1134-1143.
Miyazaki et al., "Characterization of deletion breakpoints in patients with dystrophinopathy carrying a deletion of exons 45-55 of the Duchenne muscular dystrophy (DMD) gene," Journal of Human Genetics, 2009, 54: 127-130.
Razzouk, "CRISPR-Cas9: A cornerstone for the evolution of precision medicine," Annal of Human Genetics, 2018, 82(6): 331-357.
Simeonov et al., "Discovery of stimulation-responsive immune enhancers with CRISPR activation," Nature, 2017, 549 (7670): 111-115.

\* cited by examiner

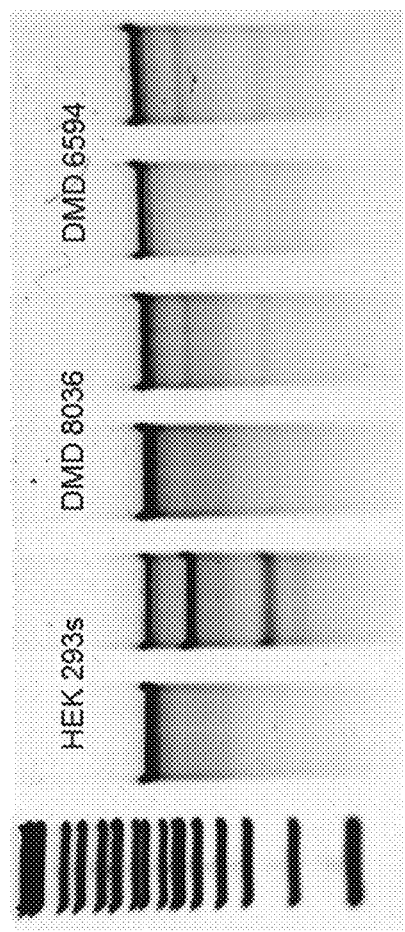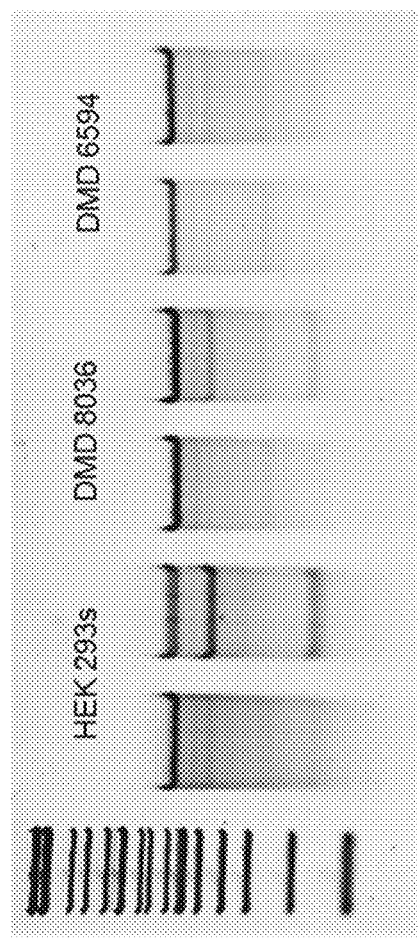
FIG. 1

| gRNA | Where | # of reads (n1) | % indel SEM | Human off-target (matches his in genome) | Results off target |
|---|---|---|---|---|---|
| JCR156 | upstream | 1300 | 7.28% ± 0.66 | 4 mismatch: 23<br>3 mismatch: 6<br>2,1 mismatch: 0 | 4 mismatch: 19<br>3 mismatch: 7<br>2 mismatch: 1<br><2: 0 |
| JCR157 | upstream | 1284 | 9.45% ± 1.48 | *did not find protospacer in human genome*<br>4 mismatch: 6<br><4 mismatch: 0 | 4 mismatch: 5<br><4 mismatch: 0 |
| JCR159 | upstream | 101 | 7.88% ± 1.07 | 4 mismatch: 16<br><4 mismatch: 0 | 4 mismatch: 15<br>3 mismatch: 1<br><3 mismatch: 0 |
| JCR168 | upstream | 1824 | 9.17% ± 0.35 | 4 mismatch: 21<br>3 mismatch: 1<br><3 mismatch: 0 | 4 mismatch: 13<br><4 mismatch: 0 |
| JCR170 | upstream | 2851 | 6.66% ± 0.74 | 4 mismatch: 1<br>3 mismatch: 1<br><3 mismatch: 0 | 4 mismatch: 3<br><4 mismatch: 0 |
| JCR171 | upstream | 2947 | 5.82% ± 0.59 | 4 mismatch: 5<br>3 mismatch: 1<br><3 mismatch: 0 | 4 mismatch: 2<br>3 mismatch: 1<br>2 mismatch: 1<br><2 mismatch: 0 |
| JCR160 | downstream | 78 | 5.25% ± 0.50 | 4 mismatch: 2<br><4 mismatch: 0 | 4 mismatch: 4<br><4 mismatch: 0 |
| JCR166 | downstream | 1266 | 5.09% ± 1.21 | 4 mismatch: 25<br>3 mismatch: 5<br><3: 0 | 4 mismatch: 17<br>3 mismatch: 5<br><3 mismatch: 0 |
| JCR167 | downstream | 1534 | 6.59% ± 0.44 | 4 mismatch: 4<br>3 mismatch: 2<br><3 mismatch: 0 | 4 mismatch: 10<br><4 mismatch: 0 |

FIG. 8

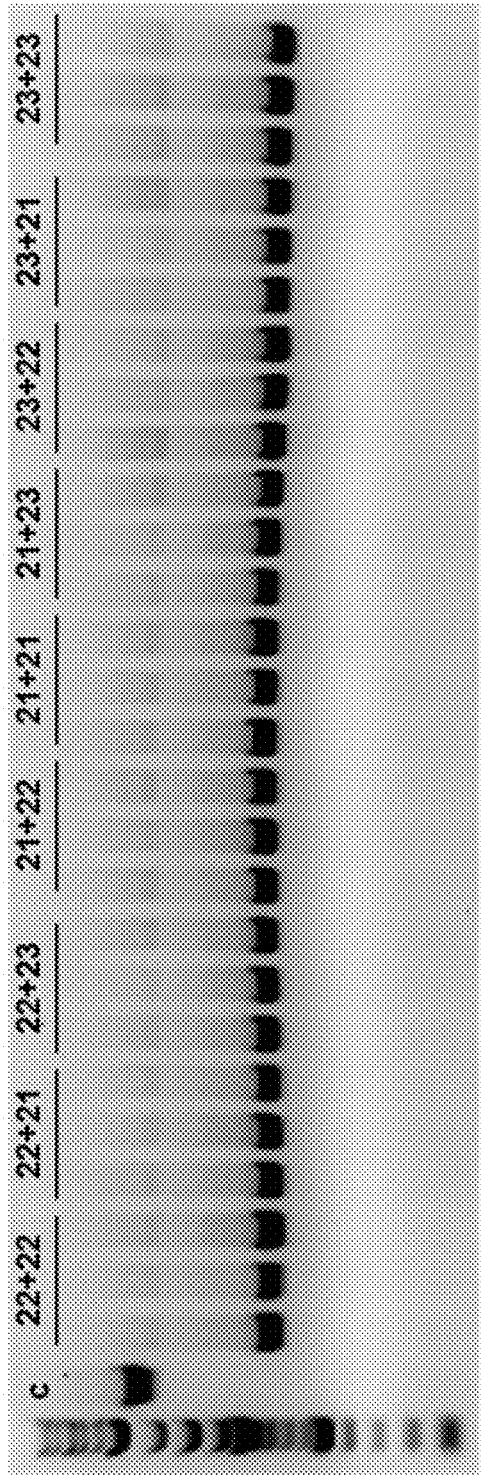
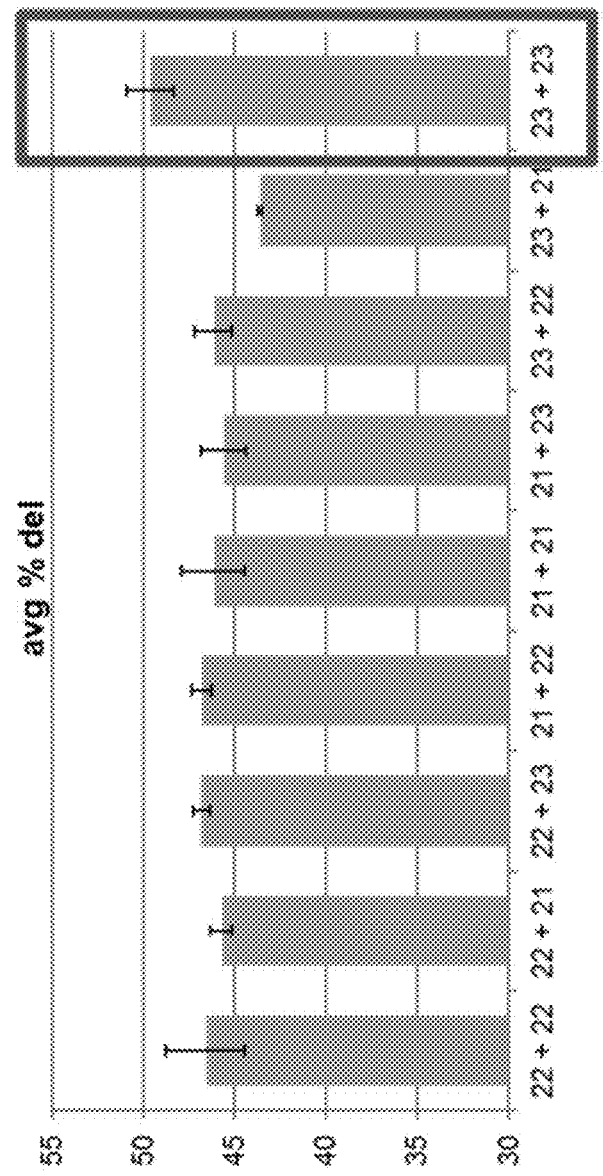
FIG. 12

Purple Bold: JCR94; <u>Green Underlined</u>: JCR99; *Grey Italicized: Insertions/deletions*

Delta 52: AACGCTGAAGAACCCTGAT<u>AATAGAAGAAATACAT</u>*TT*<u>TAAATCAATTCAGG</u> (SEQ ID NO: 46)

Founder 76: AAGAACCCTGAT<u>A</u> --- *TTATCTTAGTAGATTA* --- <u>ATAGAAGAAATACAT</u>*TTTT*<u>ATCAATTCAG</u>*T*<u>TAAA</u> (SEQ ID NO: 47)

Founder 63: GCTGAAGAACCCTGA --- *AAAATACATTTTT*<u>ATCAATTCAGG</u> (SEQ ID NO: 48)

Founder 7: GAAT --- *(19x)* --- GAT - *TTTCTTGTAG*<u>AAGAAATAACAATT</u> --- AAATC (SEQ ID NO: 49)

FIG. 23

Purple Bold: JCR94; <u>Green Underlined</u>: JCR99; *Grey Italicized*: Insertions/deletions Delta 52: AACGCTGAAGAACCCTGAT<u>AATAGAAGAAATACAT</u>TTTAAATCAATTCAGG (SEQ ID NO: 50)

54497: AACGCTGAAGAACCCTGAT*A*<u>TTATCTTAGTAGATTAATAGAAGAAATACAT</u>TTTAAAT (SEQ ID NO: 51)

54498: AACGCTGAAGAACCCTGAT*A*<u>TTATCTTAGTAGATTAATAGAAGAAATACAT</u>TTTAAAT (SEQ ID NO: 52)

FIG. 27

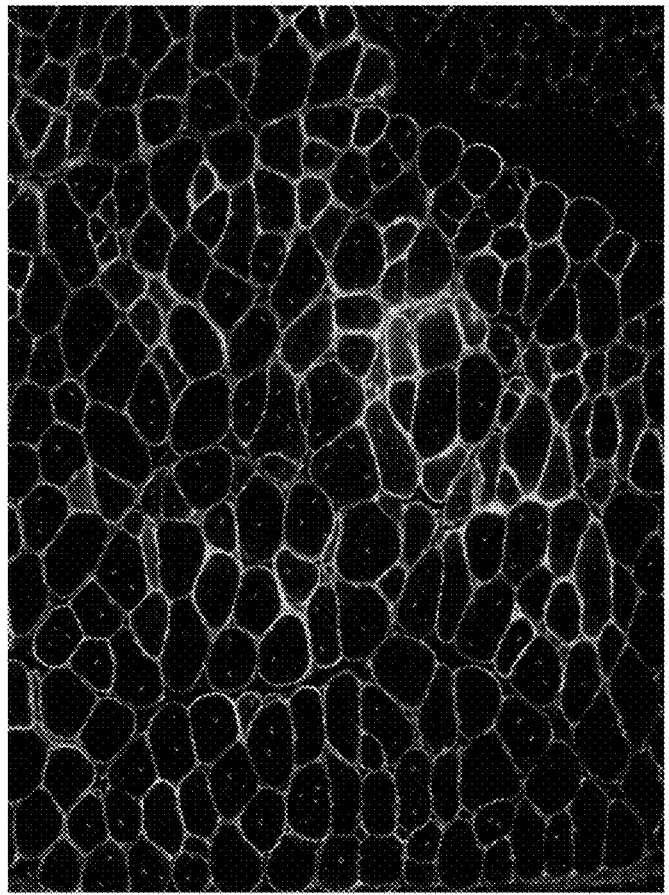
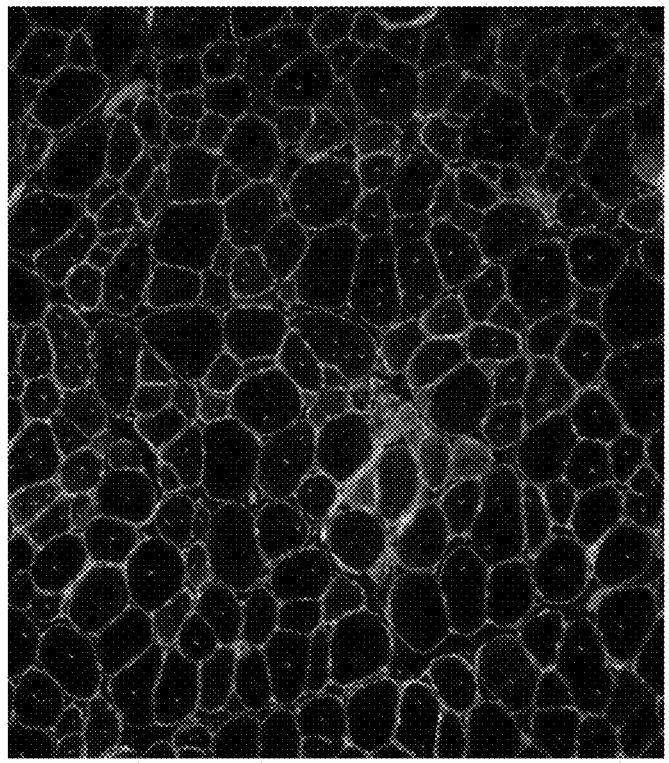
Dystrophin (green) Laminin (red) DAPI (blue)
FIG. 37

THERAPEUTIC TARGETS FOR THE CORRECTION OF THE HUMAN DYSTROPHIN GENE BY GENE EDITING AND METHODS OF USE

CROSS-REFERENCE TO RELATED APPLICATIONS

This application is a national stage filing under 35 U.S.C. § 371 of International Patent Application No. PCT/US2016/064285, which claims priority to U.S. Provisional Application No. 62/260,712, filed Nov. 30, 2015, and U.S. Provisional Application No. 62/330,336, filed May 2, 2016, all of which are incorporated herein by reference in their entirety.

The instant application includes a Sequence Listing which has been submitted electronically in ASCII format and is hereby incorporated by reference in its entirety. Said ASCII copy, created on Sep. 1, 2020, is named 028193-9251-US02Asjiled_Sequence_Listing.txt and is 143,854 bytes in size.

STATEMENT OF GOVERNMENT INTEREST

This invention was made with government support under DGE-1644868 awarded by the National Science Foundation. The government has certain rights in the invention.

TECHNICAL FIELD

The present disclosure relates to the field of gene expression alteration, genome engineering and genomic alteration of genes using Clustered Regularly Interspaced Short Palindromic Repeats (CRISPR)/CRISPR-associated (Cas) 9-based systems and viral delivery systems. The present disclosure also relates to the field of genome engineering and genomic alteration of genes in muscle, such as skeletal muscle and cardiac muscle.

BACKGROUND

Synthetic transcription factors have been engineered to control gene expression for many different medical and scientific applications in mammalian systems, including stimulating tissue regeneration, drug screening, compensating for genetic defects, activating silenced tumor suppressors, controlling stem cell differentiation, performing genetic screens, and creating synthetic gene circuits. These transcription factors can target promoters or enhancers of endogenous genes, or be purposefully designed to recognize sequences orthogonal to mammalian genomes for transgene regulation. The most common strategies for engineering novel transcription factors targeted to user-defined sequences have been based on the programmable DNA-binding domains of zinc finger proteins and transcription-activator like effectors (TALEs). Both of these approaches involve applying the principles of protein-DNA interactions of these domains to engineer new proteins with unique DNA-binding specificity. Although these methods have been widely successful for many applications, the protein engineering necessary for manipulating protein-DNA interactions can be laborious and require specialized expertise.

Additionally, these new proteins are not always effective. The reasons for this are not yet known but may be related to the effects of epigenetic modifications and chromatin state on protein binding to the genomic target site. In addition, there are challenges in ensuring that these new proteins, as well as other components, are delivered to each cell. Existing methods for delivering these new proteins and their multiple components include delivery to cells on separate plasmids or vectors which leads to highly variable expression levels in each cell due to differences in copy number. Additionally, gene activation following transfection is transient due to dilution of plasmid DNA, and temporary gene expression may not be sufficient for inducing therapeutic effects. Furthermore, this approach is not amenable to cell types that are not easily transfected. Thus another limitation of these new proteins is the potency of transcriptional activation.

CRISPR/Cas9-based gene editing systems can be used to introduce site-specific double strand breaks at targeted genomic loci. This DNA cleavage stimulates the natural DNA-repair machinery, leading to one of two possible repair pathways. In the absence of a donor template, the break will be repaired by non-homologous end joining (NHEJ), an error-prone repair pathway that leads to small insertions or deletions of DNA. This method can be used to intentionally disrupt, delete, or alter the reading frame of targeted gene sequences. However, if a donor template is provided along with the nucleases, then the cellular machinery will repair the break by homologous recombination, which is enhanced several orders of magnitude in the presence of DNA cleavage. This method can be used to introduce specific changes in the DNA sequence at target sites. Engineered nucleases have been used for gene editing in a variety of human stem cells and cell lines, and for gene editing in the mouse liver. However, the major hurdle for implementation of these technologies is delivery to particular tissues in vivo in a way that is effective, efficient, and facilitates successful genome modification.

Hereditary genetic diseases have devastating effects on children in the United States. These diseases currently have no cure and can only be managed by attempts to alleviate the symptoms. For decades, the field of gene therapy has promised a cure to these diseases. However technical hurdles regarding the safe and efficient delivery of therapeutic genes to cells and patients have limited this approach. Duchenne muscular dystrophy (DMD) is a fatal genetic disease, clinically characterized by muscle wasting, loss of ambulation, and death typically in the third decade of life due to the loss of functional dystrophin. DMD is the result of inherited or spontaneous mutations in the dystrophin gene. Most mutations causing DMD are a result of deletions of exon(s), pushing the translational reading frame out of frame.

Dystrophin is a key component of a protein complex that is responsible for regulating muscle cell integrity and function. DMD patients typically lose the ability to physically support themselves during childhood, become progressively weaker during the teenage years, and die in their twenties. Current experimental gene therapy strategies for DMD require repeated administration of transient gene delivery vehicles or rely on permanent integration of foreign genetic material into the genomic DNA. Both of these methods have serious safety concerns. Furthermore, these strategies have been limited by an inability to deliver the large and complex dystrophin gene sequence. There remains a need for more precise and efficient gene editing tools for correcting and treating patients with mutations in the dystrophin gene.

SUMMARY

The present invention is directed to a guide RNA (gRNA) comprising a targeting domain that comprises a nucleotide sequence set forth in SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 41, SEQ ID NO: 42 or a complement thereof.

The present invention is also directed to a DNA targeting composition comprising a first gRNA and a second gRNA. The first gRNA molecule and the second gRNA molecule comprise a targeting domain that comprises a nucleotide sequence set forth in SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 41, SEQ ID NO: 42, or a complement thereof. The first gRNA molecule and the second gRNA molecule comprise different targeting domains.

The present invention is also directed to an isolated polynucleotide comprising the gRNA molecule described above or the DNA targeting composition described above.

The present invention is directed to a vector comprising the gRNA described above, the DNA targeting composition described above, or the isolated polynucleotide described above.

The present invention is also directed to a vector comprising the DNA targeting composition described above.

The present invention is also directed to a vector encoding: (a) a first guide RNA (gRNA) molecule, (b) a second gRNA molecule, and (c) at least one Cas9 molecule that recognizes a Protospacer Adjacent Motif (PAM) of either NNGRRT (SEQ ID NO: 24) or NNGRRV (SEQ ID NO: 25). The first gRNA molecule and the second gRNA molecule comprise a targeting domain that comprises a nucleotide sequence set forth in SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 41, SEQ ID NO: 42, or a complement thereof. The first gRNA molecule and the second gRNA molecule comprise different targeting domains.

The present invention is also directed to a cell comprising the gRNA described above, the DNA targeting composition described above, the isolated polynucleotide described above, or the vector of described above.

The present invention is also directed to a kit comprising the gRNA described above, the DNA targeting system described above, the isolated polynucleotide described above, the vector described above, or the cell described above and optionally instructions for use.

The present invention is also directed to a method of correcting a mutant dystrophin gene in a cell. The method comprises administering to a cell the gRNA described above, the DNA targeting system described above, the isolated polynucleotide described above, or the vector described above.

The present invention is also directed to a method of genome editing a mutant dystrophin gene in a subject. The method comprises administering to the subject a genome editing composition comprising the gRNA described above, the DNA targeting system described above, the isolated polynucleotide described above, the vector described above, or the cell described above.

The present invention is also directed to a method of treating a subject in need thereof having a mutant dystrophin gene. The method comprises administering to the subject the gRNA described above, the DNA targeting system described above, the isolated polynucleotide described above, the vector described above, or the cell described above.

The present invention is also directed to a modified adeno-associated viral vector for genome editing a mutant dystrophin gene in a subject comprising a first polynucleotide sequence encoding the gRNA described above, and a second polynucleotide sequence encoding a Cas9 molecule that recognizes a Protospacer Adjacent Motif (PAM) of either NNGRRT (SEQ ID NO: 24) or NNGRRV (SEQ ID NO: 25).

The present invention is also directed to a composition for deleting a segment of a dystrophin gene comprising exon 51, the composition comprising: (a) a first vector comprising a polynucleotide sequence encoding a first guide RNA (gRNA) molecule and a polynucleotide sequence encoding a first Cas9 molecule that recognizes a Protospacer Adjacent Motif (PAM) of either NNGRRT (SEQ ID NO: 24) or NNGRRV (SEQ ID NO: 25), and (b) a second vector comprising a polynucleotide sequence encoding a second gRNA molecule and a polynucleotide sequence encoding a second Cas9 molecule that recognizes a Protospacer Adjacent Motif (PAM) of either NNGRRT (SEQ ID NO: 24) or NNGRRV (SEQ ID NO: 25). Each of the first and second gRNA molecules have a targeting domain of 19 to 24 nucleotides in length, and wherein the first vector and second vector are configured to form a first and a second double strand break in a first intron and a second intron flanking exon 51 of the human DMD gene, respectively, thereby deleting a segment of the dystrophin gene comprising exon 51.

The present invention is also directed to a cell comprising the composition described above.

The present invention is also directed to a method of correcting a mutant dystrophin gene in a cell, comprising administering to the cell: (a) a first vector comprising a polynucleotide sequence encoding a first guide RNA (gRNA) molecule and a polynucleotide sequence encoding a first Cas9 molecule that recognizes a Protospacer Adjacent Motif (PAM) of either NNGRRT (SEQ ID NO: 24) or NNGRRV (SEQ ID NO: 25), and (b) a second vector comprising a polynucleotide sequence encoding a second gRNA molecule and a polynucleotide sequence encoding a second Cas9 molecule that recognizes a Protospacer Adjacent Motif (PAM) of either NNGRRT (SEQ ID NO: 24) or NNGRRV (SEQ ID NO: 25). Each of the first gRNA and second gRNA molecules have a targeting domain of 19 to 24 nucleotides in length, and wherein the vector is configured to form a first and a second double strand break in a first and a second intron flanking exon 51 of the human dystrophin gene, respectively, thereby deleting a segment of the dystrophin gene comprising exon 51.

The present invention is also directed to a method of treating a subject in need thereof having a mutant dystrophin gene. The method comprises administering to the subject: (a) a first vector comprising a polynucleotide sequence encoding a first guide RNA (gRNA) molecule and a polynucleotide sequence encoding a first Cas9 molecule that recognizes a Protospacer Adjacent Motif (PAM) of either NNGRRT (SEQ ID NO: 24) or NNGRRV (SEQ ID NO: 25), and (b) a second vector comprising a polynucleotide sequence encoding a second gRNA molecule and a polynucleotide sequence encoding a second Cas9 molecule that recognizes a Protospacer Adjacent Motif (PAM) of either NNGRRT (SEQ ID NO: 24) or NNGRRV (SEQ ID NO: 25). Each of the first gRNA and second gRNA molecules have a targeting domain of 19 to 24 nucleotides in length, and wherein the vector is configured to form a first and a second double strand break in a first and a second intron flanking exon 51 of the human dystrophin gene, respectively, thereby deleting a segment of the dystrophin gene comprising exon 51.

The present invention is also directed to a method of generating a transgenic rodent embryo having a human dystrophin gene (hDMD) with an exon 52 deletion (Δ52). The method comprises administering to a rodent embryo the gRNA described above, the DNA targeting system described above, the isolated polynucleotide described above, the vector described above, the modified adeno-associated viral vector described above, or the composition described above, thereby deleting exon 52 of the human dystrophin gene, and selecting for a transgenic rodent embryo having a deletion of exon 52 of the human dystrophin gene, wherein the rodent embryo comprises a normal human dystrophin gene.

The present invention is also directed to a transgenic rodent embryo produced by the method described above.

The present invention is also directed to a transgenic rodent produced from the transgenic rodent embryo described above.

BRIEF DESCRIPTION OF THE DRAWINGS

FIG. 1 shows the activity of individual gRNAs JCR89 and JCR91 that target the human dystrophin gene in HEK293T cells (wild-type dystrophin gene) and DMD patient myoblast lines (DMD 8036 and DMD 6594, each of which has a mutant form of the dystrophin gene), as determined by the Surveyor Assay.

FIG. 8 shows the specificity of the candidate gRNAs as predicted using CasOFFinder program (Bae et al. (2014) *Bioinformatics* 30: 1473-1475).

FIG. 12 shows the deletions generated by combining JCR157 and JCR160 of various lengths (21, 22, or 23 nucleotides) as determined by PCR of genomic DNA.

FIG. 23 shows a portion of sequencing results from founder mice 7, 63, and 76.

FIG. 27 shows a portion of a 392 bp sequencing read of pups 54497 and 54498.

FIG. 37 shows in vivo dystrophin protein restoration in treated TA muscle.

DETAILED DESCRIPTION

Figure 2:
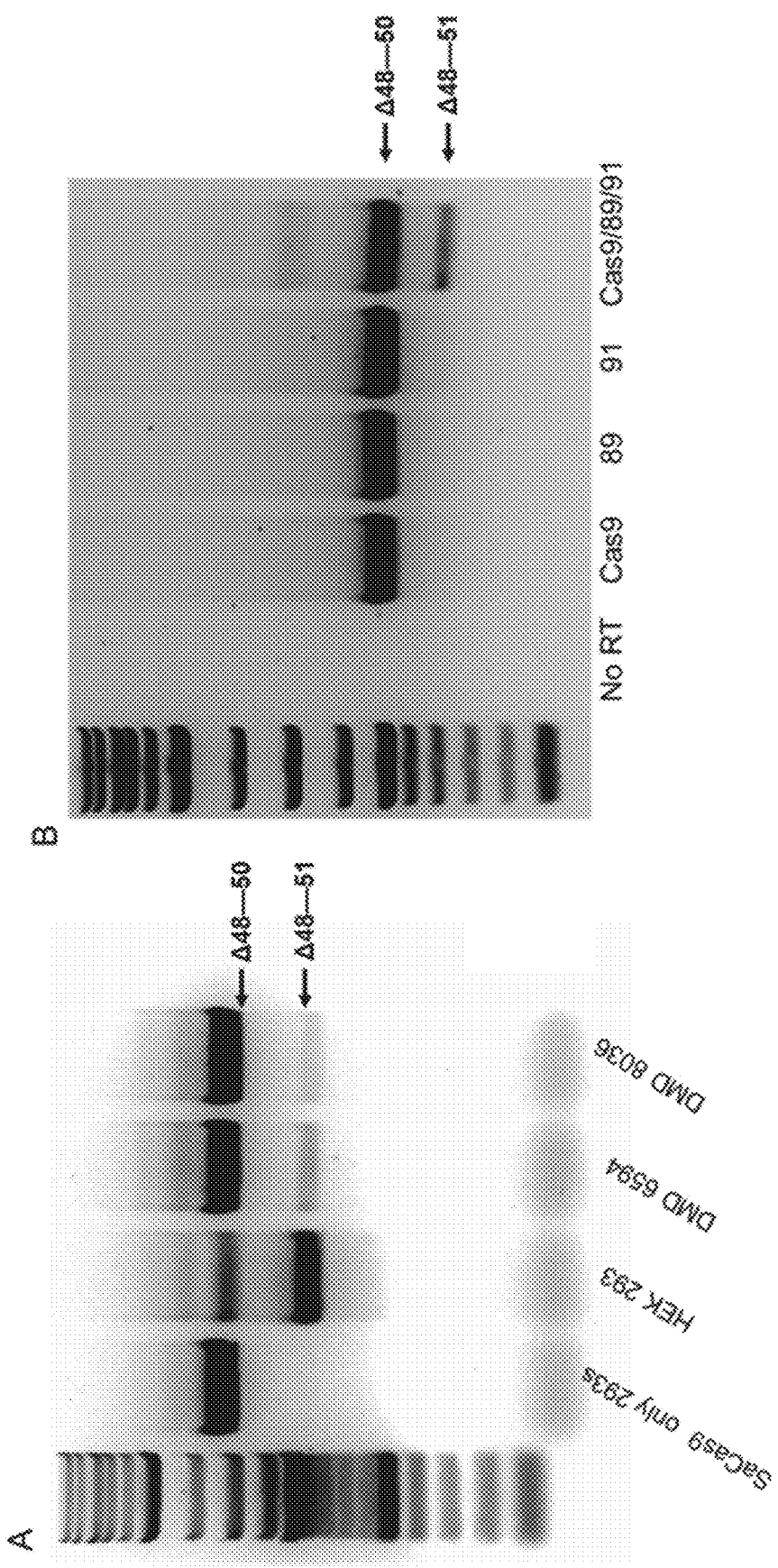
FIGS. 2A and 2B show the deletion of exon 51 in genomic DNA of HEK293T cells and DMD myoblasts (DMD 8036 and DMD 6594) (FIG. 2A) and cDNA from DMD myoblasts myoblasts (FIG. 2B) by co-treatment with SaCas9 and gRNAs JCR89 and JCR91.

As described herein, certain methods and engineered gRNAs have been discovered to be useful with CRISPR/CRISPR-associated (Cas) 9-based gene editing systems for altering the expression, genome engineering, and correcting or reducing the effects of mutations in the dystrophin gene involved in genetic diseases, e.g., DMD. The disclosed gRNAs were generated to target sites that are more amenable to clinical translation. For example, the gene encoding S. pyogenes Cas9 (SpCas9) is too large to be delivered by adeno-associated virus (AAV), a vector used for the systemic gene delivery to muscle when all other necessary regulatory sequences are included. Instead, the disclosed gRNAs were selected and screened for use with S. aureus Cas9 (SaCas9), which is about 1 kb smaller than SpCas9. The target selections were screened for being SaCas9-compatible targets on sequences that were conserved between the human and rhesus macaque genomes, which greatly limits the number of possible gene targets. This selection criterion was chosen to allow for gRNA candidates that could be active in both humans and rhesus monkeys so as to facilitate preclinical testing in non-human primate models. The disclosed gRNAs, which target both human and rhesus monkey dystrophin gene sequences, can be used with the CRISPR/Cas9-based system to target intronic regions surrounding exon 51 of the human dystrophin gene, causing genomic deletions of this region in order to restore expression of functional dystrophin in cells from DMD patients.

Also described herein are genetic constructs, compositions and methods for delivering CRISPR/Cas9-based gene editing system and multiple gRNAs to target the dystrophin gene. The presently disclosed subject matter also provides for methods for delivering the genetic constructs (e.g., vectors) or compositions comprising thereof to skeletal muscle and cardiac muscle. The vector can be an AAV, including modified AAV vectors. The presently disclosed subject matter describes a way to deliver active forms of this class of therapeutics to skeletal muscle or cardiac muscle that is effective, efficient and facilitates successful genome modification, as well as provide a means to rewrite the human genome for therapeutic applications and target model species for basic science applications.

Section headings as used in this section and the entire disclosure herein are merely for organizational purposes and are not intended to be limiting.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

As used herein, the term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

"Adeno-associated virus" or "AAV" as used interchangeably herein refers to a small virus belonging to the genus *Dependovirus* of the Parvoviridae family that infects humans and some other primate species. AAV is not currently known to cause disease and consequently the virus causes a very mild immune response.

"Binding region" as used herein refers to the region within a nuclease target region that is recognized and bound by the nuclease.

"Cardiac muscle" or "heart muscle" as used interchangeably herein means a type of involuntary striated muscle found in the walls and histological foundation of the heart, the myocardium. Cardiac muscle is made of cardiomyocytes or myocardiocytes. Myocardiocytes show striations similar to those on skeletal muscle cells but contain only one, unique nucleus, unlike the multinucleated skeletal cells. In certain embodiments, "cardiac muscle condition" refers to a condition related to the cardiac muscle, such as cardiomyopathy, heart failure, arrhythmia, and inflammatory heart disease.

"Coding sequence" or "encoding nucleic acid" as used herein means the nucleic acids (RNA or DNA molecule) that comprise a nucleotide sequence which encodes a protein. The coding sequence can further include initiation and termination signals operably linked to regulatory elements including a promoter and polyadenylation signal capable of directing expression in the cells of an individual or mammal to which the nucleic acid is administered. The coding sequence may be codon optimize.

"Complement" or "complementary" as used herein means a nucleic acid can mean Watson-Crick (e.g., A-T/U and C-G) or Hoogsteen base pairing between nucleotides or nucleotide analogs of nucleic acid molecules. "Complementarity" refers to a property shared between two nucleic acid sequences, such that when they are aligned antiparallel to each other, the nucleotide bases at each position will be complementary.

"Correcting", "genome editing" and "restoring" as used herein refers to changing a mutant gene that encodes a truncated protein or no protein at all, such that a full-length functional or partially full-length functional protein expression is obtained. Correcting or restoring a mutant gene may include replacing the region of the gene that has the mutation or replacing the entire mutant gene with a copy of the gene that does not have the mutation with a repair mechanism such as homology-directed repair (HDR). Correcting or restoring a mutant gene may also include repairing a frameshift mutation that causes a premature stop codon, an aberrant splice acceptor site or an aberrant splice donor site, by generating a double stranded break in the gene that is then repaired using non-homologous end joining (NHEJ). NHEJ may add or delete at least one base pair during repair which may restore the proper reading frame and eliminate the premature stop codon. Correcting or restoring a mutant gene may also include disrupting an aberrant splice acceptor site or splice donor sequence. Correcting or restoring a mutant gene may also include deleting a non-essential gene segment by the simultaneous action of two nucleases on the same DNA strand in order to restore the proper reading frame by removing the DNA between the two nuclease target sites and repairing the DNA break by NHEJ.

"Donor DNA", "donor template" and "repair template" as used interchangeably herein refers to a double-stranded DNA fragment or molecule that includes at least a portion of the gene of interest. The donor DNA may encode a full-functional protein or a partially-functional protein.

"Duchenne Muscular Dystrophy" or "DMD" as used interchangeably herein refers to a recessive, fatal, X-linked disorder that results in muscle degeneration and eventual death. DMD is a common hereditary monogenic disease and occurs in 1 in 3500 males. DMD is the result of inherited or spontaneous mutations that cause nonsense or frame shift mutations in the dystrophin gene. The majority of dystrophin mutations that cause DMD are deletions of exons that disrupt the reading frame and cause premature translation termination in the dystrophin gene. DMD patients typically lose the ability to physically support themselves during childhood, become progressively weaker during the teenage years, and die in their twenties.

"Dystrophin" as used herein refers to a rod-shaped cytoplasmic protein which is a part of a protein complex that connects the cytoskeleton of a muscle fiber to the surrounding extracellular matrix through the cell membrane. Dystrophin provides structural stability to the dystroglycan complex of the cell membrane that is responsible for regulating muscle cell integrity and function. The dystrophin gene or "DMD gene" as used interchangeably herein is 2.2 megabases at locus Xp21. The primary transcription measures about 2,400 kb with the mature mRNA being about 14 kb. 79 exons code for the protein which is over 3500 amino acids.

"Exon 51" as used herein refers to the $51^{st}$ exon of the dystrophin gene. Exon 51 is frequently adjacent to frame-disrupting deletions in DMD patients and has been targeted in clinical trials for oligonucleotide-based exon skipping. A clinical trial for the exon 51 skipping compound eteplirsen recently reported a significant functional benefit across 48 weeks, with an average of 47% dystrophin positive fibers compared to baseline. Mutations in exon 51 are ideally suited for permanent correction by NHEJ-based genome editing.

"Frameshift" or "frameshift mutation" as used interchangeably herein refers to a type of gene mutation wherein the addition or deletion of one or more nucleotides causes a shift in the reading frame of the codons in the mRNA. The shift in reading frame may lead to the alteration in the amino acid sequence at protein translation, such as a missense mutation or a premature stop codon.

"Functional" and "full-functional" as used herein describes protein that has biological activity. A "functional gene" refers to a gene transcribed to mRNA, which is translated to a functional protein.

"Fusion protein" as used herein refers to a chimeric protein created through the joining of two or more genes that originally coded for separate proteins. The translation of the fusion gene results in a single polypeptide with functional properties derived from each of the original proteins.

"Genetic construct" as used herein refers to the DNA or RNA molecules that comprise a nucleotide sequence that encodes a protein. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operable linked to a coding sequence that encodes a protein such that when present in the cell of the individual, the coding sequence will be expressed.

"Genetic disease" as used herein refers to a disease, partially or completely, directly or indirectly, caused by one or more abnormalities in the genome, especially a condition that is present from birth. The abnormality may be a mutation, an insertion or a deletion. The abnormality may affect the coding sequence of the gene or its regulatory sequence. The genetic disease may be, but not limited to DMD, Becker Muscular Dystrophy (BMD), hemophilia, cystic fibrosis, Huntington's chorea, familial hypercholesterolemia (LDL receptor defect), hepatoblastoma, Wilson's disease, congenital hepatic porphyria, inherited disorders of hepatic metabolism, Lesch Nyhan syndrome, sickle cell anemia, thalassaemias, xeroderma pigmentosum, Fanconi's anemia, retinitis pigmentosa, ataxia telangiectasia, Bloom's syndrome, retinoblastoma, and Tay-Sachs disease.

"Homology-directed repair" or "HDR" as used interchangeably herein refers to a mechanism in cells to repair double strand DNA lesions when a homologous piece of DNA is present in the nucleus, mostly in G2 and S phase of the cell cycle. HDR uses a donor DNA template to guide repair and may be used to create specific sequence changes to the genome, including the targeted addition of whole genes. If a donor template is provided along with the CRISPR/Cas9-based gene editing system, then the cellular machinery will repair the break by homologous recombination, which is enhanced several orders of magnitude in the presence of DNA cleavage. When the homologous DNA piece is absent, non-homologous end joining may take place instead.

"Genome editing" as used herein refers to changing a gene. Genome editing may include correcting or restoring a mutant gene. Genome editing may include knocking out a gene, such as a mutant gene or a normal gene. Genome editing may be used to treat disease or enhance muscle repair by changing the gene of interest.

"Identical" or "identity" as used herein in the context of two or more nucleic acids or polypeptide sequences means that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

"Mutant gene" or "mutated gene" as used interchangeably herein refers to a gene that has undergone a detectable mutation. A mutant gene has undergone a change, such as the loss, gain, or exchange of genetic material, which affects the normal transmission and expression of the gene. A "disrupted gene" as used herein refers to a mutant gene that has a mutation that causes a premature stop codon. The disrupted gene product is truncated relative to a full-length undisrupted gene product.

"Non-homologous end joining (NHEJ) pathway" as used herein refers to a pathway that repairs double-strand breaks in DNA by directly ligating the break ends without the need for a homologous template. The template-independent re-ligation of DNA ends by NHEJ is a stochastic, error-prone repair process that introduces random micro-insertions and micro-deletions (indels) at the DNA breakpoint. This method may be used to intentionally disrupt, delete, or alter the reading frame of targeted gene sequences. NHEJ typically uses short homologous DNA sequences called micro-homologies to guide repair. These microhomologies are often present in single-stranded overhangs on the end of double-strand breaks. When the overhangs are perfectly compatible, NHEJ usually repairs the break accurately, yet imprecise repair leading to loss of nucleotides may also occur, but is much more common when the overhangs are not compatible.

"Normal gene" as used herein refers to a gene that has not undergone a change, such as a loss, gain, or exchange of genetic material. The normal gene undergoes normal gene transmission and gene expression.

"Nuclease mediated NHEJ" as used herein refers to NHEJ that is initiated after a nuclease, such as a Cas9 molecule, cuts double stranded DNA.

"Nucleic acid" or "oligonucleotide" or "polynucleotide" as used herein means at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

"Operably linked" as used herein means that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function.

"Partially-functional" as used herein describes a protein that is encoded by a mutant gene and has less biological activity than a functional protein but more than a non-functional protein.

"Premature stop codon" or "out-of-frame stop codon" as used interchangeably herein refers to nonsense mutation in a sequence of DNA, which results in a stop codon at location not normally found in the wild-type gene. A premature stop codon may cause a protein to be truncated or shorter compared to the full-length version of the protein.

"Promoter" as used herein means a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which may be located as much as several thousand base pairs from the start site of transcription. A promoter may be derived from sources including viral, bacterial, fungal, plants, insects, and animals. A promoter may regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter, human U6 (hU6) promoter, and CMV IE promoter.

"Skeletal muscle" as used herein refers to a type of striated muscle, which is under the control of the somatic nervous system and attached to bones by bundles of collagen fibers known as tendons. Skeletal muscle is made up of individual components known as myocytes, or "muscle cells", sometimes colloquially called "muscle fibers." Myocytes are formed from the fusion of developmental myoblasts (a type of embryonic progenitor cell that gives rise to a muscle cell) in a process known as myogenesis. These long, cylindrical, multinucleated cells are also called myofibers.

"Skeletal muscle condition" as used herein refers to a condition related to the skeletal muscle, such as muscular dystrophies, aging, muscle degeneration, wound healing, and muscle weakness or atrophy.

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous or rhesus monkey, chimpanzee, etc.) and a human). In some embodiments, the subject may be a human or a non-human. The subject or patient may be undergoing other forms of treatment.

"Target gene" as used herein refers to any nucleotide sequence encoding a known or putative gene product. The target gene may be a mutated gene involved in a genetic disease. In certain embodiments, the target gene is a human dystrophin gene. In certain embodiments, the target gene is a mutant human dystrophin gene.

"Target region" as used herein refers to the region of the target gene to which the CRISPR/Cas9-based gene editing system is designed to bind and cleave.

"Transgene" as used herein refers to a gene or genetic material containing a gene sequence that has been isolated from one organism and is introduced into a different organism. This non-native segment of DNA may retain the ability to produce RNA or protein in the transgenic organism, or it may alter the normal function of the transgenic organism's genetic code. The introduction of a transgene has the potential to change the phenotype of an organism.

"Variant" used herein with respect to a nucleic acid means (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

"Variant" with respect to a peptide or polypeptide that differs in amino acid sequence by the insertion, deletion, or conservative substitution of amino acids, but retain at least one biological activity. Variant may also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes may be identified, in part, by considering the hydropathic index of amino acids, as understood in the art. Kyte et al., *J. Mol. Biol.* 157:105-132 (1982). The hydropathic index of an amino acid is based on a consideration of its hydrophobicity and charge. It is known in the art that amino acids of similar hydropathic indexes may be substituted and still retain protein function. In one aspect, amino acids having hydropathic indexes of ±2 are substituted. The hydrophilicity of amino acids may also be used to reveal substitutions that would result in proteins retaining biological function. A consideration of the hydrophilicity of amino acids in the context of a peptide permits calculation of the greatest local average hydrophilicity of that peptide. Substitutions may be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

"Vector" as used herein means a nucleic acid sequence containing an origin of replication. A vector may be a viral vector, bacteriophage, bacterial artificial chromosome or yeast artificial chromosome. A vector may be a DNA or RNA vector. A vector may be a self-replicating extrachromosomal vector, and preferably, is a DNA plasmid. For example, the vector may encode a Cas9 protein and at least one gRNA molecule, such as a gRNA comprising a targeting domain of any one of SEQ ID NOs: 1-19, 41, 42, or complement thereof. In some embodiments, the Cas9 protein may have an amino acid sequence of SEQ ID NO: 27, SEQ ID NO: 33, or SEQ ID NO: 45. In some embodiments, the Cas9 protein may be a *S. aureus* Cas9, such as a SaCas9 having an amino acid sequence of SEQ ID NO: 33 or 45. In some embodiments, the Cas9 protein is encoded by a nucleic acid sequence comprising a nucleic sequence of SEQ ID NO: 26, SEQ ID NO: 28, SEQ ID NO: 29, SEQ ID NO: 30, SEQ ID NO: 31, SEQ ID NO: 32, SEQ ID NO: 34, SEQ ID NO: 35, SEQ ID NO: 43, or SEQ ID NO: 44.

Unless otherwise defined herein, scientific and technical terms used in connection with the present disclosure shall have the meanings that are commonly understood by those of ordinary skill in the art. For example, any nomenclatures used in connection with, and techniques of, cell and tissue culture, molecular biology, immunology, microbiology, genetics and protein and nucleic acid chemistry and hybridization described herein are those that are well known and commonly used in the art. The meaning and scope of the terms should be clear; in the event however of any latent ambiguity, definitions provided herein take precedent over any dictionary or extrinsic definition. Further, unless otherwise required by context, singular terms shall include pluralities and plural terms shall include the singular.

2. GENETIC CONSTRUCTS FOR GENOME EDITING OF DYSTROPHIN GENE

The present invention is directed to genetic constructs for genome editing, genomic alteration or altering gene expression of a dystrophin gene (e.g., human dystrophin gene). The genetic constructs include at least one gRNA that targets both human and rhesus monkey dystrophin gene sequences, such as SaCas9-compatible targets. The disclosed gRNAs can be included in a CRISPR/Cas9-based gene editing system, including systems that use SaCas9, to target intronic regions surrounding exon 51 of the human dystrophin gene, causing genomic deletions of this region in order to restore expression of functional dystrophin in cells from DMD patients.

a. Dystrophin Gene

Dystrophin is a rod-shaped cytoplasmic protein which is a part of a protein complex that connects the cytoskeleton of a muscle fiber to the surrounding extracellular matrix through the cell membrane. Dystrophin provides structural stability to the dystroglycan complex of the cell membrane. The dystrophin gene is 2.2 megabases at locus Xp21. The primary transcription measures about 2,400 kb with the mature mRNA being about 14 kb. 79 exons code for the protein which is over 3500 amino acids. Normal skeleton muscle tissue contains only small amounts of dystrophin but its absence of abnormal expression leads to the development of severe and incurable symptoms. Some mutations in the dystrophin gene lead to the production of defective dystrophin and severe dystrophic phenotype in affected patients. Some mutations in the dystrophin gene lead to partially-functional dystrophin protein and a much milder dystrophic phenotype in affected patients.

DMD is the result of inherited or spontaneous mutations that cause nonsense or frame shift mutations in the dystrophin gene. Naturally occurring mutations and their consequences are relatively well understood for DMD. It is known that in-frame deletions that occur in the exon 45-55 regions (e.g., exon 51) contained within the rod domain can produce highly functional dystrophin proteins, and many carriers are asymptomatic or display mild symptoms. Furthermore, more than 60% of patients may theoretically be treated by targeting exons in this region of the dystrophin gene (e.g., targeting exon 51). Efforts have been made to restore the disrupted dystrophin reading frame in DMD patients by skipping non-essential exon(s) (e.g., exon 51 skipping) during mRNA splicing to produce internally deleted but functional dystrophin proteins. The deletion of internal dystrophin exon(s) (e.g., deletion of exon 51) retains the proper reading frame but cause the less severe Becker muscular dystrophy, or BMD. The Becker muscular dystrophy, or BMD, genotype is similar to DMD in that deletions are present in the dystrophin gene. However, these deletions leave the reading frame intact. Thus an internally truncated but partially functional dystrophin protein is created. BMD has a wide array of phenotypes, but often if deletions are between exons 45-55 of dystrophin the phenotype is much milder compared to DMD. Thus changing a DMD genotype to a BMD genotype is a common strategy to correct dystrophin. There are many strategies to correct dystrophin, many of which rely on restoring the reading frame of the endogenous dystrophin. This shifts the disease genotype from DMD to Becker muscular dystrophy. Many BMD patients have intragenic deletions that maintain the translational reading frame, leading to a shorter but largely functional dystrophin protein.

In certain embodiments, modification of exon 51 (e.g., deletion or excision of exon 51 by, e.g., NHEJ) to restore reading frame ameliorates the phenotype DMD subjects, including DMD subjects with deletion mutations. In certain embodiments, exon 51 of a dystrophin gene refers to the $51^{st}$ exon of the dystrophin gene. Exon 51 is frequently adjacent to frame-disrupting deletions in DMD patients and has been targeted in clinical trials for oligonucleotide-based exon skipping. A clinical trial for the exon 51 skipping compound eteplirsen reported a significant functional benefit across 48 weeks, with an average of 47% dystrophin positive fibers compared to baseline. Mutations in exon 51 are ideally suited for permanent correction by NHEJ-based genome editing.

The presently disclosed vectors can generate deletions in the dystrophin gene, e.g., the human dystrophin gene. In certain embodiments, the vector is configured to form two double stand breaks (a first double strand break and a second double strand break) in two introns (a first intron and a second intron) flanking a target position of the dystrophin gene, thereby deleting a segment of the dystrophin gene comprising the dystrophin target position. A "dystrophin target position" can be a dystrophin exonic target position or a dystrophin intra-exonic target position, as described herein. Deletion of the dystrophin exonic target position can optimize the dystrophin sequence of a subject suffering from Duchenne muscular dystrophy, e.g., it can increase the function or activity of the encoded dystrophin protein, or results in an improvement in the disease state of the subject. In certain embodiments, excision of the dystrophin exonic target position restores reading frame. The dystrophin exonic target position can comprise one or more exons of the dystrophin gene. In certain embodiments, the dystrophin target position comprises exon 51 of the dystrophin gene (e.g., human dystrophin gene).

A presently disclosed genetic construct (e.g., a vector) can mediate highly efficient gene editing at exon 51 of a dystrophin gene (e.g., the human dystrophin gene). A presently disclosed genetic construct (e.g., a vector) restores dystrophin protein expression in cells from DMD patients.

Exon 51 is frequently adjacent to frame-disrupting deletions in DMD. Elimination of exon 51 from the dystrophin transcript by exon skipping can be used to treat approximately 15% of all DMD patients. This class of dystrophin mutations is ideally suited for permanent correction by NHEJ-based genome editing and HDR. The genetic constructs (e.g., vectors) described herein have been developed for targeted modification of exon 51 in the human dystrophin gene. A presently disclosed genetic construct (e.g., a vector) is transfected into human DMD cells and mediates efficient gene modification and conversion to the correct reading frame. Protein restoration is concomitant with frame restoration and detected in a bulk population of CRISPR/Cas9-based gene editing system-treated cells.

b. CRISPR System

A presently disclosed genetic construct (e.g., a vector) encodes a CRISPR/Cas9-based gene editing system that is specific for a dystrophin gene (e.g., human dystrophin gene). "Clustered Regularly Interspaced Short Palindromic Repeats" and "CRISPRs", as used interchangeably herein refers to loci containing multiple short direct repeats that are found in the genomes of approximately 40% of sequenced bacteria and 90% of sequenced archaea. The CRISPR system is a microbial nuclease system involved in defense against invading phages and plasmids that provides a form of acquired immunity. The CRISPR loci in microbial hosts contain a combination of CRISPR-associated (Cas) genes as well as non-coding RNA elements capable of programming the specificity of the CRISPR-mediated nucleic acid cleavage. Short segments of foreign DNA, called spacers, are incorporated into the genome between CRISPR repeats, and serve as a 'memory' of past exposures. Cas9 forms a complex with the 3' end of the sgRNA (also referred interchangeably herein as "gRNA"), and the protein-RNA pair recognizes its genomic target by complementary base pairing between the 5' end of the sgRNA sequence and a predefined 20 bp DNA sequence, known as the protospacer. This complex is directed to homologous loci of pathogen DNA via regions encoded within the crRNA, i.e., the protospacers, and protospacer-adjacent motifs (PAMs) within the pathogen genome. The non-coding CRISPR array is transcribed and cleaved within direct repeats into short crRNAs containing individual spacer sequences, which direct Cas nucleases to the target site (protospacer). By simply exchanging the 20 bp recognition sequence of the expressed sgRNA, the Cas9 nuclease can be directed to new genomic targets. CRISPR spacers are used to recognize and silence exogenous genetic elements in a manner analogous to RNAi in eukaryotic organisms.

Three classes of CRISPR systems (Types I, II and III effector systems) are known. The Type II effector system carries out targeted DNA double-strand break in four sequential steps, using a single effector enzyme, Cas9, to cleave dsDNA. Compared to the Type I and Type III effector systems, which require multiple distinct effectors acting as a complex, the Type II effector system may function in alternative contexts such as eukaryotic cells. The Type II effector system consists of a long pre-crRNA, which is transcribed from the spacer-containing CRISPR locus, the Cas9 protein, and a tracrRNA, which is involved in pre-crRNA processing. The tracrRNAs hybridize to the repeat regions separating the spacers of the pre-crRNA, thus initiating dsRNA cleavage by endogenous RNase III. This cleavage is followed by a second cleavage event within each spacer by Cas9, producing mature crRNAs that remain associated with the tracrRNA and Cas9, forming a Cas9:crRNA-tracrRNA complex.

The Cas9:crRNA-tracrRNA complex unwinds the DNA duplex and searches for sequences matching the crRNA to cleave. Target recognition occurs upon detection of complementarity between a "protospacer" sequence in the target DNA and the remaining spacer sequence in the crRNA. Cas9 mediates cleavage of target DNA if a correct protospacer-adjacent motif (PAM) is also present at the 3' end of the protospacer. For protospacer targeting, the sequence must be immediately followed by the protospacer-adjacent motif (PAM), a short sequence recognized by the Cas9 nuclease that is required for DNA cleavage. Different Type II systems have differing PAM requirements. The *S. pyogenes* CRISPR system may have the PAM sequence for this Cas9 (SpCas9) as 5'-NRG-3', where R is either A or G, and characterized the specificity of this system in human cells. A unique capability of the CRISPR/Cas9-based gene editing system is the straightforward ability to simultaneously target multiple distinct genomic loci by co-expressing a single Cas9 protein with two or more sgRNAs. For example, the *Streptococcus pyogenes* Type II system naturally prefers to use an "NGG" sequence, where "N" can be any nucleotide, but also accepts other PAM sequences, such as "NAG" in engineered systems (Hsu et al., Nature Biotechnology (2013) doi:10.1038/nbt.2647). Similarly, the Cas9 derived from *Neisseria meningitidis* (NmCas9) normally has a native PAM of NNNNGATT, but has activity across a variety of PAMs, including a highly degenerate NNNNGNNN PAM (Esvelt et al. Nature Methods (2013) doi:10.1038/nmeth.2681).

A Cas9 molecule of *S. aureus* recognizes the sequence motif NNGRR (R=A or G) (SEQ ID NO: 22) and directs cleavage of a target nucleic acid sequence 1 to 10, e.g., 3 to 5, bp upstream from that sequence. In certain embodiments, a Cas9 molecule of *S. aureus* recognizes the sequence motif NNGRRN (R=A or G) (SEQ ID NO: 23) and directs cleavage of a target nucleic acid sequence 1 to 10, e.g., 3 to 5, bp upstream from that sequence. In certain embodiments, a Cas9 molecule of *S. aureus* recognizes the sequence motif NNGRRT (R=A or G) (SEQ ID NO: 24) and directs cleavage of a target nucleic acid sequence 1 to 10, e.g., 3 to 5, bp upstream from that sequence. In certain embodiments, a Cas9 molecule of *S. aureus* recognizes the sequence motif NNGRRV (R=A or G) (SEQ ID NO: 25) and directs cleavage of a target nucleic acid sequence 1 to 10, e.g., 3 to 5, bp upstream from that sequence. In the aforementioned embodiments, N can be any nucleotide residue, e.g., any of A, G, C, or T. Cas9 molecules can be engineered to alter the PAM specificity of the Cas9 molecule.

(1) CRISPR/Cas9-Based Gene Editing System

An engineered form of the Type II effector system of *Streptococcus pyogenes* was shown to function in human cells for genome engineering. In this system, the Cas9 protein was directed to genomic target sites by a synthetically reconstituted "guide RNA" ("gRNA", also used interchangeably herein as a chimeric single guide RNA ("sgRNA")), which is a crRNA-tracrRNA fusion that obviates the need for RNase III and crRNA processing in general. Provided herein are CRISPR/Cas9-based engineered systems for use in genome editing and treating genetic diseases. The CRISPR/Cas9-based engineered systems can be designed to target any gene, including genes involved in a genetic disease, aging, tissue regeneration, or wound healing. The CRISPR/Cas9-based gene editing systems can include a Cas9 protein or Cas9 fusion protein and at least one gRNA. In certain embodiments, the system comprises two gRNA molecules. The Cas9 fusion protein may, for example, include a domain that has a different activity that what is endogenous to Cas9, such as a trans-activation domain.

The target gene (e.g., a dystrophin gene, e.g., human dystrophin gene) can be involved in differentiation of a cell or any other process in which activation of a gene can be desired, or can have a mutation such as a frameshift mutation or a nonsense mutation. If the target gene has a mutation that causes a premature stop codon, an aberrant splice acceptor site or an aberrant splice donor site, the CRISPR/Cas9-based gene editing system can be designed to recognize and bind a nucleotide sequence upstream or downstream from the premature stop codon, the aberrant splice acceptor site or the aberrant splice donor site. The CRISPR-Cas9-based system can also be used to disrupt normal gene splicing by targeting splice acceptors and donors to induce skipping of premature stop codons or restore a disrupted reading frame. The CRISPR/Cas9-based gene editing system may or may not mediate off-target changes to protein-coding regions of the genome.

(a) Cas9 Molecules and Cas9 Fusion Proteins

The CRISPR/Cas9-based gene editing system can include a Cas9 protein or a Cas9 fusion protein. Cas9 protein is an endonuclease that cleaves nucleic acid and is encoded by the CRISPR loci and is involved in the Type II CRISPR system. The Cas9 protein can be from any bacterial or archaea species, including, but not limited to, *Streptococcus pyogenes, Staphylococcus aureus* (*S. aureus*), *Acidovorax avenae, Actinobacillus pleuropneumonias, Actinobacillus succinogenes, Actinobacillus suis, Actinomyces* sp., *cycliphilus denitrificans, Aminomonas paucivorans, Bacillus cereus, Bacillus smithii, Bacillus thuringiensis, Bacteroides* sp., *Blastopirellula marina, Bradyrhizobium* sp., *Brevibacillus laterosporus, Campylobacter coli, Campylobacter jejuni, Campylobacter lari, Candidatus Puniceispirillum, Clostridium cellulolyticum, Clostridium perfringens, Corynebacterium accolens, Corynebacterium diphtheria, Corynebacterium matruchotii, Dinoroseobacter shibae, Eubacterium dolichum, gamma proteobacterium, Gluconacetobacter diazotrophicus, Haemophilus parainfluenzae, Haemophilus sputorum, Helicobacter canadensis, Helicobacter cinaedi, Helicobacter mustelae, Ilyobacter polytropus, Kingella kingae, Lactobacillus crispatus, Listeria ivanovii, Listeria monocytogenes, Listeriaceae bacterium, Methylocystis* sp., *Methylosinus trichosporium, Mobiluncus mulieris, Neisseria bacilliformis, Neisseria cinerea, Neisseria flavescens, Neisseria lactamica, Neisseria* sp., *Neisseria wadsworthii, Nitrosomonas* sp., *Parvibaculum lavamentivorans, Pasteurella multocida, Phascolarctobacterium succinatutens, Ralstonia syzygii, Rhodopseudomonas palustris, Rhodovulum* sp., *Simonsiella muelleri, Sphingomonas* sp., *Sporolactobacillus vineae, Staphylococcus lugdunensis, Streptococcus* sp., *Subdoligranulum* sp., *Tistrella mobilis, Treponema* sp., or *Verminephrobacter eiseniae*. In certain embodiments, the Cas9 molecule is a The Cas9 protein is a *Streptococcus pyogenes* Cas9 molecule (also referred herein as "SpCas9"). In certain embodiments, the Cas9 molecule is a *Staphylococcus aureus* Cas9 molecule (also referred herein as "SaCas9").

A Cas9 molecule or a Cas9 fusion protein can interact with one or more gRNA molecule and, in concert with the gRNA molecule(s), localizes to a site which comprises a target domain, and in certain embodiments, a PAM sequence. The ability of a Cas9 molecule or a Cas9 fusion protein to recognize a PAM sequence can be determined, e.g., using a transformation assay as described previously (Jinek 2012).

In certain embodiments, the ability of a Cas9 molecule or a Cas9 fusion protein to interact with and cleave a target nucleic acid is PAM sequence dependent. A PAM sequence is a sequence in the target nucleic acid. In certain embodiments, cleavage of the target nucleic acid occurs upstream from the PAM sequence. Cas9 molecules from different bacterial species can recognize different sequence motifs (e.g., PAM sequences). In certain embodiments, a Cas9 molecule of *S. pyogenes* recognizes the sequence motif NGG and directs cleavage of a target nucleic acid sequence 1 to 10, e.g., 3 to 5, bp upstream from that sequence (see, e.g., *Mali* 2013). In certain embodiments, a Cas9 molecule of *S. thermophilus* recognizes the sequence motif NGGNG (SEQ ID NO: 36) and/or NNAGAAW (W=A or T) (SEQ ID NO: 20) and directs cleavage of a target nucleic acid sequence 1 to 10, e.g., 3 to 5, bp upstream from these sequences (see, e.g., Horvath 2010; Deveau 2008). In certain embodiments, a Cas9 molecule of *S. mutans* recognizes the sequence motif NGG and/or NAAR (R=A or G) (SEQ ID NO: 21) and directs cleavage of a target nucleic acid sequence 1 to 10, e.g., 3 to 5 bp, upstream from this sequence (see, e.g., Deveau 2008). In certain embodiments, a Cas9 molecule of *S. aureus* recognizes the sequence motif NNGRR (R=A or G) (SEQ ID NO: 22) and directs cleavage of a target nucleic acid sequence 1 to 10, e.g., 3 to 5, bp upstream from that sequence. In certain embodiments, a Cas9 molecule of *S. aureus* recognizes the sequence motif NNGRRN (R=A or G) (SEQ ID NO: 23) and directs cleavage of a target nucleic acid sequence 1 to 10, e.g., 3 to 5, bp upstream from that sequence. In certain embodiments, a Cas9 molecule of *S. aureus* recognizes the sequence motif NNGRRT (R=A or G) (SEQ ID NO: 24) and directs cleavage of a target nucleic acid sequence 1 to 10, e.g., 3 to 5, bp upstream from that sequence. In certain embodiments, a Cas9 molecule of *S. aureus* recognizes the sequence motif NNGRRV (R=A or G; V=A or C or G) (SEQ ID NO: 25) and directs cleavage of a target nucleic acid sequence 1 to 10, e.g., 3 to 5, bp upstream from that sequence. In the aforementioned embodiments, N can be any nucleotide residue, e.g., any of A, G, C, or T. Cas9 molecules can be engineered to alter the PAM specificity of the Cas9 molecule.

In certain embodiments, the vector encodes at least one Cas9 molecule that recognizes a Protospacer Adjacent Motif (PAM) of either NNGRRT (SEQ ID NO: 24) or NNGRRV (SEQ ID NO: 25). In certain embodiments, the at least one Cas9 molecule is an *S. aureus* Cas9 molecule. In certain embodiments, the at least one Cas9 molecule is a mutant *S. aureus* Cas9 molecule.

The Cas9 protein can be mutated so that the nuclease activity is inactivated. An inactivated Cas9 protein ("iCas9", also referred to as "dCas9") with no endonuclease activity has been recently targeted to genes in bacteria, yeast, and human cells by gRNAs to silence gene expression through steric hindrance. Exemplary mutations with reference to the *S. pyogenes* Cas9 sequence include: D10A, E762A, H840A, N854A, N863A and/or D986A. Exemplary mutations with reference to the *S. aureus* Cas9 sequence include D10A and N580A. In certain embodiments, the Cas9 molecule is a mutant *S. aureus* Cas9 molecule. In certain embodiments, the mutant *S. aureus* Cas9 molecule comprises a D10A mutation. The nucleotide sequence encoding this mutant *S. aureus* Cas9 is set forth in SEQ ID NO: 34, which is provided below:

[SEQ ID NO: 34]
```
atgaaaagga actacattct ggggctggcc atcgggatta caagcgtggg gtatgggatt attgactatg aaacaaggga cgtgatcgac gcaggcgtca gactgttcaa ggaggccaac gtggaaaaca atgagggacg gagaagcaag aggggagcca ggcgcctgaa acgacggaga aggcacagaa tccagagggt gaagaaactg ctgttcgatt acaacctgct gaccgaccat tctgagctga gtggaattaa tccttatgaa gccagggtga aaggcctgag tcagaagctg tcagaggaag agttttccgc agctctgctg cacctggcta agcgccgagg agtgcataac gtcaatgagg tggaagagga caccggcaac gagctgtcta caaaggaaca gatctcacgc aatagcaaag ctctggaaga gaagtatgtc gcagagctgc agctggaacg gctgaagaaa gatggcgagg tgagagggtc aattaatagg ttcaagacaa gcgactacgt caaagaagcc aagcagctgc tgaaagtgca gaaggcttac caccagctgg atcagagctt catcgatact tatatcgacc tgctggagac tcggagaacc tactatgagg gaccaggaga agggagcccc ttcggatgga aagacatcaa ggaatggtac gagatgctga tgggacattg cacctatttt ccagaagagc tgagaagcgt caagtacgct tataacgcag atctgtacaa cgccctgaat gacctgaaca acctggtcat caccagggat gaaaacgaga aactggaata ctatgagaag ttccagatca tcgaaaacgt gtttaagcag aagaaaagc ctacactgaa acagattgct aaggagatcc tggtcaacga agaggacatc aagggctacc gggtgacaag cactggaaaa ccagagttca ccaatctgaa agtgtatcac gatattaagg acatcacagc acggaaagaa atcattgaga acgccgaact gctggatcag attgctaaga tcctgactat ctaccagagc tccgaggaca tccaggaaga gctgactaac ctgaacagcg agctgaccca ggaagagatc
```

-continued

```
gaacagatta gtaatctgaa ggggtacacc ggaacacaca acctgtccct gaaagctatc aatctgattc tggatgagct gtggcataca aacgacaatc agattgcaat ctttaaccgg ctgaagctgg tcccaaaaaa ggtggacctg agtcagcaga aagagatccc aaccacactg gtggacgatt tcattctgtc acccgtggtc aagcggagct tcatccagag catcaaagtg atcaacgcca tcatcaagaa gtacggcctg cccaatgata tcattatcga gctggctagg gagaagaaca gcaaggacgc acagaagatg atcaatgaga tgcagaaacg aaaccggcag accaatgaac gcattgaaga gattatccga actaccggga aagagaacgc aaagtacctg attgaaaaaa tcaagctgca cgatatgcag gagggaaagt gtctgtattc tctggaggcc atcccctgg aggacctgct gaacaatcca ttcaactacg aggtcgatca tattatcccc agaagcgtgt ccttcgacaa ttcctttaac aacaaggtgc tggtcaagca ggaagagaac tctaaaaagg gcaataggac tcctttccag tacctgtcta gttcagattc caagatctct tacgaaacct taaaaagca cattctgaat ctggccaaag gaaagggccg catcagcaag accaaaaagg agtacctgct ggaagagcgg gacatcaaca gattctccgt ccagaaggat tttattaacc ggaatctggt ggacacaaga tacgctactc gcggcctgat gaatctgctg cgatcctatt tccgggtgaa caatctggat gtgaaagtca agtccatcaa cggcgggttc acatcttttc tgaggcgcaa atggaagttt aaaaaggagc gcaacaaagg gtacaagcac catgccgaag atgctctgat tatcgcaaat gccgacttca tctttaagga gtggaaaaag ctggacaaag ccaagaaagt gatggagaac cagatgttcg aagagaagca ggccgaatct atgcccgaaa tcgagacaga acaggagtac aaggagattt tcatcactcc tcaccagatc aagcatatca aggatttcaa ggactacaag tactctcacc gggtggataa aaagcccaac agagagctga tcaatgacac cctgtatagt acaagaaaag acgataaggg gaatacctg attgtgaaca atctgaacgg actgtacgac aaagataatg acaagctgaa aaagctgatc aacaaaagtc ccgagaagct gctgatgtac caccatgatc ctcagacata tcagaaactg aagctgatta tggagcagta cggcgacgag aagaacccac tgtataagta ctatgaagag actgggaact acctgaccaa gtatagcaaa aaggataatg gccccgtgat caagaagatc aagtactatg gaacaagct gaatgcccat ctggacatca cagacgatta ccctaacagt cgcaacaagg tggtcaagct gtcactgaag ccatacagat cgatgtcta tctggacaac ggcgtgtata aatttgtgac tgtcaagaat ctggatgtca tcaaaaagga gaactactat gaagtgaata gcaagtgcta cgaagaggct aaaaagctga aaaagattag caaccaggca gagttcatcg cctccttta caacaacgac ctgattaaga tcaatggcga actgtatagg gtcatcgggg tgaacaatga tctgctgaac cgcattgaag tgaatatgat tgacatcact taccgagagt atctggaaaa catgaatgat aagcgccccc tcgaattat caaaacaatt gcctctaaga ctcagagtat caaaaagtac tcaaccgaca ttctgggaaa cctgtatgag gtgaagagca aaaagcaccc tcagattatc aaaaagggc.
```

In certain embodiments, the mutant *S. aureus* Cas9 molecule comprises a N580A mutation. The nucleotide sequence encoding this mutant *S. aureus* Cas9 molecule is set forth in SEQ ID NO: 35, which is provided below:

```
                                                    [SEQ ID NO: 35]
                   atgaaaagga actacattct ggggctggac atcgggatta caagcgtggg gtatgggatt attgactatg aaacaaggga cgtgatcgca gcaggcgtca gactgttcaa ggaggccaac gtggaaaaca atgagggacg gagaagcaag aggggagcca ggcgcctgaa acgacggaga
```

-continued

```
aggcacagaa tccagagggt gaagaaactg ctgttcgatt acaacctgct gaccgaccat
tctgagctga gtggaattaa tccttatgaa gccagggtga aaggcctgag tcagaagctg
tcagaggaag agttttccgc agctctgctg cacctggcta agcgccgagg agtgcataac
gtcaatgagg tggaagagga caccggcaac gagctgtcta caaaggaaca gatctcacgc
aatagcaaag ctctggaaga gaagtatgtc gcagagctgc agctggaacg gctgaagaaa
gatggcgagg tgagagggtc aattaatagg ttcaagacaa gcgactacgt caaagaagcc
aagcagctgc tgaaagtgca gaaggcttac caccagctgg atcagagctt catcgatact
tatatcgacc tgctggagac tcggagaacc tactatgagg gaccaggaga agggagcccc
ttcggatgga aagacatcaa ggaatggtac gagatgctga tgggacattg cacctatttt
ccagaagagc tgagaagcgt caagtacgct tataacgcag atctgtacaa cgccctgaat
gacctgaaca acctggtcat caccagggat gaaaacgaga aactggaata ctatgagaag
ttccagatca tcgaaaacgt gtttaagcag aagaaaaagc ctacactgaa acagattgct
aaggagatcc tggtcaacga agaggacatc aagggctacc gggtgacaag cactggaaaa
ccagagttca ccaatctgaa agtgtatcac gatattaagg acatcacagc acggaaagaa
atcattgaga acgccgaact gctggatcag attgctaaga tcctgactat ctaccagagc
tccgaggaca tccaggaaga gctgactaac ctgaacagcg agctgaccca ggaagagatc
gaacagatta gtaatctgaa ggggtacacc ggaacacaca acctgtccct gaaagctatc
aatctgattc tggatgagct gtggcataca aacgacaatc agattgcaat ctttaaccgg
ctgaagctgg tcccaaaaaa ggtggacctg agtcagcaga aagagatccc aaccacactg
gtggacgatt tcattctgtc acccgtggtc aagcggagct catccagag catcaaagtg
atcaacgcca tcatcaagaa gtacggcctg cccaatgata tcattatcga gctggctagg
gagaagaaca gcaaggacgc acagaagatg atcaatgaga tgcagaaacg aaaccggcag
accaatgaac gcattgaaga gattatccga actaccggga agagaacgc aaagtacctg
attgaaaaaa tcaagctgca cgatatgcag gagggaaagt gtctgtattc tctggaggcc
atccccctgg aggacctgct gaacaatcca ttcaactacg aggtcgatca tattatcccc
agaagcgtgt ccttcgacaa ttcctttaac aacaaggtgc tggtcaagca ggaagaggcc
tctaaaaagg gcaataggac tccttttccag tacctgtcta gttcagattc caagatctct
tacgaaacct ttaaaaagca cattctgaat ctggccaaag gaaagggccg catcagcaag
accaaaaagg agtacctgct ggaagagcgg gacatcaaca gattctccgt ccagaaggat
tttattaacc ggaatctggt ggacacaaga tacgctactc gcggcctgat gaatctgctg
cgatcctatt tccgggtgaa caatctggat gtgaaagtca gtccatcaa cggcgggttc
acatcttttc tgaggcgcaa atggaagttt aaaaaggagc gcaacaaagg gtacaagcac
catgccgaag atgctctgat tatcgcaaat gccgacttca tctttaagga gtggaaaaag
ctggacaaag ccaagaaagt gatggagaac cagatgttcg aagagaagca ggccgaatct
atgcccgaaa tcgagacaga acaggagtac aaggagattt tcatcactcc tcaccagatc
aagcatatca aggatttcaa ggactacaag tactctcacc gggtggataa aaagcccaac
agagagctga tcaatgacac cctgtatagt acaagaaaag acgataaggg gaatacctg
attgtgaaca atctgaacgg actgtacgac aaagataatg acaagctgaa aaagctgatc
aacaaaagtc ccgagaagct gctgatgtac caccatgatc ctcagacata tcagaaactg
aagctgatta tggagcagta cggcgacgag aagaacccac tgtataagta ctatgaagag
actgggaact acctgaccaa gtatagcaaa aaggataatg gccccgtgat caagaagatc
```

-continued

```
aagtactatg ggaacaagct gaatgcccat ctggacatca cagacgatta ccctaacagt cgcaacaagg tggtcaagct gtcactgaag ccatacagat tcgatgtcta tctggacaac ggcgtgtata aatttgtgac tgtcaagaat ctggatgtca tcaaaaagga gaactactat gaagtgaata gcaagtgcta cgaagaggct aaaaagctga aaaagattag caaccaggca gagttcatcg cctccttta caacaacgac ctgattaaga tcaatggcga actgtatagg gtcatcgggg tgaacaatga tctgctgaac cgcattgaag tgaatatgat tgacatcact taccgagagt atctggaaaa catgaatgat aagcgccccc ctcgaattat caaaacaatt gcctctaaga ctcagagtat caaaaagtac tcaaccgaca ttctgggaaa cctgtatgag gtgaagagca aaaagcaccc tcagattatc aaaaagggc.
```

A nucleic acid encoding a Cas9 molecule can be a synthetic nucleic acid sequence. For example, the synthetic nucleic acid molecule can be chemically modified. The synthetic nucleic acid sequence can be codon optimized, e.g., at least one non-common codon or less-common codon has been replaced by a common codon. For example, the synthetic nucleic acid can direct the synthesis of an optimized messenger mRNA, e.g., optimized for expression in a mammalian expression system, e.g., described herein.

Additionally or alternatively, a nucleic acid encoding a Cas9 molecule or Cas9 polypeptide may comprise a nuclear localization sequence (NLS). Nuclear localization sequences are known in the art.

An exemplary codon optimized nucleic acid sequence encoding a Cas9 molecule of *S. pyogenes* is set forth in SEQ ID NO: 26, which is provided below:

[SEQ ID NO: 26]
```
atggataaaa agtacagcat cgggctggac atcggtacaa actcagtggg gtgggccgtg attacggacg agtacaaggt accctccaaa aatttaaag tgctgggtaa cacggacaga cactctataa agaaaaatct tattggagcc ttgctgttcg actcaggcga gacagccgaa gccacaaggt tgaagcggac cgccaggagg cggtatacca ggagaaagaa ccgcatatgc tacctgcaag aaatcttcag taacgagatg gcaaaggttg acgatagctt tttccatcgc ctggaagaat cctttcttgt tgaggaagac aagaagcacg aacggcaccc catctttggc aatattgtcg acgaagtggc atatcacgaa aagtacccga ctatctacca cctcaggaag aagctggtgg actctaccga taaggcggac ctcagactta tttatttggc actcgcccac atgattaaat ttagaggaca tttcttgatc gagggcgacc tgaacccgga caacagtgac gtcgataagc tgttcatcca acttgtgcag acctacaatc aactgttcga agaaaaccct ataaatgctt caggagtcga cgctaaagca atcctgtccg cgcgcctctc aaaatctaga agacttgaga atctgattgc tcagttgccc ggggaaaaga aaaatggatt gtttggcaac ctgatcgccc tcagtctcgg actgaccca aatttcaaaa gtaacttcga cctggccgaa gacgctaagc tccagctgtc caaggacaca tacgatgacg acctcgacaa tctgctggcc cagattgggg atcagtacgc cgatctcttt ttggcagcaa agaacctgtc cgacgccatc ctgttgagcg atatcttgag agtgaacacc gaaattacta agcaccct tagcgcatct atgatcaagc ggtacgacga gcatcatcag gatctgaccc tgctgaaggc tcttgtgagg caacagctcc ccgaaaaata caaggaaatc ttctttgacc agagcaaaaa cggctacgct ggctatatag atggtgggc cagtcaggag gaattctata aattcatcaa gcccattctc gagaaaatgg acggcacaga ggagttgctg gtcaaactta caggagga cctgctgcgg aagcagcgga cctttgacaa cgggtctatc ccccaccaga ttcatctggg cgaactgcac gcaatcctga ggaggcagga ggattttat ccttttctta agataaccg cgagaaaata gaaaagattc ttacattcag gatccccgta cgtgggac ctctcgcccg ggcaattca cggtttgcct ggatgacaag gaagtcagag gagactatta caccttggaa cttcgaagaa
```

-continued

```
gtggtggaca agggtgcatc tgcccagtct ttcatcgagc ggatgacaaa ttttgacaag aacctcccta atgagaaggt gctgcccaaa cattctctgc tctacgagta ctttaccgtc tacaatgaac tgactaaagt caagtacgtc accgagggaa tgaggaagcc ggcattcctt agtggagaac agaagaaggc gattgtagac ctgttgttca agaccaacag gaaggtgact gtgaagcaac ttaaagaaga ctactttaag aagatcgaat gttttgacag tgtggaaatt tcagggggttg aagaccgctt caatgcgtca ttggggactt accatgatct tctcaagatc ataaaggaca aagacttcct ggacaacgaa gaaaatgagg atattctcga agacatcgtc ctcaccctga ccctgttcga agacagggaa atgatagaag agcgcttgaa aacctatgcc cacctcttcg acgataaagt tatgaagcag ctgaagcgca ggagatacac aggatgggga agattgtcaa ggaagctgat caatggaatt agggataaac agagtggcaa gaccatactg gatttcctca aatctgatgg cttcgccaat aggaacttca tgcaactgat tcacgatgac tctcttacct tcaaggagga cattcaaaag gctcaggtga gcgggcaggg agactccctt catgaacaca tcgcgaattt ggcaggttcc cccgctatta aaagggcat ccttcaaact gtcaaggtgg tggatgaatt ggtcaaggta atgggcagac ataagccaga aaatattgtg atcgagatgg cccgcgaaaa ccagaccaca cagaagggcc agaaaaatag tagagagcgg atgaagagga tcgaggaggg catcaaagag ctgggatctc agattctcaa agaacacccc gtagaaaaca cacagctgca gaacgaaaaa ttgtacttgt actatctgca gaacggcaga gacatgtacg tcgaccaaga acttgatatt aatagactgt ccgactatga cgtagaccat atcgtgcccc agtccttcct gaaggacgac tccattgata caaagtctt gacaagaagc gacaagaaca ggggtaaaag tgataatgtg cctagcgagg aggtggtgaa aaaaatgaag aactactggc gacagctgct taatgcaaag ctcattacac aacggaagtt cgataatctg acgaaagcag agagaggtgg cttgtctgag ttggacaagg cagggtttat taagcggcag ctggtggaaa ctaggcagat cacaaagcac gtggcgcaga ttttggacag ccggatgaac acaaaatacg acgaaaatga taaactgata cgagaggtca agttatcac gctgaaaagc aagctggtgt ccgattttcg gaaagacttc cagttctaca aagttcgcga gattaataac taccatcatg ctcacgatgc gtacctgaac gctgttgtcg ggaccgcctt gataaagaag tacccaaagc tggaatccga gttcgtatac ggggattaca aagtgtacga tgtgaggaaa atgatagcca gtccgagca ggagattgga aaggccacag ctaagtactt cttttattct aacatcatga atttttttaa gacggaaatt accctggcca acggagagat cagaaagcgg cccctttatag agacaaatgg tgaaacaggt gaaatcgtct gggataaggg cagggatttc gctactgtga ggaaggtgct gagtatgcca caggtaaata tcgtgaaaaa accgaagta cagaccggag gatttccaa ggaaagcatt ttgcctaaaa gaaactcaga caagctcatc gcccgcaaga aagattggga ccctaagaaa tacggggat ttgactcacc caccgtagcc tattctgtgc tggtggtagc taaggtggaa aaaggaaagt ctaagaagct gaagtccgtg aaggaactct tgggaatcac tatcatggaa agatcatcct ttgaaaagaa ccctatcgat ttcctggagg ctaagggtta caaggaggtc aagaaagacc tcatcattaa actgccaaaa tactctctct tcgagctgga aaatggcagg aagagaatgt tggccagcgc cggagagctg caaaagggaa acgagcttgc tctgccctcc aaatatgtta ttttctctc tctcgcttcc cactatgaaa agctgaaagg gtctcccgaa gataacgagc agaagcagct gttcgtcgaa cagcacaagc actatctgga tgaaataatc gaacaaataa gcgagttcag caaaagggtt
```

```
atcctggcgg atgctaattt ggacaaagta ctgtctgctt ataacaagca ccgggataag cctattaggg aacaagccga gaatataatt cacctcttta cactcacgaa tctcggagcc cccgccgcct tcaaatactt tgatacgact atcgaccgga aacggtatac cagtaccaaa gaggtcctcg atgccaccct catccaccag tcaattactg gcctgtacga aacacggatc gacctctctc aactgggcgg cgactag.
```

The corresponding amino acid sequence of an *S. pyogenes* Cas9 molecule is set forth in SEQ ID NO: 27, which is provided below:

[SEQ ID NO: 27]
MDKKYSIGLDIGTNSVGWAVITDEYKVPSKKFKVLGNTDRHSIKKNLIG
ALLFDSGETAEATRLKRTARRRYTRRKNRICYLQEIFSNEMAKVDDSFF
HRLEESFLVEEDKKHERHPIFGNIVDEVAYHEKYPTIYHLRKKLVDSTD
KADLRLIYLALAHMIKFRGHFLIEGDLNPDNSDVDKLFIQLVQTYNQLF
EENPINASGVDAKAILSARLSKSRRLENLIAQLPGEKKNGLFGNLIALS
LGLTPNFKSNFDLAEDAKLQLSKDTYDDDLDNLLAQIGDQYADLFLAAK
NLSDAILLSDILRVNTEITKAPLSASMIKRYDEHHQDLTLLKALVRQQL
PEKYKEIFFDQSKNGYAGYIDGGASQEEFYKFIKPILEKMDGTEELLVK
LNREDLLRKQRTFDNGSIPHQIHLGELHAILRRQEDFYPFLKDNREKIE
KILTFRIPYYVGPLARGNSRFAWMTRKSEETITPWNFEEVVDKGASAQS
FIERMTNFDKNLPNEKVLPKHSLLYEYFTVYNELTKVKYVTEGMRKPAF
LSGEQKKAIVDLLFKTNRKVTVKQLKEDYFKKIECFDSVEISGVEDRFN
ASLGTYHDLLKIIKDKDFLDNEENEDILEDIVLTLTLFEDREMIEERLK
TYAHLFDDKVMKQLKRRRYTGWGRLSRKLINGIRDKQSGKTILDFLKSD
GFANRNFMQLIHDDSLTFKEDIQKAQVSGQGDSLHEHIANLAGSPAIKK
GILQTVKVVDELVKVMGRHKPENIVIEMARENQTTQKGQKNSRERMKRI
EEGIKELGSQILKEHPVENTQLQNEKLYLYYLQNGRDMYVDQELDINRL
SDYDVDHIVPQSFLKDDSIDNKVLTRSDKNRGKSDNVPSEEVVKKMKNY
WRQLLNAKLITQRKFDNLTKAERGGLSELDKAGFIKRQLVETRQITKHV
AQILDSRMNTKYDENDKLIREVKVITLKSKLVSDFRKDFQFYKVREINN
YHHAHDAYLNAVVGTALIKKYPKLESEFVYGDYKVYDVRKMIAKSEQEI
GKATAKYFFYSNIMNFFKTEITLANGEIRKRPLIETNGETGEIVWDKGR
DFATVRKVLSMPQVNIVKKTEVQTGGFSKESILPKRNSDKLIARKKDWD
PKKYGGFDSPTVAYSVLVVAKVEKGKSKKLKSVKELLGITIMERSSFEK
NPIDFLEAKGYKEVKKDLIIKLPKYSLFELENGRKRMLASAGELQKGNE
LALPSKYVNFLYLASHYEKLKGSPEDNEQKQLFVEQHKHYLDEIIEQIS
EFSKRVILADANLDKVLSAYNKHRDKPIREQAENIIHLFTLTNLGAPAA
FKYFDTTIDRKRYTSTKEVLDATLIHQSITGLYETRIDLSQLGGD

Exemplary codon optimized nucleic acid sequences encoding a Cas9 molecule of *S. aureus*, and optionally containing nuclear localization sequences (NLSs), are set forth in SEQ ID NOs: 28-32, 43, and 44, which are provided below. Another exemplary codon optimized nucleic acid sequence encoding a Cas9 molecule of *S. aureus* comprises the nucleotides 1293-4451 of SEQ ID NO: 83.

SEQ ID NO: 28 is set forth below:

```
[SEQ ID NO: 28]
atgaaaagga actacattct ggggctggac atcgggatta caagcgtggg gtatgggatt attgactatg aaacaaggga cgtgatcgac gcaggcgtca gactgttcaa ggaggccaac gtggaaaaca atgaggacg gagaagcaag aggggagcca ggcgcctgaa acgacggaga aggcacagaa tccagagggt gaagaaactg ctgttcgatt acaacctgct gaccgaccat tctgagctga gtggaattaa tccttatgaa gccagggtga aaggcctgag tcagaagctg tcagaggaag agttttccgc agctctgctg cacctggcta agcgccgagg agtgcataac gtcaatgagg tggaagagga caccggcaac gagctgtcta caaaggaaca gatctcacgc aatagcaaag ctctggaaga gaagtatgtc gcagagctgc agctggaacg gctgaagaaa gatggcgagg tgagagggtc aattaatagg ttcaagacaa gcgactacgt caaagaagcc aagcagctgc tgaaagtgca gaaggcttac caccagctgg atcagagctt catcgatact tatatcgacc tgctggagac tcggagaacc tactatgagg gaccaggaga agggagcccc ttcggatgga agacatcaa ggaatggtac gagatgctga tgggacattg cacctatttt ccagaagagc tgagaagcgt caagtacgct tataacgcag atctgtacaa cgccctgaat gacctgaaca acctggtcat caccagggat gaaaacgaga actggaata ctatgagaag ttccagatca tcgaaaacgt gtttaagcag aagaaaaagc ctacactgaa acagattgct
```

-continued

```
aaggagatcc tggtcaacga agaggacatc aagggctacc gggtgacaag cactggaaaa ccagagttca ccaatctgaa agtgtatcac gatattaagg acatcacagc acggaaagaa atcattgaga acgccgaact gctggatcag attgctaaga tcctgactat ctaccagagc tccgaggaca tccaggaaga gctgactaac ctgaacagcg agctgaccca ggaagagatc gaacagatta gtaatctgaa ggggtacacc ggaacacaca acctgtccct gaaagctatc aatctgattc tggatgagct gtggcataca aacgacaatc agattgcaat ctttaaccgg ctgaagctgg tcccaaaaaa ggtggacctg agtcagcaga agagatccc aaccacactg gtggacgatt tcattctgtc acccgtggtc aagcggagct tcatccagag catcaaagtg atcaacgcca tcatcaagaa gtacggcctg cccaatgata tcattatcga gctggctagg gagaagaaca gcaaggacgc acagaagatg atcaatgaga tgcagaaacg aaaccggcag accaatgaac gcattgaaga gattatccga actaccggga agagaacgc aaagtacctg attgaaaaaa tcaagctgca cgatatgcag gagggaaagt gtctgtattc tctggaggcc tcccccctgg aggacctgct gaacaatcca ttcaactacg aggtcgatca tattatcccc agaagcgtgt ccttcgacaa ttcctttaac aacaaggtgc tggtcaagca ggaagagaac tctaaaaagg gcaataggac tcctttccag tacctgtcta gttcagattc caagatctct tacgaaacct ttaaaaagca cattctgaat ctggccaaag gaaagggccg catcagcaag accaaaaagg agtacctgct ggaagagcgg gacatcaaca gattctccgt ccagaaggat tttattaacc ggaatctggt ggacacaaga tacgctactc gcggcctgat gaatctgctg cgatcctatt tccgggtgaa caatctggat gtgaaagtca agtccatcaa cggcgggttc acatcttttc tgaggcgcaa atggaagttt aaaaaggagc gcaacaaagg gtacaagcac catgccgaag atgctctgat tatcgcaaat gccgacttca tctttaagga gtggaaaaag ctggacaaag ccaagaaagt gatggagaac cagatgttcg aagagaagca ggccgaatct atgcccgaaa tcgagacaga acaggagtac aaggagattt tcatcactcc tcaccagatc aagcatatca aggatttcaa ggactacaag tactctcacc gggtggataa aaagcccaac agagagctga tcaatgacac cctgtatagt acaagaaaag acgataaggg gaatacctg attgtgaaca atctgaacgg actgtacgac aaagataatg acaagctgaa aaagctgatc aacaaaagtc ccgagaagct gctgatgtac caccatgatc ctcagacata tcagaaactg aagctgatta tggagcagta cggcgacgag aagaacccac tgtataagta ctatgaagag actgggaact acctgaccaa gtatagcaaa aaggataatg cccccgtgat caagaagatc aagtactatg ggaacaagct gaatgcccat ctggacatca cagacgatta ccctaacagt cgcaacaagg tggtcaagct gtcactgaag ccatacagat cgatgtcta tctggacaac ggcgtgtata aatttgtgac tgtcaagaat ctggatgtca tcaaaaagga gaactactat gaagtgaata gcaagtgcta cgaagaggct aaaaagctga aaaagattag caaccaggca gagttcatcg cctccttta caacaacgac ctgattaaga tcaatggcga actgtatagg gtcatcgggg tgaacaatga tctgctgaac cgcattgaag tgaatatgat tgacatcact taccgagagt atctggaaaa catgaatgat aagcgccccc ctcgaattat caaaacaatt
```

-continued

```
gcctctaaga ctcagagtat caaaaagtac tcaaccgaca ttctgggaaa cctgtatgag gtgaagagca aaaagcaccc tcagattatc aaaaagggc
```

SEQ ID NO: 29 is set forth below.

[SEQ ID NO: 29]
```
atgaagcgga actacatcct gggcctggac atcggcatca ccagcgtggg ctacggcatc atcgactacg agacacggga cgtgatcgat gccggcgtgc ggctgttcaa agaggccaac gtggaaaaca acgagggcag gcggagcaag agaggcgcca aaggctgaa gcggcggagg cggcatagaa tccagagagt gaagaagctg ctgttcgact acaacctgct gaccgaccac agcgagctga gcggcatcaa ccctacgag gccagagtga agggcctgag ccagaagctg agcgaggaag agttctctgc cgccctgctg cacctggcca agagaagagg cgtgcacaac gtgaacgagg tggaagagga caccggcaac gagctgtcca ccaaagagca gatcagccgg aacagcaagg ccctggaaga aaatacgtg gccgaactgc agctggaacg gctgaagaaa gacggcgaag tgcggggcag catcaacaga ttcaagacca gcgactacgt gaaagaagcc aaacagctgc tgaaggtgca gaaggcctac accagctgg accagagctt catcgacacc tacatcgacc tgctggaaac ccggcggacc tactatgagg acctggcga gggcagcccc ttcggctgga aggacatcaa agaatggtac gagatgctga tgggccactg cacctacttc cccgaggaac tgcggagcgt gaagtacgcc tacaacgccg acctgtacaa cgccctgaac gacctgaaca atctcgtgat caccagggac gagaacgaga gctggaata ttacgagaag ttccagatca tcgagaacgt gttcaagcag aagaagaagc ccaccctgaa gcagatcgcc aaagaaatcc tcgtgaacga agaggatatt aagggctaca gagtgaccag caccggcaag cccgagttca ccaacctgaa ggtgtaccac gacatcaagg acattaccgc ccggaaagag attattgaga cgccgagct gctggatcag attgccaaga tcctgaccat ctaccagagc agcgaggaca tccaggaaga actgaccaat ctgaactccg agctgaccca ggaagagatc gagcagatct ctaatctgaa gggctatacc ggcacccaca acctgagcct gaaggccatc aacctgatcc tggacgagct gtggcacacc aacgacaacc agatcgctat cttcaaccgg ctgaagctgg tgcccaagaa ggtggacctg tcccagcaga aagagatccc caccaccctg gtggacgact tcatcctgag ccccgtcgtg aagagaagct tcatccagag catcaaagtg atcaacgcca tcatcaagaa gtacggcctg cccaacgaca tcattatcga gctggcccgc gagaagaact ccaaggacgc ccagaaaatg atcaacgaga tgcagaagcg gaaccggcag accaacgagc ggatcgagga aatcatccgg accaccggca agagaacgc caagtacctg atcgagaaga tcaagctgca cgacatgcag gaaggcaagt gcctgtacag cctggaagcc atccctctgg aagatctgct gaacaacccc ttcaactatg aggtggacca catcatcccc agaagcgtgt ccttcgacaa cagcttcaac aacaaggtgc tcgtgaagca ggaagaaaac agcaagaagg caaccggac cccattccag tacctgagca gcagcgacag caagatcagc tacgaaacct tcaagaagca catcctgaat ctggccaagg gcaagggcag aatcagcaag accaagaaag agtatctgct ggaagaacgg gacatcaaca ggttctccgt gcagaaagac ttcatcaacc ggaacctggt ggataccaga tacgccacca gaggcctgat gaacctgctg cggagctact tcagagtgaa caacctggac gtgaaagtga agtccatcaa tggcggcttc accagctttc tgcggcggaa gtggaagttt aagaaagagc ggaacaaggg gtacaagcac cacgccgagg acgccctgat cattgccaac gccgatttca tcttcaaaga gtggaagaaa
```

-continued

```
ctggacaagg ccaaaaaagt gatggaaaac cagatgttcg aggaaaagca ggccgagagc atgcccgaga tcgaaaccga gcaggagtac aaagagatct tcatcacccc ccaccagatc aagcacatta aggacttcaa ggactacaag tacagccacc gggtggacaa gaagcctaat agagagctga ttaacgacac cctgtactcc acccggaagg acgacaaggg caacaccctg atcgtgaaca atctgaacgg cctgtacgac aaggacaatg acaagctgaa aaagctgatc aacaagagcc ccgaaaagct gctgatgtac caccacgacc cccagaccta ccagaaactg aagctgatta tggaacagta cggcgacgag aagaatcccc tgtacaagta ctacgaggaa accgggaact acctgaccaa gtactccaaa aaggacaacg cccccgtgat caagaagatt aagtattacg gcaacaaact gaacgcccat ctggacatca ccgacgacta ccccaacagc agaaacaagg tcgtgaagct gtccctgaag ccctacagat cgacgtgta cctggacaat ggcgtgtaca agttcgtgac cgtgaagaat ctggatgtga tcaaaaaga aaactactac gaagtgaata gcaagtgcta tgaggaagct aagaagctga agaagatcag caaccaggcc gagtttatcg cctccttcta caacaacgat ctgatcaaga tcaacggcga gctgtataga gtgatcggcg tgaacaacga cctgctgaac cggatcgaag tgaacatgat cgacatcacc taccgcgagt acctggaaaa catgaacgac aagaggcccc ccaggatcat taagacaatc gcctccaaga cccagagcat taagaagtac agcacagaca ttctgggcaa cctgtatgaa gtgaaatcta agaagcaccc tcagatcatc aaaaagggc
```

SEQ ID NO: 30 is set forth below.

[SEQ ID NO: 30]
```
atgaagcgca actacatcct cggactggac atcggcatta cctccgtggg atacggcatc atcgattacg aaactaggga tgtgatcgac gctggagtca ggctgttcaa agaggcgaac gtggagaaca acgaggggcg gcgctcaaag aggggggccc gccggctgaa gcgccgccgc agacatagaa tccagcgcgt gaagaagctg ctgttcgact acaaccttct gaccgaccac tccgaacttt ccggcatcaa cccatatgag gctagagtga agggattgtc ccaaaagctg tccgaggaag agttctccgc cgcgttgctc caccctcgcca agcgcagggg agtgcacaat gtgaacgaag tggaagaaga taccggaaac gagctgtcca ccaaggagca gatcagccgg aactccaagg ccctggaaga gaaatacgtg gcggaactgc aactggagcg gctgaagaaa gacggagaag tgcgcggctc gatcaaccgc ttcaagacct cggactacgt gaaggaggcc aagcagctcc tgaaagtgca aaaggcctat caccaacttg accagtcctt tatcgatacc tacatcgatc tgctcgagac tcggcggact tactacgagg gtccagggga gggctcccca tttggttgga aggatattaa ggagtggtac gaaatgctga tgggacactg cacatacttc cctgaggagc tgcggagcgt gaaatacgca tacaacgcag acctgtacaa cgcgctgaac gacctgaaca atctcgtgat cacccgggac gagaacgaaa agctcgagta ttacgaaaag ttccagatta ttgagaacgt gttcaaacag aagaagaagc cgacactgaa gcagattgcc aaggaaatcc tcgtgaacga agaggacatc aagggctatc gagtgaccct caacgggaaag ccggagttca ccaatctgaa ggtctaccac gacatcaaag acattaccgc ccggaaggag atcattgaga acgcggagct gttggaccag attgcgaaga ttctgaccat ctaccaatcc tccgaggata ttcaggaaga actcaccaac ctcaacagcg aactgaccca ggaggagata gagcaaatct ccaacctgaa gggctacacc ggaactcata acctgagcct gaaggccatc aacttgatcc tggacgagct gtggcacacc aacgataacc agatcgctat tttcaatcgg
```

-continued ctgaagctgg tccccaagaa agtggacctc tcacaacaaa aggagatccc tactacccttt gtggacgatt tcattctgtc ccccgtggtc aagagaagct tcatacagtc aatcaaagtg atcaatgcca ttatcaagaa atacggtctg cccaacgaca ttatcattga gctcgcccgc gagaagaact cgaaggacgc ccagaagatg attaacgaaa tgcagaagag aaccgacag actaacgaac ggatcgaaga aatcatccgg accaccggga aggaaaacgc gaagtacctg atcgaaaaga tcaagctcca tgacatgcag gaaggaaagt gtctgtactc gctggaggcc attccgctgg aggacttgct gaacaaccct tttaactacg aagtggatca tatcattccg aggagcgtgt cattcgacaa ttccttcaac aacaaggtcc tcgtgaagca ggaggaaaac tcgaagaagg gaaaccgcac gccgttccag tacctgagcg cagcgactc caagatttcc tacgaaacct tcaagaagca catcctcaac ctggcaaagg ggaagggtcg catctccaag accaagaagg aatatctgct ggaagaaaga gacatcaaca gattctccgt gcaaaaggac ttcatcaacc gcaacctcgt ggatactaga tacgctactc ggggtctgat gaacctcctg agaagctact ttagagtgaa caatctggac gtgaaggtca agtcgattaa cggaggtttc acctccttcc tgcggcgcaa gtggaagttc aagaaggaac ggaacaaggg ctacaagcac cacgccgagg acgccctgat cattgccaac gccgacttca tcttcaaaga atggaagaaa cttgacaagg ctaagaaggt catggaaaac cagatgttcg aagaaaagca ggccgagtct atgcctgaaa tcgagactga acaggagtac aaggaaatct ttattacgcc acaccagatc aaacacatca aggatttcaa ggattacaag tactcacatc gcgtggacaa aaagccgaac agggaactga tcaacgacac cctctactcc acccggaagg atgacaaagg gaataccctc atcgtcaaca accttaacgg cctgtacgac aaggacaacg ataagctgaa gaagctcatt aacaagtcgc ccgaaaagtt gctgatgtac caccacgacc ctcagactta ccagaagctc aagctgatca tggagcagta tggggacgag aaaaacccgt tgtacaagta ctacgaagaa actgggaatt atctgactaa gtactccaag aaagataacg gccccgtgat taagaagatt aagtactacg gcaacaagct gaacgcccat ctggacatca ccgatgacta ccctaattcc cgcaacaagg tcgtcaagct gagcctcaag ccctaccggt ttgatgtgta ccttgacaat ggagtgtaca agttcgtgac tgtgaagaac cttgacgtga tcaagaagga gaactactac gaagtcaact ccaagtgcta cgaggaagca aagaagttga agaagatctc gaaccaggcc gagttcattg cctccttcta taacaacgac ctgattaaga tcaacggcga actgtaccgc gtcattggcg tgaacaacga tctcctgaac cgcatcgaag tgaacatgat cgacatcact taccgggaat acctggagaa tatgaacgac aagcgcccgc cccggatcat taagactatc gcctcaaaga cccagtcgat caagaagtac agcaccgaca tcctgggcaa cctgtacgag gtcaaatcga agaagcaccc ccagatcatc aagaaggga SEQ ID NO: 31 is set forth below.

[SEQ ID NO: 31]

ATGGCCCCAAAGAAGAAGCGGAAGGTCGGTATCCACGGAGTCCCAGCAGC

CAAGCGGAACTACATCCTGGGCCTGGACATCGGCATCACCAGCGTGGGCT

ACGGCATCATCGACTACGAGACACGGGACGTGATCGATGCCGGCGTGCGG

CTGTTCAAAGAGGCCAACGTGGAAAACAACGAGGGCAGGCGGAGCAAGAG

AGGCGCCAGAAGGCTGAAGCGGCGGAGGCGGCATAGAATCCAGAGAGTGA

AGAAGCTGCTGTTCGACTACAACCTGCTGACCGACCACAGCGAGCTGAGC

GGCATCAACCCCTACGAGGCCAGAGTGAAGGGCCTGAGCCAGAAGCTGAG

CGAGGAAGAGTTCTCTGCCGCCCTGCTGCACCTGGCCAAGAGAAGAGGCG

TGCACAACGTGAACGAGGTGGAAGAGGACACCGGCAACGAGCTGTCCACC

AGAGAGCAGATCAGCCGGAACAGCAAGGCCCTGGAAGAGAAATACGTGGC

CGAACTGCAGCTGGAACGGCTGAAGAAAGACGGCGAAGTGCGGGGCAGCA

TCAACAGATTCAAGACCAGCGACTACGTGAAAGAAGCCAAACAGCTGCTG

AAGGTGCAGAAGGCCTACCACCAGCTGGACCAGAGCTTCATCGACACCTA

-continued

```
CATCGACCTGCTGGAAACCCGGCGGACCTACTATGAGGGACCTGGCGAGG
GCAGCCCCTTCGGCTGGAAGGACATCAAAGAATGGTACGAGATGCTGATG
GGCCACTGCACCTACTTCCCCGAGGAACTGCGGAGCGTGAAGTACGCCTA
CAACGCCGACCTGTACAACGCCCTGAACGACCTGAACAATCTCGTGATCA
CCAGGGACGAGAACGAGAAGCTGGAATATTACGAGAAGTTCCAGATCATC
GAGAACGTGTTCAAGCAGAAGAAGAAGCCCACCCTGAAGCAGATCGCCAA
AGAAATCCTCGTGAACGAAGAGGATATTAAGGGCTACAGAGTGACCAGCA
CCGGCAAGCCCGAGTTCACCAACCTGAAGGTGTACCACGACATCAAGGAC
ATTACCGCCCGGAAAGAGATTATTGAGAACGCCGAGCTGCTGGATCAGAT
TGCCAAGATCCTGACCATCTACCAGAGCAGCGAGGACATCCAGGAAGAAC
TGACCAATCTGAACTCCGAGCTGACCCAGGAAGAGATCGAGCAGATCTCT
AATCTGAAGGGCTATACCGGCACCCACAACCTGAGCCTGAAGGCCATCAA
CCTGATCCTGGACGAGCTGTGGCACACCAACGACAACCAGATCGCTATCT
TCAACCGGCTGAAGCTGGTGCCCAAGAAGGTGGACCTGTCCCAGCAGAAA
GAGATCCCCACCACCCTGGTGGACGACTTCATCCTGAGCCCCGTCGTGAA
GAGAAGCTTCATCCAGAGCATCAAAGTGATCAACGCCATCATCAAGAAGT
ACGGCCTGCCCAACGACATCATTATCGAGCTGGCCCGCGAGAAGAACTCC
AAGGACGCCCAGAAAATGATCAACGAGATGCAGAAGCGGAACCGGCAGAC
CAACGAGCGGATCGAGGAAATCATCCGGACCACCGGCAAAGAGAACGCCA
AGTACCTGATCGAGAAGATCAAGCTGCACGACATGCAGGAAGGCAAGTGC
CTGTACAGCCTGGAAGCCATCCCTCTGGAAGATCTGCTGAACAACCCCTT
CAACTATGAGGTGGACCACATCATCCCCAGAAGCGTGTCCTTCGACAACA
GCTTCAACAACAAGGTGCTCGTGAAGCAGGAAGAAAACAGCAAGAAGGGC
AACCGGACCCCATTCCAGTACCTGAGCAGCAGCGACAGCAAGATCAGCTA
CGAAACCTTCAAGAAGCACATCCTGAATCTGGCCAAGGGCAAGGGCAGAA
TCAGCAAGACCAAGAAAGAGTATCTGCTGGAAGAACGGGACATCAACAGG
TTCTCCGTGCAGAAAGACTTCATCAACCGGAACCTGGTGGATACCAGATA
```

```
CGCCACCAGAGGCCTGATGAACCTGCTGCGGAGCTACTTCAGAGTGAACA
ACCTGGACGTGAAAGTGAAGTCCATCAATGGCGGCTTCACCAGCTTTCTG
CGGCGGAAGTGGAAGTTTAAGAAAGAGCGGAACAAGGGGTACAAGCACCA
CGCCGAGGACGCCCTGATCATTGCCAACGCCGATTTCATCTTCAAAGAGT
GGAAGAAACTGGACAAGGCCAAAAAAGTGATGGAAAACCAGATGTTCGAG
GAAAGGCAGGCCGAGAGCATGCCCGAGATCGAAACCGAGCAGGAGTACAA
AGAGATCTTCATCACCCCCCACCAGATCAAGCACATTAAGGACTTCAAGG
ACTACAAGTACAGCCACCGGGTGGACAAGAAGCCTAATAGAGAGCTGATT
AACGACACCCTGTACTCCACCCGGAAGGACGACAAGGGCAACACCCTGAT
CGTGAACAATCTGAACGGCCTGTACGACAAGGACAATGACAAGCTGAAAA
AGCTGATCAACAAGAGCCCCGAAAAGCTGCTGATGTACCACCACGACCCC
CAGACCTACCAGAAACTGAAGCTGATTATGGAACAGTACGGCGACGAGAA
GAATCCCCTGTACAAGTACTACGAGGAAACCGGGAACTACCTGACCAAGT
ACTCCAAAAAGGACAACGGCCCCGTGATCAAGAAGATTAAGTATTACGGC
AACAAACTGAACGCCCATCTGGACATCACCGACGACTACCCCAACAGCAG
AAACAAGGTCGTGAAGCTGTCCCTGAAGCCCTACAGATTCGACGTGTACC
TGGACAATGGCGTGTACAAGTTCGTGACCGTGAAGAATCTGGATGTGATC
AAAAAAGAAAACTACTACGAAGTGAATAGCAAGTGCTATGAGGAAGCTAA
GAAGCTGAAGAAGATCAGCAACCAGGCCGAGTTTATCGCCTCCTTCTACA
ACAACGATCTGATCAAGATCAACGGCGAGCTGTATAGAGTGATCGGCGTG
AACAACGACCTGCTGAACCGGATCGAAGTGAACATGATCGACATCACCTA
CCGCGAGTACCTGGAAAACATGAACGACAAGAGGCCCCCCAGGATCATTA
AGACAATCGCCTCCAAGACCCAGAGCATTAAGAAGTACAGCACAGACATT
CTGGGCAACCTGTATGAAGTGAAATCTAAGAAGCACCCTCAGATCATCAA
AAAGGGCAAAAGGCCGGCGGCCACGAAAAAGGCCGGCCAGGCAAAAAAGA
AAAAG
```

SEQ ID NO: 32 is set forth below.

[SEQ ID NO: 32]
```
ACCGGTGCCA CCATGTACCC ATACGATGTT CCAGATTACG CTTCGCCGAA GAAAAAGCGC
AAGGTCGAAG CGTCCATGAA AGGAACTAC ATTCTGGGGC TGGACATCGG GATTACAAGC
GTGGGGTATG GGATTATTGA CTATGAAACA AGGGACGTGA TCGACGCAGG CGTCAGACTG
TTCAAGGAGG CCAACGTGGA AAACAATGAG GGACGGAGAA GCAAGAGGGG AGCCAGGCGC
CTGAAACGAC GGAGAAGGCA CAGAATCCAG AGGGTGAAGA AACTGCTGTT CGATTACAAC
CTGCTGACCG ACCATTCTGA GCTGAGTGGA ATTAATCCTT ATGAAGCCAG GGTGAAAGGC
CTGAGTCAGA AGCTGTCAGA GGAAGAGTTT TCCGCAGCTC TGCTGCACCT GGCTAAGCGC
CGAGGAGTGC ATAACGTCAA TGAGGTGGAA GAGGACACCG GCAACGAGCT GTCTACAAAG
GAACAGATCT CACGCAATAG CAAAGCTCTG GAAGAGAAGT ATGTCGCAGA GCTGCAGCTG
GAACGGCTGA AGAAAGATGG CGAGGTGAGA GGGTCAATTA ATAGGTTCAA GACAAGCGAC
TACGTCAAAG AAGCCAAGCA GCTGCTGAAA GTGCAGAAGG CTTACCACCA GCTGGATCAG
```

-continued
```
AGCTTCATCG ATACTTATAT CGACCTGCTG GAGACTCGGA GAACCTACTA TGAGGGACCA

GGAGAAGGGA GCCCCTTCGG ATGGAAAGAC ATCAAGGAAT GGTACGAGAT GCTGATGGGA

CATTGCACCT ATTTTCCAGA AGAGCTGAGA AGCGTCAAGT ACGCTTATAA CGCAGATCT

TACAACGCCC TGAATGACCT GAACAACCTG GTCATCACCA GGGATGAAAA CGAGAAACTG

GAATACTATG AGAAGTTCCA GATCATCGAA AACGTGTTTA AGCAGAAGAA AAAGCCTACA

CTGAAACAGA TTGCTAAGGA GATCCTGGTC AACGAAGAGG ACATCAAGGG CTACCGGGTG

ACAAGCACTG GAAAACCAGA GTTCACCAAT CTGAAAGTGT ATCACGATAT TAAGGACATC

ACAGCACGGA AAGAAATCAT TGAGAACGCC GAACTGCTGG ATCAGATTGC TAAGATCCTG

ACTATCTACC AGAGCTCCGA GGACATCCAG GAAGAGCTGA CTAACCTGAA CAGCGAGCTG

ACCCAGGAAG AGATCGAACA GATTAGTAAT CTGAAGGGGT ACACCGGAAC ACACAACCTG

TCCCTGAAAG CTATCAATCT GATTCTGGAT GAGCTGTGGC ATACAAACGA CAATCAGATT

GCAATCTTTA ACCGGCTGAA GCTGGTCCCA AAAAAGGTGG ACCTGAGTCA GCAGAAAGAG

ATCCCAACCA CACTGGTGGA CGATTTCATT CTGTCACCCG TGGTCAAGCG GAGCTTCATC

CAGAGCATCA AAGTGATCAA CGCCATCATC AAGAAGTACG GCCTGCCCAA TGATATCATT

ATCGAGCTGG CTAGGGAGAA GAACAGCAAG GACGCACAGA AGATGATCAA TGAGATGCAG

AAACGAAACC GGCAGACCAA TGAACGCATT GAAGAGATTA TCCGAACTAC CGGGAAAGAG

AACGCAAAGT ACCTGATTGA AAAAATCAAG CTGCACGATA TGCAGGAGGG AAAGTGTCTG

TATTCTCTGG AGGCCATCCC CCTGGAGGAC CTGCTGAACA ATCCATTCAA CTACGAGGTC

GATCATATTA TCCCCAGAAG CGTGTCCTTC GACAATTCCT TTAACAACAA GGTGCTGGTC

AAGCAGGAAG AGAACTCTAA AAAGGGCAAT AGGACTCCTT TCCAGTACCT GTCTAGTTCA

GATTCCAAGA TCTCTTACGA AACCTTTAAA AGCACATTC TGAATCTGGC CAAAGGAAAG

GGCCGCATCA GCAAGACCAA AAAGGAGTAC CTGCTGGAAG AGCGGGACAT CAACAGATTC

TCCGTCCAGA AGGATTTTAT TAACCGGAAT CTGGTGGACA CAAGATACGC TACTCGCGGC

CTGATGAATC TGCTGCGATC CTATTTCCGG GTGAACAATC TGGATGTGAA AGTCAAGTCC

ATCAACGGCG GGTTCACATC TTTTCTGAGG CGCAAATGGA AGTTTAAAAA GGAGCGCAAC

AAAGGGTACA AGCACCATGC CGAAGATGCT CTGATTATCG CAAATGCCGA CTTCATCTTT

AAGGAGTGGA AAAAGCTGGA CAAAGCCAAG AAAGTGATGG AGAACCAGAT GTTCGAAGAG

AAGCAGGCCG AATCTATGCC CGAAATCGAG ACAGAACAGG AGTACAAGGA GATTTTCATC

ACTCCTCACC AGATCAAGCA TATCAAGGAT TTCAAGGACT ACAAGTACTC TCACCGGGTG

GATAAAAAGC CCAACAGAGA GCTGATCAAT GACACCCTGT ATAGTACAAG AAAAGACGAT

AAGGGGAATA CCCTGATTGT GAACAATCTG AACGGACTGT ACGACAAAGA TAATGACAAG

CTGAAAAAGC TGATCAACAA AGTCCCGAG AAGCTGCTGA TGTACCACCA TGATCCTCAG

ACATATCAGA AACTGAAGCT GATTATGGAG CAGTACGGCG ACGAGAAGAA CCCACTGTAT

AAGTACTATG AAGAGACTGG GAACTACCTG ACCAAGTATA GCAAAAAGGA TAATGGCCCC

GTGATCAAGA AGATCAAGTA CTATGGGAAC AAGCTGAATG CCCATCTGGA CATCACAGAC

GATTACCCTA ACAGTCGCAA CAAGGTGGTC AAGCTGTCAC TGAAGCCATA CAGATTCGAT

GTCTATCTGG ACAACGGCGT GTATAAATTT GTGACTGTCA AGAATCTGGA TGTCATCAAA

AAGGAGAACT ACTATGAAGT GAATAGCAAG TGCTACGAAG AGGCTAAAAA GCTGAAAAAG

ATTAGCAACC AGGCAGAGTT CATCGCCTCC TTTTACAACA ACGACCTGAT TAAGATCAAT

GGCGAACTGT ATAGGGTCAT CGGGGTGAAC AATGATCTGC TGAACCGCAT TGAAGTGAAT

ATGATTGACA TCACTTACCG AGAGTATCTG GAAAACATGA ATGATAAGCG CCCCCCTCGA
```

-continued

```
ATTATCAAAA CAATTGCCTC TAAGACTCAG AGTATCAAAA AGTACTCAAC CGACATTCTG
GGAAACCTGT ATGAGGTGAA GAGCAAAAAG CACCCTCAGA TTATCAAAAA GGGCTAAGAA
TTC
```

SEQ ID NO: 43 is set forth below.

[SEQ ID NO: 43]
```
ATGGCCCCAAAGAAGAAGCGGAAGGTCGGTATCCACGGAGTCCCAGCAGC
CAAGCGGAACTACATCCTGGGCCTGGACATCGGCATCACCAGCGTGGGCT
ACGGCATCATCGACTACGAGACACGGGACGTGATCGATGCCGGCGTGCGG
CTGTTCAAAGAGGCCAACGTGGAAAACAACGAGGGCAGGCGGAGCAAGAG
AGGCGCCAGAAGGCTGAAGCGGCGGAGGCGGCATAGAATCCAGAGAGTGA
AGAAGCTGCTGTTCGACTACAACCTGCTGACCGACCACAGCGAGCTGAGC
GGCATCAACCCCTACGAGGCCAGAGTGAAGGGCCTGAGCCAGAAGCTGAG
CGAGGAAGAGTTCTCTGCCGCCCTGCTGCACCTGGCCAAGAGAAGAGGCG
TGCACAACGTGAACGAGGTGGAAGAGGACACCGGCAACGAGCTGTCCACC
AAAGAGCAGATCAGCCGGAACAGCAAGGCCCTGGAAGAGAAATACGTGGC
CGAACTGCAGCTGGAACGGCTGAAGAAAGACGGCGAAGTGCGGGGCAGCA
TCAACAGATTCAAGACCAGCGACTACGTGAAAGAAGCCAAACAGCTGCTG
AAGGTGCAGAAGGCCTACCACCAGCTGGACCAGAGCTTCATCGACACCTA
CATCGACCTGCTGGAAACCCGGCGGACCTACTATGAGGGACCTGGCGAGG
GCAGCCCCTTCGGCTGGAAGGACATCAAAGAATGGTACGAGATGCTGATG
GGCCACTGCACCTACTTCCCCGAGGAACTGCGGAGCGTGAAGTACGCCTA
CAACGCCGACCTGTACAACGCCCTGAACGACCTGAACAATCTCGTGATCA
CCAGGGACGAGAACGAGAAGCTGGAATATTACGAGAAGTTCCAGATCATC
GAGAACGTGTTCAAGCAGAAGAAGAAGCCCACCCTGAAGCAGATCGCCAA
AGAAATCCTCGTGAACGAAGAGGATATTAAGGGCTACAGAGTGACCAGCA
CCGGCAAGCCCGAGTTCACCAACCTGAAGGTGTACCACGACATCAAGGAC
ATTACCGCCCGGAAAGAGATTATTGAGAACGCCGAGCTGCTGGATCAGAT
TGCCAAGATCCTGACCATCTACCAGAGCAGCGAGGACATCCAGGAAGAAC
TGACCAATCTGAACTCCGAGCTGACCCAGGAAGAGATCGAGCAGATCTCT
AATCTGAAGGGCTATACCGGCACCCACAACCTGAGCCTGAAGGCCATCAA
CCTGATCCTGGACGAGCTGTGGCACACCAACGACAACCAGATCGCTATCT
TCAACCGGCTGAAGCTGGTGCCCAAGAAGGTGGACCTGTCCCAGCAGAAA
GAGATCCCCACCACCCTGGTGGACGACTTCATCCTGAGCCCCGTCGTGAA
GAGAAGCTTCATCCAGAGCATCAAAGTGATCAACGCCATCATCAAGAAGT
ACGGCCTGCCCAACGACATCATTATCGAGCTGGCCCGCGAGAAGAACTCC
AAGGACGCCCAGAAAATGATCAACGAGATGCAGAAGCGGAACCGGCAGAC
CAACGAGCGGATCGAGGAAATCATCCGGACCACCGGCAAAGAGAACGCCA
AGTACCTGATCGAGAAGATCAAGCTGCACGACATGCAGGAAGGCAAGTGC
CTGTACAGCCTGGAAGCCATCCCTCTGGAAGATCTGCTGAACAACCCCTT
CAACTATGAGGTGGACCACATCATCCCCAGAAGCGTGTCCTTCGACAACA
GCTTCAACAACAAGGTGCTCGTGAAGCAGGAAGAAAACAGCAAGAAGGGC
AACCGGACCCCATTCCAGTACCTGAGCAGCAGCGACAGCAAGATCAGCTA
CGAAACCTTCAAGAAGCACATCCTGAATCTGGCCAAGGGCAAGGGCAGAA
TCAGCAAGACCAAGAAAGAGTATCTGCTGGAAGAACGGGACATCAACAGG
TTCTCCGTGCAGAAAGACTTCATCAACCGGAACCTGGTGGATACCAGATA
CGCCACCAGAGGCCTGATGAACCTGCTGCGGAGCTACTTCAGAGTGAACA
ACCTGGACGTGAAAGTGAAGTCCATCAATGGCGGCTTCACCAGCTTTCTG
CGGCGGAAGTGGAAGTTTAAGAAAGAGCGGAACAAGGGGTACAAGCACCA
CGCCGAGGACGCCCTGATCATTGCCAACGCCGATTTCATCTTCAAAGAGT
GGAAGAAACTGGACAAGGCCAAAAAAGTGATGGAAAACCAGATGTTCGAG
GAAAAGCAGGCCGAGAGCATGCCCGAGATCGAAACCGAGCAGGAGTACAA
AGAGATCTTCATCACCCCCCACCAGATCAAGCACATTAAGGACTTCAAGG
ACTACAAGTACAGCCACCGGGTGGACAAGAAGCCTAATAGAGAGCTGATT
AACGACACCCTGTACTCCACCCGGAAGGACGACAAGGGCAACACCCTGAT
CGTGAACAATCTGAACGGCCTGTACGACAAGGACAATGACAAGCTGAAAA
AGCTGATCAACAAGAGCCCCGAAAAGCTGCTGATGTACCACCACGACCCC
CAGACCTACCAGAAACTGAAGCTGATTATGGAACAGTACGGCGACGAGAA
GAATCCCCTGTACAAGTACTACGAGGAAACCGGGAACTACCTGACCAAGT
ACTCCAAAAAGGACAACGGCCCCGTGATCAAGAAGATTAAGTATTACGGC
AACAAACTGAACGCCCATCTGGACATCACCGACGACTACCCCAACAGCAG
AAACAAGGTCGTGAAGCTGTCCCTGAAGCCCTACAGATTCGACGTGTACC
TGGACAATGGCGTGTACAAGTTCGTGACCGTGAAGAATCTGGATGTGATC
AAAAAAGAAAACTACTACGAAGTGAATAGCAAGTGCTATGAGGAAGCTAA
GAAGCTGAAGAAGATCAGCAACCAGGCCGAGTTTATCGCCTCCTTCTACA
ACAACGATCTGATCAAGATCAACGGCGAGCTGTATAGAGTGATCGGCGTG
AACAACGACCTGCTGAACCGGATCGAAGTGAACATGATCGACATCACCTA
CCGCGAGTACCTGGAAAACATGAACGACAAGAGGCCCCCCAGGATCATTA
AGACAATCGCCTCCAAGACCCAGAGCATTAAGAAGTACAGCACAGACATT
CTGGGCAACCTGTATGAAGTGAAATCTAAGAAGCACCCTCAGATCATCAA
AAAGGGCAAAGGCCGGCGGCCACGAAAAAGGCCGGCCAGGCAAAAAAGA
AAAAG
```

In some embodiments, the nucleotide sequence encoding a S. aureus Cas9 molecule includes a nucleotide sequence of SEQ ID NO: 44, which is provided below:

[SEQ ID NO: 44]
AAGCGGAACTACATCCTGGGCCTGGACATCGGCATCACCAGCGTGGGCTA
CGGCATCATCGACTACGAGACACGGGACGTGATCGATGCCGGCGTGCGGC
TGTTCAAAGAGGCCAACGTGGAAAACAACGAGGGCAGGCGGAGCAAGAGA
GGCGCCAGAAGGCTGAAGCGGCGGAGGCGGCATAGAATCCAGAGAGTGAA
GAAGCTGCTGTTCGACTACAACCTGCTGACCGACCACAGCGAGCTGAGCG
GCATCAACCCCTACGAGGCCAGAGTGAAGGGCCTGAGCCAGAAGCTGAGC
GAGGAAGAGTTCTCTGCCGCCCTGCTGCACCTGGCCAAGAGAAGAGGCGT
GCACAACGTGAACGAGGTGGAAGAGGACACCGGCAACGAGCTGTCCACCA
AGGAGCAGATCAGCCGGAACAGCAAGGCCCTGGAAGAGAAATACGTGGCC
GAACTGCAGCTGGAACGGCTGAAGAAAGACGGCGAAGTGCGGGGCAGCAT
CAACAGATTCAAGACCAGCGACTACGTGAAAGAAGCCAAACAGCTGCTGA
AGGTGCAGAAGGCCTACCACCAGCTGGACCAGAGCTTCATCGACACCTAC
ATCGACCTGCTGGAAACCCGGCGGACCTACTATGAGGGACCTGGCGAGGG
CAGCCCCTTCGGCTGGAAGGACATCAAAGAATGGTACGAGATGCTGATGG
GCCACTGCACCTACTTCCCCGAGGAACTGCGGAGCGTGAAGTACGCCTAC
AACGCCGACCTGTACAACGCCCTGAACGACCTGAACAATCTCGTGATCAC
CAGGGACGAGAACGAGAAGCTGGAATATTACGAGAAGTTCCAGATCATCG
AGAACGTGTTCAAGCAGAAGAAGAAGCCCACCCTGAAGCAGATCGCCAAA
GAAATCCTCGTGAACGAAGAGGATATTAAGGGCTACAGAGTGACCAGCAC
CGGCAAGCCCGAGTTCACCAACCTGAAGGTGTACCACGACATCAAGGACA
TTACCGCCCGGAAAGAGATTATTGAGAACGCCGAGCTGCTGGATCAGATT
GCCAAGATCCTGACCATCTACCAGAGCAGCGAGGACATCCAGGAAGAACT
GACCAATCTGAACTCCGAGCTGACCCAGGAAGAGATCGAGCAGATCTCTA
ATCTGAAGGGCTATACCGGCACCCACAACCTGAGCCTGAAGGCCATCAAC
CTGATCCTGGACGAGCTGTGGCACACCAACGACAACCAGATCGCTATCTT
CAACCGGCTGAAGCTGGTGCCCAAGAAGGTGGACCTGTCCCAGCAGAAAG
AGATCCCCACCACCCTGGTGGACGACTTCATCCTGAGCCCCGTCGTGAAG
AGAAGCTTCATCCAGAGCATCAAAGTGATCAACGCCATCATCAAGAAGTA
CGGCCTGCCCAACGACATCATTATCGAGCTGGCCCGCGAGAAGAACTCCA
AGGACGCCCAGAAAATGATCAACGAGATGCAGAAGCGGAACCGGCAGACC
AACGAGCGGATCGAGGAAATCATCCGGACCACCGGCAAGAGAACGCCAA
GTACCTGATCGAGAAGATCAAGCTGCACGACATGCAGGAAGGCAAGTGCC
TGTACAGCCTGGAAGCCATCCCTCTGGAAGATCTGCTGAACAACCCCTTC
AACTATGAGGTGGACCACATCATCCCCAGAAGCGTGTCCTTCGACAACAG
CTTCAACAACAAGGTGCTCGTGAAGCAGGAAGAAAACAGCAAGAAGGCA
ACCGGACCCCATTCCAGTACCTGAGCAGCAGCGACAGCAAGATCAGCTAC
GAAACCTTCAAGAAGCACATCCTGAATCTGGCCAAGGGCAAGGGCAGAAT
CAGCAAGACCAAGAAAGAGTATCTGCTGGAAGAACGGGACATCAACAGGT

TCTCCGTGCAGAAAGACTTCATCAACCGGAACCTGGTGGATACCAGATAC
GCCACCAGAGGCCTGATGAACCTGCTGCGGAGCTACTTCAGAGTGAACAA
CCTGGACGTGAAAGTGAAGTCCATCAATGGCGGCTTCACCAGCTTTCTGC
GGCGGAAGTGGAAGTTTAAGAAAGAGCGGAACAAGGGGTACAAGCACCAC
GCCGAGGACGCCCTGATCATTGCCAACGCCGATTTCATCTTCAAAGAGTG
GAAGAAACTGGACAAGGCCAAAAAAGTGATGGAAACCAGATGTTCGAGG
AAAAGCAGGCCGAGAGCATGCCCGAGATCGAAACCGAGCAGGAGTACAAA
GAGATCTTCATCACCCCCCCACCAGATCAAGCACATTAAGGACTTCAAGGA
CTACAAGTACAGCCACCGGGTGGACAAGAAGCCTAATAGAGAGCTGATTA
ACGACACCCTGTACTCCACCCGGAAGGACGACAAGGGCAACACCCTGATC
GTGAACAATCTGAACGGCCTGTACGACAAGGACAATGACAAGCTGAAAAA
GCTGATCAACAAGAGCCCCGAAAAGCTGCTGATGTACCACCACGACCCCC
AGACCTACCAGAAACTGAAGCTGATTATGGAACAGTACGGCGACGAGAAG
AATCCCCTGTACAAGTACTACGAGGAAACCGGGAACTACCTGACCAAGTA
CTCCAAAAAGGACAACGGCCCCGTGATCAAGAAGATTAAGTATTACGGCA
ACAAACTGAACGCCCATCTGGACATCACCGACGACTACCCCAACAGCAGA
AACAAGGTCGTGAAGCTGTCCCTGAAGCCCTACAGATTCGACGTGTACCT
GGACAATGGCGTGTACAAGTTCGTGACCGTGAAGAATCTGGATGTGATCA
AAAAAGAAAACTACTACGAAGTGAATAGCAAGTGCTATGAGGAAGCTAAG
AAGCTGAAGAAGATCAGCAACCAGGCCGAGTTTATCGCCTCCTTCTACAA
CAACGATCTGATCAAGATCAACGGCGAGCTGTATAGAGTGATCGGCGTGA
ACAACGACCTGCTGAACCGGATCGAAGTGAACATGATCGACATCACCTAC
CGCGAGTACCTGGAAAACATGAACGACAAGAGGCCCCCCAGGATCATTAA
GACAATCGCCTCCAAGACCCAGAGCATTAAGAAGTACAGCACAGACATTC
TGGGCAACCTGTATGAAGTGAAATCTAAGAAGCACCCTCAGATCATCAAA
AAGGGC

An amino acid sequence of an S. aureus Cas9 molecule is set forth in SEQ ID NO: 33, which is provided below.

[SEQ ID NO: 33]
MKRNYILGLDIGITSVGYGIIDYETRDVIDAGVRLFKEANVENNEGRRSK
RGARRLKRRRRHRIQRVKKLLFDYNLLTDHSELSGINPYEARVKGLSQKL
SEEEFSAALLHLAKRRGVHNVNEVEEDTGNELSTKEQISRNSKALEEKYV
AELQLERLKKDGEVRGSINRFKTSDYVKEAKQLLKVQKAYHQLDQSFIDT
YIDLLETRRTYYEGPGEGSPFGWKDIKEWYEMLMGHCTYFPEELRSVKYA
YNADLYNALNDLNNLVITRDENEKLEYYEKFQIIENVFKQKKKPTLKQIA
KEILVNEEDIKGYRVTSTGKPEFTNLKVYHDIKDITARKEIIENAELLDQ
IAKILTIYQSSEDIQEELTNLNSELTQEEIEQISNLKGYTGTHNLSLKAI
NLILDELWHTNDNQIAIFNRLKLVPKKVDLSQQKEIPTTLVDDFILSPVV
KRSFIQSIKVINAIIKKYGLPNDIIIELAREKNSKDAQKMINEMQKRNRQ
TNERIEEIIRTTGKENAKYLIEKIKLHDMQEGKCLYSLEAIPLEDLLNNP

-continued

FNYEVDHIIPRSVSFDNSFNNKVLVKQEENSKKGNRTPFQYLSSSDSKIS

YETFKKHILNLAKGKGRISKTKKEYLLEERDINRFSVQKDFINRNLVDTR

YATRGLMNLLRSYFRVNNLDVKVKSINGGFTSFLRRKWKFKKERNKGYKH

HAEDALIIANADFIFKEWKKLDKAKKVMENQMFEEKQAESMPEIETEQEY

KEIFITPHQIKHIKDFKDYKYSHRVDKKPNRELINDTLYSTRKDDKGNTL

IVNNLNGLYDKDNDKLKKLINKSPEKLLMYHHDPQTYQKLKLIMEQYGDE

KNPLYKYYEETGNYLTKYSKKDNGPVIKKIKYYGNKLNAHLDITDDYPNS

RNKVVKLSLKPYRFDVYLDNGVYKFVTVKNLDVIKKENYYEVNSKCYEEA

KKLKKISNQAEFIASFYNNDLIKINGELYRVIGVNNDLLNRIEVNMIDIT

YREYLENMNDKRPPRIIKTIASKTQSIKKYSTDILGNLYEVKSKKHPQII

KKG

An amino acid sequence of an *S. aureus* Cas9 molecule is set forth in SEQ ID NO: 45, which is provided below.

[SEQ ID NO: 45]
KRNYILGLDIGITSVGYGIIDYETRDVIDAGVRLFKEANVENNEGRRSKR

GARRLKRRRRHRIQRVKKLLFDYNLLTDHSELSGINPYEARVKGLSQKLS

EEEFSAALLHLAKRRGVHNVNEVEEDTGNELSTKEQISRNSKALEEKYVA

ELQLERLKKDGEVRGSINRFKTSDYVKEAKQLLKVQKAYHQLDQSFIDTY

IDLLETRRTYYEGPGEGSPFGWKDIKEWYEMLMGHCTYFPEELRSVKYAY

NADLYNALNDLNNLVITRDENEKLEYYEKFQIIENVFKQKKKPTLKQIAK

EILVNEEDIKGYRVTSTGKPEFTNLKVYHDIKDITARKEIIENAELLDQI

AKILTIYQSSEDIQEELTNLNSELTQEEIEQISNLKGYTGTHNLSLKAIN

LILDELWHTNDNQIAIFNRLKLVPKKVDLSQQKEIPTTLVDDFILSPVVK

RSFIQSIKVINAIIKKYGLPNDIIIELAREKNSKDAQKMINEMQKRNRQT

NERIEEIIRTTGKENAKYLIEKIKLHDMQEGKCLYSLEAIPLEDLLNNPF

NYEVDHIIPRSVSFDNSFNNKVLVKQEENSKKGNRTPFQYLSSSDSKISY

ETFKKHILNLAKGKGRISKTKKEYLLEERDINRFSVQKDFINRNLVDTRY

ATRGLMNLLRSYFRVNNLDVKVKSINGGFTSFLRRKWKFKKERNKGYKHH

AEDALIIANADFIFKEWKKLDKAKKVMENQMFEEKQAESMPEIETEQEYK

EIFITPHQIKHIKDFKDYKYSHRVDKKPNRELINDTLYSTRKDDKGNTLI

VNNLNGLYDKDNDKLKKLINKSPEKLLMYHHDPQTYQKLKLIMEQYGDEK

NPLYKYYEETGNYLTKYSKKDNGPVIKKIKYYGNKLNAHLDITDDYPNSR

NKVVKLSLKPYRFDVYLDNGVYKFVTVKNLDVIKKENYYEVNSKCYEEAK

KLKKISNQAEFIASFYNNDLIKINGELYRVIGVNNDLLNRIEVNMIDITY

REYLENMNDKRPPRIIKTIASKTQSIKKYSTDILGNLYEVKSKKHPQIIK

KG

Alternatively or additionally, the CRISPR/Cas9-based gene editing system can include a fusion protein. The fusion protein can comprise two heterologous polypeptide domains, wherein the first polypeptide domain comprises a Cas protein and the second polypeptide domain has an activity such as transcription activation activity, transcription repression activity, transcription release factor activity, histone modification activity, nuclease activity, nucleic acid association activity, methylase activity, or demethylase activity. The fusion protein can include a Cas9 protein or a mutated Cas9 protein, fused to a second polypeptide domain that has an activity such as transcription activation activity, transcription repression activity, transcription release factor activity, histone modification activity, nuclease activity, nucleic acid association activity, methylase activity, or demethylase activity.

(a) Transcription Activation Activity

The second polypeptide domain can have transcription activation activity, i.e., a transactivation domain. For example, gene expression of endogenous mammalian genes, such as human genes, can be achieved by targeting a fusion protein of iCas9 and a transactivation domain to mammalian promoters via combinations of gRNAs. The transactivation domain can include a VP 16 protein, multiple VP 16 proteins, such as a VP48 domain or VP64 domain, or p65 domain of NF kappa B transcription activator activity. For example, the fusion protein may be iCas9-VP64.

(b) Transcription Repression Activity

The second polypeptide domain can have transcription repression activity. The second polypeptide domain can have a Kruppel associated box activity, such as a KRAB domain, ERF repressor domain activity, Mxil repressor domain activity, SID4X repressor domain activity, Mad-SID repressor domain activity or TATA box binding protein activity. For example, the fusion protein may be dCas9-KRAB.

(c) Transcription Release Factor Activity

The second polypeptide domain can have transcription release factor activity. The second polypeptide domain can have eukaryotic release factor 1 (ERF1) activity or eukaryotic release factor 3 (ERF3) activity.

(d) Histone Modification Activity

The second polypeptide domain can have histone modification activity. The second polypeptide domain can have histone deacetylase, histone acetyltransferase, histone demethylase, or histone methyltransferase activity. The histone acetyltransferase may be p300 or CREB-binding protein (CBP) protein, or fragments thereof. For example, the fusion protein may be dCas9-p300.

(e) Nuclease Activity

The second polypeptide domain can have nuclease activity that is different from the nuclease activity of the Cas9 protein. A nuclease, or a protein having nuclease activity, is an enzyme capable of cleaving the phosphodiester bonds between the nucleotide subunits of nucleic acids. Nucleases are usually further divided into endonucleases and exonucleases, although some of the enzymes may fall in both categories. Well known nucleases are deoxyribonuclease and ribonuclease.

(f) Nucleic Acid Association Activity

The second polypeptide domain can have nucleic acid association activity or nucleic acid binding protein-DNA-binding domain (DBD) is an independently folded protein domain that contains at least one motif that recognizes double- or single-stranded DNA. A DBD can recognize a specific DNA sequence (a recognition sequence) or have a general affinity to DNA. nucleic acid association region selected from the group consisting of helix-turn-helix region, leucine zipper region, winged helix region, winged helix-turn-helix region, helix-loop-helix region, immunoglobulin fold, B3 domain, Zinc finger, HMG-box, Wor3 domain, TAL effector DNA-binding domain.

(g) Methylase Activity

The second polypeptide domain can have methylase activity, which involves transferring a methyl group to DNA, RNA, protein, small molecule, cytosine or adenine. The second polypeptide domain may include a DNA methyltransferase.

(h) Demethylase Activity

The second polypeptide domain can have demethylase activity. The second polypeptide domain can include an enzyme that remove methyl (CH3-) groups from nucleic acids, proteins (in particular histones), and other molecules. Alternatively, the second polypeptide can covert the methyl group to hydroxymethylcytosine in a mechanism for demethylating DNA. The second polypeptide can catalyze this reaction. For example, the second polypeptide that catalyzes this reaction can be Tet1.

(b) gRNA Targeting the Dystrophin Gene

The CRISPR/Cas9-based gene editing system includes at least one gRNA molecule, e.g., two gRNA molecules. The gRNA provides the targeting of a CRISPR/Cas9-based gene editing system. The gRNA is a fusion of two noncoding RNAs: a crRNA and a tracrRNA. The sgRNA may target any desired DNA sequence by exchanging the sequence encoding a 20 bp protospacer which confers targeting specificity through complementary base pairing with the desired DNA target. gRNA mimics the naturally occurring crRNA:tracrRNA duplex involved in the Type II Effector system. This duplex, which may include, for example, a 42-nucleotide crRNA and a 75-nucleotide tracrRNA, acts as a guide for the Cas9 to cleave the target nucleic acid. The "target region", "target sequence" or "protospacer" as used interchangeably herein refers to the region of the target gene (e.g., a dystrophin gene) to which the CRISPR/Cas9-based gene editing system targets. The CRISPR/Cas9-based gene editing system may include at least one gRNA, wherein the gRNAs target different DNA sequences. The target DNA sequences may be overlapping. The target sequence or protospacer is followed by a PAM sequence at the 3' end of the protospacer. Different Type II systems have differing PAM requirements. For example, the *Streptococcus pyogenes* Type II system uses an "NGG" sequence, where "N" can be any nucleotide. In some embodiments, the PAM sequence may be "NGG", where "N" can be any nucleotide. In some embodiments, the PAM sequence may be NNGRRT (SEQ ID NO: 24) or NNGRRV (SEQ ID NO: 25).

The number of gRNA molecule encoded by a presently disclosed genetic construct (e.g., an AAV vector) can be at least 1 gRNA, at least 2 different gRNA, at least 3 different gRNA at least 4 different gRNA, at least 5 different gRNA, at least 6 different gRNA, at least 7 different gRNA, at least 8 different gRNA, at least 9 different gRNA, at least 10 different gRNAs, at least 11 different gRNAs, at least 12 different gRNAs, at least 13 different gRNAs, at least 14 different gRNAs, at least 15 different gRNAs, at least 16 different gRNAs, at least 17 different gRNAs, at least 18 different gRNAs, at least 18 different gRNAs, at least 20 different gRNAs, at least 25 different gRNAs, at least 30 different gRNAs, at least 35 different gRNAs, at least 40 different gRNAs, at least 45 different gRNAs, or at least 50 different gRNAs. The number of gRNA encoded by a presently disclosed vector can be between at least 1 gRNA to at least 50 different gRNAs, at least 1 gRNA to at least 45 different gRNAs, at least 1 gRNA to at least 40 different gRNAs, at least 1 gRNA to at least 35 different gRNAs, at least 1 gRNA to at least 30 different gRNAs, at least 1 gRNA to at least 25 different gRNAs, at least 1 gRNA to at least 20 different gRNAs, at least 1 gRNA to at least 16 different gRNAs, at least 1 gRNA to at least 12 different gRNAs, at least 1 gRNA to at least 8 different gRNAs, at least 1 gRNA to at least 4 different gRNAs, at least 4 gRNAs to at least 50 different gRNAs, at least 4 different gRNAs to at least 45 different gRNAs, at least 4 different gRNAs to at least 40 different gRNAs, at least 4 different gRNAs to at least 35 different gRNAs, at least 4 different gRNAs to at least 30 different gRNAs, at least 4 different gRNAs to at least 25 different gRNAs, at least 4 different gRNAs to at least 20 different gRNAs, at least 4 different gRNAs to at least 16 different gRNAs, at least 4 different gRNAs to at least 12 different gRNAs, at least 4 different gRNAs to at least 8 different gRNAs, at least 8 different gRNAs to at least 50 different gRNAs, at least 8 different gRNAs to at least 45 different gRNAs, at least 8 different gRNAs to at least 40 different gRNAs, at least 8 different gRNAs to at least 35 different gRNAs, 8 different gRNAs to at least 30 different gRNAs, at least 8 different gRNAs to at least 25 different gRNAs, 8 different gRNAs to at least 20 different gRNAs, at least 8 different gRNAs to at least 16 different gRNAs, or 8 different gRNAs to at least 12 different gRNAs. In certain embodiments, the genetic construct (e.g., an AAV vector) encodes one gRNA molecule, i.e., a first gRNA molecule, and optionally a Cas9 molecule. In certain embodiments, a first genetic construct (e.g., a first AAV vector) encodes one gRNA molecule, i.e., a first gRNA molecule, and optionally a Cas9 molecule, and a second genetic construct (e.g., a second AAV vector) encodes one gRNA molecule, i.e., a second gRNA molecule, and optionally a Cas9 molecule.

The gRNA molecule comprises a targeting domain, which is a complementary polynucleotide sequence of the target DNA sequence followed by a PAM sequence. The gRNA may comprise a "G" at the 5' end of the targeting domain or complementary polynucleotide sequence. The targeting domain of a gRNA molecule may comprise at least a 10 base pair, at least a 11 base pair, at least a 12 base pair, at least a 13 base pair, at least a 14 base pair, at least a 15 base pair, at least a 16 base pair, at least a 17 base pair, at least a 18 base pair, at least a 19 base pair, at least a 20 base pair, at least a 21 base pair, at least a 22 base pair, at least a 23 base pair, at least a 24 base pair, at least a 25 base pair, at least a 30 base pair, or at least a 35 base pair complementary polynucleotide sequence of the target DNA sequence followed by a PAM sequence. In certain embodiments, the targeting domain of a gRNA molecule has 19-25 nucleotides in length. In certain embodiments, the targeting domain of a gRNA molecule is 20 nucleotides in length. In certain embodiments, the targeting domain of a gRNA molecule is 21 nucleotides in length. In certain embodiments, the targeting domain of a gRNA molecule is 22 nucleotides in length. In certain embodiments, the targeting domain of a gRNA molecule is 23 nucleotides in length.

The gRNA may target a region of the dystrophin gene (DMD). In certain embodiments, the gRNA can target at least one of exons, introns, the promoter region, the enhancer region, the transcribed region of the dystrophin gene. In certain embodiments, the gRNA molecule targets intron 50 of the human dystrophin gene. In certain embodiments, the gRNA molecule targets intron 51 of the human dystrophin gene. In certain embodiments, the gRNA molecule targets exon 51 of the human dystrophin gene. The gRNA may include a targeting domain that comprises a nucleotide sequence set forth in SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, or a complement thereof.

Single or multiplexed gRNAs can be designed to restore the dystrophin reading frame by targeting the mutational hotspot at exon 51 or and introducing either intraexonic small insertions and deletions, or excision of exon 51. Following treatment with a presently disclosed vector, dystrophin expression can be restored in Duchenne patient muscle cells in vitro. Human dystrophin was detected in vivo following transplantation of genetically corrected patient cells into immunodeficient mice. Significantly, the unique multiplex gene editing capabilities of the CRISPR/Cas9-based gene editing system enable efficiently generating large deletions of this mutational hotspot region that can correct up to 62% of patient mutations by universal or patient-specific gene editing approaches. In some embodiments, candidate gRNAs are evaluated and chosen based on off-target activity, on-target activity as measured by surveyor, and distance from the exon.

3. DNA TARGETING COMPOSITIONS

The present invention is also directed to DNA targeting compositions that comprise such genetic constructs. The DNA targeting compositions include at least one gRNA molecule (e.g., two gRNA molecules) that targets a dystrophin gene (e.g., human dystrophin gene), as described above. The at least one gRNA molecule can bind and recognize a target region. The target regions can be chosen immediately upstream of possible out-of-frame stop codons such that insertions or deletions during the repair process restore the dystrophin reading frame by frame conversion. Target regions can also be splice acceptor sites or splice donor sites, such that insertions or deletions during the repair process disrupt splicing and restore the dystrophin reading frame by splice site disruption and exon exclusion. Target regions can also be aberrant stop codons such that insertions or deletions during the repair process restore the dystrophin reading frame by eliminating or disrupting the stop codon.

In certain embodiments, the presently disclosed DNA targeting composition includes a first gRNA and a second gRNA, wherein the first gRNA molecule and the second gRNA molecule comprise a targeting domain that comprises a nucleotide sequence set forth in SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, or a complement thereof. In certain embodiments, the first gRNA molecule and the second gRNA molecule comprise different targeting domains. In certain embodiments, the first gRNA molecule is SEQ ID NO: 1, SEQ ID NO: 3, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, or SEQ ID NO: 15, and the second gRNA molecule is SEQ ID NO: 2, SEQ ID NO: 4, SEQ ID NO: 5, SEQ ID NO: 6, SEQ ID NO: 16, SEQ ID NO: 17, SEQ ID NO: 18, or SEQ ID NO: 19. In certain embodiments, the first gRNA molecule is selected from the group consisting of SEQ ID NO: 1, SEQ ID NO: 11, SEQ ID NO: 12, SEQ ID NO: 13, SEQ ID NO: 14 and SEQ ID NO: 15, and the second gRNA molecule is selected from the group consisting of SEQ ID NO: 2, SEQ ID NO: 4, SEQ ID NO: 16, SEQ ID NO: 17, SEQ ID NO: 18, and SEQ ID NO: 19.

In certain embodiments, the first gRNA molecule and the second gRNA molecule are selected from the group consisting of: (i) a first gRNA molecule comprising a targeting domain that comprises a nucleotide sequence set forth in SEQ ID NO: 1, and a second gRNA molecule comprising a targeting domain that comprises a nucleotide sequence set forth in SEQ ID NO: 2; (ii) a first gRNA molecule comprising a targeting domain that comprises a nucleotide sequence set forth in SEQ ID NO: 11, and a second gRNA molecule comprising a targeting domain that comprises a nucleotide sequence set forth in SEQ ID NO: 4; (iii) a first gRNA molecule comprising a targeting domain that comprises a nucleotide sequence set forth in SEQ ID NO: 15, and a second gRNA molecule comprising a targeting domain that comprises a nucleotide sequence set forth in SEQ ID NO: 19; (iv) a first gRNA molecule comprising a targeting domain that comprises a nucleotide sequence set forth in SEQ ID NO: 15, and a second gRNA molecule comprising a targeting domain that comprises a nucleotide sequence set forth in SEQ ID NO: 18; (v) a first gRNA molecule comprising a targeting domain that comprises a nucleotide sequence set forth in SEQ ID NO: 15, and a second gRNA molecule comprising a targeting domain that comprises a nucleotide sequence set forth in SEQ ID NO: 4; (vi) a first gRNA molecule comprising a targeting domain that comprises a nucleotide sequence set forth in SEQ ID NO: 14, and a second gRNA molecule comprising a targeting domain that comprises a nucleotide sequence set forth in SEQ ID NO: 19; (vii) a first gRNA molecule comprising a targeting domain that comprises a nucleotide sequence set forth in SEQ ID NO: 14, and a second gRNA molecule comprising a targeting domain that comprises a nucleotide sequence set forth in SEQ ID NO: 18; (viii) a first gRNA molecule comprising a targeting domain that comprises a nucleotide sequence set forth in SEQ ID NO: 14, and a second gRNA molecule comprising a targeting domain that comprises a nucleotide sequence set forth in SEQ ID NO: 4; (ix) a first gRNA molecule comprising a targeting domain that comprises a nucleotide sequence set forth in SEQ ID NO: 11, and a second gRNA molecule comprising a targeting domain that comprises a nucleotide sequence set forth in SEQ ID NO: 19; (x) a first gRNA molecule comprising a targeting domain that comprises a nucleotide sequence set forth in SEQ ID NO: 14, and a second gRNA molecule comprising a targeting domain that comprises a nucleotide sequence set forth in SEQ ID NO: 15; (xi) a first gRNA molecule comprising a targeting domain that comprises a nucleotide sequence set forth in SEQ ID NO: 11, and a second gRNA molecule comprising a targeting domain that comprises a nucleotide sequence set forth in SEQ ID NO: 18; and (xii) a first gRNA molecule comprising a targeting domain that comprises a nucleotide sequence set forth in SEQ ID NO: 41, and a second gRNA molecule comprising a targeting domain that comprises a nucleotide sequence set forth in SEQ ID NO: 42. In some embodiments, the DNA targeting composition includes a nucleotide sequence set forth in SEQ ID NO: 37 and/or a nucleotide sequence set forth in SEQ ID NO: 38.

In certain embodiments, the DNA targeting composition may further include at least one Cas9 molecule or a Cas9 fusion protein that recognizes a PAM of either NNGRRT (SEQ ID NO: 24) or NNGRRV (SEQ ID NO: 25). In some embodiments, the DNA targeting composition includes a nucleotide sequence set forth in SEQ ID NO: 83 or SEQ ID NO: 84 In certain embodiments, the vector is configured to form a first and a second double strand break in a first and a second intron flanking exon 51 of the human dystrophin gene, respectively, thereby deleting a segment of the dystrophin gene comprising exon 51.

The deletion efficiency of the presently disclosed vectors can be related to the deletion size, i.e., the size of the segment deleted by the vectors. In certain embodiments, the length or size of specific deletions is determined by the distance between the PAM sequences in the gene being targeted (e.g., a dystrophin gene). In certain embodiments, a specific deletion of a segment of the dystrophin gene, which is defined in terms of its length and a sequence it comprises (e.g., exon 51), is the result of breaks made adjacent to specific PAM sequences within the target gene (e.g., a dystrophin gene).

In certain embodiments, the deletion size is about 50 to about 2,000 base pairs (bp), e.g., about 50 to about 1999 bp, about 50 to about 1900 bp, about 50 to about 1800 bp, about 50 to about 1700 bp, about 50 to about 1650 bp, about 50 to about 1600 bp, about 50 to about 1500 bp, about 50 to about 1400 bp, about 50 to about 1300 bp, about 50 to about 1200 bp, about 50 to about 1150 bp, about 50 to about 1100 bp, about 50 to about 1000 bp, about 50 to about 900 bp, about 50 to about 850 bp, about 50 to about 800 bp, about 50 to about 750 bp, about 50 to about 700 bp, about 50 to about 600 bp, about 50 to about 500 bp, about 50 to about 400 bp, about 50 to about 350 bp, about 50 to about 300 bp, about 50 to about 250 bp, about 50 to about 200 bp, about 50 to about 150 bp, about 50 to about 100 bp, about 100 to about 1999 bp, about 100 to about 1900 bp, about 100 to about 1800 bp, about 100 to about 1700 bp, about 100 to about 1650 bp, about 100 to about 1600 bp, about 100 to about 1500 bp, about 100 to about 1400 bp, about 100 to about 1300 bp, about 100 to about 1200 bp, about 100 to about 1150 bp, about 100 to about 1100 bp, about 100 to about 1000 bp, about 100 to about 900 bp, about 100 to about 850 bp, about 100 to about 800 bp, about 100 to about 750 bp, about 100 to about 700 bp, about 100 to about 600 bp, about 100 to about 1000 bp, about 100 to about 400 bp, about 100 to about 350 bp, about 100 to about 300 bp, about 100 to about 250 bp, about 100 to about 200 bp, about 100 to about 150 bp, about 200 to about 1999 bp, about 200 to about 1900 bp, about 200 to about 1800 bp, about 200 to about 1700 bp, about 200 to about 1650 bp, about 200 to about 1600 bp, about 200 to about 1500 bp, about 200 to about 1400 bp, about 200 to about 1300 bp, about 200 to about 1200 bp, about 200 to about 1150 bp, about 200 to about 1100 bp, about 200 to about 1000 bp, about 200 to about 900 bp, about 200 to about 850 bp, about 200 to about 800 bp, about 200 to about 750 bp, about 200 to about 700 bp, about 200 to about 600 bp, about 200 to about 2000 bp, about 200 to about 400 bp, about 200 to about 350 bp, about 200 to about 300 bp, about 200 to about 250 bp, about 300 to about 1999 bp, about 300 to about 1900 bp, about 300 to about 1800 bp, about 300 to about 1700 bp, about 300 to about 1650 bp, about 300 to about 1600 bp, about 300 to about 1500 bp, about 300 to about 1400 bp, about 300 to about 1300 bp, about 300 to about 1200 bp, about 300 to about 1150 bp, about 300 to about 1100 bp, about 300 to about 1000 bp, about 300 to about 900 bp, about 300 to about 850 bp, about 300 to about 800 bp, about 300 to about 750 bp, about 300 to about 700 bp, about 300 to about 600 bp, about 300 to about 3000 bp, about 300 to about 400 bp, or about 300 to about 350 bp. In certain embodiments, the deletion size can be about 118 base pairs, about 233 base pairs, about 326 base pairs, about 766 base pairs, about 805 base pairs, or about 1611 base pairs.

4. COMPOSITIONS FOR GENOME EDITING IN MUSCLE

The present invention is directed to genetic constructs (e.g., vectors) or a composition thereof for genome editing a target gene in skeletal muscle or cardiac muscle of a subject. The composition includes a modified AAV vector and a nucleotide sequence encoding a CRISPR/Cas9-based gene editing system, e.g., a gRNA molecule and a Cas9 molecule. The composition delivers active forms of CRISPR/Cas9-based gene editing systems to skeletal muscle or cardiac muscle. The presently disclosed genetic constructs (e.g., vectors) can be used in correcting or reducing the effects of mutations in the dystrophin gene involved in genetic diseases and/or other skeletal or cardiac muscle conditions, e.g., DMD. The composition may further comprise a donor DNA or a transgene. These compositions may be used in genome editing, genome engineering, and correcting or reducing the effects of mutations in genes involved in genetic diseases and/or other skeletal or cardiac muscle conditions.

a. CRISPR/Cas9-Based Gene Editing System for Targeting Dystrophin

A CRISPR/Cas9-based gene editing system specific for dystrophin gene are disclosed herein. The CRISPR/Cas9-based gene editing system may include Cas9 and at least one gRNA to target the dystrophin gene. The CRISPR/Cas9-based gene editing system may bind and recognize a target region. The target regions may be chosen immediately upstream of possible out-of-frame stop codons such that insertions or deletions during the repair process restore the dystrophin reading frame by frame conversion. Target regions may also be splice acceptor sites or splice donor sites, such that insertions or deletions during the repair process disrupt splicing and restore the dystrophin reading frame by splice site disruption and exon exclusion. Target regions may also be aberrant stop codons such that insertions or deletions during the repair process restore the dystrophin reading frame by eliminating or disrupting the stop codon.

The gRNA may target a nucleotide sequence selected from the group consisting of SEQ ID NO: 1-19, 41, 42, or a complement thereof. For example, the disclosed CRISPR/Cas9-based gene editing systems were engineered to mediate highly efficient gene editing at exon 51 of the dystrophin gene. These CRISPR/Cas9-based gene editing systems restored dystrophin protein expression in cells from DMD patients. In some embodiments, the DNA targeting composition includes a nucleotide sequence set forth in SEQ ID NO: 37, a nucleotide sequence set forth in SEQ ID NO: 38, a nucleotide sequence set forth in SEQ ID NO: 83, and/or a nucleotide sequence set forth in SEQ ID NO: 84. For example, the DNA targeting composition includes a nucleotide sequence set forth in SEQ ID NO: 37, a nucleotide sequence set forth in SEQ ID NO: 38, and a nucleotide sequence set forth in SEQ ID NO: 83, or the DNA targeting composition includes a nucleotide sequence set forth in SEQ ID NO: 37, a nucleotide sequence set forth in SEQ ID NO: 38, and a nucleotide sequence set forth in SEQ ID NO: 84.

b. Adeno-Associated Virus Vectors

The composition may also include a viral delivery system. In certain embodiments, the vector is an adeno-associated virus (AAV) vector. The AAV vector is a small virus belonging to the genus *Dependovirus* of the Parvoviridae family that infects humans and some other primate species. AAV vectors may be used to deliver CRISPR/Cas9-based gene editing systems using various construct configurations. For example, AAV vectors may deliver Cas9 and gRNA expression cassettes on separate vectors or on the same vector. Alternatively, if the small Cas9 proteins, derived from species such as *Staphylococcus aureus* or *Neisseria meningitidis*, are used then both the Cas9 and up to two gRNA expression cassettes may be combined in a single AAV vector within the 4.7 kb packaging limit.

In certain embodiments, the AAV vector is a modified AAV vector. The modified AAV vector may have enhanced cardiac and skeletal muscle tissue tropism. The modified AAV vector may be capable of delivering and expressing the CRISPR/Cas9-based gene editing system in the cell of a mammal. For example, the modified AAV vector may be an AAV-SASTG vector (Piacentino et al. (2012) Human Gene Therapy 23:635-646). The modified AAV vector may deliver nucleases to skeletal and cardiac muscle in vivo. The modified AAV vector may be based on one or more of several capsid types, including AAV1, AAV2, AAV5, AAV6, AAV8, and AAV9. The modified AAV vector may be based on AAV2 pseudotype with alternative muscle-tropic AAV capsids, such as AAV2/1, AAV2/6, AAV2/7, AAV2/8, AAV2/9, AAV2.5 and AAV/SASTG vectors that efficiently transduce skeletal muscle or cardiac muscle by systemic and local delivery (Seto et al. Current Gene Therapy (2012) 12:139-151). The modified AAV vector may be AAV2i8G9 (Shen et al. J. Biol. Chem. (2013) 288:28814-28823). In some embodiments, the composition includes a nucleotide sequence set forth in SEQ ID NO: 39 and/or a nucleotide sequence set forth in SEQ ID NO: 40. In some embodiments, the composition includes a first vector comprises a nucleotide sequence set forth in SEQ ID NO; 39 and the second vector comprises a nucleotide sequence set forth in SEQ ID NO: 40.

5. METHODS OF GENOME EDITING IN MUSCLE

The present disclosure is directed to a method of genome editing in a skeletal muscle or cardiac muscle of a subject. The method comprises administering to the skeletal muscle or cardiac muscle of the subject the composition for genome editing in skeletal muscle or cardiac muscle, as described above. The genome editing may include correcting a mutant gene or inserting a transgene. Correcting the mutant gene may include deleting, rearranging, or replacing the mutant gene. Correcting the mutant gene may include nuclease-mediated NHEJ or HDR.

6. METHODS OF CORRECTING A MUTANT GENE AND TREATING A SUBJECT

The presently disclosed subject matter provides for methods of correcting a mutant gene (e.g., a mutant dystrophin gene, e.g., a mutant human dystrophin gene) in a cell and treating a subject suffering from a genetic disease, such as DMD. The method can include administering to a cell or a subject a presently disclosed genetic construct (e.g., a vector) or a composition comprising thereof as described above. The method can comprises administering to the skeletal muscle or cardiac muscle of the subject the presently disclosed genetic construct (e.g., a vector) or a composition comprising thereof for genome editing in skeletal muscle or cardiac muscle, as described above. Use of presently disclosed genetic construct (e.g., a vector) or a composition comprising thereof to deliver the CRISPR/Cas9-based gene editing system to the skeletal muscle or cardiac muscle may restore the expression of a full-functional or partially-functional protein with a repair template or donor DNA, which can replace the entire gene or the region containing the mutation. The CRISPR/Cas9-based gene editing system may be used to introduce site-specific double strand breaks at targeted genomic loci. Site-specific double-strand breaks are created when the CRISPR/Cas9-based gene editing system binds to a target DNA sequences, thereby permitting cleavage of the target DNA. This DNA cleavage may stimulate the natural DNA-repair machinery, leading to one of two possible repair pathways: homology-directed repair (HDR) or the non-homologous end joining (NHEJ) pathway.

The present disclosure is directed to genome editing with a CRISPR/Cas9-based gene editing system without a repair template, which can efficiently correct the reading frame and restore the expression of a functional protein involved in a genetic disease. The disclosed CRISPR/Cas9-based gene editing systems may involve using homology-directed repair or nuclease-mediated non-homologous end joining (NHEJ)-based correction approaches, which enable efficient correction in proliferation-limited primary cell lines that may not be amenable to homologous recombination or selection-based gene correction. This strategy integrates the rapid and robust assembly of active CRISPR/Cas9-based gene editing systems with an efficient gene editing method for the treatment of genetic diseases caused by mutations in nonessential coding regions that cause frameshifts, premature stop codons, aberrant splice donor sites or aberrant splice acceptor sites.

a. Nuclease Mediated Non-Homologous End Joining

Restoration of protein expression from an endogenous mutated gene may be through template-free NHEJ-mediated DNA repair. In contrast to a transient method targeting the target gene RNA, the correction of the target gene reading frame in the genome by a transiently expressed CRISPR/Cas9-based gene editing system may lead to permanently restored target gene expression by each modified cell and all of its progeny. In certain embodiments, NHEJ is a nuclease mediated NHEJ, which in certain embodiments, refers to NHEJ that is initiated a Cas9 molecule, cuts double stranded DNA. The method comprises administering a presently disclosed genetic construct (e.g., a vector) or a composition comprising thereof to the skeletal muscle or cardiac muscle of the subject for genome editing in skeletal muscle or cardiac muscle.

Nuclease mediated NHEJ gene correction may correct the mutated target gene and offers several potential advantages over the HDR pathway. For example, NHEJ does not require a donor template, which may cause nonspecific insertional mutagenesis. In contrast to HDR, NHEJ operates efficiently in all stages of the cell cycle and therefore may be effectively exploited in both cycling and post-mitotic cells, such as muscle fibers. This provides a robust, permanent gene restoration alternative to oligonucleotide-based exon skipping or pharmacologic forced read-through of stop codons and could theoretically require as few as one drug treatment. NHEJ-based gene correction using a CRISPR/Cas9-based gene editing system, as well as other engineered nucleases including meganucleases and zinc finger nucleases, may be combined with other existing ex vivo and in vivo platforms for cell- and gene-based therapies, in addition to the plasmid electroporation approach described here. For example, delivery of a CRISPR/Cas9-based gene editing system by mRNA-based gene transfer or as purified cell permeable proteins could enable a DNA-free genome editing approach that would circumvent any possibility of insertional mutagenesis.

b. Homology-Directed Repair

Restoration of protein expression from an endogenous mutated gene may involve homology-directed repair. The method as described above further includes administrating a donor template to the cell. The donor template may include a nucleotide sequence encoding a full-functional protein or a partially-functional protein. For example, the donor template may include a miniaturized dystrophin construct, termed minidystrophin ("minidys"), a full-functional dystrophin construct for restoring a mutant dystrophin gene, or a fragment of the dystrophin gene that after homology-directed repair leads to restoration of the mutant dystrophin gene.

c. Methods of Correcting a Mutant Gene and Treating a Subject Using CRISPR/Cas9

The present disclosure is also directed to genome editing with the CRISPR/Cas9-based gene editing system to restore the expression of a full-functional or partially-functional protein with a repair template or donor DNA, which can replace the entire gene or the region containing the mutation. The CRISPR/Cas9-based gene editing system may be used to introduce site-specific double strand breaks at targeted genomic loci. Site-specific double-strand breaks are created when the CRISPR/Cas9-based gene editing system binds to a target DNA sequences using the gRNA, thereby permitting cleavage of the target DNA. The CRISPR/Cas9-based gene editing system has the advantage of advanced genome editing due to their high rate of successful and efficient genetic modification. This DNA cleavage may stimulate the natural DNA-repair machinery, leading to one of two possible repair pathways: homology-directed repair (HDR) or the non-homologous end joining (NHEJ) pathway. For example, a CRISPR/Cas9-based gene editing system directed towards the dystrophin gene may include a gRNA having a nucleic acid sequence of any one of SEQ ID NOs: 1-19, 41, 42, or complement thereof.

The present disclosure is directed to genome editing with CRISPR/Cas9-based gene editing system without a repair template, which can efficiently correct the reading frame and restore the expression of a functional protein involved in a genetic disease. The disclosed CRISPR/Cas9-based gene editing system and methods may involve using homology-directed repair or nuclease-mediated non-homologous end joining (NHEJ)-based correction approaches, which enable efficient correction in proliferation-limited primary cell lines that may not be amenable to homologous recombination or selection-based gene correction. This strategy integrates the rapid and robust assembly of active CRISPR/Cas9-based gene editing system with an efficient gene editing method for the treatment of genetic diseases caused by mutations in nonessential coding regions that cause frameshifts, premature stop codons, aberrant splice donor sites or aberrant splice acceptor sites.

The present disclosure provides methods of correcting a mutant gene in a cell and treating a subject suffering from a genetic disease, such as DMD. The method may include administering to a cell or subject a CRISPR/Cas9-based gene editing system, a polynucleotide or vector encoding said CRISPR/Cas9-based gene editing system, or composition of said CRISPR/Cas9-based gene editing system as described above. The method may include administering a CRISPR/Cas9-based gene editing system, such as administering a Cas9 protein or Cas9 fusion protein containing a second domain having nuclease activity, a nucleotide sequence encoding said Cas9 protein or Cas9 fusion protein, and/or at least one gRNA, wherein the gRNAs target different DNA sequences. The target DNA sequences may be overlapping. The number of gRNA administered to the cell may be at least 1 gRNA, at least 2 different gRNA, at least 3 different gRNA, at least 4 different gRNA, at least 5 different gRNA, at least 6 different gRNA, at least 7 different gRNA, at least 8 different gRNA, at least 9 different gRNA, at least 10 different gRNA, at least 15 different gRNA, at least 20 different gRNA, at least 30 different gRNA, or at least 50 different gRNA, as described above. The gRNA may include a nucleic acid sequence of at least one of SEQ ID NOs: 1-19, 41, 42, or complement thereof. The method may involve homology-directed repair or non-homologous end joining.

7. METHODS OF TREATING DISEASE

The present disclosure is directed to a method of treating a subject in need thereof. The method comprises administering to a tissue of a subject the presently disclosed genetic construct (e.g., a vector) or a composition comprising thereof, as described above. In certain embodiments, the method may comprises administering to the skeletal muscle or cardiac muscle of the subject the presently disclosed genetic construct (e.g., a vector) or composition comprising thereof, as described above. In certain embodiments, the method may comprises administering to a vein of the subject the presently disclosed genetic construct (e.g., a vector) or composition comprising thereof, as described above. In certain embodiments, the subject is suffering from a skeletal muscle or cardiac muscle condition causing degeneration or weakness or a genetic disease. For example, the subject may be suffering from Duchenne muscular dystrophy, as described above.

a. Duchenne Muscular Dystrophy

The method, as described above, may be used for correcting the dystrophin gene and recovering full-functional or partially-functional protein expression of said mutated dystrophin gene. In some aspects and embodiments the disclosure provides a method for reducing the effects (e.g., clinical symptoms/indications) of DMD in a patient. In some aspects and embodiments the disclosure provides a method for treating DMD in a patient. In some aspects and embodiments the disclosure provides a method for preventing DMD in a patient. In some aspects and embodiments the disclosure provides a method for preventing further progression of DMD in a patient.

8. METHODS OF GENERATING A TRANSGENIC RODENT HAVING Δ52 hDMD

The present disclosure is directed to a method of generating a transgenic rodent embryo having a human dystrophin gene with an exon 52 deletion. The method includes administering to a rodent embryo the gRNA thereby deleting exon 52 of the human dystrophin gene, and selecting for a transgenic rodent embryo having a deletion of exon 52 of the human dystrophin gene, wherein the rodent embryo comprises a normal human dystrophin gene. In some embodiments, the rodent embryo is a mouse embryo. In some embodiments, the transgenic rodent embryo is heterozygous hDMD or heterozygous hDMD-Δ52. In some embodiments, a first gRNA molecule comprising a targeting domain that includes a nucleotide sequence set forth in SEQ ID NO: 41, and a second gRNA molecule comprising a targeting domain that includes a nucleotide sequence set forth in SEQ ID NO: 42 are administered to the rodent embryo to delete exon 52 of the human dystrophin gene. In some embodiments, the method further includes administering to the rodent embryo a Cas protein comprising an amino acid sequence set forth in SEQ ID NO: 27. The present disclosure is directed to a transgenic rodent embryo that is produced by this method. The present disclosure is also directed to a transgenic rodent produced from the transgenic rodent embryo.

9. CONSTRUCTS AND PLASMIDS

The compositions, as described above, may comprise genetic constructs that encodes the CRISPR/Cas9-based gene editing system, as disclosed herein. The genetic construct, such as a plasmid, may comprise a nucleic acid that encodes the CRISPR/Cas9-based gene editing system, such as the Cas9 protein and Cas9 fusion proteins and/or at least one of the gRNAs. The compositions, as described above, may comprise genetic constructs that encodes the modified AAV vector and a nucleic acid sequence that encodes the CRISPR/Cas9-based gene editing system, as disclosed herein. The genetic construct, such as a plasmid, may comprise a nucleic acid that encodes the CRISPR/Cas9-based gene editing system. The compositions, as described above, may comprise genetic constructs that encodes the modified lentiviral vector, as disclosed herein.

The genetic construct, such as a recombinant plasmid or recombinant viral particle, may comprise a nucleic acid that encodes the Cas9-fusion protein and at least one gRNA. In some embodiments, the genetic construct may comprise a nucleic acid that encodes the Cas9-fusion protein and at least two different gRNAs. In some embodiments, the genetic construct may comprise a nucleic acid that encodes the Cas9-fusion protein and more than two different gRNAs. In some embodiments, the genetic construct may comprise a promoter that operably linked to the nucleotide sequence encoding the at least one gRNA molecule and/or a Cas9 molecule. In some embodiments, the promoter is operably linked to the nucleotide sequence encoding a first gRNA molecule, a second gRNA molecule, and/or a Cas9 molecule. The genetic construct may be present in the cell as a functioning extrachromosomal molecule. The genetic construct may be a linear minichromosome including centromere, telomeres or plasmids or cosmids.

The genetic construct may also be part of a genome of a recombinant viral vector, including recombinant lentivirus, recombinant adenovirus, and recombinant adenovirus associated virus. The genetic construct may be part of the genetic material in attenuated live microorganisms or recombinant microbial vectors which live in cells. The genetic constructs may comprise regulatory elements for gene expression of the coding sequences of the nucleic acid. The regulatory elements may be a promoter, an enhancer, an initiation codon, a stop codon, or a polyadenylation signal.

In certain embodiments, the genetic construct is a vector. The vector can be an Adeno-associated virus (AAV) vector, which encode at least one Cas9 molecule and at least one gRNA molecule; the vector is capable of expressing the at least one Cas9 molecule and the at least gRNA molecule, in the cell of a mammal. The vector can be a plasmid. The vectors can be used for in vivo gene therapy. The vector may be recombinant. The vector may comprise heterologous nucleic acid encoding the fusion protein, such as the Cas9-fusion protein or CRISPR/Cas9-based gene editing system. The vector may be a plasmid. The vector may be useful for transfecting cells with nucleic acid encoding the Cas9-fusion protein or CRISPR/Cas9-based gene editing system, which the transformed host cell is cultured and maintained under conditions wherein expression of the Cas9-fusion protein or the CRISPR/Cas9-based gene editing system takes place.

Coding sequences may be optimized for stability and high levels of expression. In some instances, codons are selected to reduce secondary structure formation of the RNA such as that formed due to intramolecular bonding.

The vector may comprise heterologous nucleic acid encoding the CRISPR/Cas9-based gene editing system and may further comprise an initiation codon, which may be upstream of the CRISPR/Cas9-based gene editing system coding sequence, and a stop codon, which may be downstream of the CRISPR/Cas9-based gene editing system coding sequence. The initiation and termination codon may be in frame with the CRISPR/Cas9-based gene editing system coding sequence. The vector may also comprise a promoter that is operably linked to the CRISPR/Cas9-based gene editing system coding sequence. The promoter that is operably linked to the CRISPR/Cas9-based gene editing system coding sequence may be a promoter from simian virus 40 (SV40), a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, a U6 promoter, such as the human U6 promoter, or a Rous sarcoma virus (RSV) promoter. The promoter may also be a promoter from a human gene such as human ubiquitin C (hUbC), human actin, human myosin, human hemoglobin, human muscle creatine, or human metalothionein. The promoter may also be a tissue specific promoter, such as a muscle or skin specific promoter, natural or synthetic. Examples of such promoters are described in US Patent Application Publication Nos. US20040175727 and US20040192593, the contents of which are incorporated herein in their entirety. Examples of muscle-specific promoters include a Spc5-12 promoter (described in US Patent Application Publication No. US 20040192593, which is incorporated by reference herein in its entirety; Hakim et al, Mol. Ther. Methods Clin. Dev. (2014) 1:14002; and Lai et al. Hum Mol Genet. (2014) 23(12): 3189-3199), a MHCK7 promoter (described in Salva et al., Mol. Ther. (2007) 15:320-329), a CK8 promoter (described in Park et al. PLoS ONE (2015) 10(4): e0124914), and a CK8e promoter (described in Muir et al., Mol. Ther. Methods Clin. Dev. (2014) 1:14025). In some embodiments, the expression of the gRNA and/or Cas9 protein is driven by tRNAs.

Each of the polynucleotide sequences encoding the gRNA molecule and/or Cas9 molecule may each be operably linked to a promoter. The promoters that are operably linked to the gRNA molecule and/or Cas9 molecule may be the same promoter. The promoters that are operably linked to the gRNA molecule and/or Cas9 molecule may be different promoters. The promoter may be a constitutive promoter, an inducible promoter, a repressible promoter, or a regulatable promoter.

The vector may also comprise a polyadenylation signal, which may be downstream of the CRISPR/Cas9-based gene editing system. The polyadenylation signal may be a SV40 polyadenylation signal, LTR polyadenylation signal, bovine growth hormone (bGH) polyadenylation signal, human growth hormone (hGH) polyadenylation signal, or human β-globin polyadenylation signal. The SV40 polyadenylation signal may be a polyadenylation signal from a pCEP4 vector (Invitrogen, San Diego, CA).

The vector may also comprise an enhancer upstream of the CRISPR/Cas9-based gene editing system, i.e., the Cas9 protein or Cas9 fusion protein coding sequence or sgRNAs, or the CRISPR/Cas9-based gene editing system. The enhancer may be necessary for DNA expression. The enhancer may be human actin, human myosin, human hemoglobin, human muscle creatine or a viral enhancer such as one from CMV, HA, RSV or EBV. Polynucleotide function enhancers are described in U.S. Pat. Nos. 5,593,972, 5,962,428, and WO94/016737, the contents of each are fully incorporated by reference. The vector may also comprise a mammalian origin of replication in order to maintain the vector extrachromosomally and produce multiple copies of the vector in a cell. The vector may also comprise a regulatory sequence, which may be well suited for gene expression in a mammalian or human cell into which the vector is administered. The vector may also comprise a reporter gene, such as green fluorescent protein ("GFP") and/or a selectable marker, such as hygromycin ("Hygro").

The vector may be expression vectors or systems to produce protein by routine techniques and readily available starting materials including Sambrook et al., Molecular Cloning and Laboratory Manual, Second Ed., Cold Spring Harbor (1989), which is incorporated fully by reference. In some embodiments the vector may comprise the nucleic acid sequence encoding the CRISPR/Cas9-based gene editing system, including the nucleic acid sequence encoding the Cas9 protein or Cas9 fusion protein and the nucleic acid sequence encoding the at least one gRNA comprising the nucleic acid sequence of at least one of SEQ ID NOs: 1-19, 41, 42, or complement thereof. In some embodiments, the Cas9 protein or Cas9 fusion protein is encoded by a nucleic acid sequence of any one of SEQ ID NO: 26. In some embodiments, the vector comprises a nucleic acid sequence of SEQ ID NO: 39 or SEQ ID NO: 40.

10. PHARMACEUTICAL COMPOSITIONS

The presently disclosed subject matter provides for compositions comprising the above-described genetic constructs. The pharmaceutical compositions according to the present invention can be formulated according to the mode of administration to be used. In cases where pharmaceutical compositions are injectable pharmaceutical compositions, they are sterile, pyrogen free and particulate free. An isotonic formulation is preferably used. Generally, additives for isotonicity may include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation.

The composition may further comprise a pharmaceutically acceptable excipient. The pharmaceutically acceptable excipient may be functional molecules as vehicles, adjuvants, carriers, or diluents. The pharmaceutically acceptable excipient may be a transfection facilitating agent, which may include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and more preferably, the poly-L-glutamate is present in the composition for genome editing in skeletal muscle or cardiac muscle at a concentration less than 6 mg/ml. The transfection facilitating agent may also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the genetic construct. In some embodiments, the DNA vector encoding the composition may also include a transfection facilitating agent such as lipids, liposomes, including lecithin liposomes or other liposomes known in the art, as a DNA-liposome mixture (see for example International Patent Publication No. WO9324640), calcium ions, viral proteins, polyanions, polycations, or nanoparticles, or other known transfection facilitating agents. Preferably, the transfection facilitating agent is a polyanion, polycation, including poly-L-glutamate (LGS), or lipid.

11. METHODS OF DELIVERY

Provided herein is a method for delivering the presently disclosed genetic construct (e.g., a vector) or a composition thereof to a cell. The delivery of the compositions may be the transfection or electroporation of the composition as a nucleic acid molecule that is expressed in the cell and delivered to the surface of the cell. The nucleic acid molecules may be electroporated using BioRad Gene Pulser Xcell or Amaxa Nucleofector IIb devices. Several different buffers may be used, including BioRad electroporation solution, Sigma phosphate-buffered saline product #D8537 (PBS), Invitrogen OptiMEM I (OM), or Amaxa Nucleofector solution V (N. V.). Transfections may include a transfection reagent, such as Lipofectamine 2000.

Upon delivery of the presently disclosed genetic construct or composition to the tissue, and thereupon the vector into the cells of the mammal, the transfected cells will express the gRNA molecule(s) and the Cas9 molecule. The genetic construct or composition may be administered to a mammal to alter gene expression or to re-engineer or alter the genome. For example, the genetic construct or composition may be administered to a mammal to correct the dystrophin gene in a mammal. The mammal may be human, non-human primate, cow, pig, sheep, goat, antelope, bison, water buffalo, bovids, deer, hedgehogs, elephants, llama, alpaca, mice, rats, or chicken, and preferably human, cow, pig, or chicken.

The genetic construct (e.g., a vector) encoding the gRNA molecule(s) and the Cas9 molecule can be delivered to the mammal by DNA injection (also referred to as DNA vaccination) with and without in vivo electroporation, liposome mediated, nanoparticle facilitated, and/or recombinant vectors. The recombinant vector can be delivered by any viral mode. The viral mode can be recombinant lentivirus, recombinant adenovirus, and/or recombinant adeno-associated virus.

A presently disclosed genetic construct (e.g., a vector) or a composition comprising thereof can be introduced into a cell to genetically correct a dystrophin gene (e.g., human dystrophin gene). In certain embodiments, a presently disclosed genetic construct (e.g., a vector) or a composition comprising thereof is introduced into a myoblast cell from a DMD patient. In certain embodiments, the genetic construct (e.g., a vector) or a composition comprising thereof is introduced into a fibroblast cell from a DMD patient, and the genetically corrected fibroblast cell can be treated with MyoD to induce differentiation into myoblasts, which can be implanted into subjects, such as the damaged muscles of a subject to verify that the corrected dystrophin protein is functional and/or to treat the subject. The modified cells can also be stem cells, such as induced pluripotent stem cells, bone marrow-derived progenitors, skeletal muscle progenitors, human skeletal myoblasts from DMD patients, CD 133+ cells, mesoangioblasts, and MyoD- or Pax7-transduced cells, or other myogenic progenitor cells. For example, the CRISPR/Cas9-based gene editing system may cause neuronal or myogenic differentiation of an induced pluripotent stem cell.

12. ROUTES OF ADMINISTRATION

The presently disclosed genetic constructs (e.g., vectors) or a composition comprising thereof may be administered to a subject by different routes including orally, parenterally, sublingually, transdermally, rectally, transmucosally, topically, via inhalation, via buccal administration, intrapleurally, intravenous, intraarterial, intraperitoneal, subcutaneous, intramuscular, intranasal intrathecal, and intraarticular or combinations thereof. In certain embodiments, the presently disclosed genetic construct (e.g., a vector) or a composition is administered to a subject (e.g., a subject suffering from DMD) intramuscularly, intravenously or a combination thereof. For veterinary use, the presently disclosed genetic constructs (e.g., vectors) or compositions may be administered as a suitably acceptable formulation in accordance with normal veterinary practice. The veterinarian may readily determine the dosing regimen and route of administration that is most appropriate for a particular animal. The compositions may be administered by traditional syringes, needleless injection devices, "microprojectile bombardment gone guns", or other physical methods such as electroporation ("EP"), "hydrodynamic method", or ultrasound.

The presently disclosed genetic construct (e.g., a vector) or a composition may be delivered to the mammal by several technologies including DNA injection (also referred to as DNA vaccination) with and without in vivo electroporation, liposome mediated, nanoparticle facilitated, recombinant vectors such as recombinant lentivirus, recombinant adenovirus, and recombinant adenovirus associated virus. The composition may be injected into the skeletal muscle or cardiac muscle. For example, the composition may be injected into the tibialis anterior muscle or tail.

In some embodiments, the presently disclosed genetic construct (e.g., a vector) or a composition thereof is administered by 1) tail vein injections (systemic) into adult mice; 2) intramuscular injections, for example, local injection into a muscle such as the TA or gastrocnemius in adult mice; 3) intraperitoneal injections into P2 mice; or 4) facial vein injection (systemic) into P2 mice.

13. CELL TYPES

Any of these delivery methods and/or routes of administration can be utilized with a myriad of cell types, for example, those cell types currently under investigation for cell-based therapies of DMD, including, but not limited to, immortalized myoblast cells, such as wild-type and DMD patient derived lines, for example Δ48-50 DMD, DMD 6594 (del48-50), DMD 8036 (del48-50), C25C14 and DMD-7796 cell lines, primal DMD dermal fibroblasts, induced pluripotent stem cells, bone marrow-derived progenitors, skeletal muscle progenitors, human skeletal myoblasts from DMD patients, CD 133$^+$ cells, mesoangioblasts, cardiomyocytes, hepatocytes, chondrocytes, mesenchymal progenitor cells, hematopoetic stem cells, smooth muscle cells, and MyoD- or Pax7-transduced cells, or other myogenic progenitor cells. Immortalization of human myogenic cells can be used for clonal derivation of genetically corrected myogenic cells. Cells can be modified ex vivo to isolate and expand clonal populations of immortalized DMD myoblasts that include a genetically corrected dystrophin gene and are free of other nuclease-introduced mutations in protein coding regions of the genome. Alternatively, transient in vivo delivery of CRISPR/Cas9-based systems by non-viral or non-integrating viral gene transfer, or by direct delivery of purified proteins and gRNAs containing cell-penetrating motifs may enable highly specific correction in situ with minimal or no risk of exogenous DNA integration.

14. KITS

Provided herein is a kit, which may be used to correct a mutated dystrophin gene. The kit comprises at least a gRNA for correcting a mutated dystrophin gene and instructions for using the CRISPR/Cas9-based gene editing system. Also provided herein is a kit, which may be used for genome editing of a dystrophin gene in skeletal muscle or cardiac muscle. The kit comprises genetic constructs (e.g., vectors) or a composition comprising thereof for genome editing in skeletal muscle or cardiac muscle, as described above, and instructions for using said composition.

Instructions included in kits may be affixed to packaging material or may be included as a package insert. While the instructions are typically written or printed materials they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" may include the address of an internet site that provides the instructions.

The genetic constructs (e.g., vectors) or a composition comprising thereof for correcting a mutated dystrophin or genome editing of a dystrophin gene in skeletal muscle or cardiac muscle may include a modified AAV vector that includes a gRNA molecule(s) and a Cas9 molecule, as described above, that specifically binds and cleaves a region of the dystrophin gene. The CRISPR/Cas9-based gene editing system, as described above, may be included in the kit to specifically bind and target a particular region in the mutated dystrophin gene. The kit may further include donor DNA, a different gRNA, or a transgene, as described above.

15. EXAMPLES

It will be readily apparent to those skilled in the art that other suitable modifications and adaptations of the methods of the present disclosure described herein are readily applicable and appreciable, and may be made using suitable equivalents without departing from the scope of the present disclosure or the aspects and embodiments disclosed herein. Having now described the present disclosure in detail, the same will be more clearly understood by reference to the following examples, which are merely intended only to illustrate some aspects and embodiments of the disclosure, and should not be viewed as limiting to the scope of the disclosure. The disclosures of all journal references, U.S. patents, and publications referred to herein are hereby incorporated by reference in their entireties.

The present invention has multiple aspects, illustrated by the following non-limiting examples.

Example 1

Targeting Human Dystrophin Gene

Figure 3:
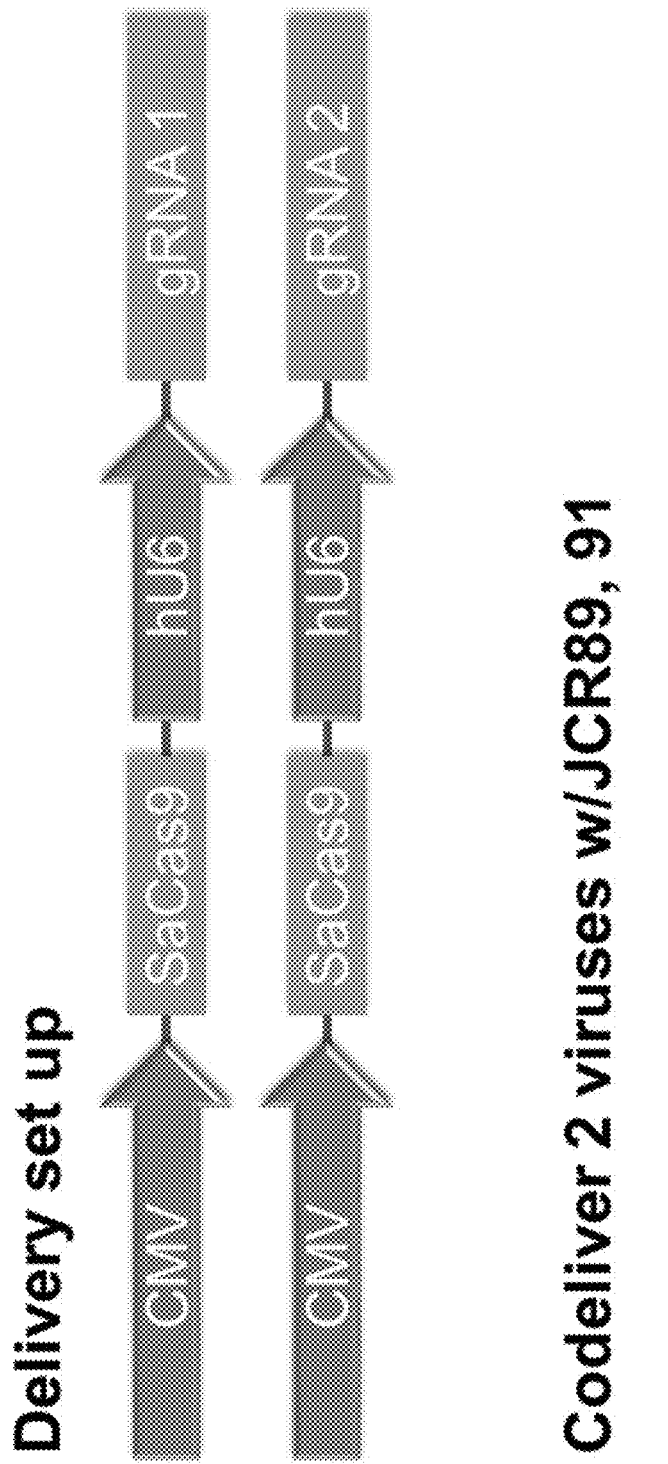
FIG. 3 shows an AAV-based in vivo system for co-delivery of SaCas9 and gRNAs JCR89 and JCR91 on two viral vectors to muscle tissues.

A CRISPR/Cas9-based gene editing system was used to target and delete exon 51 of the human dystrophin gene. The *S. aureus* Cas9 (SaCas9), which is about 1 kb smaller than S. pyogenes Cas9, was used with a adeno-associate virus (AAV) to deliver the CRISPR/Cas9-based gene editing system. The codon optimized nucleic acid sequence encoding the S. aureus Cas9 molecule is set forth in SEQ ID NO: 43 or SEQ ID NO: 44. FIG. 3 shows a schematic of the AAV-based in vivo co-delivery of SaCas9 and two gRNAs on two viral vectors to muscle tissues. Each vector had a copy of SaCas9 and one gRNA driven by the CMV and hU6 promoters, respectively (PT366-179 (SEQ ID NO: 39) and PT366-183 (SEQ ID NO: 40)).

The activity of individual gRNAs that target the human dystrophin gene, JCR89 (targets upstream of exon 51) and JCR91 (targets downstream of exon 51), which were designed against the human genome, was determined by Surveyor Assay in HEK293T cells (has normal version of dystrophin gene) and DMD patient myoblast lines (DMD 8036 and DMD 6594, which each have mutant form of dystrophin gene) (see FIG. 1). The Surveyor assay detects mismatches in the genomic DNA, which is indicative of indels from the CRISPR/Cas9-based gene editing system. For JCR89, the parent band size was 555 nt and the primer used were: forward primer—aagttacttgtccaggcatga (SEQ ID NO: 91); and reverse primer—gaaaaacttctgccaacttttatca (SEQ ID NO: 92). The expected cut band sizes were 134 nt and 421 nt. For JCR91, the parent band size was 632 nt and the primer used were: forward primer—tgcaaataacaaaagtagccataca (SEQ ID NO: 93); and reverse primer—tctttagaaaggcttgaaagctg (SEQ ID NO: 94). The expected cut band sizes were 210 nt and 422 nt.

HEK293T cells and DMD myoblasts (DMD 8036 and DMD 6594) were co-treated with SaCas9 and gRNAs JCR89 and JCR91 (SEQ ID NO: 37 and SEQ ID NO: 38). Genomic DNA was amplified with forward primer—cttcactgctggccagttta (SEQ ID NO: 95); and reverse primer—tctttagaaaggcttgaaagctg (SEQ ID NO: 94). The expected parent band size was 1646 nt and the expected "perfect" deletion band was 766 nt (the actual deletion size between the gRNA cut sites varied from the 766 nt due to the occurrence of indels). FIG. 2A shows the deletion of exon 51 in genomic DNA of the HEK293T cells and DMD myoblasts. FIG. 2B shows the deletion of exon 51 in cDNA from DMD myoblasts. "No RT" is a negative control where no reverse transcriptase was added.

The CRISPR/Cas9-based gene editing system was injected into transgenic mice carrying the human DMD gene (hDMD/mdx mice) to delete exon 51. Local AAV8 delivery of the viral vectors carrying the SaCas9 and gRNAs was applied to tibialis anterior (TA) muscle. See Table 1. 3 mice were injected with AAV8:1 mouse was injected with a high dose of AAV8 in both TAs ("HH"), 1 mouse was injected with low dose of AAV8 in both TAs ("LL"), and 1 mouse was injected with the low dose in the left TA and the high dose in the right TA ("LH"). Doses are listed in column 2 of Table 1. The mice were sacrificed 8 weeks post treatment ("Weeks PT") to harvest tissues for analysis. Nested PCR revealed deletion of exon 51 in both of the limbs in the HH mouse, in the right TA of the LL mouse, and in the right limb of the LH mouse.

TABLE 1

| Experiment | AAV8 dosage | Delivery | Weeks PT | Nested PCR - gDNA Δ51 |
|---|---|---|---|---|
| HH, LL, LH | HH: 6.6E11 LL: 1E11 | Intramuscular tibialis anterior (TA) | 8 | HH: both, LL: R, LH: R |

Figure 4:
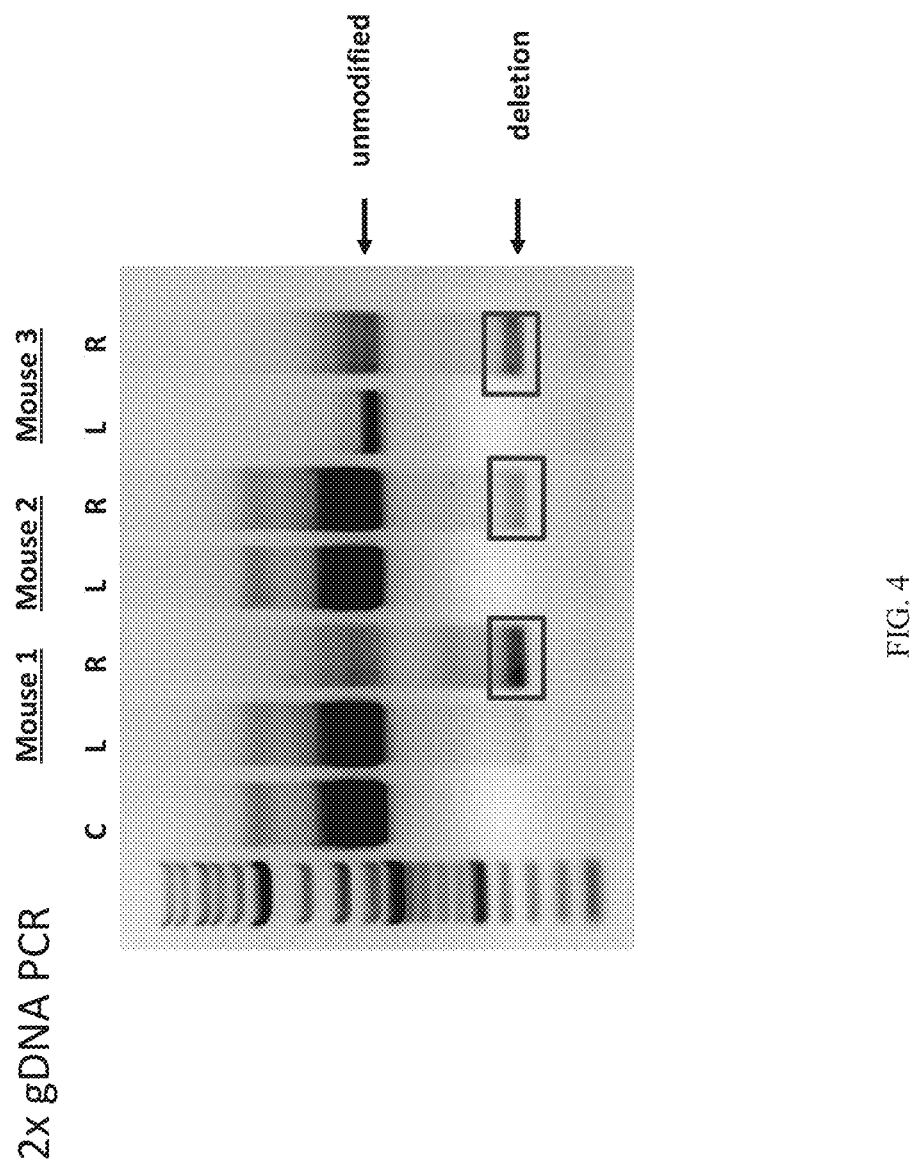
FIG. 4 shows the detection of the deletion of human exon 51 in transgenic mice carrying the human DMD gene (hDMD/mdx mice) following local AAV8 delivery of viral vectors carrying the SaCas9 and gRNAs to tibialis anterior (TA) muscle.
Figure 5:
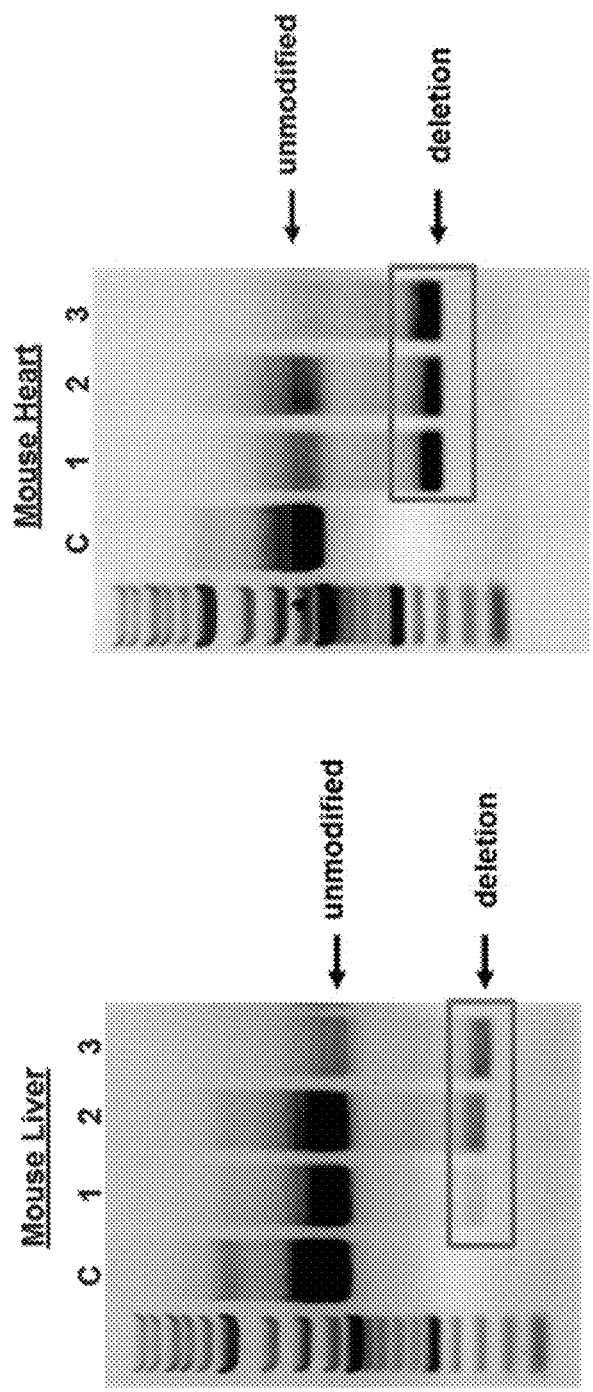
FIG. 5 shows the detection of the deletion of human exon 51 in transgenic mice carrying the hDMD gene following systemic AAV8 delivery via tail vein injection.

Genomic DNA harvested from mouse TA muscle was amplified in a first PCR reaction using forward primer: cttcactgctggccagttta (SEQ ID NO: 95) and reverse primer: tctttagaaaggcttgaaagctg (SEQ ID NO: 94). 1-3 μL of the PCR product was used in a second PCR reaction (2×gDNA PCR) using forward primer—aagttacttgtccaggcatga (SEQ ID NO: 91); and reverse primer—ttgaacatggcattgcataaA (SEQ ID NO: 96). This second PCR had an expected parent band of 1089 nt and an expected deletion band of 323 nt (the actual deletion size between the gRNA cut sites varied from the 323 nt due to the occurrence of indels). FIG. 4 shows the second PCR results. The "L" lanes show the results for the left TA muscle, which was used as a control and received saline solution. The "R" lanes show the results for the right TA muscle, which were injected with the 2 viral vectors that were pre-mixed in equal amounts. The CRISPR/Cas9-based gene editing system was also injected into the tail vein of hDMD/mdx mice via systemic AAV8 delivery (see FIG. 5). Genomic DNA harvested from mouse liver (FIG. 5—left panel) and heart (FIG. 5—right panel) was also amplified using the same protocol as for FIG. 4. The expected band of approximately 300 nucleotides indicated the deletion of exon 51.

Figure 6:
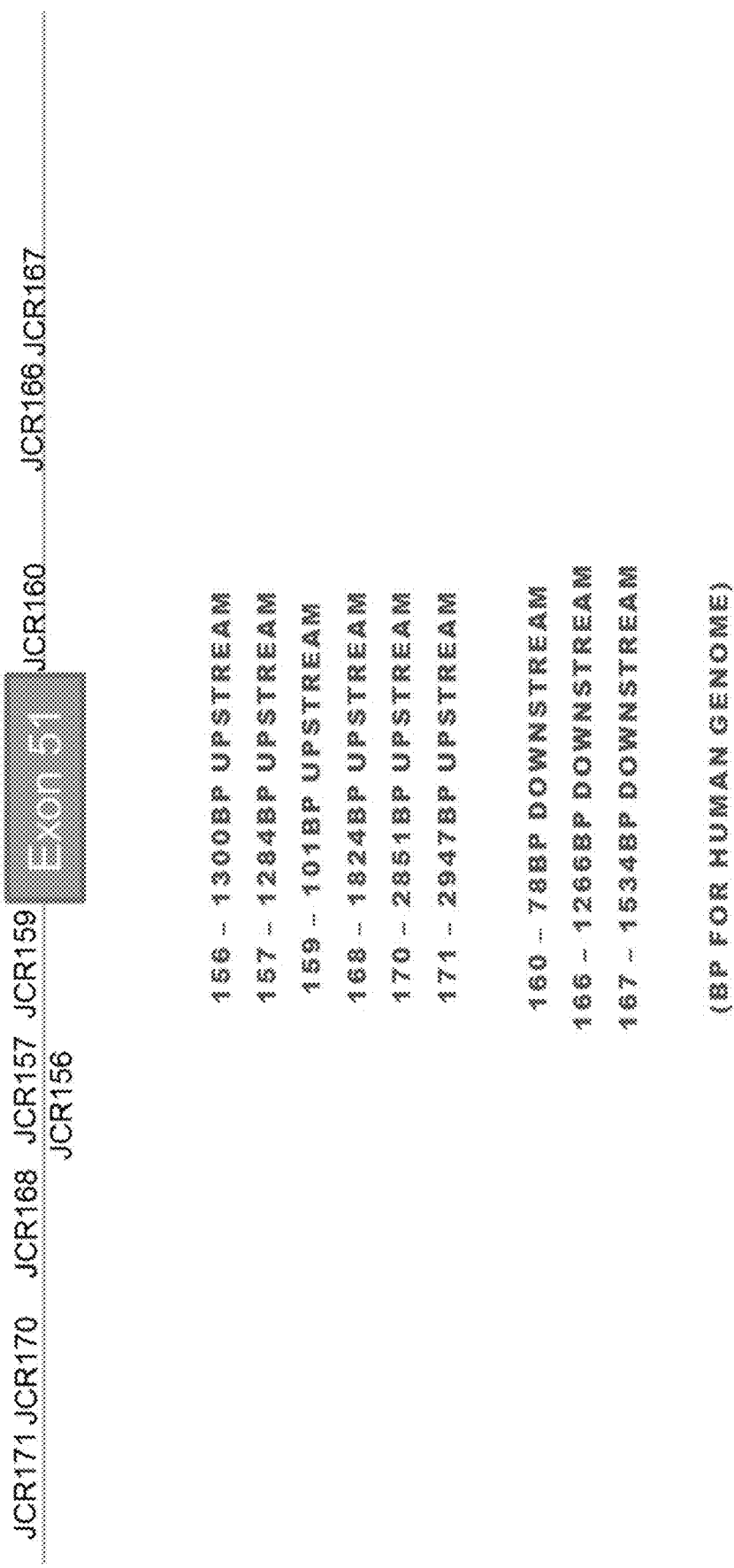
FIG. 6 shows the various gRNA targets that are conserved between human and rhesus macaque genomes (see sequences of gRNA in Table 2). The location of each gRNA is indicated in relation to Exon 51 of the human dystrophin gene.
Figure 10:
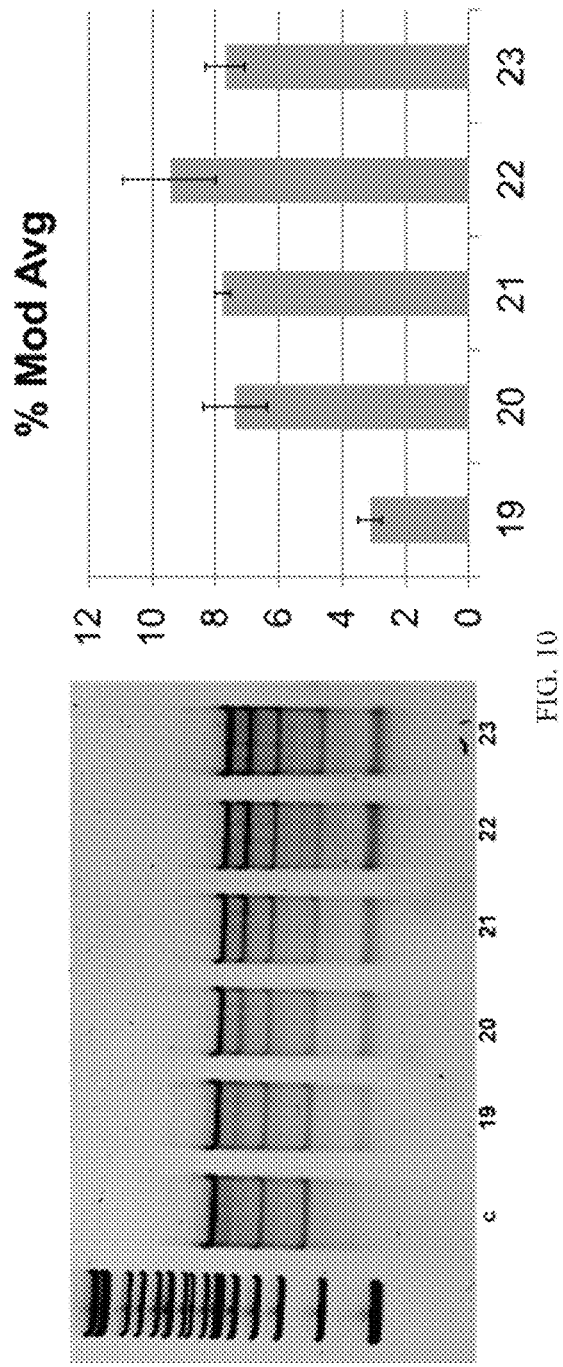
FIG. 10 shows the activity, as determined by the Surveyor Assay, of various target lengths of gRNA JCR157: 19, 20, 21, 22, and 23 nucleotides.
Figure 11:
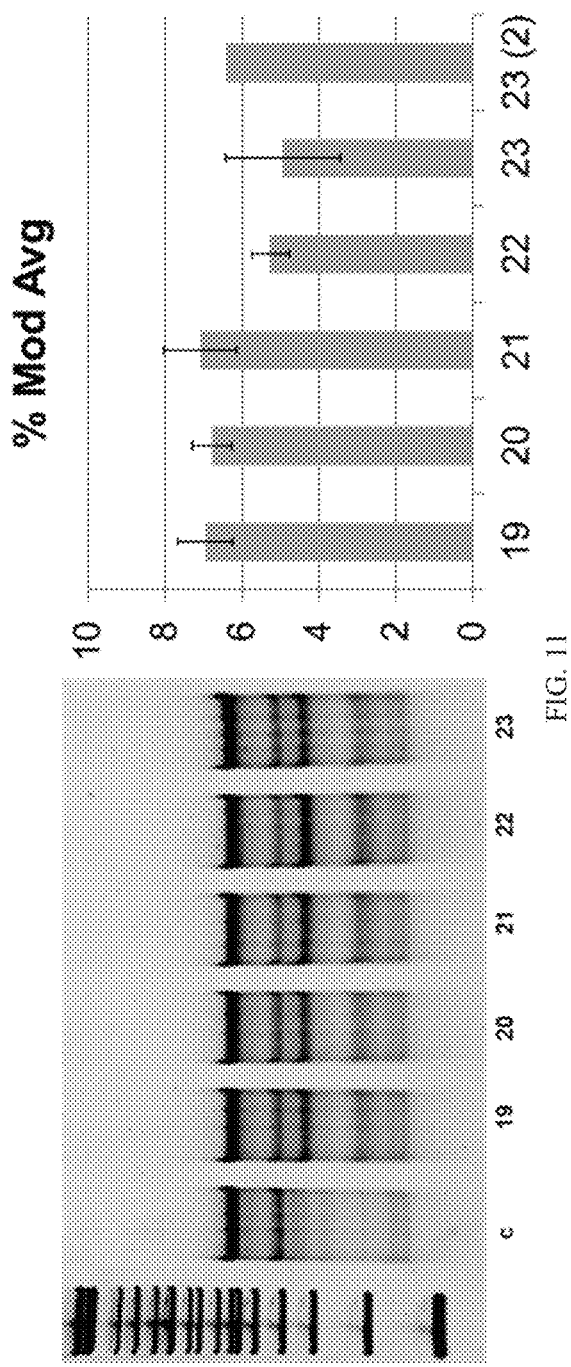
FIG. 11 shows the activity, as determined by the Surveyor Assay, of various target lengths of gRNA JCR160: 19, 20, 21, 22, and 23 nucleotides.

Further gRNAs that target human and rhesus monkey dystrophin gene sequences or human dystrophin gene sequences were generated and selected (see FIG. 6 and Table 2). Table 2 lists the general target of the gRNAs, the genomic strand that is recognized, the gRNA sequence, and the PAM sequence associated with the gRNA. The target genome sequences for the gRNAs, as indicated on the genomic plus strand, are listed in Table 3. These gRNAs were tested in cultured human cells to find optimal activity and combinations of gRNAs to generate deletions. Selected gRNAs were also prioritized based on predicted specificity in the human genome (FIG. 8) and screened for optimal target sequence lengths varying from 19-23 nucleotides (FIGS. 10 and 11). FIG. 6 shows the various gRNA targets listed in Table 2 that are conserved between human and rhesus macaque genomes. The location of each gRNA is indicated in relation to exon 51 of the human dystrophin gene.

TABLE 2

List of gRNAs

| gRNA | General target | Strand | gRNA sequence (5'-3') | SEQ ID NO: | PAM Sequence | SEQ ID NO: |
|---|---|---|---|---|---|---|
| JCR89 | Human DMD exon 51 (upstream) | plus | AAAGATATATAATGTCATGAAT | 1 | AAGAGT | 53 |

TABLE 2-continued

List of gRNAs

| gRNA | General target | Strand | gRNA sequence (5'-3') | SEQ ID NO: | PAM Sequence | SEQ ID NO: |
|---|---|---|---|---|---|---|
| JCR91 | Human DMD exon 51 (downstream) | plus | GCAGAATCAAATATAATAGTCT | 2 | GGGAAT | 54 |
| JCR94 | Human DMD exon 52 (upstream) | minus | AACAAATATCCCTTAGTATC | 41 | AGG | 55 |
| JCR99 | Human DMD exon 52 (downstream) | minus | AATGTATTTCTTCTATTCAA | 42 | TGG | 56 |
| JCR159 | Human and rhesus DMD exon 51 (upstream) | minus | AACAATAAGTCAAATTTAATTG | 3 | AAGAGT | 53 |
| JCR160 | Human and rhesus DMD exon 51 (downstream) | minus | GAACTGGTGGGAAATGGTCTAG | 4 | GAGAGT | 57 |
| JCR167 | Human and rhesus DMD exon 51 (downstream) | minus | TCCTTTGGTAAATAAAAGTCCT | 5 | GGGAGT | 58 |
| JCR166 | Human and rhesus DMD exon 51 (downstream) | minus | TAGGAATCAAATGGACTTGGAT | 6 | TTGAAT | 59 |
| JCR168 | Human and rhesus DMD exon 51 (upstream) | plus | TAATTCTTTCTAGAAAGAGCCT | 7 | CAGAGT | 60 |
| JCR170 | Human and rhesus DMD exon 51 (upstream) | minus | CTCTTGCATCTTGCACATGTCC | 8 | TGGAGT | 61 |
| JCR171 | Human and rhesus DMD exon 51 (upstream) | minus | ACTTAGAGGTCTTCTACATACA | 9 | ATGAGT | 62 |
| JCR156 | Human and rhesus DMD exon 51 (upstream) | minus | TCAGAGGTGAGTGGTGAGGGGA | 10 | AGGAAT | 63 |
| JCR157 | Human and rhesus DMD exon 51 (upstream) | minus | ACACACAGCTGGGTTATCAGAG | 11 | GAGAGT | 57 |
| JCR176 | Human and rhesus DMD exon 51 (upstream) | minus | CACAGCTGGGTTATCAGAG | 12 | GAGAGT | 57 |
| JCR177 | Human and rhesus DMD exon 51 (upstream) | minus | ACACAGCTGGGTTATCAGAG | 13 | GAGAGT | 57 |
| JCR178 | Human and rhesus DMD exon 51 (upstream) | minus | CACACAGCTGGGTTATCAGAG | 14 | GAGAGT | 57 |

TABLE 2-continued

List of gRNAs

| gRNA | General target | Strand | gRNA sequence (5'-3') | SEQ ID NO: | PAM Sequence | SEQ ID NO: |
|---|---|---|---|---|---|---|
| JCR179 | Human and rhesus DMD exon 51 (upstream) | minus | AACACACAGCTGGGTTATCAGAG | 15 | GAGAGT | 57 |
| JCR180 | Human and rhesus DMD exon 51 (downstream) | minus | CTGGTGGGAAATGGTCTAG | 16 | GAGAGT | 57 |
| JCR181 | Human and rhesus DMD exon 51 (downstream) | minus | ACTGGTGGGAAATGGTCTAG | 17 | GAGAGT | 57 |
| JCR182 | Human and rhesus DMD exon 51 (downstream) | minus | AACTGGTGGGAAATGGTCTAG | 18 | GAGAGT | 57 |
| JCR183 | Human and rhesus DMD exon 51 (downstream) | minus | AGAACTGGTGGGAAATGGTCTAG | 19 | GAGAGT | 57 |

TABLE 3

Target sequences of gRNAs

| gRNA Name | Target Sequence (Plus Strand 5'-3') | SEQ ID NO: | Comments |
|---|---|---|---|
| JCR89 | AAAGATATATAATGTCATGAAT | 64 | |
| JCR91 | GCAGAATCAAATATAATAGTCT | 65 | |
| JCR159 | CAATTAAATTTGACTTATTGTT | 66 | 101 upstream of exon 51 |
| JCR160 | CTAGACCATTTCCCACCAGTTC | 67 | 78 downstream of exon 51 |
| JCR167 | AGGACTTTTATTTACCAAAGGA | 68 | 1534 downstream of exon 51 |
| JCR166 | ATCCAAGTCCATTTGATTCCTA | 69 | 1266 downstream of exon 51 |
| JCR168 | TAATTCTTTCTAGAAAGAGCCT | 70 | 1824 upstream of exon 51 |
| JCR170 | GGACATGTGCAAGATGCAAGAG | 71 | 2851 upstream of exon 51 |
| JCR171 | TGTATGTAGAAGACCTCTAAGT | 72 | 2947 upstream of exon 51 |
| JCR156 | TCCCCTCACCACTCACCTCTGA | 73 | 1300 upstream of exon 51 |
| JCR157 | CTCTGATAACCCAGCTGTGTGT | 74 | 1284 upstream of exon 51 |
| JCR176 | CTCTGATAACCCAGCTGTG | 75 | JCR157 - 19 nucleotide |
| JCR177 | CTCTGATAACCCAGCTGTGT | 76 | JCR157 - 20 nucleotide |
| JCR178 | CTCTGATAACCCAGCTGTGTG | 77 | JCR157 - 21 nucleotide |
| JCR179 | CTCTGATAACCCAGCTGTGTGTT | 78 | JCR157 - 23 nucleotide |
| JCR180 | CTAGACCATTTCCCACCAG | 79 | JCR160 - 19 nucleotide |
| JCR181 | CTAGACCATTTCCCACCAGT | 80 | JCR160 - 20 nucleotide |
| JCR182 | CTAGACCATTTCCCACCAGTT | 81 | JCR160 - 21 nucleotide |
| JCR183 | CTAGACCATTTCCCACCAGTTCT | 82 | JCR160 - 23 nucleotide |

Human HEK293T cells were transfected with the individual candidate gRNAs listed in Table 2. The activity of the candidate gRNAs was determined by the Surveyor assay (see FIG. 7). For JCR160, the parent band size was 483 nt and the primer used were: forward primer—cgggcttggacagaacttac (SEQ ID NO: 97); and reverse primer—ctgcgtagtgccaaaacaaa (SEQ ID NO: 98). The expected cut band sizes were 192 nt and 291 nt. For JCR157, the parent band size was 631 nt and the primer used were: forward primer—gagatgtcttttgcagctttcc (SEQ ID NO: 99); and reverse primer—gggaccttggtaaagccaca (SEQ ID NO: 100). The expected cut band sizes were 147 nt and 484 nt.

The specificity of the candidate gRNAs was predicted using CasOFFinder program (Bae et al. (2014) *Bioinformatics* 30: 1473-1475; see FIG. 8). Candidate gRNAs were evaluated and chosen based on off-target activity, on-target activity as measured by Surveyor assay, and distance from the exon. The gRNAs JCR157 and JCR160 had low predicted off-target binding and were used for further testing.

Figure 9:
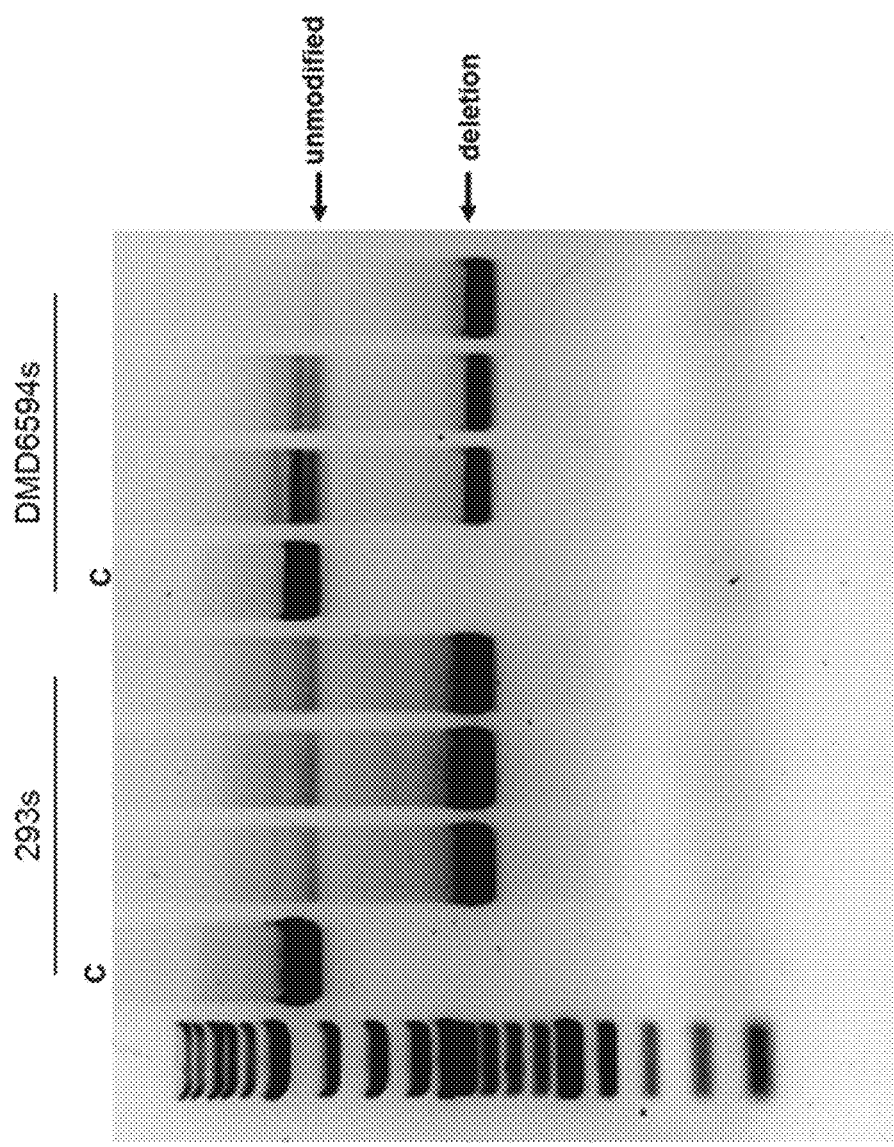
FIG. 9 shows the deletion of exon 51 by gRNAs JCR157 and JCR160 in HEK293T cells and DMD 6594 cells as determined by PCR of genomic DNA.

HEK293T cells were transfected with and DMD 6594 cells were electroporated with a modified pDO240 plasmid containing the gRNA JCR157, a modified pDO240 plasmid containing the gRNA JCR160, and a plasmid containing SaCas9 (pDO242; SEQ ID NO:83). The parent band was predicted to be 2451 nt and the deletion band is predicted to be about 840-850 nt. FIG. 9 shows the deletion of exon 51 as determined by PCR of genomic DNA (approximately 850 nucleotides) using forward primer—tgcctttcaatcattgtttcg (SEQ ID NO: 101) and reverse primer—agaaggcaaattggcacaga (SEQ ID NO: 102). The deletion created between the gRNA cut sites was approximately 1611 nt.

Figure 7:
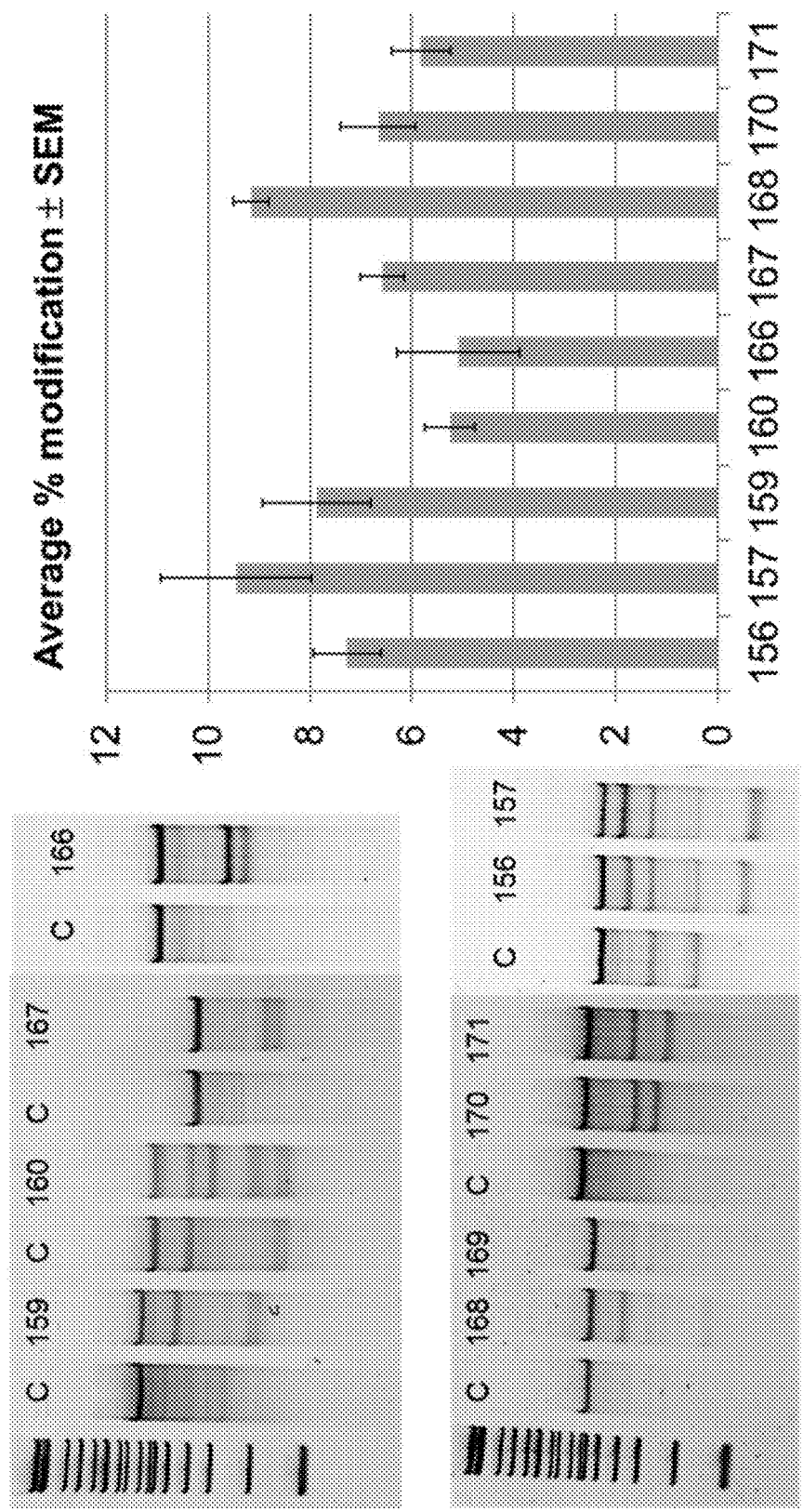
FIG. 7 shows the activity of individual gRNAs following transfection of human HEK293T cells as determined by the Surveyor assay.

FIG. 10 shows the activity of various target lengths of gRNA JCR157 (19, 20, 21, 22, and 23 nucleotides) determined by the Surveyor Assay in HEK293T cells using the primers and PCR conditions used for JCR157 in FIG. 7. FIG. 11 shows the activity of various target lengths of gRNA JCR160 (19, 20, 21, 22, and 23 nucleotides) determined by the Surveyor Assay in HEK293T cells using forward primer—cgggcttggacagaacttac (SEQ ID NO: 97); and reverse primer—ctgcgtagtgccaaaacaaa (SEQ ID NO: 98). The parent band size was predicted to be 483 nt and expected cut band sizes were 209 nt and 274 nt.

Combinations of the various target lengths of gRNA JCR157 and JCR160 (21, 22, or 23 nucleotides) were used in HEK293T cells using the conditions used in FIG. 9. FIG. 12 shows PCR of genomic DNA. The combination of JCR157 and JCR160 each having 23 nucleotide targets, had almost 50% deletion.

Figure 13:
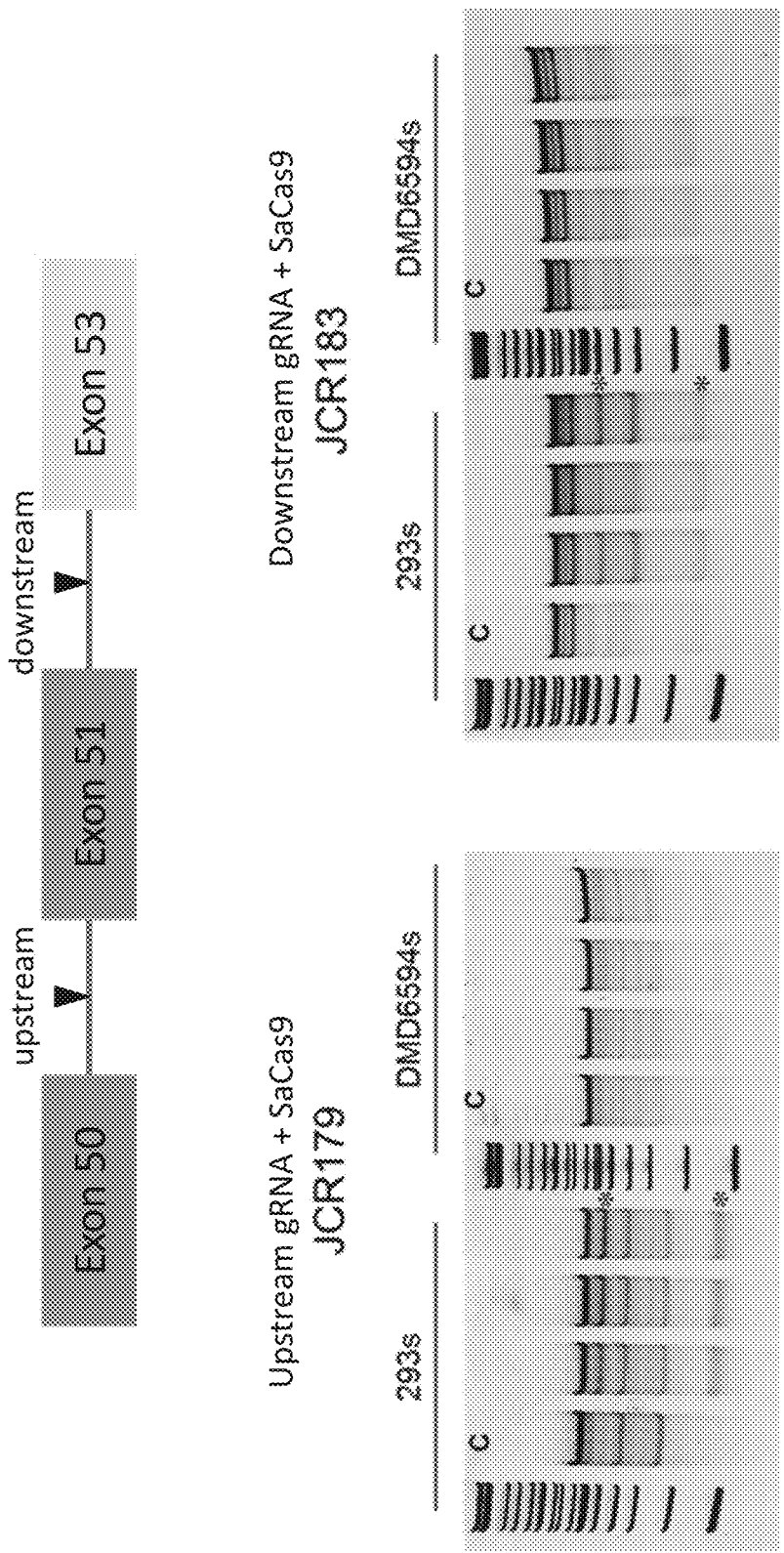
FIG. 13 shows in vitro on-target nuclease activity by Surveyor assay.

Each gRNA flanking exon 51 (upstream JCR179 and downstream JCR183) was performed individually with SaCas9 using a target sequences of 23 nt to demonstrate on-target nuclease activity in HEK293T cells ("293s") and DMD6594 cells ("DMD6594s") (see FIG. 13). For JCR179, the parent band size was 594 nt and the primer used were: forward primer—tgcctttcaatcattgtttcg (SEQ ID NO: 101); and reverse primer—aaggccccaaaatgtgaaat (SEQ ID NO: 103). The expected cut band sizes were 594 nt and 130 nt. For JCR183, the parent band size was 731 nt and the primer used were: forward primer—gagtttggctcaaattgttactctt (SEQ ID NO: 104); and reverse primer—ctgcgtagtgccaaaacaaa (SEQ ID NO: 98). The expected cut band sizes were 440 nt and 291 nt. FIG. 13 shows in vitro on-target nuclease activity by Surveyor assay.

Figure 14:
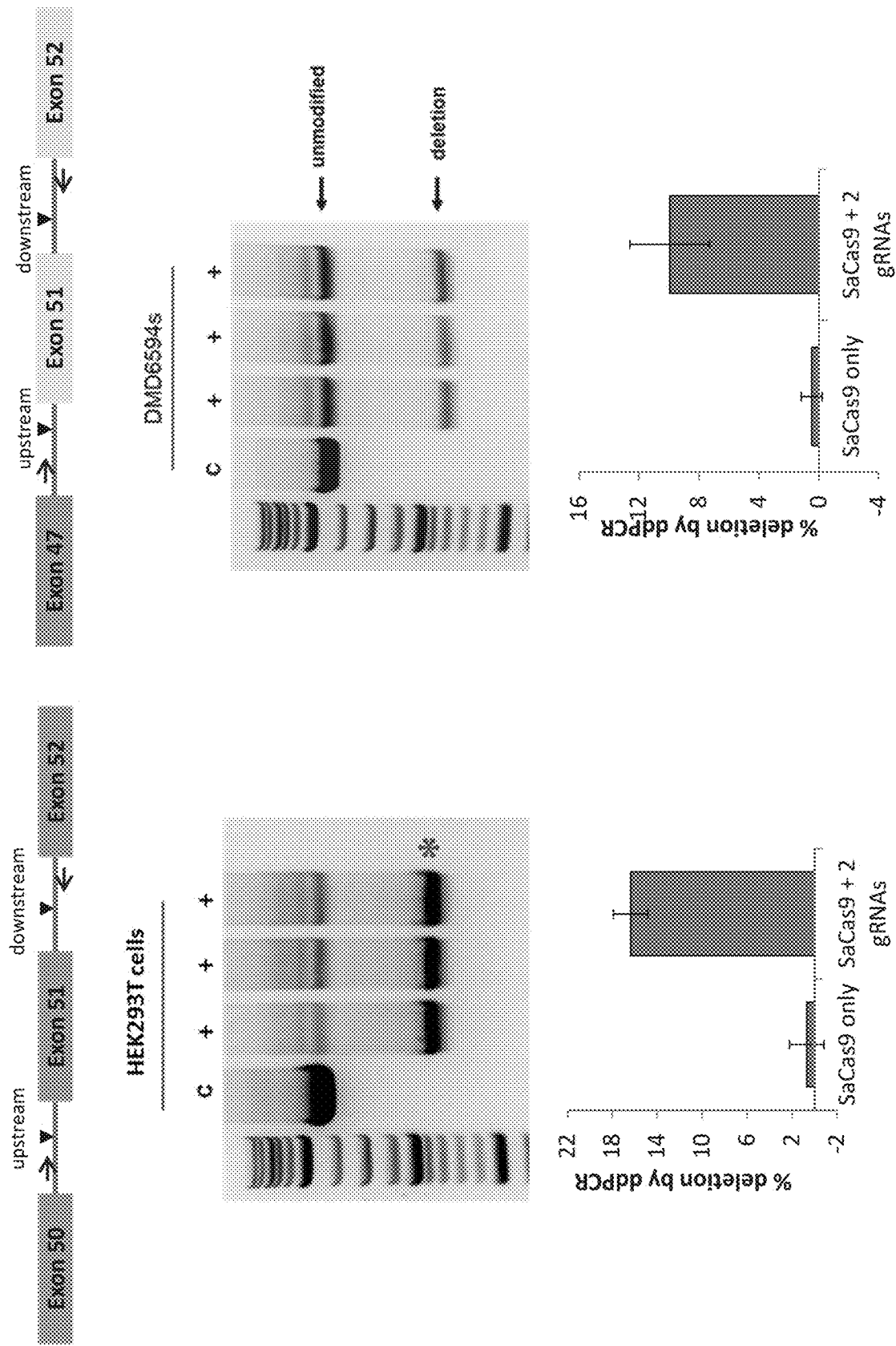
FIG. 14 shows the in vitro deletion of exon 51 in genomic DNA.

Human HEK293T cells were transfected with and DMD myoblasts (DMD 6594s) were electroporated with plasmids containing SaCas9 and gRNAs JCR179 and JCR183 (23 nt targets of JCR157 and JCR160; SEQ ID NO: 37 and SEQ ID NO: 38). The DMD 6594 cells are immortalized DMD patient myoblasts that are already lacking exons 48-50. The parent band was predicted to be 2451 nt and the deletion band is predicted to be about 823 nt. FIG. 14 shows the in vitro deletion of exon 51 in genomic DNA in human HEK293T cells (left panels) and DMD 6594s cells (right panels) as determined by PCR of genomic DNA using forward primer—tgcctttcaatcattgtttcg (SEQ ID NO: 101) and reverse primer—agaaggcaaattggcacaga (SEQ ID NO: 102). The deletion created between the gRNA cut sites was approximately 1628 nt. The top panels show a schematic of the target gene of the upstream and downstream gRNAs in the HEK293T cells and DMD 6594 cells, wherein the purple indicates normally processed exons and yellow indicates mutant exons. The middle panels show the result of PCR across the genomic deletion region, wherein the asterisk indicates the deletion. The bottom panels shows the droplet digital PCR of genomic DNA. In the HEK293T cells, the gRNAs and SaCas9 had 16% deletion, wherein the DMD 6594 cells had editing of about 10%.

Figure 15:
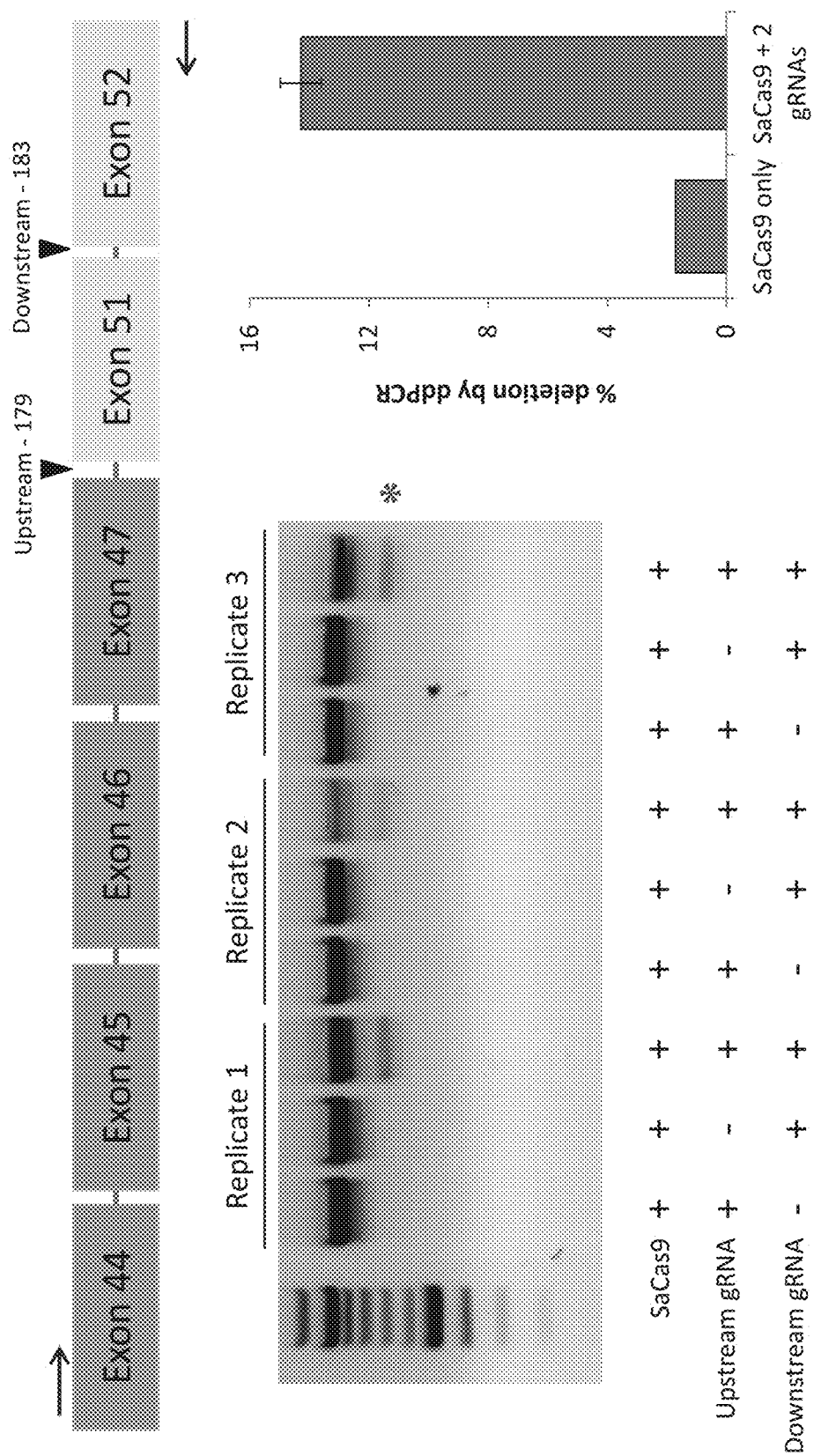
FIG. 15 shows the in vitro deletion of exon 51 in cDNA in human DMD myoblasts differentiated for 7 days.
Figure 16:
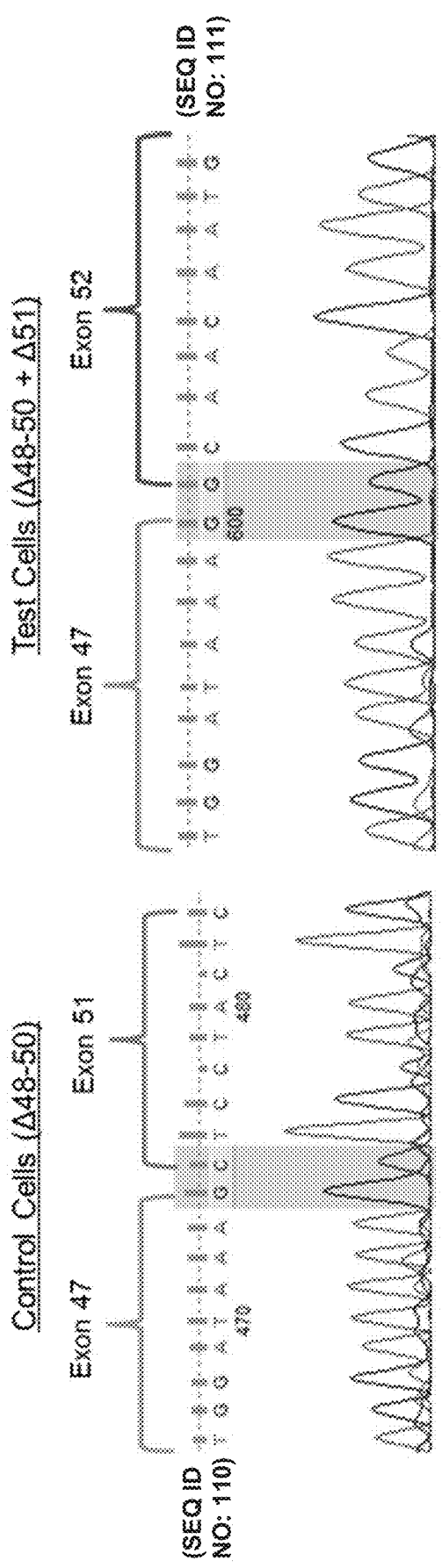
FIG. 16 shows in vitro exon 47 to 52 junction in cDNA of DMD patient myoblasts.

To determine if the changes in genomic DNA were transcribed to the RNA, RNA was harvested from DMD myoblasts that were co-transfected with SaCas9 and both gRNAs and differentiated for 7 days (see FIG. 15). The RNA was reverse transcribed to cDNA and the cDNA was PCR amplified using standard methods known in the art. In FIG. 15, the bottom left panel shows PCR amplification from exon 44 to exon 52 using forward primer—tggcggcgttttcattat (SEQ ID NO: 105) and reverse primer—TTCGATCCGTAATGATTGTTCTAGCC (SEQ ID NO: 106). The parent band was predicted to be 948 nt and the deletion band is predicted to be about 715 nt. FIG. 15 shows a deletion band only in cells treated with SaCas9 and both gRNAs. The bottom right panel shows ddPCR revealing editing of about 14% of the cDNA. The in vitro exon 47 to 52 junction in cDNA of DMD patient myoblasts was sequenced (see FIG. 16). In FIG. 16, the sequence of the bands from the untreated cells (Control cells Δ48-50) indicated that exons 47 to 51 were joined as expected, while the deletion band in the treated cells (Δ48-50+Δ51) showed the junction of exon 47 to 52. Thus a distinct lack of exon 51 and the disclosed system aimed at the genomic DNA level was being carried through transcription.

Example 2

Generation of Δ52/mdx Mouse

Figure 17:
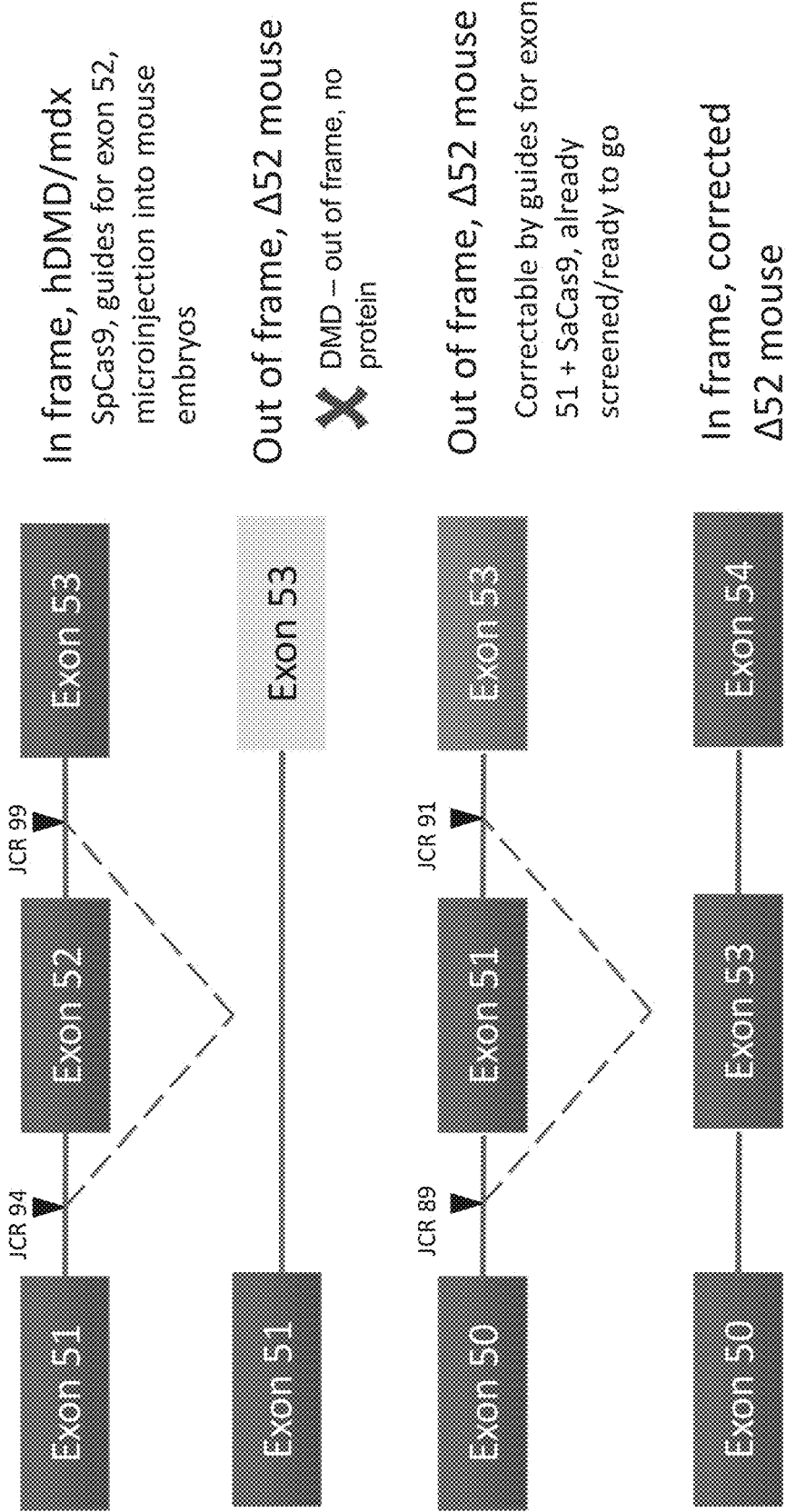
FIG. 17 shows the design for the Δ52/mdx mouse starting from healthy hDMD/mdx mouse.

FIG. 17 shows the design for the Δ52/mdx mouse. The hDMD/mdx mouse was obtained from Leiden University and manipulated to generate a relevant model for DMD, in which exon 52 is removed and the deletion results in an out-of reading frame shift and DMD genotype. The hDMD/mdx mouse contains a full length, wild-type human dystrophin gene on chromosome 5 in the mdx background such that no mouse dystrophin is expressed.

Figure 18:
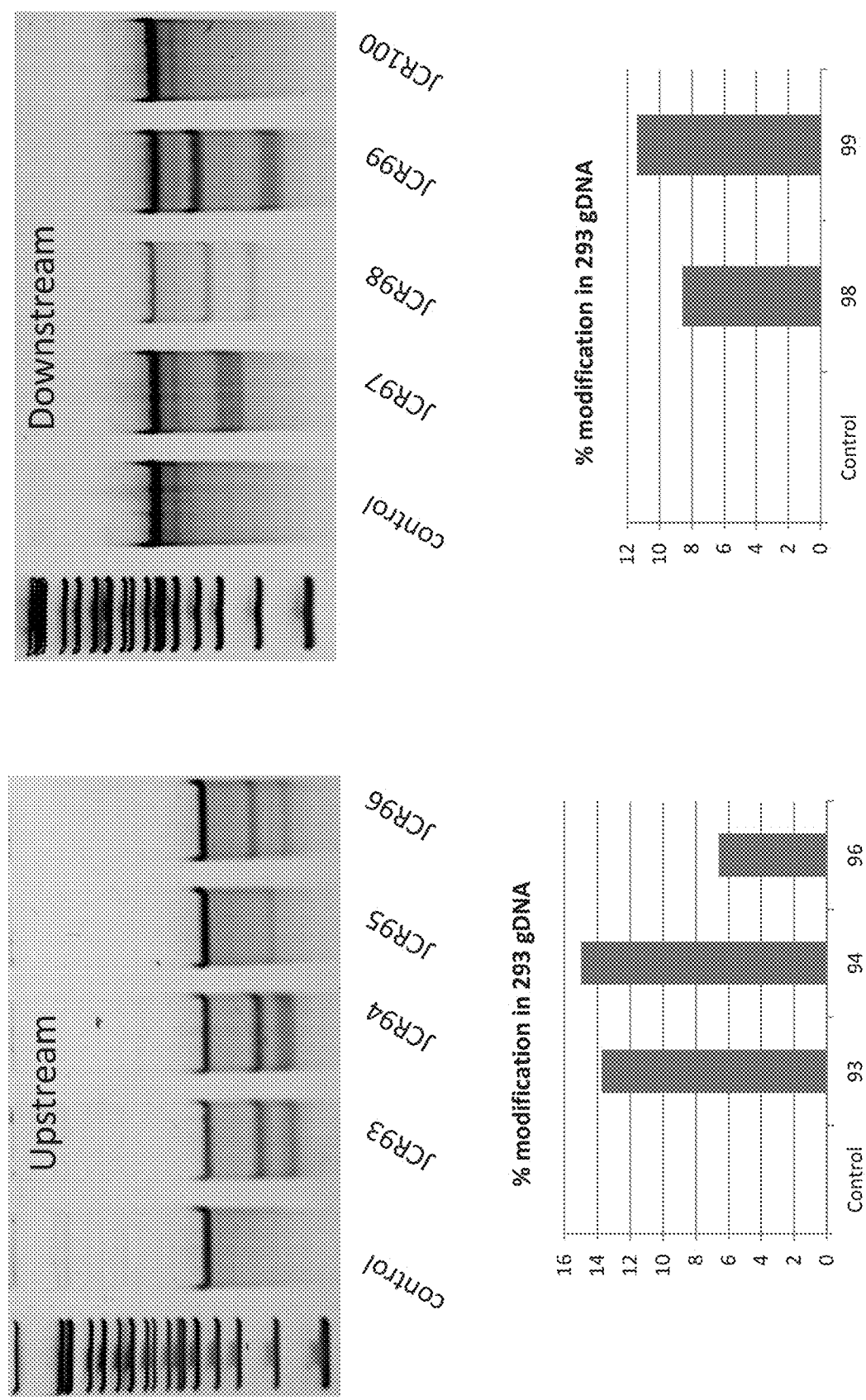
FIG. 18 shows in vitro guide validation: individual (Surveyor assay).
Figure 19:
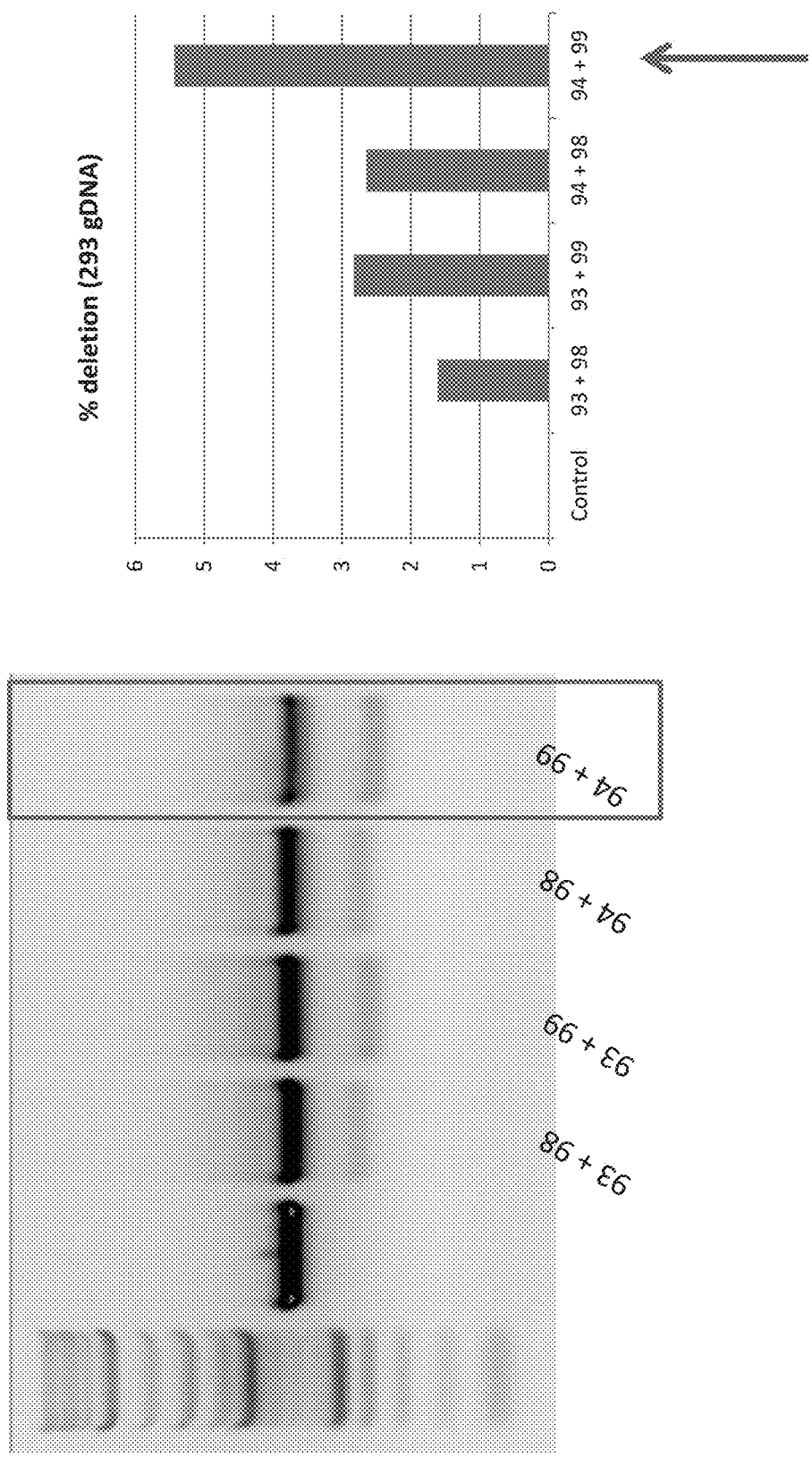
FIG. 19 shows in vitro guide validation: paired: the deletion of exon 51 in genomic DNA of HEK293T cells was generated using pairs of gRNAs.

To generate a relevant model for DMD, the SpCas9 CRISPR/Cas9 editing system and gRNAs were used to target and delete exon 52 of the human dystrophin gene. Various gRNAs targeting upstream and downstream of exon 52 were tested and validated using Surveyor assay (see FIG. 18). For the upstream gRNAs, the forward primer—ctccggaatgtctccatttg (SEQ ID NO: 87) and reverse primer—TTGTGTGTCCCATGCTTGTT (SEQ ID NO: 107) were used and the parent band size was 402 nt. For JCR94 (AACAAATATCCCTTAGTATC (SEQ ID NO: 41)), the expected cut sizes were 243 nt and 159 nt. For the downstream gRNAs, the forward primer—CAACGCT-GAAGAACCCTGAT (SEQ ID NO: 108) and reverse—atgagggagagactggcatc (SEQ ID NO: 88) were used and the parent band size was 509 nt. For JCR99 (AATGTAT-TTCTTCTATTCAA (SEQ ID NO: 42)), the expected cut sizes were 346 nt and 163 nt. Pairs of gRNAs were tested and validated by detecting the deletion of exon 51 in genomic DNA of HEK293T cells, including JCR94 and JCR99, using forward primer—ctccggaatgtctccatttg (SEQ ID NO: 87) and reverse primer—atgagggagagactggcatc (SEQ ID NO: 88) (see FIG. 19). The parent band size was 718 nt, the deletion band was 392 nt, and the deletion between gRNAs was 326 nt. The pair of JCR94 and JCR99 was used in the genome editing system to generate the Δ52/mdx mouse. Specifically, the mouse was created by injecting JCR94 gRNA, JCR99 gRNA, and SaCas9 mRNA into mice embryos.

Figure 20:
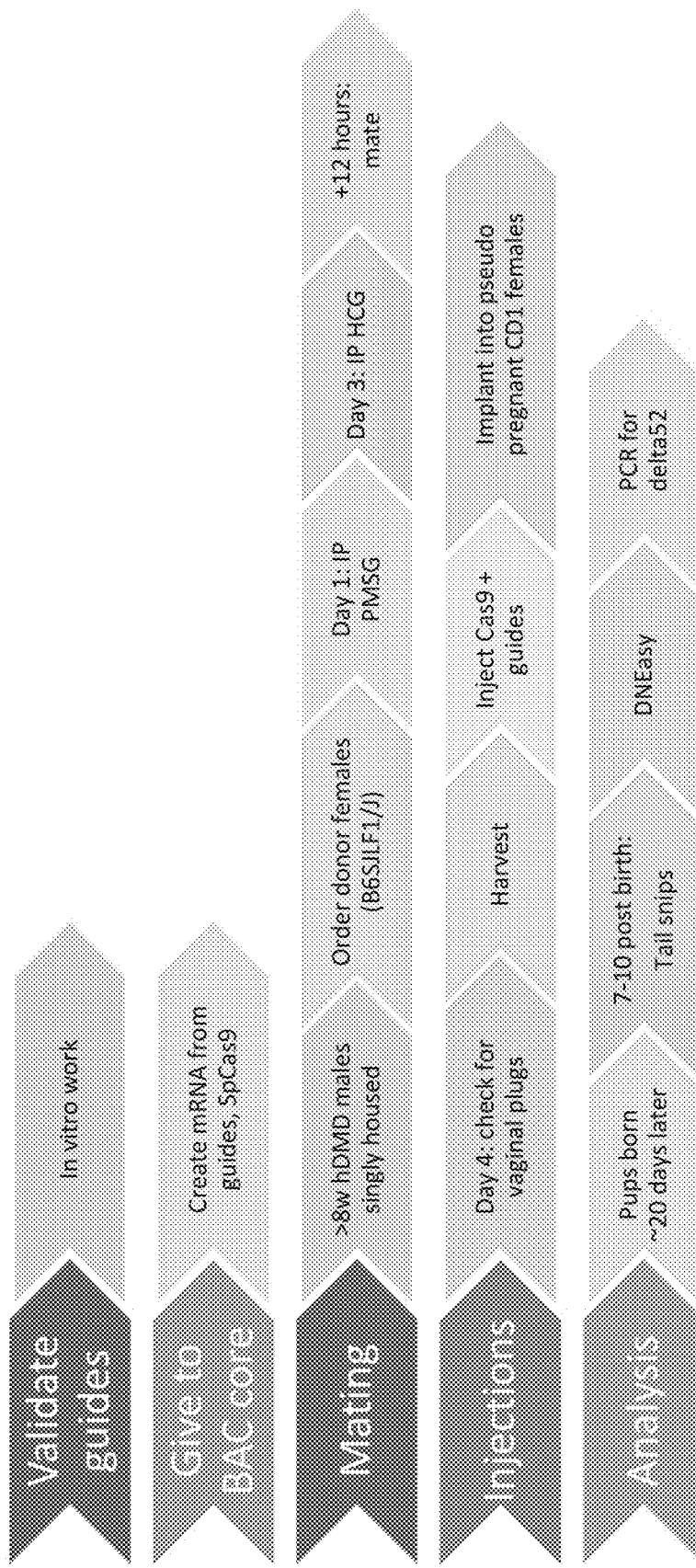
FIG. 20 shows schematic of DNA microinjection protocol.
Figure 21:
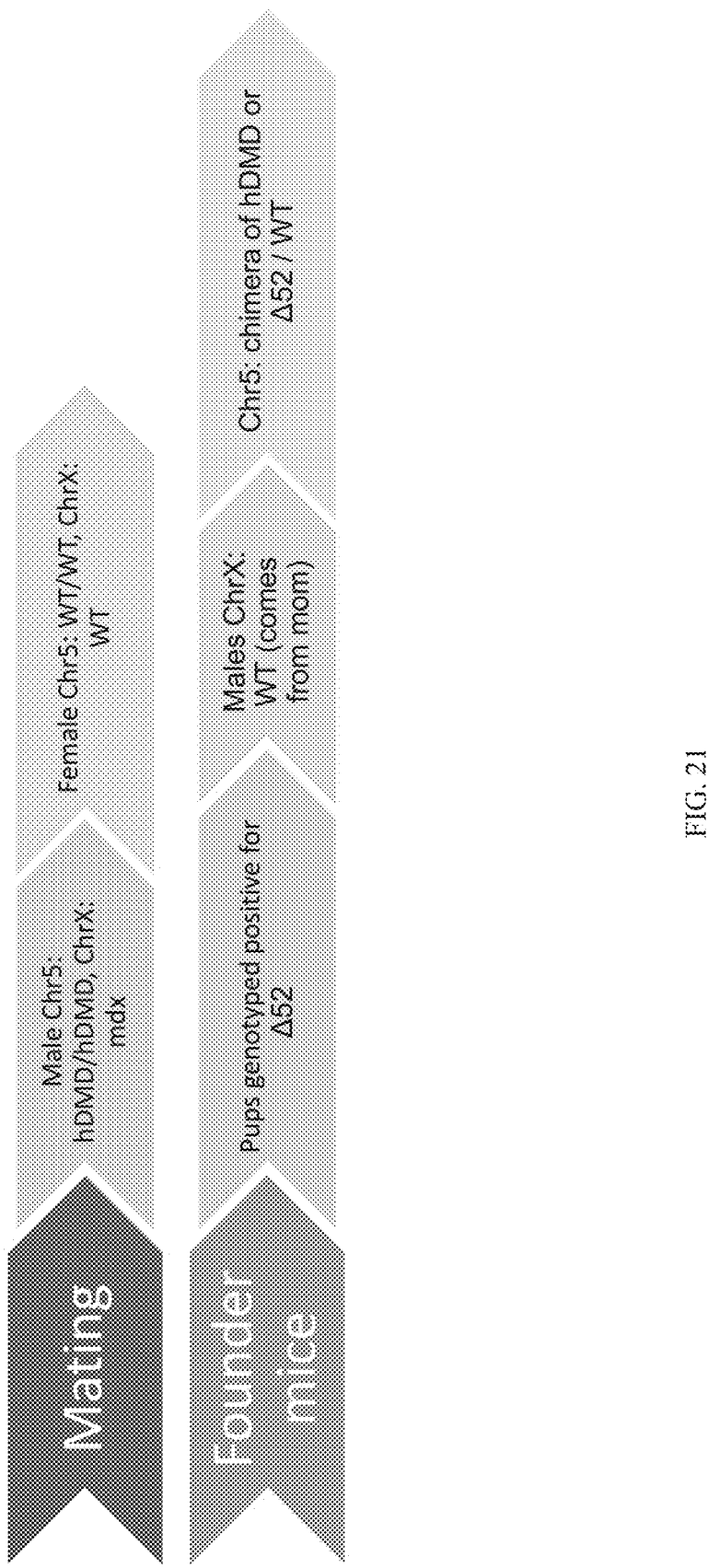
FIG. 21 shows a schematic of mouse breeding.

FIG. 20 shows DNA microinjection protocol which includes BAC recombineering service. Day 1: pregnant mares were intraperitoneally treated with serum gonadotropin to induce ovulation. Day 3: pregnant mares were intraperitoneally treated with human chorionic gonadotropin. In the 1$^{st}$ round, 471 embryos were produced, but only 5 plugs were visualized. 150 fertilized embryos were used (14 females superovulated). Pronuclear injections were performed with less than 50 ng Cas9, and 20 ng each guide. FIG. 21 shows the mouse breeding protocol to generate the transgenic mice.

Figure 22:
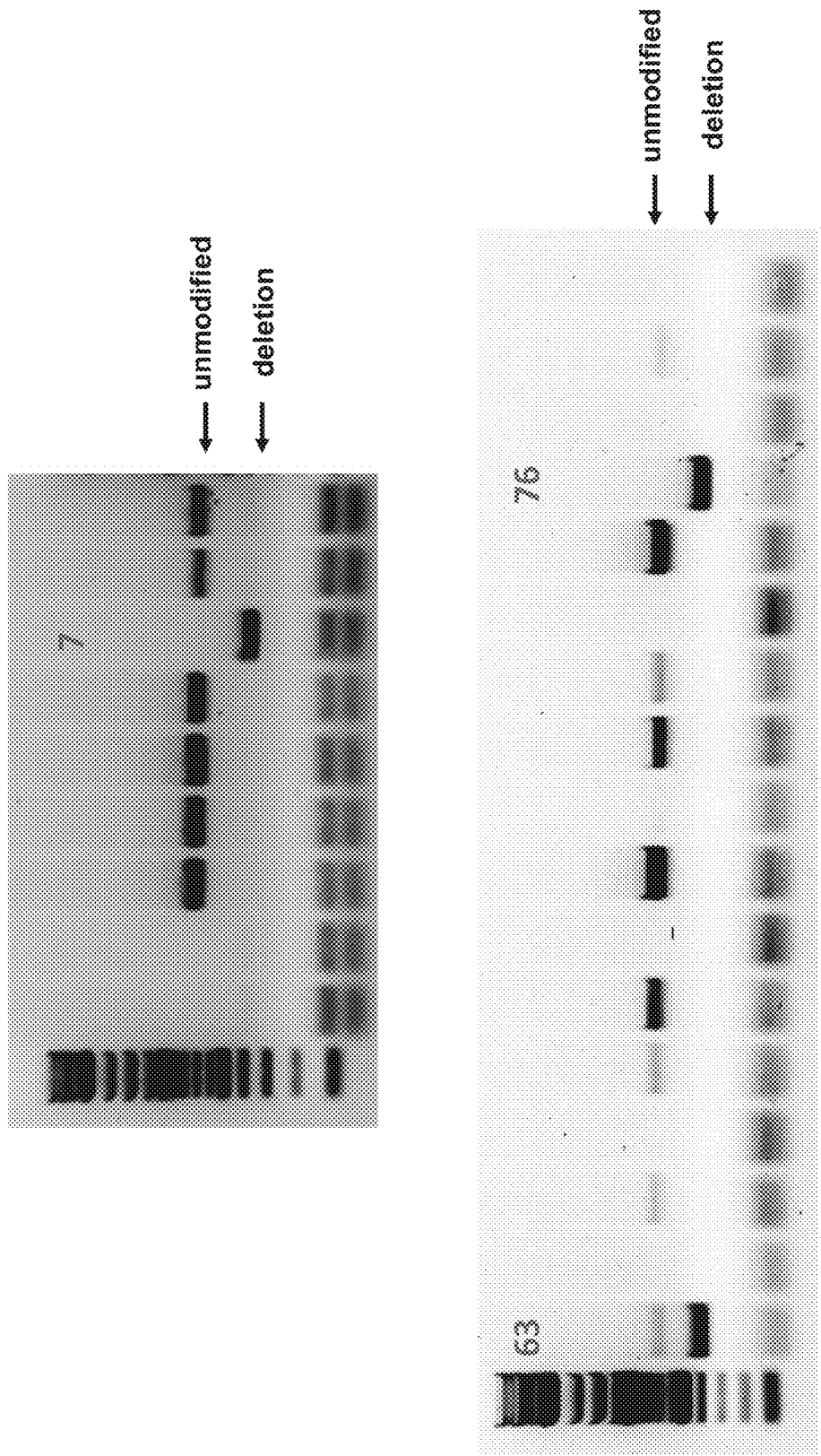
FIG. 22 shows founder mice genotyping results.

The founder mice were genotyped using the following genotyping protocol. Genomic DNA (gDNA) was extracted from the tail snips of the mice using a DNEasy Blood and Tissue kit (Qiagen). To genotype each pup, gDNA was amplified using AccuPrime HiFi Taq kit as follows: i. 100 ng gDNA; ii. 2.5 µL AccuPrime Buffer II; iii. 0.1 µL AccuPrime HiFi Taq; iv. 1 µL JRH261 (ctccggaatgtctccatttg (SEQ ID NO: 87)) (10 µM); v. 1 µL JRH264 (atgagggagagactggcatc (SEQ ID NO: 88)) (10 µM); and vi. water up to 25 µL total volume. The reactions were run on a thermocycler as follows: i. 95 degrees for 4 minutes; ii. 95 degrees for 30 sec; iii. 52 degrees for 30 sec; iv. 68 degrees for 1:00 min; v. Cycle steps ii-iv 35 times; and 4 degrees forever. The PCR reactions were separated on a gel (FIG. 22). The expected band sizes were 718 nt if no deletion was present (i.e., exon 52 was still present) and approximately 392 nt if there was a deletion of exon 52. As shown in FIG. 22, the founder mice 7, 63, and 76 had the exon 52 deletion.

The amplified bands were sequenced using the JRH264 primer (see FIG. 23) to sequence the rejoined ends of the targeted regions. FIG. 23 shows the sequenced region, where the bolded, underlined, and normal letters indicate native sequences and the italicized letters indicate insertions or deletions. In the expected sequence ("delta 52"), the bold letters are ligated to the underlined letters. In the founder mice, there were insertions (italicized letters) and deletions (hyphens) in this region.

Figure 24:
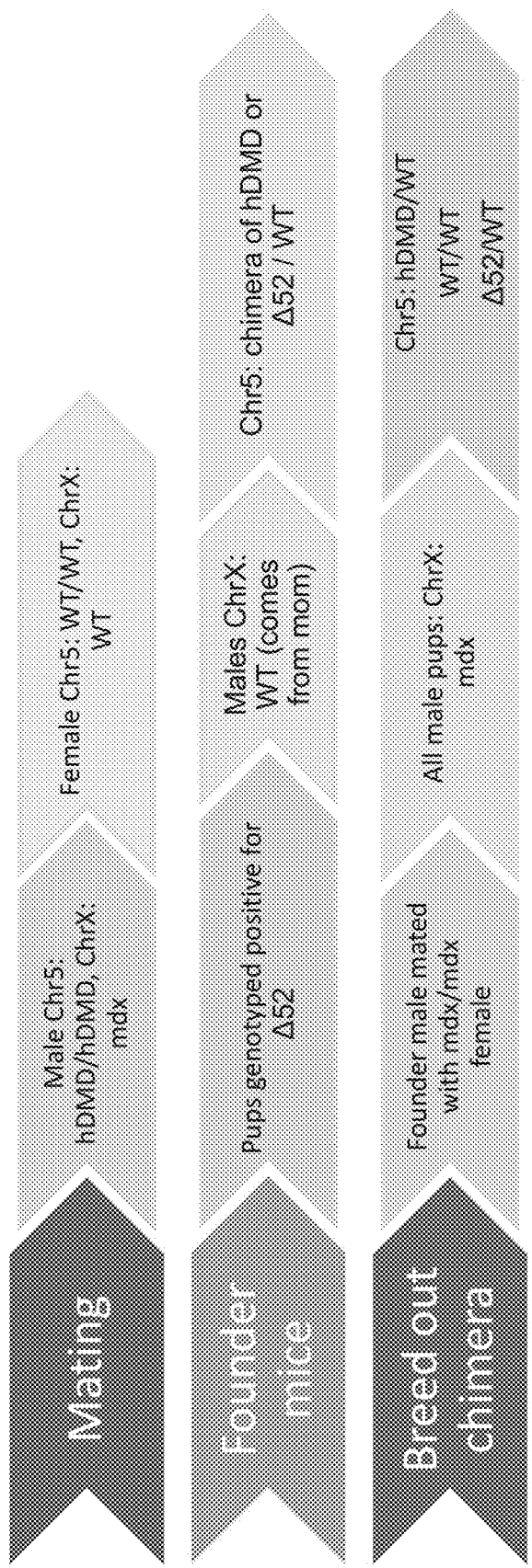
FIG. 24 shows a schematic of further mouse breeding.
Figure 25:
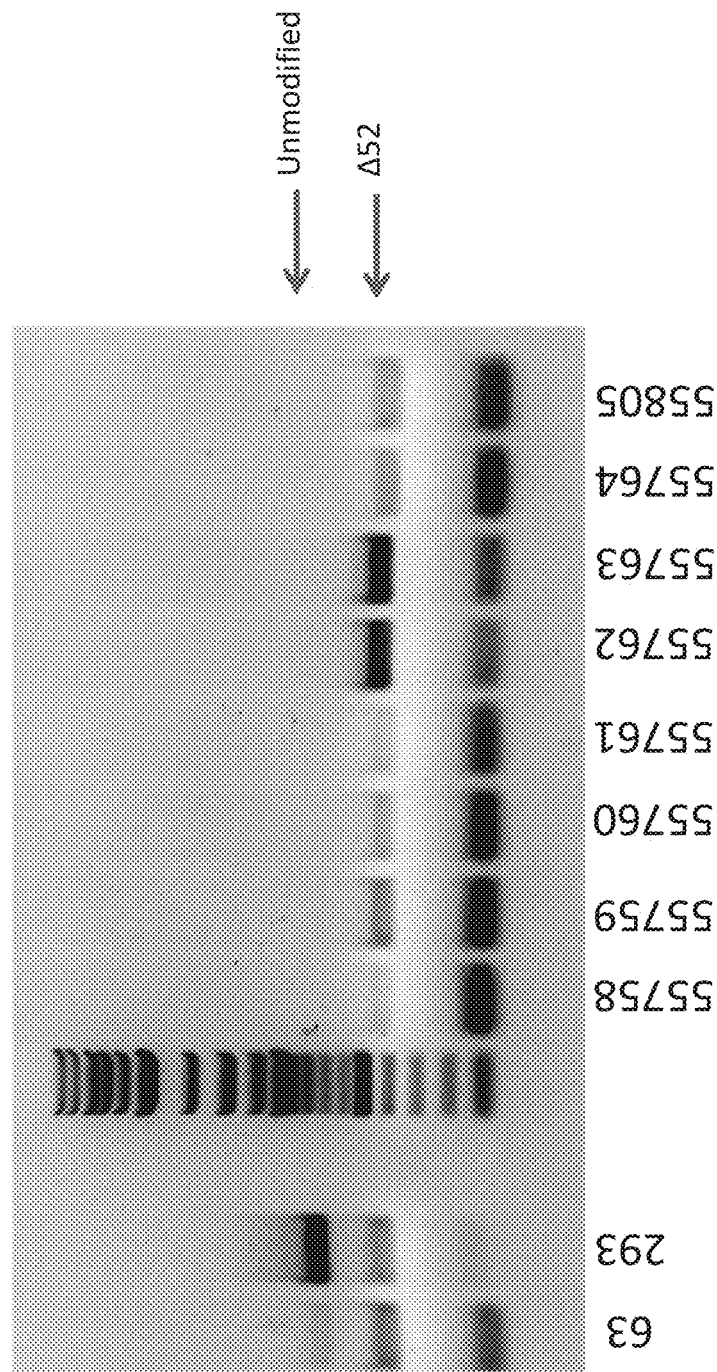
FIG. 25 shows the genotyping of litter 5 (males only) from the founder male 76+mdx/mdx breeding results. "63" is a founder male (but was not the parent in this case). "293" represents HEK293T cell genomic DNA control.
Figure 26:
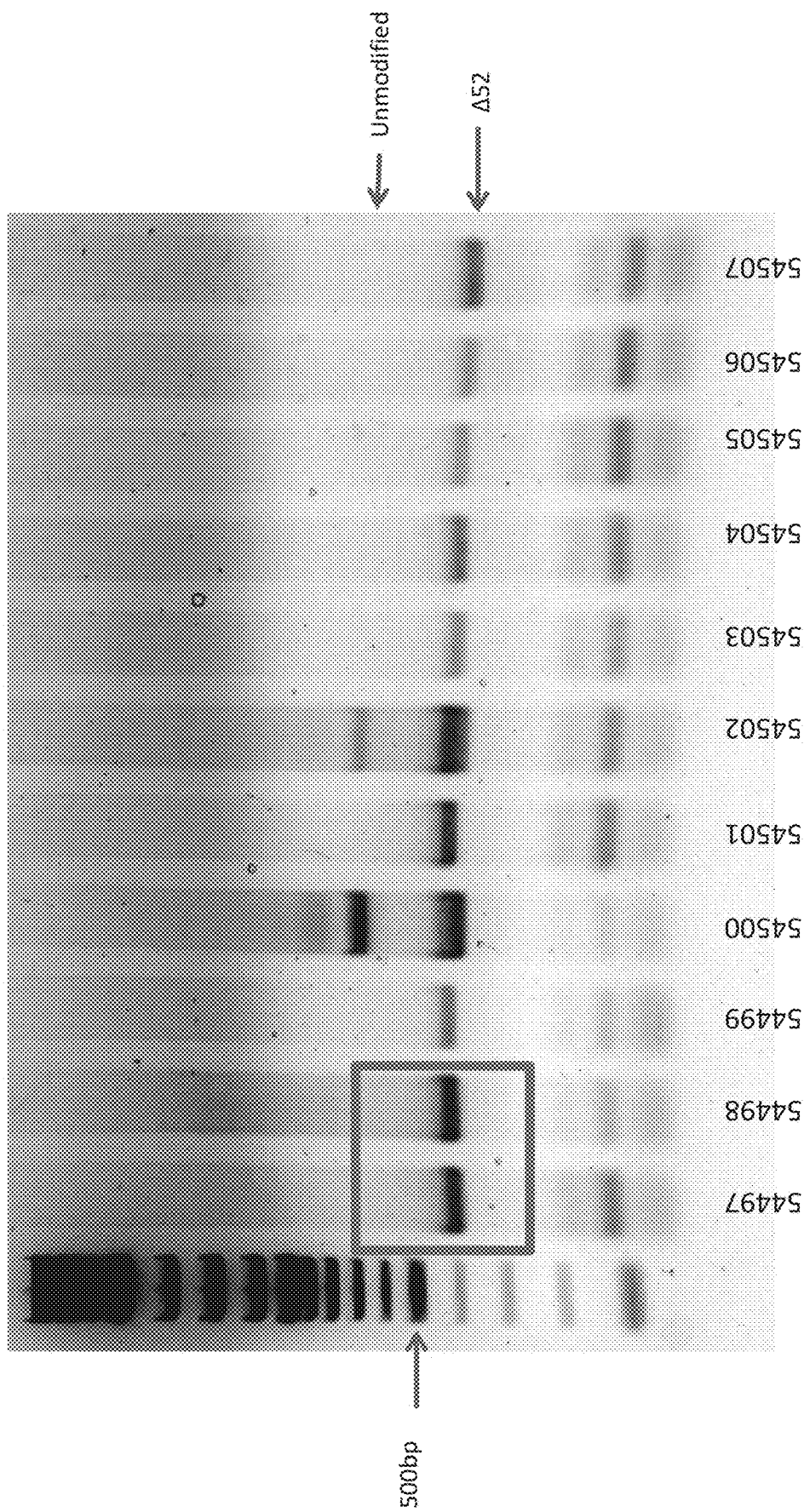
FIG. 26 shows the genotyping of litter 1 from the founder male 63+mdx/mdx breeding results.

The male founder mice were mated with mdx/mdx female to breed out chimera (FIG. 24). The litters generated from founder male 76 or founder male 63 with mdx/mdx female were screened and genotyped for the exon 52 deletion using the conditions used in FIG. 22 (FIG. 25 and FIG. 26, respectively). If exon 52 was deleted, then the expected band size was about 392 nt. If exon 52 was present, then the expected band size was about 718 nt. The pups 54497 and 54498 (from founder male 63+mdx/mdx female breeding pair) had the exon 52 deletion and were sequenced (FIG. 27). Pups 54497 and 54498 had 92.86% identity with each other in a 392 bp sequencing read and the indels were identical.

Figure 28:
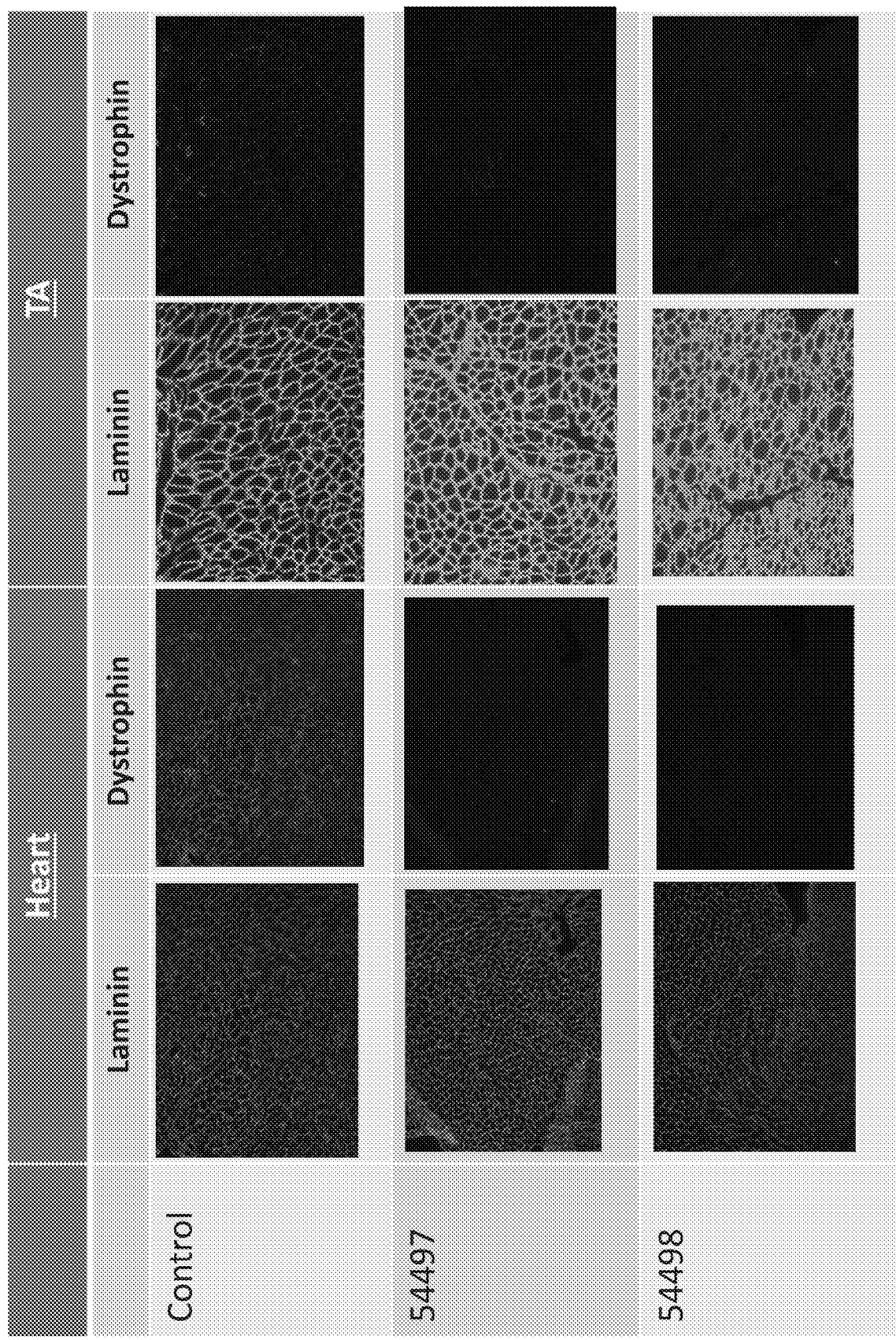
FIG. 28 shows immunohistochemical staining of heart and TA from pups 54497 and 54498.
Figure 29:
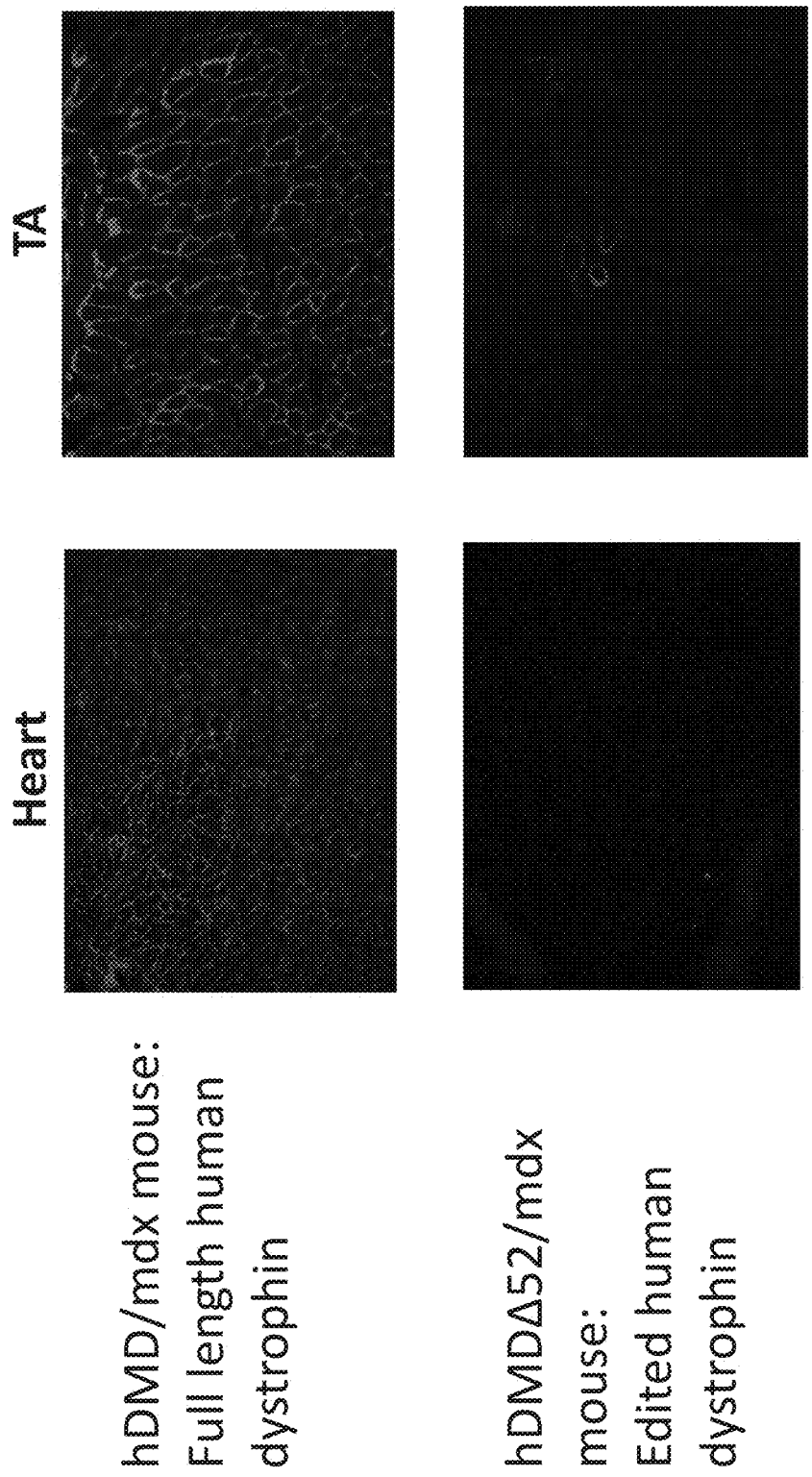
FIG. 29 shows that the Δ52/mdx mouse lacks dystrophin protein.
Figure 30:
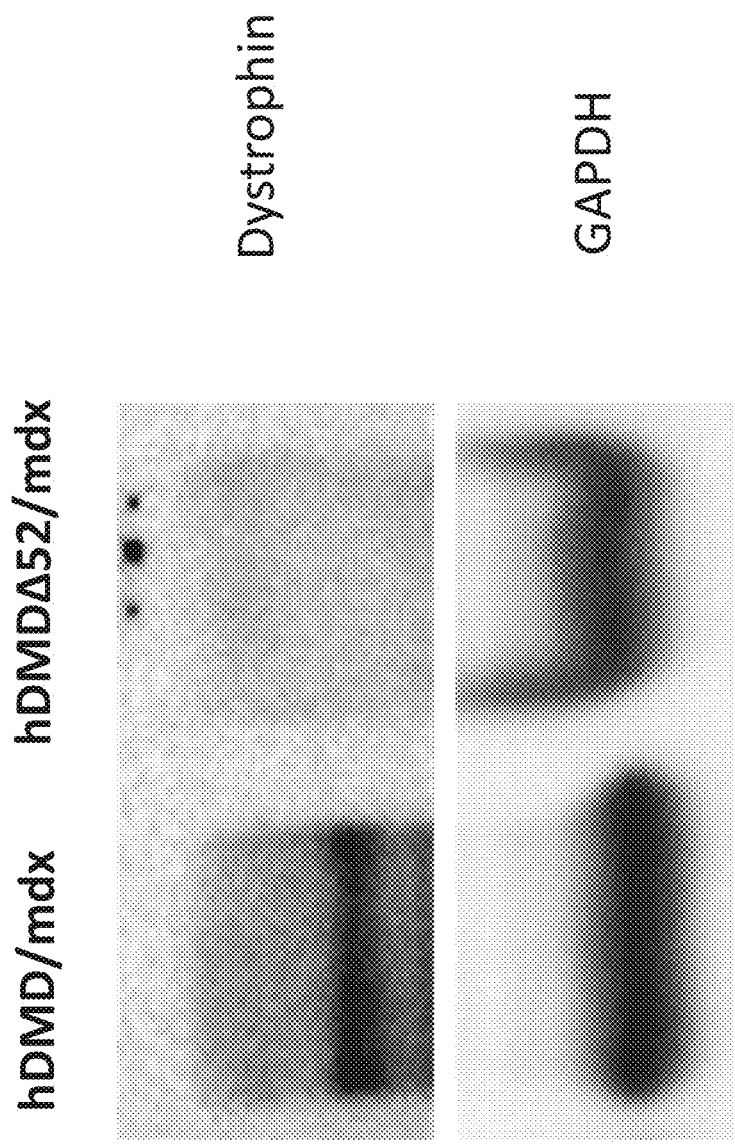
FIG. 30 shows a Western blot indicating that the Δ52/mdx mouse lacks dystrophin protein which is consistent with the DMD genotype, while the healthy hDMD/mdx mouse expresses dystrophin.

The expression of dystrophin in healthy hDMD/mdx mouse and the Δ52/mdx mouse was compared using fluorescent immunohistochemistry. As shown in FIG. 28, Δ52/mdx mice pups 54497 and 54498 lacked dystrophin protein. For the heart staining, exposure for laminin probe was 100 ms, while exposure for dystrophin was 900 ms. For the TA muscle sample, exposure for the laminin and dystrophin probes was 2.0 s. See also FIG. 29 which shows that the Δ52/mdx mouse lacked dystrophin protein. In both the heart and TA muscle, dystrophin expression was lost in the Δ52/mdx mouse. In the TA muscle, there were a few spontaneous revertant fibers (random splice events, or somatic mutations), but this was consistent with the mdx mouse model. Western blotting also indicated that the Δ52/mdx mouse lacked dystrophin protein which was consistent with the DMD genotype, while the healthy hDMD/mdx mouse expresses dystrophin. See FIG. 30.

Figure 31:
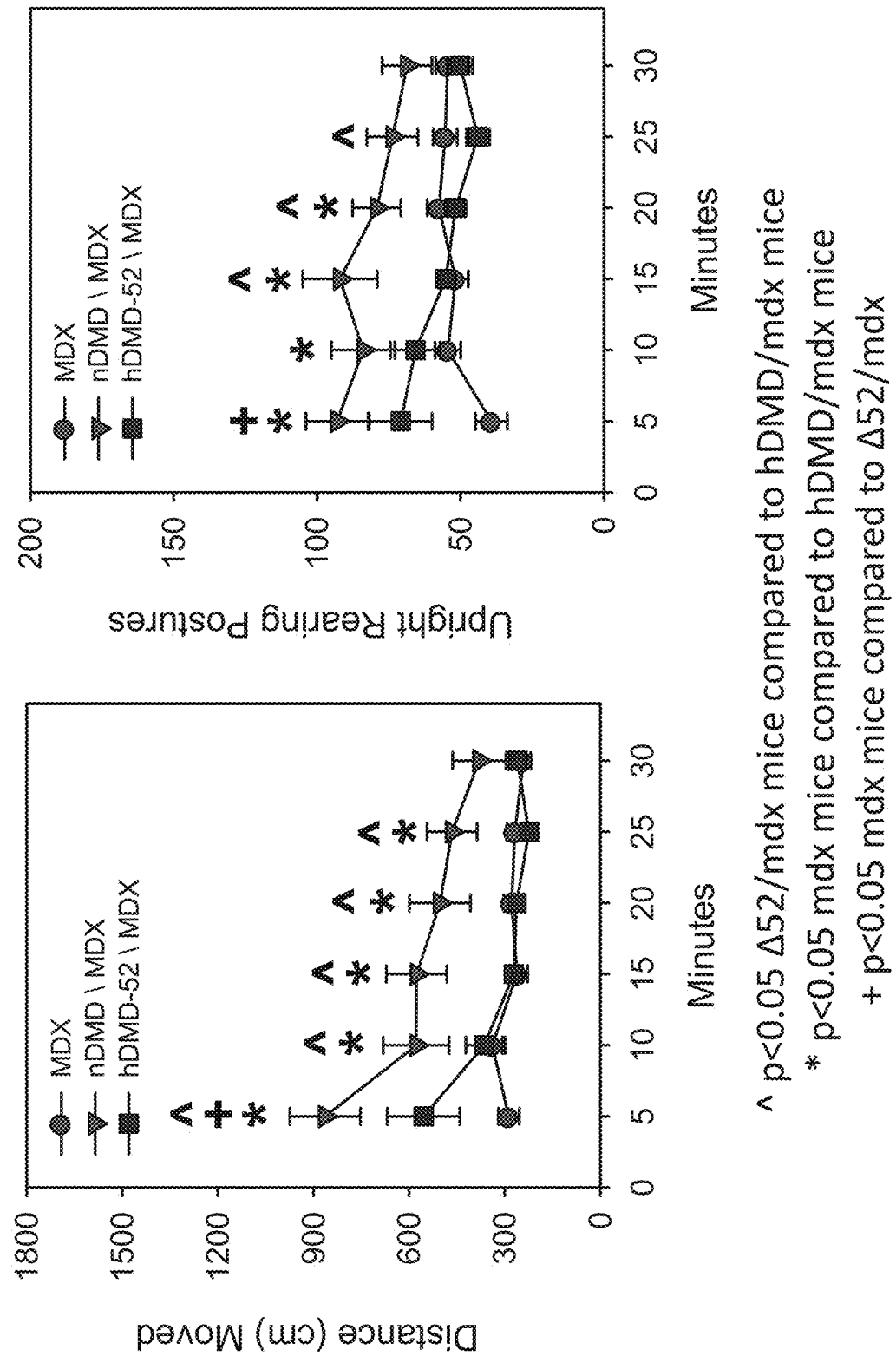
FIG. 31 shows the overall activity of the Δ52/mdx mouse compared to mdx mice and hDMD/mdx mice as indicated by locomotion and exploration.

The Δ52/mdx mouse showed similar levels of activity to the mdx mice after the first five minutes of an open field test. In the open field test, the mice were allowed to freely explore an open field arena (20×20×30 cm) for 30 minutes. The activity and location of the animal was automatically monitored using infrared diodes (x, y, and z axis) interfaced to a computer running Fusion Activity software (version 5.3, Omnitech, Columbus, OH). FIG. 31 shows the overall activity of the Δ52/mdx mouse compared to mdx mice and hDMD/mdx mice as indicated by locomotion and exploration. The distance traveled and the upright vertical activities are shown in the left and right panels, respectively.

Example 3

Dystrophin Restoration by Removal of Exon 51

Figure 32:
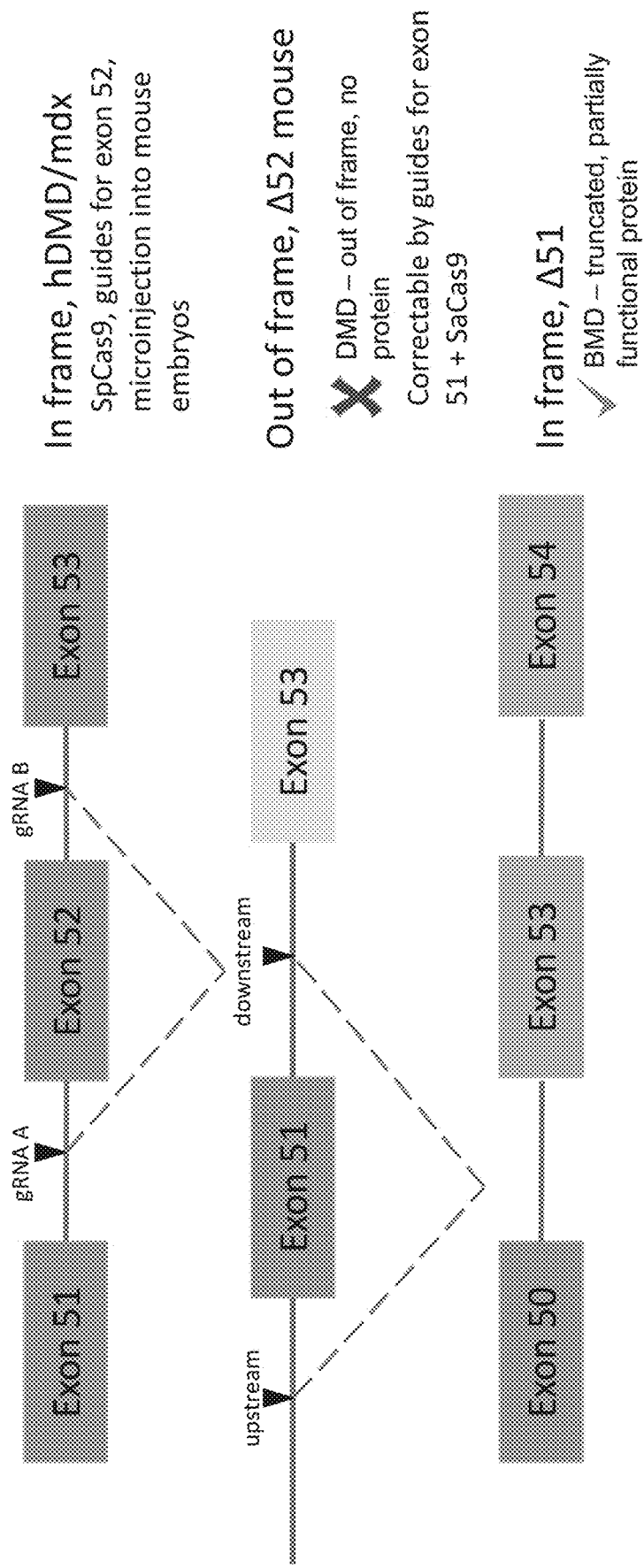
FIG. 32 shows the corrections strategy for the Δ52/mdx mouse using SaCas9 and gRNAs to skip exon 51 by targeting gRNAs upstream and downstream of exon 51 in the intronic region for removal.

The removal of exon 51 can generate a Becker Muscular Dystrophy (BMD)-like genotype in the Δ52/mdx mouse, and in theory restore dystrophin expression. The Δ52/mdx mouse was used to demonstrate the restoration of dystrophin expression by the removal of exon 51 using the disclosed CRISPR/Cas9-based gene editing system. FIG. 32 shows the corrections strategy using SaCas9 and gRNAs to skip exon 51 by targeting the gRNAs upstream and downstream of exon 51 in the intronic region.

Figure 33:
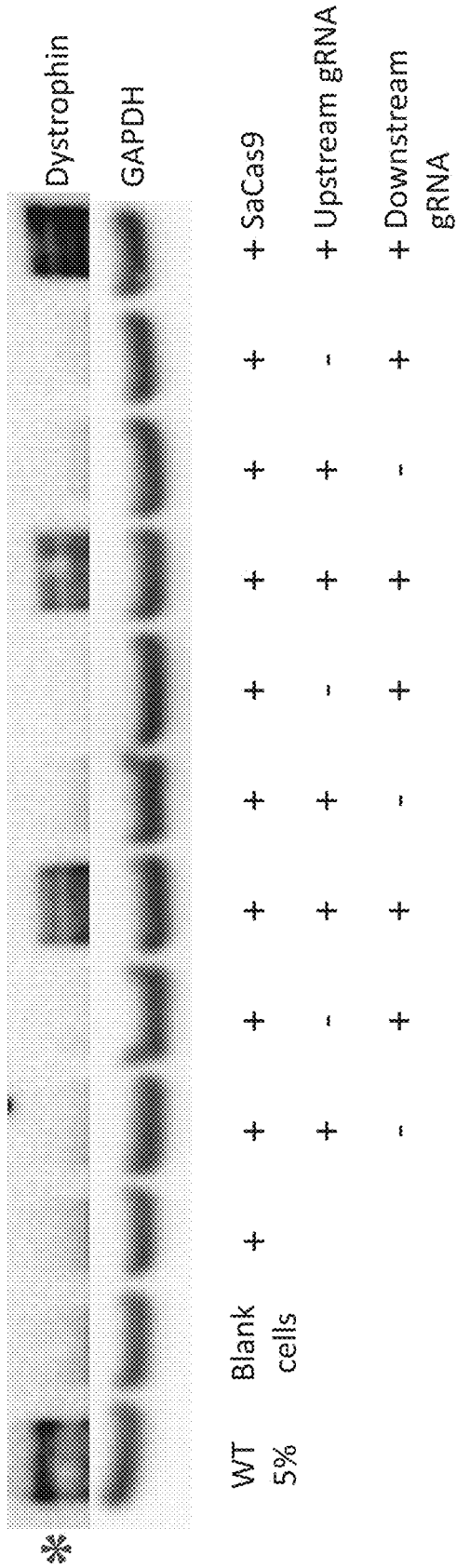
FIG. 33 shows in vitro restoration of dystrophin protein from exon 51 deletion in DMD patient myoblasts (DMD 6594 cells) using SaCas9 and gRNAs JCR179 and JCR183.

Standard: plasmids containing gRNAs JCR179 (upstream) or JCR183 (downstream) (SEQ ID NO: 37 and SEQ ID NO: 38, respectively) and SaCas9 were electroporated into DMD patient myoblasts. Protein was harvested from differentiated cells and analyzed using a Western blot with a dystrophin antibody. FIG. 33 shows that the genomic DNA can be edited to restore the dystrophin protein as cells treated with all 3 components (i.e., both gRNAs and SaCas9) showed dystrophin expression.

Figure 34:
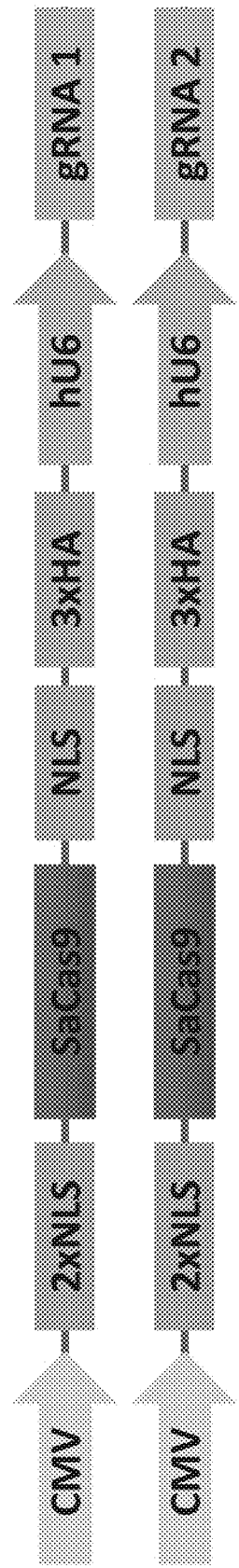
FIG. 34 shows the experimental design to treat Δ52/mdx mouse using the gRNAs and SaCas9 system.
Figure 35:
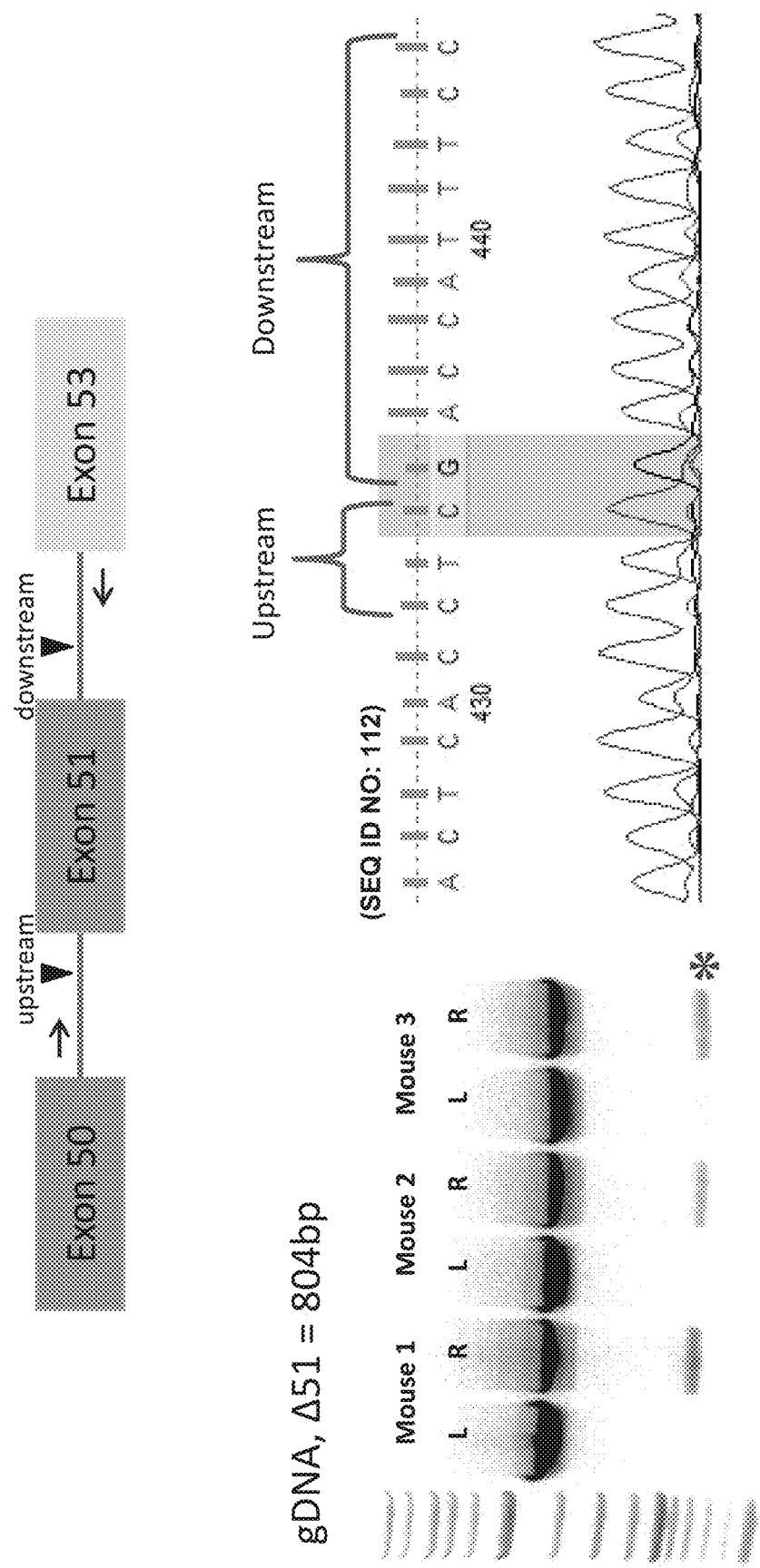
FIG. 35 shows in vivo exon 51 deletion in right TA muscle.

The system was then tested with the Δ52/mdx mouse. FIG. 34 shows the experimental design to treat Δ52/mdx mouse using the gRNAs and SaCas9 system, including schematics of 2 viral vectors used in the experimental design. AAV8 recombinant viral constructs were created using vectors PT366-179 (SEQ ID NO: 39) and PT366-183 (SEQ ID NO: 40) and methods known in the art to produce viral particles. These viral vectors (AAV8) were co-delivered in vivo as two viral particles. Each viral particle contained SaCas9 and one of the gRNAs (see FIG. 3). Δ52/mdx mice were treated with 5E11 of AAV8 recombinant viral constructs. The virus was injected intramuscularly into the right TA muscle, while the left TA muscle served as a contralateral control and was injected with PBS. After treatment, both the left and right TA muscles were removed and sections of each were taken for genomic DNA analyses. As shown in FIG. 35, PCR was performed across the region of interest and the deletion bands were noted in the treated right TA muscle on the left gel, indicating some level of gene editing. The deletion band was sequenced and the dominant product was the expected ligation 3 base pairs in from the PAM of each gRNA. FIG. 35 shows in vivo exon 51 deletion in right TA muscle.

Figure 36:
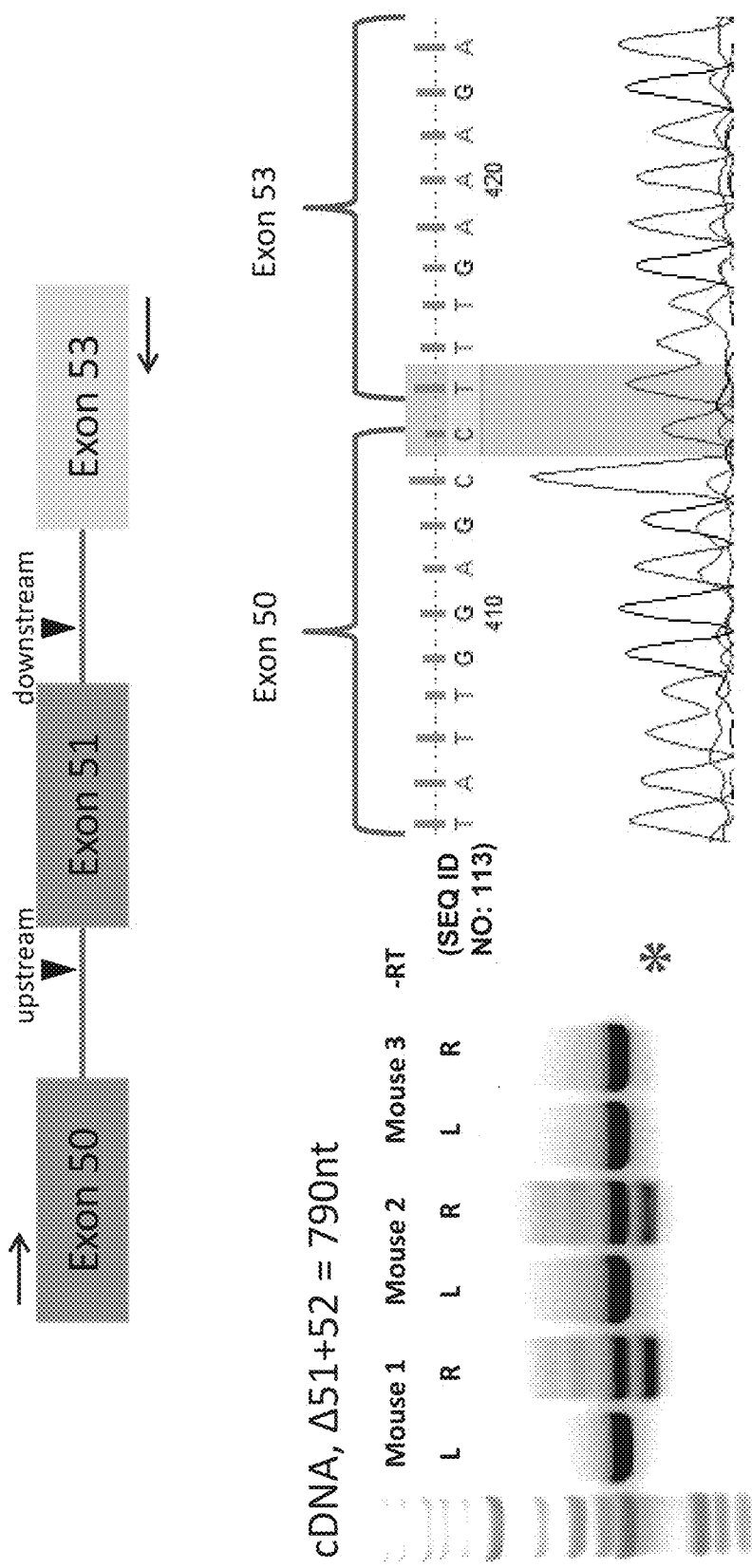
FIG. 36 shows in vivo exon 51 deletion in right TA muscle.

Similarly, sections of the treated right TA and control left TA muscles were analyzed to determine if editing carried through to the RNA. PCR was performed across exons 50 to 53 in the cDNA. As shown in the right gel of FIG. 36, there is a lack of exon 51 and 52 in two of the treated samples. The deletion band was sequenced and the dominant product was the ligation of exon 50 to 53, as expected given the mouse already lacked exon 52 and the CRISPR/Cas9-based gene editing system removed exon 51 (see bottom right sequence chromatogram). FIG. 36 shows in vivo exon 51 deletion in right TA muscle.

FIG. 37 shows representative fluorescent immunohistochemical staining indicating that little dystrophin was present in the control PBS injected left TA muscle of the Δ52/mdx mouse. Some degree of dystrophin staining in green on the control left TA may be due to revertant fibers or dead cells, which sometimes also stain green. There is a clear increase in the green dystrophin staining in the treated right TA muscle, as shown in the right photo. FIG. 37 shows in vivo dystrophin protein restoration in treated TA muscle.

Figure 38:
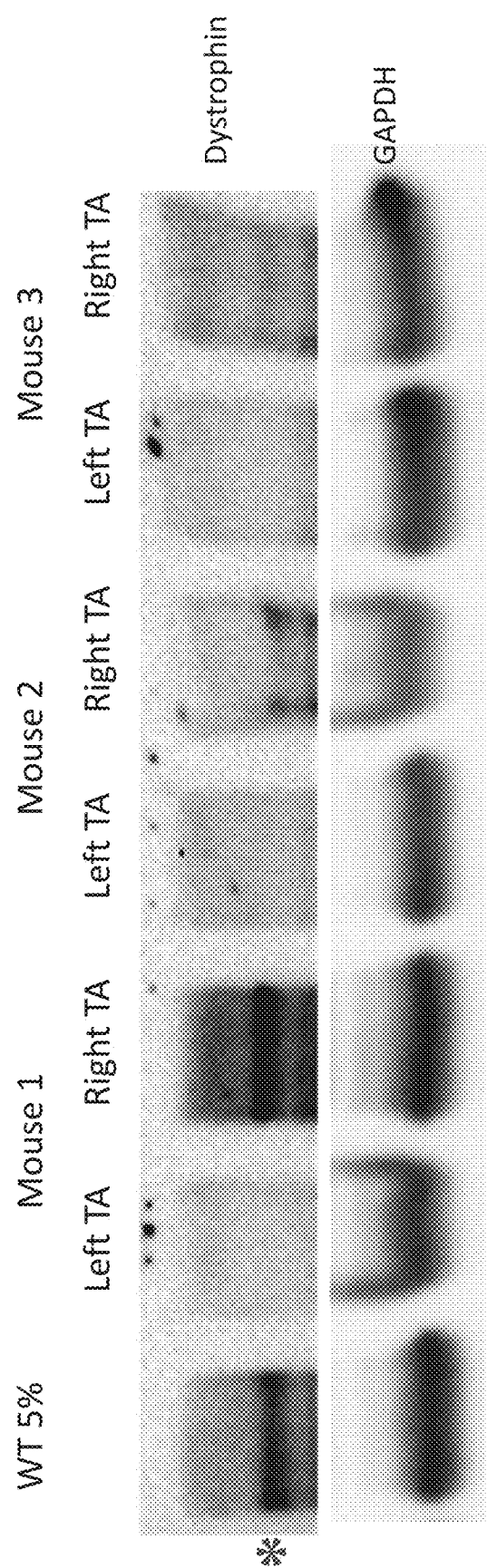
FIG. 38 shows in vivo dystrophin protein restoration in treated TA muscle.

Protein was extracted from the left and right TA muscles from 3 test mice and Western blot analysis was performed. FIG. 38 shows in vivo dystrophin protein restoration in treated TA muscle. No protein expression was seen in the control left TA muscles, while all three right TA muscles displayed varying levels of dystrophin protein expression. The protein expression from the right TA of mouse 1 was the strongest, while mouse 2 and 3 had faint but nonetheless present bands. The disclosed CRISPR/Cas9-based gene editing system worked in vivo to restore dystrophin protein expression to some degree in the Δ52/mdx mouse.

Mouse Physiology Testing. Treated mice (all male hDMD-Δ52(het)/mdx(hemi) mice) were treated with SaCas9- and gRNA-containing AAV8 (n=10) or AAV9 (n=10) recombinant viral constructs and compared with untreated mice (hDMD—Δ52/mdx) (n=10.). The AAV recombinant viral constructs were created using vectors PT366-179 (SEQ ID NO: 39) and PT366-183 (SEQ ID NO: 40) and using methods known in the art. The treated mice had 200 of virus injected into the tail vein between 6 and 8 weeks old. Mice were tested 8 weeks later.

Figure 40:
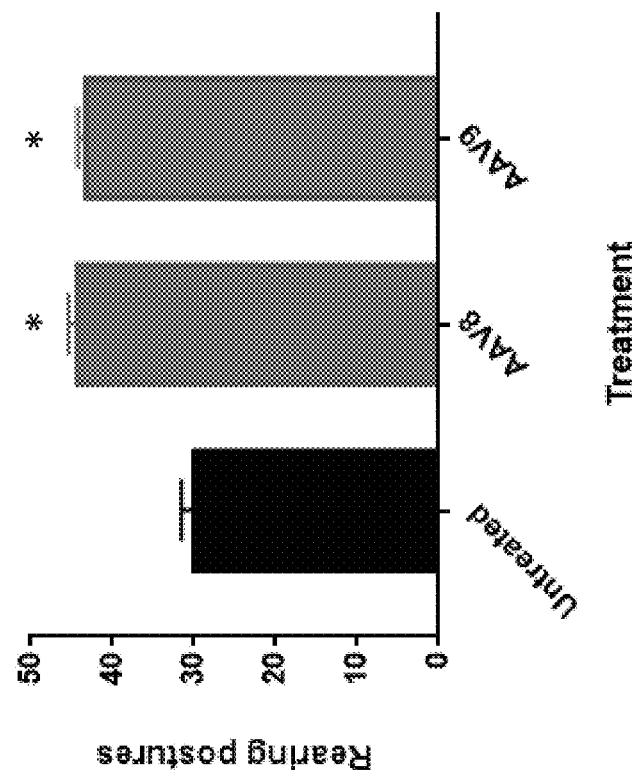
FIG. 40 shows average of all time points for total rearing postures.
Figure 39:
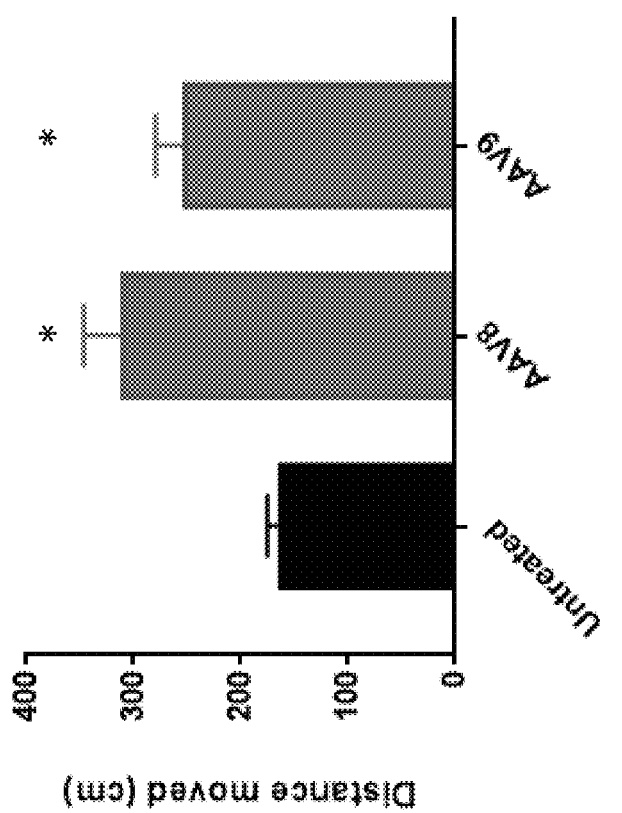
FIG. 39 shows average of all time points for total distance moved.

Open field distance test. Mice were allowed free exploration of an open field arena for 30 minutes. The activity and location of animals was automatically monitored with infrared diodes interfaced to a computer running Fusion Activity software. Data was collected continuously and binned into 5 minute intervals. FIG. 39 shows the average of all time points for total distance moved in 16 week old mice that were treated at 8 weeks old compared to 16 week old mice that were not treated. The average of all time points for total rearing postures after 16 weeks is shown in FIG. 40. Statistics were: one way ANOVA, compared each column mean to the untreated mean, and Dunnett post hoc (Mean+/−SEM). The AAV8 and AAV9 treated mice show statistically significant more distance traveled than untreated age matched mice (statistically significant). All treated mice show statistically significant increased amounts of rearing postures compared to untreated age matched control.

Figure 41:
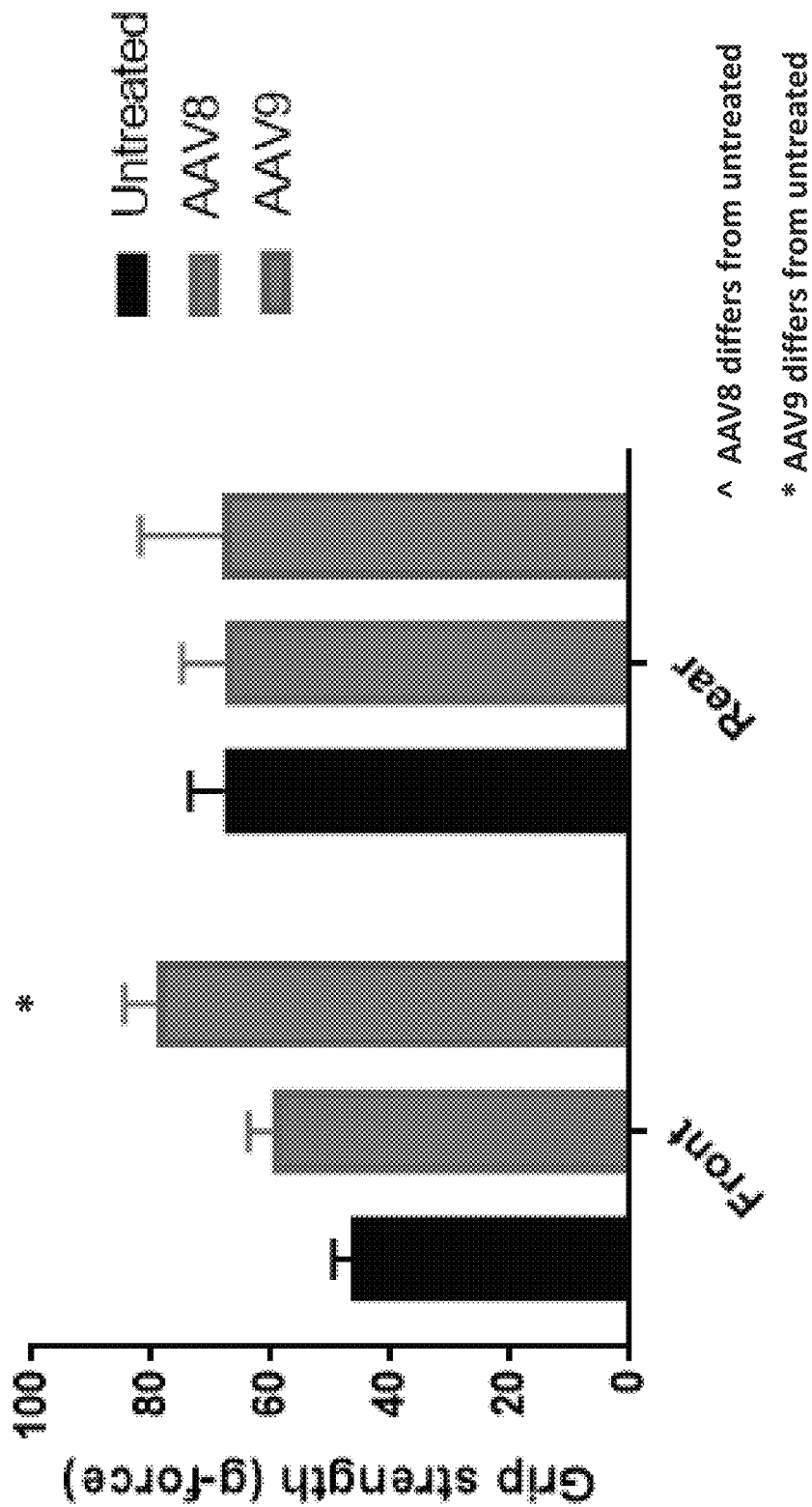
FIG. 41 shows the grip strength of 16 week untreated and treated mice.
Figure 42:
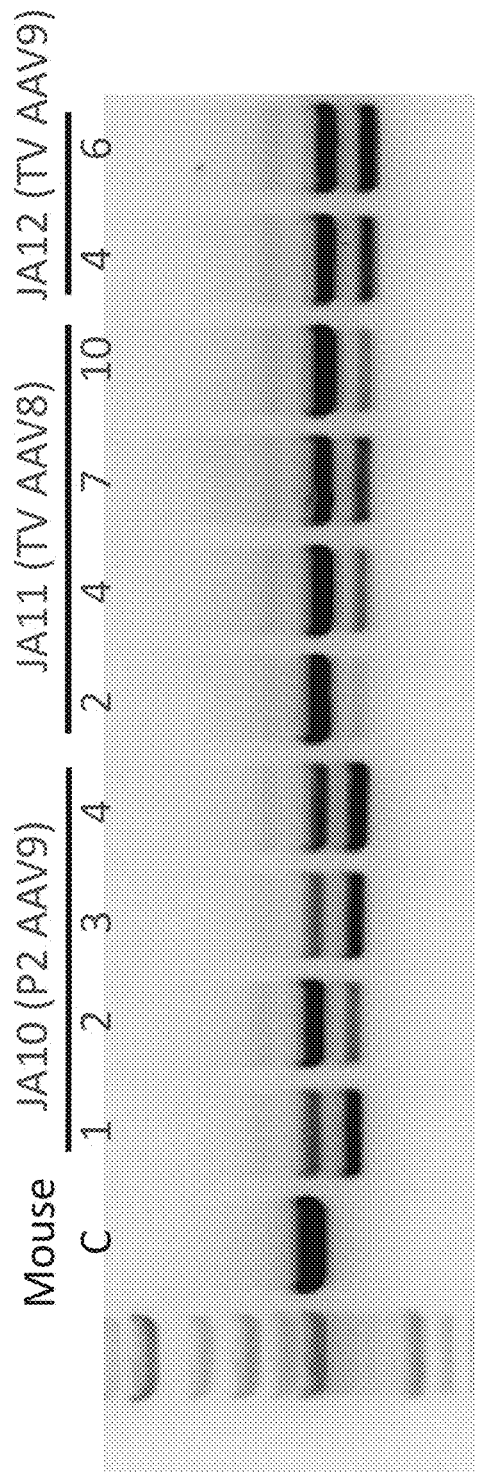
FIG. 42 shows cDNA PCR results of heart tissue.
Figure 43:
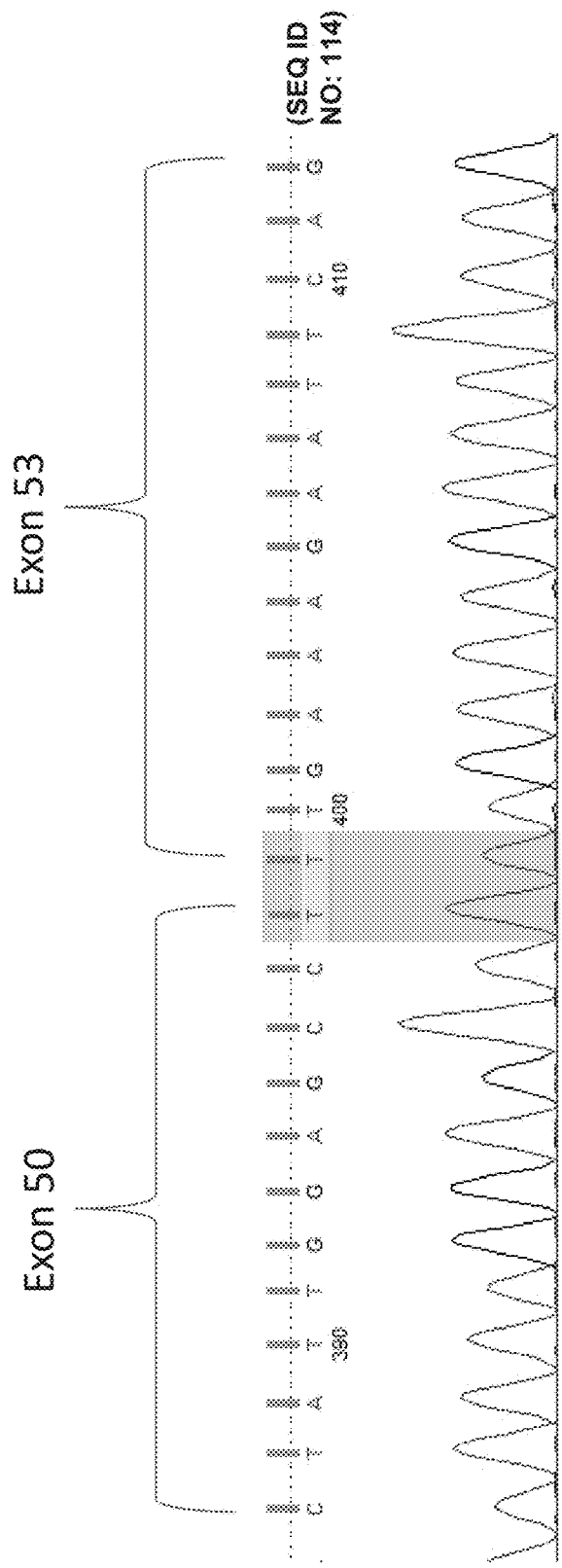
FIG. 43 shows sequencing of the amplified cDNA PCR bands from FIG. 42.

Grip strength. The grip strength of 16 week untreated and treated mice were tested. Mice were given 3-5 trials each for the front and rear feet to test grip strength. The average trial is shown in FIG. 41. Grip strength is reported as grams force. As shown in FIG. 41, AAV9 treated mice showed statistically significant increased grip strength force in the front paws compared to untreated age matched mice. Statistics were: Two-way ANOVA, Tukey's test post hoc.

cDNA PCR. Tissues from the hearts of mice were processed using the RNEasy Plus Universal mini kit (Qiagen). The resulting RNA was reversed transcribed to cDNA using SuperScript VILO cDNA synthesis kit. 1 μL of cDNA was PCR amplified using AccuPrime DNA Polymerase and primers in exon 48 (forward primer: gtttccagagctttacctgagaa (SEQ ID NO: 89)) and exon 54 (reverse primer: CTTTTAT-GAATGCTTCTCCAAG (SEQ ID NO: 90)). The expected band sizes were 997 nt if no deletion was present (i.e., exon 52 was still present) and approximately 764 nt if there was a deletion of exon 52. FIG. 42 shows P2 mice injected via facial vein with AAV9 ("JA10 (P2 AAV9)") at between 36-50 hrs old, and adult mice injected via tail vein with 3.3-7.7E12 of AAV8 ("JA11 (TV AAV8)") or 4.3-7.5E12 of AAV9 ("JA12 (TV AAV9)"). As shown in FIG. 42, editing occurred to varying degrees in P2 mice (48-54 hrs old mice) AAV9 treated mice, and AAV8 and AAV9 adult treated mice, which was further confirmed by sequencing the deletion band using the primer tttctgtgattttcttttggattg (SEQ ID NO: 109) which binds to exon 53. FIG. 43 shows a representative chromatogram showing the deletion of exons 51 and 52 in the sequence of the deletion band from Ja10 mouse 1.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

For reasons of completeness, various aspects of the invention are set out in the following numbered clause:

Clause 1. A guide RNA (gRNA) comprising a targeting domain that comprises a nucleotide sequence set forth in SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 41, SEQ ID NO: 42 or a complement thereof.

Clause 2. A DNA targeting composition comprising a first gRNA and a second gRNA, the first gRNA molecule and the second gRNA molecule comprise a targeting domain that comprises a nucleotide sequence set forth in SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 41, SEQ ID NO: 42, or a complement thereof, wherein the first gRNA molecule and the second gRNA molecule comprise different targeting domains.

Clause 3. The DNA targeting composition clause 2, wherein the first gRNA molecule is SEQ ID NO: 1, SEQ ID NO: 3, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, or SEQ ID NO: 41, and the second gRNA molecule is SEQ ID NO: 2, SEQ ID NO: 4, SEQ ID NO: 5, SEQ ID NO: 6, SEQ ID NO: 16, SEQ ID NO: 17, SEQ ID NO: 18, SEQ ID NO: 19, or SEQ ID NO: 42.

Clause 4. The DNA targeting composition of clause 2 or 3, wherein the first gRNA molecule is selected from the group consisting of SEQ ID NO: 1, SEQ ID NO: 11, SEQ ID NO: 12, SEQ ID NO: 13, SEQ ID NO: 14 and SEQ ID NO: 15, and the second gRNA molecule is selected from the group consisting of SEQ ID NO: 2, SEQ ID NO: 4, SEQ ID NO: 16, SEQ ID NO: 17, SEQ ID NO: 18, and SEQ ID NO: 19.

Clause 5. The DNA targeting composition of any one of clauses 2-4, wherein the first gRNA molecule and the second gRNA molecule are selected from the group consisting of: (i) a first gRNA molecule comprising a targeting domain that comprises a nucleotide sequence set forth in SEQ ID NO: 1, and a second gRNA molecule comprising a targeting domain that comprises a nucleotide sequence set forth in SEQ ID NO: 2; (ii) a first gRNA molecule comprising a targeting domain that comprises a nucleotide sequence set forth in SEQ ID NO: 11, and a second gRNA molecule comprising a targeting domain that comprises a nucleotide sequence set forth in SEQ ID NO: 4; (iii) a first gRNA molecule comprising a targeting domain that comprises a nucleotide sequence set forth in SEQ ID NO: 15, and a second gRNA molecule comprising a targeting domain that comprises a nucleotide sequence set forth in SEQ ID NO: 19; (iv) a first gRNA molecule comprising a targeting domain that comprises a nucleotide sequence set forth in SEQ ID NO: 15, and a second gRNA molecule comprising a targeting domain that comprises a nucleotide sequence set forth in SEQ ID NO: 18; (v) a first gRNA molecule comprising a targeting domain that comprises a nucleotide sequence set forth in SEQ ID NO: 15, and a second gRNA molecule comprising a targeting domain that comprises a nucleotide sequence set forth in SEQ ID NO: 4; (vi) a first gRNA molecule comprising a targeting domain that comprises a nucleotide sequence set forth in SEQ ID NO: 14, and a second gRNA molecule comprising a targeting domain that comprises a nucleotide sequence set forth in SEQ ID NO: 19; (vii) a first gRNA molecule comprising a targeting domain that comprises a nucleotide sequence set forth in SEQ ID NO: 14, and a second gRNA molecule comprising a targeting domain that comprises a nucleotide sequence set forth in SEQ ID NO: 18; (viii) a first gRNA molecule comprising a targeting domain that comprises a nucleotide sequence set forth in SEQ ID NO: 14, and a second gRNA molecule comprising a targeting domain that comprises a nucleotide sequence set forth in SEQ ID NO: 4; (ix) a first gRNA molecule comprising a targeting domain that comprises a nucleotide sequence set forth in SEQ ID NO: 11, and a second gRNA molecule comprising a targeting domain that comprises a nucleotide sequence set forth in SEQ ID NO: 19; (x) a first gRNA molecule comprising a targeting domain that comprises a nucleotide sequence set forth in SEQ ID NO: 14, and a second gRNA molecule comprising a targeting domain that comprises a nucleotide sequence set forth in SEQ ID NO: 15; (xi) a first gRNA molecule comprising a targeting domain that comprises a nucleotide sequence set forth in SEQ ID NO: 11, and a second gRNA molecule comprising a targeting domain that comprises a nucleotide sequence set forth in SEQ ID NO: 18; and (xii) a first gRNA molecule comprising a targeting domain that comprises a nucleotide sequence set forth in SEQ ID NO: 41, and a second gRNA molecule comprising a targeting domain that comprises a nucleotide sequence set forth in SEQ ID NO: 42.

Clause 6. The DNA targeting composition of any one of clauses 2-5, further comprising a Clustered Regularly Interspaced Short Palindromic Repeats associated (Cas) protein.

Clause 7. The DNA targeting composition of clause 6, wherein the Cas protein comprises a Cas9 molecule that recognizes a Protospacer Adjacent Motif (PAM) of either NNGRRT (SEQ ID NO: 24) or NNGRRV (SEQ ID NO: 25).

Clause 8. The DNA targeting composition of clause 6 or 7, wherein the Cas protein comprises a *Staphylococcus aureus* Cas9 molecule having an amino acid sequence of SEQ ID NO: 45.

Clause 9. The DNA targeting composition of any one of clauses 2-8, wherein the DNA targeting composition comprises a nucleotide sequence of SEQ ID NO: 83, a nucleotide sequence of SEQ ID NO: 84, a nucleotide sequence of SEQ ID NO: 37, and/or a nucleotide sequence of SEQ ID NO: 38.

Clause 10. An isolated polynucleotide comprising the gRNA molecule of clause 1 or the DNA targeting composition of any one of clauses 2-9.

Clause 11. A vector comprising the gRNA of clause 1, the DNA targeting composition of any one of clauses 2-9, or the isolated polynucleotide of clause 10.

Clause 12. A vector comprising the DNA targeting composition of any one of clauses 6-9.

Clause 13. A vector encoding: (a) a first guide RNA (gRNA) molecule, (b) a second gRNA molecule, and (c) at least one Cas9 molecule that recognizes a Protospacer Adjacent Motif (PAM) of either NNGRRT (SEQ ID NO: 24) or NNGRRV (SEQ ID NO: 25), wherein the first gRNA molecule and the second gRNA molecule comprise a targeting domain that comprises a nucleotide sequence set forth in SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 41, SEQ ID NO: 42, or a complement thereof, wherein the first gRNA molecule and the second gRNA molecule comprise different targeting domains.

Clause 14. The vector of clause 13, wherein the vector is configured to form a first and a second double strand break in a first and a second intron flanking exon 51 of the human DMD gene.

Clause 15. The vector of clause 13 or 14, wherein the first gRNA molecule is SEQ ID NO: 1, SEQ ID NO: 3, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, or SEQ ID NO: 41, and the second gRNA molecule is SEQ ID NO: 2, SEQ ID NO: 4, SEQ ID NO: 5, SEQ ID NO: 6, SEQ ID NO: 16, SEQ ID NO: 17, SEQ ID NO: 18, SEQ ID NO: 19, or SEQ ID NO: 42.

Clause 16. The vector of any one of clauses 13-15, wherein the first gRNA molecule is selected from the group consisting of SEQ ID NO: 1, SEQ ID NO: 11, SEQ ID NO: 12, SEQ ID NO: 13, SEQ ID NO: 14 and SEQ ID NO: 15, and the second gRNA molecule is selected from the group consisting of SEQ ID NO: 2, SEQ ID NO: 4, SEQ ID NO: 16, SEQ ID NO: 17, SEQ ID NO: 18, and SEQ ID NO: 19.

Clause 17. The vector of any one of clauses 13-16, the first gRNA molecule and the second gRNA molecule are selected from the group consisting of: (i) a first gRNA molecule comprising a targeting domain that comprises a nucleotide sequence set forth in SEQ ID NO: 1, and a second gRNA molecule comprising a targeting domain that comprises a nucleotide sequence set forth in SEQ ID NO: 2; (ii) a first gRNA molecule comprising a targeting domain that comprises a nucleotide sequence set forth in SEQ ID NO: 11, and a second gRNA molecule comprising a targeting domain that comprises a nucleotide sequence set forth in SEQ ID NO: 4; (iii) a first gRNA molecule comprising a targeting domain that comprises a nucleotide sequence set forth in SEQ ID NO: 15, and a second gRNA molecule comprising a targeting domain that comprises a nucleotide sequence set forth in SEQ ID NO: 19; (iv) a first gRNA molecule comprising a targeting domain that comprises a nucleotide sequence set forth in SEQ ID NO: 15, and a second gRNA molecule comprising a targeting domain that comprises a nucleotide sequence set forth in SEQ ID NO: 18; (v) a first gRNA molecule comprising a targeting domain that comprises a nucleotide sequence set forth in SEQ ID NO: 15, and a second gRNA molecule comprising a targeting domain that comprises a nucleotide sequence set forth in SEQ ID NO: 4; (vi) a first gRNA molecule comprising a targeting domain that comprises a nucleotide sequence set forth in SEQ ID NO: 14, and a second gRNA molecule comprising a targeting domain that comprises a nucleotide sequence set forth in SEQ ID NO: 19; (vii) a first gRNA molecule comprising a targeting domain that comprises a nucleotide sequence set forth in SEQ ID NO: 14, and a second gRNA molecule comprising a targeting domain that comprises a nucleotide sequence set forth in SEQ ID NO: 18; (viii) a first gRNA molecule comprising a targeting domain that comprises a nucleotide sequence set forth in SEQ ID NO: 14, and a second gRNA molecule comprising a targeting domain that comprises a nucleotide sequence set forth in SEQ ID NO: 4; (ix) a first gRNA molecule comprising a targeting domain that comprises a nucleotide sequence set forth in SEQ ID NO: 11, and a second gRNA molecule comprising a targeting domain that comprises a nucleotide sequence set forth in SEQ ID NO: 19; (x) a first gRNA molecule comprising a targeting domain that comprises a nucleotide sequence set forth in SEQ ID NO: 14, and a second gRNA molecule comprising a targeting domain that comprises a nucleotide sequence set forth in SEQ ID NO: 15; and (xi) a first gRNA molecule comprising a targeting domain that comprises a nucleotide sequence set forth in SEQ ID NO: 11, and a second gRNA molecule comprising a targeting domain that comprises a nucleotide sequence set forth in SEQ ID NO: 18.

Clause 18. The vector of any one of clauses 11-17, wherein the vector is a viral vector.

Clause 19. The vector of clause 18, wherein the vector is an Adeno-associated virus (AAV) vector.

Clause 20. The vector of clause 19, wherein the AAV vector is an AAV8 vector or an AAV9 vector.

Clause 21. The vector of any one of clauses 11-20, wherein the vector comprises a tissue-specific promoter operably linked to the nucleotide sequence encoding the first gRNA molecule, the second gRNA molecule, and/or the Cas9 molecule.

Clause 22. The vector of clause 21, wherein the tissue-specific promoter is a muscle specific promoter.

Clause 23. A cell comprising the gRNA of clause 1, the DNA targeting composition of any one of clauses 2-9, the isolated polynucleotide of clause 10, or the vector of any one of clauses 11-22.

Clause 24. A kit comprising the gRNA of clause 1, the DNA targeting system of any one of clauses 2-9, the isolated polynucleotide of clause 10, the vector of any one of clauses 11-22, or the cell of clause 23, and optionally instructions for use.

Clause 25. A method of correcting a mutant dystrophin gene in a cell, the method comprising administering to a cell the gRNA of clause 1, the DNA targeting system of any one of clauses 2-9, the isolated polynucleotide of clause 10, or the vector of any one of clauses 11-22.

Clause 26. A method of genome editing a mutant dystrophin gene in a subject, the method comprising administering to the subject a genome editing composition comprising the gRNA of clause 1, the DNA targeting system of any one of clauses 2-9, the isolated polynucleotide of clause 10, the vector of any one of clauses 11-22, or the cell of clause 23.

Clause 27. The method of clause 26, wherein the genome editing composition is administered the subject intramuscularly, intravenously or a combination thereof.

Clause 28. The method of any one of clauses 25-27, wherein correcting the mutant dystrophin gene comprises nuclease-mediated non-homologous end joining.

Clause 29. A method of treating a subject in need thereof having a mutant dystrophin gene, the method comprising administering to the subject the gRNA of clause 1, the DNA targeting system of any one of clauses 2-9, the isolated polynucleotide of clause 10, the vector of any one of clauses 11-22, or the cell of clause 23.

Clause 30. A modified adeno-associated viral vector for genome editing a mutant dystrophin gene in a subject comprising a first polynucleotide sequence encoding the gRNA of clause 1, and a second polynucleotide sequence encoding a Cas9 molecule that recognizes a Protospacer Adjacent Motif (PAM) of either NNGRRT (SEQ ID NO: 24) or NNGRRV (SEQ ID NO: 25).

Clause 31. The modified adeno-associated viral vector of clause 30, wherein the modified adeno-associated viral vector comprises the nucleotide sequence set forth in SEQ ID NO: 39 or SEQ ID NO: 40.

Clause 32. A composition for deleting a segment of a dystrophin gene comprising exon 51, the composition comprising: (a) a first vector comprising a polynucleotide sequence encoding a first guide RNA (gRNA) molecule and a polynucleotide sequence encoding a first Cas9 molecule that recognizes a Protospacer Adjacent Motif (PAM) of either NNGRRT (SEQ ID NO: 24) or NNGRRV (SEQ ID NO: 25), and (b) a second vector comprising a polynucleotide sequence encoding a second gRNA molecule and a polynucleotide sequence encoding a second Cas9 molecule that recognizes a Protospacer Adjacent Motif (PAM) of either NNGRRT (SEQ ID NO: 24) or NNGRRV (SEQ ID NO: 25), wherein each of the first and second gRNA molecules have a targeting domain of 19 to 24 nucleotides in length, and wherein the first vector and second vector are configured to form a first and a second double strand break in a first intron and a second intron flanking exon 51 of the human DMD gene, respectively, thereby deleting a segment of the dystrophin gene comprising exon 51.

Clause 33. The composition of clause 32, wherein the segment has a length of about 50 base pairs to about 2,000 base pairs.

Clause 34. The composition of clause 33, wherein the segment has a length of about 118 base pairs, about 233 base pairs, about 326 base pairs, about 766 base pairs, about 805 base pairs, or about 1611 base pairs.

Clause 35. The composition of any one of clauses 32-34, wherein the first Cas9 molecule and the second Cas9 molecule are the same.

Clause 36. The composition of clause 35, wherein the first Cas9 molecule and the second Cas9 molecule is a *Staphylococcus aureus* Cas9 molecule.

Clause 37. The composition of clause 36, wherein the first Cas9 molecule and the second Cas9 molecule is a mutant *Staphylococcus aureus* Cas9 molecule.

Clause 38. The composition of any one of clauses 32-34, wherein the first Cas9 molecule and the second Cas9 molecule are different.

Clause 39. The composition of clause 38, wherein the first Cas9 molecule or the second Cas9 molecule is a *Staphylococcus aureus* Cas9 molecule.

Clause 40. The composition of any one of clauses 32-39, wherein the first Cas9 molecule and/or the second Cas9 molecule comprises a SaCas9 molecule having an amino acid sequence of SEQ ID NO: 45.

Clause 41. The composition of any one of clauses 32-40, wherein the first vector and/or the second vector is a viral vector.

Clause 42. The composition of clause 41, wherein the first vector and/or the second vector is an Adeno-associated virus (AAV) vector.

Clause 43. The composition of clause 42, wherein the AAV vector is an AAV8 vector or an AAV9 vector.

Clause 44. The composition of any one of clauses 32-43, wherein the dystrophin gene is a human dystrophin gene.

Clause 45. The composition of any one of clauses 32-44, wherein the first gRNA molecule and the second gRNA molecule comprise a targeting domain that comprises a nucleotide sequence set forth in SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, or a complement thereof, wherein the first gRNA molecule and the second gRNA molecule comprise different targeting domains.

Clause 46. The composition of any one of clauses 32-45, wherein the first gRNA molecule is SEQ ID NO: 1, SEQ ID NO: 3, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, or SEQ ID NO: 15, and the second gRNA molecule is SEQ ID NO: 2, SEQ ID NO: 4, SEQ ID NO: 5, SEQ ID NO: 6, SEQ ID NO: 16, SEQ ID NO: 17, SEQ ID NO: 18, or SEQ ID NO: 19.

Clause 47. The composition of any one of clauses 32-46, wherein the first gRNA molecule is selected from the group consisting of SEQ ID NO: 1, SEQ ID NO: 11, SEQ ID NO: 12, SEQ ID NO: 13, SEQ ID NO: 14 and SEQ ID NO: 15, and the second gRNA molecule is selected from the group consisting of SEQ ID NO: 2, SEQ ID NO: 4, SEQ ID NO: 16, SEQ ID NO: 17, SEQ ID NO: 18, and SEQ ID NO: 19.

Clause 48. The composition of any one of clauses 32-47, wherein the first gRNA molecule and the second gRNA molecule are selected from the group consisting of: (i) a first gRNA molecule comprising a targeting domain that comprises a nucleotide sequence set forth in SEQ ID NO: 1, and a second gRNA molecule comprising a targeting domain that comprises a nucleotide sequence set forth in SEQ ID NO: 2; (ii) a first gRNA molecule comprising a targeting domain that comprises a nucleotide sequence set forth in SEQ ID NO: 11, and a second gRNA molecule comprising a targeting domain that comprises a nucleotide sequence set forth in SEQ ID NO: 4; (iii) a first gRNA molecule comprising a targeting domain that comprises a nucleotide sequence set forth in SEQ ID NO: 15, and a second gRNA molecule comprising a targeting domain that comprises a nucleotide sequence set forth in SEQ ID NO: 19; (iv) a first gRNA molecule comprising a targeting domain that comprises a nucleotide sequence set forth in SEQ ID NO: 15, and a second gRNA molecule comprising a targeting domain that comprises a nucleotide sequence set forth in SEQ ID NO: 18; (v) a first gRNA molecule comprising a targeting domain that comprises a nucleotide sequence set forth in SEQ ID NO: 15, and a second gRNA molecule comprising a targeting domain that comprises a nucleotide sequence set forth in SEQ ID NO: 4; (vi) a first gRNA molecule comprising a targeting domain that comprises a nucleotide sequence set forth in SEQ ID NO: 14, and a second gRNA molecule comprising a targeting domain that comprises a nucleotide sequence set forth in SEQ ID NO: 19; (vii) a first gRNA molecule comprising a targeting domain that comprises a nucleotide sequence set forth in SEQ ID NO: 14, and a second gRNA molecule comprising a targeting domain that comprises a nucleotide sequence set forth in SEQ ID NO: 18; (viii) a first gRNA molecule comprising a targeting domain that comprises a nucleotide sequence set forth in SEQ ID NO: 14, and a second gRNA molecule comprising a targeting domain that comprises a nucleotide sequence set forth in SEQ ID NO: 4; (ix) a first gRNA molecule comprising a targeting domain that comprises a nucleotide sequence set forth in SEQ ID NO: 11, and a second gRNA molecule comprising a targeting domain that comprises a nucleotide sequence set forth in SEQ ID NO: 19; (x) a first gRNA molecule comprising a targeting domain that comprises a nucleotide sequence set forth in SEQ ID NO: 14, and a second gRNA molecule comprising a targeting domain that comprises a nucleotide sequence set forth in SEQ ID NO: 15; and (xi) a first gRNA molecule comprising a targeting domain that comprises a nucleotide sequence set forth in SEQ ID NO: 11, and a second gRNA molecule comprising a targeting domain that comprises a nucleotide sequence set forth in SEQ ID NO: 18.

Clause 49. The composition of any one of clauses 32-48, wherein the first vector comprises a nucleotide sequence set forth in SEQ ID NO; 39 and the second vector comprises a nucleotide sequence set forth in SEQ ID NO: 40.

Clause 50. The composition of any one of clauses 32-49, for use in a medicament.

Clause 51. The composition of any one of clauses 32-50, for use in the treatment of Duchenne Muscular Dystrophy.

Clause 52. A cell comprising the composition of any one of clauses 32-51.

Clause 53. A method of correcting a mutant dystrophin gene in a cell, comprising administering to the cell: (a) a first vector comprising a polynucleotide sequence encoding a first guide RNA (gRNA) molecule and a polynucleotide sequence encoding a first Cas9 molecule that recognizes a Protospacer Adjacent Motif (PAM) of either NNGRRT (SEQ ID NO: 24) or NNGRRV (SEQ ID NO: 25), and (b) a second vector comprising a polynucleotide sequence encoding a second gRNA molecule and a polynucleotide sequence encoding a second Cas9 molecule that recognizes a Protospacer Adjacent Motif (PAM) of either NNGRRT (SEQ ID NO: 24) or NNGRRV (SEQ ID NO: 25), wherein each of the first gRNA and second gRNA molecules have a targeting domain of 19 to 24 nucleotides in length, and wherein the vector is configured to form a first and a second double strand break in a first and a second intron flanking exon 51 of the human dystrophin gene, respectively, thereby deleting a segment of the dystrophin gene comprising exon 51.

Clause 54. The method of clause 53, wherein the first gRNA molecule and the second gRNA molecule are selected from the group consisting of: (i) a first gRNA molecule comprising a targeting domain that comprises a nucleotide sequence set forth in SEQ ID NO: 1, and a second gRNA molecule comprising a targeting domain that comprises a nucleotide sequence set forth in SEQ ID NO: 2; (ii) a first gRNA molecule comprising a targeting domain that comprises a nucleotide sequence set forth in SEQ ID NO: 11, and a second gRNA molecule comprising a targeting domain that comprises a nucleotide sequence set forth in SEQ ID NO: 4; (iii) a first gRNA molecule comprising a targeting domain that comprises a nucleotide sequence set forth in SEQ ID NO: 15, and a second gRNA molecule comprising a targeting domain that comprises a nucleotide sequence set forth in SEQ ID NO: 19; (iv) a first gRNA molecule comprising a targeting domain that comprises a nucleotide sequence set forth in SEQ ID NO: 15, and a second gRNA molecule comprising a targeting domain that comprises a nucleotide sequence set forth in SEQ ID NO: 18; (v) a first gRNA molecule comprising a targeting domain that comprises a nucleotide sequence set forth in SEQ ID NO: 15, and a second gRNA molecule comprising a targeting domain that comprises a nucleotide sequence set forth in SEQ ID NO: 4; (vi) a first gRNA molecule comprising a targeting domain that comprises a nucleotide sequence set forth in SEQ ID NO: 14, and a second gRNA molecule comprising a targeting domain that comprises a nucleotide sequence set forth in SEQ ID NO: 19; (vii) a first gRNA molecule comprising a targeting domain that comprises a nucleotide sequence set forth in SEQ ID NO: 14, and a second gRNA molecule comprising a targeting domain that comprises a nucleotide sequence set forth in SEQ ID NO: 18; (viii) a first gRNA molecule comprising a targeting domain that comprises a nucleotide sequence set forth in SEQ ID NO: 14, and a second gRNA molecule comprising a targeting domain that comprises a nucleotide sequence set forth in SEQ ID NO: 4; (ix) a first gRNA molecule comprising a targeting domain that comprises a nucleotide sequence set forth in SEQ ID NO: 11, and a second gRNA molecule comprising a targeting domain that comprises a nucleotide sequence set forth in SEQ ID NO: 19; (x) a first gRNA molecule comprising a targeting domain that comprises a nucleotide sequence set forth in SEQ ID NO: 14, and a second gRNA molecule comprising a targeting domain that comprises a nucleotide sequence set forth in SEQ ID NO: 15; and (xi) a first gRNA molecule comprising a targeting domain that comprises a nucleotide sequence set forth in SEQ ID NO: 11, and a second gRNA molecule comprising a targeting domain that comprises a nucleotide sequence set forth in SEQ ID NO: 18.

Clause 55. The method of clause 53 or 54, wherein the mutant dystrophin gene comprises a premature stop codon, disrupted reading frame, an aberrant splice acceptor site, or an aberrant splice donor site.

Clause 56. The method of any one of clauses 53-55, wherein the mutant dystrophin gene comprises a frameshift mutation which causes a premature stop codon and a truncated gene product.

Clause 57. The method of any one of clauses 53-55, wherein the mutant dystrophin gene comprises a deletion of one or more exons which disrupts the reading frame.

Clause 58. The method of any one of clauses 53-57, wherein the correction of the mutant dystrophin gene comprises a deletion of a premature stop codon, correction of a disrupted reading frame, or modulation of splicing by disruption of a splice acceptor site or disruption of a splice donor sequence.

Clause 59. The method of any one of clauses 53-58, wherein the correction of the mutant dystrophin gene comprises deletion of exon 51.

Clause 60. The method of any one of clauses 53-59, wherein the correction of the mutant dystrophin gene comprises homology-directed repair.

Clause 61. The method of clause 60, further comprising administering to the cell a donor DNA.

Clause 62. The method of any one of clauses 53-61, wherein the correction of the mutant dystrophin gene comprises nuclease mediated non-homologous end joining.

Clause 63. The method of any one of clauses 53-62, wherein the cell is a myoblast cell.

Clause 64. The method of any one of clauses 53-63, wherein the cell is from a subject suffering from Duchenne muscular dystrophy.

Clause 65. The method of any one of clauses 53-64, wherein the cell is a myoblast from a human subject suffering from Duchenne muscular dystrophy.

Clause 66. The method of any one of clauses 53-65, wherein the first gRNA molecule and the second gRNA molecule are selected from the group consisting of: (i) a first gRNA molecule comprising a targeting domain that comprises a nucleotide sequence set forth in SEQ ID NO: 1, and a second gRNA molecule comprising a targeting domain that comprises a nucleotide sequence set forth in SEQ ID NO: 2; (ii) a first gRNA molecule comprising a targeting domain that comprises a nucleotide sequence set forth in SEQ ID NO: 11, and a second gRNA molecule comprising a targeting domain that comprises a nucleotide sequence set forth in SEQ ID NO: 4; and (iii) a first gRNA molecule comprising a targeting domain that comprises a nucleotide sequence set forth in SEQ ID NO: 15, and a second gRNA molecule comprising a targeting domain that comprises a nucleotide sequence set forth in SEQ ID NO: 19.

Clause 67. A method of treating a subject in need thereof having a mutant dystrophin gene, the method comprising administering to the subject: (a) a first vector comprising a polynucleotide sequence encoding a first guide RNA (gRNA) molecule and a polynucleotide sequence encoding a first Cas9 molecule that recognizes a Protospacer Adjacent Motif (PAM) of either NNGRRT (SEQ ID NO: 24) or NNGRRV (SEQ ID NO: 25), and (b) a second vector comprising a polynucleotide sequence encoding a second gRNA molecule and a polynucleotide sequence encoding a second Cas9 molecule that recognizes a Protospacer Adjacent Motif (PAM) of either NNGRRT (SEQ ID NO: 24) or NNGRRV (SEQ ID NO: 25), wherein each of the first gRNA and second gRNA molecules have a targeting domain of 19 to 24 nucleotides in length, and wherein the vector is configured to form a first and a second double strand break in a first and a second intron flanking exon 51 of the human dystrophin gene, respectively, thereby deleting a segment of the dystrophin gene comprising exon 51.

Clause 68. The method of clause 67, wherein the first gRNA molecule and the second gRNA molecule are selected from the group consisting of: (i) a first gRNA molecule comprising a targeting domain that comprises a nucleotide sequence set forth in SEQ ID NO: 1, and a second gRNA molecule comprising a targeting domain that comprises a nucleotide sequence set forth in SEQ ID NO: 2; (ii) a first gRNA molecule comprising a targeting domain that comprises a nucleotide sequence set forth in SEQ ID NO: 11, and a second gRNA molecule comprising a targeting domain that comprises a nucleotide sequence set forth in SEQ ID NO: 4; (iii) a first gRNA molecule comprising a targeting domain that comprises a nucleotide sequence set forth in SEQ ID NO: 15, and a second gRNA molecule comprising a targeting domain that comprises a nucleotide sequence set forth in SEQ ID NO: 19; (iv) a first gRNA molecule comprising a targeting domain that comprises a nucleotide sequence set forth in SEQ ID NO: 15, and a second gRNA molecule comprising a targeting domain that comprises a nucleotide sequence set forth in SEQ ID NO: 18; (v) a first gRNA molecule comprising a targeting domain that comprises a nucleotide sequence set forth in SEQ ID NO: 15, and a second gRNA molecule comprising a targeting domain that comprises a nucleotide sequence set forth in SEQ ID NO: 4; (vi) a first gRNA molecule comprising a targeting domain that comprises a nucleotide sequence set forth in SEQ ID NO: 14, and a second gRNA molecule comprising a targeting domain that comprises a nucleotide sequence set forth in SEQ ID NO: 19; (vii) a first gRNA molecule comprising a targeting domain that comprises a nucleotide sequence set forth in SEQ ID NO: 14, and a second gRNA molecule comprising a targeting domain that comprises a nucleotide sequence set forth in SEQ ID NO: 18; (viii) a first gRNA molecule comprising a targeting domain that comprises a nucleotide sequence set forth in SEQ ID NO: 14, and a second gRNA molecule comprising a targeting domain that comprises a nucleotide sequence set forth in SEQ ID NO: 4; (ix) a first gRNA molecule comprising a targeting domain that comprises a nucleotide sequence set forth in SEQ ID NO: 11, and a second gRNA molecule comprising a targeting domain that comprises a nucleotide sequence set forth in SEQ ID NO: 19; (x) a first gRNA molecule comprising a targeting domain that comprises a nucleotide sequence set forth in SEQ ID NO: 14, and a second gRNA molecule comprising a targeting domain that comprises a nucleotide sequence set forth in SEQ ID NO: 15; and (xi) a first gRNA molecule comprising a targeting domain that comprises a nucleotide sequence set forth in SEQ ID NO: 11, and a second gRNA molecule comprising a targeting domain that comprises a nucleotide sequence set forth in SEQ ID NO: 18.

Clause 69. The method of clause 68, wherein the subject is suffering from Duchenne muscular dystrophy.

Clause 70. The method of any one of clauses 67-69, wherein the first vector and second vector are administered to a muscle of the subject.

Clause 71. The method of clause 70, wherein the muscle is skeletal muscle or cardiac muscle.

Clause 72. The method of clause 71, wherein the skeletal muscle is tibialis anterior muscle.

Clause 73. The method of any one of clauses 67-72, wherein the first vector and second vector are administered to the subject intramuscularly, intravenously or a combination thereof.

Clause 74. A method of generating a transgenic rodent embryo having a human dystrophin gene (hDMD) with an exon 52 deletion (Δ52), the method comprising administering to a rodent embryo the gRNA of clause 1, the DNA targeting system of any one of clauses 2-9, the isolated polynucleotide of clause 10, the vector of any one of clauses 11-22, the modified adeno-associated viral vector of clause 30 or 31, or the composition of any one of clauses 32-51, thereby deleting exon 52 of the human dystrophin gene, and selecting for a transgenic rodent embryo having a deletion of exon 52 of the human dystrophin gene, wherein the rodent embryo comprises a normal human dystrophin gene.

Clause 75. The method of clause 74, wherein the rodent embryo is a mouse embryo.

Clause 76. The method of clause 74 or 75, wherein the transgenic rodent embryo is heterozygous hDMD or heterozygous hDMD-Δ52.

Clause 77. The method of any one of clauses 74-76, wherein a first gRNA molecule comprising a targeting domain that comprises a nucleotide sequence set forth in SEQ ID NO: 41, and a second gRNA molecule comprising a targeting domain that comprises a nucleotide sequence set forth in SEQ ID NO: 42 are administered to the rodent embryo to delete exon 52 of the human dystrophin gene.

Clause 78. The method of any one of clauses 74-77, further comprising administering to the rodent embryo a Cas protein comprising an amino acid sequence set forth in SEQ ID NO: 27.

Clause 79. A transgenic rodent embryo produced by the method of any one of clauses 74-78.

Clause 80. A transgenic rodent produced from the transgenic rodent embryo of clause 79.

APPENDIX pDO240 with JCR179 (SEQ ID NO: 37) (gRNA in bold)
ctaaattgtaagcgttaatattttgttaaaattcgcgttaaattttgttaaatcagctcatttttttaaccaatagg ccgaaatcggcaaaatcccttataaatcaaaagaatagaccgagatagggttgagtgttgttccagtttggaacaag agtccactattaaagaacgtggactccaacgtcaaagggcgaaaaaccgtctatcagggcgatggcccactacgtga accatcaccctaatcaagttttttggggtcgaggtgccgtaaagcactaaatcggaaccctaaagggagcccccgat ttagagcttgacggggaaagccggcgaacgtggcgagaaaggaagggaagaaagcgaaaggagcgggcgctagggcg ctggcaagtgtagcggtcacgctgcgcgtaaccaccacacccgccgcgcttaatgcgccgctacagggcgcgtccca ttcgccattcaggctgcgcaactgttgggaagggcgatcggtgcgggcctcttcgctattacgccagctggcgaaag ggggatgtgctgcaaggcgattaagttgggtaacgccagggttttcccagtcacgacgttgtaaaacgacggccagt gagcgcgcgtaatacgactcactatagggcgaattgggtaccaagcttgcctatttcccatgattccttcatatttg catatacgatacaaggctgttagagagataattggaattaatttgactgtaaacacaaagatattagtacaaaatac gtgacgtagaaagtaataatttcttgggtagtttgcagttttaaaattatgttttaaaatggactatcatatgctta ccgtaacttgaaagtatttcgatttcttggctttatatatcttgtggaaaggacgaaacaccAACACACAGCTGGGT

TATCAGAGgttttagtactctggaaacagaatctactaaaacaaggcaaaatgccgtgtttatctcgtcaacttgtt ggcgagattttttgcggccgcccgcggtggagctccagcttttgttccctttagtgagggttaattgcgcgcttgg cgtaatcatggtcatagctgtttcctgtgtgaaattgttatccgctcacaattccacacaacatacgagccggaagc ataaagtgtaaagcctggggtgcctaatgagtgagctaactcacattaattgcgttgcgctcactgcccgctttcca gtcgggaaacctgtcgtgccagctgcattaatgaatcggccaacgcgcggggagaggcggtttgcgtattgggcgct cttccgcttcctcgctcactgactcgctgcgctcggtcgttcggctgcggcgagcggtatcagctcactcaaaggcg gtaatacggttatccacagaatcaggggataacgcaggaaagaacatgtgagcaaaaggccagcaaaaggccaggaa ccgtaaaaaggccgcgttgctggcgtttttccataggctccgcccccctgacgagcatcacaaaaatcgacgctcaa gtcagaggtggcgaaacccgacaggactataaagataccaggcgtttccccctggaagctccctcgtgcgctctcct gttccgaccctgccgcttaccggatacctgtccgcctttctcccttcgggaagcgtggcgctttctcatagctcacg ctgtaggtatctcagttcggtgtaggtcgttcgctccaagctgggctgtgtgcacgaaccccccgttcagcccgacc gctgcgccttatccggtaactatcgtcttgagtccaacccggtaagacacgacttatcgccactggcagcagccact ggtaacaggattagcagagcgaggtatgtaggcggtgctacagagttcttgaagtggtggcctaactacggctacac tagaaggacagtatttggtatctgcgctctgctgaagccagttaccttcggaaaaagagttggtagctcttgatccg gcaaacaaaccaccgctggtagcggtggtttttttgtttgcaagcagcagattacgcgcagaaaaaaaggatctcaa gaagatcctttgatcttttctacggggtctgacgctcagtggaacgaaaactcacgttaagggattttggtcatgag attatcaaaaaggatcttcacctagatccttttaaattaaaaatgaagttttaaatcaatctaaagtatatatgagt gtcgggaaacctgtcgtgccagctgcattaatgaatcggccaacgcgcggggagaggcggtttgcgtattgggcgct cttccgcttcctcgctcactgactcgctgcgctcggtcgttcggctgcggcgagcggtatcagctcactcaaaggcg gtaatacggttatccacagaatcaggggataacgcaggaaagaacatgtgagcaaaaggccagcaaaaggccaggaa ccgtaaaaaggccgcgttgctggcgtttttccataggctccgcccccctgacgagcatcacaaaaatcgacgctcaa gtcagaggtggcgaaacccgacaggactataaagataccaggcgtttccccctggaagctccctcgtgcgctctcct gttccgaccctgccgcttaccggatacctgtccgcctttctcccttcgggaagcgtggcgctttctcatagctcacg ctgtaggtatctcagttcggtgtaggtcgttcgctccaagctgggctgtgtgcacgaaccccccgttcagcccgacc gctgcgccttatccggtaactatcgtcttgagtccaacccggtaagacacgacttatcgccactggcagcagccact ggtaacaggattagcagagcgaggtatgtaggcggtgctacagagttcttgaagtggtggcctaactacggctacac tagaaggacagtatttggtatctgcgctctgctgaagccagttaccttcggaaaaagagttggtagctcttgatccg -continued gcaaacaaaccaccgctggtagcggtggttttttgtttgcaagcagcagattacgcgcagaaaaaaggatctcaa gaagatcctttgatcttttctacggggtctgacgctcagtggaacgaaaactcacgttaagggattttggtcatgag attatcaaaaaggatcttcacctagatccttttaaattaaaaatgaagttttaaatcaatctaaagtatatatgagt aaacttggtctgacagttaccaatgcttaatcagtgaggcacctatctcagcgatctgtctatttcgttcatccata gttgcctgactccccgtcgtgtagataactacgatacgggagggcttaccatctggccccagtgctgcaatgatacc gcgagacccacgctcaccggctccagatttatcagcaataaaccagccagccggaagggccgagcgcagaagtggtc ctgcaactttatccgcctccatccagtctattaattgttgccgggaagctagagtaagtagttcgccagttaatagt ttgcgcaacgttgttgccattgctacaggcatcgtggtgtcacgctcgtcgtttggtatggcttcattcagctccgg ttcccaacgatcaaggcgagttacatgatccccatgttgtgcaaaaaagcggttagctccttcggtcctccgatcg ttgtcagaagtaagttggccgcagtgttatcactcatggttatggcagcactgcataattctcttactgtcatgcca tccgtaagatgcttttctgtgactggtgagtactcaaccaagtcattctgagaatagtgtatgcggcgaccgagttg ctcttgcccggcgtcaatacgggataataccgcgccacatagcagaactttaaaagtgctcatcattggaaaacgtt cttcggggcgaaaactctcaaggatcttaccgctgttgagatccagttcgatgtaacccactcgtgcacccaactga tcttcagcatcttttactttcaccagcgtttctgggtgagcaaaaacaggaaggcaaaatgccgcaaaaaagggaat aagggcgacacggaaatgttgaatactcatactcttcctttttcaatattattgaagcatttatcagggttattgtc tcatgagcggatacatatttgaatgtatttagaaaaataaacaaataggggttccgcgcacatttccccgaaaagtg ccac pDO240 with JCR183 (SEQ ID NO: 38) (gRNA in bold)
ctaaattgtaagcgttaatattttgttaaaattcgcgttaaattttgttaaatcagctcatttttttaaccaatagg ccgaaatcggcaaaatcccttataaatcaaaagaatagaccgagatagggttgagtgttgttccagtttggaacaag agtccactattaaagaacgtggactccaacgtcaaagggcgaaaaaccgtctatcagggcgatggcccactacgtga accatcaccctaatcaagttttttggggtcgaggtgccgtaaagcactaaatcggaaccctaaagggagcccccgat ttagagcttgacggggaaagccggcgaacgtggcgagaaaggaagggaagaaagcgaaaggagcgggcgctagggcg ctggcaagtgtagcggtcacgctgcgcgtaaccaccacacccgccgcgcttaatgcgccgctacagggcgcgtccca ttcgccattcaggctgcgcaactgttgggaagggcgatcggtgcgggcctcttcgctattacgccagctggcgaaag ggggatgtgctgcaaggcgattaagttgggtaacgccagggttttcccagtcacgacgttgtaaaacgacggccagt gagcgcgcgtaatacgactcactatagggcgaattgggtaccaagcttgcctatttcccatgattccttcatatttg catatacgatacaaggctgttagagagataattggaattaatttgactgtaaacacaaagatattagtacaaaatac gtgacgtagaaagtaataatttcttgggtagtttgcagttttaaaattatgttttaaaatggactatcatatgctta ccgtaacttgaaagtatttcgatttcttggctttatatatcttgtggaaaggacgaaacaccAGAACTGGTGGGAAA

TGGTCTAGgttttagtactctggaaacagaatctactaaaacaaggcaaaatgccgtgtttatctcgtcaacttgtt ggcgagattttttgcggccgcccgcggtggagctccagcttttgttcccttagtgagggttaattgcgcgcttgg cgtaatcatggtcatagctgtttcctgtgtgaaattgttatccgctcacaattccacacaacatacgagccggaagc ataaagtgtaaagcctggggtgcctaatgagtgagctaactcacattaattgcgttgcgctcactgcccgctttcca gtcgggaaacctgtcgtgccagctgcattaatgaatcggccaacgcgcggggagaggcggtttgcgtattgggcgct cttccgcttcctcgctcactgactcgctgcgctcggtcgttcggctgcggcgagcggtatcagctcactcaaaggcg gtaatacggttatccacagaatcaggggataacgcaggaaagaacatgtgagcaaaaggccagcaaaaggccaggaa ccgtaaaaaggccgcgttgctggcgtttttccataggctccgcccccctgacgagcatcacaaaaatcgacgctcaa gtcagaggtggcgaaacccgacaggactataaagataccaggcgtttccccctggaagctccctcgtgcgctctcct gttccgaccctgccgcttaccggatacctgtccgcctttctcccttcgggaagcgtggcgctttctcatagctcacg ctgtaggtatctcagttcggtgtaggtcgttcgctccaagctgggctgtgtgcacgaaccccccgttcagcccgacc gctgcgccttatccggtaactatcgtcttgagtccaacccggtaagacacgacttatcgccactggcagcagccact -continued ggtaacaggattagcagagcgaggtatgtaggcggtgctacagagttcttgaagtggtggcctaactacggctacac tagaaggacagtatttggtatctgcgctctgctgaagccagttaccttcggaaaaagagttggtagctcttgatccg gcaaacaaccaccgctggtagcggtggttttttttgtttgcaagcagcagattacgcgcagaaaaaaaggatctcaa gaagatcctttgatcttttctacggggtctgacgctcagtggaacgaaaactcacgttaagggattttggtcatgag attatcaaaaaggatcttcacctagatccttttaaattaaaaatgaagttttaaatcaatctaaagtatatatgagt gtcgggaaacctgtcgtgccagctgcattaatgaatcggccaacgcgcggggagaggcggtttgcgtattgggcgct cttccgcttcctcgctcactgactcgctgcgctcggtcgttcggctgcggcgagcggtatcagctcactcaaaggcg gtaatacggttatccacagaatcaggggataacgcaggaaagaacatgtgagcaaaaggccagcaaaaggccaggaa ccgtaaaaaggccgcgttgctggcgtttttccataggctccgcccccctgacgagcatcacaaaaatcgacgctcaa gtcagaggtggcgaaacccgacaggactataaagataccaggcgtttccccctggaagctccctcgtgcgctctcct gttccgaccctgccgcttaccggatacctgtccgcctttctcccttcgggaagcgtggcgctttctcatagctcacg ctgtaggtatctcagttcggtgtaggtcgttcgctccaagctgggctgtgtgcacgaaccccccgttcagcccgacc gctgcgccttatccggtaactatcgtcttgagtccaacccggtaagacacgacttatcgccactggcagcagccact ggtaacaggattagcagagcgaggtatgtaggcggtgctacagagttcttgaagtggtggcctaactacggctacac tagaaggacagtatttggtatctgcgctctgctgaagccagttaccttcggaaaaagagttggtagctcttgatccg gcaaacaaccaccgctggtagcggtggttttttttgtttgcaagcagcagattacgcgcagaaaaaaaggatctcaa gaagatcctttgatcttttctacggggtctgacgctcagtggaacgaaaactcacgttaagggattttggtcatgag attatcaaaaaggatcttcacctagatccttttaaattaaaaatgaagttttaaatcaatctaaagtatatatgagt aaacttggtctgacagttaccaatgcttaatcagtgaggcacctatctcagcgatctgtctatttcgttcatccata gttgcctgactccccgtcgtgtagataactacgatacgggagggcttaccatctggccccagtgctgcaatgatacc gcgagacccacgctcaccggctccagatttatcagcaataaaccagccagccggaagggccgagcgcagaagtggtc ctgcaactttatccgcctccatccagtctattaattgttgccgggaagctagagtaagtagttcgccagttaatagt ttgcgcaacgttgttgccattgctacaggcatcgtggtgtcacgctcgtcgtttggtatggcttcattcagctccgg ttcccaacgatcaaggcgagttacatgatcccccatgttgtgcaaaaaagcggttagctccttcggtcctccgatcg ttgtcagaagtaagttggccgcagtgttatcactcatggttatggcagcactgcataattctcttactgtcatgcca tccgtaagatgcttttctgtgactggtgagtactcaaccaagtcattctgagaatagtgtatgcggcgaccgagttg ctcttgcccggcgtcaatacgggataataccgcgccacatagcagaactttaaaagtgctcatcattggaaaacgtt cttcggggcgaaaactctcaaggatcttaccgctgttgagatccagttcgatgtaacccactcgtgcacccaactga tcttcagcatcttttactttcaccagcgtttctgggtgagcaaaaacaggaaggcaaaatgccgcaaaaaagggaat aagggcgacacggaaatgttgaatactcatactcttcctttttcaatattattgaagcatttatcagggttattgtc tcatgagcggatacatatttgaatgtatttagaaaaataaacaaataggggttccgcgcacatttccccgaaaagtg ccac PT366 with JCR179 PT366AAV 179 (SEQ ID NO: 39) - AAV plasmid used for in vivo
work (gRNA in bold; SaCas9 is uppercase; NLS is lowercase, bold, and underlined)
cctgcaggcagctgcgcgctcgctcgctcactgaggccgcccgggcgtcgggcgacctttggtcgcccggcctcagt gagcgagcgagcgcgcagagagggagtggccaactccatcactaggggttcctgcggcctctagactcgaggcgttg acattgattattgactagttattaatagtaatcaattacgggtcattagttcatagcccatatatggagttccgcg ttacataacttacggtaaatggcccgcctggctgaccgcccaacgacccccgcccattgacgtcaataatgacgtat gttcccatagtaacgccaatagggactttccattgacgtcaatgggtggagtatttacggtaaactgcccacttggc agtacatcaagtgtatcatatgccaagtacgccccctattgacgtcaatgacggtaaatggcccgcctggcattatg cccagtacatgaccttatgggactttcctacttggcagtacatctacgtattagtcatcgctattaccatggtgatg cggttttggcagtacatcaatgggcgtggatagcggtttgactcacggggatttccaagtctccaccccattgacgt -continued caatgggagtttgttttggcaccaaaatcaacgggactttccaaaatgtcgtaacaactccgccccattgacgcaaa tgggcggtaggcgtgtacggtgggaggtctatataagcagagctctctggctaactaccggtgccaccatggcccca aagaagaagcggaaggtcggtatccacggagtcccagcagccAAGCGGAACTACATCCTGGGCCTGGACAT

CGGCATCACCAGCGTGGGCTACGGCATCATCGACTACGAGACACGGGACGTGATCG

ATGCCGGCGTGCGGCTGTTCAAAGAGGCCAACGTGGAAAACAACGAGGGCAGGCG

GAGCAAGAGAGGCGCCAGAAGGCTGAAGCGGCGGAGGCGGCATAGAATCCAGAGA

GTGAAGAAGCTGCTGTTCGACTACAACCTGCTGACCGACCACAGCGAGCTGAGCGG

CATCAACCCCTACGAGGCCAGAGTGAAGGGCCTGAGCCAGAAGCTGAGCGAGGAA

GAGTTCTCTGCCGCCCTGCTGCACCTGGCCAAGAGAAAGGCGTGCACAACGTGAAC

GAGGTGGAAGAGGACACCGGCAACGAGCTGTCCACCAAAGAGCAGATCAGCCGGA

ACAGCAAGGCCCTGGAAGAGAAATACGTGGCCGAACTGCAGCTGGAACGGCTGAA

GAAAGACGGCGAAGTGCGGGGCAGCATCAACAGATTCAAGACCAGCGACTACGTG

AAAGAAGCCAAACAGCTGCTGAAGGTGCAGAAGGCCTACCACCAGCTGGACCAGA

GCTTCATCGACACCTACATCGACCTGCTGGAAACCCGGCGGACCTACTATGAGGGA

CCTGGCGAGGGCAGCCCCTTCGGCTGGAAGGACATCAAAGAATGGTACGAGATGCT

GATGGGCCACTGCACCTACTTCCCCGAGGAACTGCGGAGCGTGAAGTACGCCTACA

ACGCCGACCTGTACAACGCCCTGAACGACCTGAACAATCTCGTGATCACCAGGGAC

GAGAACGAGAAGCTGGAATATTACGAGAAGTTCCAGATCATCGAGAACGTGTTCAA

GCAGAAGAAGAAGCCCACCCTGAAGCAGATCGCCAAAGAAATCCTCGTGAACGAA

GAGGATATTAAGGGCTACAGAGTGACCAGCACCGGCAAGCCGAGTTCACCAACCTG

AAGGTGTACCACGACATCAAGGACATTACCGCCCGGAAAGAGATTATTGAGAACGC

CGAGCTGCTGGATCAGATTGCCAAGATCCTGACCATCTACCAGAGCAGCGAGGACA

TCCAGGAAGAACTGACCAATCTGAACTCCGAGCTGACCCAGGAAGAGATCGAGCAG

ATCTCTAATCTGAAGGGCTATACCGGCACCCACAACCTGAGCCTGAAGGCCATCAA

CCTGATCCTGGACGAGCTGTGGCACACCAACGACAACCAGATCGCTATCTTCAACCG

GCTGAAGCTGGTGCCCAAGAAGGTGGACCTGTCCCAGCAGAAAGAGATCCCCACCA

CCCTGGTGGACGACTTCATCCTGAGCCCCGTCGTGAAGAGAAGCTTCATCCAGAGCA

TCAAAGTGATCAACGCCATCATCAAGAAGTACGGCCTGCCCAACGACATCATTATC

GAGCTGGCCCGCGAGAAGAACTCCAAGGACGCCCAGAAAATGATCAACGAGATGC

AGAAGCGGAACCGGCAGACCAACGAGCGGATCGAGGAAATCATCCGGACCACCGG

CAAAGAGAACGCCAAGTACCTGATCGAGAAGATCAAGCTGCACGACATGCAGGAA

GGCAAGTGCCTGTACAGCCTGGAAGCCATCCCTCTGGAAGATCTGCTGAACAACCC

CTTCAACTATGAGGTGGACCACATCATCCCCAGAAGCGTGTCCTTCGACAACAGCTT

CAACAACAAGGTGCTCGTGAAGCAGGAAGAAAACAGCAAGAAGGGCAACCGGACC

CCATTCCAGTACCTGAGCAGCAGCGACAGCAAGATCAGCTACGAAACCTTCAAGAA

GCACATCCTGAATCTGGCCAAGGGCAAGGGCAGAATCAGCAAGACCAAGAAAGAG

TATCTGCTGGAAGAACGGGACATCAACAGGTTCTCCGTGCAGAAAGACTTCATCAA

CCGGAACCTGGTGGATACCAGATACGCCACCAGAGGCCTGATGAACCTGCTGCGGA

GCTACTTCAGAGTGAACAACCTGGACGTGAAAGTGAAGTCCATCAATGGCGGCTTC

ACCAGCTTTCTGCGGCGGAAGTGGAAGTTTAAGAAAGAGCGGAACAAGGGGTACAA

GCACCACGCCGAGGACGCCCTGATCATTGCCAACGCCGATTTCATCTTCAAAGAGTG

-continued

```
GAAGAAACTGGACAAGGCCAAAAAAGTGATGGAAAACCAGATGTTCGAGGAAAAG
CAGGCCGAGAGCATGCCCGAGATCGAAACCGAGCAGGAGTACAAAGAGATCTTCAT
CACCCCCCACCAGATCAAGCACATTAAGGACTTCAAGGACTACAAGTACAGCCACC
GGGTGGACAAGAAGCCTAATAGAGAGCTGATTAACGACACCCTGTACTCCACCCGG
AAGGACGACAAGGGCAACACCCTGATCGTGAACAATCTGAACGGCCTGTACGACAA
GGACAATGACAAGCTGAAAAAGCTGATCAACAAGAGCCCCGAAAAGCTGCTGATGT
ACCACCACGACCCCCAGACCTACCAGAAACTGAAGCTGATTATGGAACAGTACGGC
GACGAGAAGAATCCCCTGTACAAGTACTACGAGGAAACCGGGAACTACCTGACCAA
GTACTCCAAAAAGGACAACGGCCCCGTGATCAAGAAGATTAAGTATTACGGCAACA
AACTGAACGCCCATCTGGACATCACCGACGACTACCCCAACAGCAGAAACAAGGTC
GTGAAGCTGTCCCTGAAGCCCTACAGATTCGACGTGTACCTGGACAATGGCGTGTAC
AAGTTCGTGACCGTGAAGAATCTGGATGTGATCAAAAAAGAAAACTACTACGAAGT
GAATAGCAAGTGCTATGAGGAAGCTAAGAAGCTGAAGAAGATCAGCAACCAGGCC
GAGTTTATCGCCTCCTTCTACAACAACGATCTGATCAAGATCAACGGCGAGCTGTAT
AGAGTGATCGGCGTGAACAACGACCTGCTGAACCGGATCGAAGTGAACATGATCGA
CATCACCTACCGCGAGTACCTGGAAAACATGAACGACAAGAGGCCCCCCAGGATCA
TTAAGACAATCGCCTCCAAGACCCAGAGCATTAAGAAGTACAGCACAGACATTCTG
GGCAACCTGTATGAAGTGAAATCTAAGAAGCACCCTCAGATCATCAAAAAGGGCaaa
aggccggcggccacgaaaaaggccggccaggca
aaaagaaaaaggatcctacccatacgatgttccagattacgcttacccatacgatgttccagattacgcttaccc
atacgatgttccagattacgcttaagaattcctagagctcgctgatcagcctcgactgtgccttctagttgccagcc
atctgttgtttgcccctccccgtgccttccttgaccctggaaggtgccactccactgtcctttcctaataaaatg
aggaaattgcatcgcattgtctgagtaggtgtcattctattctgggggtgggtggggcaggacagcaaggggag
gattgggaagagaatagcaggcatgctggggaggtaccgagggcctattttcccatgattccttcatatttgcatata
cgatacaaggctgttagagagataattggaattaatttgactgtaaacaaagatattagtacaaaatacgtgacg
tagaaagtaataatttcttgggtagtttgcagttttaaaattatgttttaaaatggactatcatatgcttaccgtaa
cttgaaagtatttcgatttcttggctttatatatcttgtggaaaggacgaaacaccgAACACACAGCTGGGTTATCA
GAGgttttagtactctggaaacagaatctactaaaacaaggcaaaatgccgtgtttatctcgtcaacttgttggcga
gattttttgcggccgcaggaaccccctagtgatggagttggccactccctctctgcgcgctcgctcgctcactgaggcc
gggcgaccaaaggtcgcccgacgcccgggctttgcccgggcggcctcagtgagcgagcgagcgcgcagctgcctgca
ggggcgcctgatgcggtattttctccttacgcatctgtgcggtatttcacaccgcatacgtcaaagcaaccatagta
cgcgccctgtagcggcgcattaagcgcggcgggtgtggtggttacgcgcagcgtgaccgctacacttgccagcgccc
tagcgcccgctcctttcgctttcttcccttcctttctcgccacgttcgccggctttccccgtcaagctctaaatcgg
gggctcccttagggttccgatttagtgctttacggcacctcgaccccaaaaaacttgatttgggtgatggttcacg
tagtgggccatcgccctgatagacggttttttcgccctttgacgttggagtccacgttctttaatagtggactcttgt
tccaaactggaacaacactcaaccctatctcgggctattcttttgatttataagggattttgccgatttcggcctat
tggttaaaaaatgagctgatttaacaaaaatttaacgcgaattttaacaaaatattaacgtttacaattttatggtg
cactctcagtacaatctgctctgatgccgcatagttaagccagccccgacacccgccaacacccgctgacgcgccct
gacgggcttgtctgctcccggcatccgcttacagacaagctgtgaccgtctccgggagctgcatgtgtcagaggttt
tcaccgtcatcaccgaaacgcgcgagacgaaagggcctcgtgatacgcctatttttataggttaatgtcatgataat
```

-continued

```
aatggtttcttagacgtcaggtggcacttttcggggaaatgtgcgcggaaccccctatttgtttattttttctaaatac attcaaatatgtatccgctcatgagacaataaccctgataaatgcttcaataatattgaaaaggaagagtatgagt attcaacatttccgtgtcgcccttattccctttttttgcggcattttgccttcctgttttttgctcacccagaaacgct ggtgaaagtaaaagatgctgaagatcagttgggtgcacgagtgggttacatcgaactggatctcaacagcggtaaga tccttgagagttttcgccccgaagaacgttttccaatgatgagcacttttaaagttctgctatgtggcgcggtatta tcccgtattgacgccgggcaagagcaactcggtcgccgcatacactattctcagaatgacttggttgagtactcacc agtcacagaaaagcatcttacggatggcatgacagtaagagaattatgcagtgctgccataaccatgagtgataaca ctgcggccaacttacttctgacaacgatcggaggaccgaaggagctaaccgcttttttgcacaacatggggatcat gtaactcgccttgatcgttgggaaccggagctgaatgaagccataccaaacgacgagcgtgacaccacgatgcctgt agcaatggcaacaacgttgcgcaaactattaactggcgaactacttactctagcttcccggcaacaattaatagact ggatggaggcggataaagttgcaggaccacttctgcgctcggcccttccggctggctggtttattgctgataaatct ggagccggtgagcgtggaagccgcggtatcattgcagcactggggccagatggtaagccctcccgtatcgtagttat ctacacgacggggagtcaggcaactatggatgaacgaaatagacagatcgctgagataggtgcctcactgattaagc attggtaactgtcagaccaagtttactcatatatactttagattgatttaaaacttcattttttaatttaaaaggatc taggtgaagatcctttttgataatctcatgaccaaaatcccttaacgtgagttttcgttccactgagcgtcagaccc cgtagaaaagatcaaaggatcttcttgagatcctttttttctgcgcgtaatctgctgcttgcaaacaaaaaaaccac cgctaccagcggtggtttgtttgccggatcaagagctaccaactctttttccgaaggtaactggcttcagcagagcg cagataccaaatactgtccttctagtgtagccgtagttaggccaccacttcaagaactctgtagcaccgcctacata cctcgctctgctaatcctgttaccagtggctgctgccagtggcgataagtcgtgtcttaccgggttggactcaagac gatagttaccggataaggcgcagcggtcgggctgaacggggggttcgtgcacacagcccagcttggagcgaacgacc tacaccgaactgagatacctacagcgtgagctatgagaaagcgccacgcttcccgaagggagaaaggcggacaggta tccggtaagcggcagggtcggaacaggagagcgcacgagggagcttccaggggaaacgcctggtatctttatagtc ctgtcgggtttcgccacctctgacttgagcgtcgatttttgtgatgctcgtcaggggggcggagcctatggaaaaac gccagcaacgcggcctttttacggttcctggccttttgctggccttttgctcacatgt
```

PT366 with JCR183 (SEQ ID NO: 40) - used for in vivo work (gRNA in bold; SaCas9 is uppercase; NLS is lowercase, bold, and underlined)

```
cctgcaggcagctgcgcgctcgctcgctcactgaggccgcccgggcgtcgggcgacctttggtcgcccggcctcagt gagcgagcgagcgcgcagagagggagtggccaactccatcactagggggttcctgcggcctctagactcgaggcgttg acattgattattgactagttattaatagtaatcaattacggggtcattagttcatagcccatatatggagttccgcg ttacataacttacggtaaatggcccgcctggctgaccgcccaacgacccccgcccattgacgtcaataatgacgtat gttcccatagtaacgccaatagggactttccattgacgtcaatgggtggagtatttacggtaaactgcccacttggc agtacatcaagtgtatcatatgccaagtacgccccctattgacgtcaatgacggtaaatggcccgcctggcattatg cccagtacatgaccttatgggactttcctacttggcagtacatctacgtattagtcatcgctattaccatggtgatg cggttttggcagtacatcaatgggcgtggatagcggtttgactcacggggatttccaagtctccaccccattgacgt caatgggagtttgttttggcaccaaaatcaacgggactttccaaaatgtcgtaacaactccgccccattgacgcaaa tgggcggtaggcgtgtacggtgggaggtctatataagcagagctctctggctaactaccggtgccaccatggcccca aagaagaagcggaaggtcggtatccacggagtcccagcagccAAGCGGAACTACATCCTGGGCCTGGACAT

CGGCATCACCAGCGTGGGCTACGGCATCATCGACTACGAGACACGGGACGTGATCG

ATGCCGGCGTGCGGCTGTTCAAAGAGGCCAACGTGGAAAACAACGAGGGCAGGCG

GAGCAAGAGAGGCGCCAGAAGGCTGAAGCGGCGGAGGCGGCATAGAATCCAGAGA

GTGAAGAAGCTGCTGTTCGACTACAACCTGCTGACCGACCACAGCGAGCTGAGCGG

CATCAACCCCTACGAGGCCAGAGTGAAGGGCCTGAGCCAGAAGCTGAGCGAGGAA
```

-continued

```
GAGTTCTCTGCCGCCCTGCTGCACCTGGCCAAGAGAAGAGGCGTGCACAACGTGAA
CGAGGTGGAAGAGGACACCGGCAACGAGCTGTCCACCAAAGAGCAGATCAGCCGG
AACAGCAAGGCCCTGGAAGAGAAATACGTGGCCGAACTGCAGCTGGAACGGCTGA
AGAAAGACGGCGAAGTGCGGGGCAGCATCAACAGATTCAAGACCAGCGACTACGT
GAAAGAAGCCAAACAGCTGCTGAAGGTGCAGAAGGCCTACCACCAGCTGGACCAG
AGCTTCATCGACACCTACATCGACCTGCTGGAAACCCGGCGGACCTACTATGAGGG
ACCTGGCGAGGGCAGCCCCTTCGGCTGGAAGGACATCAAAGAATGGTACGAGATGC
TGATGGGCCACTGCACCTACTTCCCCGAGGAACTGCGGAGCGTGAAGTACGCCTAC
AACGCCGACCTGTACAACGCCCTGAACGACCTGAACAATCTCGTGATCACCAGGGA
CGAGAACGAGAAGCTGGAATATTACGAGAAGTTCCAGATCATCGAGAACGTGTTCA
AGCAGAAGAAGAAGCCCACCCTGAAGCAGATCGCCAAAGAAATCCTCGTGAACGA
AGAGGATATTAAGGGCTACAGAGTGACCAGCACCGGCAAGCCCGAGTTCACCAACC
TGAAGGTGTACCACGACATCAAGGACATTACCGCCCGGAAAGAGATTATTGAGAAC
GCCGAGCTGCTGGATCAGATTGCCAAGATCCTGACCATCTACCAGAGCAGCGAGGA
CATCCAGGAAGAACTGACCAATCTGAACTCCGAGCTGACCCAGGAAGAGATCGAGC
AGATCTCTAATCTGAAGGGCTATACCGGCACCCACAACCTGAGCCTGAAGGCCATC
AACCTGATCCTGGACGAGCTGTGGCACACCAACGACAACCAGATCGCTATCTTCAA
CCGGCTGAAGCTGGTGCCCAAGAAGGTGGACCTGTCCCAGCAGAAAGAGATCCCCA
CCACCCTGGTGGACGACTTCATCCTGAGCCCCGTCGTGAAGAGAAGCTTCATCCAGA
GCATCAAAGTGATCAACGCCATCATCAAGAAGTACGGCCTGCCCAACGACATCATT
ATCGAGCTGGCCCGCGAGAAGAACTCCAAGGACGCCCAGAAAATGATCAACGAGAT
GCAGAAGCGGAACCGGCAGACCAACGAGCGGATCGAGGAAATCATCCGGACCACC
GGCAAAGAGAACGCCAAGTACCTGATCGAGAAGATCAAGCTGCACGACATGCAGG
AAGGCAAGTGCCTGTACAGCCTGGAAGCCATCCCTCTGGAAGATCTGCTGAACAAC
CCCTTCAACTATGAGGTGGACCACATCATCCCCAGAAGCGTGTCCTTCGACAACAGC
TTCAACAACAAGGTGCTCGTGAAGCAGGAAGAAAACAGCAAGAAGGGCAACCGGA
CCCCATTCCAGTACCTGAGCAGCAGCGACAGCAAGATCAGCTACGAAACCTTCAAG
AAGCACATCCTGAATCTGGCCAAGGGCAAGGGCAGAATCAGCAAGACCAAGAAAG
AGTATCTGCTGGAAGAACGGGACATCAACAGGTTCTCCGTGCAGAAAGACTTCATC
AACCGGAACCTGGTGGATACCAGATACGCCACCAGAGGCCTGATGAACCTGCTGCG
GAGCTACTTCAGAGTGAACAACCTGGACGTGAAAGTGAAGTCCATCAATGGCGGCT
TCACCAGCTTTCTGCGGCGGAAGTGGAAGTTTAAGAAAGAGCGGAACAAGGGGTAC
AAGCACCACGCCGAGGACGCCCTGATCATTGCCAACGCCGATTTCATCTTCAAAGA
GTGGAAGAAACTGGACAAGGCCAAAAAAGTGATGGAAAACCAGATGTTCGAGGAA
AAGCAGGCCGAGAGCATGCCCGAGATCGAAACCGAGCAGGAGTACAAAGAGATCT
TCATCACCCCCCACCAGATCAAGCACATTAAGGACTTCAAGGACTACAAGTACAGC
CACCGGGTGGACAAGAAGCCTAATAGAGAGCTGATTAACGACACCCTGTACTCCAC
CCGGAAGGACGACAAGGGCAACACCCTGATCGTGAACAATCTGAACGGCCTGTACG
ACAAGGACAATGACAAGCTGAAAAAGCTGATCAACAAGAGCCCCGAAAAGCTGCT
GATGTACCACCACGACCCCCAGACCTACCAGAAACTGAAGCTGATTATGGAACAGT
```

```
ACGGCGACGAGAAGAATCCCCTGTACAAGTACTACGAGGAAACCGGGAACTACCTG

ACCAAGTACTCCAAAAAGGACAACGGCCCCGTGATCAAGAAGATTAAGTATTACGG

CAACAAACTGAACGCCCATCTGGACATCACCGACGACTACCCCAACAGCAGAAACA

AGGTCGTGAAGCTGTCCCTGAAGCCCTACAGATTCGACGTGTACCTGGACAATGGCG

TGTACAAGTTCGTGACCGTGAAGAATCTGGATGTGATCAAAAAGAAAACTACTAC

GAAGTGAATAGCAAGTGCTATGAGGAAGCTAAGAAGCTGAAGAAGATCAGCAACC

AGGCCGAGTTTATCGCCTCCTTCTACAACAACGATCTGATCAAGATCAACGGCGAGC

TGTATAGAGTGATCGGCGTGAACAACGACCTGCTGAACCGGATCGAAGTGAACATG

ATCGACATCACCTACCGCGAGTACCTGGAAAACATGAACGACAAGAGGCCCCCCAG

GATCATTAAGACAATCGCCTCCAAGACCCAGAGCATTAAGAAGTACAGCACAGACA

TTCTGGGCAACCTGTATGAAGTGAAATCTAAGAAGCACCCTCAGATCATCAAAAAG
```
GGCaaaaggccggcggccacgaaaaaggccggccaggca aaaagaaaagggatcctacccatacgatgttccagattacgcttacccatacgatgttccagattacgcttaccc atacgatgttccagattacgcttaagaattcctagagctcgctgatcagcctcgactgtgccttctagttgccagcc atctgttgtttgcccctcccccgtgccttccttgaccctggaaggtgccactcccactgtccttcctaataaaatg aggaaattgcatcgcattgtctgagtaggtgtcattctattctggggggtggggtggggcaggacagcaagggggag gattgggaagagaatagcaggcatgctggggaggtaccgagggcctatttcccatgattccttcatatttgcatata cgatacaaggctgttagagagataattggaattaatttgactgtaaacacaaagatattagtacaaaatacgtgacg tagaaagtaataatttcttgggtagtttgcagttttaaaattatgttttaaaatggactatcatatgcttaccgtaa cttgaaagtatttcgatttcttggctttatatatcttgtggaaaggacgaaacaccgAGAACTGGTGGGAAATGGTC

TAGgttttagtactctggaaacagaatctactaaaacaaggcaaaatgccgtgtttatctcgtcaacttgttggcga gattttttgcggccgcaggaaccctagtgatggagttggccactccctctctgcgcgctcgctcgctcactgaggcc gggcgaccaaaggtcgcccgacgcccgggctttgcccgggcggcctcagtgagcgagcgagcgcgcagctgcctgca ggggcgcctgatgcggtattttctccttacgcatctgtgcggtatttcacaccgcatacgtcaaagcaaccatagta cgcgccctgtagcggcgcattaagcgcggcgggtgtggtggttacgcgcagcgtgaccgctacacttgccagcgccc tagcgcccgctcctttcgctttcttcccttcctttctcgccacgttcgccggctttccccgtcaagctctaaatcgg gggctccctttagggttccgatttagtgctttacggcacctcgaccccaaaaaacttgatttgggtgatggttcacg tagtgggccatcgccctgatagacggtttttcgccctttgacgttggagtccacgttctttaatagtggactcttgt tccaaactggaacaacactcaaccctatctcgggctattcttttgatttataagggattttgccgatttcggcctat tggttaaaaaatgagctgatttaacaaaaatttaacgcgaattttaacaaaatattaacgtttacaattttatggtg cactctcagtacaatctgctctgatgccgcatagttaagccagccccgacacccgccaacacccgctgacgcgccct gacgggcttgtctgctcccggcatccgcttacagacaagctgtgaccgtctccgggagctgcatgtgtcagaggttt tcaccgtcatcaccgaaacgcgcgagacgaaagggcctcgtgatacgcctatttttataggttaatgtcatgataat aatggtttcttagacgtcaggtggcacttttcggggaaatgtgcgcggaaccccatttgttatttttctaaatac attcaaatatgtatccgctcatgagacaataaccctgataaatgcttcaataatattgaaaaaggaagagtatgagt attcaacatttccgtgtcgcccttattcccttttttgcggcattttgccttcctgtttttgctcacccagaaacgct ggtgaaagtaaaagatgctgaagatcagttgggtgcacgagtgggttacatcgaactggatctcaacagcggtaaga tccttgagagttttcgccccgaagaacgttttccaatgatgagcacttttaaagttctgctatgtggcgcggtatta tcccgtattgacgccgggcaagagcaactcggtcgccgcatacactattctcagaatgacttggttgagtactcacc agtcacagaaaagcatcttacggatggcatgacagtaagagaattatgcagtgctgccataaccatgagtgataaca ctgcggccaacttacttctgacaacgatcggaggaccgaaggagctaaccgcttttttgcacaacatggggatcat -continued

```
gtaactcgccttgatcgttgggaaccggagctgaatgaagccataccaaacgacgagcgtgacaccacgatgcctgt agcaatggcaacaacgttgcgcaaactattaactggcgaactacttactctagcttcccggcaacaattaatagact ggatggaggcggataaagttgcaggaccacttctgcgctcggcccttccggctggctggtttattgctgataaatct ggagccggtgagcgtggaagccgcggtatcattgcagcactggggccagatggtaagccctcccgtatcgtagttat ctacacgacggggagtcaggcaactatggatgaacgaaatagacagatcgctgagataggtgcctcactgattaagc attggtaactgtcagaccaagtttactcatatatactttagattgatttaaaacttcattttttaatttaaaaggatc taggtgaagatccttttttgataatctcatgaccaaaatcccttaacgtgagttttcgttccactgagcgtcagaccc cgtagaaaagatcaaaggatcttcttgagatcctttttttctgcgcgtaatctgctgcttgcaaacaaaaaaaccac cgctaccagcggtggtttgtttgccggatcaagagctaccaactcttttccgaaggtaactggcttcagcagagcg cagataccaaatactgtccttctagtgtagccgtagttaggccaccacttcaagaactctgtagcaccgcctacata cctcgctctgctaatcctgttaccagtggctgctgccagtggcgataagtcgtgtcttaccgggttggactcaagac gatagttaccggataaggcgcagcggtcgggctgaacggggggttcgtgcacacagcccagcttggagcgaacgacc tacaccgaactgagatacctacagcgtgagctatgagaaagcgccacgcttcccgaagggagaaaggcggacaggta tccggtaagcggcagggtcggaacaggagagcgcacgagggagcttccaggggaaacgcctggtatctttatagtc ctgtcgggtttcgccacctctgacttgagcgtcgatttttgtgatgctcgtcaggggggcggagcctatggaaaaac gccagcaacgcggcctttttacggttcctggccttttgctggccttttgctcacatgt
``` pDO242 (SaCas9 used in all JCR89/91 projects and JCR157/160
projects for in vitro work; SaCas9 in uppercase)(SEQ ID NO: 83)

```
ctaaattgtaagcgttaatattttgttaaaattcgcgttaaattttgttaaatcagctcatttttttaaccaatagg ccgaaatcggcaaaatcccttataaatcaaaagaatagaccgagataggggttgagtgttgttccagtttggaacaag agtccactattaaagaacgtggactccaacgtcaaagggcgaaaaaccgtctatcagggcgatggcccactacgtga accatcaccctaatcaagttttttggggtcgaggtgccgtaaagcactaaatcggaaccctaaagggagccccgat ttagagcttgacggggaaagccggcgaacgtggcgagaaaggaagggaagaaagcgaaaggagcgggcgctagggcg ctggcaagtgtagcggtcacgctgcgcgtaaccaccacccgccgcgcttaatgcgccgctacagggcgcgtccca ttcgccattcaggctgcgcaactgttgggaagggcgatcggtgcgggcctcttcgctattacgccagctggcgaaag ggggatgtgctgcaaggcgattaagttgggtaacgccagggttttcccagtcacgacgttgtaaaacgacggccagt gagcgcgcgtaatacgactcactatagggcgaattgggtacCtttaattctagtactatgcaTgcgttgacattgat tattgactagttattaatagtaatcaattacggggtcattagttcatagcccatatatggagttccgcgttacataa cttacggtaaatggcccgcctggctgaccgcccaacgacccccgcccattgacgtcaataatgacgtatgttcccat agtaacgccaatagggactttccattgacgtcaatgggtggagtatttacggtaaactgcccacttggcagtacatc aagtgtatcatatgccaagtacgccccctattgacgtcaatgacggtaaatggcccgcctggcattatgcccagtac atgaccttatgggactttcctacttggcagtacatctacgtattagtcatcgctattaccatggtgatgcggttttg gcagtacatcaatgggcgtggatagcggtttgactcacggggatttccaagtctccaccccattgacgtcaatggga gtttgttttggcaccaaaatcaacgggactttccaaaatgtcgtaacaactccgccccattgacgcaaatgggcggt aggcgtgtacggtgggaggtctatataagcagagctctctggctaactaccggtgccaccATGAAAAGGAACTACAT

TCTGGGGCTGGACATCGGGATTACAAGCGTGGGGTATGGGATTATTGACTATGAAA

CAAGGGACGTGATCGACGCAGGCGTCAGACTGTTCAAGGAGGCCAACGTGGAAAAC

AATGAGGGACGGAGAAGCAAGAGGGGAGCCAGGCGCCTGAAACGACGGAGAAGGC

ACAGAATCCAGAGGGTGAAGAAACTGCTGTTCGATTACAACCTGCTGACCGACCAT

TCTGAGCTGAGTGGAATTAATCCTTATGAAGCCAGGGTGAAAGGCCTGAGTCAGAA

GCTGTCAGAGGAAGAGTTTTCCGCAGCTCTGCTGCACCTGGCTAAGCGCCGAGGAGT
```

-continued

```
GCATAACGTCAATGAGGTGGAAGAGGACACCGGCAACGAGCTGTCTACAAAGGAAC

AGATCTCACGCAATAGCAAAGCTCTGGAAGAGAAGTATGTCGCAGAGCTGCAGCTG

GAACGGCTGAAGAAAGATGGCGAGGTGAGAGGGTCAATTAATAGGTTCAAGACAA

GCGACTACGTCAAAGAAGCCAAGCAGCTGCTGAAAGTGCAGAAGGCTTACCACCAG

CTGGATCAGAGCTTCATCGATACTTATATCGACCTGCTGGAGACTCGGAGAACCTAC

ATGAGGGACCAGGAGAAGGGAGCCCCTTCGGATGGAAAGACATCAAGGAATGGTA

CGAGATGCTGATGGGACATTGCACCTATTTTCCAGAAGAGCTGAGAAGCGTCAAGT

ACGCTTATAACGCAGATCTGTACAACGCCCTGAATGACCTGAACAACCTGGTCATCA

CCAGGGATGAAAACGAGAAACTGGAATACTATGAGAAGTTCCAGATCATCGAAAAC

GTGTTTAAGCAGAAGAAAAAGCCTACACTGAAACAGATTGCTAAGGAGATCCTGGT

CAACGAAGAGGACATCAAGGGCTACCGGGTGACAAGCACTGGAAAACCAGAGTTC

ACCAATCTGAAAGTGTATCACGATATTAAGGACATCACAGCACGGAAAGAATCATT

GAGAACGCCGAACTGCTGGATCAGATTGCTAAGATCCTGACTATCTACCAGAGCTCC

GAGGACATCCAGGAAGAGCTGACTAACCTGAACAGCGAGCTGACCCAGGAAGAGA

TCGAACAGATTAGTAATCTGAAGGGGTACACCGGAACACACAACCTGTCCCTGAAA

GCTATCAATCTGATTCTGGATGAGCTGTGGCATACAAACGACAATCAGATTGCAATC

TTTAACCGGCTGAAGCTGGTCCCAAAAAAGGTGGACCTGAGTCAGCAGAAAGAGAT

CCCAACCACACTGGTGGACGATTTCATTCTGTCACCCGTGGTCAAGCGGAGCTTCAT

CCAGAGCATCAAAGTGATCAACGCCATCATCAAGAAGTACGGCCTGCCCAATGATA

TCATTATCGAGCTGGCTAGGGAGAAGAACAGCAAGGACGCACAGAAGATGATCAAT

GAGATGCAGAAACGAAACCGGCAGACCAATGAACGCATTGAAGAGATTATCCGAAC

TACCGGGAAAGAGAACGCAAAGTACCTGATTGAAAAAATCAAGCTGCACGATATGC

AGGAGGGAAAGTGTCTGTATTCTCTGGAGGCCATCCCCCTGGAGGACCTGCTGAAC

AATCCATTCAACTACGAGGTCGATCATATTATCCCCAGAAGCGTGTCCTTCGACAAT

TCCTTTAACAACAAGGTGCTGGTCAAGCAGGAAGAGAACTCTAAAAAGGGCAATAG

GACTCCTTTCCAGTACCTGTCTAGTTCAGATTCCAAGATCTCTTACGAAACCTTTAAA

AAGCACATTCTGAATCTGGCCAAAGGAAAGGGCCGCATCAGCAAGACCAAAAAGG

AGTACCTGCTGGAAGAGCGGGACATCAACAGATTCTCCGTCCAGAAGGATTTTATTA

ACCGGAATCTGGTGGACACAAGATACGCTACTCGCGGCCTGATGAATCTGCTGCGAT

CCTATTTCCGGGTGAACAATCTGGATGTGAAAGTCAAGTCCATCAACGGCGGGTTCA

CATCTTTTCTGAGGCGCAAATGGAAGTTTAAAAAGGAGCGCAACAAAGGGTACAAG

CACCATGCCGAAGATGCTCTGATTATCGCAAATGCCGACTTCATCTTTAAGGAGTGG

AAAAAGCTGGACAAAGCCAAGAAAGTGATGGAGAACCAGATGTTCGAAGAGAAGC

AGGCCGAATCTATGCCCGAAATCGAGACAGAACAGGAGTACAAGGAGATTTTCATC

ACTCCTCACCAGATCAAGCATATCAAGGATTTCAAGGACTACAAGTACTCTCACCGG

GTGGATAAAAAGCCCAACAGAGAGCTGATCAATGACACCCTGTATAGTACAAGAAA

AGACGATAAGGGGAATACCCTGATTGTGAACAATCTGAACGGACTGTACGACAAAG

ATAATGACAAGCTGAAAAAGCTGATCAACAAAAGTCCCGAGAAGCTGCTGATGTAC

CACCATGATCCTCAGACATATCAGAAACTGAAGCTGATTATGGAGCAGTACGGCGA

CGAGAAGAACCCACTGTATAAGTACTATGAAGAGACTGGGAACTACCTGACCAAGT

ATAGCAAAAAGGATAATGGCCCCGTGATCAAGAAGATCAAGTACTATGGGAACAAG
```

```
CTGAATGCCCATCTGGACATCACAGACGATTACCCTAACAGTCGCAACAAGGTGGT

CAAGCTGTCACTGAAGCCATACAGATTCGATGTCTATCTGGACAACGGCGTGTATAA

ATTTGTGACTGTCAAGAATCTGGATGTCATCAAAAAGGAGAACTACTATGAAGTGA

ATAGCAAGTGCTACGAAGAGGCTAAAAAGCTGAAAAAGATTAGCAACCAGGCAGA

GTTCATCGCCTCCTTTTACAACAACGACCTGATTAAGATCAATGGCGAACTGTATAG

GGTCATCGGGGTGAACAATGATCTGCTGAACCGCATTGAAGTGAATATGATTGACAT

CACTTACCGAGAGTATCTGGAAAACATGAATGATAAGCGCCCCCCTCGAATTATCAA

AACAATTGCCTCTAAGACTCAGAGTATCAAAAAGTACTCAACCGACATTCTGGGAA

ACCTGTATGAGGTGAAGAGCAAAAAGCACCCTCAGATTATCAAAAAGGGCagcggaggc aagcgtcctgctgctactaagaaagctggtcaagctaagaaaaagaaaggatcctacccatacgatgttccagattacgctta agaattcctagagctcgctgatcagcctcgactgtgccttctagttgccagccatctgttgtttgcccctcccccgt gccttccttgaccctggaaggtgccactcccactgtcctttcctaataaaatgaggaaattgcatcgcattgtctga gtaggtgtcattctattctgggggtggggtggggcaggacagcaaggggaggattgggaagagaatagcaggcat gctggggaggtagcggccgcCCgcggtggagctccagcttttgttcccttttagtgagggttaattgcgcgcttggcg taatcatggtcatagctgtttcctgtgtgaaattgttatccgctcacaattccacacaacatacgagccggaagcat aaagtgtaaagcctggggtgcctaatgagtgagctaactcacattaattgcgttgcgctcactgcccgctttccagt cgggaaacctgtcgtgccagctgcattaatgaatcggccaacgcgcggggagaggcggtttgcgtattgggcgctct tccgcttcctcgctcactgactcgctgcgctcggtcgttcggctgcggcgagcggtatcagctcactcaaaggcggt aatacggttatccacagaatcaggggataacgcaggaaagaacatgtgagcaaaaggccagcaaaaggccaggaacc gtaaaaaggccgcgttgctggcgtttttccataggctccgcccccctgacgagcatcacaaaaatcgacgctcaagt cagaggtggcgaaacccgacaggactataaagataccaggcgtttccccctggaagctccctcgtgcgctctcctgt tccgaccctgccgcttaccggatacctgtccgcctttctcccttcgggaagcgtggcgctttctcatagctcacgct gtaggtatctcagttcggtgtaggtcgttcgctccaagctgggctgtgtgcacgaaccccccgttcagcccgaccgc tgcgccttatccggtaactatcgtcttgagtccaacccggtaagacacgacttatcgccactggcagcagccactgg taacaggattagcagagcgaggtatgtaggcggtgctacagagttcttgaagtggtggcctaactacggctacacta gaaggacagtatttggtatctgcgctctgctgaagccagttaccttcggaaaaagagttggtagctcttgatccggc aaacaaaccaccgctggtagcggtggtttttttgtttgcaagcagcagattacgcgcagaaaaaaaggatctcaaga agatcctttgatcttttctacggggtctgacgctcagtggaacgaaaactcacgttaagggattttggtcatgagat tatcaaaaaggatcttcacctagatccttttaaattaaaaatgaagttttaaatcaatctaaagtatatatgagtaa acttggtctgacagttaccaatgcttaatcagtgaggcacctatctcagcgatctgtctatttcgttcatccatagt tgcctgactccccgtcgtgtagataactacgatacgggagggcttaccatctggccccagtgctgcaatgataccgc gagacccacgctcaccggctccagatttatcagcaataaaccagccagccggaagggccgagcgcagaagtggtcct gcaactttatccgcctccatccagtctattaattgttgccgggaagctagagtaagtagttcgccagttaatagttt gcgcaacgttgttgccattgctacaggcatcgtggtgtcacgctcgtcgtttggtatggcttcattcagctccggtt cccaacgatcaaggcgagttacatgatccccatgttgtgcaaaaaagcggttagctccttcggtcctccgatcgtt gtcagaagtaagttggccgcagtgttatcactcatggttatggcagcactgcataattctcttactgtcatgccatc cgtaagatgcttttctgtgactggtgagtactcaaccaagtcattctgagaatagtgtatgcggcgaccgagttgct cttgcccggcgtcaatacgggataataccgcgccacatagcagaactttaaaagtgctcatcattggaaaacgttct tcggggcgaaaactctcaaggatcttaccgctgttgagatccagttcgatgtaacccactcgtgcacccaactgatc ttcagcatcttttactttcaccagcgtttctgggtgagcaaaaacaggaaggcaaaatgccgcaaaaaagggaataa
```

-continued gggcgacacggaaatgttgaatactcatactcttccttttcaatattattgaagcatttatcagggttattgtctc atgagcggatacatatttgaatgtatttagaaaaataaacaaatagggggttccgcgcacatttccccgaaaagtgccac pJRH1 (SaCas9 used for all JCR179/183 projects, SaCas9 is in uppercase; NLS is lowercase, bolded, and underlined)(SEQ ID NO: 84)
ctaaattgtaagcgttaatattttgttaaaattcgcgttaaattttttgttaaatcagctcatttttttaaccaatagg ccgaaatcggcaaaatcccttataaatcaaaagaatagaccgagatagggttgagtgttgttccagtttggaacaag agtccactattaaagaacgtggactccaacgtcaaagggcgaaaaaccgtctatcagggcgatggcccactacgtga accatcaccctaatcaagttttttgggggtcgaggtgccgtaaagcactaaatcggaaccctaaagggagcccccgat ttagagcttgacggggaaagccggcgaacgtggcgagaaaggaagggaagaaagcgaaaggagcgggcgctagggcg ctggcaagtgtagcggtcacgctgcgcgtaaccaccacacccgccgcgcttaatgcgccgctacagggcgcgtccca ttcgccattcaggctgcgcaactgttgggaagggcgatcggtgcgggcctcttcgctattacgccagctggcgaaag ggggatgtgctgcaaggcgattaagttgggtaacgccagggttttcccagtcacgacgttgtaaaacgacggccagt gagcgcgcgtaatacgactcactatagggcgaattgggtacctttaattctagtactatgcatgcgttgacattgat tattgactagttattaatagtaatcaattacgggtcattagttcatagcccatatatggagttccgcgttacataa cttacggtaaatggcccgcctggctgaccgcccaacgacccccgcccattgacgtcaataatgacgtatgttcccat agtaacgccaatagggactttccattgacgtcaatgggtggagtatttacggtaaactgcccacttggcagtacatc aagtgtatcatatgccaagtacgccccctattgacgtcaatgacggtaaatggcccgcctggcattatgcccagtac atgaccttatgggactttcctacttggcagtacatctacgtattagtcatcgctattaccatggtgatgcggttttg gcagtacatcaatgggcgtggatagcggtttgactcacggggatttccaagtctccaccccattgacgtcaatggga gtttgttttggcaccaaaatcaacgggactttccaaaatgtcgtaacaactccgccccattgacgcaaatgggcggt aggcgtgtacggtgggaggtctatataagcagagctctctggctaactaccggtgccaccatggccccaaagaagaa gcggaaggtcggtatccacggagtcccagcagccAAGCGGAACTACATCCTGGGCCTGGACATCGGCA

TCACCAGCGTGGGCTACGGCATCATCGACTACGAGACACGGGACGTGATCGATGCC

GGCGTGCGGCTGTTCAAAGAGGCCAACGTGGAAAACAACGAGGGCAGGCGGAGCA

AGAGAGGCGCCAGAAGGCTGAAGCGGCGGAGGCGGCATAGAATCCAGAGAGTGAA

GAAGCTGCTGTTCGACTACAACCTGCTGACCGACCACAGCGAGCTGAGCGGCATCA

ACCCCTACGAGGCCAGAGTGAAGGGCCTGAGCCAGAAGCTGAGCGAGGAAGAGTT

CTCTGCCGCCCTGCTGCACCTGGCCAAGAGAAGAGGCGTGCACAACGTGAACGAGG

TGGAAGAGGACACCGGCAACGAGCTGTCCACCAAAGAGCAGATCAGCCGGAACAG

CAAGGCCCTGGAAGAGAAATACGTGGCCGAACTGCAGCTGGAACGGCTGAAGAAA

GACGGCGAAGTGCGGGGCAGCATCAACAGATTCAAGACCAGCGACTACGTGAAAG

AAGCCAAACAGCTGCTGAAGGTGCAGAAGGCCTACCACCAGCTGGACCAGAGCTTC

ATCGACACCTACATCGACCTGCTGGAAACCCGGCGGACCTACTATGAGGGACCTGG

CGAGGGCAGCCCCTTCGGCTGGAAGGACATCAAAGAATGGTACGAGATGCTGATGG

GCCACTGCACCTACTTCCCCGAGGAACTGCGGAGCGTGAAGTACGCCTACAACGCC

GACCTGTACAACGCCCTGAACGACCTGAACAATCTCGTGATCACCAGGGACGAGAA

CGAGAAGCTGGAATATTACGAGAAGTTCCAGATCATCGAGAACGTGTTCAAGCAGA

AGAAGAAGCCCACCCTGAAGCAGATCGCCAAAGAAATCCTCGTGAACGAAGAGGA

TATTAAGGGCTACAGAGTGACCAGCACCGGCAAGCCCGAGTTCACCAACCTGAAGG

TGTACCACGACATCAAGGACATTACCGCCCGGAAAGAGATTATTGAGAACGCCGAG

CTGCTGGATCAGATTGCCAAGATCCTGACCATCTACCAGAGCAGCGAGGACATCCA

GGAAGAACTGACCAATCTGAACTCCGAGCTGACCCAGGAAGAGATCGAGCAGATCT

-continued

```
CTAATCTGAAGGGCTATACCGGCACCCACAACCTGAGCCTGAAGGCCATCAACCTG
ATCCTGGACGAGCTGTGGCACACCAACGACAACCAGATCGCTATCTTCAACCGGCT
GAAGCTGGTGCCCAAGAAGGTGGACCTGTCCCAGCAGAAAGAGATCCCCACCACCC
TGGTGGACGACTTCATCCTGAGCCCCGTCGTGAAGAGAAGCTTCATCCAGAGCATCA
AAGTGATCAACGCCATCATCAAGAAGTACGGCCTGCCCAACGACATCATTATCGAG
CTGGCCCGCGAGAAGAACTCCAAGGACGCCCAGAAAATGATCAACGAGATGCAGA
AGCGGAACCGGCAGACCAACGAGCGGATCGAGGAAATCATCCGGACCACCGGCAA
AGAGAACGCCAAGTACCTGATCGAGAAGATCAAGCTGCACGACATGCAGGAAGGC
AAGTGCCTGTACAGCCTGGAAGCCATCCCTCTGGAAGATCTGCTGAACAACCCCTTC
AACTATGAGGTGGACCACATCATCCCCAGAAGCGTGTCCTTCGACAACAGCTTCAAC
AACAAGGTGCTCGTGAAGCAGGAAGAAAACAGCAAGAAGGGCAACCGGACCCCAT
TCCAGTACCTGAGCAGCAGCGACAGCAAGATCAGCTACGAAACCTTCAAGAAGCAC
ATCCTGAATCTGGCCAAGGGCAAGGGCAGAATCAGCAAGACCAAGAAAGAGTATCT
GCTGGAAGAACGGGACATCAACAGGTTCTCCGTGCAGAAAGACTTCATCAACCGGA
ACCTGGTGGATACCAGATACGCCACCAGAGGCCTGATGAACCTGCTGCGGAGCTAC
TTCAGAGTGAACAACCTGGACGTGAAAGTGAAGTCCATCAATGGCGGCTTCACCAG
CTTTCTGCGGCGGAAGTGGAAGTTTAAGAAAGAGCGGAACAAGGGGTACAAGCACC
ACGCCGAGGACGCCCTGATCATTGCCAACGCCGATTTCATCTTCAAAGAGTGGAAG
AAACTGGACAAGGCCAAAAAAGTGATGGAAAACCAGATGTTCGAGGAAAAGCAGG
CCGAGAGCATGCCCGAGATCGAAACCGAGCAGGAGTACAAAGAGATCTTCATCACC
CCCCACCAGATCAAGCACATTAAGGACTTCAAGGACTACAAGTACAGCCACCGGGT
GGACAAGAAGCCTAATAGAGAGCTGATTAACGACACCCTGTACTCCACCCGGAAGG
ACGACAAGGGCAACACCCTGATCGTGAACAATCTGAACGGCCTGTACGACAAGGAC
AATGACAAGCTGAAAAAGCTGATCAACAAGAGCCCCGAAAAGCTGCTGATGTACCA
CCACGACCCCCAGACCTACCAGAAACTGAAGCTGATTATGGAACAGTACGGCGACG
AGAAGAATCCCCTGTACAAGTACTACGAGGAAACCGGGAACTACCTGACCAAGTAC
TCCAAAAAGGACAACGGCCCCGTGATCAAGAAGATTAAGTATTACGGCAACAAACT
GAACGCCCATCTGGACATCACCGACGACTACCCCAACAGCAGAAACAAGGTCGTGA
AGCTGTCCCTGAAGCCCTACAGATTCGACGTGTACCTGGACAATGGCGTGTACAAGT
TCGTGACCGTGAAGAATCTGGATGTGATCAAAAAAGAAAACTACTACGAAGTGAAT
AGCAAGTGCTATGAGGAAGCTAAGAAGCTGAAGAAGATCAGCAACCAGGCCGAGTT
TATCGCCTCCTTCTACAACAACGATCTGATCAAGATCAACGGCGAGCTGTATAGAGT
GATCGGCGTGAACAACGACCTGCTGAACCGGATCGAAGTGAACATGATCGACATCA
CCTACCGCGAGTACCTGGAAAACATGAACGACAAGAGGCCCCCCAGGATCATTAAG
ACAATCGCCTCCAAGACCCAGAGCATTAAGAAGTACAGCACAGACATTCTGGGCAA
CCTGTATGAAGTGAAATCTAAGAAGCACCCTCAGATCATCAAAAAGGGCaaaaggccgg
cggccacgaaaaaggccggccaggcaaaaaagaa
aaagggatcctacccatacgatgttccagattacgcttaagaattcctagagctcgctgatcagcctcgactgtgcc
ttctagttgccagccatctgttgtttgcccctcccccgtgccttccttgaccctggaaggtgccactcccactgtcc
tttcctaataaaatgaggaaattgcatcgcattgtctgagtaggtgtcattctattctggggggtggggtggggcag
```

```
gacagcaaggggaggattgggaagagaatagcaggcatgctggggaggtagcggccgcccgcggtggagctccagc ttttgttcccttagtgagggttaattgcgcgcttggcgtaatcatggtcatagctgtttcctgtgtgaaattgtta tccgctcacaattccacacaacatacgagccggaagcataaagtgtaaagcctggggtgcctaatgagtgagctaac tcacattaattgcgttgcgctcactgcccgctttccagtcgggaaacctgtcgtgccagctgcattaatgaatcggc caacgcgcggggagaggcggtttgcgtattgggcgctcttccgcttcctcgctcactgactcgctgcgctcggtcgt tcggctgcggcgagcggtatcagctcactcaaaggcggtaatacggttatccacagaatcaggggataacgcaggaa agaacatgtgagcaaaaggccagcaaaaggccaggaaccgtaaaaaggccgcgttgctggcgtttttccataggctc cgcccccctgacgagcatcacaaaaatcgacgctcaagtcagaggtggcgaaacccgacaggactataaagatacca ggcgtttccccctggaagctccctcgtgcgctctcctgttccgaccctgccgcttaccggatacctgtccgcctttc tcccttcgggaagcgtggcgctttctcatagctcacgctgtaggtatctcagttcggtgtaggtcgttcgctccaag ctgggctgtgtgcacgaaccccccgttcagcccgaccgctgcgccttatccggtaactatcgtcttgagtccaaccc ggtaagacacgacttatcgccactggcagcagccactggtaacaggattagcagagcgaggtatgtaggcggtgcta cagagttcttgaagtggtggcctaactacggctacactagaaggacagtatttggtatctgcgctctgctgaagcca gttaccttcggaaaaagagttggtagctcttgatccggcaaacaaaccaccgctggtagcggtggtttttttgtttg caagcagcagattacgcgcagaaaaaaaggatctcaagaagatcctttgatcttttctacggggtctgacgctcagt ggaacgaaaactcacgttaagggattttggtcatgagattatcaaaaaggatcttcacctagatccttttaaattaa aaatgaagttttaaatcaatctaaagtatatatgagtaaacttggtctgacagttaccaatgcttaatcagtgaggc acctatctcagcgatctgtctatttcgttcatccatagttgcctgactccccgtcgtgtagataactacgatacggg agggcttaccatctggccccagtgctgcaatgataccgcgagacccacgctcaccggctccagatttatcagcaata aaccagccagccggaagggccgagcgcagaagtggtcctgcaactttatccgcctccatccagtctattaattgttg ccgggaagctagagtaagtagttcgccagttaatagtttgcgcaacgttgttgccattgctacaggcatcgtggtgt cacgctcgtcgtttggtatggcttcattcagctccggttcccaacgatcaaggcgagttacatgatcccccatgttg tgcaaaaaagcggttagctccttcggtcctccgatcgttgtcagaagtaagttggccgcagtgttatcactcatggt tatggcagcactgcataattctcttactgtcatgccatccgtaagatgcttttctgtgactggtgagtactcaacca agtcattctgagaatagtgtatgcggcgaccgagttgctcttgcccggcgtcaatacgggataataccgcgccacat agcagaactttaaaagtgctcatcattggaaaacgttcttcggggcgaaaactctcaaggatcttaccgctgttgag atccagttcgatgtaacccactcgtgcacccaactgatcttcagcatcttttactttcaccagcgtttctgggtgag caaaaacaggaaggcaaaatgccgcaaaaaagggaataagggcgacacggaaatgttgaatactcatactcttcctt tttcaatattattgaagcatttatcagggttattgtctcatgagcggatacatatttgaatgtatttagaaaaataa acaaataggggttccgcgcacatttccccgaaaagtgccac
```

NLS sequence in PT366 (SEQ ID NO: 85)
AAAAGGCCGGCGGCCACGAAAAAGGCCGGCCAGGCAAAAAAGAAAAAG pDO203 - Generic backbone to clone gRNAs into for SpCas9; JCR94 and JCR99 were put into the site in bold to test in cells then to make mRNA from for making the hDMD-delta52/mdx mouse (SEQ ID NO: 86)

```
ctaaattgtaagcgttaatattttgttaaaattcgcgttaaattttgttaaatcagctcatttttaaccaatagg ccgaaatcggcaaaatcccttataaatcaaaagaatagaccgagatagggttgagtgttgttccagtttggaacaag agtccactattaaagaacgtggactccaacgtcaaagggcgaaaaaccgtctatcagggcgatggcccactacgtga accatcaccctaatcaagttttttggggtcgaggtgccgtaaagcactaaatcggaaccctaaagggagcccccgat ttagagcttgacggggaaagccggcgaacgtggcgagaaaggaagggaagaaagcgaaaggagcgggcgctagggcg ctggcaagtgtagcggtcacgctgcgcgtaaccaccacacccgccgcgcttaatgcgccgctacagggcgcgtccca ttcgccattcaggctgcgcaactgttgggaagggcgatcggtgcgggcctcttcgctattacgccagctggcgaaag ggggatgtgctgcaaggcgattaagttgggtaacgccagggttttcccagtcacgacgttgtaaaacgacggccagt
```

-continued

```
gagcgcgcgtaatacgactcactatagggcgaattgggtaccgagggcctatttcccatgattccttcatatttgca tatacgatacaaggctgttagagagataattggaattaatttgactgtaaacacaaagatattagtacaaaatacgt gacgtagaaagtaataatttcttgggtagtttgcagttttaaaattatgttttaaaatggactatcatatgcttatc gtaacttgaaagtatttcgatttcttggctttatatatcttgtggaaaggacgaaacaccGGGTCTTCGAGAAGACC

Tgttttagagctagaaatagcaagttaaaataaggctagtccgttatcaacttgaaaaagtggcaccgagtcggtgc ttttttccgcggtggagctccagcttttgttccctttagtgagggtaattgcgcgcttggcgtaatcatggtcat agctgtttcctgtgtgaaattgttatccgctcacaattccacacaacatacgagccggaagcataaagtgtaaagcc tggggtgcctaatgagtgagctaactcacattaattgcgttgcgctcactgcccgctttccagtcgggaaacctgtc gtgccagctgcattaatgaatcggccaacgcgcggggagaggcggtttgcgtattgggcgctcttccgcttcctcgc tcactgactcgctgcgctcggtcgttcggctgcggcgagcggtatcagctcactcaaaggcggtaatacggttatcc acagaatcaggggataacgcaggaaagaacatgtgagcaaaaggccagcaaaaggccaggaaccgtaaaaaggccgc gttgctggcgtttttccataggctccgcccccctgacgagcatcacaaaaatcgacgctcaagtcagaggtggcgaa acccgacaggactataaagataccaggcgtttccccctggaagctccctcgtgcgctctcctgttccgaccctgccg cttaccggatacctgtccgcctttctcccttcgggaagcgtggcgctttctcatagctcacgctgtaggtatctcag ttcggtgtaggtcgttcgctccaagctgggctgtgtgcacgaaccccccgttcagcccgaccgctgcgccttatccg gtaactatcgtcttgagtccaacccggtaagacacgacttatcgccactggcagcagccactggtaacaggattagc agagcgaggtatgtaggcggtgctacagagttcttgaagtggtggcctaactacggctacactagaaggacagtatt tggtatctgcgctctgctgaagccagttaccttcggaaaaagagttggtagctcttgatccggcaaacaaaccaccg ctggtagcggtggtttttttgtttgcaagcagcagattacgcgcagaaaaaaaggatctcaagaagatcctttgatc ttttctacggggtctgacgctcagtggaacgaaaactcacgttaagggattttggtcatgagattatcaaaaaggat cttcacctagatccttttaaattaaaaatgaagttttaaatcaatctaaagtatatatgagtaaacttggtctgaca gttaccaatgcttaatcagtgaggcacctatctcagcgatctgtctatttcgttcatccatagttgcctgactcccc gtcgtgtagataactacgatacgggagggcttaccatctggccccagtgctgcaatgataccgcgagacccacgctc accggctccagatttatcagcaataaaccagccagccggaagggccgagcgcagaagtggtcctgcaactttatccg cctccatccagtctattaattgttgccgggaagctagagtaagtagttcgccagttaatagtttgcgcaacgttgtt gccattgctacaggcatcgtggtgtcacgctcgtcgtttggtatggcttcattcagctccggttcccaacgatcaag gcgagttacatgatccccatgttgtgcaaaaaagcggttagctccttcggtcctccgatcgttgtcagaagtaagt tggccgcagtgttatcactcatggttatggcagcactgcataattctcttactgtcatgccatccgtaagatgcttt tctgtgactggtgagtactcaaccaagtcattctgagaatagtgtatgcggcgaccgagttgctcttgcccggcgtc aatacgggataataccgcgccacatagcagaactttaaaagtgctcatcattggaaaacgttcttcggggcgaaaac tctcaaggatcttaccgctgttgagatccagttcgatgtaacccactcgtgcacccaactgatcttcagcatctttt actttcaccagcgtttctgggtgagcaaaaacaggaaggcaaaatgccgcaaaaaagggaataagggcgacacggaa atgttgaatactcatactcttcctttttcaatattattgaagcatttatcagggttattgtctcatgagcggataca tatttgaatgtatttagaaaaataaacaataggggttccgcgcacatttccccgaaaagtgccac
```

---

What is claimed is:

1. A DNA targeting composition comprising a first gRNA molecule and a second gRNA molecule, wherein the first gRNA molecule and the second gRNA molecule are selected from the group consisting of:
   (i) a first gRNA molecule comprising a targeting domain that is encoded by a polynucleotide comprising a nucleotide sequence set forth in SEQ ID NO: 1, and a second gRNA molecule comprising a targeting domain that is encoded by a polynucleotide comprising a nucleotide sequence set forth in SEQ ID NO: 2;
   (ii) a first gRNA molecule comprising a targeting domain that is encoded by a polynucleotide comprising a nucleotide sequence set forth in SEQ ID NO: 11, and a second gRNA molecule comprising a targeting domain that is encoded by a polynucleotide comprising a nucleotide sequence set forth in SEQ ID NO: 4;
   (iii) a first gRNA molecule comprising a targeting domain that is encoded by a polynucleotide comprising a nucleotide sequence set forth in SEQ ID NO: 15, and a second gRNA molecule comprising a targeting domain that is encoded by a polynucleotide comprising a nucleotide sequence set forth in SEQ ID NO: 19;
   (iv) a first gRNA molecule comprising a targeting domain that is encoded by a polynucleotide comprising a nucleotide sequence set forth in SEQ ID NO: 15, and a second gRNA molecule comprising a targeting domain that is encoded by a polynucleotide comprising a nucleotide sequence set forth in SEQ ID NO: 18;
   (v) a first gRNA molecule comprising a targeting domain that is encoded by a polynucleotide comprising a nucleotide sequence set forth in SEQ ID NO: 15, and a second gRNA molecule comprising a targeting domain that is encoded by a polynucleotide comprising a nucleotide sequence set forth in SEQ ID NO: 4;
   (vi) a first gRNA molecule comprising a targeting domain that is encoded by a polynucleotide comprising a nucleotide sequence set forth in SEQ ID NO: 14, and a second gRNA molecule comprising a targeting domain that is encoded by a polynucleotide comprising a nucleotide sequence set forth in SEQ ID NO: 19;
   (vii) a first gRNA molecule comprising a targeting domain that is encoded by a polynucleotide comprising a nucleotide sequence set forth in SEQ ID NO: 14, and a second gRNA molecule comprising a targeting domain that is encoded by a polynucleotide comprising a nucleotide sequence set forth in SEQ ID NO: 18;
   (viii) a first gRNA molecule comprising a targeting domain that is encoded by a polynucleotide comprising a nucleotide sequence set forth in SEQ ID NO: 14, and a second gRNA molecule comprising a targeting domain that is encoded by a polynucleotide comprising a nucleotide sequence set forth in SEQ ID NO: 4;
   (ix) a first gRNA molecule comprising a targeting domain that is encoded by a polynucleotide comprising a nucleotide sequence set forth in SEQ ID NO: 11, and a second gRNA molecule comprising a targeting domain that is encoded by a polynucleotide comprising a nucleotide sequence set forth in SEQ ID NO: 19;
   (x) a first gRNA molecule comprising a targeting domain that is encoded by a polynucleotide comprising a nucleotide sequence set forth in SEQ ID NO: 14, and a second gRNA molecule comprising a targeting domain that is encoded by a polynucleotide comprising a nucleotide sequence set forth in SEQ ID NO: 15;
   (xi) a first gRNA molecule comprising a targeting domain that is encoded by a polynucleotide comprising a nucleotide sequence set forth in SEQ ID NO: 11, and a second gRNA molecule comprising a targeting domain that is encoded by a polynucleotide comprising a nucleotide sequence set forth in SEQ ID NO: 18; and
   (xii) a first gRNA molecule comprising a targeting domain that is encoded by a polynucleotide comprising a nucleotide sequence set forth in SEQ ID NO: 41, and a second gRNA molecule comprising a targeting domain that is encoded by a polynucleotide comprising a nucleotide sequence set forth in SEQ ID NO: 42.

2. The DNA targeting composition of claim 1, further comprising a Clustered Regularly Interspaced Short Palindromic Repeats associated (Cas) protein.

3. An isolated polynucleotide encoding the DNA targeting composition of claim 1.

4. A vector encoding the DNA targeting composition of claim 1.

5. A vector encoding:
   (a) the DNA targeting composition of claim 1, and
   (b) at least one Cas9 molecule that recognizes a Protospacer Adjacent Motif (PAM) of either NNGRRT (SEQ ID NO: 24) or NNGRRV (SEQ ID NO: 25).

6. The vector of claim 5, wherein the vector is configured to form a first and a second double strand break in a first and a second intron flanking exon 51 of the human DMD gene.

7. The vector of claim 5, wherein the vector is a viral vector.

8. The vector of claim 5, wherein the vector comprises a tissue-specific promoter operably linked to the nucleotide sequence encoding the first gRNA molecule, and/or the second gRNA molecule, and/or the Cas9 molecule.

9. An isolated cell comprising the DNA targeting composition of claim 5.

10. A kit comprising the vector of claim 5.

11. A method of correcting a mutant dystrophin gene in a cell, the method comprising administering to a cell the gRNA of claim 3.

12. A method of genome editing a mutant dystrophin gene in a subject, the method comprising administering to the subject a genome editing composition comprising the gRNA of claim 3.

13. A method of treating a subject in need thereof having a mutant dystrophin gene, the method comprising administering to the subject the gRNA of claim 3.

14. A composition for deleting a segment of a dystrophin gene comprising exon 51, the composition comprising:
(a) a first vector comprising a polynucleotide sequence encoding a first guide RNA (gRNA) molecule and a polynucleotide sequence encoding a first Cas9 molecule that recognizes a Protospacer Adjacent Motif (PAM) of either NNGRRT (SEQ ID NO: 24) or NNGRRV (SEQ ID NO: 25), and
(b) a second vector comprising a polynucleotide sequence encoding a second gRNA molecule and a polynucleotide sequence encoding a second Cas9 molecule that recognizes a Protospacer Adjacent Motif (PAM) of either NNGRRT (SEQ ID NO: 24) or NNGRRV (SEQ ID NO: 25),
wherein each of the first and second gRNA molecules have a targeting domain of 19 to 24 nucleotides in length, and wherein the first vector and second vector are configured to form a first and a second double strand break in a first intron and a second intron flanking exon 51 of the human DMD gene, respectively, thereby deleting a segment of the dystrophin gene comprising exon 51, and wherein the first gRNA molecule and the second gRNA molecule are selected from the group consisting of:
(i) a first gRNA molecule comprising a targeting domain that is encoded by a polynucleotide comprising a nucleotide sequence set forth in SEQ ID NO: 1, and a second gRNA molecule comprising a targeting domain that is encoded by a polynucleotide comprising a nucleotide sequence set forth in SEQ ID NO: 2;
(ii) a first gRNA molecule comprising a targeting domain that is encoded by a polynucleotide comprising a nucleotide sequence set forth in SEQ ID NO: 11, and a second gRNA molecule comprising a targeting domain that is encoded by a polynucleotide comprising a nucleotide sequence set forth in SEQ ID NO: 4;
(iii) a first gRNA molecule comprising a targeting domain that is encoded by a polynucleotide comprising a nucleotide sequence set forth in SEQ ID NO: 15, and a second gRNA molecule comprising a targeting domain that is encoded by a polynucleotide comprising a nucleotide sequence set forth in SEQ ID NO: 19;
(iv) a first gRNA molecule comprising a targeting domain that is encoded by a polynucleotide comprising a nucleotide sequence set forth in SEQ ID NO: 15, and a second gRNA molecule comprising a targeting domain that is encoded by a polynucleotide comprising a nucleotide sequence set forth in SEQ ID NO: 18;
(v) a first gRNA molecule comprising a targeting domain that is encoded by a polynucleotide comprising a nucleotide sequence set forth in SEQ ID NO: 15, and a second gRNA molecule comprising a targeting domain that is encoded by a polynucleotide comprising a nucleotide sequence set forth in SEQ ID NO: 4;
(vi) a first gRNA molecule comprising a targeting domain that is encoded by a polynucleotide comprising a nucleotide sequence set forth in SEQ ID NO: 14, and a second gRNA molecule comprising a targeting domain that is encoded by a polynucleotide comprising a nucleotide sequence set forth in SEQ ID NO: 19;
(vii) a first gRNA molecule comprising a targeting domain that is encoded by a polynucleotide comprising a nucleotide sequence set forth in SEQ ID NO: 14, and a second gRNA molecule comprising a targeting domain that is encoded by a polynucleotide comprising a nucleotide sequence set forth in SEQ ID NO: 18;
(viii) a first gRNA molecule comprising a targeting domain that is encoded by a polynucleotide comprising a nucleotide sequence set forth in SEQ ID NO: 14, and a second gRNA molecule comprising a targeting domain that is encoded by a polynucleotide comprising a nucleotide sequence set forth in SEQ ID NO: 4;
(ix) a first gRNA molecule comprising a targeting domain that is encoded by a polynucleotide comprising a nucleotide sequence set forth in SEQ ID NO: 11, and a second gRNA molecule comprising a targeting domain that is encoded by a polynucleotide comprising a nucleotide sequence set forth in SEQ ID NO: 19;
(x) a first gRNA molecule comprising a targeting domain that is encoded by a polynucleotide comprising a nucleotide sequence set forth in SEQ ID NO: 14, and a second gRNA molecule comprising a targeting domain that is encoded by a polynucleotide comprising a nucleotide sequence set forth in SEQ ID NO: 15;
(xi) a first gRNA molecule comprising a targeting domain that is encoded by a polynucleotide comprising a nucleotide sequence set forth in SEQ ID NO: 11, and a second gRNA molecule comprising a targeting domain that is encoded by a polynucleotide comprising a nucleotide sequence set forth in SEQ ID NO: 18; and
(xii) a first gRNA molecule comprising a targeting domain that is encoded by a polynucleotide comprising a nucleotide sequence set forth in SEQ ID NO: 41, and a second gRNA molecule comprising a targeting domain that is encoded by a polynucleotide comprising a nucleotide sequence set forth in SEQ ID NO: 42.

15. A method of correcting a mutant dystrophin gene in a cell, comprising administering to the cell:
(a) a first vector comprising a polynucleotide sequence encoding a first guide RNA (gRNA) molecule and a polynucleotide sequence encoding a first Cas9 molecule that recognizes a Protospacer Adjacent Motif (PAM) of either NNGRRT (SEQ ID NO: 24) or NNGRRV (SEQ ID NO: 25), and
(b) a second vector comprising a polynucleotide sequence encoding a second gRNA molecule and a polynucleotide sequence encoding a second Cas9 molecule that recognizes a Protospacer Adjacent Motif (PAM) of either NNGRRT (SEQ ID NO: 24) or NNGRRV (SEQ ID NO: 25),
wherein each of the first gRNA and second gRNA molecules have a targeting domain of 19 to 24 nucleotides in length, wherein the vector is configured to form a first and a second double strand break in a first and a second intron flanking exon 51 of the human dystrophin gene, respectively, thereby deleting a segment of the dystrophin gene comprising exon 51, and wherein the first gRNA molecule and the second gRNA molecule are selected from the group consisting of:
(i) a first gRNA molecule comprising a targeting domain that is encoded by a polynucleotide comprising a nucleotide sequence set forth in SEQ ID NO: 1, and a second gRNA molecule comprising a targeting domain that is encoded by a polynucleotide comprising a nucleotide sequence set forth in SEQ ID NO: 2;

(ii) a first gRNA molecule comprising a targeting domain that is encoded by a polynucleotide comprising a nucleotide sequence set forth in SEQ ID NO: 11, and a second gRNA molecule comprising a targeting domain that is encoded by a polynucleotide comprising a nucleotide sequence set forth in SEQ ID NO: 4;
(iii) a first gRNA molecule comprising a targeting domain that is encoded by a polynucleotide comprising a nucleotide sequence set forth in SEQ ID NO: 15, and a second gRNA molecule comprising a targeting domain that is encoded by a polynucleotide comprising a nucleotide sequence set forth in SEQ ID NO: 19;
(iv) a first gRNA molecule comprising a targeting domain that is encoded by a polynucleotide comprising s a nucleotide sequence set forth in SEQ ID NO: 15, and a second gRNA molecule comprising a targeting domain that is encoded by a polynucleotide comprising a nucleotide sequence set forth in SEQ ID NO: 18;
(v) a first gRNA molecule comprising a targeting domain that is encoded by a polynucleotide comprising a nucleotide sequence set forth in SEQ ID NO: 15, and a second gRNA molecule comprising a targeting domain that is encoded by a polynucleotide comprising a nucleotide sequence set forth in SEQ ID NO: 4;
(vi) a first gRNA molecule comprising a targeting domain that is encoded by a polynucleotide comprising a nucleotide sequence set forth in SEQ ID NO: 14, and a second gRNA molecule comprising a targeting domain that is encoded by a polynucleotide comprising a nucleotide sequence set forth in SEQ ID NO: 19;
(vii) a first gRNA molecule comprising a targeting domain that is encoded by a polynucleotide comprising a nucleotide sequence set forth in SEQ ID NO: 14, and a second gRNA molecule comprising a targeting domain that is encoded by a polynucleotide comprising a nucleotide sequence set forth in SEQ ID NO: 18;
(viii) a first gRNA molecule comprising a targeting domain that is encoded by a polynucleotide comprising a nucleotide sequence set forth in SEQ ID NO: 14, and a second gRNA molecule comprising a targeting domain that is encoded by a polynucleotide comprising a nucleotide sequence set forth in SEQ ID NO: 4;
(ix) a first gRNA molecule comprising a targeting domain that is encoded by a polynucleotide comprising a nucleotide sequence set forth in SEQ ID NO: 11, and a second gRNA molecule comprising a targeting domain that is encoded by a polynucleotide comprising a nucleotide sequence set forth in SEQ ID NO: 19;
(x) a first gRNA molecule comprising a targeting domain that is encoded by a polynucleotide comprising a nucleotide sequence set forth in SEQ ID NO: 14, and a second gRNA molecule comprising a targeting domain that is encoded by a polynucleotide comprising a nucleotide sequence set forth in SEQ ID NO: 15;
(xi) a first gRNA molecule comprising a targeting domain that is encoded by a polynucleotide comprising a nucleotide sequence set forth in SEQ ID NO: 11, and a second gRNA molecule comprising a targeting domain that is encoded by a polynucleotide comprising a nucleotide sequence set forth in SEQ ID NO: 18; and
(xii) a first gRNA molecule comprising a targeting domain that is encoded by a polynucleotide comprising a nucleotide sequence set forth in SEQ ID NO: 41, and a second gRNA molecule comprising a targeting domain that is encoded by a polynucleotide comprising a nucleotide sequence set forth in SEQ ID NO: 42.

16. A method of treating a subject in need thereof having a mutant dystrophin gene, the method comprising administering to the subject:
(a) a first vector comprising a polynucleotide sequence encoding a first guide RNA (gRNA) molecule and a polynucleotide sequence encoding a first Cas9 molecule that recognizes a Protospacer Adjacent Motif (PAM) of either NNGRRT (SEQ ID NO: 24) or NNGRRV (SEQ ID NO: 25), and
(b) a second vector comprising a polynucleotide sequence encoding a second gRNA molecule and a polynucleotide sequence encoding a second Cas9 molecule that recognizes a Protospacer Adjacent Motif (PAM) of either NNGRRT (SEQ ID NO: 24) or NNGRRV (SEQ ID NO: 25),
wherein each of the first gRNA and second gRNA molecules have a targeting domain of 19 to 24 nucleotides in length, wherein the vector is configured to form a first and a second double strand break in a first and a second intron flanking exon 51 of the human dystrophin gene, respectively, thereby deleting a segment of the dystrophin gene comprising exon 51, and wherein the first gRNA molecule and the second gRNA molecule are selected from the group consisting of:
(i) a first gRNA molecule comprising a targeting domain that is encoded by a polynucleotide comprising a nucleotide sequence set forth in SEQ ID NO: 1, and a second gRNA molecule comprising a targeting domain that is encoded by a polynucleotide comprising a nucleotide sequence set forth in SEQ ID NO: 2;
(ii) a first gRNA molecule comprising a targeting domain that is encoded by a polynucleotide comprising a nucleotide sequence set forth in SEQ ID NO: 11, and a second gRNA molecule comprising a targeting domain that is encoded by a polynucleotide comprising a nucleotide sequence set forth in SEQ ID NO: 4;
(iii) a first gRNA molecule comprising a targeting domain that is encoded by a polynucleotide comprising a nucleotide sequence set forth in SEQ ID NO: 15, and a second gRNA molecule comprising a targeting domain that is encoded by a polynucleotide comprising a nucleotide sequence set forth in SEQ ID NO: 19;
(iv) a first gRNA molecule comprising a targeting domain that is encoded by a polynucleotide comprising a nucleotide sequence set forth in SEQ ID NO: 15, and a second gRNA molecule comprising a targeting domain that is encoded by a polynucleotide comprising a nucleotide sequence set forth in SEQ ID NO: 18;
(v) a first gRNA molecule comprising a targeting domain that is encoded by a polynucleotide comprising a nucleotide sequence set forth in SEQ ID NO: 15, and a second gRNA molecule comprising a targeting domain that is encoded by a polynucleotide comprising a nucleotide sequence set forth in SEQ ID NO: 4;
(vi) a first gRNA molecule comprising a targeting domain that is encoded by a polynucleotide comprising a nucleotide sequence set forth in SEQ ID NO: 14, and a second gRNA molecule comprising a targeting domain that is encoded by a polynucleotide comprising a nucleotide sequence set forth in SEQ ID NO: 19;
(vii) a first gRNA molecule comprising a targeting domain that is encoded by a polynucleotide comprising a nucleotide sequence set forth in SEQ ID NO: 14, and a second gRNA molecule comprising a targeting domain that is encoded by a polynucleotide comprising a nucleotide sequence set forth in SEQ ID NO: 18;
(viii) a first gRNA molecule comprising a targeting domain that is encoded by a polynucleotide comprising a nucleotide sequence set forth in SEQ ID NO: 14, and a second gRNA molecule comprising a targeting domain that is encoded by a polynucleotide comprising a nucleotide sequence set forth in SEQ ID NO: 4;

(ix) a first gRNA molecule comprising a targeting domain that is encoded by a polynucleotide comprising a nucleotide sequence set forth in SEQ ID NO: 11, and a second gRNA molecule comprising a targeting domain that is encoded by a polynucleotide comprising a nucleotide sequence set forth in SEQ ID NO: 19;

(x) a first gRNA molecule comprising a targeting domain that is encoded by a polynucleotide comprising a nucleotide sequence set forth in SEQ ID NO: 14, and a second gRNA molecule comprising a targeting domain that is encoded by a polynucleotide comprising a nucleotide sequence set forth in SEQ ID NO: 15;

(xi) a first gRNA molecule comprising a targeting domain that is encoded by a polynucleotide comprising a nucleotide sequence set forth in SEQ ID NO: 11, and a second gRNA molecule comprising a targeting domain that is encoded by a polynucleotide comprising a nucleotide sequence set forth in SEQ ID NO: 18; and (xii) a first gRNA molecule comprising a targeting domain that is encoded by a polynucleotide comprising a nucleotide sequence set forth in SEQ ID NO: 41, and a second gRNA molecule comprising a targeting domain that is encoded by a polynucleotide comprising a nucleotide sequence set forth in SEQ ID NO: 42.

* * * * *

SEQUENCE LISTING

<160> NUMBER OF SEQ ID NOS: 114

<210> SEQ ID NO 1
<211> LENGTH: 22
<212> TYPE: DNA
<213> ORGANISM: Artificial sequence

```
<220> FEATURE:
<223> OTHER INFORMATION: Synthetic

<400> SEQUENCE: 1
aaagatatat aatgtcatga at                                              22

<210> SEQ ID NO 2
<211> LENGTH: 22
<212> TYPE: DNA
<213> ORGANISM: Artificial sequence
<220> FEATURE:
<223> OTHER INFORMATION: Synthetic

<400> SEQUENCE: 2
gcagaatcaa atataatagt ct                                              22

<210> SEQ ID NO 3
<211> LENGTH: 22
<212> TYPE: DNA
<213> ORGANISM: Artificial sequence
<220> FEATURE:
<223> OTHER INFORMATION: Synthetic

<400> SEQUENCE: 3
caattaaatt tgacttattg tt                                              22

<210> SEQ ID NO 4
<211> LENGTH: 22
<212> TYPE: DNA
<213> ORGANISM: Artificial sequence
<220> FEATURE:
<223> OTHER INFORMATION: Synthetic

<400> SEQUENCE: 4
ctagaccatt tcccaccagt tc                                              22

<210> SEQ ID NO 5
<211> LENGTH: 22
<212> TYPE: DNA
<213> ORGANISM: Artificial sequence
<220> FEATURE:
<223> OTHER INFORMATION: Synthetic

<400> SEQUENCE: 5 aggacttttta tttaccaaag ga                                             22

<210> SEQ ID NO 6
<211> LENGTH: 22
<212> TYPE: DNA
<213> ORGANISM: Artificial sequence
<220> FEATURE:
<223> OTHER INFORMATION: Synthetic

<400> SEQUENCE: 6
atccaagtcc atttgattcc ta                                              22

<210> SEQ ID NO 7
<211> LENGTH: 22
<212> TYPE: DNA
<213> ORGANISM: Artificial sequence
<220> FEATURE:
<223> OTHER INFORMATION: Synthetic

<400> SEQUENCE: 7
taattctttc tagaaagagc ct                                              22
```

<210> SEQ ID NO 8
<211> LENGTH: 22
<212> TYPE: DNA
<213> ORGANISM: Artificial sequence
<220> FEATURE:
<223> OTHER INFORMATION: Synthetic

<400> SEQUENCE: 8
ggacatgtgc aagatgcaag ag                                          22

<210> SEQ ID NO 9
<211> LENGTH: 22
<212> TYPE: DNA
<213> ORGANISM: Artificial sequence
<220> FEATURE:
<223> OTHER INFORMATION: Synthetic

<400> SEQUENCE: 9
tgtatgtaga agacctctaa gt                                          22

<210> SEQ ID NO 10
<211> LENGTH: 22
<212> TYPE: DNA
<213> ORGANISM: Artificial sequence
<220> FEATURE:
<223> OTHER INFORMATION: Synthetic

<400> SEQUENCE: 10
tcccctcacc actcacctct ga                                          22

<210> SEQ ID NO 11
<211> LENGTH: 22
<212> TYPE: DNA
<213> ORGANISM: Artificial sequence
<220> FEATURE:
<223> OTHER INFORMATION: Synthetic

<400> SEQUENCE: 11
ctctgataac ccagctgtgt gt                                          22

<210> SEQ ID NO 12
<211> LENGTH: 19
<212> TYPE: DNA
<213> ORGANISM: Artificial sequence
<220> FEATURE:
<223> OTHER INFORMATION: Synthetic

<400> SEQUENCE: 12
ctctgataac ccagctgtg                                              19

<210> SEQ ID NO 13
<211> LENGTH: 20
<212> TYPE: DNA
<213> ORGANISM: Artificial sequence
<220> FEATURE:
<223> OTHER INFORMATION: Synthetic

<400> SEQUENCE: 13
ctctgataac ccagctgtgt                                             20

<210> SEQ ID NO 14
<211> LENGTH: 21
<212> TYPE: DNA
<213> ORGANISM: Artificial sequence
<220> FEATURE:
<223> OTHER INFORMATION: Synthetic

```
<400> SEQUENCE: 14
ctctgataac ccagctgtgt g                                           21

<210> SEQ ID NO 15
<211> LENGTH: 23
<212> TYPE: DNA
<213> ORGANISM: Artificial sequence
<220> FEATURE:
<223> OTHER INFORMATION: Synthetic

<400> SEQUENCE: 15
ctctgataac ccagctgtgt gtt                                         23

<210> SEQ ID NO 16
<211> LENGTH: 19
<212> TYPE: DNA
<213> ORGANISM: Artificial sequence
<220> FEATURE:
<223> OTHER INFORMATION: Synthetic

<400> SEQUENCE: 16
ctagaccatt tcccaccag                                              19

<210> SEQ ID NO 17
<211> LENGTH: 20
<212> TYPE: DNA
<213> ORGANISM: Artificial sequence
<220> FEATURE:
<223> OTHER INFORMATION: Synthetic

<400> SEQUENCE: 17
ctagaccatt tcccaccagt                                             20

<210> SEQ ID NO 18
<211> LENGTH: 21
<212> TYPE: DNA
<213> ORGANISM: Artificial sequence
<220> FEATURE:
<223> OTHER INFORMATION: Synthetic

<400> SEQUENCE: 18
ctagaccatt tcccaccagt t                                           21

<210> SEQ ID NO 19
<211> LENGTH: 23
<212> TYPE: DNA
<213> ORGANISM: Artificial sequence
<220> FEATURE:
<223> OTHER INFORMATION: Synthetic

<400> SEQUENCE: 19
ctagaccatt tcccaccagt tct                                         23

<210> SEQ ID NO 20
<211> LENGTH: 7
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: w
<222> LOCATION: (7)..(7)
```

```
<223> OTHER INFORMATION: a or t

<400> SEQUENCE: 20 nnagaaw                                                                        7

<210> SEQ ID NO 21
<211> LENGTH: 4
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: r
<222> LOCATION: (4)..(4)
<223> OTHER INFORMATION: a or g

<400> SEQUENCE: 21 naar                                                                           4

<210> SEQ ID NO 22
<211> LENGTH: 5
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: r
<222> LOCATION: (4)..(5)
<223> OTHER INFORMATION: a or g

<400> SEQUENCE: 22 nngrr                                                                          5

<210> SEQ ID NO 23
<211> LENGTH: 6
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: r
<222> LOCATION: (4)..(5)
<223> OTHER INFORMATION: a or g
<220> FEATURE:
<221> NAME/KEY: misc_feature
<222> LOCATION: (6)..(6)
<223> OTHER INFORMATION: n is a, c, g, or t

<400> SEQUENCE: 23 nngrrn                                                                         6

<210> SEQ ID NO 24
<211> LENGTH: 6
<212> TYPE: DNA
<213> ORGANISM: Artificial sequence
<220> FEATURE:
<223> OTHER INFORMATION: Synthetic
<220> FEATURE:
<221> NAME/KEY: misc_feature
```

```
<222> LOCATION: (1)..(2)
<223> OTHER INFORMATION: n is a, c, g, or t
<220> FEATURE:
<221> NAME/KEY: r
<222> LOCATION: (4)..(5)
<223> OTHER INFORMATION: a or g

<400> SEQUENCE: 24 nngrrt                                                                6

<210> SEQ ID NO 25
<211> LENGTH: 6
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: r
<222> LOCATION: (4)..(5)
<223> OTHER INFORMATION: a or g

<400> SEQUENCE: 25 nngrrv                                                                6

<210> SEQ ID NO 26
<211> LENGTH: 4107
<212> TYPE: DNA
<213> ORGANISM: Artificial sequence
<220> FEATURE:
<223> OTHER INFORMATION: Synthetic

<400> SEQUENCE: 26
atggataaaa agtacagcat cgggctggac atcggtacaa actcagtggg gtgggccgtg      60
attacggacg agtacaaggt accctccaaa aaatttaaag tgctgggtaa cacggacaga     120
cactctataa agaaaaatct tattggagcc ttgctgttcg actcaggcga gacagccgaa     180
gccacaaggt tgaagcggac cgccaggagg cggtatacca ggagaaagaa ccgcatatgc     240
tacctgcaag aaatcttcag taacgagatg gcaaaggttg acgatagctt tttccatcgc     300
ctggaagaat cctttcttgt tgaggaagac aagaagcacg aacggcaccc catctttggc     360
aatattgtcg acgaagtggc atatcacgaa agtacccga ctatctacca cctcaggaag     420
aagctggtgg actctaccga taaggcggac ctcagactta tttatttggc actcgcccac     480
atgattaaat ttagaggaca tttcttgatc gagggcgacc tgaacccgga caacagtgac     540
gtcgataagc tgttcatcca acttgtgcag acctacaatc aactgttcga agaaaaccct     600
ataaatgctt caggagtcga cgctaaagca atcctgtccg cgcgcctctc aaaatctaga     660
agacttgaga atctgattgc tcagttgccc ggggaaaaga aaatggatt gtttggcaac     720 ctgatcgccc tcagtctcgg actgaccca aatttcaaaa gtaacttcga cctgccgaa     780 gacgctaagc tccagctgtc caaggacaca tacgatgacg acctcgacaa tctgctggcc     840
cagattgggg atcagtacgc cgatctcttt ttggcagcaa agaacctgtc cgacgccatc     900
ctgttgagcg atatcttgag agtgaacacc gaaattacta agcacccct agcgcatct     960 atgatcaagc ggtacgacga gcatcatcag gatctgaccc tgctgaaggc tcttgtgagg    1020
caacagctcc ccgaaaaata caaggaaatc ttctttgacc agagcaaaaa cggctacgct    1080
ggctatatag atggtggggc cagtcaggag gaattctata aattcatcaa gcccattctc    1140
```

-continued

```
gagaaaatgg acggcacaga ggagttgctg gtcaaactta acaggagga cctgctgcgg    1200 aagcagcgga cctttgacaa cgggtctatc ccccaccaga ttcatctggg cgaactgcac    1260
gcaatcctga ggaggcagga ggattttat ccttttctta aagataaccg cgagaaaata    1320
gaaaagattc ttacattcag gatcccgtac tacgtgggac ctctcgcccg ggcaattca    1380 cggtttgcct ggatgacaag gaagtcagag gagactatta caccttggaa cttcgaagaa    1440
gtggtggaca agggtgcatc tgcccagtct ttcatcgagc ggatgacaaa ttttgacaag    1500
aacctcccta atgagaaggt gctgcccaaa cattctctgc tctacgagta ctttaccgtc    1560
tacaatgaac tgactaaagt caagtacgtc accgagggaa tgaggaagcc ggcattcctt    1620
agtggagaac agaagaaggc gattgtagac ctgttgttca agaccaacag gaaggtgact    1680
gtgaagcaac ttaaagaaga ctactttaag aagatcgaat gttttgacag tgtggaaatt    1740
tcaggggttg aagaccgctt caatgcgtca ttggggactt accatgatct tctcaagatc    1800
ataaaggaca aagacttcct ggacaacgaa gaaaatgagg atattctcga agacatcgtc    1860
ctcaccctga ccctgttcga agacagggaa atgatagaag agcgcttgaa aacctatgcc    1920
cacctcttcg acgataaagt tatgaagcag ctgaagcgca ggagatacac aggatgggga    1980
agattgtcaa ggaagctgat caatggaatt agggataaac agagtggcaa gaccatactg    2040
gatttcctca aatctgatgg cttcgccaat aggaacttca tgcaactgat tcacgatgac    2100
tctcttacct tcaaggagga cattcaaaag gctcaggtga gcgggcaggg agactccctt    2160
catgaacaca tcgcgaattt ggcaggttcc cccgctatta aaagggcat ccttcaaact    2220 gtcaaggtgg tggatgaatt ggtcaaggta atgggcagac ataagccaga aaatattgtg    2280
atcgagatgg cccgcgaaaa ccagaccaca cagaagggcc agaaaaatag tagagagcgg    2340
atgaagagga tcgaggaggg catcaaagag ctgggatctc agattctcaa agaacacccc    2400
gtagaaaaca cacagctgca gaacgaaaaa ttgtacttgt actatctgca gaacggcaga    2460
gacatgtacg tcgaccaaga acttgatatt aatagactgt ccgactatga cgtagaccat    2520
atcgtgcccc agtccttcct gaaggacgac tccattgata caaagtctt gacaagaagc    2580 gacaagaaca ggggtaaaag tgataatgtg cctagcgagg aggtggtgaa aaaaatgaag    2640
aactactggc gacagctgct taatgcaaag ctcattacac aacggaagtt cgataatctg    2700
acgaaagcag agagaggtgg cttgtctgag ttggacaagg cagggtttat taagcggcag    2760
ctggtggaaa ctaggcagat cacaaagcac gtggcgcaga ttttggacag ccggatgaac    2820
acaaaatacg acgaaaatga taaactgata cgagaggtca agttatcac gctgaaaagc    2880 aagctggtgt ccgattttcg gaaagacttc cagttctaca aagttcgcga gattaataac    2940
taccatcatg ctcacgatgc gtacctgaac gctgttgtcg ggaccgcctt gataaagaag    3000
tacccaaagc tggaatccga gttcgtatac ggggattaca agtgtacga tgtgaggaaa    3060 atgatagcca gtccgagca ggagattgga aaggccacag ctaagtactt ctttattct    3120 aacatcatga ttttttaa gacggaaatt accctggcca acggagagat cagaaagcgg    3180 cccttatag agacaaatgg tgaaacaggt gaaatcgtct gggataaggg cagggattc    3240 gctactgtga ggaaggtgct gagtatgcca caggtaaata tcgtgaaaaa accgaagta    3300 cagaccggag gattttccaa ggaaagcatt ttgcctaaaa gaaactcaga caagctcatc    3360
gcccgcaaga aagattggga ccctaagaaa tacgggggat tgactcacc caccgtagcc    3420 tattctgtgc tggtggtagc taaggtggaa aaggaaaagt ctaagaagct gaagtccgtg    3480
aaggaactct tgggaatcac tatcatggaa agatcatcct ttgaaaagaa ccctatcgat    3540
```

```
ttcctggagg ctaagggtta caaggaggtc aagaaagacc tcatcattaa actgccaaaa    3600
tactctctct tcgagctgga aaatggcagg aagagaatgt tggccagcgc cggagagctg    3660
caaaagggaa acgagcttgc tctgccctcc aaatatgtta attttctcta tctcgcttcc    3720
cactatgaaa agctgaaagg gtctcccgaa gataacgagc agaagcagct gttcgtcgaa    3780
cagcacaagc actatctgga tgaaataatc gaacaaataa gcgagttcag caaaagggtt    3840
atcctggcgg atgctaattt ggacaaagta ctgtctgctt ataacaagca ccgggataag    3900
cctattaggg aacaagccga gaatataatt cacctcttta cactcacgaa tctcggagcc    3960
cccgccgcct tcaaatactt tgatacgact atcgaccgga acggtatac cagtaccaaa    4020 gaggtcctcg atgccaccct catccaccag tcaattactg gcctgtacga aacacggatc    4080
gacctctctc aactgggcgg cgactag                                       4107
```

<210> SEQ ID NO 27
<211> LENGTH: 1368
<212> TYPE: PRT
<213> ORGANISM: Artificial sequence
<220> FEATURE:
<223> OTHER INFORMATION: Synthetic

<400> SEQUENCE: 27

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255
```

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe

```
            675                 680                 685
Ala Asn Arg Asn Phe Met Gln Leu Ile His Asp Asp Ser Leu Thr Phe
690                 695                 700
Lys Glu Asp Ile Gln Lys Ala Gln Val Ser Gly Gln Gly Asp Ser Leu
705                 710                 715                 720
His Glu His Ile Ala Asn Leu Ala Gly Ser Pro Ala Ile Lys Lys Gly
                725                 730                 735
Ile Leu Gln Thr Val Lys Val Val Asp Glu Leu Val Lys Val Met Gly
                740                 745                 750
Arg His Lys Pro Glu Asn Ile Val Ile Glu Met Ala Arg Glu Asn Gln
                755                 760                 765
Thr Thr Gln Lys Gly Gln Lys Asn Ser Arg Glu Arg Met Lys Arg Ile
770                 775                 780
Glu Glu Gly Ile Lys Glu Leu Gly Ser Gln Ile Leu Lys Glu His Pro
785                 790                 795                 800
Val Glu Asn Thr Gln Leu Gln Asn Glu Lys Leu Tyr Leu Tyr Tyr Leu
                805                 810                 815
Gln Asn Gly Arg Asp Met Tyr Val Asp Gln Glu Leu Asp Ile Asn Arg
                820                 825                 830
Leu Ser Asp Tyr Asp Val Asp His Ile Val Pro Gln Ser Phe Leu Lys
                835                 840                 845
Asp Asp Ser Ile Asp Asn Lys Val Leu Thr Arg Ser Asp Lys Asn Arg
                850                 855                 860
Gly Lys Ser Asp Asn Val Pro Ser Glu Glu Val Val Lys Lys Met Lys
865                 870                 875                 880
Asn Tyr Trp Arg Gln Leu Leu Asn Ala Lys Leu Ile Thr Gln Arg Lys
                885                 890                 895
Phe Asp Asn Leu Thr Lys Ala Glu Arg Gly Gly Leu Ser Glu Leu Asp
                900                 905                 910
Lys Ala Gly Phe Ile Lys Arg Gln Leu Val Glu Thr Arg Gln Ile Thr
                915                 920                 925
Lys His Val Ala Gln Ile Leu Asp Ser Arg Met Asn Thr Lys Tyr Asp
                930                 935                 940
Glu Asn Asp Lys Leu Ile Arg Glu Val Lys Val Ile Thr Leu Lys Ser
945                 950                 955                 960
Lys Leu Val Ser Asp Phe Arg Lys Asp Phe Gln Phe Tyr Lys Val Arg
                965                 970                 975
Glu Ile Asn Asn Tyr His His Ala His Asp Ala Tyr Leu Asn Ala Val
                980                 985                 990
Val Gly Thr Ala Leu Ile Lys Lys Tyr Pro Lys Leu Glu Ser Glu Phe
                995                 1000                1005
Val Tyr Gly Asp Tyr Lys Val Tyr Asp Val Arg Lys Met Ile Ala
                1010                1015                1020
Lys Ser Glu Gln Glu Ile Gly Lys Ala Thr Ala Lys Tyr Phe Phe
                1025                1030                1035
Tyr Ser Asn Ile Met Asn Phe Phe Lys Thr Glu Ile Thr Leu Ala
                1040                1045                1050
Asn Gly Glu Ile Arg Lys Arg Pro Leu Ile Glu Thr Asn Gly Glu
                1055                1060                1065
Thr Gly Glu Ile Val Trp Asp Lys Gly Arg Asp Phe Ala Thr Val
                1070                1075                1080
Arg Lys Val Leu Ser Met Pro Gln Val Asn Ile Val Lys Lys Thr
                1085                1090                1095
```

| Glu | Val | Gln | Thr | Gly | Gly | Phe | Ser | Lys | Glu | Ser | Ile | Leu | Pro | Lys |
|     |     |     |     | 1100 |     |     | 1105 |     |     |     | 1110 |     |     |     |

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

<210> SEQ ID NO 28
<211> LENGTH: 3158
<212> TYPE: DNA
<213> ORGANISM: Artificial sequence
<220> FEATURE:
<223> OTHER INFORMATION: Synthetic

<400> SEQUENCE: 28
atgaaaagga actacattct ggggctggac atcgggatta caagcgtggg gtatgggatt      60
attgactatg aaacaaggga cgtgatcgac gcaggcgtca gactgttcaa ggaggccaac     120
gtggaaaaca atgagggacg gagaagcaag aggggagcca ggcgcctgaa acgacggaga     180
aggcacagaa tccagagggt gaagaaactg ctgttcgatt acaacctgct gaccgaccat     240
tctgagctga gtggaattaa tccttatgaa gccagggtga aggcctgag tcagaagctg     300 tcagaggaag agttttccgc agctctgctg cacctggcta agcgccgagg agtgcataac     360
gtcaatgagg tggaagagga caccggcaac gagctgtcta caaggaaca gatctcacgc     420

```
aatagcaaag ctctggaaga gaagtatgtc gcagagctgc agctggaacg gctgaagaaa    480
gatggcgagg tgagagggtc aattaatagg ttcaagacaa gcgactacgt caaagaagcc    540
aagcagctgc tgaaagtgca gaaggcttac caccagctgg atcagagctt catcgatact    600
tatatcgacc tgctggagac tcggagaacc tactatgagg gaccaggaga agggagcccc    660
ttcggatgga agacatcaa ggaatggtac gagatgctga tgggacattg cacctatttt    720
ccagaagagc tgagaagcgt caagtacgct tataacgcag atctgtacaa cgccctgaat    780
gacctgaaca acctggtcat caccagggat gaaaacgaga aactggaata ctatgagaag    840
ttccagatca tcgaaaacgt gtttaagcag aagaaaaagc ctacactgaa acagattgct    900
aaggagatcc tggtcaacga gaggacatc aagggctacc gggtgacaag cactggaaaa    960
ccagagttca ccaatctgaa agtgtatcac gatattaagg acatcacagc acggaaagaa   1020
atcattgaga acgccgaact gctggatcag attgctaaga tcctgactat ctaccagagc   1080
tccgaggaca tccaggaaga gctgactaac ctgaacagcg agctgaccca ggaagagatc   1140
gaacagatta gtaatctgaa ggggtacacc ggaacacaca acctgtccct gaaagctatc   1200
aatctgattc tggatgagct gtggcataca aacgacaatc agattgcaat cttttaaccgg   1260
ctgaagctgg tcccaaaaaa ggtggacctg agtcagcaga aagagatccc aaccacactg   1320
gtggacgatt tcattctgtc acccgtggtc aagcggagct tcatccagag catcaaagtg   1380
atcaacgcca tcatcaagaa gtacggcctg cccaatgata tcattatcga gctggctagg   1440
gagaagaaca gcaaggacgc acagaagatg atcaatgaga tgcagaaacg aaaccggcag   1500
accaatgaac gcattgaaga gattatccga actaccggga agagaacgc aaagtacctg   1560
attgaaaaaa tcaagctgca cgatatgcag gagggaaagt gtctgtattc tctggaggcc   1620
tcccccctgga ggacctgctg aacaatccat tcaactacga ggtcgatcat attatcccca   1680
gaagcgtgtc cttcgacaat tcctttaaca acaaggtgct ggtcaagcag gaagagaact   1740
ctaaaaaggg caataggact cctttccagt acctgtctag ttcagattcc aagatctctt   1800
acgaaacctt taaaaagcac attctgaatc tggccaaagg aaagggccgc atcagcaaga   1860
ccaaaaagga gtacctgctg gaagagcggg acatcaacag attctccgtc agaaggatt    1920
ttattaaccg gaatctggtg gacacaagat acgctactcg cggcctgatg aatctgctgc   1980
gatcctattt ccgggtgaac aatctggatg tgaaagtcaa gtccatcaac ggcgggttca   2040
catcttttct gaggcgcaaa tggaagttta aaaaggagcg caacaagggg tacaagcacc   2100
atgccgaaga tgctctgatt atcgcaaatg ccgacttcat cttttaaggag tggaaaaagc   2160
tggacaaagc caagaaagtg atggagaacc agatgttcga agagaagcag gccgaatcta   2220
tgcccgaaat cgagacagaa caggagtaca aggagattt catcactcct caccagatca   2280
agcatatcaa ggattcaag gactacaagt actctcaccg ggtggataaa aagcccaaca   2340
gagagctgat caatgacacc ctgtatagta caagaaaaga cgataagggg aatacccctga   2400
ttgtgaacaa tctgaacgga ctgtacgaca agataatga caagctgaaa aagctgatca   2460
acaaaagtcc cgagaagctg ctgatgtacc accatgatcc tcagacatat cagaaactga   2520
agctgattat ggagcagtac ggcgacgaga agaacccact gtataagtac tatgaagaga   2580
ctgggaacta cctgaccaag tatagcaaaa aggataatgg ccccgtgatc aagaagatca   2640
agtactatgg gaacaagctg aatgcccatc tggacatcac agacgattac cctaacagtc   2700
gcaacaaggt ggtcaagctg tcactgaagc catacagatt cgatgtctat ctggacaacg   2760
gcgtgtataa atttgtgact gtcaagaatc tggatgtcat caaaaaggag aactactatg   2820
```

```
aagtgaatag caagtgctac gaagaggcta aaaagctgaa aaagattagc aaccaggcag    2880
agttcatcgc ctccttttac aacaacgacc tgattaagat caatggcgaa ctgtataggg    2940
tcatcggggt gaacaatgat ctgctgaacc gcattgaagt gaatatgatt gacatcactt    3000
accgagagta tctggaaaac atgaatgata agcgcccccc tcgaattatc aaaacaattg    3060
cctctaagac tcagagtatc aaaaagtact caaccgacat tctgggaaac ctgtatgagg    3120
tgaagagcaa aaagcaccct cagattatca aaaagggc                           3158
```

<210> SEQ ID NO 29
<211> LENGTH: 3159
<212> TYPE: DNA
<213> ORGANISM: Artificial sequence
<220> FEATURE:
<223> OTHER INFORMATION: Synthetic

<400> SEQUENCE: 29

```
atgaagcgga actacatcct gggcctggac atcggcatca ccagcgtggg ctacggcatc      60
atcgactacg agacacggga cgtgatcgat gccggcgtgc ggctgttcaa agaggccaac     120
gtggaaaaca acgagggcag gcggagcaag agaggcgcca aaggctgaa gcggcggagg      180 cggcatagaa tccagagagt gaagaagctg ctgttcgact acaacctgct gaccgaccac     240
agcgagctga gcggcatcaa cccctacgag gccagagtga agggcctgag ccagaagctg     300
agcgaggaag agttctctgc cgccctgctg cacctggcca gagaagagg cgtgcacaac     360 gtgaacgagg tggaagagga caccggcaac gagctgtcca ccaaagagca gatcagccgg     420
aacagcaagg ccctggaaga gaaatacgtg gccgaactgc agctggaacg gctgaagaaa     480
gacggcgaag tgcgggggcag catcaacaga ttcaagacca gcgactacgt gaaagaagcc     540
aaacagctgc tgaaggtgca gaaggcctac caccagctgg accagagctt catcgacacc     600
tacatcgacc tgctggaaaac ccggcggacc tactatgagg acctggcga gggcagcccc     660 ttcggctgga aggacatcaa agaatggtac gagatgctga tgggccactg cacctacttc     720
cccgaggaac tgcggagcgt gaagtacgcc tacaacgccg acctgtacaa cgccctgaac     780
gacctgaaca atctcgtgat caccagggac gagaacgaga agctggaata ttacgagaag     840
ttccagatca tcgagaacgt gttcaagcag aagaagaagc ccaccctgaa gcagatcgcc     900
aaagaaatcc tcgtgaacga agaggatatt aagggctaca gagtgaccag caccggcaag     960
cccgagttca ccaacctgaa ggtgtaccac gacatcaagg acattaccgc ccggaaagag    1020
attattgaga cgccgagct gctggatcag attgccaaga tcctgaccat ctaccagagc    1080
agcgaggaca tccaggaaga actgaccaat ctgaactccg agctgaccca ggaagagatc    1140
gagcagatct ctaatctgaa gggctatacc ggcacccaca acctgagcct gaaggccatc    1200
aacctgatcc tggacgagct gtggcacacc aacgacaacc agatcgctat cttcaaccgg    1260
ctgaagctgg tgcccaagaa ggtggacctg tcccagcaga aagagatccc caccaccctg    1320
gtggacgact tcatcctgag ccccgtcgtg aagagaagct tcatccagag catcaaagtg    1380
atcaacgcca tcatcaagaa gtacggcctg cccaacgaca tcattatcga gctggcccgc    1440
gagaagaact ccaaggacgc ccagaaaatg atcaacgaga tgcagaagcg gaaccggcag    1500
accaacgagc ggatcgagga aatcatccgg accaccggca agagaacgc caagtacctg    1560 atcgagaaga tcaagctgca cgacatgcag gaaggcaagt gcctgtacag cctggaagcc    1620
atccctctgg aagatctgct gaacaacccc ttcaactatg aggtggacca catcatcccc    1680
```

| | |
|---|---|
| agaagcgtgt ccttcgacaa cagcttcaac aacaaggtgc tcgtgaagca ggaagaaaac | 1740 |
| agcaagaagg gcaaccggac cccattccag tacctgagca gcagcgacag caagatcagc | 1800 |
| tacgaaacct tcaagaagca catcctgaat ctggccaagg gcaagggcag aatcagcaag | 1860 |
| accaagaaag agtatctgct ggaagaacgg gacatcaaca ggttctccgt gcagaaagac | 1920 |
| ttcatcaacc ggaacctggt ggataccaga tacgccacca gaggcctgat gaacctgctg | 1980 |
| cggagctact tcagagtgaa caacctggac gtgaaagtga agtccatcaa tggcggcttc | 2040 |
| accagctttc tgcggcggaa gtggaagttt aagaaagagc ggaacaaggg gtacaagcac | 2100 |
| cacgccgagg acgccctgat cattgccaac gccgatttca tcttcaaaga gtggaagaaa | 2160 |
| ctggacaagg ccaaaaaagt gatggaaaac cagatgttcg aggaaaagca ggccgagagc | 2220 |
| atgcccgaga tcgaaaccga gcaggagtac aaagagatct tcatcacccc ccaccagatc | 2280 |
| aagcacatta aggacttcaa ggactacaag tacagccacc gggtggacaa gaagcctaat | 2340 |
| agagagctga ttaacgacac cctgtactcc acccggaagg acgacaaggg caacaccctg | 2400 |
| atcgtgaaca atctgaacgg cctgtacgac aaggacaatg acaagctgaa aaagctgatc | 2460 |
| aacaagagcc ccgaaaagct gctgatgtac caccacgacc cccagaccta ccagaaactg | 2520 |
| aagctgatta tggaacagta cggcgacgag aagaatcccc tgtacaagta ctacgaggaa | 2580 |
| accgggaact acctgaccaa gtactccaaa aaggacaacg cccccgtgat caagaagatt | 2640 |
| aagtattacg gcaacaaact gaacgcccat ctggacatca ccgacgacta ccccaacagc | 2700 |
| agaaacaagg tcgtgaagct gtccctgaag ccctacagat cgacgtgta cctggacaat | 2760 |
| ggcgtgtaca agttcgtgac cgtgaagaat ctggatgtga tcaaaaaaga aaactactac | 2820 |
| gaagtgaata gcaagtgcta tgaggaagct aagaagctga agaagatcag caaccaggcc | 2880 |
| gagtttatcg cctccttcta caacaacgat ctgatcaaga tcaacggcga gctgtataga | 2940 |
| gtgatcggcg tgaacaacga cctgctgaac cggatcgaag tgaacatgat cgacatcacc | 3000 |
| taccgcgagt acctggaaaa catgaacgac aagaggcccc ccaggatcat taagacaatc | 3060 |
| gcctccaaga cccagagcat taagaagtac agcacagaca ttctgggcaa cctgtatgaa | 3120 |
| gtgaaatcta agaagcaccc tcagatcatc aaaaagggc | 3159 |

<210> SEQ ID NO 30
<211> LENGTH: 3159
<212> TYPE: DNA
<213> ORGANISM: Artificial sequence
<220> FEATURE:
<223> OTHER INFORMATION: Synthetic

<400> SEQUENCE: 30

| | |
|---|---|
| atgaagcgca actacatcct cggactggac atcggcatta cctccgtggg atacggcatc | 60 |
| atcgattacg aaactaggga tgtgatcgac gctggagtca ggctgttcaa agaggcgaac | 120 |
| gtggagaaca cgaggggcg cgctcaaag aggggggccc gccggctgaa gcgccgccgc | 180 |
| agacatagaa tccagcgcgt gaagaagctg ctgttcgact acaaccttct gaccgaccac | 240 |
| tccgaacttt ccggcatcaa cccatatgag gctagagtga agggattgtc ccaaaagctg | 300 |
| tccgaggaag agttctccgc cgcgttgctc cacctcgcca gcgcagggg agtgcacaat | 360 |
| gtgaacgaag tggaagaaga taccggaaac gagctgtcca ccaaggagca gatcagccgg | 420 |
| aactccaagg ccctggaaga gaaatacgtg gcggaactgc aactggagcg gctgaagaaa | 480 |
| gacgagaag tgcgcggctc gatcaaccgc ttcaagacct cggactacgt gaaggaggcc | 540 |
| aagcagctcc tgaaagtgca aaaggcctat accaacttg accagtcctt tatcgatacc | 600 |

```
tacatcgatc tgctcgagac tcggcggact tactacgagg gtccagggga gggctcccca    660
tttggttgga aggatattaa ggagtggtac gaaatgctga tgggacactg cacatacttc    720
cctgaggagc tgcggagcgt gaaatacgca tacaacgcag acctgtacaa cgcgctgaac    780
gacctgaaca atctcgtgat cacccgggac gagaacgaaa agctcgagta ttacgaaaag    840
ttccagatta ttgagaacgt gttcaaacag aagaagaagc cgacactgaa gcagattgcc    900
aaggaaatcc tcgtgaacga agaggacatc aagggctatc gagtgacctc aacgggaaag    960
ccggagttca ccaatctgaa ggtctaccac gacatcaaag acattaccgc ccggaaggag   1020
atcattgaga acgcggagct gttggaccag attgcgaaga ttctgaccat ctaccaatcc   1080
tccgaggata ttcaggaaga actcaccaac ctcaacagcg aactgaccca ggaggagata   1140
gagcaaatct ccaacctgaa gggctacacc ggaactcata acctgagcct gaaggccatc   1200
aacttgatcc tggacgagct gtggcacacc aacgataacc agatcgctat tttcaatcgg   1260
ctgaagctgg tccccaagaa agtggacctc tcacaacaaa aggagatccc tactacccct   1320
gtggacgatt tcattctgtc ccccgtggtc aagagaagct tcatacagtc aatcaaagtg   1380
atcaatgcca ttatcaagaa atacggtctg cccaacgaca ttatcattga gctcgcccgc   1440
gagaagaact cgaaggacgc ccagaagatg attaacgaaa tgcagaagag gaaccgacag   1500
actaacgaac ggatcgaaga aatcatccgg accaccggga aggaaaacgc gaagtacctg   1560
atcgaaaaga tcaagctcca tgacatgcag gaaggaaagt gtctgtactc gctggaggcc   1620
attccgctgg aggacttgct gaacaaccct tttaactacg aagtggatca tatcattccg   1680
aggagcgtgt cattcgacaa ttccttcaac aacaaggtcc tcgtgaagca ggaggaaaac   1740
tcgaagaagg gaaaccgcac gccgttccag tacctgagca gcagcgactc caagatttcc   1800
tacgaaacct tcaagaagca catcctcaac ctggcaaagg ggaagggtcg catctccaag   1860
accaagaagg aatatctgct ggaagaaaga gacatcaaca gattctccgt gcaaaaggac   1920
ttcatcaacc gcaacctcgt ggatactaga tacgctactc ggggtctgat gaacctcctg   1980
agaagctact ttagagtgaa caatctggac gtgaaggtca agtcgattaa cggaggtttc   2040
acctccttcc tgcggcgcaa gtggaagttc aagaaggaac ggaacaaggg ctacaagcac   2100
cacgccgagg acgccctgat cattgccaac gccgacttca tcttcaaaga atggaagaaa   2160
cttgacaagg ctaagaaggt catggaaaac cagatgttcg aagaaaagca ggccgagtct   2220
atgcctgaaa tcgagactga acaggagtac aaggaaatct ttattacgcc acaccagatc   2280
aaacacatca aggatttcaa ggattacaag tactcacatc gcgtggacaa aaagccgaac   2340
agggaactga tcaacgacac cctctactcc acccggaagg atgacaaagg gaataccctc   2400
atcgtcaaca accttaacgg cctgtacgac aaggacaacg ataagctgaa gaagctcatt   2460
aacaagtcgc ccgaaaagtt gctgatgtac caccacgacc ctcagactta ccagaagctc   2520
aagctgatca tggagcagta tgggacgag aaaaacccgt tgtacaagta ctacgaagaa   2580
actgggaatt atctgactaa gtactccaag aaaagataacg gccccgtgat taagaagatt   2640
aagtactacg gcaacaagct gaacgcccat ctggacatca ccgatgacta ccctaattcc   2700
cgcaacaagg tcgtcaagct gagcctcaag ccctaccggt tgatgtgta ccttgacaat   2760 ggagtgtaca agttcgtgac tgtgaagaac cttgacgtga tcaagaagga aactactac   2820 gaagtcaact ccagtgctca cgaggaagca aagaagttga agaagatctc gaaccaggcc   2880
gagttcattg cctccttcta taacaacgac ctgattaaga tcaacggcga actgtaccgc   2940
```

```
gtcattggcg tgaacaacga tctcctgaac cgcatcgaag tgaacatgat cgacatcact   3000
taccgggaat acctggagaa tatgaacgac aagcgcccgc cccggatcat taagactatc   3060
gcctcaaaga cccagtcgat caagaagtac agcaccgaca tcctgggcaa cctgtacgag   3120
gtcaaatcga agaagcaccc ccagatcatc aagaaggga                          3159
```

<210> SEQ ID NO 31
<211> LENGTH: 3255
<212> TYPE: DNA
<213> ORGANISM: Artificial sequence
<220> FEATURE:
<223> OTHER INFORMATION: Synthetic

<400> SEQUENCE: 31

```
atggccccaa agaagaagcg gaaggtcggt atccacggag tcccagcagc caagcggaac     60
tacatcctgg gcctggacat cggcatcacc agcgtgggct acggcatcat cgactacgag    120
acacgggacg tgatcgatgc cggcgtgcgg ctgttcaaag aggccaacgt ggaaaacaac    180
gagggcaggc ggagcaagag aggcgccaga aggctgaagc ggcggaggcg catagaatc    240 cagagagtga agaagctgct gttcgactac aacctgctga ccgaccacag cgagctgagc    300
ggcatcaacc cctacgaggc cagagtgaag ggcctgagcc agaagctgag cgaggaagag    360
ttctctgccg ccctgctgca cctggccaag agaagaggcg tgcacaacgt gaacgaggtg    420
gaagaggaca ccggcaacga gctgtccacc agagagcaga tcagccggaa cagcaaggcc    480
ctggaagaga atacgtggc cgaactgcag ctggaacggc tgaagaaaga cggcgaagtg    540
cggggcagca tcaacagatt caagaccagc gactacgtga agaagccaa acagctgctg    600 aaggtgcaga aggcctacca ccagctggac cagagcttca tcgacaccta catcgacctg    660
ctggaaaccc ggcggaccta ctatgaggga cctggcgagg cagccccctt cggctggaag    720
gacatcaaag aatggtacga gatgctgatg ggccactgca cctacttccc cgaggaactg    780
cggagcgtga gtacgccta caacgccgac ctgtacaacg ccctgaacga cctgaacaat    840
ctcgtgatca ccagggacga gaacgagaag ctggaatatt acgagaagtt ccagatcatc    900
gagaacgtgt tcaagcagaa gaagaagccc accctgaagc agatcgccaa agaaatcctc    960
gtgaacgaag aggatattaa ggctacaga gtgaccagca ccggcaagcc cgagttcacc   1020
aacctgaagg tgtaccacga catcaaggac attaccgccc ggaaagagat tattgagaac   1080
gccgagctgc tggatcagat tgccaagatc ctgaccatct accagagcag cgaggacatc   1140
caggaagaac tgaccaatct gaactccgag ctgacccagg aagagatcga gcagatctct   1200
aatctgaagg gctataccgg cacccacaac ctgagcctga aggccatcaa cctgatcctg   1260
gacgagctgt ggcacaccaa cgacaaccag atcgctatct tcaaccggct gaagctggtg   1320
cccaagaagg tggacctgtc ccagcagaaa gagatcccca ccaccctggt ggacgacttc   1380
atcctgagcc ccgtcgtgaa gagaagcttc atccagagca tcaaagtgat caacgccatc   1440
atcaagaagt acggcctgcc caacgacatc attatcgagc tggcccgcga gaagaactcc   1500
aaggacgccc agaaaatgat caacgagatg cagaagcgga accggcagac aacgagcgg   1560 atcgaggaaa tcatccggac caccggcaaa gagaacgcca gtacctgat cgagaagatc   1620 aagctgcacg acatgcagga aggcaagtgc ctgtacagcc tggaagccat ccctctggaa   1680
gatctgctga acaaccccct taactatgag gtggaccaca tcatcccag aagcgtgtcc   1740 ttcgacaaca gcttcaacaa caaggtgctc gtgaagcagg aagaaaacag caagaagggc   1800
aaccggaccc cattccagta cctgagcagc agcgacagca agatcagcta cgaaaccttc   1860
```

| | | |
|---|---|---|
| aagaagcaca tcctgaatct ggccaagggc aagggcagaa tcagcaagac caagaaagag | 1920 | |
| tatctgctgg aagaacggga catcaacagg ttctccgtgc agaaagactt catcaaccgg | 1980 | |
| aacctggtgg ataccagata cgccaccaga ggcctgatga acctgctgcg gagctacttc | 2040 | |
| agagtgaaca acctggacgt gaaagtgaag tccatcaatg gcggcttcac cagctttctg | 2100 | |
| cggcggaagt ggaagtttaa gaaagagcgg aacaaggggt acaagcacca cgccgaggac | 2160 | |
| gccctgatca ttgccaacgc cgatttcatc ttcaaagagt ggaagaaact ggacaaggcc | 2220 | |
| aaaaagtga tggaaaacca gatgttcgag gaaaggcagg ccgagagcat gcccgagatc | 2280 | |
| gaaaccgagc aggagtacaa agagatcttc atcaccccc accagatcaa gcacattaag | 2340 | |
| gacttcaagg actacaagta cagccaccgg gtggacaaga agcctaatag agagctgatt | 2400 | |
| aacgacaccc tgtactccac ccggaaggac gacaagggca cacccctgat cgtgaacaat | 2460 | |
| ctgaacggcc tgtacgacaa ggacaatgac aagctgaaaa agctgatcaa caagagcccc | 2520 | |
| gaaaagctgc tgatgtacca ccacgacccc cagacctacc agaaactgaa gctgattatg | 2580 | |
| gaacagtacg gcgacgagaa gaatcccctg tacaagtact acgaggaaac cgggaactac | 2640 | |
| ctgaccaagt actccaaaaa ggacaacggc cccgtgatca agaagattaa gtattacggc | 2700 | |
| aacaaactga acgcccatct ggacatcacc gacgactacc ccaacagcag aaacaaggtc | 2760 | |
| gtgaagctgt ccctgaagcc ctacagattc gacgtgtacc tggacaatgg cgtgtacaag | 2820 | |
| ttcgtgaccg tgaagaatct ggatgtgatc aaaaagaaa actactacga agtgaatagc | 2880 | |
| aagtgctatg aggaagctaa gaagctgaag aagatcagca accaggccga gtttatcgcc | 2940 | |
| tccttctaca caacgatct gatcaagatc aacggcgagc tgtatagagt gatcggcgtg | 3000 | |
| aacaacgacc tgctgaaccg gatcgaagtg aacatgatcg acatcaccta ccgcgagtac | 3060 | |
| ctggaaaaca tgaacgacaa gaggcccccc aggatcatta agacaatcgc ctccaagacc | 3120 | |
| cagagcatta agaagtacag cacagacatt ctgggcaacc tgtatgaagt gaaatctaag | 3180 | |
| aagcaccctc agatcatcaa aaagggcaaa aggccggcgg ccacgaaaaa ggccggccag | 3240 | |
| gcaaaaaaga aaaag | 3255 | |

<210> SEQ ID NO 32
<211> LENGTH: 3242
<212> TYPE: DNA
<213> ORGANISM: Artificial sequence
<220> FEATURE:
<223> OTHER INFORMATION: Synthetic

<400> SEQUENCE: 32

| | | |
|---|---|---|
| accggtgcca ccatgtaccc atacgatgtt ccagattacg cttcgccgaa gaaaaagcgc | 60 | |
| aaggtcgaag cgtccatgaa aaggaactac attctggggc tggacatcgg gattacaagc | 120 | |
| gtggggtatg ggattattga ctatgaaaca agggacgtga tcgacgcagg cgtcagactg | 180 | |
| ttcaaggagg ccaacgtgga aaacaatgag ggacggagaa gcaagagggg agccaggcgc | 240 | |
| ctgaaacgac ggagaaggca cagaatccag agggtgaaga aactgctgtt cgattacaac | 300 | |
| ctgctgaccg accattctga gctgagtgga attaatcctt atgaagccag ggtgaaaggc | 360 | |
| ctgagtcaga agctgtcaga ggaagagttt tccgcagctc tgctgcacct ggctaagcgc | 420 | |
| cgaggagtgc ataacgtcaa tgaggtggaa gaggacaccg gcaacgagct gtctacaaag | 480 | |
| gaacagatct cacgcaatag caaagctctg gaagagaagt atgtcgcaga gctgcagctg | 540 | |
| gaacggctga agaaagatgg cgaggtgaga gggtcaatta ataggttcaa gacaagcgac | 600 | |

```
tacgtcaaag aagccaagca gctgctgaaa gtgcagaagg cttaccacca gctggatcag    660
agcttcatcg atacttatat cgacctgctg gagactcgga gaacctacta tgagggacca    720
ggagaaggga gccccttcgg atggaaagac atcaaggaat ggtacgagat gctgatggga    780
cattgcacct attttccaga gagctgaga agcgtcaagt acgcttataa cgcagatctt    840
acaacgccct gaatgacctg aacaacctgg tcatcaccag ggatgaaaac gagaaactgg    900
aatactatga gaagttccag atcatcgaaa acgtgtttaa gcagaagaaa aagcctacac    960
tgaaacagat tgctaaggag atcctggtca acgaagagga catcaagggc taccgggtga   1020
caagcactgg aaaaccagag ttcaccaatc tgaaagtgta tcacgatatt aaggacatca   1080
cagcacggaa agaaatcatt gagaacgccg aactgctgga tcagattgct aagatcctga   1140
ctatctacca gagctccgag gacatccagg aagagctgac taacctgaac agcgagctga   1200
cccaggaaga gatcgaacag attagtaatc tgaaggggta caccggaaca cacaacctgt   1260
ccctgaaagc tatcaatctg attctggatg agctgtggca tacaaacgac aatcagattg   1320
caatctttaa ccggctgaag ctggtcccaa aaaaggtgga cctgagtcag cagaaagaga   1380
tcccaaccac actggtggac gatttcattc tgtcacccgt ggtcaagcgg agcttcatcc   1440
agagcatcaa agtgatcaac gccatcatca agaagtacgg cctgcccaat gatatcatta   1500
tcgagctggc tagggagaag aacagcaagg acgcacagaa gatgatcaat gagatgcaga   1560
aacgaaaccg gcagaccaat gaacgcattg aagagattat ccgaactacc gggaagagaa   1620
acgcaaagta cctgattgaa aaaatcaagc tgcacgatat gcaggaggga aagtgtctgt   1680
attctctgga ggccatcccc ctggaggacc tgctgaacaa tccattcaac tacgaggtcg   1740
atcatattat ccccagaagc gtgtccttcg acaattcctt taacaacaag gtgctggtca   1800
agcaggaaga gaactctaaa aagggcaata ggactccttt ccagtacctg tctagttcag   1860
attccaagat ctcttacgaa acctttaaaa agcacattct gaatctggcc aaaggaaagg   1920
gccgcatcag caagaccaaa aaggagtacc tgctggaaga gcgggacatc aacagattct   1980
ccgtccagaa ggatttttatt aaccggaatc tggtggacac aagatacgct actcgcggcc   2040
tgatgaatct gctgcgatcc tatttccggg tgaacaatct ggatgtgaaa gtcaagtcca   2100
tcaacggcgg gttcacatct tttctgaggc gcaaatggaa gtttaaaaag gagcgcaaca   2160
aagggtacaa gcaccatgcc gaagatgctc tgattatcgc aaatgccgac ttcatcttta   2220
aggagtggaa aaagctggac aaagccaaga agtgatggga gaaccagatg ttcgaagaga   2280
agcaggccga atctatgccc gaaatcgaga cagaacagga gtacaaggag atttcatca   2340 ctcctcacca gatcaagcat atcaaggatt tcaaggacta caagtactct caccgggtgg   2400
ataaaaagcc caacagagag ctgatcaatg acaccctgta tagtacaaga aaagacgata   2460
aggggaatac cctgattgtg aacaatctga acggactgta cgacaaagat aatgacaagc   2520
tgaaaaagct gatcaacaaa agtcccgaga gctgctgat gtaccaccat gatcctcaga   2580
catatcagaa actgaagctg attatggagc agtacggcga cgagaagaac ccactgtata   2640
agtactatga agagactggg aactacctga ccaagtatag caaaaaggat aatggccccg   2700
tgatcaagaa gatcaagtac tatgggaaca agctgaatgc ccatctggac atcacagacg   2760
attaccctaa cagtcgcaac aaggtggtca agctgtcact gaagccatac agattcgatg   2820
tctatctgga caacggcgtg tataaatttg tgactgtcaa gaatctggat gtcatcaaaa   2880
aggagaacta ctatgaagtg aatagcaagt gctacgaaga ggctaaaaag ctgaaaaaga   2940
ttagcaacca ggcagagttc atcgcctcct tttacaacaa cgacctgatt aagatcaatg   3000
```

```
gcgaactgta tagggtcatc ggggtgaaca atgatctgct gaaccgcatt gaagtgaata    3060
tgattgacat cacttaccga gagtatctgg aaaacatgaa tgataagcgc ccccctcgaa    3120
ttatcaaaac aattgcctct aagactcaga gtatcaaaaa gtactcaacc gacattctgg    3180
gaaacctgta tgaggtgaag agcaaaaagc accctcagat tatcaaaaag ggctaagaat    3240
tc                                                                  3242
```

<210> SEQ ID NO 33
<211> LENGTH: 1053
<212> TYPE: PRT
<213> ORGANISM: Artificial sequence
<220> FEATURE:
<223> OTHER INFORMATION: Synthetic

<400> SEQUENCE: 33

```
Met Lys Arg Asn Tyr Ile Leu Gly Leu Asp Ile Gly Ile Thr Ser Val
1               5                   10                  15

Gly Tyr Gly Ile Ile Asp Tyr Glu Thr Arg Asp Val Ile Asp Ala Gly
            20                  25                  30

Val Arg Leu Phe Lys Glu Ala Asn Val Glu Asn Asn Glu Gly Arg Arg
        35                  40                  45

Ser Lys Arg Gly Ala Arg Arg Leu Lys Arg Arg Arg His Arg Ile
    50                  55                  60

Gln Arg Val Lys Lys Leu Leu Phe Asp Tyr Asn Leu Leu Thr Asp His
65                  70                  75                  80

Ser Glu Leu Ser Gly Ile Asn Pro Tyr Glu Ala Arg Val Lys Gly Leu
                85                  90                  95

Ser Gln Lys Leu Ser Glu Glu Phe Ser Ala Ala Leu Leu His Leu
            100                 105                 110

Ala Lys Arg Arg Gly Val His Asn Val Asn Glu Val Glu Glu Asp Thr
        115                 120                 125

Gly Asn Glu Leu Ser Thr Lys Glu Gln Ile Ser Arg Asn Ser Lys Ala
    130                 135                 140

Leu Glu Glu Lys Tyr Val Ala Glu Leu Gln Leu Glu Arg Leu Lys Lys
145                 150                 155                 160

Asp Gly Glu Val Arg Gly Ser Ile Asn Arg Phe Lys Thr Ser Asp Tyr
                165                 170                 175

Val Lys Glu Ala Lys Gln Leu Leu Lys Val Gln Lys Ala Tyr His Gln
            180                 185                 190

Leu Asp Gln Ser Phe Ile Asp Thr Tyr Ile Asp Leu Leu Glu Thr Arg
        195                 200                 205

Arg Thr Tyr Tyr Glu Gly Pro Gly Glu Gly Ser Pro Phe Gly Trp Lys
    210                 215                 220

Asp Ile Lys Glu Trp Tyr Glu Met Leu Met Gly His Cys Thr Tyr Phe
225                 230                 235                 240

Pro Glu Glu Leu Arg Ser Val Lys Tyr Ala Tyr Asn Ala Asp Leu Tyr
                245                 250                 255

Asn Ala Leu Asn Asp Leu Asn Asn Leu Val Ile Thr Arg Asp Glu Asn
            260                 265                 270

Glu Lys Leu Glu Tyr Tyr Glu Lys Phe Gln Ile Ile Glu Asn Val Phe
        275                 280                 285

Lys Gln Lys Lys Lys Pro Thr Leu Lys Gln Ile Ala Lys Glu Ile Leu
    290                 295                 300

Val Asn Glu Glu Asp Ile Lys Gly Tyr Arg Val Thr Ser Thr Gly Lys
```

-continued

```
            305                 310                 315                 320
        Pro Glu Phe Thr Asn Leu Lys Val Tyr His Asp Ile Lys Asp Ile Thr
                        325                 330                 335
        Ala Arg Lys Glu Ile Ile Glu Asn Ala Glu Leu Leu Asp Gln Ile Ala
                        340                 345                 350
        Lys Ile Leu Thr Ile Tyr Gln Ser Ser Glu Asp Ile Gln Glu Glu Leu
                        355                 360                 365
        Thr Asn Leu Asn Ser Glu Leu Thr Gln Glu Glu Ile Glu Gln Ile Ser
        370                 375                 380
        Asn Leu Lys Gly Tyr Thr Gly Thr His Asn Leu Ser Leu Lys Ala Ile
        385                 390                 395                 400
        Asn Leu Ile Leu Asp Glu Leu Trp His Thr Asn Asp Asn Gln Ile Ala
                        405                 410                 415
        Ile Phe Asn Arg Leu Lys Leu Val Pro Lys Lys Val Asp Leu Ser Gln
                        420                 425                 430
        Gln Lys Glu Ile Pro Thr Thr Leu Val Asp Asp Phe Ile Leu Ser Pro
                        435                 440                 445
        Val Val Lys Arg Ser Phe Ile Gln Ser Ile Lys Val Ile Asn Ala Ile
                        450                 455                 460
        Ile Lys Lys Tyr Gly Leu Pro Asn Asp Ile Ile Glu Leu Ala Arg
        465                 470                 475                 480
        Glu Lys Asn Ser Lys Asp Ala Gln Lys Met Ile Asn Glu Met Gln Lys
                        485                 490                 495
        Arg Asn Arg Gln Thr Asn Glu Arg Ile Glu Glu Ile Ile Arg Thr Thr
                        500                 505                 510
        Gly Lys Glu Asn Ala Lys Tyr Leu Ile Glu Lys Ile Lys Leu His Asp
                        515                 520                 525
        Met Gln Glu Gly Lys Cys Leu Tyr Ser Leu Glu Ala Ile Pro Leu Glu
                        530                 535                 540
        Asp Leu Leu Asn Asn Pro Phe Asn Tyr Glu Val Asp His Ile Ile Pro
        545                 550                 555                 560
        Arg Ser Val Ser Phe Asp Asn Ser Phe Asn Asn Lys Val Leu Val Lys
                        565                 570                 575
        Gln Glu Glu Asn Ser Lys Lys Gly Asn Arg Thr Pro Phe Gln Tyr Leu
                        580                 585                 590
        Ser Ser Ser Asp Ser Lys Ile Ser Tyr Glu Thr Phe Lys Lys His Ile
                        595                 600                 605
        Leu Asn Leu Ala Lys Gly Lys Gly Arg Ile Ser Lys Thr Lys Lys Glu
        610                 615                 620
        Tyr Leu Leu Glu Glu Arg Asp Ile Asn Arg Phe Ser Val Gln Lys Asp
        625                 630                 635                 640
        Phe Ile Asn Arg Asn Leu Val Asp Thr Arg Tyr Ala Thr Arg Gly Leu
                        645                 650                 655
        Met Asn Leu Leu Arg Ser Tyr Phe Arg Val Asn Asn Leu Asp Val Lys
                        660                 665                 670
        Val Lys Ser Ile Asn Gly Gly Phe Thr Ser Phe Leu Arg Arg Lys Trp
                        675                 680                 685
        Lys Phe Lys Lys Glu Arg Asn Lys Gly Tyr Lys His His Ala Glu Asp
                        690                 695                 700
        Ala Leu Ile Ile Ala Asn Ala Asp Phe Ile Phe Lys Glu Trp Lys Lys
        705                 710                 715                 720
        Leu Asp Lys Ala Lys Lys Val Met Glu Asn Gln Met Phe Glu Glu Lys
                        725                 730                 735
```

Gln Ala Glu Ser Met Pro Glu Ile Glu Thr Glu Gln Glu Tyr Lys Glu
        740                 745                 750

Ile Phe Ile Thr Pro His Gln Ile Lys His Ile Lys Asp Phe Lys Asp
        755                 760                 765

Tyr Lys Tyr Ser His Arg Val Asp Lys Pro Asn Arg Glu Leu Ile
770                 775                 780

Asn Asp Thr Leu Tyr Ser Thr Arg Lys Asp Lys Gly Asn Thr Leu
785                 790                 795                 800

Ile Val Asn Asn Leu Asn Gly Leu Tyr Asp Lys Asp Asn Asp Lys Leu
                805                 810                 815

Lys Lys Leu Ile Asn Lys Ser Pro Glu Lys Leu Leu Met Tyr His His
                820                 825                 830

Asp Pro Gln Thr Tyr Gln Lys Leu Lys Leu Ile Met Glu Gln Tyr Gly
                835                 840                 845

Asp Glu Lys Asn Pro Leu Tyr Lys Tyr Glu Glu Thr Gly Asn Tyr
850                 855                 860

Leu Thr Lys Tyr Ser Lys Lys Asp Asn Gly Pro Val Ile Lys Lys Ile
865                 870                 875                 880

Lys Tyr Tyr Gly Asn Lys Leu Asn Ala His Leu Asp Ile Thr Asp Asp
                885                 890                 895

Tyr Pro Asn Ser Arg Asn Lys Val Val Lys Leu Ser Leu Lys Pro Tyr
                900                 905                 910

Arg Phe Asp Val Tyr Leu Asp Asn Gly Val Tyr Lys Phe Val Thr Val
                915                 920                 925

Lys Asn Leu Asp Val Ile Lys Lys Glu Asn Tyr Tyr Glu Val Asn Ser
930                 935                 940

Lys Cys Tyr Glu Glu Ala Lys Lys Leu Lys Lys Ile Ser Asn Gln Ala
945                 950                 955                 960

Glu Phe Ile Ala Ser Phe Tyr Asn Asn Asp Leu Ile Lys Ile Asn Gly
                965                 970                 975

Glu Leu Tyr Arg Val Ile Gly Val Asn Asn Asp Leu Leu Asn Arg Ile
                980                 985                 990

Glu Val Asn Met Ile Asp Ile Thr Tyr Arg Glu Tyr Leu Glu Asn Met
                995                 1000                1005

Asn Asp Lys Arg Pro Pro Arg Ile Ile Lys Thr Ile Ala Ser Lys
        1010                1015                1020

Thr Gln Ser Ile Lys Lys Tyr Ser Thr Asp Ile Leu Gly Asn Leu
        1025                1030                1035

Tyr Glu Val Lys Ser Lys Lys His Pro Gln Ile Ile Lys Lys Gly
        1040                1045                1050

<210> SEQ ID NO 34
<211> LENGTH: 3159
<212> TYPE: DNA
<213> ORGANISM: Artificial sequence
<220> FEATURE:
<223> OTHER INFORMATION: Synthetic

<400> SEQUENCE: 34
atgaaaagga actacattct ggggctggcc atcgggatta caagcgtggg gtatgggatt      60
attgactatg aaacaaggga cgtgatcgac gcaggcgtca gactgttcaa ggaggccaac     120
gtggaaaaca atgagggacg gagaagcaag aggggagcca ggcgcctgaa acgacggaga     180
aggcacagaa tccagagggt gaagaaactg ctgttcgatt acaacctgct gaccgaccat     240

```
tctgagctga gtggaattaa tccttatgaa gccagggtga aaggcctgag tcagaagctg    300
tcagaggaag agttttccgc agctctgctg cacctggcta agcgccgagg agtgcataac    360
gtcaatgagg tggaagagga caccggcaac gagctgtcta caaaggaaca gatctcacgc    420
aatagcaaag ctctggaaga gaagtatgtc gcagagctgc agctgaacg gctgaagaaa    480 gatggcgagg tgagagggtc aattaatagg ttcaagacaa gcgactacgt caaagaagcc    540
aagcagctgc tgaaagtgca gaaggcttac caccagctgg atcagagctt catcgatact    600
tatatcgacc tgctggagac tcggagaacc tactatgagg accaggaga agggagcccc    660 ttcggatgga agacatcaa ggaatggtac gagatgctga tgggacattg cacctatttt    720
ccagaagagc tgagaagcgt caagtacgct tataacgcag atctgtacaa cgccctgaat    780
gacctgaaca acctggtcat caccagggat gaaaacgaga actggaata ctatgagaag    840 ttccagatca tcgaaaacgt gtttaagcag aagaaaaagc ctacactgaa acagattgct    900
aaggagatcc tggtcaacga gaggacatc aagggctacc gggtgacaag cactggaaaa    960
ccagagttca ccaatctgaa agtgtatcac gatattaagg acatcacagc acggaaagaa   1020
atcattgaga acgccgaact gctggatcag attgctaaga tcctgactat ctaccagagc   1080
tccgaggaca tccaggaaga gctgactaac ctgaacagcg agctgaccca ggaagagatc   1140
gaacagatta gtaatctgaa ggggtacacc ggaacacaca acctgtccct gaaagctatc   1200
aatctgattc tggatgagct gtggcataca acgacaatc agattgcaat ctttaaccgg   1260
ctgaagctgg tcccaaaaaa ggtggacctg agtcagcaga agagatcccc aaccacactg   1320
gtggacgatt tcattctgtc acccgtggtc aagcggagct tcatccagag catcaaagtg   1380
atcaacgcca tcatcaagaa gtacggcctg cccaatgata tcattatcga gctggctagg   1440
gagaagaaca gcaaggacgc acagaagatg atcaatgaga tgcagaaacg aaaccggcag   1500
accaatgaac gcattgaaga gattatccga actaccggga agagaacgc aaagtacctg   1560 attgaaaaaa tcaagctgca cgatatgcag gagggaaagt gtctgtattc tctggaggcc   1620
atccccctgg aggacctgct gaacaatcca ttcaactacg aggtcgatca tattatcccc   1680
agaagcgtgt ccttcgacaa ttccctttaac aacaaggtgc tggtcaagca ggaagagaac   1740
tctaaaaagg gcaataggac tccctttccag tacctgtcta gttcagattc caagatctct   1800
tacgaaacct ttaaaagca cattctgaat ctggccaaag gaaagggccg catcagcaag   1860
accaaaaagg agtacctgct ggaagagcgg gacatcaaca gattctccgt ccagaaggat   1920
tttattaacc ggaatctggt ggacacaaga tacgctactc gcggcctgat gaatctgctg   1980
cgatcctatt tccgggtgaa caatctggat gtgaaagtca agtccatcaa cggcgggttc   2040
acatcttttc tgaggcgcaa atggaagttt aaaaaggagc gcaacaaagg gtacaagcac   2100
catgccgaag atgctctgat tatcgcaaat gccgacttca tctttaagga gtggaaaaag   2160
ctggacaaag ccaagaaagt gatggagaac cagatgttcg aagagaagca ggccgaatct   2220
atgcccgaaa tcgagacaga acaggagtac aaggagattt tcatcactcc tcaccagatc   2280
aagcatatca aggatttcaa ggactacaag tactctcacc gggtggataa aaagcccaac   2340
agagagctga tcaatgacac cctgtatagt acaagaaaag acgataaggg gaatacctg   2400 attgtgaaca atctgaacgg actgtacgac aaagataatg acaagctgaa aaagctgatc   2460
aacaaaagtc ccgagaagct gctgatgtac caccatgatc ctcagacata tcagaaactg   2520
aagctgatta tggagcagta cggcgacgag aagaacccac tgtataagta ctatgaagag   2580
actgggaact acctgaccaa gtatagcaaa aaggataatg gccccgtgat caagaagatc   2640
```

```
aagtactatg ggaacaagct gaatgcccat ctggacatca cagacgatta ccctaacagt    2700
cgcaacaagg tggtcaagct gtcactgaag ccatacagat tcgatgtcta tctggacaac    2760
ggcgtgtata aatttgtgac tgtcaagaat ctggatgtca tcaaaaagga gaactactat    2820
gaagtgaata gcaagtgcta cgaagaggct aaaaagctga aaaagattag caaccaggca    2880
gagttcatcg cctccttta caacaacgac ctgattaaga tcaatggcga actgtatagg    2940
gtcatcgggg tgaacaatga tctgctgaac cgcattgaag tgaatatgat tgacatcact    3000
taccgagagt atctggaaaa catgaatgat aagcgccccc ctcgaattat caaaacaatt    3060
gcctctaaga ctcagagtat caaaaagtac tcaaccgaca ttctgggaaa cctgtatgag    3120
gtgaagagca aaaagcaccc tcagattatc aaaaagggc                          3159
```

<210> SEQ ID NO 35
<211> LENGTH: 3159
<212> TYPE: DNA
<213> ORGANISM: Artificial sequence
<220> FEATURE:
<223> OTHER INFORMATION: Synthetic

<400> SEQUENCE: 35

```
atgaaaagga actacattct ggggctggac atcgggatta caagcgtggg gtatgggatt      60
attgactatg aaacaaggga cgtgatcgac gcaggcgtca gactgttcaa ggaggccaac     120
gtggaaaaca atgagggacg gagaagcaag aggggagcca ggcgcctgaa cgacggaga     180 aggcacagaa tccagagggt gaagaaactg ctgttcgatt acaacctgct gaccgaccat     240
tctgagctga gtggaattaa tccttatgaa gccaggtgaa aaggcctgag tcagaagctg     300
tcagaggaag agttttccgc agctctgctg cacctggcta agcgccgagg agtgcataac     360
gtcaatgagg tggaagagga caccggcaac gagctgtcta caaggaaca gatctcacgc     420 aatagcaaag ctctggaaga agtatgtc gcagagctgc agctggaacg gctgaagaaa     480
gatggcgagg tgagagggtc aattaatagg ttcaagacaa gcgactacgt caaagaagcc     540
aagcagctgc tgaaagtgca gaaggcttac caccagctgg atcagagctt catcgatact     600
tatatcgacc tgctggagac tcggagaacc tactatgagg gaccaggaga agggagccccc     660 ttcggatgga agacatcaa ggaatggtac gagatgctga tgggacattg cacctattt      720 ccagaagagc tgagaagcgt caagtacgct ataacgcag atctgtacaa cgccctgaat     780
gacctgaaca acctggtcat caccagggat gaaaacgaga actggaata ctatgagaag     840 ttccagatca tcgaaaacgt gtttaagcag aagaaaagc ctacactgaa acagattgct     900
aaggagatcc tggtcaacga agaggacatc aagggctacc gggtgacaag cactggaaaa     960
ccagagttca ccaatctgaa agtgtatcac gatattaagg acatcacagc acggaaagaa    1020
atcattgaga acgccgaact gctggatcag attgctaaga tcctgactat ctaccagagc    1080
tccgaggaca tccaggaaga gctgactaac ctgaacagcg agctgaccca ggaagagatc    1140
gaacagatta gtaatctgaa ggggtacacc ggaacacaca acctgtccct gaaagctatc    1200
aatctgattc tggatgagct gtggcataca aacgacaatc agattgcaat ctttaaccgg    1260
ctgaagctgg tcccaaaaaa ggtggacctg agtcagcaga aagagatccc aaccacactg    1320
gtggacgatt tcattctgtc acccgtggtc aagcggagct tcatccagag catcaaagtg    1380
atcaacgcca tcatcaagaa gtacggcctg cccaatgata tcattatcga gctggctagg    1440
gagaagaaca gcaaggacgc acagaagatg atcaatgaga tgcagaaacg aaaccggcag    1500
```

```
accaatgaac gcattgaaga gattatccga actaccggga aagagaacgc aaagtacctg    1560
attgaaaaaa tcaagctgca cgatatgcag gagggaaagt gtctgtattc tctggaggcc    1620 atcccctgg aggacctgct gaacaatcca ttcaactacg aggtcgatca tattatcccc    1680
agaagcgtgt ccttcgacaa ttcctttaac aacaaggtgc tggtcaagca ggaagaggcc    1740
tctaaaaagg gcaataggac tcctttccag tacctgtcta gttcagattc caagatctct    1800
tacgaaacct ttaaaaagca cattctgaat ctggccaaag aaagggccg catcagcaag    1860 accaaaaagg agtacctgct ggaagagcgg gacatcaaca gattctccgt ccagaaggat    1920
tttattaacc ggaatctggt ggacacaaga tacgctactc gcggcctgat gaatctgctg    1980
cgatcctatt tccgggtgaa caatctggat gtgaaagtca agtccatcaa cggcgggttc    2040
acatcttttc tgaggcgcaa atggaagttt aaaaaggagc gcaacaaagg gtacaagcac    2100
catgccgaag atgctctgat tatcgcaaat gccgacttca tctttaagga gtggaaaaag    2160
ctggacaaag ccaagaaagt gatggagaac cagatgttcg aagagaagca ggccgaatct    2220
atgcccgaaa tcgagacaga acaggagtac aaggagattt tcatcactcc tcaccagatc    2280
aagcatatca aggatttcaa ggactacaag tactctcacc gggtggataa aaagcccaac    2340
agagagctga tcaatgacac cctgtatagt acaagaaaag acgataaggg gaataccctg    2400
attgtgaaca atctgaacgg actgtacgac aaagataatg acaagctgaa aaagctgatc    2460
aacaaaagtc ccgagaagct gctgatgtac caccatgatc ctcagacata tcagaaactg    2520
aagctgatta tggagcagta cggcgacgag aagaacccac tgtataagta ctatgaagag    2580
actgggaact acctgaccaa gtatagcaaa aaggataatg gccccgtgat caagaagatc    2640
aagtactatg gaacaagct gaatgcccat ctggacatca cagacgatta ccctaacagt    2700
cgcaacaagg tggtcaagct gtcactgaag ccatacagat cgatgtcta tctggacaac    2760 ggcgtgtata aatttgtgac tgtcaagaat ctggatgtca tcaaaaagga gaactactat    2820
gaagtgaata gcaagtgcta cgaagaggct aaaaagctga aaagattag caaccaggca    2880 gagttcatcg cctccttta caacaacgac ctgattaaga tcaatggcga actgtatagg    2940
gtcatcgggg tgaacaatga tctgctgaac cgcattgaag tgaatatgat tgacatcact    3000
taccgagagt atctggaaaa catgaatgat aagcgccccc tcgaattat caaaacaatt    3060 gcctctaaga ctcagagtat caaaaagtac tcaaccgaca ttctgggaaa cctgtatgag    3120
gtgaagagca aaaagcaccc tcagattatc aaaaagggc                          3159
```

<210> SEQ ID NO 36
<211> LENGTH: 5
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t

<400> SEQUENCE: 36 nggng                                                                   5

<210> SEQ ID NO 37
<211> LENGTH: 3238

```
<212> TYPE: DNA
<213> ORGANISM: Artificial sequence
<220> FEATURE:
<223> OTHER INFORMATION: Synthetic

<400> SEQUENCE: 37
ctaaattgta agcgttaata ttttgttaaa attcgcgtta aatttttgtt aaatcagctc      60
atttttaac  caataggccg aaatcggcaa atcccttat  aaatcaaaag aatagaccga     120
gatagggttg agtgttgttc cagtttggaa caagagtcca ctattaaaga acgtggactc     180
caacgtcaaa gggcgaaaaa ccgtctatca gggcgatggc ccactacgtg aaccatcacc    240
ctaatcaagt tttttggggt cgaggtgccg taaagcacta aatcggaacc ctaaagggag    300
cccccgattt agagcttgac ggggaaagcc ggcgaacgtg gcgagaaagg aagggaagaa    360
agcgaaagga gcgggcgcta gggcgctggc aagtgtagcg gtcacgctgc gcgtaaccac    420
cacacccgcc gcgcttaatg cgccgctaca gggcgcgtcc cattcgccat tcaggctgcg    480
caactgttgg gaagggcgat cggtgcgggc ctcttcgcta ttacgccagc tggcgaaagg    540
gggatgtgct gcaaggcgat taagttgggt aacgccaggg ttttcccagt cacgacgttg    600
taaaacgacg gccagtgagc gcgcgtaata cgactcacta tagggcgaat tgggtaccaa    660
gcttgcctat ttcccatgat tccttcatat ttgcatatac gatacaaggc tgttagagag    720
ataattggaa ttaatttgac tgtaaacaca agatattag  tacaaaatac gtgacgtaga    780
aagtaataat ttcttgggta gtttgcagtt ttaaaattat gttttaaaat ggactatcat    840
atgcttaccg taacttgaaa gtatttcgat tccttggctt tatatatctt gtggaaagga    900
cgaaacacca acacacagct gggttatcag aggttttagt actctggaaa cagaatctac    960
taaaacaagg caaaatgccg tgtttatctc gtcaacttgt tggcgagatt tttttgcggc   1020
cgcccgcggt ggagctccag cttttgttcc ctttagtgag ggttaattgc gcgcttggcg   1080
taatcatggt catagctgtt tcctgtgtga aattgttatc cgctcacaat tccacacaac   1140
atacgagccg gaagcataaa gtgtaaagcc tggggtgcct aatgagtgag ctaactcaca   1200
ttaattgcgt tgcgctcact gcccgctttc cagtcgggaa acctgtcgtg ccagctgcat   1260
taatgaatcg gccaacgcgc ggggagaggc ggtttgcgta ttgggcgctc ttccgcttcc   1320
tcgctcactg actcgctgcg ctcggtcgtt cggctgcggc gagcggtatc agctcactca   1380
aaggcggtaa tacggttatc cacagaatca ggggataacg caggaaagaa catgtgagca   1440
aaaggccagc aaaaggccag gaaccgtaaa aaggccgcgt tgctggcgtt tttccatagg   1500
ctccgccccc ctgacgagca tcacaaaaat cgacgctcaa gtcagaggtg gcgaaacccg   1560
acaggactat aaagatacca ggcgtttccc cctggaagct ccctcgtgcg ctctcctgtt   1620
ccgaccctgc cgcttaccgg atacctgtcc gcctttctcc cttcgggaag cgtggcgctt   1680
tctcatagct cacgctgtag gtatctcagt tcggtgtagg tcgttcgctc caagctgggc   1740
tgtgtgcacg aaccccccgt tcagcccgac cgctgcgcct tatccggtaa ctatcgtctt   1800
gagtccaacc cggtaagaca cgacttatcg ccactggcag cagccactgg taacaggatt   1860
agcagagcga ggtatgtagg cggtgctaca gagttcttga agtggtggcc taactacggc   1920
tacactagaa ggacagtatt tggtatctgc gctctgctga agccagttac cttcggaaaa   1980
agagttggta gctcttgatc cggcaaacaa accaccgctg gtagcggtgg ttttttgtt   2040
tgcaagcagc agattacgcg cagaaaaaaa ggatctcaag aagatccttt gatcttttct   2100
acggggtctg acgctcagtg gaacgaaaac tcacgttaag ggattttggt catgagatta   2160
```

| | |
|---|---:|
| tcaaaaagga tcttcaccta gatccttttta aattaaaaat gaagttttaa atcaatctaa | 2220 |
| agtatatatg agtaaacttg gtctgacagt taccaatgct taatcagtga ggcacctatc | 2280 |
| tcagcgatct gtctatttcg ttcatccata gttgcctgac tccccgtcgt gtagataact | 2340 |
| acgatacggg agggcttacc atctggcccc agtgctgcaa tgataccgcg agacccacgc | 2400 |
| tcaccggctc cagatttatc agcaataaac cagccagccg aagggccga gcgcagaagt | 2460 |
| ggtcctgcaa ctttatccgc ctccatccag tctattaatt gttgccggga agctagagta | 2520 |
| agtagttcgc cagttaatag tttgcgcaac gttgttgcca ttgctacagg catcgtggtg | 2580 |
| tcacgctcgt cgtttggtat ggcttcattc agctccggtt cccaacgatc aaggcgagtt | 2640 |
| acatgatccc ccatgttgtg caaaaaagcg gttagctcct tcggtcctcc gatcgttgtc | 2700 |
| agaagtaagt tggccgcagt gttatcactc atggttatgg cagcactgca taattctctt | 2760 |
| actgtcatgc catccgtaag atgcttttct gtgactggtg agtactcaac caagtcattc | 2820 |
| tgagaatagt gtatgcggcg accgagttgc tcttgcccgg cgtcaatacg ggataatacc | 2880 |
| gcgccacata gcagaacttt aaaagtgctc atcattggaa aacgttcttc ggggcgaaaa | 2940 |
| ctctcaagga tcttaccgct gttgagatcc agttcgatgt aacccactcg tgcacccaac | 3000 |
| tgatcttcag catcttttac tttcaccagc gtttctgggt gagcaaaaac aggaaggcaa | 3060 |
| aatgccgcaa aaaagggaat aagggcgaca cggaaatgtt gaatactcat actcttcctt | 3120 |
| tttcaatatt attgaagcat ttatcagggt tattgtctca tgagcggata catatttgaa | 3180 |
| tgtatttaga aaaataaaca aataggggtt ccgcgcacat ttccccgaaa agtgccac | 3238 |

<210> SEQ ID NO 38
<211> LENGTH: 3238
<212> TYPE: DNA
<213> ORGANISM: Artificial sequence
<220> FEATURE:
<223> OTHER INFORMATION: Synthetic

<400> SEQUENCE: 38

| | |
|---|---:|
| ctaaattgta agcgttaata ttttgttaaa attcgcgtta aattttttgtt aaatcagctc | 60 |
| attttttaac caataggccg aaatcggcaa atcccttat aaatcaaaag aatagaccga | 120 |
| gatagggttg agtgttgttc cagtttggaa caagagtcca ctattaaaga acgtggactc | 180 |
| caacgtcaaa gggcgaaaaa ccgtctatca gggcgatggc ccactacgtg aaccatcacc | 240 |
| ctaatcaagt tttttggggt cgaggtgccg taaagcacta aatcggaacc ctaaagggag | 300 |
| cccccgattt agagcttgac ggggaaagcc ggcgaacgtg gcgagaaagg aagggaagaa | 360 |
| agcgaaagga gcgggcgcta gggcgctggc aagtgtagcg gtcacgctgc gcgtaaccac | 420 |
| cacacccgcc gcgcttaatg cgccgctaca gggcgcgtcc cattcgccat tcaggctgcg | 480 |
| caactgttgg gaagggcgat cggtgcgggc ctcttcgcta ttacgccagc tggcgaaagg | 540 |
| gggatgtgct gcaaggcgat taagttgggt aacgccaggg ttttcccagt cacgacgttg | 600 |
| taaaacgacg gccagtgagc gcgcgtaata cgactcacta tagggcgaat tgggtaccaa | 660 |
| gcttgcctat ttcccatgat tccttcatat ttgcatatac gatacaaggc tgttagagag | 720 |
| ataattggaa ttaatttgac tgtaaacaca aagatattag tacaaaatac gtgacgtaga | 780 |
| aagtaataat ttcttgggta gtttgcagtt ttaaaattat gttttaaaat ggactatcat | 840 |
| atgcttaccg taacttgaaa gtatttcgat ttcttggctt tatatatctt gtggaaagga | 900 |
| cgaaacacca gaactggtgg gaatggtct aggttttagt actctggaaa cagaatctac | 960 |
| taaaacaagg caaaatgccg tgtttatctc gtcaacttgt tggcgagatt ttttttgcggc | 1020 |

-continued

```
cgcccgcggt ggagctccag cttttgttcc ctttagtgag ggttaattgc gcgcttggcg    1080
taatcatggt catagctgtt tcctgtgtga aattgttatc cgctcacaat tccacacaac    1140
atacgagccg aagcataaa gtgtaaagcc tggggtgcct aatgagtgag ctaactcaca    1200
ttaattgcgt tgcgctcact gcccgctttc cagtcgggaa acctgtcgtg ccagctgcat    1260
taatgaatcg gccaacgcgc ggggagaggc ggtttgcgta ttgggcgctc ttccgcttcc    1320
tcgctcactg actcgctgcg ctcggtcgtt cggctgcggc gagcggtatc agctcactca    1380
aaggcggtaa tacggttatc cacagaatca ggggataacg caggaaagaa catgtgagca    1440
aaaggccagc aaaaggccag gaaccgtaaa aaggccgcgt tgctggcgtt tttccatagg    1500
ctccgccccc ctgacgagca tcacaaaaat cgacgctcaa gtcagaggtg gcgaaacccg    1560
acaggactat aaagatacca ggcgtttccc cctggaagct ccctcgtgcg ctctcctgtt    1620
ccgaccctgc cgcttaccgg atacctgtcc gcctttctcc cttcgggaag cgtggcgctt    1680
tctcatagct cacgctgtag gtatctcagt tcggtgtagg tcgttcgctc caagctgggc    1740
tgtgtgcacg aaccccccgt tcagcccgac cgctgcgcct tatccggtaa ctatcgtctt    1800
gagtccaacc cggtaagaca cgacttatcg ccactggcag cagccactgg taacaggatt    1860
agcagagcga ggtatgtagg cggtgctaca gagttcttga agtggtggcc taactacggc    1920
tacactagaa ggacagtatt tggtatctgc gctctgctga gccagttac cttcggaaaa    1980 agagttggta gctcttgatc cggcaaacaa accaccgctg gtagcggtgg tttttttgtt    2040
tgcaagcagc agattacgcg cagaaaaaaa ggatctcaag aagatccttt gatcttttct    2100
acggggtctg acgctcagtg gaacgaaaac tcacgttaag ggattttggt catgagatta    2160
tcaaaaagga tcttcaccta gatcctttta aattaaaaat gaagttttaa atcaatctaa    2220
agtatatatg agtaaacttg gtctgacagt taccaatgct taatcagtga ggcacctatc    2280
tcagcgatct gtctatttcg ttcatccata gttgcctgac tccccgtcgt gtagataact    2340
acgatacggg agggcttacc atctggcccc agtgctgcaa tgataccgcg agacccacgc    2400
tcaccggctc cagatttatc agcaataaac cagccagccg aagggccga gcgcagaagt    2460 ggtcctgcaa ctttatccgc ctccatccag tctattaatt gttgccggga agctagagta    2520
agtagttcgc cagttaatag tttgcgcaac gttgttgcca ttgctacagg catcgtggtg    2580
tcacgctcgt cgtttggtat ggcttcattc agctccggtt cccaacgatc aaggcgagtt    2640
acatgatccc ccatgttgtg caaaaaagcg gttagctcct tcggtcctcc gatcgttgtc    2700
agaagtaagt tggccgcagt gttatcactc atggttatgg cagcactgca taattctctt    2760
actgtcatgc catccgtaag atgcttttct gtgactggtg agtactcaac caagtcattc    2820
tgagaatagt gtatgcggcg accgagttgc tcttgcccgg cgtcaatacg ggataatacc    2880
gcgccacata gcagaacttt aaaagtgctc atcattggaa aacgttcttc ggggcgaaaa    2940
ctctcaagga tcttaccgct gttgagatcc agttcgatgt aacccactcg tgcacccaac    3000
tgatcttcag catcttttac tttcaccagc gtttctgggt gagcaaaaac aggaaggcaa    3060
aatgccgcaa aaaagggaat aagggcgaca cggaaatgtt gaatactcat actcttcctt    3120
tttcaatatt attgaagcat ttatcagggt tattgtctca tgagcggata catatttgaa    3180
tgtatttaga aaaataaaca ataggggtt ccgcgcacat ttccccgaaa agtgccac      3238
```

<210> SEQ ID NO 39
<211> LENGTH: 7450
<212> TYPE: DNA

<213> ORGANISM: Artificial sequence
<220> FEATURE:
<223> OTHER INFORMATION: Synthetic

<400> SEQUENCE: 39

```
cctgcaggca gctgcgcgct cgctcgctca ctgaggccgc ccgggcgtcg ggcgaccttt      60
ggtcgcccgg cctcagtgag cgagcgagcg cgcagagagg gagtggccaa ctccatcact     120
aggggttcct gcggcctcta gactcgaggc gttgacattg attattgact agttattaat     180
agtaatcaat tacggggtca ttagttcata gcccatatat ggagttccgc gttacataac     240
ttacggtaaa tggcccgcct ggctgaccgc ccaacgaccc ccgcccattg acgtcaataa     300
tgacgtatgt tcccatagta acgccaatag ggactttcca ttgacgtcaa tgggtggagt     360
atttacggta aactgcccac ttggcagtac atcaagtgta tcatatgcca agtacgcccc     420
ctattgacgt caatgacggt aaatggcccg cctggcatta tgcccagtac atgaccttat     480
gggactttcc tacttggcag tacatctacg tattagtcat cgctattacc atggtgatgc     540
ggttttggca gtacatcaat gggcgtggat agcggtttga ctcacgggga tttccaagtc     600
tccaccccat tgacgtcaat gggagtttgt tttggcacca aaatcaacgg gactttccaa     660
aatgtcgtaa caactccgcc ccattgacgc aaatgggcgg taggcgtgta cggtgggagg     720
tctatataag cagagctctc tggctaacta ccggtgccac catggcccca agaagaagc      780
ggaaggtcgg tatccacgga gtcccagcag ccaagcggaa ctacatcctg gcctggaca      840
tcggcatcac cagcgtgggc tacggcatca tcgactacga gacacgggac gtgatcgatg     900
ccggcgtgcg gctgttcaaa gaggccaacg tggaaaacaa cgagggcagg cggagcaaga     960
gaggcgccag aaggctgaag cggcggaggc ggcatagaat ccagagagtg aagaagctgc    1020
tgttcgacta caacctgctg accgaccaca gcgagctgag cggcatcaac ccctacgagg    1080
ccagagtgaa gggcctgagc cagaagctga gcgaggaaga gttctctgcc gccctgctgc    1140
acctggccaa gagaagaggc gtgcacaacg tgaacgaggt ggaagaggac accggcaacg    1200
agctgtccac caaagagcag atcagccgga acagcaaggc cctggaagag aaatacgtgg    1260
ccgaactgca gctggaacgg ctgaagaaag acggcgaagt gcggggcagc atcaacagat    1320
tcaagaccag cgactacgtg aaagaagcca acagctgct gaaggtgcag aaggcctacc     1380
accagctgga ccagagcttc atcgacacct acatcgacct gctggaaacc cggcggacct    1440
actatgaggg acctggcgag ggcagccct tcggctggaa ggacatcaaa gaatggtacg     1500
agatgctgat gggccactgc acctacttcc ccgaggaact cgcgagcgtg aagtacgcct     1560
acaacgccga cctgtacaac gccctgaacg acctgaacaa tctcgtgatc accagggacg    1620
agaacgagaa gctggaatat tacgagaagt tccagatcat cgagaacgtg ttcaagcaga    1680
agaagaagcc caccctgaag cagatcgcca agaaatcct cgtgaacgaa gaggatatta    1740
agggctacag agtgaccagc accggcaagc ccgagttcac caacctgaag gtgtaccacg    1800
acatcaagga cattaccgcc cggaaagaga ttattgagaa cgccgagctg ctggatcaga    1860
ttgccaagat cctgaccatc taccagagca gcgaggacat ccaggaagaa ctgaccaatc    1920
tgaactccga gctgacccag gaagagatcg agcagatctc taatctgaag ggctataccg    1980
gcacccacaa cctgagcctg aaggccatca acctgatcct ggacgagctg tggcacacca    2040
acgacaacca gatcgctatc ttcaaccggc tgaagctggt gcccaagaag gtggacctgt    2100
cccagcagaa agagatcccc accacctggt ggacgactt catcctgagc ccgtcgtga     2160
agagaagctt catccagagc atcaaagtga tcaacgccat catcaagaag tacggcctgc    2220
```

```
ccaacgacat cattatcgag ctggcccgcg agaagaactc caaggacgcc cagaaaatga    2280
tcaacgagat gcagaagcgg aaccggcaga ccaacgagcg gatcgaggaa atcatccgga    2340
ccaccggcaa agagaacgcc aagtacctga tcgagaagat caagctgcac gacatgcagg    2400
aaggcaagtg cctgtacagc ctggaagcca tccctctgga agatctgctg aacaacccct    2460
tcaactatga ggtggaccac atcatcccca gaagcgtgtc cttcgacaac agcttcaaca    2520
acaaggtgct cgtgaagcag gaagaaaaca gcaagaaggg caaccggacc ccattccagt    2580
acctgagcag cagcgacagc aagatcagct acgaaacctt caagaagcac atcctgaatc    2640
tggccaaggg caagggcaga atcagcaaga ccaagaaaga gtatctgctg gaagaacggg    2700
acatcaacag gttctccgtg cagaaagact tcatcaaccg gaacctggtg ataccagat     2760 acgccaccga aggcctgatg aacctgctgc ggagctactt cagagtgaac aacctggacg    2820
tgaaagtgaa gtccatcaat ggcggcttca ccagctttct gcggcggaag tggaagttta    2880
agaaagagcg gaacaagggg tacaagcacc acgccgagga cgccctgatc attgccaacg    2940
ccgatttcat cttcaaagag tggaagaaac tggacaaggc caaaaagtg atggaaaacc     3000 agatgttcga ggaaaagcag gccgagagca tgcccgagat cgaaaccgag caggagtaca    3060
aagagatctt catcacccccc caccagatca agcacattaa ggacttcaag gactacaagt    3120
acagccaccg ggtggacaag aagcctaata gagagctgat taacgacacc ctgtactcca    3180
cccggaagga cgacaagggc aacacccctga tcgtgaacaa tctgaacggc ctgtacgaca    3240
aggacaatga caagctgaaa aagctgatca acaagagccc cgaaaagctg ctgatgtacc    3300
accacgaccc ccagacctac cagaaactga agctgattat ggaacagtac ggcgacgaga    3360
agaatcccct gtacaagtac tacgaggaaa ccgggaacta cctgaccaag tactccaaaa    3420
aggacaacgg cccccgtgatc aagaagatta agtattacgg caacaaactg aacgcccatc    3480
tggacatcac cgacgactac cccaacagca gaaacaaggt cgtgaagctg tccctgaagc    3540
cctacagatt cgacgtgtac ctggacaatg gcgtgtacaa gttcgtgacc gtgaagaatc    3600
tggatgtgat caaaaaagaa aactactacg aagtgaatag caagtgctat gaggaagcta    3660
agaagctgaa gaagatcagc aaccaggccg agtttatcgc ctccttctac aacaacgatc    3720
tgatcaagat caacggcgag ctgtatagag tgatcggcgt gaacaacgac ctgctgaacc    3780
ggatcgaagt gaacatgatc gacatcacct accgcgagta cctggaaaac atgaacgaca    3840 agaggcccccc caggatcatt aagacaatcg cctccaagac ccagagcatt aagaagtaca    3900
gcacagacat tctgggcaac ctgtatgaag tgaaatctaa gaagcaccct cagatcatca    3960
aaaagggcaa aaggccggcg gccacgaaaa aggccggcca ggcaaaaaag aaaaagggat    4020
cctacccata cgatgttcca gattacgctt acccatacga tgttccagat acgcttacc    4080 catacgatgt tccagattac gcttaagaat cctagagct cgctgatcag cctcgactgt     4140
gccttctagt tgccagccat ctgttgtttg ccctccccc gtgccttcct tgacctgga     4200 aggtgccact cccactgtcc tttcctaata aaatgaggaa attgcatcgc attgtctgag    4260
taggtgtcat tctattctgg ggggtgggt gggcaggac agcaagggg aggattggga      4320 agagaatagc aggcatgctg gggaggtacc gagggcctat tcccatgat ccttcatat     4380 ttgcatatac gatacaaggc tgttagagag ataattggaa ttaatttgac tgtaaacaca    4440
aagatattag tacaaaatac gtgacgtaga aagtaataat ttcttgggta gtttgcagtt    4500
ttaaaattat gttttaaaat ggactatcat atgcttaccg taacttgaaa gtatttcgat    4560
```

```
ttcttggctt tatatatctt gtggaaagga cgaaacaccg aacacacagc tgggttatca    4620
gaggttttag tactctggaa acagaatcta ctaaaacaag gcaaaatgcc gtgtttatct    4680
cgtcaacttg ttggcgagat ttttgcggcc gcaggaaccc ctagtgatgg agttggccac    4740
tccctctctg cgcgctcgct cgctcactga ggccgggcga ccaaaggtcg cccgacgccc    4800
gggctttgcc cgggcggcct cagtgagcga gcgagcgcgc agctgcctgc aggggcgcct    4860
gatgcggtat tttctcctta cgcatctgtg cggtatttca caccgcatac gtcaaagcaa    4920
ccatagtacg cgccctgtag cggcgcatta agcgcggcgg gtgtggtggt tacgcgcagc    4980
gtgaccgcta cacttgccag cgccctagcg cccgctcctt tcgctttctt cccttccttt    5040
ctcgccacgt tcgccggctt tccccgtcaa gctctaaatc gggggctccc tttagggttc    5100
cgatttagtg ctttacggca cctcgacccc aaaaaacttg atttgggtga tggttcacgt    5160
agtgggccat cgccctgata acggttttt cgcccttga cgttggagtc cacgttcttt    5220
aatagtggac tcttgttcca aactggaaca cactcaacc ctatctcggg ctattctttt    5280
gatttataag ggattttgcc gatttcggcc tattggttaa aaaatgagct gatttaacaa    5340
aaatttaacg cgaattttaa caaaatatta cgtttacaa ttttatggtg cactctcagt    5400
acaatctgct ctgatgccgc atagttaagc cagccccgac acccgccaac acccgctgac    5460
gcgccctgac gggcttgtct gctcccggca tccgcttaca gacaagctgt gaccgtctcc    5520
gggagctgca tgtgtcagag gttttcaccg tcatcaccga aacgcgcgag acgaaagggc    5580
ctcgtgatac gcctatttt ataggttaat gtcatgataa taatggtttc ttagacgtca    5640
ggtggcactt ttcggggaaa tgtgcgcgga acccctattt gtttatttt ctaaatacat    5700 tcaaatatgt atccgctcat gagacaataa ccctgataaa tgcttcaata atattgaaaa    5760
aggaagagta tgagtattca acatttccgt gtcgcccta ttcccttttt tgcggcattt    5820
tgccttcctg ttttttgctca cccagaaacg ctggtgaaag taaaagatgc tgaagatcag    5880
ttgggtgcac gagtgggtta catcgaactg gatctcaaca gcggtaagat ccttgagagt    5940
tttcgccccg aagaacgttt tccaatgatg agcacttta aagttctgct atgtggcgcg    6000
gtattatccc gtattgacgc cgggcaagag caactcggtc gccgcataca ctattctcag    6060
aatgacttgg ttgagtactc accagtcaca gaaaagcatc ttacggatgg catgacagta    6120
agagaattat gcagtgctgc cataaccatg agtgataaca ctgcggccaa cttacttctg    6180
acaacgatcg gaggaccgaa ggagctaacc gcttttttgc acaacatggg ggatcatgta    6240
actcgccttg atcgttggga accggagctg aatgaagcca taccaaacga cgagcgtgac    6300
accacgatgc ctgtagcaat ggcaacaacg ttgcgcaaac tattaactgg cgaactactt    6360
actctagctt cccggcaaca attaatagac tggatggagg cggataaagt tgcaggacca    6420
cttctgcgct cggcccttcc ggctggctgg tttattgctg ataaatctgg agccggtgag    6480
cgtggaagcc gcggtatcat tgcagcactg gggccagatg gtaagccctc ccgtatcgta    6540
gttatctaca cgacggggag tcaggcaact atggatgaac gaaatagaca gatcgctgag    6600
ataggtgcct cactgattaa gcattggtaa ctgtcagacc aagtttactc atatatactt    6660
tagattgatt taaaacttca ttttttaattt aaaaggatct aggtgaagat cctttttgat    6720
aatctcatga ccaaaatccc ttaacgtgag ttttcgttcc actgagcgtc agaccccgta    6780
gaaaagatca aaggatcttc ttgagatcct ttttttctgc gcgtaatctg ctgcttgcaa    6840
acaaaaaaac caccgctacc agcggtggtt tgtttgccgg atcaagagct accaactctt    6900
tttccgaagg taactggctt cagcagagcg cagataccaa atactgtcct tctagtgtag    6960
```

```
ccgtagttag gccaccactt caagaactct gtagcaccgc ctacatacct cgctctgcta    7020
atcctgttac cagtggctgc tgccagtggc gataagtcgt gtcttaccgg gttggactca    7080
agacgatagt taccggataa ggcgcagcgg tcgggctgaa cggggggttc gtgcacacag    7140
cccagcttgg agcgaacgac ctacaccgaa ctgagatacc tacagcgtga gctatgagaa    7200
agcgccacgc ttcccgaagg gagaaaggcg gacaggtatc cggtaagcgg cagggtcgga    7260
acaggagagc gcacgaggga gcttccaggg ggaaacgcct ggtatcttta tagtcctgtc    7320
gggtttcgcc acctctgact tgagcgtcga ttttttgtgat gctcgtcagg ggggcggagc    7380
ctatggaaaa acgccagcaa cgcggccttt ttacggttcc tggccttttg ctggccttt    7440 gctcacatgt                                                           7450
```

<210> SEQ ID NO 40
<211> LENGTH: 7450
<212> TYPE: DNA
<213> ORGANISM: Artificial sequence
<220> FEATURE:
<223> OTHER INFORMATION: Synthetic

<400> SEQUENCE: 40

```
cctgcaggca gctgcgcgct cgctcgctca ctgaggccgc ccgggcgtcg gcgacctttt     60
ggtcgcccgg cctcagtgag cgagcgagcg cgcagagagg gagtggccaa ctccatcact    120
aggggttcct gcggcctcta gactcgaggc gttgacattg attattgact agttattaat    180
agtaatcaat tacggggtca ttagttcata gcccatatat ggagttccgc gttacataac    240
ttacggtaaa tggcccgcct ggctgaccgc ccaacgaccc ccgcccattg acgtcaataa    300
tgacgtatgt tcccatagta acgccaatag ggactttcca ttgacgtcaa tgggtggagt    360
atttacggta aactgcccac ttggcagtac atcaagtgta tcatatgcca agtacgcccc    420
ctattgacgt caatgacggt aaatggcccg cctggcatta tgcccagtac atgaccttat    480
gggactttcc tacttggcag tacatctacg tattagtcat cgctattacc atggtgatgc    540
ggttttggca gtacatcaat gggcgtggat agcggtttga ctcacgggga tttccaagtc    600
tccaccccat tgacgtcaat gggagtttgt tttggcacca aaatcaacgg gactttccaa    660
aatgtcgtaa caactccgcc ccattgacgc aaatgggcgg taggcgtgta cggtgggagg    720
tctatataag cagagctctc tggctaacta ccggtgccac catggcccca agaagaagc    780 ggaaggtcgg tatccacgga gtcccagcag ccaagcggaa ctacatcctg gcctggaca    840 tcggcatcac cagcgtgggc tacggcatca tcgactacga gacacgggac gtgatcgatg    900
ccggcgtgcg gctgttcaaa gaggccaacg tggaaaacaa cgagggcagg cggagcaaga    960
gaggcgccag aaggctgaag cggcggaggc ggcatagaat ccagagagtg aagaagctgc    1020
tgttcgacta caacctgctg accgaccaca gcgagctgag cggcatcaac ccctacgagg    1080
ccagagtgaa gggcctgagc cagaagctga gcgaggaaga gttctctgcc gccctgctgc    1140
acctggccaa gagaagaggc gtgcacaacg tgaacgaggt ggaagaggac accggcaacg    1200
agctgtccac caaagagcag atcagccgga acagcaaggc cctggaagag aaatacgtgg    1260
ccgaactgca gctggaacgg ctgaagaaag acggcgaagt gcggggcagc atcaacagat    1320
tcaagaccag cgactacgtg aaagaagcca acagctgct gaaggtgcag aaggcctacc    1380
accagctgga ccagagcttc atcgacacct acatcgacct gctggaaacc cggcggacct    1440
actatgaggg acctggcgag ggcagccct tcggctggaa ggacatcaaa gaatggtacg    1500
```

```
agatgctgat gggccactgc acctacttcc ccgaggaact gcggagcgtg aagtacgcct    1560
acaacgccga cctgtacaac gccctgaacg acctgaacaa tctcgtgatc accagggacg    1620
agaacgagaa gctggaatat tacgagaagt tccagatcat cgagaacgtg ttcaagcaga    1680
agaagaagcc caccctgaag cagatcgcca agaaatcct cgtgaacgaa gaggatatta    1740
agggctacag agtgaccagc accggcaagc ccgagttcac caacctgaag gtgtaccacg    1800
acatcaagga cattaccgcc cggaaagaga ttattgagaa cgccgagctg ctggatcaga    1860
ttgccaagat cctgaccatc taccagagca gcgaggacat ccaggaagaa ctgaccaatc    1920
tgaactccga gctgacccag gaagagatcg agcagatctc taatctgaag ggctataccg    1980
gcacccacaa cctgagcctg aaggccatca acctgatcct ggacgagctg tggcacacca    2040
acgacaacca gatcgctatc ttcaaccggc tgaagctggt gcccaagaag gtggacctgt    2100
cccagcagaa agagatcccc accaccctgg tggacgactt catcctgagc cccgtcgtga    2160
agagaagctt catccagagc atcaaagtga tcaacgccat catcaagaag tacggcctgc    2220
ccaacgacat cattatcgag ctggcccgcg agaagaactc caaggacgcc agaaaatga    2280 tcaacgagat gcagaagcgg aaccggcaga ccaacgagcg gatcgaggaa atcatccgga    2340
ccaccggcaa agagaacgcc aagtacctga tcgagaagat caagctgcac gacatgcagg    2400
aaggcaagtg cctgtacagc ctggaagcca tccctctgga agatctgctg aacaaccct    2460 tcaactatga ggtggaccac atcatcccca gaagcgtgtc cttcgacaac agcttcaaca    2520
acaaggtgct cgtgaagcag gaagaaaaca gcaagaaggg caaccggacc ccattccagt    2580
acctgagcag cagcgacagc aagatcagct acgaaacctt caagaagcac atcctgaatc    2640
tggccaaggg caagggcaga atcagcaaga ccaagaaaga gtatctgctg gaagaacggg    2700
acatcaacag gttctccgtg cagaaagact tcatcaaccg gaacctggtg gataccagat    2760
acgccaccag aggcctgatg aacctgctgc ggagctactt cagagtgaac aacctggacg    2820
tgaaagtgaa gtccatcaat ggcggcttca ccagctttct cgcggcggaag tggaagttta    2880 agaaagagcg gaacaagggg tacaagcacc acgccgagga cgccctgatc attgccaacg    2940
ccgatttcat cttcaaagag tggaagaaac tggacaaggc caaaaagtg atggaaaacc    3000 agatgttcga ggaaaagcag gccgagagca tgcccgagat cgaaaccgag caggagtaca    3060
aagagatctt catcaccccc caccagatca agcacattaa ggacttcaag gactacaagt    3120
acagccaccg ggtggacaag aagcctaata gagagctgat taacgacacc ctgtactcca    3180
cccggaagga cgacaagggc aacacccctga tcgtgaacaa tctgaacggc ctgtacgaca    3240
aggacaatga caagctgaaa aagctgatca acaagagccc cgaaaagctg ctgatgtacc    3300
accacgaccc ccagacctac cagaaactga agctgattat ggaacagtac ggcgacgaga    3360
agaatcccct gtacaagtac tacgaggaaa ccgggaacta cctgaccaag tactccaaaa    3420 aggcaacgg ccccgtgatc aagaagatta agtattacgg caacaaactg aacgcccatc    3480
tggacatcac cgacgactac cccaacagca gaaacaaggt cgtgaagctg tccctgaagc    3540
cctacagatt cgacgtgtac ctggacaatg gcgtgtacaa gttcgtgacc gtgaagaatc    3600
tggatgtgat caaaaaagaa aactactacg aagtgaatag caagtgctat gaggaagcta    3660
agaagctgaa gaagatcagc aaccaggccg agtttatcgc ctccttctac aacaacgatc    3720
tgatcaagat caacggcgag ctgtatagag tgatcggcgt gaacaacgac ctgctgaacc    3780
ggatcgaagt gaacatgatc gacatcacct accgcgagta cctggaaaac atgaacgaca    3840
agaggccccc caggatcatt aagacaatcg cctccaagac ccagagcatt aagaagtaca    3900
```

```
gcacagacat tctgggcaac ctgtatgaag tgaaatctaa gaagcaccct cagatcatca   3960
aaaagggcaa aaggccggcg gccacgaaaa aggccggcca ggcaaaaaag aaaaagggat   4020
cctacccata cgatgttcca gattacgctt acccatacga tgttccagat tacgcttacc   4080
catacgatgt tccagattac gcttaagaat cctagagct cgctgatcag cctcgactgt   4140
gccttctagt tgccagccat ctgttgtttg cccctccccc gtgccttcct tgaccctgga   4200
aggtgccact cccactgtcc tttcctaata aaatgaggaa attgcatcgc attgtctgag   4260
taggtgtcat tctattctgg ggggtggggt ggggcaggac agcaaggggg aggattggga   4320
agagaatagc aggcatgctg gggaggtacc gagggcctat ttcccatgat tccttcatat   4380
ttgcatatac gatacaaggc tgttagagag ataattggaa ttaatttgac tgtaaacaca   4440
aagatattag tacaaaatac gtgacgtaga aagtaataat ttcttgggta gtttgcagtt   4500
ttaaaattat gttttaaaat ggactatcat atgcttaccg taacttgaaa gtatttcgat   4560
ttcttggctt tatatatctt gtggaaagga cgaaacaccg agaactggtg ggaaatggtc   4620
taggttttag tactctggaa acagaatcta ctaaaacaag gcaaatgcc gtgtttatct   4680 cgtcaacttg ttggcgagat ttttgcggcc gcaggaaccc ctagtgatgg agttggccac   4740
tccctctctg cgcgctcgct cgctcactga ggccgggcga ccaaaggtcg cccgacgccc   4800
gggctttgcc cgggcggcct cagtgagcga gcgagcgcgc agctgcctgc aggggcgcct   4860
gatgcggtat tttctcctta cgcatctgtg cggtatttca caccgcatac gtcaaagcaa   4920
ccatagtacg cgccctgtag cggcgcatta agcgcggcgg gtgtggtggt tacgcgcagc   4980
gtgaccgcta cacttgccag cgccctagcg cccgctcctt tcgctttctt cccttccttt   5040
ctcgccacgt tcgccggctt tccccgtcaa gctctaaatc ggggggctcc ctttagggttc   5100 cgatttagtg ctttacggca cctcgacccc aaaaaacttg atttgggtga tggttcacgt   5160
agtgggccat cgccctgata gacggttttt cgccctttga cgttggagtc cacgttcttt   5220
aatagtggac tcttgttcca aactggaaca acactcaacc ctatctcggg ctattctttt   5280
gatttataag ggattttgcc gatttcggcc tattggttaa aaaatgagct gatttaacaa   5340
aaatttaacg cgaattttaa caaaatatta acgtttacaa ttttatggtg cactctcagt   5400
acaatctgct ctgatgccgc atagttaagc cagccccgac acccgccaac acccgctgac   5460
gcgccctgac gggcttgtct gctcccggca tccgcttaca gacaagctgt gaccgtctcc   5520
gggagctgca tgtgtcagag gttttcaccg tcatcaccga aacgcgcgag acgaaagggc   5580
ctcgtgatac gcctattttt ataggttaat gtcatgataa taatggttc ttagacgtca   5640 ggtggcactt ttcggggaaa tgtgcgcgga accctattt gtttatttt ctaaatacat   5700 tcaaatatgt atccgctcat gagacaataa ccctgataaa tgcttcaata atattgaaaa   5760
aggaagagta tgagtattca acatttccgt gtcgccctta ttcccttttt tgcggcattt   5820
tgccttcctg ttttgctca cccagaaacg ctggtgaaag taaagatgc tgaagatcag   5880 ttgggtgcac gagtgggtta catcgaactg gatctcaaca gcggtaagat ccttgagagt   5940
tttcgccccg aagaacgttt tccaatgatg agcactttta aagttctgct atgtggcgcg   6000
gtattatccc gtattgacgc cgggcaagag caactcggtc gccgcataca ctattctcag   6060
aatgacttgg ttgagtactc accagtcaca gaaaagcatc ttacggatgg catgacagta   6120
agagaattat gcagtgctgc cataaccatg agtgataaca ctgcggccaa cttacttctg   6180
acaacgatcg gaggaccgaa ggagctaacc gcttttttgc acaacatggg ggatcatgta   6240
```

```
actcgccttg atcgttggga accggagctg aatgaagcca taccaaacga cgagcgtgac   6300
accacgatgc ctgtagcaat ggcaacaacg ttgcgcaaac tattaactgg cgaactactt   6360
actctagctt cccggcaaca attaatagac tggatggagg cggataaagt tgcaggacca   6420
cttctgcgct cggcccttcc ggctggctgg tttattgctg ataaatctgg agccggtgag   6480
cgtggaagcc gcggtatcat tgcagcactg gggccagatg gtaagccctc ccgtatcgta   6540
gttatctaca cgacggggag tcaggcaact atggatgaac gaaatagaca gatcgctgag   6600
ataggtgcct cactgattaa gcattggtaa ctgtcagacc aagtttactc atatatactt   6660
tagattgatt taaaacttca ttttttaattt aaaaggatct aggtgaagat ccttttttgat   6720 aatctcatga ccaaaatccc ttaacgtgag ttttcgttcc actgagcgtc agaccccgta   6780
gaaaagatca aaggatcttc ttgagatcct ttttttctgc gcgtaatctg ctgcttgcaa   6840
acaaaaaaac caccgctacc agcggtggtt tgtttgccgg atcaagagct accaactctt   6900
tttccgaagg taactggctt cagcagagcg cagataccaa atactgtcct tctagtgtag   6960
ccgtagttag gccaccactt caagaactct gtagcaccgc ctacatacct cgctctgcta   7020
atcctgttac cagtggctgc tgccagtggc gataagtcgt gtcttaccgg gttggactca   7080
agacgatagt taccggataa ggcgcagcgg tcgggctgaa cggggggttc gtgcacacag   7140
cccagcttgg agcgaacgac ctacaccgaa ctgagatacc tacagcgtga gctatgagaa   7200
agcgccacgc ttcccgaagg gagaaaggcg gacaggtatc cggtaagcgg cagggtcgga   7260
acaggagagc gcacgaggga gcttccaggg ggaaacgcct ggtatcttta tagtcctgtc   7320
gggtttcgcc acctctgact tgagcgtcga ttttttgtgat gctcgtcagg ggggcggagc   7380
ctatggaaaa acgccagcaa cgcggccttt ttacggttcc tggccttttg ctggcctttt   7440
gctcacatgt                                                          7450

<210> SEQ ID NO 41
<211> LENGTH: 20
<212> TYPE: DNA
<213> ORGANISM: Artificial sequence
<220> FEATURE:
<223> OTHER INFORMATION: Synthetic

<400> SEQUENCE: 41
aacaaatatc ccttagtatc                                                 20

<210> SEQ ID NO 42
<211> LENGTH: 20
<212> TYPE: DNA
<213> ORGANISM: Artificial sequence
<220> FEATURE:
<223> OTHER INFORMATION: Synthetic

<400> SEQUENCE: 42
aatgtatttc ttctattcaa                                                 20

<210> SEQ ID NO 43
<211> LENGTH: 3255
<212> TYPE: DNA
<213> ORGANISM: Artificial sequence
<220> FEATURE:
<223> OTHER INFORMATION: Synthetic

<400> SEQUENCE: 43
atggccccaa agaagaagcg gaaggtcggt atccacggag tcccagcagc caagcggaac     60
tacatcctgg gcctggacat cggcatcacc agcgtgggct acggcatcat cgactacgag    120
```

-continued

```
acacgggacg tgatcgatgc cggcgtgcgg ctgttcaaag aggccaacgt ggaaaacaac    180
gagggcaggc ggagcaagag aggcgccaga aggctgaagc ggcggaggcg catagaatc     240 cagagagtga agaagctgct gttcgactac aacctgctga ccgaccacag cgagctgagc    300
ggcatcaacc cctacgaggc cagagtgaag ggcctgagcc agaagctgag cgaggaagag    360
ttctctgccg ccctgctgca cctggccaag agaagaggcg tgcacaacgt gaacgaggtg    420
gaagaggaca ccggcaacga gctgtccacc aagagcagat cagccggaac agcaaggcc     480 ctggaagaga aatacgtggc cgaactgcag ctggaacggc tgaagaaaga cggcgaagtg    540
cggggcagca tcaacagatt caagaccagc gactacgtga agaagccaa acagctgctg     600 aaggtgcaga aggcctacca ccagctggac cagagcttca tcgacaccta catcgacctg    660
ctggaacccc ggcggaccta ctatgaggga cctggcgagg gcagccctt cggctggaag     720 gacatcaaag aatggtacga gatgctgatg gccactgca cctacttccc cgaggaactg     780
cggagcgtga agtacgccta caacgccgac ctgtacaacg ccctgaacga cctgaacaat    840
ctcgtgatca ccagggacga gaacgagaag ctggaatatt acgagaagtt ccagatcatc    900
gagaacgtgt tcaagcagaa gaagaagccc accctgaagc agatcgccaa agaaatcctc    960
gtgaacgaag aggatattaa gggctacaga gtgaccagca ccggcaagcc cgagttcacc    1020
aacctgaagg tgtaccacga catcaaggac attaccgccc ggaaagagat tattgagaac    1080
gccgagctgc tggatcagat tgccaagatc ctgaccatct accagagcag cgaggacatc    1140
caggaagaac tgaccaatct gaactccgag ctgacccagg aagagatcga gcagatctct    1200
aatctgaagg gctataccgg cacccacaac ctgagcctga aggccatcaa cctgatcctg    1260
gacgagctgt ggcacaccaa cgacaaccag atcgctatct tcaaccggct gaagctggtg    1320
cccaagaagg tggacctgtc ccagcagaaa gagatcccca ccaccctggt ggacgacttc    1380
atcctgagcc ccgtcgtgaa gagaagcttc atccagagca tcaaagtgat caacgccatc    1440
atcaagaagt acggcctgcc caacgacatc attatcgagc tggcccgcga agaactcc     1500 aaggacgccc agaaaatgat caacgagatg cagaagcgga accggcagac caacgagcgg    1560
atcgaggaaa tcatccggac caccggcaaa gagaacgcca agtacctgat cgagaagatc    1620
aagctgcacg acatgcagga aggcaagtgc ctgtacagcc tggaagccat ccctctggaa    1680
gatctgctga acaacccctt caactatgag gtggaccaca tcatccccag aagcgtgtcc    1740
ttcgacaaca gcttcaacaa caaggtgctc gtgaagcagg aagaaaacag caagaagggc    1800
aaccggaccc cattccagta cctgagcagc agcgacagca gatcagcta cgaaaccttc    1860 aagaagcaca tcctgaatct ggccaagggc aagggcagaa tcagcaagac caagaaagag    1920
tatctgctga agaacggga catcaacagg ttctccgtgc agaaagactt catcaaccgg    1980
aacctggtgg ataccagata cgccaccaga ggcctgatga acctgctgcg gagctacttc    2040
agagtgaaca acctggacgt gaaagtgaag tccatcaatg gcggcttcac cagctttctg    2100
cggcggaagt ggaagtttaa aaagagcgg aacaagggt acaagcacca cgccgaggac    2160
gccctgatca ttgccaacgc cgatttcatc ttcaaagagt ggaagaaact ggacaaggcc    2220
aaaaaagtga tggaaaacca gatgttcgag gaaaagcagg ccgagcat gcccgagatc    2280 gaaaccgagc aggagtacaa agagatcttc atcacccccc accagatcaa gcacattaag    2340
gacttcaagg actacaagta cagccaccgg gtggacaaga gcctaatag agagctgatt    2400 aacgacaccc tgtactccac ccggaaggac gacaagggca cacccctgat cgtgaacaat    2460
```

```
ctgaacggcc tgtacgacaa ggacaatgac aagctgaaaa agctgatcaa caagagcccc    2520
gaaaagctgc tgatgtacca ccacgacccc cagacctacc agaaactgaa gctgattatg    2580
gaacagtacg gcgacgagaa gaatcccctg tacaagtact acgaggaaac cgggaactac    2640
ctgaccaagt actccaaaaa ggacaacggc cccgtgatca agaagattaa gtattacggc    2700
aacaaactga acgcccatct ggacatcacc gacgactacc ccaacagcag aaacaaggtc    2760
gtgaagctgt ccctgaagcc ctacagattc gacgtgtacc tggacaatgg cgtgtacaag    2820
ttcgtgaccg tgaagaatct ggatgtgatc aaaaagaaa actactacga agtgaatagc    2880
aagtgctatg aggaagctaa gaagctgaag aagatcagca accaggccga gtttatcgcc    2940
tccttctaca caacgatct gatcaagatc aacggcgagc tgtatagagt gatcggcgtg    3000
aacaacgacc tgctgaaccg gatcgaagtg aacatgatcg acatcaccta ccgcgagtac    3060
ctggaaaaca tgaacgacaa gaggcccccc aggatcatta agacaatcgc ctccaagacc    3120
cagagcatta agaagtacag cacagacatt ctgggcaacc tgtatgaagt gaaatctaag    3180
aagcaccctc agatcatcaa aaagggcaaa aggccggcgg ccacgaaaaa ggccggccag    3240
gcaaaaaaga aaaag                                                    3255

<210> SEQ ID NO 44
<211> LENGTH: 3156
<212> TYPE: DNA
<213> ORGANISM: Artificial sequence
<220> FEATURE:
<223> OTHER INFORMATION: Synthetic

<400> SEQUENCE: 44
aagcggaact acatcctggg cctggacatc ggcatcacca gcgtgggcta cggcatcatc      60
gactacgaga cacgggacgt gatcgatgcc ggcgtgcggc tgttcaaaga ggccaacgtg     120
gaaaacaacg agggcaggcg gagcaagaga ggcgccagaa ggctgaagcg gcggaggcgg     180
catagaatcc agagagtgaa gaagctgctg ttcgactaca acctgctgac cgaccacagc     240
gagctgagcg gcatcaaccc ctacgaggcc agagtgaagg gcctgagcca aagctgagc     300 gaggaagagt tctctgccgc cctgctgcac ctggccaaga agagggcgt gcacaacgtg     360 aacgaggtgg aagaggacac cggcaacgag ctgtccacca agagcagat cagccggaac     420 agcaaggccc tggaagagaa atacgtggcc gaactgcagc tggaacggct gaagaaagac     480
ggcgaagtgc ggggcagcat caacagattc aagaccagcg actacgtgaa gaagccaaa     540 cagctgctga aggtgcagaa ggcctaccac cagctggacc agagcttcat cgacacctac     600
atcgacctgc tggaaacccg gcggacctac tatgagggac ctggcgaggg cagccccttc     660
ggctggaagg acatcaaaga atggtacgag atgctgatgg ccactgcac ctacttcccc     720 gaggaactgc ggagcgtgaa gtacgcctac aacgccgacc tgtacaacgc cctgaacgac     780
ctgaacaatc tcgtgatcac cagggacgag aacgagaagc tggaatatta cgagaagttc     840
cagatcatcg agaacgtgtt caagcagaag aagaagccca ccctgaagca gatcgccaaa     900
gaaatcctcg tgaacgaaga ggatattaag ggctacagag tgaccagcac cggcaagccc     960
gagttcacca acctgaaggt gtaccacgac atcaaggaca ttaccgcccg gaaagagatt    1020
attgagaacg ccgagctgct ggatcagatt gccaagatcc tgaccatcta ccagagcagc    1080
gaggacatcc aggaagaact gaccaatctg aactccgagc tgacccagga agagatcgag    1140
cagatctcta atctgaaggg ctataccggc acccacaacc tgagcctgaa ggccatcaac    1200
ctgatcctgg acgagctgtg gcacaccaac gacaaccaga tcgctatctt caaccggctg    1260
```

```
aagctggtgc ccaagaaggt ggacctgtcc cagcagaaag agatcccac caccctggtg    1320 gacgacttca tcctgagccc cgtcgtgaag agaagcttca tccagagcat caaagtgatc    1380
aacgccatca tcaagaagta cggcctgccc aacgacatca ttatcgagct ggcccgcgag    1440
aagaactcca aggacgccca gaaaatgatc aacgagatgc agaagcggaa ccggcagacc    1500
aacgagcgga tcgaggaaat catccggacc accggcaaag agaacgccaa gtacctgatc    1560
gagaagatca agctgcacga catgcaggaa ggcaagtgcc tgtacagcct ggaagccatc    1620
cctctggaag atctgctgaa caacccttc aactatgagg tggaccacat catccccaga    1680
agcgtgtcct tcgacaacag cttcaacaac aaggtgctcg tgaagcagga agaaaacagc    1740
aagaagggca accggacccc attccagtac ctgagcagca gcgacagcaa gatcagctac    1800
gaaaccttca gaagcacat cctgaatctg gccaagggca agggcagaat cagcaagacc    1860
aagaaagagt atctgctgga agaacgggac atcaacaggt tctccgtgca gaaagacttc    1920
atcaaccgga acctggtgga taccagatac gccaccagag gcctgatgaa cctgctgcgg    1980
agctacttca gagtgaacaa cctggacgtg aaagtgaagt ccatcaatgg cggcttcacc    2040
agctttctgc ggcggaagtg gaagtttaag aaagagcgga caaggggta caagcaccac    2100 gccgaggacg ccctgatcat tgccaacgcc gatttcatct tcaaagagtg aagaaactg    2160 gacaaggcca aaaagtgat ggaaaaccag atgttcgagg aaaagcaggc cgagagcatg    2220
cccgagatcg aaaccgagca ggagtacaaa gagatcttca tcaccccca ccagatcaag    2280 cacattaagg acttcaagga ctacaagtac agccaccggg tggacaagaa gcctaataga    2340
gagctgatta acgacaccct gtactccacc cggaaggacg acaagggcaa caccctgatc    2400
gtgaacaatc tgaacggcct gtacgacaag gacaatgaca agctgaaaaa gctgatcaac    2460
aagagccccg aaaagctgct gatgtaccac cacgacccc agacctacca gaaactgaag    2520
ctgattatgg aacagtacgg cgacgagaag aatcccctgt acaagtacta cgaggaaacc    2580
gggaactacc tgaccaagta ctccaaaaag gacaacggcc ccgtgatcaa gaagattaag    2640
tattacggca caaactgaa cgcccatctg gacatcaccg cgactaccc caacagcaga    2700 aacaaggtcg tgaagctgtc cctgaagccc tacagattcg acgtgtacct ggacaatggc    2760
gtgtacaagt tcgtgaccgt gaagaatctg gatgtgatca aaaagaaaa ctactacgaa    2820 gtgaatagca agtgctatga ggaagctaag aagctgaaga agatcagcaa ccaggccgag    2880
tttatcgcct ccttctacaa caacgatctg atcaagatca acggcgagct gtatagagtg    2940
atcggcgtga caacgacct gctgaaccgg atcgaagtga acatgatcga catcacctac    3000
cgcgagtacc tggaaaacat gaacgacaag aggccccca ggatcattaa gacaatcgcc    3060
tccaagaccc agagcattaa gaagtacagc acagacattc tgggcaacct gtatgaagtg    3120
aaatctaaga agcaccctca gatcatcaaa aagggc    3156
```

<210> SEQ ID NO 45
<211> LENGTH: 1052
<212> TYPE: PRT
<213> ORGANISM: Artificial sequence
<220> FEATURE:
<223> OTHER INFORMATION: Synthetic

<400> SEQUENCE: 45

```
Lys Arg Asn Tyr Ile Leu Gly Leu Asp Ile Gly Ile Thr Ser Val Gly
1               5                   10                  15

Tyr Gly Ile Ile Asp Tyr Glu Thr Arg Asp Val Ile Asp Ala Gly Val
```

```
                    20                  25                  30
Arg Leu Phe Lys Glu Ala Asn Val Glu Asn Glu Gly Arg Arg Ser
                35                  40                  45
Lys Arg Gly Ala Arg Arg Leu Lys Arg Arg Arg His Arg Ile Gln
        50                  55                  60
Arg Val Lys Lys Leu Leu Phe Asp Tyr Asn Leu Thr Asp His Ser
65                  70                  75                  80
Glu Leu Ser Gly Ile Asn Pro Tyr Glu Ala Arg Val Lys Gly Leu Ser
                85                  90                  95
Gln Lys Leu Ser Glu Glu Phe Ser Ala Ala Leu Leu His Leu Ala
            100                 105                 110
Lys Arg Gly Val His Asn Val Asn Glu Val Glu Glu Asp Thr Gly
            115                 120                 125
Asn Glu Leu Ser Thr Lys Glu Gln Ile Ser Arg Asn Ser Lys Ala Leu
                130                 135                 140
Glu Glu Lys Tyr Val Ala Glu Leu Gln Leu Glu Arg Leu Lys Lys Asp
145                 150                 155                 160
Gly Glu Val Arg Gly Ser Ile Asn Arg Phe Lys Thr Ser Asp Tyr Val
                165                 170                 175
Lys Glu Ala Lys Gln Leu Leu Lys Val Gln Lys Ala Tyr His Gln Leu
            180                 185                 190
Asp Gln Ser Phe Ile Asp Thr Tyr Ile Asp Leu Leu Glu Thr Arg Arg
                195                 200                 205
Thr Tyr Tyr Glu Gly Pro Gly Glu Gly Ser Pro Phe Gly Trp Lys Asp
            210                 215                 220
Ile Lys Glu Trp Tyr Glu Met Leu Met Gly His Cys Thr Tyr Phe Pro
225                 230                 235                 240
Glu Glu Leu Arg Ser Val Lys Tyr Ala Tyr Asn Ala Asp Leu Tyr Asn
                245                 250                 255
Ala Leu Asn Asp Leu Asn Asn Leu Val Ile Thr Arg Asp Glu Asn Glu
            260                 265                 270
Lys Leu Glu Tyr Tyr Glu Lys Phe Gln Ile Ile Glu Asn Val Phe Lys
            275                 280                 285
Gln Lys Lys Lys Pro Thr Leu Lys Gln Ile Ala Lys Glu Ile Leu Val
            290                 295                 300
Asn Glu Glu Asp Ile Lys Gly Tyr Arg Val Thr Ser Thr Gly Lys Pro
305                 310                 315                 320
Glu Phe Thr Asn Leu Lys Val Tyr His Asp Ile Lys Asp Ile Thr Ala
                325                 330                 335
Arg Lys Glu Ile Ile Glu Asn Ala Glu Leu Leu Asp Gln Ile Ala Lys
            340                 345                 350
Ile Leu Thr Ile Tyr Gln Ser Ser Glu Asp Ile Gln Glu Glu Leu Thr
            355                 360                 365
Asn Leu Asn Ser Glu Leu Thr Gln Glu Glu Ile Glu Gln Ile Ser Asn
            370                 375                 380
Leu Lys Gly Tyr Thr Gly Thr His Asn Leu Ser Leu Lys Ala Ile Asn
385                 390                 395                 400
Leu Ile Leu Asp Glu Leu Trp His Thr Asn Asp Asn Gln Ile Ala Ile
                405                 410                 415
Phe Asn Arg Leu Lys Leu Val Pro Lys Lys Val Asp Leu Ser Gln Gln
            420                 425                 430
Lys Glu Ile Pro Thr Thr Leu Val Asp Asp Phe Ile Leu Ser Pro Val
            435                 440                 445
```

-continued

```
Val Lys Arg Ser Phe Ile Gln Ser Ile Lys Val Ile Asn Ala Ile Ile
    450                 455                 460
Lys Lys Tyr Gly Leu Pro Asn Asp Ile Ile Glu Leu Ala Arg Glu
465                 470                 475                 480
Lys Asn Ser Lys Asp Ala Gln Lys Met Ile Asn Glu Met Gln Lys Arg
                    485                 490                 495
Asn Arg Gln Thr Asn Glu Arg Ile Glu Glu Ile Ile Arg Thr Thr Gly
                500                 505                 510
Lys Glu Asn Ala Lys Tyr Leu Ile Glu Lys Ile Lys Leu His Asp Met
            515                 520                 525
Gln Glu Gly Lys Cys Leu Tyr Ser Leu Glu Ala Ile Pro Leu Glu Asp
530                 535                 540
Leu Leu Asn Asn Pro Phe Asn Tyr Glu Val Asp His Ile Ile Pro Arg
545                 550                 555                 560
Ser Val Ser Phe Asp Asn Ser Phe Asn Asn Lys Val Leu Val Lys Gln
                565                 570                 575
Glu Glu Asn Ser Lys Lys Gly Asn Arg Thr Pro Phe Gln Tyr Leu Ser
                580                 585                 590
Ser Ser Asp Ser Lys Ile Ser Tyr Glu Thr Phe Lys Lys His Ile Leu
            595                 600                 605
Asn Leu Ala Lys Gly Lys Gly Arg Ile Ser Lys Thr Lys Lys Glu Tyr
        610                 615                 620
Leu Leu Glu Glu Arg Asp Ile Asn Arg Phe Ser Val Gln Lys Asp Phe
625                 630                 635                 640
Ile Asn Arg Asn Leu Val Asp Thr Arg Tyr Ala Thr Arg Gly Leu Met
                645                 650                 655
Asn Leu Leu Arg Ser Tyr Phe Arg Val Asn Asn Leu Asp Val Lys Val
                660                 665                 670
Lys Ser Ile Asn Gly Gly Phe Thr Ser Phe Leu Arg Arg Lys Trp Lys
            675                 680                 685
Phe Lys Lys Glu Arg Asn Lys Gly Tyr Lys His His Ala Glu Asp Ala
        690                 695                 700
Leu Ile Ile Ala Asn Ala Asp Phe Ile Phe Lys Glu Trp Lys Lys Leu
705                 710                 715                 720
Asp Lys Ala Lys Lys Val Met Glu Asn Gln Met Phe Glu Glu Lys Gln
                725                 730                 735
Ala Glu Ser Met Pro Glu Ile Glu Thr Glu Gln Glu Tyr Lys Glu Ile
                740                 745                 750
Phe Ile Thr Pro His Gln Ile Lys His Ile Lys Asp Phe Lys Asp Tyr
            755                 760                 765
Lys Tyr Ser His Arg Val Asp Lys Lys Pro Asn Arg Glu Leu Ile Asn
        770                 775                 780
Asp Thr Leu Tyr Ser Thr Arg Lys Asp Asp Lys Gly Asn Thr Leu Ile
785                 790                 795                 800
Val Asn Asn Leu Asn Gly Leu Tyr Asp Lys Asp Asn Asp Lys Leu Lys
                805                 810                 815
Lys Leu Ile Asn Lys Ser Pro Glu Lys Leu Leu Met Tyr His His Asp
            820                 825                 830
Pro Gln Thr Tyr Gln Lys Leu Lys Leu Ile Met Glu Gln Tyr Gly Asp
        835                 840                 845
Glu Lys Asn Pro Leu Tyr Lys Tyr Tyr Glu Glu Thr Gly Asn Tyr Leu
850                 855                 860
```

```
Thr Lys Tyr Ser Lys Lys Asp Asn Gly Pro Val Ile Lys Lys Ile Lys
865                 870                 875                 880

Tyr Tyr Gly Asn Lys Leu Asn Ala His Leu Asp Ile Thr Asp Asp Tyr
            885                 890                 895

Pro Asn Ser Arg Asn Lys Val Val Lys Leu Ser Leu Lys Pro Tyr Arg
                900                 905                 910

Phe Asp Val Tyr Leu Asp Asn Gly Val Tyr Lys Phe Val Thr Val Lys
                915                 920                 925

Asn Leu Asp Val Ile Lys Lys Glu Asn Tyr Tyr Glu Val Asn Ser Lys
930                 935                 940

Cys Tyr Glu Glu Ala Lys Lys Leu Lys Lys Ile Ser Asn Gln Ala Glu
945                 950                 955                 960

Phe Ile Ala Ser Phe Tyr Asn Asn Asp Leu Ile Lys Ile Asn Gly Glu
                965                 970                 975

Leu Tyr Arg Val Ile Gly Val Asn Asn Asp Leu Leu Asn Arg Ile Glu
                980                 985                 990

Val Asn Met Ile Asp Ile Thr Tyr  Arg Glu Tyr Leu Glu  Asn Met Asn
                995                 1000                1005

Asp Lys Arg Pro Arg Ile  Ile Lys Thr Ile Ala  Ser Lys Thr
    1010                1015                1020

Gln Ser  Ile Lys Lys Tyr Ser  Thr Asp Ile Leu Gly  Asn Leu Tyr
    1025                1030                1035

Glu Val Lys Ser Lys Lys His  Pro Gln Ile Ile Lys  Lys Gly
        1040                1045                1050

<210> SEQ ID NO 46
<211> LENGTH: 52
<212> TYPE: DNA
<213> ORGANISM: Artificial sequence
<220> FEATURE:
<223> OTHER INFORMATION: Synthetic

<400> SEQUENCE: 46
aacgctgaag aaccctgata atagaagaaa tacatttta aatcaattca gg            52

<210> SEQ ID NO 47
<211> LENGTH: 51
<212> TYPE: DNA
<213> ORGANISM: Artificial sequence
<220> FEATURE:
<223> OTHER INFORMATION: Synthetic

<400> SEQUENCE: 47
aagaaccctg atattatctt agtagattaa tagaagaaat cattttaa a              51

<210> SEQ ID NO 48
<211> LENGTH: 42
<212> TYPE: DNA
<213> ORGANISM: Artificial sequence
<220> FEATURE:
<223> OTHER INFORMATION: Synthetic

<400> SEQUENCE: 48
gctgaagaac cctgaaaaaa tacatttttt tatcaattca gg                      42

<210> SEQ ID NO 49
<211> LENGTH: 36
<212> TYPE: DNA
<213> ORGANISM: Artificial sequence
<220> FEATURE:
<223> OTHER INFORMATION: Synthetic
```

```
<400> SEQUENCE: 49
gaatgatttt cttgtagaag aaataacaat taaatc                       36

<210> SEQ ID NO 50
<211> LENGTH: 52
<212> TYPE: DNA
<213> ORGANISM: Artificial sequence
<220> FEATURE:
<223> OTHER INFORMATION: Synthetic

<400> SEQUENCE: 50
aacgctgaag aaccctgata atagaagaaa tacattttta aatcaattca gg     52

<210> SEQ ID NO 51
<211> LENGTH: 59
<212> TYPE: DNA
<213> ORGANISM: Artificial sequence
<220> FEATURE:
<223> OTHER INFORMATION: Synthetic

<400> SEQUENCE: 51
aacgctgaag aaccctgata ttatcttagt agattaatag aagaaataca tttttaaat  59

<210> SEQ ID NO 52
<211> LENGTH: 59
<212> TYPE: DNA
<213> ORGANISM: Artificial sequence
<220> FEATURE:
<223> OTHER INFORMATION: Synthetic

<400> SEQUENCE: 52
aacgctgaag aaccctgata ttatcttagt agattaatag aagaaataca tttttaaat  59

<210> SEQ ID NO 53
<211> LENGTH: 6
<212> TYPE: DNA
<213> ORGANISM: Artificial sequence
<220> FEATURE:
<223> OTHER INFORMATION: Synthetic

<400> SEQUENCE: 53 aagagt                                                        6

<210> SEQ ID NO 54
<211> LENGTH: 6
<212> TYPE: DNA
<213> ORGANISM: Artificial sequence
<220> FEATURE:
<223> OTHER INFORMATION: Synthetic

<400> SEQUENCE: 54 gggaat                                                        6

<210> SEQ ID NO 55
<211> LENGTH: 3
<212> TYPE: DNA
<213> ORGANISM: Artificial sequence
<220> FEATURE:
<223> OTHER INFORMATION: Synthetic

<400> SEQUENCE: 55 agg                                                           3

<210> SEQ ID NO 56
```

```
<211> LENGTH: 3
<212> TYPE: DNA
<213> ORGANISM: Artificial sequence
<220> FEATURE:
<223> OTHER INFORMATION: Synthetic

<400> SEQUENCE: 56 tgg                                                                        3

<210> SEQ ID NO 57
<211> LENGTH: 6
<212> TYPE: DNA
<213> ORGANISM: Artificial sequence
<220> FEATURE:
<223> OTHER INFORMATION: Synthetic

<400> SEQUENCE: 57 gagagt                                                                     6

<210> SEQ ID NO 58
<211> LENGTH: 6
<212> TYPE: DNA
<213> ORGANISM: Artificial sequence
<220> FEATURE:
<223> OTHER INFORMATION: Synthetic

<400> SEQUENCE: 58 gggagt                                                                     6

<210> SEQ ID NO 59
<211> LENGTH: 6
<212> TYPE: DNA
<213> ORGANISM: Artificial sequence
<220> FEATURE:
<223> OTHER INFORMATION: Synthetic

<400> SEQUENCE: 59 ttgaat                                                                     6

<210> SEQ ID NO 60
<211> LENGTH: 6
<212> TYPE: DNA
<213> ORGANISM: Artificial sequence
<220> FEATURE:
<223> OTHER INFORMATION: Synthetic

<400> SEQUENCE: 60 cagagt                                                                     6

<210> SEQ ID NO 61
<211> LENGTH: 6
<212> TYPE: DNA
<213> ORGANISM: Artificial sequence
<220> FEATURE:
<223> OTHER INFORMATION: Synthetic

<400> SEQUENCE: 61 tggagt                                                                     6

<210> SEQ ID NO 62
<211> LENGTH: 6
<212> TYPE: DNA
<213> ORGANISM: Artificial sequence
<220> FEATURE:
<223> OTHER INFORMATION: Synthetic

<400> SEQUENCE: 62
```

```
atgagt                                                              6

<210> SEQ ID NO 63
<211> LENGTH: 6
<212> TYPE: DNA
<213> ORGANISM: Artificial sequence
<220> FEATURE:
<223> OTHER INFORMATION: Synthetic

<400> SEQUENCE: 63 aggaat                                                              6

<210> SEQ ID NO 64
<211> LENGTH: 22
<212> TYPE: DNA
<213> ORGANISM: Artificial sequence
<220> FEATURE:
<223> OTHER INFORMATION: Synthetic

<400> SEQUENCE: 64
aaagatatat aatgtcatga at                                           22

<210> SEQ ID NO 65
<211> LENGTH: 22
<212> TYPE: DNA
<213> ORGANISM: Artificial sequence
<220> FEATURE:
<223> OTHER INFORMATION: Synthetic

<400> SEQUENCE: 65
gcagaatcaa atataatagt ct                                           22

<210> SEQ ID NO 66
<211> LENGTH: 22
<212> TYPE: DNA
<213> ORGANISM: Artificial sequence
<220> FEATURE:
<223> OTHER INFORMATION: Synthetic

<400> SEQUENCE: 66
caattaaatt tgacttattg tt                                           22

<210> SEQ ID NO 67
<211> LENGTH: 22
<212> TYPE: DNA
<213> ORGANISM: Artificial sequence
<220> FEATURE:
<223> OTHER INFORMATION: Synthetic

<400> SEQUENCE: 67
ctagaccatt tcccaccagt tc                                           22

<210> SEQ ID NO 68
<211> LENGTH: 22
<212> TYPE: DNA
<213> ORGANISM: Artificial sequence
<220> FEATURE:
<223> OTHER INFORMATION: Synthetic

<400> SEQUENCE: 68
aggactttta tttaccaaag ga                                           22

<210> SEQ ID NO 69
<211> LENGTH: 22
<212> TYPE: DNA
```

```
<213> ORGANISM: Artificial sequence
<220> FEATURE:
<223> OTHER INFORMATION: Synthetic

<400> SEQUENCE: 69
atccaagtcc atttgattcc ta                                              22

<210> SEQ ID NO 70
<211> LENGTH: 22
<212> TYPE: DNA
<213> ORGANISM: Artificial sequence
<220> FEATURE:
<223> OTHER INFORMATION: Synthetic

<400> SEQUENCE: 70
taattctttc tagaaagagc ct                                              22

<210> SEQ ID NO 71
<211> LENGTH: 22
<212> TYPE: DNA
<213> ORGANISM: Artificial sequence
<220> FEATURE:
<223> OTHER INFORMATION: Synthetic

<400> SEQUENCE: 71
ggacatgtgc aagatgcaag ag                                              22

<210> SEQ ID NO 72
<211> LENGTH: 22
<212> TYPE: DNA
<213> ORGANISM: Artificial sequence
<220> FEATURE:
<223> OTHER INFORMATION: Synthetic

<400> SEQUENCE: 72
tgtatgtaga agacctctaa gt                                              22

<210> SEQ ID NO 73
<211> LENGTH: 22
<212> TYPE: DNA
<213> ORGANISM: Artificial sequence
<220> FEATURE:
<223> OTHER INFORMATION: Synthetic

<400> SEQUENCE: 73
tcccctcacc actcacctct ga                                              22

<210> SEQ ID NO 74
<211> LENGTH: 22
<212> TYPE: DNA
<213> ORGANISM: Artificial sequence
<220> FEATURE:
<223> OTHER INFORMATION: Synthetic

<400> SEQUENCE: 74
ctctgataac ccagctgtgt gt                                              22

<210> SEQ ID NO 75
<211> LENGTH: 19
<212> TYPE: DNA
<213> ORGANISM: Artificial sequence
<220> FEATURE:
<223> OTHER INFORMATION: Synthetic

<400> SEQUENCE: 75
ctctgataac ccagctgtg                                                  19
```

<210> SEQ ID NO 76
<211> LENGTH: 20
<212> TYPE: DNA
<213> ORGANISM: Artificial sequence
<220> FEATURE:
<223> OTHER INFORMATION: Synthetic

<400> SEQUENCE: 76
ctctgataac ccagctgtgt                                               20

<210> SEQ ID NO 77
<211> LENGTH: 21
<212> TYPE: DNA
<213> ORGANISM: Artificial sequence
<220> FEATURE:
<223> OTHER INFORMATION: Synthetic

<400> SEQUENCE: 77
ctctgataac ccagctgtgt g                                             21

<210> SEQ ID NO 78
<211> LENGTH: 23
<212> TYPE: DNA
<213> ORGANISM: Artificial sequence
<220> FEATURE:
<223> OTHER INFORMATION: Synthetic

<400> SEQUENCE: 78
ctctgataac ccagctgtgt gtt                                           23

<210> SEQ ID NO 79
<211> LENGTH: 19
<212> TYPE: DNA
<213> ORGANISM: Artificial sequence
<220> FEATURE:
<223> OTHER INFORMATION: Synthetic

<400> SEQUENCE: 79
ctagaccatt tcccaccag                                                19

<210> SEQ ID NO 80
<211> LENGTH: 20
<212> TYPE: DNA
<213> ORGANISM: Artificial sequence
<220> FEATURE:
<223> OTHER INFORMATION: Synthetic

<400> SEQUENCE: 80
ctagaccatt tcccaccagt                                               20

<210> SEQ ID NO 81
<211> LENGTH: 21
<212> TYPE: DNA
<213> ORGANISM: Artificial sequence
<220> FEATURE:
<223> OTHER INFORMATION: Synthetic

<400> SEQUENCE: 81
ctagaccatt tcccaccagt t                                             21

<210> SEQ ID NO 82
<211> LENGTH: 23
<212> TYPE: DNA
<213> ORGANISM: Artificial sequence
<220> FEATURE:

<223> OTHER INFORMATION: Synthetic

<400> SEQUENCE: 82
ctagaccatt tcccaccagt tct                                    23

<210> SEQ ID NO 83
<211> LENGTH: 7009
<212> TYPE: DNA
<213> ORGANISM: Artificial sequence
<220> FEATURE:
<223> OTHER INFORMATION: Synthetic

<400> SEQUENCE: 83

| | | | | | |
|---|---|---|---|---|---|
| ctaaattgta | agcgttaata | ttttgttaaa | attcgcgtta | aattttttgtt | aaatcagctc    60 |
| attttttaac | caataggccg | aaatcggcaa | aatcccttat | aaatcaaaag | aatagaccga   120 |
| gatagggttg | agtgttgttc | cagtttggaa | caagagtcca | ctattaaaga | acgtggactc   180 |
| caacgtcaaa | gggcgaaaaa | ccgtctatca | gggcgatggc | ccactacgtg | aaccatcacc   240 |
| ctaatcaagt | tttttggggt | cgaggtgccg | taaagcacta | aatcggaacc | ctaaagggag   300 |
| cccccgattt | agagcttgac | ggggaaagcc | ggcgaacgtg | gcgagaaagg | aagggaagaa   360 |
| agcgaaagga | gcgggcgcta | gggcgctggc | aagtgtagcg | gtcacgctgc | gcgtaaccac   420 |
| cacacccgcc | gcgcttaatg | cgccgctaca | gggcgcgtcc | cattcgccat | tcaggctgcg   480 |
| caactgttgg | gaagggcgat | cggtgcgggc | ctcttcgcta | ttacgccagc | tggcgaaagg   540 |
| gggatgtgct | gcaaggcgat | taagttgggt | aacgccaggg | ttttcccagt | cacgacgttg   600 |
| taaaacgacg | gccagtgagc | gcgcgtaata | cgactcacta | tagggcgaat | tgggtacctt   660 |
| taattctagt | actatgcatg | cgttgacatt | gattattgac | tagttattaa | tagtaatcaa   720 |
| ttacggggtc | attagttcat | agcccatata | tggagttccg | cgttacataa | cttacggtaa   780 |
| atggcccgcc | tggctgaccg | cccaacgacc | cccgcccatt | gacgtcaata | atgacgtatg   840 |
| ttcccatagt | aacgccaata | gggactttcc | attgacgtca | atgggtggag | tatttacggt   900 |
| aaactgccca | cttggcagta | catcaagtgt | atcatatgcc | aagtacgccc | cctattgacg   960 |
| tcaatgacgg | taaatggccc | gcctggcatt | atgcccagta | catgacctta | tgggactttc  1020 |
| ctacttggca | gtacatctac | gtattagtca | tcgctattac | catggtgatg | cggttttggc  1080 |
| agtacatcaa | tgggcgtgga | tagcggtttg | actcacgggg | atttccaagt | ctccacccca  1140 |
| ttgacgtcaa | tgggagtttg | ttttggcacc | aaaatcaacg | ggactttcca | aaatgtcgta  1200 |
| acaactccgc | cccattgacg | caaatgggcg | gtaggcgtgt | acggtgggag | gtctatataa  1260 |
| gcagagctct | ctggctaact | accggtgcca | ccatgaaaag | gaactacatt | ctggggctgg  1320 |
| acatcgggat | tacaagcgtg | gggtatggga | ttattgacta | tgaaacaagg | gacgtgatcg  1380 |
| acgcaggcgt | cagactgttc | aaggaggcca | acgtggaaaa | caatgaggga | cggagaagca  1440 |
| agagggggagc | caggcgcctg | aaacgacgga | aaggcacag | aatccagagg | gtgaagaaac  1500 |
| tgctgttcga | ttacaacctg | ctgaccgacc | attctgagct | gagtggaatt | aatccttatg  1560 |
| aagccagggt | gaaaggcctg | agtcagaagc | tgtcagagga | agagttttcc | gcagctctgc  1620 |
| tgcacctggc | taagcgccga | ggagtgcata | acgtcaatga | ggtggaagag | gacaccggca  1680 |
| acgagctgtc | tacaaaggaa | cagatctcac | gcaatagcaa | agctctggaa | gagaagtatg  1740 |
| tcgcagagct | gcagctggaa | cggctgaaga | aagatggcga | ggtgagaggg | tcaattaata  1800 |
| ggttcaagac | aagcgactac | gtcaaagaag | ccaagcagct | gctgaaagtg | cagaaggctt  1860 |
| accaccagct | ggatcagagc | ttcatcgata | cttatatcga | cctgctggag | actcggagaa  1920 |

| | |
|---|---|
| cctactatga gggaccagga gaagggagcc ccttcggatg aaagacatc aaggaatggt | 1980 |
| acgagatgct gatgggacat tgcacctatt ttccagaaga gctgagaagc gtcaagtacg | 2040 |
| cttataacgc agatctgtac aacgccctga atgacctgaa caacctggtc atcaccaggg | 2100 |
| atgaaaacga gaaactggaa tactatgaga agttccagat catcgaaaac gtgtttaagc | 2160 |
| agaagaaaaa gcctacactg aaacagattg ctaaggagat cctggtcaac gaagaggaca | 2220 |
| tcaagggcta ccgggtgaca agcactggaa accagagtt caccaatctg aaagtgtatc | 2280 |
| acgatattaa ggacatcaca gcacggaaag aaatcattga gaacgccgaa ctgctggatc | 2340 |
| agattgctaa gatcctgact atctaccaga gctccgagga catccaggaa gagctgacta | 2400 |
| acctgaacag cgagctgacc caggaagaga tcgaacagat tagtaatctg aagggtaca | 2460 |
| ccggaacaca caacctgtcc ctgaaagcta tcaatctgat tctggatgag ctgtggcata | 2520 |
| caaacgacaa tcagattgca atctttaacc ggctgaagct ggtcccaaaa aaggtggacc | 2580 |
| tgagtcagca gaaagagatc ccaaccacac tggtggacga tttcattctg tcacccgtgg | 2640 |
| tcaagcggag cttcatccag agcatcaaag tgatcaacgc catcatcaag aagtacggcc | 2700 |
| tgcccaatga tatcattatc gagctggcta gggagaagaa cagcaaggac gcacagaaga | 2760 |
| tgatcaatga gatgcagaaa cgaaaccggc agaccaatga acgcattgaa gagattatcc | 2820 |
| gaactaccgg gaaagagaac gcaaagtacc tgattgaaaa aatcaagctg cacgatatgc | 2880 |
| aggagggaaa gtgtctgtat tctctggagg ccatccccct ggaggacctg ctgaacaatc | 2940 |
| cattcaacta cgaggtcgat catattatcc ccagaagcgt gtccttcgac aattccttta | 3000 |
| acaacaaggt gctggtcaag caggaagaga actctaaaaa gggcaatagg actcctttcc | 3060 |
| agtacctgtc tagttcagat tccaagatct cttacgaaac cttaaaaag cacattctga | 3120 |
| atctggccaa aggaaagggc cgcatcagca agaccaaaaa ggagtacctg ctggaagagc | 3180 |
| gggacatcaa cagattctcc gtccagaagg attttattaa ccggaatctg gtggacacaa | 3240 |
| gatacgctac tcgcggcctg atgaatctgc tgcgatccta tttccgggtg aacaatctgg | 3300 |
| atgtgaaagt caagtccatc aacggcgggt tcacatcttt tctgaggcgc aaatggaagt | 3360 |
| ttaaaaagga gcgcaacaaa gggtacaagc accatgccga agatgctctg attatcgcaa | 3420 |
| atgccgactt catctttaag gagtggaaaa agctggacaa agccaagaaa gtgatggaga | 3480 |
| accagatgtt cgaagagaag caggccgaat ctatgcccga atcgagaca gaacaggagt | 3540 |
| acaaggagat tttcatcact cctcaccaga tcaagcatat caaggatttc aaggactaca | 3600 |
| agtactctca ccgggtggat aaaaagccca acagagagct gatcaatgac accctgtata | 3660 |
| gtacaagaaa agacgataag gggaataccc tgattgtgaa caatctgaac ggactgtacg | 3720 |
| acaaagataa tgacaagctg aaaaagctga tcaacaaaag tcccgagaag ctgctgatgt | 3780 |
| accaccatga tcctcagaca tatcagaaac tgaagctgat tatggagcag tacggcgacg | 3840 |
| agaagaaccc actgtataag tactatgaag agactgggaa ctacctgacc aagtatagca | 3900 |
| aaaaggataa tggccccgtg atcaagaaga tcaagtacta tgggaacaag ctgaatgccc | 3960 |
| atctggacat cacagacgat tacccctaaca gtcgcaacaa ggtggtcaag ctgtcactga | 4020 |
| agccatacag attcgatgtc tatctggaca acggcgtgta taaatttgtg actgtcaaga | 4080 |
| atctggatgt catcaaaaag gagaactact atgaagtgaa tagcaagtgc tacgaagagg | 4140 |
| ctaaaaagct gaaaaagatt agcaaccagg cagagttcat cgcctccttt tacaacaacg | 4200 |
| acctgattaa gatcaatggc gaactgtata ggggtcatcgg ggtgaacaat gatctgctga | 4260 |

```
accgcattga agtgaatatg attgacatca cttaccgaga gtatctggaa aacatgaatg   4320
ataagcgccc ccctcgaatt atcaaaacaa ttgcctctaa gactcagagt atcaaaaagt   4380
actcaaccga cattctggga aacctgtatg aggtgaagag caaaaagcac cctcagatta   4440
tcaaaagggg cagcggaggc aagcgtcctg ctgctactaa gaaagctggt caagctaaga   4500 aaagaaagg atcctaccca tacgatgttc cagattacgc ttaagaattc ctagagctcg    4560
ctgatcagcc tcgactgtgc cttctagttg ccagccatct gttgtttgcc ctcccccgt    4620 gccttccttg accctggaag gtgccactcc cactgtcctt tcctaataaa atgaggaaat   4680
tgcatcgcat tgtctgagta ggtgtcattc tattctgggg gtgggggtgg ggcaggacag   4740 caaggggag gattgggaag agaatagcag gcatgctggg gaggtagcgg ccgcccgcgg    4800
tggagctcca gcttttgttc cctttagtga gggttaattg cgcgcttggc gtaatcatgg   4860
tcatagctgt ttcctgtgtg aaattgttat ccgctcacaa ttccacacaa catacgagcc   4920
ggaagcataa agtgtaaagc ctggggtgcc taatgagtga gctaactcac attaattgcg   4980
ttgcgctcac tgcccgcttt ccagtcggga acctgtcgt gccagctgca ttaatgaatc     5040
ggccaacgcg cggggagagg cggtttgcgt attgggcgct cttccgcttc ctcgctcact   5100
gactcgctgc gctcggtcgt tcggctgcgg cgagcggtat cagctcactc aaaggcggta   5160
atacggttat ccacagaatc aggggataac gcaggaaaga acatgtgagc aaaaggccag   5220
caaaaggcca ggaaccgtaa aaaggccgcg ttgctggcgt ttttccatag gctccgcccc   5280
cctgacgagc atcacaaaaa tcgacgctca agtcagaggt ggcgaaaccc gacaggacta   5340
taaagatacc aggcgtttcc ccctggaagc tccctcgtgc gctctcctgt tccgaccctg   5400
ccgcttaccg gatacctgtc cgcctttctc ccttcgggaa gcgtggcgct ttctcatagc   5460
tcacgctgta ggtatctcag ttcggtgtag gtcgttcgct ccaagctggg ctgtgtgcac   5520
gaaccccccg ttcagcccga ccgctgcgcc ttatccggta actatcgtct tgagtccaac   5580
ccggtaagac acgacttatc gccactggca gcagccactg gtaacaggat tagcagagcg   5640
aggtatgtag gcggtgctac agagttcttg aagtggtggc ctaactacgg ctacactaga   5700
aggacagtat ttggtatctg cgctctgctg aagccagtta ccttcggaaa aagagttggt   5760
agctcttgat ccggcaaaca aaccaccgct ggtagcggtg gtttttttgt ttgcaagcag   5820
cagattacgc gcagaaaaaa aggatctcaa gaagatcctt tgatctttc tacgggtct     5880 gacgctcagt ggaacgaaaa ctcacgttaa gggattttgg tcatgagatt atcaaaaagg   5940
atcttcacct agatcctttt aaattaaaaa tgaagtttta atcaatcta agtatatat     6000 gagtaaactt ggtctgacag ttaccaatgc ttaatcagtg aggcacctat ctcagcgatc   6060
tgtctatttc gttcatccat agttgcctga ctccccgtcg tgtagataac tacgatacgg   6120
gagggcttac catctggccc cagtgctgca atgataccgc gagacccacg ctcaccggct   6180
ccagatttat cagcaataaa ccagccagcc ggaagggccg agcgcagaag tggtcctgca   6240
actttatccg cctccatcca gtctattaat tgttgccggg aagctagagt aagtagttcg   6300
ccagttaata gtttgcgcaa cgttgttgcc attgctacag gcatcgtggt gtcacgctcg   6360
tcgtttggta tggcttcatt cagctccggt tcccaacgat caaggcgagt tacatgatcc   6420
cccatgttgt gcaaaaaagc ggttagctcc ttcggtcctc cgatcgttgt cagaagtaag   6480
ttggccgcag tgttatcact catggttatg gcagcactgc ataattctct tactgtcatg   6540
ccatccgtaa gatgcttttc tgtgactggt gagtactcaa ccaagtcatt ctgagaatag   6600
tgtatgcggc gaccgagttg ctcttgcccg gcgtcaatac gggataatac cgcgccacat   6660
```

```
agcagaactt taaaagtgct catcattgga aaacgttctt cggggcgaaa actctcaagg    6720
atcttaccgc tgttgagatc cagttcgatg taacccactc gtgcacccaa ctgatcttca    6780 gcatcttta  ctttcaccag cgtttctggg tgagcaaaaa caggaaggca aaatgccgca    6840 aaaagggaa  taagggcgac acggaaatgt tgaatactca tactcttcct ttttcaatat    6900
tattgaagca tttatcaggg ttattgtctc atgagcggat acatatttga atgtatttag    6960
aaaaataaac aaatagggt  tccgcgcaca tttccccgaa aagtgccac              7009
```

<210> SEQ ID NO 84
<211> LENGTH: 7048
<212> TYPE: DNA
<213> ORGANISM: Artificial sequence
<220> FEATURE:
<223> OTHER INFORMATION: Synthetic

<400> SEQUENCE: 84

```
ctaaattgta agcgttaata ttttgttaaa attcgcgtta aattttttgtt aaatcagctc      60 attttttaac caataggccg aaatcggcaa atcccttat  aaatcaaaag aatagaccga     120
gatagggttg agtgttgttc cagttttgaa caagagtcca ctattaaaga acgtggactc     180
caacgtcaaa gggcgaaaaa ccgtctatca gggcgatggc ccactacgtg aaccatcacc     240
ctaatcaagt ttttggggt  cgaggtgccg taaagcacta atcggaacc  ctaaagggag     300 ccccgattt  agagcttgac ggggaaagcc ggcgaacgtg gcgagaaagg aagggaagaa     360
agcgaaagga gcggcgcta  gggcgctggc aagtgtagcg gtcacgctgc gcgtaaccac     420
cacacccgcc gcgcttaatg cgccgctaca gggcgcgtcc cattcgccat tcaggctgcg     480
caactgttgg gaagggcgat cggtgcgggc ctcttcgcta ttacgccagc tggcgaaagg     540
gggatgtgct gcaaggcgat taagttgggt aacgccaggg ttttcccagt cacgacgttg     600
taaaacgacg gccagtgagc gcgcgtaata cgactcacta gggcgaat   tgggtacctt     660 taattctagt actatgcatg cgttgacatt gattattgac tagttattaa tagtaatcaa     720
ttacggggtc attagttcat agcccatata tggagttccg cgttacataa cttacggtaa     780
atggcccgcc tggctgaccg cccaacgacc cccgcccatt gacgtcaata atgacgtatg     840
ttcccatagt aacgccaata gggactttcc attgacgtca atgggtggag tatttacggt     900
aaactgccca cttggcagta catcaagtgt atcatatgcc aagtacgccc cctattgacg     960
tcaatgacgg taaatggccc gcctggcatt atgcccagta catgacctta tgggactttc    1020
ctacttggca gtacatctac gtattagtca tcgctattac catggtgatg cggttttggc    1080
agtacatcaa tgggcgtgga tagcggtttg actcacgggg atttccaagt ctccacccca    1140
ttgacgtcaa tgggagtttg ttttggcacc aaaatcaacg ggactttcca aaatgtcgta    1200
acaactccgc cccattgacg caaatgggcg gtaggcgtgt acggtgggag gtctatataa    1260
gcagagctct ctggctaact accggtgcca ccatggcccc aaagaagaag cggaaggtcg    1320
gtatccacgg agtcccagca gccaagcgga actacatcct gggcctggac atcggcatca    1380
ccagcgtggg ctacggcatc atcgactacg agacacggga cgtgatcgat gccggcgtgc    1440
ggctgttcaa agaggccaac gtggaaaaca acgagggcag gcggagcaag agaggcgcca    1500
gaaggctgaa gcggcggagg cggcatagaa tccagagagt gaagaagctg ctgttcgact    1560
acaacctgct gaccgaccac agcgagctga cggcatcaa  ccctacgag gccagagtga    1620 agggcctgag ccagaagctg agcgaggaag agttctctgc cgccctgctg cacctggcca    1680
```

```
agagaagagg cgtgcacaac gtgaacgagg tggaagagga caccggcaac gagctgtcca    1740
ccaaagagca gatcagccgg aacagcaagg ccctggaaga gaaatacgtg gccgaactgc    1800
agctggaacg gctgaagaaa gacggcgaag tgcggggcag catcaacaga ttcaagacca    1860
gcgactacgt gaaagaagcc aaacagctgc tgaaggtgca gaaggcctac caccagctgg    1920
accagagctt catcgacacc tacatcgacc tgctggaaaa ccggcggacc tactatgagg    1980
gacctggcga gggcagcccc ttcggctgga aggacatcaa gaatggtac gagatgctga    2040 tgggccactg cacctacttc cccgaggaac tgcggagcgt gaagtacgcc tacaacgccg    2100
acctgtacaa cgccctgaac gacctgaaca atctcgtgat caccagggac gagaacgaga    2160
agctggaata ttacgagaag ttccagatca tcgaacgt gttcaagcag aagaagaagc    2220
ccaccctgaa gcagatcgcc aaagaaatcc tcgtgaacga agaggatatt aagggctaca    2280
gagtgaccag caccggcaag cccgagttca ccaacctgaa ggtgtaccac gacatcaagg    2340
acattaccgc ccggaaagag attattgaga cgccgagct gctggatcag attgccaaga    2400
tcctgaccat ctaccagagc agcgaggaca tccaggaaga actgaccaat ctgaactccg    2460
agctgaccca ggaagagatc gagcagatct ctaatctgaa gggctatacc ggcacccaca    2520
acctgagcct gaaggccatc aacctgatcc tggacgagct gtggcacacc aacgacaacc    2580
agatcgctat cttcaaccgg ctgaagctgg tgcccaagaa ggtggacctg tcccagcaga    2640
aagagatccc caccaccctg gtggacgact tcatcctgag ccccgtcgtg aagagaagct    2700
tcatccagag catcaaagtg atcaacgcca tcatcaagaa gtacggcctg cccaacgaca    2760
tcattatcga gctggcccgc gagaagaact ccaaggacgc ccagaaaatg atcaacgaga    2820
tgcagaagcg gaaccggcag accaacgagc ggatcgagga aatcatccgg accaccggca    2880
aagagaacgc caagtacctg atcgagaaga tcaagctgca cgacatgcag gaaggcaagt    2940
gcctgtacag cctggaagcc atccctctgg aagatctgct gaacaacccc ttcaactatg    3000
aggtggacca catcatcccc agaagcgtgt ccttcgacaa cagcttcaac aacaaggtgc    3060
tcgtgaagca ggaagaaaac agcaagaagg gcaaccggac cccattccag tacctgagca    3120
gcagcgacac caagatcagc tacgaaacct tcaagaagca catcctgaat ctggccaagg    3180
gcaagggcag aatcagcaag accaagaaag agtatctgct ggaagaacgg gacatcaaca    3240
ggttctccgt gcagaaagac ttcatcaacc ggaacctggt ggataccaga tacgccacca    3300
gaggcctgat gaacctgctg cggagctact tcagagtgaa caacctggac gtgaaagtga    3360
agtccatcaa tggcggcttc accagctttt gcggcggaa gtggaagttt aagaaagagc    3420
ggaacaaggg gtacaagcac cacgccgagg acgccctgat cattgccaac gccgatttca    3480
tcttcaaaga gtggaagaaa ctggacaagg ccaaaaaagt gatggaaaac cagatgttcg    3540
aggaaaagca ggccgagagc atgcccgaga tcgaaaccga gcaggagtac aaagagatct    3600
tcatcacccc ccaccagatc aagcacatta aggacttcaa ggactacaag tacagccacc    3660
gggtggacaa gaagcctaat agagagctga ttaacgacac cctgtactcc acccggaagg    3720
acgacaaggg caacaccctg atcgtgaaca atctgaacgg cctgtacgac aaggacaatg    3780
acaagctgaa aaagctgatc aacaagagcc ccgaaaagct gctgatgtac caccacgacc    3840
cccagaccta ccagaaactg aagctgatta tggaacagta cggcgacgag aagaatcccc    3900
tgtacaagta ctacgaggaa accgggaact acctgaccaa gtactccaaa aaggacaacg    3960
gccccgtgat caagaagatt aagtattacg gcaacaaact gaacgccat ctggacatca    4020 ccgacgacta ccccaacagc agaaacaagg tcgtgaagct gtccctgaag ccctacagat    4080
```

-continued

```
tcgacgtgta cctggacaat ggcgtgtaca agttcgtgac cgtgaagaat ctggatgtga   4140
tcaaaaaaga aaactactac gaagtgaata gcaagtgcta tgaggaagct aagaagctga   4200
agaagatcag caaccaggcc gagtttatcg cctccttcta caacaacgat ctgatcaaga   4260
tcaacggcga gctgtataga gtgatcgcg tgaacaacga cctgctgaac cggatcgaag   4320
tgaacatgat cgacatcacc taccgcgagt acctggaaaa catgaacgac aagaggcccc   4380
ccaggatcat taagacaatc gcctccaaga cccagagcat taagaagtac agcacagaca   4440
ttctgggcaa cctgtatgaa gtgaaatcta agaagcaccc tcagatcatc aaaaagggca   4500
aaaggccggc ggccacgaaa aaggccggcc aggcaaaaaa gaaaaaggga tcctacccat   4560
acgatgttcc agattacgct taagaattcc tagagctcgc tgatcagcct cgactgtgcc   4620
ttctagttgc cagccatctg ttgtttgccc ctcccccgtg ccttccttga ccctggaagg   4680
tgccactccc actgtccttt cctaataaaa tgaggaaatt gcatcgcatt gtctgagtag   4740
gtgtcattct attctggggg gtggggtggg gcaggacagc aagggggagg attgggaaga   4800
gaatagcagg catgctgggg aggtagcggc cgcccgcggt ggagctccag cttttgttcc   4860
ctttagtgag ggttaattgc gcgcttggcg taatcatggt catagctgtt tcctgtgtga   4920
aattgttatc cgctcacaat tccacacaac atacgagccg gaagcataaa gtgtaaagcc   4980
tggggtgcct aatgagtgag ctaactcaca ttaattgcgt tgcgctcact gcccgctttc   5040
cagtcgggaa acctgtcgtg ccagctgcat taatgaatcg gccaacgcgc ggggagaggc   5100
ggtttgcgta ttgggcgctc ttccgcttcc tcgctcactg actcgctgcg ctcggtcgtt   5160
cggctgcggc gagcggtatc agctcactca aaggcggtaa tacggttatc cacagaatca   5220
ggggataacg caggaaagaa catgtgagca aaaggccagc aaaaggccag gaaccgtaaa   5280
aaggccgcgt tgctggcgtt tttccatagg ctccgccccc ctgacgagca tcacaaaaat   5340
cgacgctcaa gtcagaggtg gcgaaacccg acaggactat aaagatacca ggcgtttccc   5400
cctggaagct ccctcgtgcg ctctcctgtt ccgaccctgc cgcttaccgg atacctgtcc   5460
gcctttctcc cttcgggaag cgtggcgctt tctcatagct cacgctgtag gtatctcagt   5520
tcggtgtagg tcgttcgctc caagctgggc tgtgtgcacg aacccccccgt tcagcccgac   5580
cgctgcgcct tatccggtaa ctatcgtctt gagtccaacc cggtaagaca cgacttatcg   5640
ccactggcag cagccactgg taacaggatt agcagagcga ggtatgtagg cggtgctaca   5700
gagttcttga agtggtggcc taactacggc tacactagaa ggacagtatt tggtatctgc   5760
gctctgctga agccagttac cttcggaaaa agagttggta gctcttgatc cggcaaacaa   5820
accaccgctg gtagcggtgg tttttttgtt tgcaagcagc agattacgcg cagaaaaaaa   5880
ggatctcaag aagatccttt gatcttttct acggggtctg acgctcagtg gaacgaaaac   5940
tcacgttaag ggattttggt catgagatta tcaaaaagga tcttcaccta gatccttta   6000
aattaaaaat gaagttttaa atcaatctaa agtatatatg agtaaacttg gtctgacagt   6060
taccaatgct taatcagtga ggcacctatc tcagcgatct gtctatttcg ttcatccata   6120
gttgcctgac tccccgtcgt gtagataact acgatacggg agggcttacc atctggcccc   6180
agtgctgcaa tgataccgcg agacccacgc tcaccggctc cagatttatc agcaataaac   6240
cagccagccg gaagggccga gcgcagaagt ggtcctgcaa ctttatccgc ctccatccag   6300
tctattaatt gttgccggga agctagagta agtagttcgc cagttaatag tttgcgcaac   6360
gttgttgcca ttgctacagg catcgtggtg tcacgctcgt cgtttggtat ggcttcattc   6420
```

```
agctccggtt cccaacgatc aaggcgagtt acatgatccc ccatgttgtg caaaaaagcg    6480
gttagctcct tcggtcctcc gatcgttgtc agaagtaagt tggccgcagt gttatcactc    6540
atggttatgg cagcactgca taattctctt actgtcatgc catccgtaag atgcttttct    6600
gtgactggtg agtactcaac caagtcattc tgagaatagt gtatgcggcg accgagttgc    6660
tcttgcccgg cgtcaatacg ggataatacc gcgccacata gcagaacttt aaaagtgctc    6720
atcattggaa aacgttcttc ggggcgaaaa ctctcaagga tcttaccgct gttgagatcc    6780
agttcgatgt aacccactcg tgcacccaac tgatcttcag catcttttac tttcaccagc    6840
gtttctgggt gagcaaaaac aggaaggcaa aatgccgcaa aaagggaat aagggcgaca    6900 cggaaatgtt gaatactcat actcttcctt tttcaatatt attgaagcat ttatcagggt    6960
tattgtctca tgagcggata catatttgaa tgtatttaga aaataaaca atagggggtt    7020 ccgcgcacat ttccccgaaa agtgccac                                       7048
```

<210> SEQ ID NO 85
<211> LENGTH: 48
<212> TYPE: DNA
<213> ORGANISM: Artificial sequence
<220> FEATURE:
<223> OTHER INFORMATION: Synthetic

<400> SEQUENCE: 85

```
aaaaggccgg cggccacgaa aaaggccggc caggcaaaaa agaaaaag                   48
```

<210> SEQ ID NO 86
<211> LENGTH: 3223
<212> TYPE: DNA
<213> ORGANISM: Artificial sequence
<220> FEATURE:
<223> OTHER INFORMATION: Synthetic

<400> SEQUENCE: 86

```
ctaaattgta agcgttaata ttttgttaaa attcgcgtta aatttttgtt aaatcagctc      60
attttttaac caataggccg aaatcggcaa aatcccttat aaatcaaaag aatagaccga     120
gatagggttg agtgttgttc cagttttgga caagagtcca ctattaaaga acgtggactc     180
caacgtcaaa gggcgaaaaa ccgtctatca gggcgatggc ccactacgtg aaccatcacc     240
ctaatcaagt ttttggggt cgaggtgccg taaagcacta atcggaacc ctaaagggag      300 cccccgattt agagcttgac ggggaaagcc ggcgaacgtg gcgagaaagg aagggaagaa    360
agcgaaagga gcgggcgcta gggcgctggc aagtgtagcg gtcacgctgc gcgtaaccac    420
cacacccgcc gcgcttaatg cgccgctaca gggcgcgtcc cattcgccat tcaggctgcg    480
caactgttgg aagggcgat cggtgcgggc ctcttcgcta ttacgccagc tggcgaaagg    540
gggatgtgct gcaaggcgat taagttgggt aacgccaggg ttttcccagt cacgacgttg    600
taaaacgacg gccagtgagc gcgcgtaata cgactcacta gggcgaat tgggtaccga     660 gggcctattt cccatgattc cttcatattt gcatatacga tacaaggctg ttagagagat    720
aattggaatt aatttgactg taaacacaaa gatattagta caaaatacgt gacgtagaaa    780
gtaataattt cttgggtagt ttgcagtttt aaaattatgt tttaaatgg actatcatat    840 gcttatcgta acttgaaagt atttcgattt cttggcttta tatcttgt ggaaaggacg     900 aaacaccggg tcttcgagaa gacctgtttt agagctagaa atagcaagtt aaaataaggc    960
tagtccgtta tcaacttgaa aaagtggcac cgagtcggtg cttttttcc gcggtggagc    1020 tccagctttt gttcccttta gtgagggtta attgcgcgct tggcgtaatc atggtcatag    1080
```

```
ctgtttcctg tgtgaaattg ttatccgctc acaattccac acaacatacg agccggaagc    1140
ataaagtgta aagcctgggg tgcctaatga gtgagctaac tcacattaat tgcgttgcgc    1200
tcactgcccg ctttccagtc gggaaacctg tcgtgccagc tgcattaatg aatcggccaa    1260
cgcgcgggga gaggcggttt gcgtattggg cgctcttccg cttcctcgct cactgactcg    1320
ctgcgctcgg tcgttcggct gcggcgagcg gtatcagctc actcaaaggc ggtaatacgg    1380
ttatccacag aatcagggga taacgcagga agaacatgt gagcaaaagg ccagcaaaag    1440
gccaggaacc gtaaaaaggc cgcgttgctg gcgtttttcc ataggctccg ccccctgac    1500 gagcatcaca aaaatcgacg ctcaagtcag aggtggcgaa acccgacagg actataaaga    1560
taccaggcgt ttccccctgg aagctccctc gtgcgctctc ctgttccgac cctgccgctt    1620
accggatacc tgtccgcctt tctcccttcg ggaagcgtgg cgctttctca tagctcacgc    1680
tgtaggtatc tcagttcggt gtaggtcgtt cgctccaagc tgggctgtgt gcacgaaccc    1740
cccgttcagc ccgaccgctg cgccttatcc ggtaactatc gtcttgagtc caacccggta    1800
agacacgact tatcgccact ggcagcagcc actggtaaca ggattagcag agcgaggtat    1860
gtaggcggtg ctacagagtt cttgaagtgg tggcctaact acggctacac tagaaggaca    1920
gtatttggta tctgcgctct gctgaagcca gttaccttcg gaaaaagagt tggtagctct    1980
tgatccggca aacaaaccac cgctggtagc ggtggttttt ttgtttgcaa gcagcagatt    2040
acgcgcagaa aaaaggatc tcaagaagat cctttgatct tttctacggg gtctgacgct    2100
cagtggaacg aaaactcacg ttaagggatt ttggtcatga gattatcaaa aaggatcttc    2160
acctagatcc ttttaaatta aaaatgaagt tttaaatcaa tctaaagtat atatgagtaa    2220
acttggtctg acagttacca atgcttaatc agtgaggcac ctatctcagc gatctgtcta    2280
tttcgttcat ccatagttgc ctgactcccc gtcgtgtaga taactacgat acgggagggc    2340
ttaccatctg gccccagtgc tgcaatgata ccgcgagacc cacgctcacc ggctccagat    2400
ttatcagcaa taaaccagcc agccggaagg gccgagcgca gaagtggtcc tgcaacttta    2460
tccgcctcca tccagtctat taattgttgc cgggaagcta gagtaagtag ttcgccagtt    2520
aatagtttgc gcaacgttgt tgccattgct acaggcatcg tggtgtcacg ctcgtcgttt    2580
ggtatggctt cattcagctc cggttcccaa cgatcaaggc gagttacatg atcccccatg    2640
ttgtgcaaaa aagcggttag ctccttcggt cctccgatcg ttgtcagaag taagttggcc    2700
gcagtgttat cactcatggt tatggcagca ctgcataatt ctcttactgt catgccatcc    2760
gtaagatgct tttctgtgac tggtgagtac tcaaccaagt cattctgaga atagtgtatg    2820
cggcgaccga gttgctcttg cccggcgtca atacgggata ataccgcgcc acatagcaga    2880
actttaaaag tgctcatcat tggaaaacgt tcttcggggc gaaaactctc aaggatctta    2940
ccgctgttga gatccagttc gatgtaaccc actcgtgcac ccaactgatc ttcagcatct    3000
tttactttca ccagcgtttc tgggtgagca aaaacaggaa ggcaaaatgc cgcaaaaaag    3060
ggaataaggg cgacacggaa atgttgaata ctcatactct tcctttttca atattattga    3120
agcatttatc agggttattg tctcatgagc ggatacatat ttgaatgtat ttagaaaaat    3180
aaacaaatag gggttccgcg cacatttccc cgaaaagtgc cac                      3223
```

<210> SEQ ID NO 87
<211> LENGTH: 20
<212> TYPE: DNA
<213> ORGANISM: Artificial sequence
<220> FEATURE:

<223> OTHER INFORMATION: Synthetic

<400> SEQUENCE: 87
ctccggaatg tctccatttg                                        20

<210> SEQ ID NO 88
<211> LENGTH: 20
<212> TYPE: DNA
<213> ORGANISM: Artificial sequence
<220> FEATURE:
<223> OTHER INFORMATION: Synthetic

<400> SEQUENCE: 88
atgagggaga gactggcatc                                        20

<210> SEQ ID NO 89
<211> LENGTH: 23
<212> TYPE: DNA
<213> ORGANISM: Artificial sequence
<220> FEATURE:
<223> OTHER INFORMATION: Synthetic

<400> SEQUENCE: 89
gtttccagag ctttacctga gaa                                    23

<210> SEQ ID NO 90
<211> LENGTH: 22
<212> TYPE: DNA
<213> ORGANISM: Artificial sequence
<220> FEATURE:
<223> OTHER INFORMATION: Synthetic

<400> SEQUENCE: 90
cttttatgaa tgcttctcca ag                                     22

<210> SEQ ID NO 91
<211> LENGTH: 21
<212> TYPE: DNA
<213> ORGANISM: Artificial sequence
<220> FEATURE:
<223> OTHER INFORMATION: Synthetic

<400> SEQUENCE: 91
aagttacttg tccaggcatg a                                      21

<210> SEQ ID NO 92
<211> LENGTH: 25
<212> TYPE: DNA
<213> ORGANISM: Artificial sequence
<220> FEATURE:
<223> OTHER INFORMATION: Synthetic

<400> SEQUENCE: 92
gaaaaacttc tgccaacttt tatca                                  25

<210> SEQ ID NO 93
<211> LENGTH: 25
<212> TYPE: DNA
<213> ORGANISM: Artificial sequence
<220> FEATURE:
<223> OTHER INFORMATION: Synthetic

<400> SEQUENCE: 93
tgcaaataac aaaagtagcc ataca                                  25

```
<210> SEQ ID NO 94
<211> LENGTH: 23
<212> TYPE: DNA
<213> ORGANISM: Artificial sequence
<220> FEATURE:
<223> OTHER INFORMATION: Synthetic

<400> SEQUENCE: 94
tctttagaaa ggcttgaaag ctg                                             23

<210> SEQ ID NO 95
<211> LENGTH: 20
<212> TYPE: DNA
<213> ORGANISM: Artificial sequence
<220> FEATURE:
<223> OTHER INFORMATION: Synthetic

<400> SEQUENCE: 95
cttcactgct ggccagttta                                                 20

<210> SEQ ID NO 96
<211> LENGTH: 21
<212> TYPE: DNA
<213> ORGANISM: Artificial sequence
<220> FEATURE:
<223> OTHER INFORMATION: Synthetic

<400> SEQUENCE: 96
ttgaacatgg cattgcataa a                                               21

<210> SEQ ID NO 97
<211> LENGTH: 20
<212> TYPE: DNA
<213> ORGANISM: Artificial sequence
<220> FEATURE:
<223> OTHER INFORMATION: Synthetic

<400> SEQUENCE: 97
cgggcttgga cagaacttac                                                 20

<210> SEQ ID NO 98
<211> LENGTH: 20
<212> TYPE: DNA
<213> ORGANISM: Artificial sequence
<220> FEATURE:
<223> OTHER INFORMATION: Synthetic

<400> SEQUENCE: 98
ctgcgtagtg ccaaaacaaa                                                 20

<210> SEQ ID NO 99
<211> LENGTH: 22
<212> TYPE: DNA
<213> ORGANISM: Artificial sequence
<220> FEATURE:
<223> OTHER INFORMATION: Synthetic

<400> SEQUENCE: 99
gagatgtctt ttgcagcttt cc                                              22

<210> SEQ ID NO 100
<211> LENGTH: 20
<212> TYPE: DNA
<213> ORGANISM: Artificial sequence
<220> FEATURE:
<223> OTHER INFORMATION: Synthetic
```

<400> SEQUENCE: 100
gggaccttgg taaagccaca                                              20

<210> SEQ ID NO 101
<211> LENGTH: 21
<212> TYPE: DNA
<213> ORGANISM: Artificial sequence
<220> FEATURE:
<223> OTHER INFORMATION: Synthetic

<400> SEQUENCE: 101
tgcctttcaa tcattgtttc g                                            21

<210> SEQ ID NO 102
<211> LENGTH: 20
<212> TYPE: DNA
<213> ORGANISM: Artificial sequence
<220> FEATURE:
<223> OTHER INFORMATION: Synthetic

<400> SEQUENCE: 102
agaaggcaaa ttggcacaga                                              20

<210> SEQ ID NO 103
<211> LENGTH: 20
<212> TYPE: DNA
<213> ORGANISM: Artificial sequence
<220> FEATURE:
<223> OTHER INFORMATION: Synthetic

<400> SEQUENCE: 103
aaggccccaa aatgtgaaat                                              20

<210> SEQ ID NO 104
<211> LENGTH: 25
<212> TYPE: DNA
<213> ORGANISM: Artificial sequence
<220> FEATURE:
<223> OTHER INFORMATION: Synthetic

<400> SEQUENCE: 104
gagtttggct caaattgtta ctctt                                        25

<210> SEQ ID NO 105
<211> LENGTH: 18
<212> TYPE: DNA
<213> ORGANISM: Artificial sequence
<220> FEATURE:
<223> OTHER INFORMATION: Synthetic

<400> SEQUENCE: 105
tggcggcgtt ttcattat                                                18

<210> SEQ ID NO 106
<211> LENGTH: 26
<212> TYPE: DNA
<213> ORGANISM: Artificial sequence
<220> FEATURE:
<223> OTHER INFORMATION: Synthetic

<400> SEQUENCE: 106
ttcgatccgt aatgattgtt ctagcc                                       26

<210> SEQ ID NO 107
<211> LENGTH: 20

```
<212> TYPE: DNA
<213> ORGANISM: Artificial sequence
<220> FEATURE:
<223> OTHER INFORMATION: Synthetic

<400> SEQUENCE: 107
ttgtgtgtcc catgcttgtt                                          20

<210> SEQ ID NO 108
<211> LENGTH: 20
<212> TYPE: DNA
<213> ORGANISM: Artificial sequence
<220> FEATURE:
<223> OTHER INFORMATION: Synthetic

<400> SEQUENCE: 108
caacgctgaa gaaccctgat                                          20

<210> SEQ ID NO 109
<211> LENGTH: 24
<212> TYPE: DNA
<213> ORGANISM: Artificial sequence
<220> FEATURE:
<223> OTHER INFORMATION: Synthetic

<400> SEQUENCE: 109
tttctgtgat tttcttttgg attg                                     24

<210> SEQ ID NO 110
<211> LENGTH: 18
<212> TYPE: DNA
<213> ORGANISM: Artificial sequence
<220> FEATURE:
<223> OTHER INFORMATION: Synthetic

<400> SEQUENCE: 110
tggataaagc tcctactc                                            18

<210> SEQ ID NO 111
<211> LENGTH: 18
<212> TYPE: DNA
<213> ORGANISM: Artificial sequence
<220> FEATURE:
<223> OTHER INFORMATION: Synthetic

<400> SEQUENCE: 111
tggataaagg caacaatg                                            18

<210> SEQ ID NO 112
<211> LENGTH: 19
<212> TYPE: DNA
<213> ORGANISM: Artificial sequence
<220> FEATURE:
<223> OTHER INFORMATION: Synthetic

<400> SEQUENCE: 112
actcacctcg accatttcc                                           19

<210> SEQ ID NO 113
<211> LENGTH: 19
<212> TYPE: DNA
<213> ORGANISM: Artificial sequence
<220> FEATURE:
<223> OTHER INFORMATION: Synthetic

<400> SEQUENCE: 113
```

```
tattggagcc tttgaaaga                                                    19

<210> SEQ ID NO 114
<211> LENGTH: 26
<212> TYPE: DNA
<213> ORGANISM: Artificial sequence
<220> FEATURE:
<223> OTHER INFORMATION: Synthetic

<400> SEQUENCE: 114
ctattggagc ctttgaaaga attcag                                            26
```